(12) United States Patent
Li et al.

(10) Patent No.: US 9,879,039 B2
(45) Date of Patent: Jan. 30, 2018

(54) TETRADENTATE AND OCTAHEDRAL METAL COMPLEXES CONTAINING NAPHTHYRIDINOCARBAZOLE AND ITS ANALOGUES

(71) Applicant: Arizona Board of Regents on behalf of Arizona State University, Scottsdale, AZ (US)

(72) Inventors: Jian Li, Tempe, AZ (US); Guijie Li, Hangzhou Zhejiang (CN)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/168,942

(22) Filed: May 31, 2016

(65) Prior Publication Data

US 2016/0359125 A1 Dec. 8, 2016

Related U.S. Application Data

(60) Provisional application No. 62/170,283, filed on Jun. 3, 2015, provisional application No. 62/254,011, filed on Nov. 11, 2015.

(51) Int. Cl.
| | | |
|---|---|---|
| *C07F 15/00* | (2006.01) | |
| *H01L 51/50* | (2006.01) | |
| *H01L 51/00* | (2006.01) | |
| *C09K 11/06* | (2006.01) | |

(52) U.S. Cl.
CPC ........ *C07F 15/0033* (2013.01); *C07F 15/006* (2013.01); *C07F 15/0086* (2013.01); *C09K 11/06* (2013.01); *H01L 51/0084* (2013.01); *H01L 51/0085* (2013.01); *H01L 51/0087* (2013.01); *H01L 51/0094* (2013.01); *C09K 2211/1007* (2013.01); *C09K 2211/1029* (2013.01); *C09K 2211/1044* (2013.01); *C09K 2211/185* (2013.01); *H01L 51/5016* (2013.01); *H01L 2251/5376* (2013.01)

(58) Field of Classification Search
CPC ................................ C07F 15/00; H01L 51/50
USPC .............................................. 546/10; 313/504
See application file for complete search history.

(56) References Cited

U.S. PATENT DOCUMENTS

| | | | |
|---|---|---|---|
| 4,769,292 A | 9/1988 | Tang et al. | |
| 5,707,745 A | 1/1998 | Forrest et al. | |
| 5,844,363 A | 12/1998 | Gu et al. | |
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,037,599 B2 | 5/2006 | Culligan et al. | |
| 7,064,228 B1 | 6/2006 | Yu et al. | |
| 7,279,704 B2 | 10/2007 | Walters et al. | |
| 7,332,232 B2 | 2/2008 | Ma et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,389,725 B2 | 3/2013 | Li et al. | |
| 8,617,723 B2 | 12/2013 | Stoessel | |
| 8,816,080 B2 | 8/2014 | Li et al. | |
| 8,871,361 B2 | 10/2014 | Xia et al. | |
| 8,927,713 B2 | 1/2015 | Li et al. | |
| 8,946,417 B2 | 2/2015 | Jian et al. | |
| 9,059,412 B2 | 6/2015 | Zeng et al. | |
| 9,221,857 B2 | 12/2015 | Li et al. | |
| 9,224,963 B2 | 12/2015 | Li et al. | |
| 9,238,668 B2 | 1/2016 | Li et al. | |
| 9,312,505 B2 | 4/2016 | Brooks et al. | |
| 9,324,957 B2 | 4/2016 | Li et al. | |
| 9,382,273 B2 | 7/2016 | Li | |
| 9,385,329 B2 | 7/2016 | Li et al. | |
| 9,425,415 B2 | 8/2016 | Li et al. | |
| 9,461,254 B2 | 10/2016 | Tsai et al. | |
| 9,550,801 B2 | 1/2017 | Li et al. | |
| 9,598,449 B2 | 3/2017 | Li et al. | |
| 2001/0019782 A1 | 9/2001 | Igarashi et al. | |
| 2002/0068190 A1 | 6/2002 | Tsuboyama et al. | |
| 2003/0062519 A1 | 4/2003 | Yamazaki et al. | |
| 2004/0230061 A1 | 11/2004 | Seo et al. | |
| 2005/0170207 A1 | 8/2005 | Ma et al. | |
| 2005/0260446 A1 | 11/2005 | Mackenzie et al. | |
| 2006/0024522 A1 | 2/2006 | Thompson et al. | |
| 2006/0073359 A1 | 4/2006 | Ise et al. | |
| 2006/0094875 A1 | 5/2006 | Itoh et al. | |
| 2006/0127696 A1 | 6/2006 | Stossel | |
| 2006/0182992 A1 | 8/2006 | Nii | |
| 2006/0202197 A1 | 9/2006 | Nakayama et al. | |
| 2006/0210831 A1 | 9/2006 | Sano et al. | |
| 2006/0255721 A1 | 11/2006 | Igarashi | |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

(Continued)

*Primary Examiner* — Charanjit Aulakh
(74) *Attorney, Agent, or Firm* — Fish & Richardson P.C.

(57) ABSTRACT

Tetradentate and octahedral metal complexes suitable for use as phosphorescent or delayed fluorescent and phosphorescent emitters in display and lighting applications.

20 Claims, 9 Drawing Sheets

(56) References Cited

U.S. PATENT DOCUMENTS

| | | |
|---|---|---|
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0141127 A1 | 6/2010 | Xia et al. |
| 2010/0171111 A1 | 7/2010 | Takada et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0264938 A1 | 10/2012 | Li |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2015/0380666 A1 | 12/2015 | Szigethy et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133861 A1 | 5/2016 | Li et al. |
| 2016/0133862 A1 | 5/2016 | Li et al. |
| 2016/0194344 A1 | 7/2016 | Li et al. |
| 2016/0197285 A1 | 7/2016 | Xia et al. |
| 2016/0285015 A1 | 9/2016 | Li et al. |
| 2016/0359120 A1 | 12/2016 | Li |
| 2017/0005278 A1 | 1/2017 | Li et al. |
| 2017/0012224 A1 | 1/2017 | Li et al. |
| 2017/0047533 A1 | 2/2017 | Li et al. |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2002105055 | 4/2002 |
| JP | 2003342284 | 12/2003 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 | 2/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 | 4/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 2006290988 | 10/2006 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201249851 | 12/2012 |
| TW | 201307365 | 2/2013 |
| WO | WO0070655 | 11/2000 |
| WO | WO2004003108 | 1/2004 |

(56) References Cited

FOREIGN PATENT DOCUMENTS

| WO | WO2004085450 | 10/2004 |
|---|---|---|
| WO | WO2004108857 | 12/2004 |
| WO | WO2005042444 | 5/2005 |
| WO | WO2005042550 | 5/2005 |
| WO | WO2005113704 | 12/2005 |
| WO | WO2006033440 | 3/2006 |
| WO | WO2006067074 | 6/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010007098 | 1/2010 |
| WO | WO2010056669 | 5/2010 |
| WO | WO2010093176 | 8/2010 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate $O^{\wedge}N^{\wedge}C^{\wedge}N$ Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate $O^{\wedge}N^{\wedge}C^{\wedge}N$ ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.

(56) References Cited

OTHER PUBLICATIONS

Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
V. Thamilarasan et al., "Green-emitting phosphorescent iridium(III) complex: Structural, photophysical and electrochemical properties," Inorganica Chimica Acta, vol. 408, 2013, pp. 240-245.
Rui Zhu et al., "Color tuning based on a six-membered chelated iridium (III) complex with aza-aromatic ligand," Chemistry Letters, vol. 34, No. 12, 2005, pp. 1668-1669.

TETRADENTATE AND OCTAHEDRAL METAL COMPLEXES CONTAINING NAPHTHYRIDINOCARBAZOLE AND ITS ANALOGUES

CROSS-REFERENCE TO RELATED APPLICATIONS

This application claims priority to U.S. Provisional Patent Application No. 62/170,283 entitled "TETRADENTATE METAL COMPLEXES CONTAINING NAPHTHYRIDINOCARBAZOLE AND ITS ANALOGUES" filed on Jun. 3, 2015, and U.S. Provisional Patent Application No. 62/254,011 entitled "TETRADENTATE AND OCTAHEDRAL METAL COMPLEXES CONTAINING NAPHTHYRIDINOCARBAZOLE AND ITS ANALOGUES" filed on Nov. 11, 2015, which are hereby incorporated by reference in their entirety.

TECHNICAL FIELD

The present disclosure relates to tetradentate and octahedral metal complexes suitable for use as phosphorescent or delayed fluorescent and phosphorescent emitters in display and lighting applications.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, and devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to metal complexes suitable for use as emitters in organic light emitting diodes (OLEDs), display and lighting applications.

Disclosed herein are complexes of Formula AI, Formula AII, Formula AIII and Formula AIV:

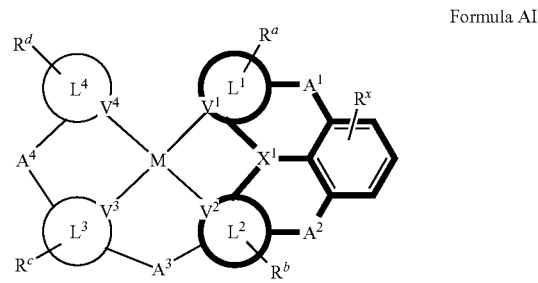
Formula AI

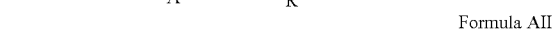
Formula AII

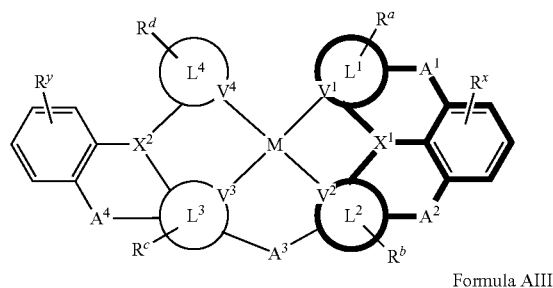

Formula AIII

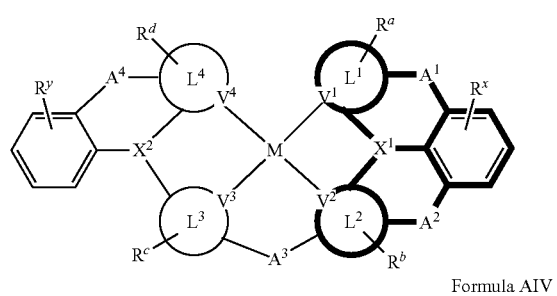

Formula AIV

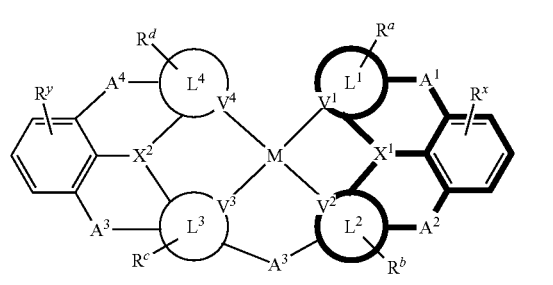

wherein:
M is Pt or Pd,
each of $V^1$, $V^2$, $V^3$, and $V^4$ is coordinated with M and is independently N, C, P, B, or Si,
each of $L^1$, $L^2$, $L^3$, and $L^4$ is independently substituted or unsubstituted aryl, cycloalkyl, cycloalkenyl, heteroaryl, heterocyclyl, carbene, or N-heterocyclic carbene,
each of $A^1$, $A^2$, $A^3$, $A^4$ and $A^5$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$,
each of $X^1$ and $X^2$ is independently $CR^1$, $SiR^1$, $GeR^1$, N, P, P=O, As, As=O, B, $R^3Bi$=O or Bi,
each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^x$ and $R^y$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination and each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula AV, Formula AVI, Formula AVII, Formula AVIII, Formula AIX, Formula AX, Formula AXI or Formula AXII:

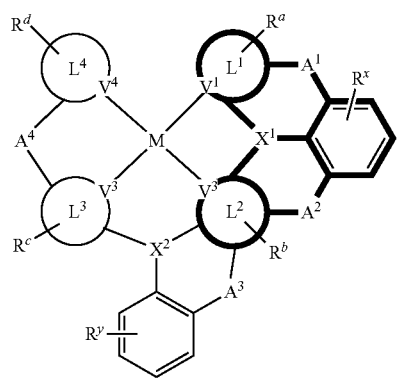

Formula AVI


Formula AVII


Formula AVIII

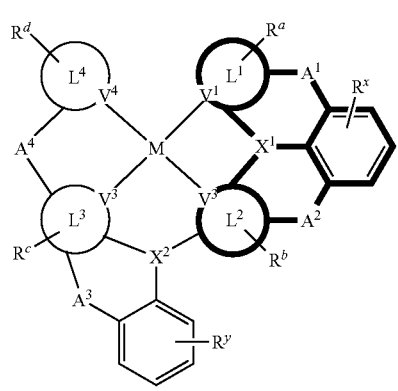

Formula AV

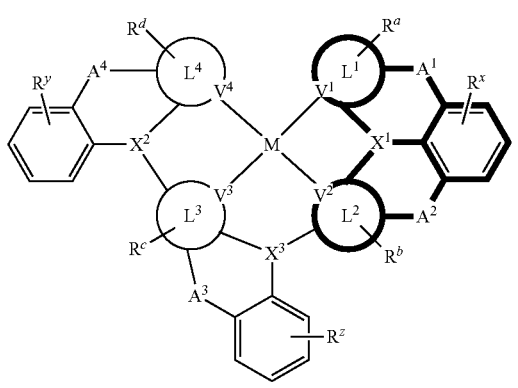

Formula AIX

-continued

Formula AX

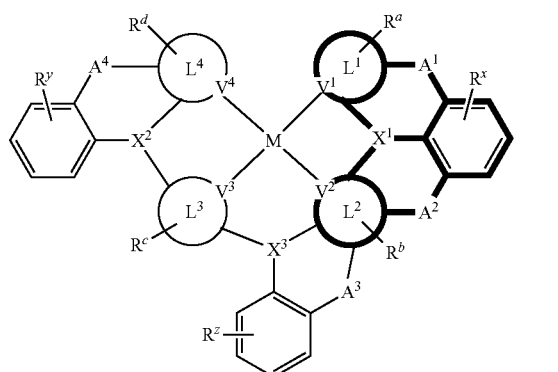

Formula AXI

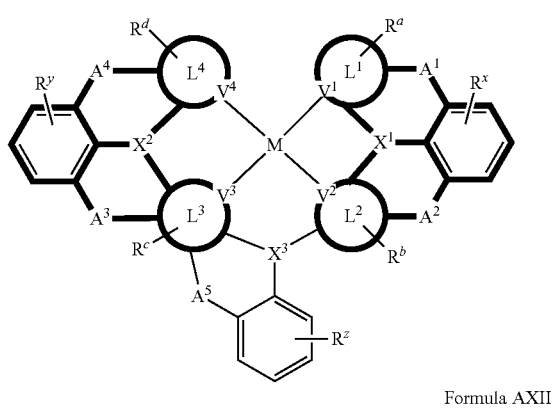

Formula AXII

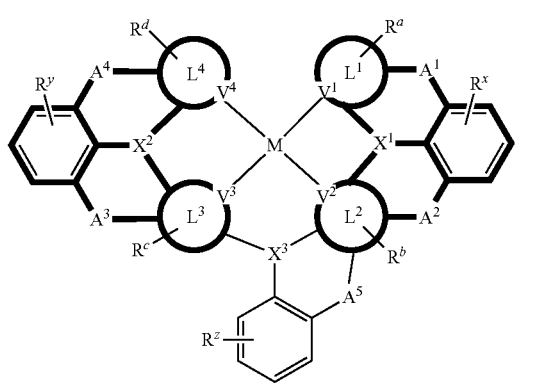

wherein:
M is Pt or Pd,
each of $V^1$, $V^2$, $V^3$, and $V^4$ is coordinated with M and is independently N, C, P, B, or Si,
each of $L^1$, $L^2$, $L^3$, and $L^4$ is independently substituted or unsubstituted aryl, cycloalkyl, cycloalkenyl, heteroaryl, heterocyclyl, carbene, or N-heterocyclic carbene,
each of $A^1$, $A^2$, $A^3$, $A^4$ and $A^5$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$,
each of $X^1$, $X^2$ and $X^3$ is independently $CR^1$, $SiR^1$, $GeR^1$, N, P, P=O, As, As=O, B, $R^3Bi$=O or Bi,
each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^x$, $R^y$ and $R^z$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination and wherein each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Disclosed herein are complexes of Formula BI, Formula BII, Formula BIII, Formula BIV, or Formula BV:

Formula BI

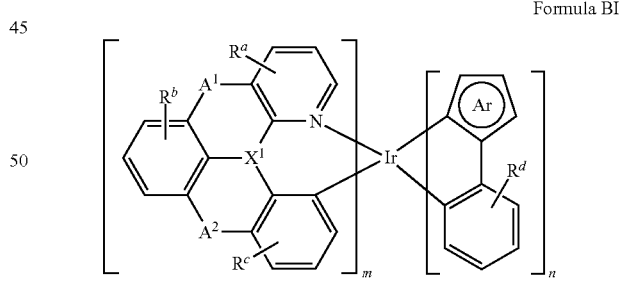

Formula BII

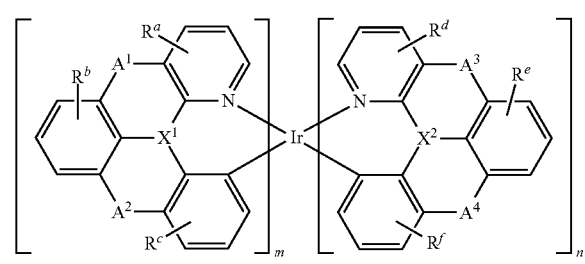

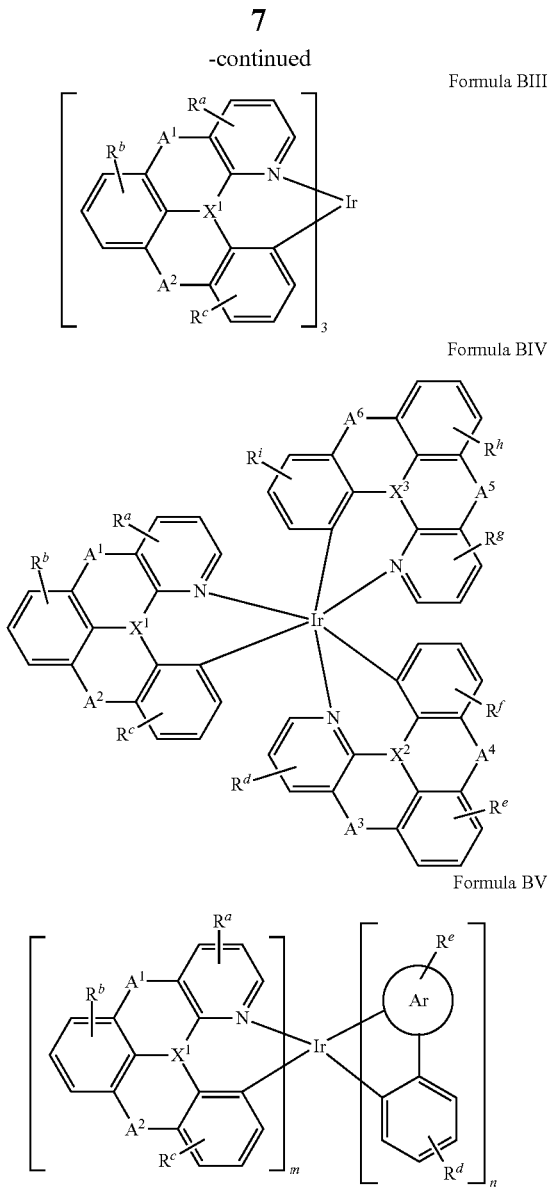

wherein:
Ar is substituted or unsubstituted aryl, cycloalkyl, cycloalkenyl, heteroaryl, heterocyclyl, carbene, or N-heterocyclic carbene,
each of $A^1$, $A^2$, $A^3$, $A^4$, $A^5$, and $A^6$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$,
each of $X^1$, $X^2$, and $X^3$ is independently $CR^1$, $SiR^1$, $GeR^1$, N, P, P=O, As, As=O, B, $R^3Bi$=O or Bi,
m=1 and n=2 or m=2 and n=1,
each of $R^a$, $R^b$, $R^c$, $R^d$, $R^e$, $R^f$, $R^g$, $R^h$, and $R^i$ is independently present or absent, and if present each of $R^a$, $R^b$, $R^c$, $R^d$, $R^e$, $R^f$, $R^g$, $R^h$, and $R^i$ is independently a mono-, di-, or tri-substitution as valency permits, and each of $R^a$, $R^b$, $R^c$, $R^d$, $R^e$, $R^f$, $R^g$, $R^h$, and $R^i$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions including one or more complexes disclosed herein.

Also disclosed herein are devices, such as OLEDs, including one or more complexes or compositions disclosed herein.

Figure 1:
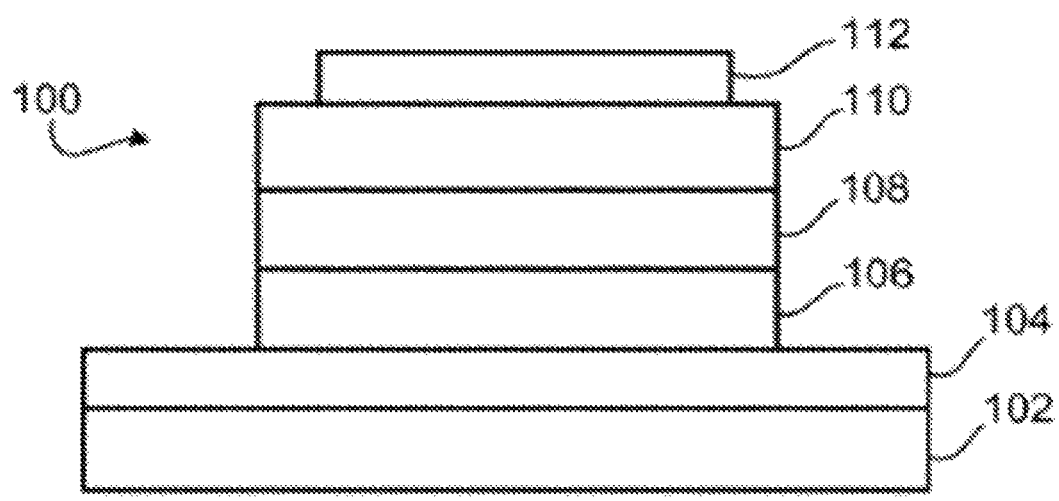
FIG. 1 depicts a cross-sectional view of an exemplary organic light-emitting diode (OLED).

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group can connect two atoms such as, for example, an N atom and a C atom. A linking atom or group is in one aspect disclosed as $X^1$, $X^2$, and/or $X^3$ herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms.

Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula —(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH (COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

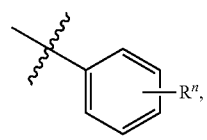

which is understood to be equivalent to a formula:

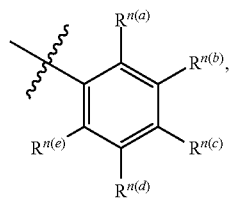

wherein n is typically an integer. That is, R'' is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs) and a great deal of attention has been received both in the academic and industrial fields. And much achievement has been made in the past decade to lead to the lucrative commercialization of the technology, for example, OLEDs have been used in advanced displays in smart phones, televisions and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state ($T_1$) energy of the blue phosphors is high, which generally means that the lowest triplet excited state ($T_1$) energy of host materials for the blue devices should be even higher. This leads to difficulty in the development of the host materials for the blue devices.

This disclosure provides a materials design route by introducing a carbon group (C, Si, Ge) bridging to the ligand of the metal complexes. It was found that chemical structures of the ligands could be modified, and also the metal could be changed to adjust the singlet states energy and the triplet states energy of the metal complexes, which all could affect the optical properties of the complexes.

The metal complexes described herein can be tailored or tuned to a specific application that is facilitated by a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can generally exhibit different optical properties, including emission and absorption spectra. The color of the metal complexes can be tuned by modifying the conjugated groups on the fluorescent luminophores and ligands.

The emission of such complexes can be tuned, for example, from the ultraviolet to near-infrared, by, for example, modifying the ligand or fluorescent luminophore structure. A fluorescent luminophore is a group of atoms in an organic molecule that can absorb energy to generate singlet excited state(s). The singlet exciton(s) produce(s) decay rapidly to yield prompt luminescence. In one aspect, the complexes can provide emission over a majority of the visible spectrum. In a specific example, the complexes described herein can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, emitters in organic light emitting diodes (OLEDs), or a combination thereof. In another aspect, the complexes can be useful in light emitting devices, such as, for example, compact fluorescent lamps (CFL), light emitting diodes (LEDs), incandescent lamps, and combinations thereof.

Disclosed herein are compounds or compound complexes comprising platinum or palladium. The terms compound or compound complex are used interchangeably herein. In one aspect, the compounds disclosed herein have a neutral charge.

The compounds disclosed herein can exhibit desirable properties and have emission and/or absorption spectra that can be tuned via the selection of appropriate ligands. In another aspect, any one or more of the compounds, structures, or portions thereof, specifically recited herein may be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency and/or operational lifetimes in lighting devices, such as, for example, organic light emitting devices, as compared to conventional materials.

Compounds described herein can be made using a variety of methods, including, but not limited to those recited in the examples.

The compounds disclosed herein include delayed fluorescent emitters, phosphorescent emitters, or a combination thereof. In one aspect, the compounds disclosed herein are delayed fluorescent emitters. In another aspect, the compounds disclosed herein are phosphorescent emitters. In yet another aspect, a compound disclosed herein is both a delayed fluorescent emitter and a phosphorescent emitter.

Disclosed herein are complexes of Formula AI, Formula AII, Formula AIII and Formula AIV:

Formula AI
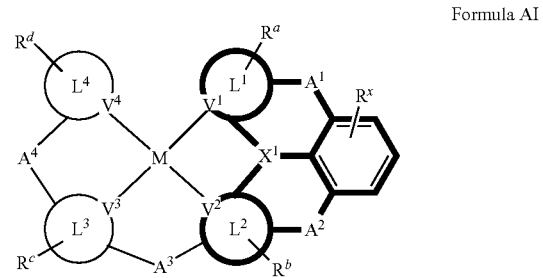

Formula AII
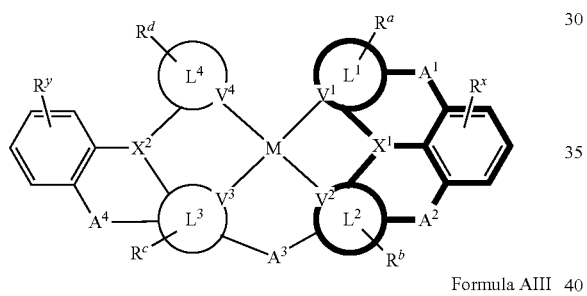

Formula AIII
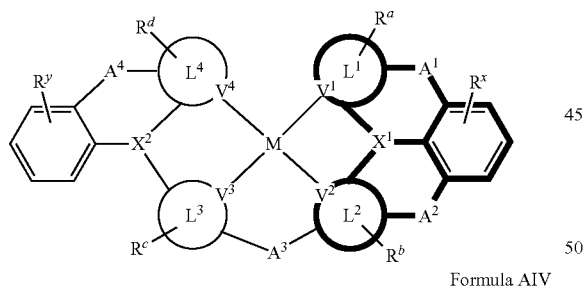

Formula AIV
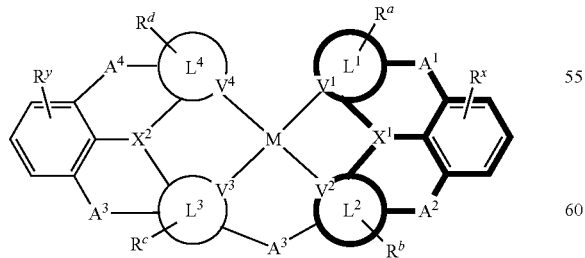

wherein:
M is Pt or Pd,
each of $V^1$, $V^2$, $V^3$, and $V^4$ is coordinated with M and is independently N, C, P, B, or Si, each of $L^1$, $L^2$, $L^3$, and $L^4$ is independently substituted or unsubstituted aryl, cycloalkyl, cycloalkenyl, heteroaryl, heterocyclyl, carbene, or N-heterocyclic carbene, each of $A^1$, $A^2$, $A^3$, $A^4$ and $A^5$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$, each of $X^1$ and $X^2$ is independently $CR^1$, $SiR^1$, $GeR^1$, N, P, P=O, As, As=O, B, $R^3Bi$=O or Bi, each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^x$ and $R^y$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination and each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula AV, Formula AVI, Formula AVII, Formula AVIII, Formula AIX, Formula AX, Formula AXI or Formula AXII:

Formula AV
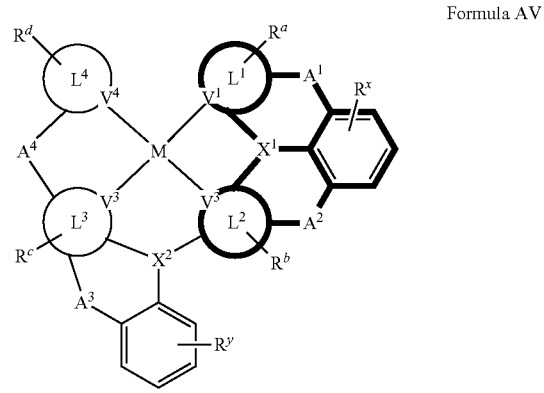

-continued

Formula AVI

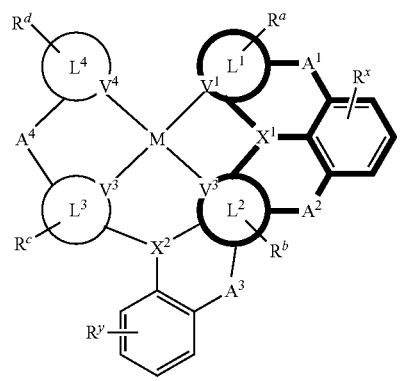

Formula AVII

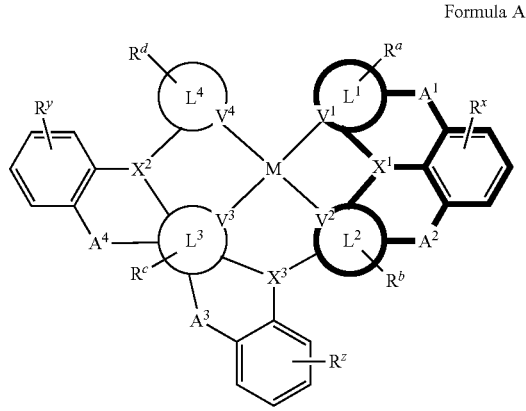

Formula AVIII

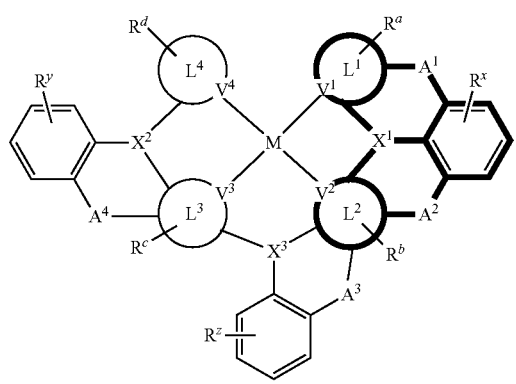

Formula AIX

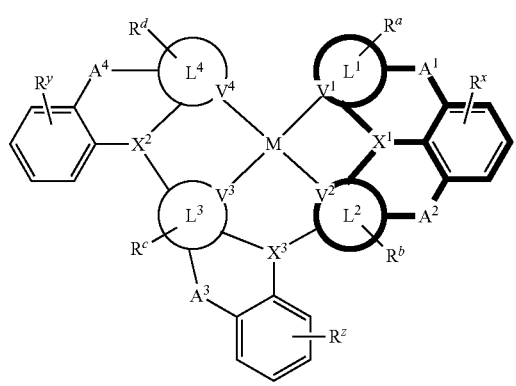

Formula AX

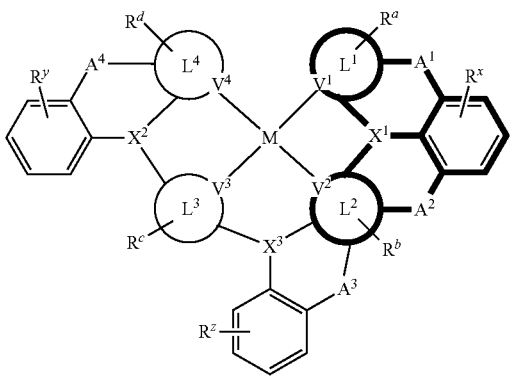

Formula AXI

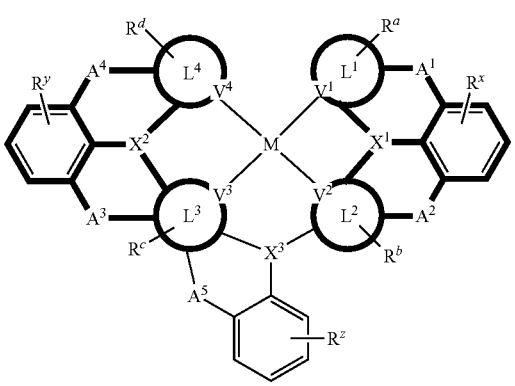

Formula AXII

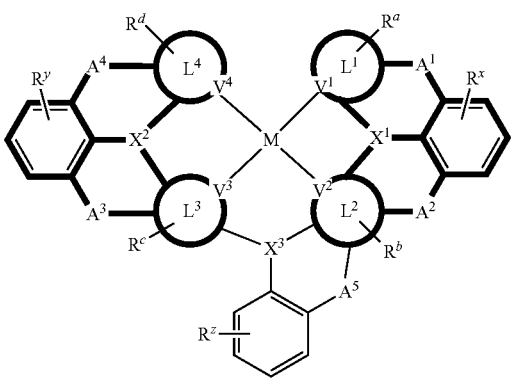

wherein:

M is Pt or Pd, each of $V^1$, $V^2$, $V^3$, and $V^4$ is coordinated with M and is independently N, C, P, B, or Si, each of $L^1$, $L^2$, $L^3$, and $L^4$ is independently substituted or unsubstituted aryl, cycloalkyl, cycloalkenyl, heteroaryl, heterocyclyl, carbene, or N-heterocyclic carbene, each of $A^1$, $A^2$, $A^3$, $A^4$ and $A^5$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$, each of $X^1$, $X^2$ and $X^3$ is independently $CR^1$, $SiR^1$, $GeR^1$, N, P, P=O, As, As=O, B, $R^3Bi$=O or Bi, each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^x$, $R^y$ and $R^z$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof and wherein each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

For Formulas AI-AXII as described herein, groups may be defined as described below.

In one aspect, M is Pt.

In another aspect, M is Pd.

In one aspect, each of $V^1$, $V^2$, $V^3$, and $V^4$ is coordinated with M and is independently N, C, P, B, or Si.

In another aspect, each of $V^1$, $V^2$, $V^3$, and $V^4$ is independently N or C.

In yet another aspect, each of $V^1$, $V^2$, $V^3$, and $V^4$ is independently P or B.

In yet another aspect, each of $V^1$, $V^2$, $V^3$, and $V^4$ is Si.

In one aspect, each of $A^1$, $A^2$, $A^3$, $A^4$, and $A^5$ is independently a single bond.

In another aspect, each of $A^1$, $A^2$, $A^3$, $A^4$, and $A^5$ is independently $CR^1R^2$.

In yet another aspect, each of $A^1$, $A^2$, $A^3$, $A^4$, and $A^5$ is independently $NR^3$.

In yet another aspect, each of $A^1$, $A^2$, $A^3$, $A^4$, and $A^5$ is independently O.

In yet another aspect, each of $A^1$, $A^2$, $A^3$, $A^4$, and $A^5$ is independently S.

In yet another aspect, each of $A^1$, $A^2$, $A^3$, $A^4$, and $A^5$ is independently $BR^3$.

In yet another aspect, each of $A^1$, $A^2$, $A^3$, $A^4$, and $A^5$ is independently $SiR^1R^2$.

In yet another aspect, each of $A^1$, $A^2$, $A^3$, $A^4$, and $A^5$ is independently $R^3P=O$.

In yet another aspect, each of $A^1$, $A^2$, $A^3$, $A^4$, and $A^5$ is independently $SO_2$.

In yet another aspect, A is independently $CH_2$, $C=O$, $SiH_2$, $GeH_2$, $GeR^1R^2$, NH, PH, $PR^3$, $AsR^3$, $R^3As=O$, $S=O$, Se, $Se=O$, $SeO_2$, BH, $R^3Bi=O$, BiH, or $BiR^3$.

In one aspect, each of $X^1$, $X^2$, and $X^3$ is independently CH.

In another aspect, each of $X^1$, $X^2$, and $X^3$ is independently $CR^1$.

In yet another aspect, each of $X^1$, $X^2$ and $X^3$, is independently N.

In yet another aspect, each of $X^1$, $X^2$ and $X^3$, is independently B.

In yet another aspect, each of $X^1$, $X^2$ and $X^3$, is independently P=O.

In yet another aspect, each of $X^1$, $X^2$ and $X^3$, is independently SiH, $SiR^1$, GeH, $GeR^1$, P, As, As=O, $R^3Bi=O$, or Bi.

In one aspect, at least one $R^a$ is present. In another aspect, $R^a$ is absent.

In one aspect, $R^a$ is a mono-substitution. In another aspect, $R^a$ is a di-substitution. In yet another aspect, $R^a$ is a tri-substitution.

In one aspect, each $R^a$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^a$ are linked together or are not linked together. In one aspect, at least one $R^a$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^a$ are linked together or are not linked together.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^b$ are linked together or are not linked together. In one aspect, at least one $R^b$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^b$ are linked together or are not linked together.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonyl amino, sulfonylamino, sulfamoyl, carbamoyl, alkylthio, ureido, phosphoramide, silyl, polymeric; or any conjugate or combination thereof, and wherein two or more of $R^c$ are linked together or are not linked together. In one aspect, at least one $R^c$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^c$ are linked together or are not linked together.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^d$ are linked together or are not linked together. In one aspect, at least one $R^d$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^d$ are linked together or are not linked together.

In one aspect, at least one $R^x$ is present. In another aspect, $R^x$ is absent.

In one aspect, $R^x$ is a mono-substitution. In another aspect, $R^x$ is a di-substitution. In yet another aspect, $R^x$ is a tri-substitution.

In one aspect, each $R^x$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^x$ are linked together or are not linked together. In one aspect, at least one $R^x$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^x$ are linked together or are not linked together.

In one aspect, at least one $R^y$ is present. In another aspect, $R^y$ is absent.

In one aspect, $R^y$ is a mono-substitution. In another aspect, $R^y$ is a di-substitution. In yet another aspect, $R^y$ is a tri-substitution.

In one aspect, each $R^y$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^y$ are linked together or are not linked together. In one aspect, at least one $R^y$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^y$ are linked together or are not linked together.

In one aspect, at least one $R^z$ is present. In another aspect, $R^z$ is absent.

In one aspect, $R^z$ is a mono-substitution. In another aspect, $R^z$ is a di-substitution. In yet another aspect, $R^z$ is a tri-substitution.

In one aspect, each $R^z$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^z$ are linked together or are not linked together. In one aspect, at least one $R^z$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^z$ are linked together or are not linked together.

In one aspect, each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino, aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, substituted silyl, polymeric, or any conjugate or combination thereof. In another aspect, each of R, $R^1$, $R^2$, $R^3$, and $R^4$ is independently hydrogen, aryl, cycloalkyl, cycloalkenyl, heterocyclyl, heteroaryl, alkyl, alkenyl, alkynyl, halogen, hydroxyl, thiol, nitro, cyano, or amino. In another aspect, each of R, $R^1$, $R^2$, $R^3$, and $R^4$ is independently hydrogen, aryl, cycloalkyl, cycloalkenyl, heterocyclyl, heteroaryl, alkyl, alkenyl, or alkynyl.

In one aspect, $L^1$ is aryl, cycloalkyl, cycloalkenyl, heteroaryl, heterocyclyl, carbene, or N-heterocyclic carbene. In one example, $L^1$ is aryl, cycloalkyl, cycloalkenyl, heteroaryl, or N-heterocyclyl. In another example, $L^1$ is aryl or heteroaryl. In yet another example, $L^2$ is aryl.

In one aspect, $L^2$ is aryl, cycloalkyl, cycloalkenyl, heteroaryl, heterocyclyl, carbene, or N-heterocyclic carbene. In one example, $L^2$ is aryl, cycloalkyl, cycloalkenyl, heteroaryl, or N-heterocyclyl. In another example, $L^2$ is aryl or heteroaryl. In yet another example, $L^2$ is aryl.

In one aspect, $L^3$ is aryl, cycloalkyl, cycloalkenyl, heteroaryl, heterocyclyl, carbene, or N-heterocyclic carbene. In one example, $L^3$ is aryl, cycloalkyl, cycloalkenyl, heteroaryl, or heterocyclyl. In another example, $L^3$ is aryl or heteroaryl. In yet another example, $L^3$ is aryl.

In one aspect, $L^4$ is aryl, cycloalkyl, cycloalkenyl, heteroaryl, heterocyclyl, carbene, or N-heterocyclic carbene. In one example, $L^4$ is aryl, cycloalkyl, cycloalkenyl, heteroaryl, or heterocyclyl. In another example, $L^4$ is aryl or heteroaryl. In yet another example, $L^4$ is heteroaryl. In yet another example, $L^4$ is heterocyclyl. It is understood that $V^4$ is or is not a part of $L^4$ and is intended to be included in the description of $L^4$ above.

In one aspect, for any of the formulas disclosed herein, each of

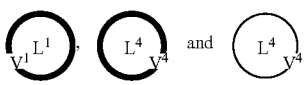

is independently one following structures:

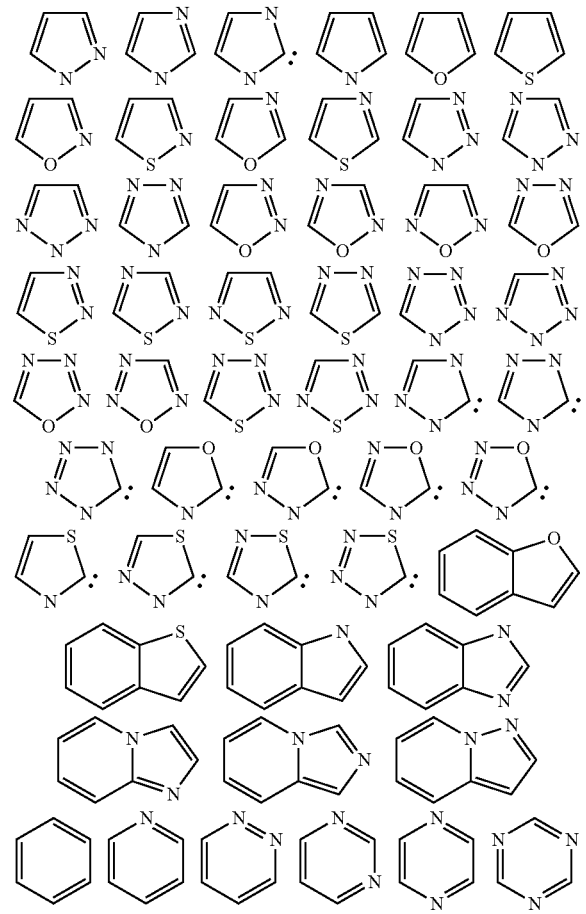

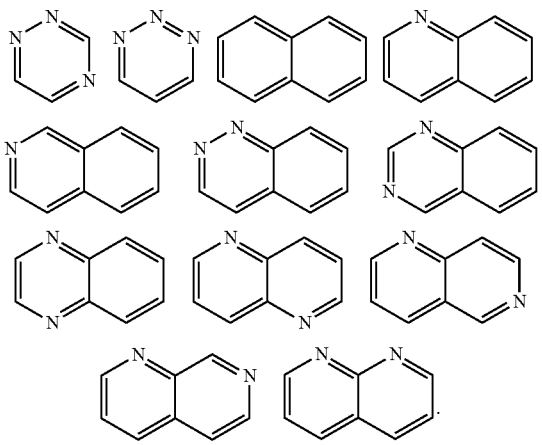

It is understood that one or more of $R^a$, $R^b$, $R^c$, and $R^d$ as described herein is or is not bonded to

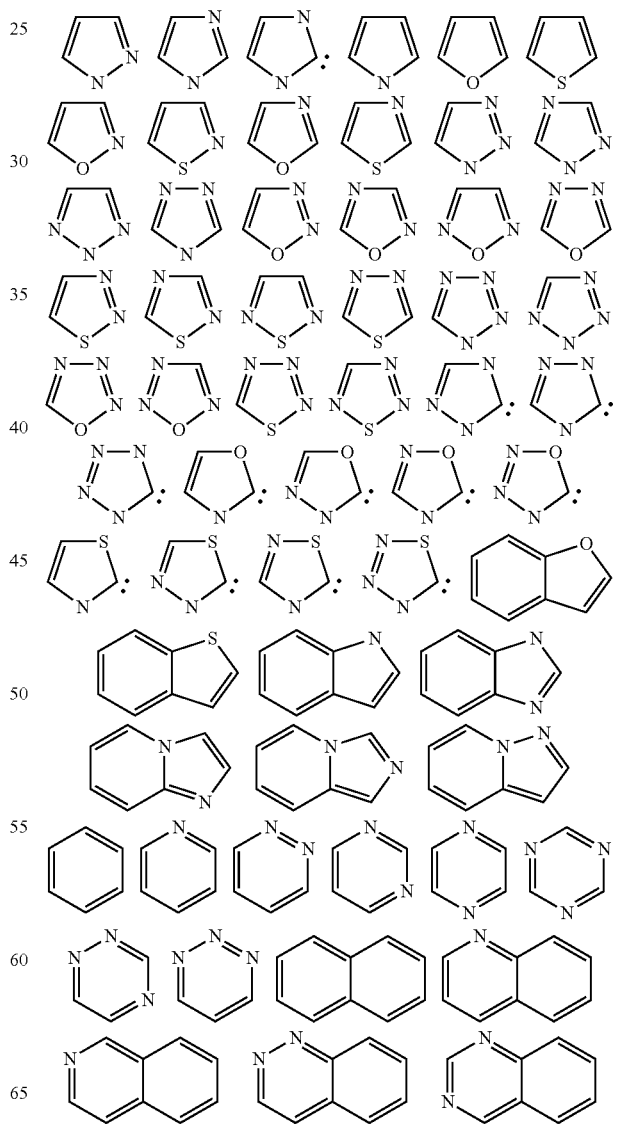

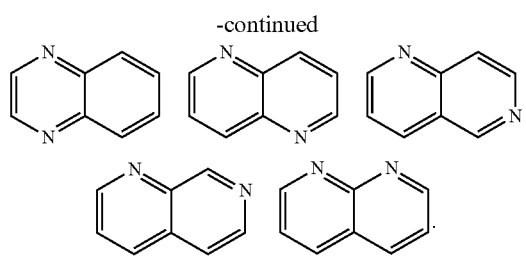
as permitted by valency.
In one aspect,
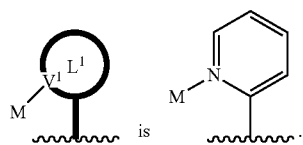
In one aspect,
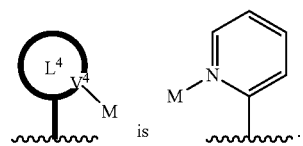
In one aspect,
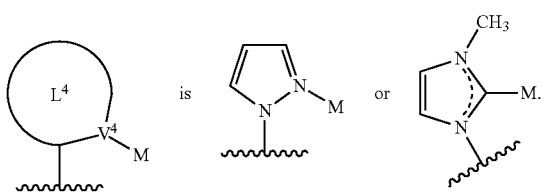
In one aspect, for any of the formulas illustrated in this disclosure, each of
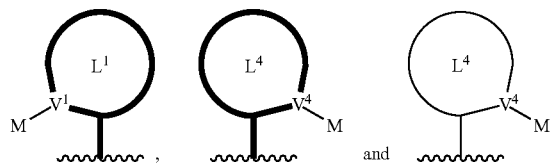
is independently one of following structures:
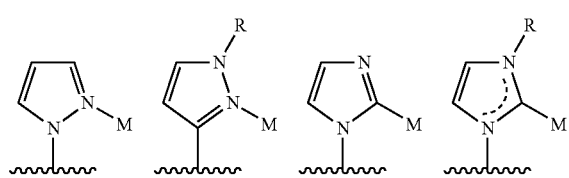
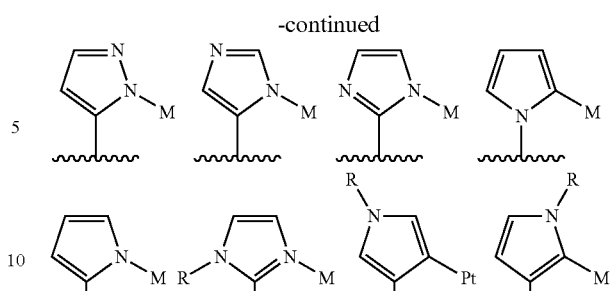
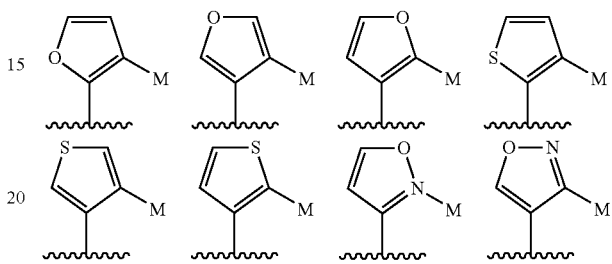
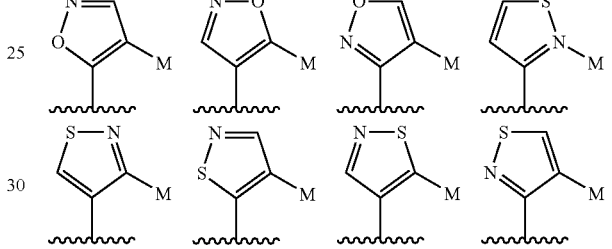
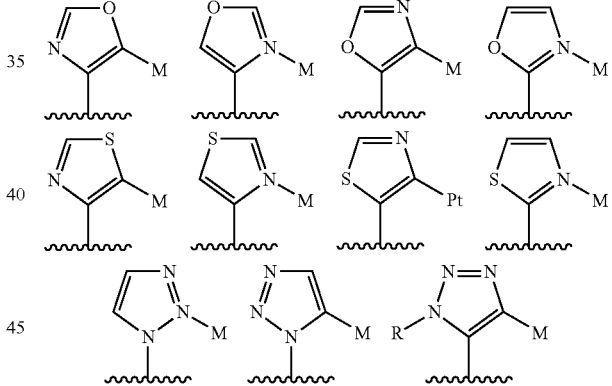
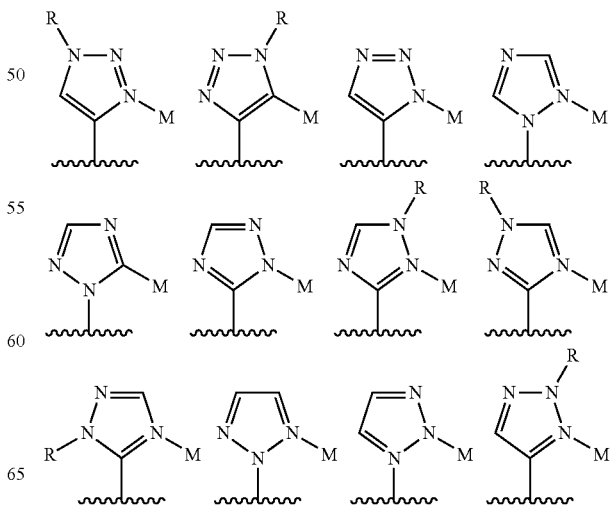

-continued
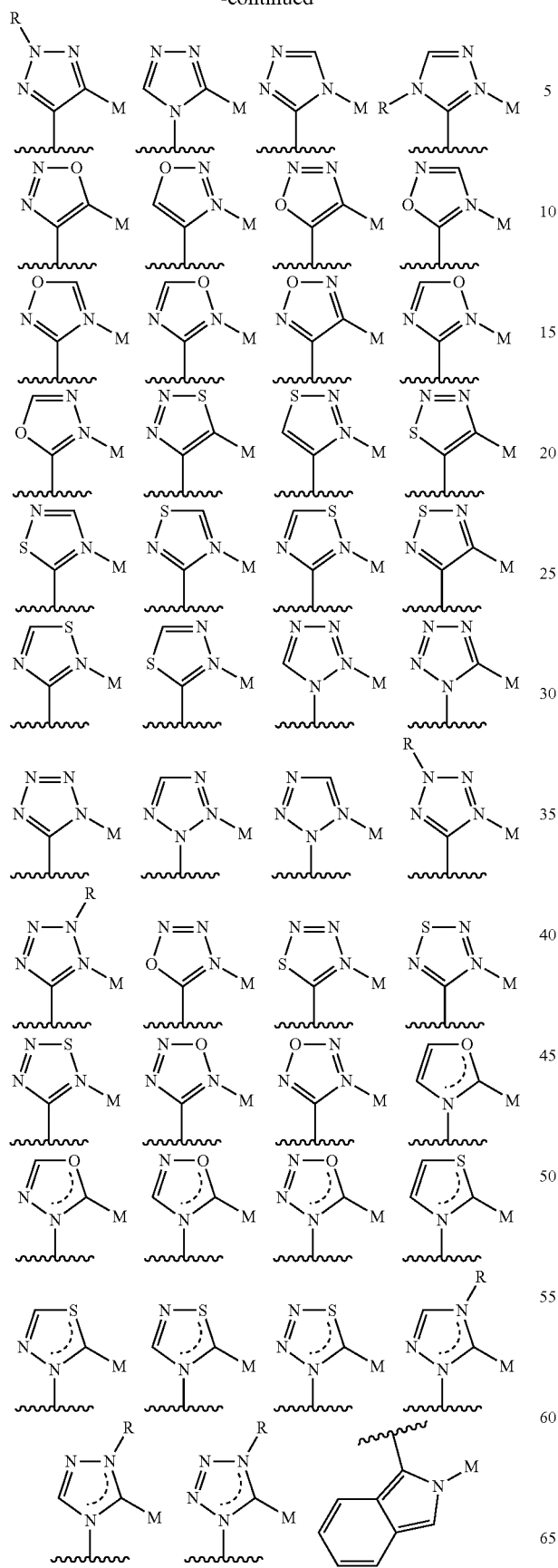
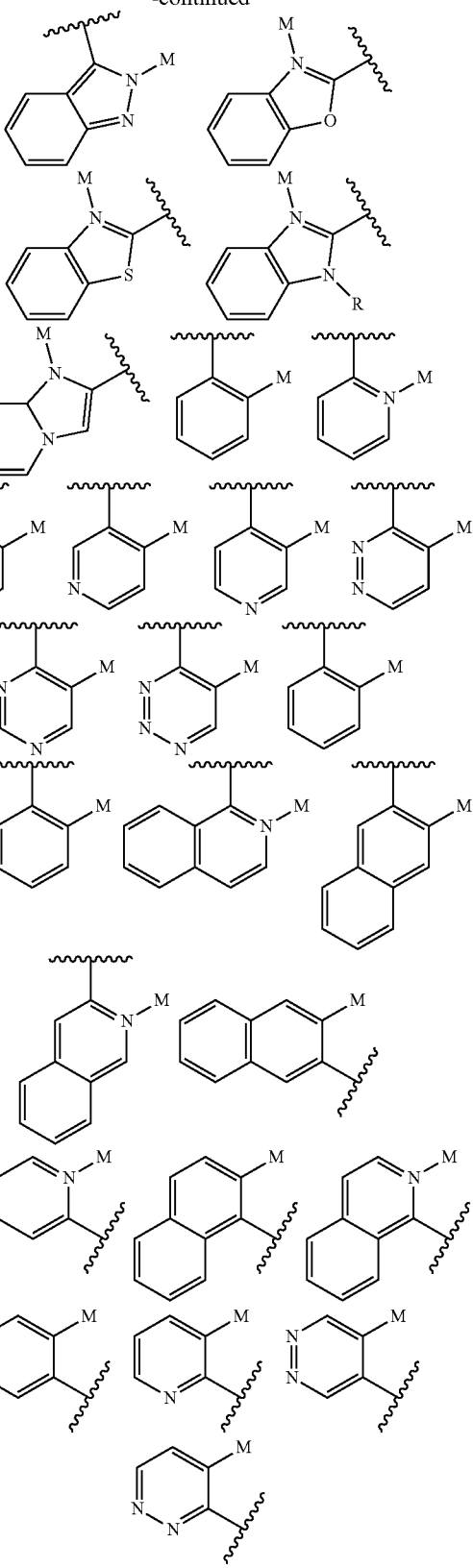
wherein R is hydrogen, deuterium, halogen, hydroxyl, thiol, nitro, cyano, nitrile, isonitrile, sulfinyl, mercapto, sulfo, carboxyl, hydrazino; substituted or unsubstituted:

aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect,

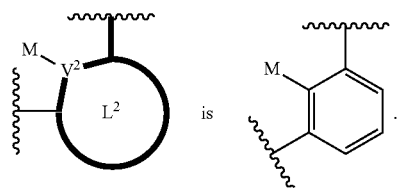

In one aspect,

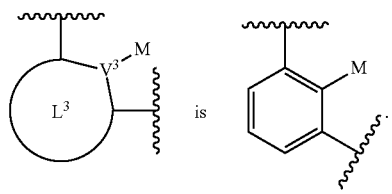

In one aspect, for any of the formulas disclosed herein, each of

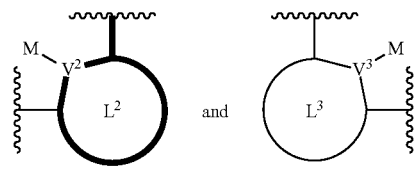

is independently one of the following structures:

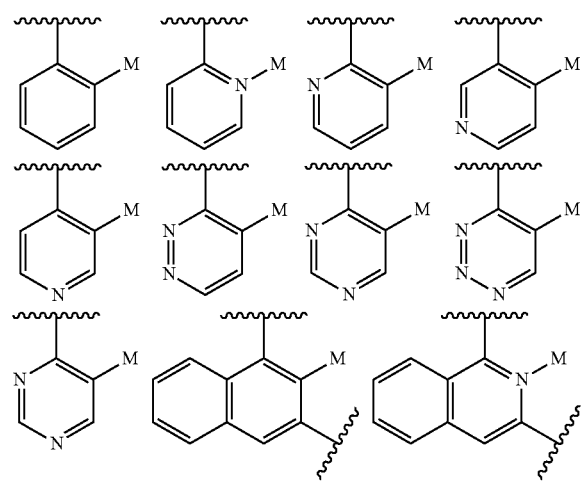

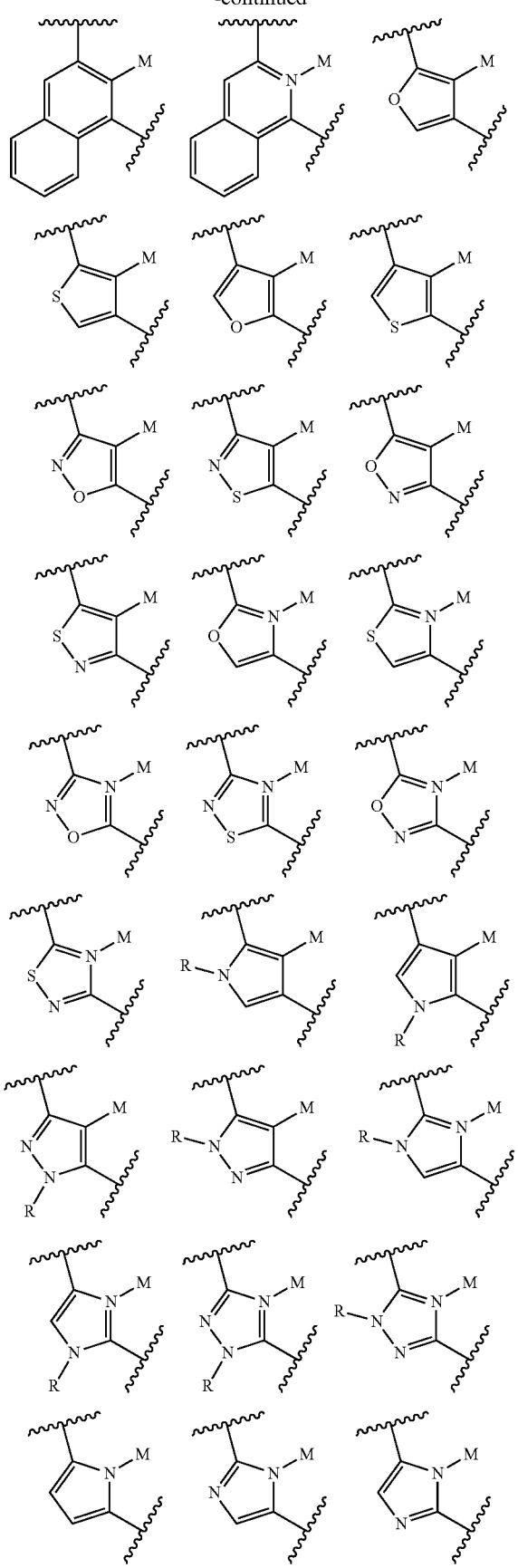

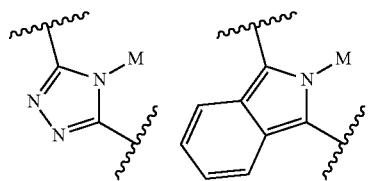

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

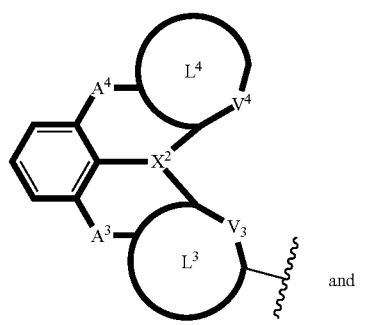

and

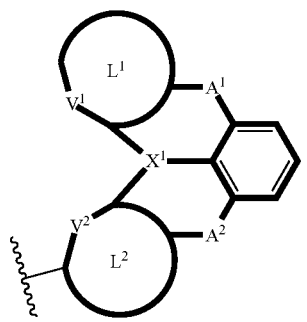

is independently one of the following structures:

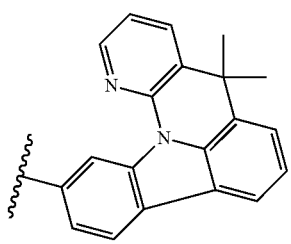

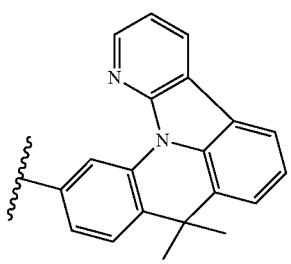

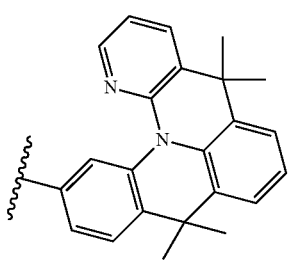

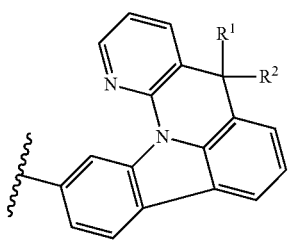

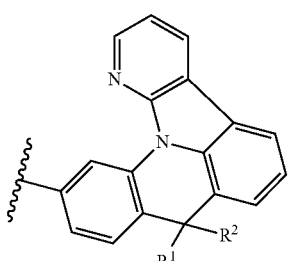

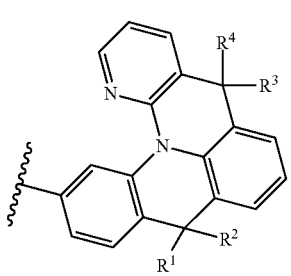

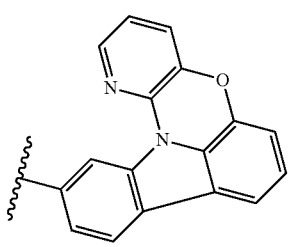

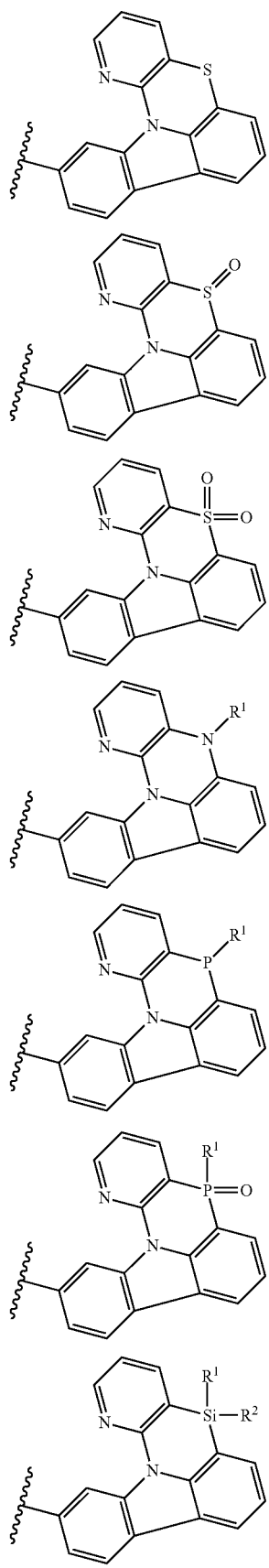
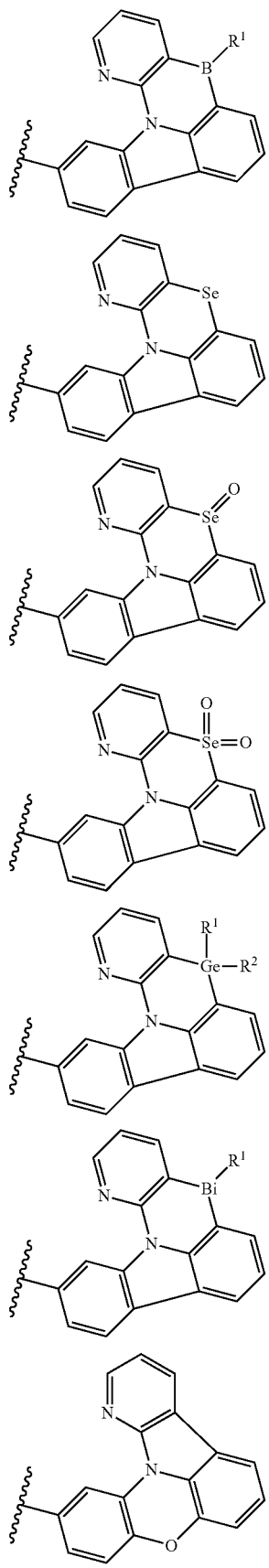

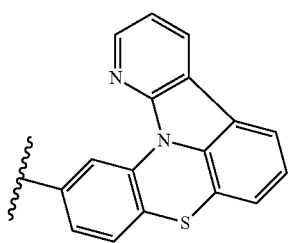
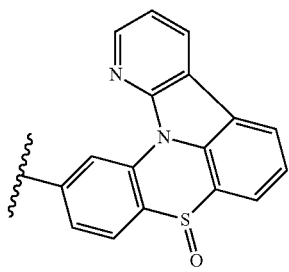
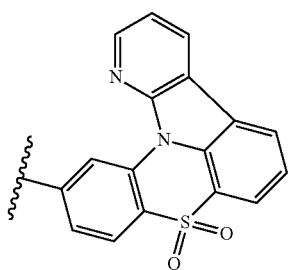
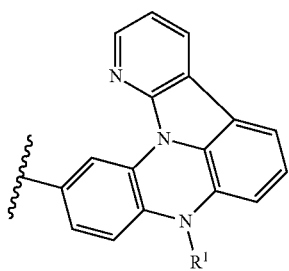
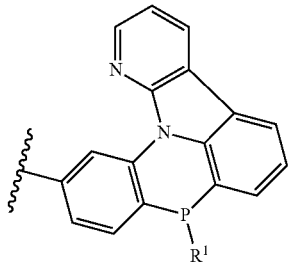
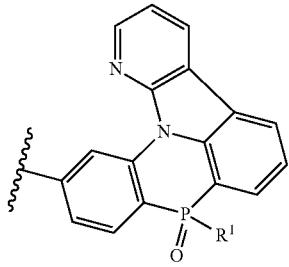
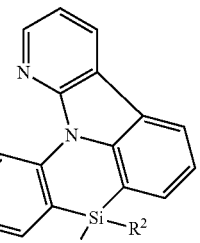
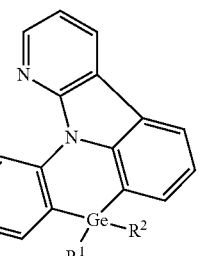
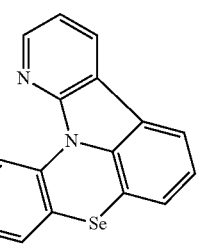
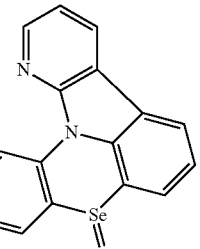
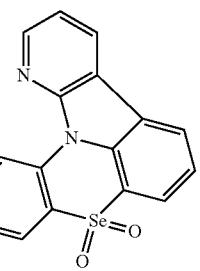
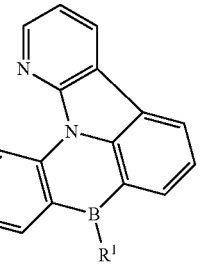

-continued
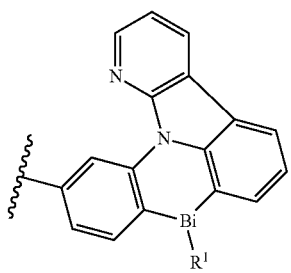
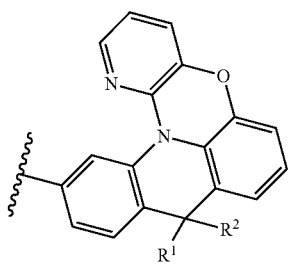
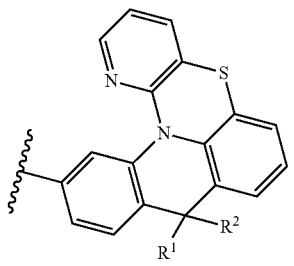
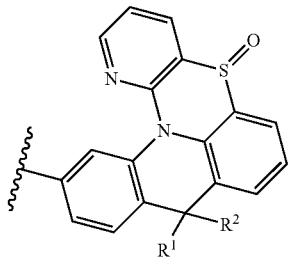
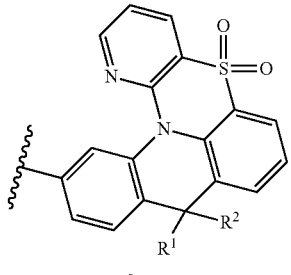
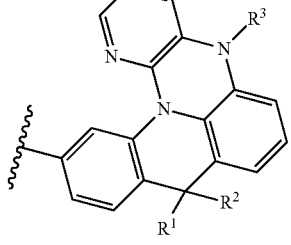
-continued
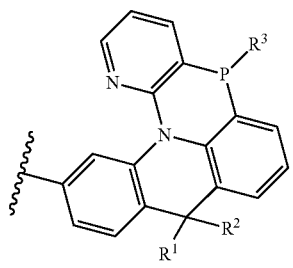
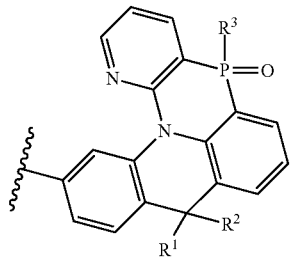
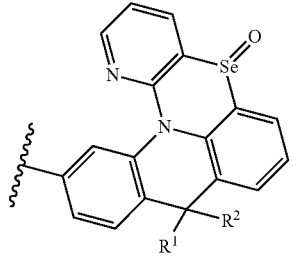
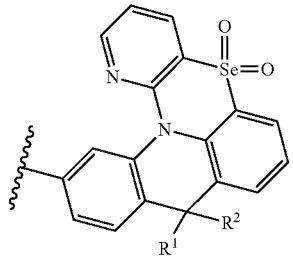
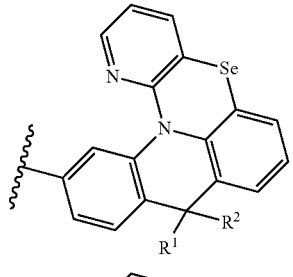
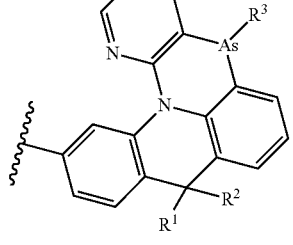

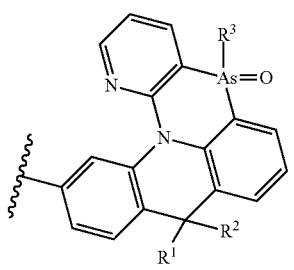
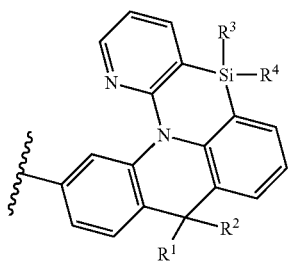
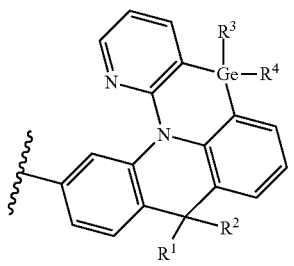
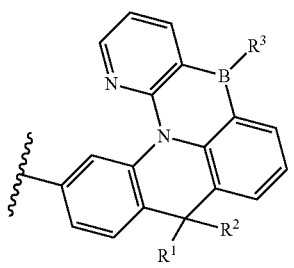
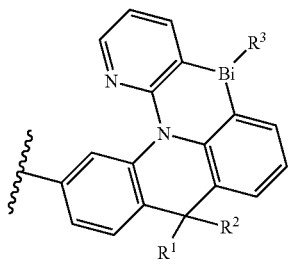
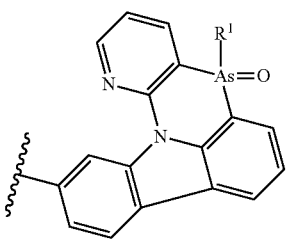
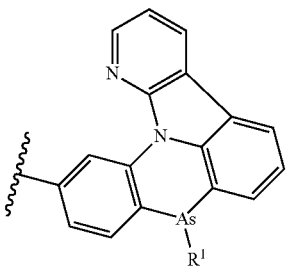
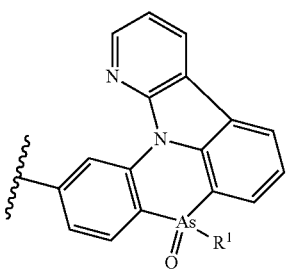
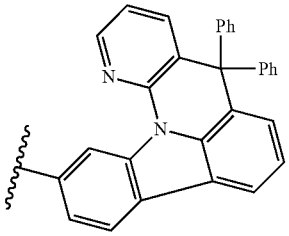
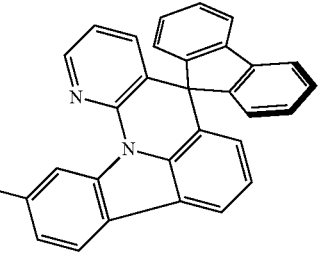
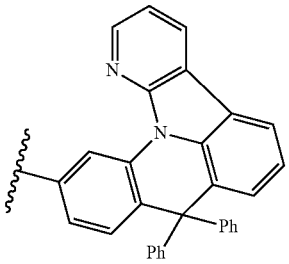

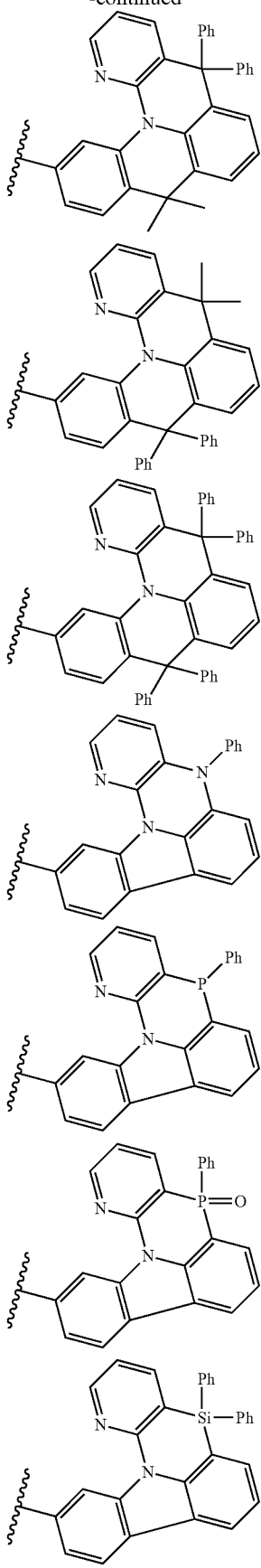
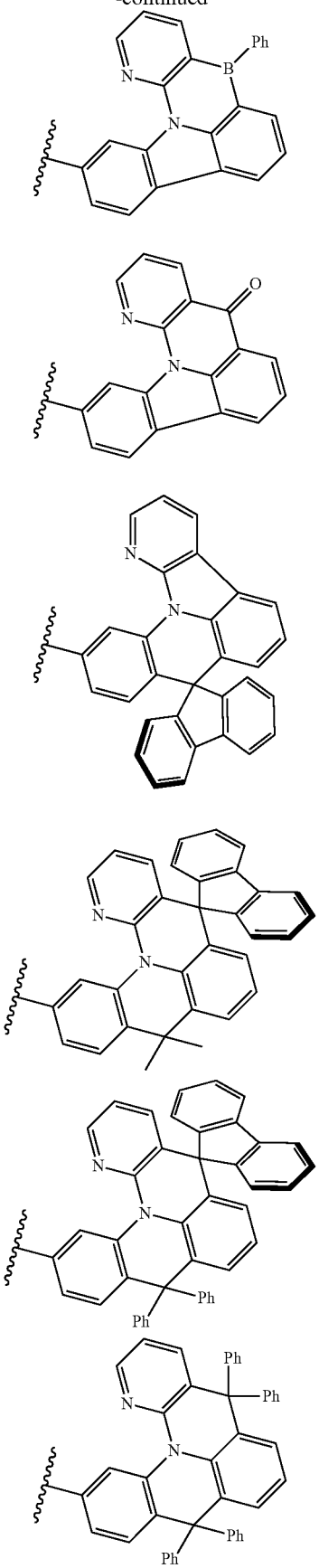

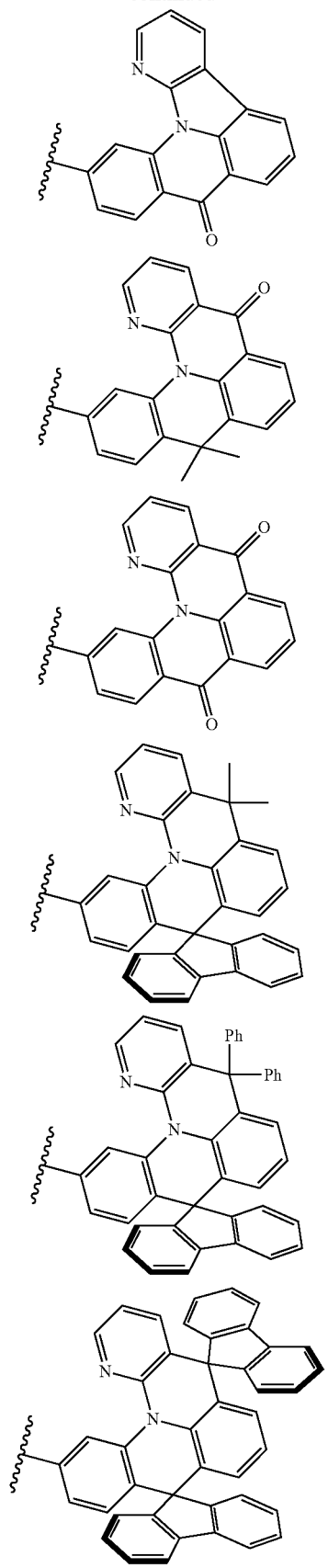
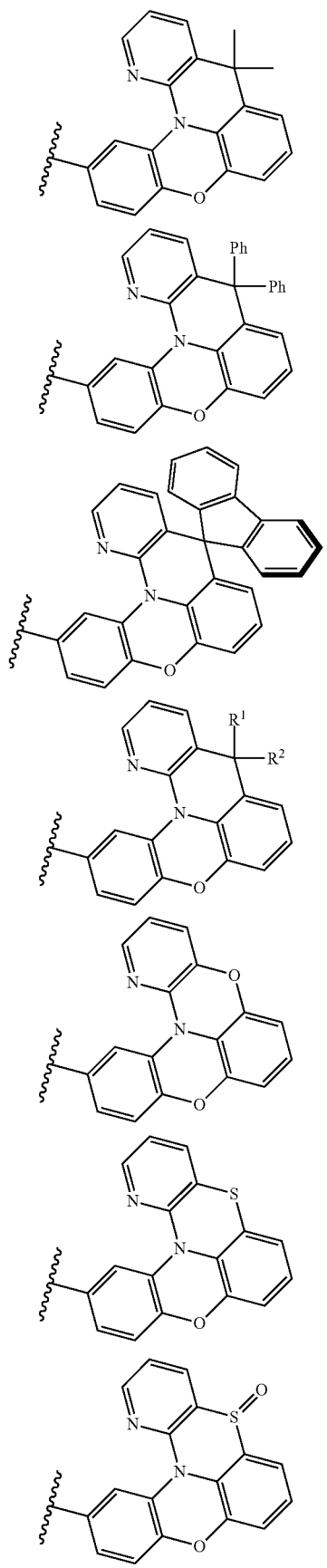

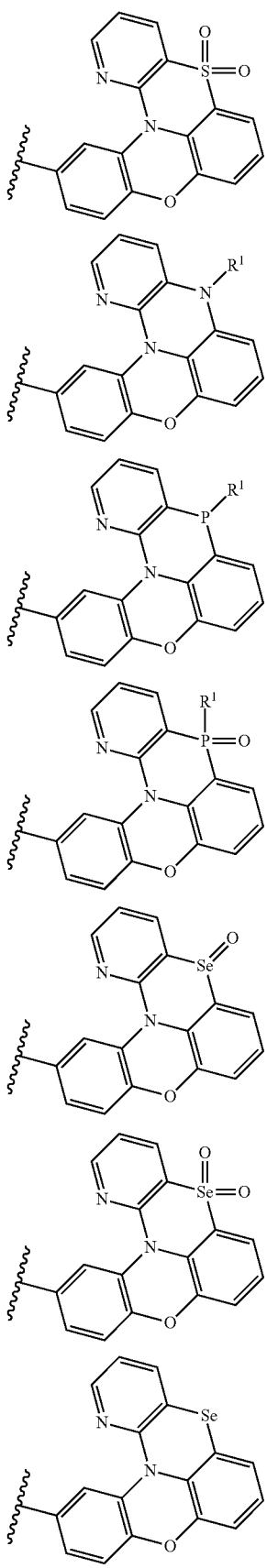
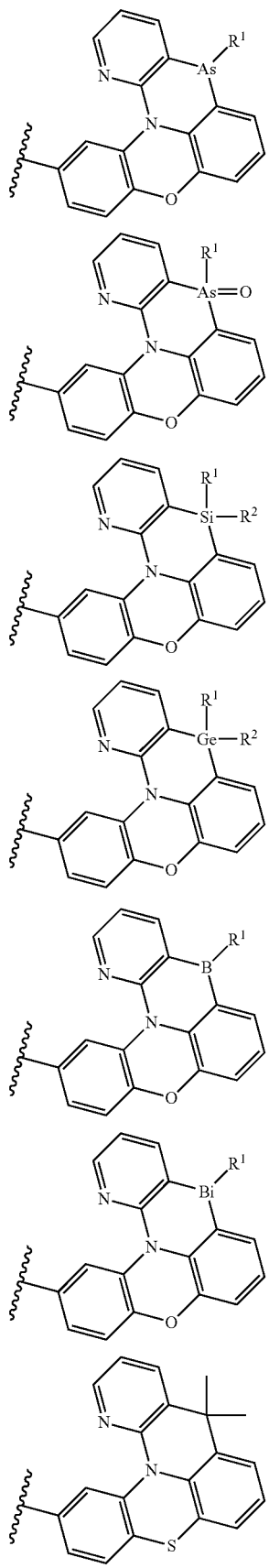

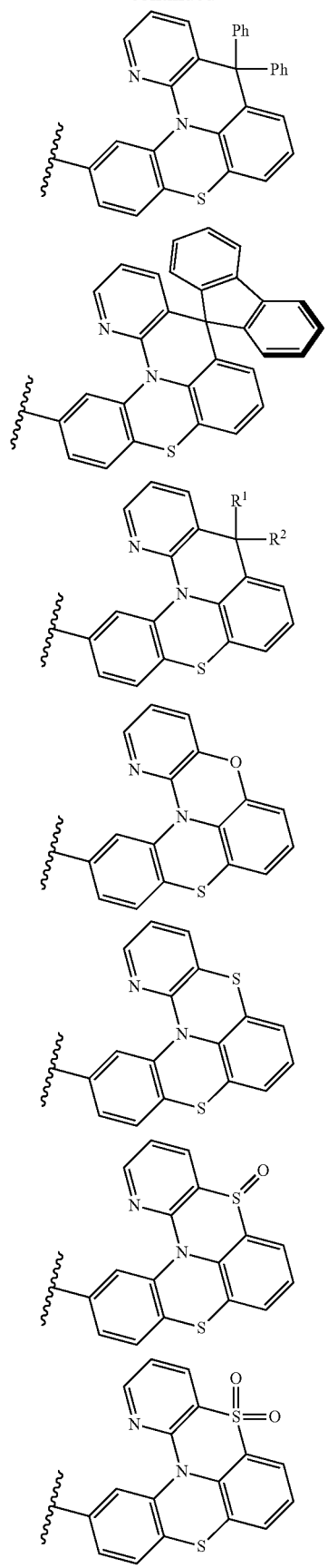
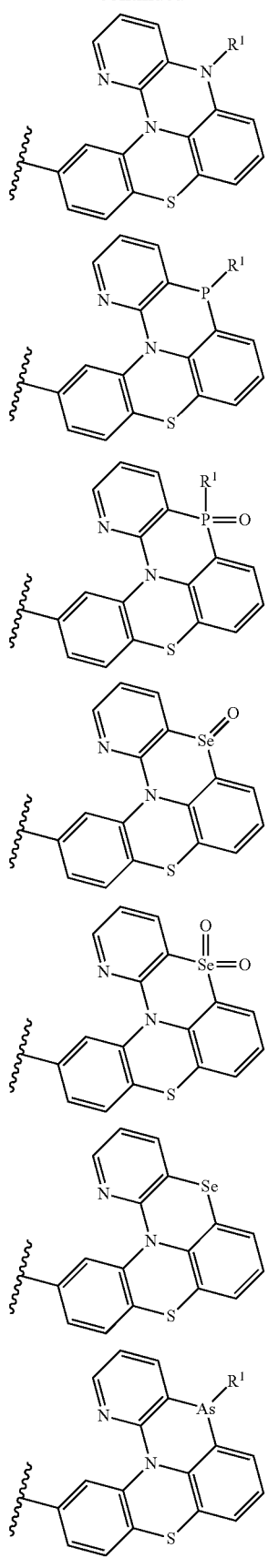

51
-continued
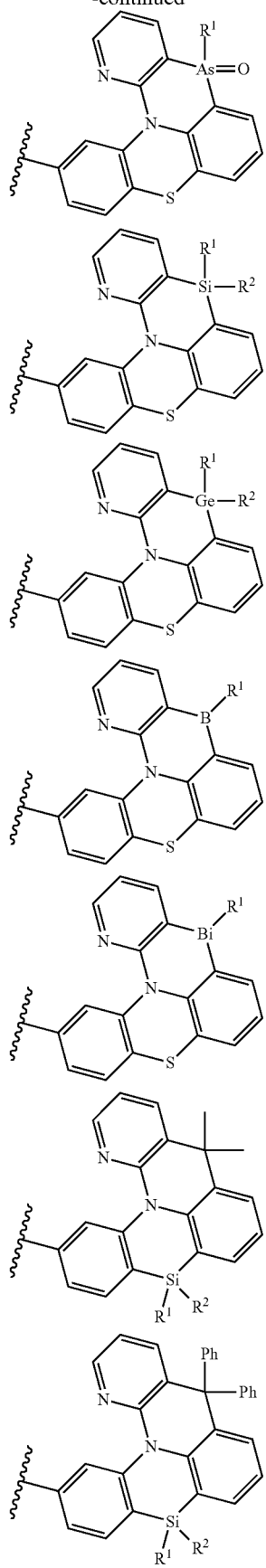
52
-continued
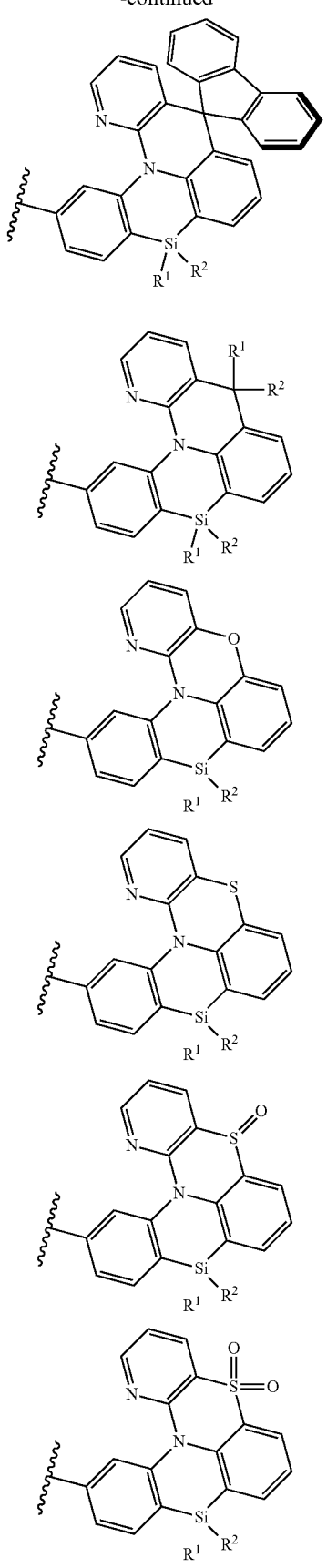

-continued
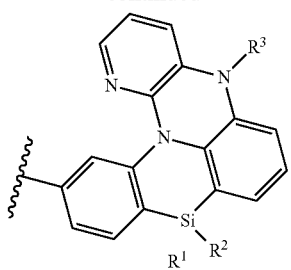
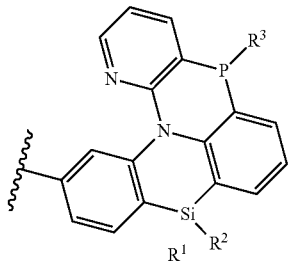
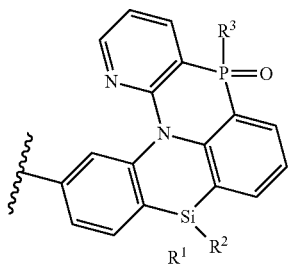
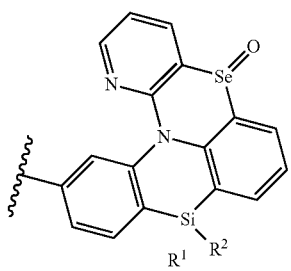
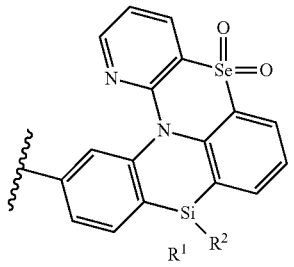
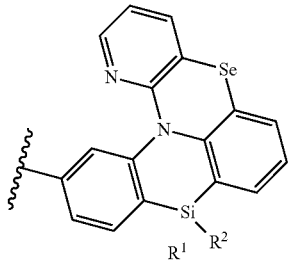
-continued
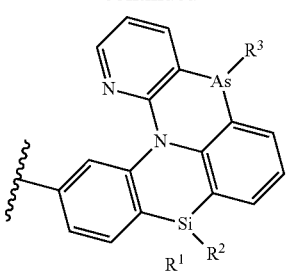
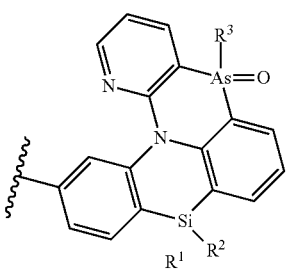
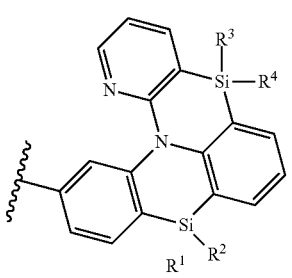
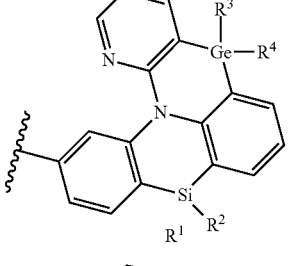
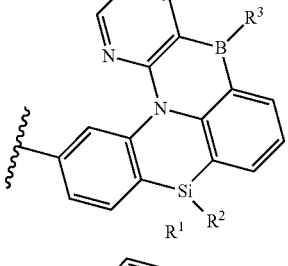
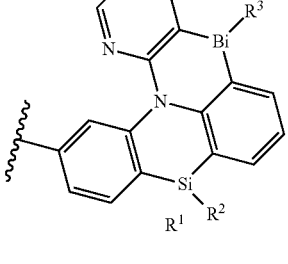

55
-continued
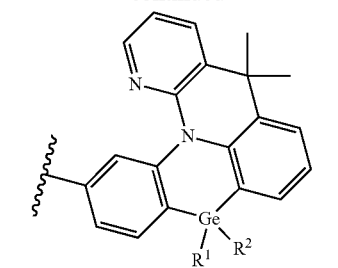
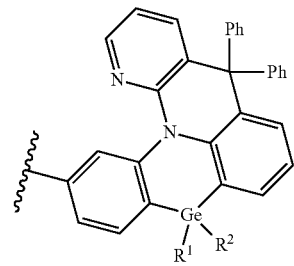
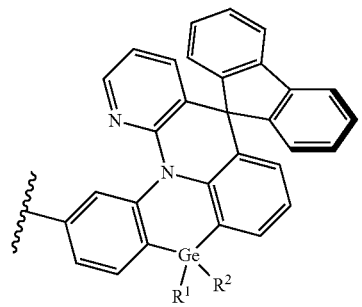
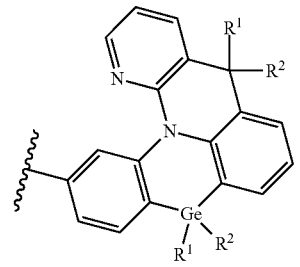
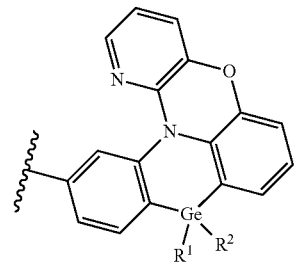
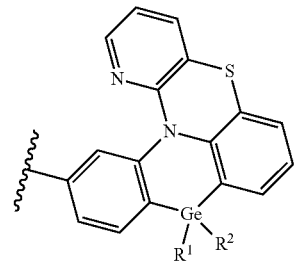
56
-continued
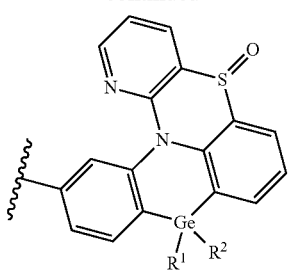
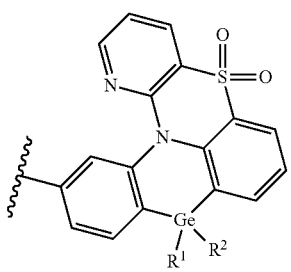
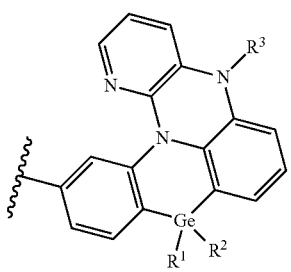
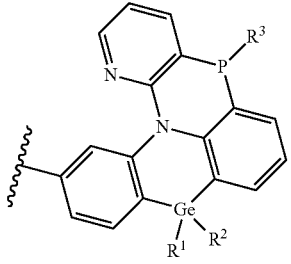
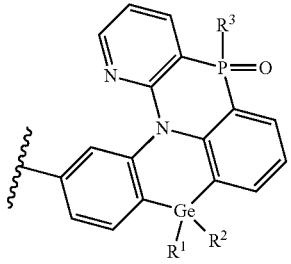
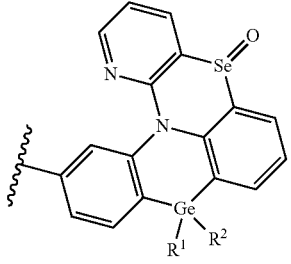

-continued
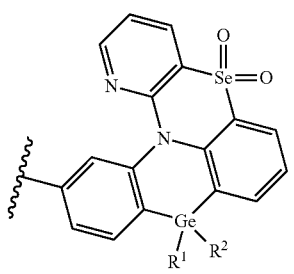
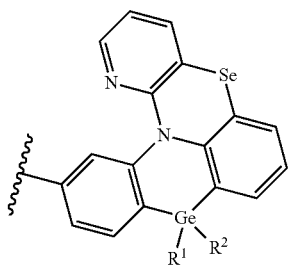
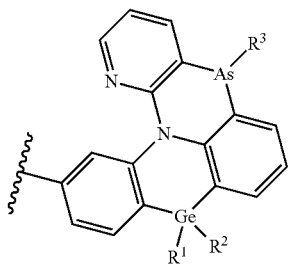
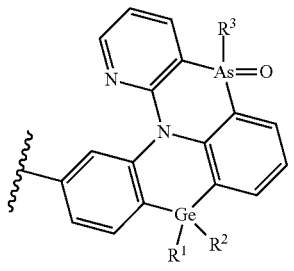
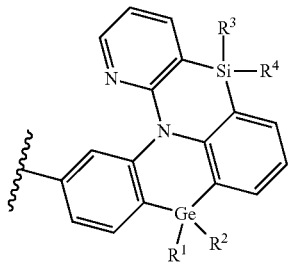
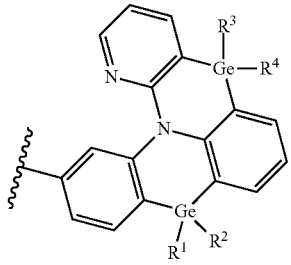
-continued
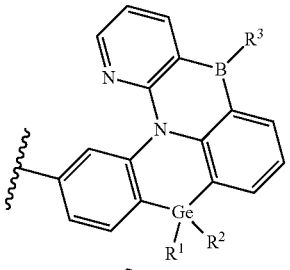
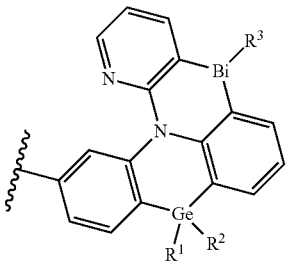
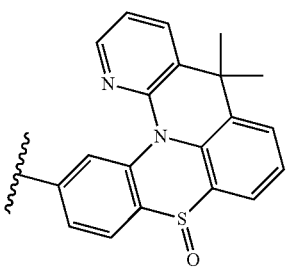
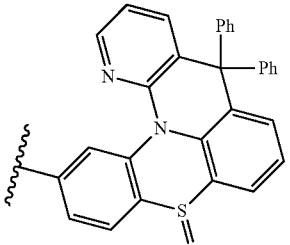
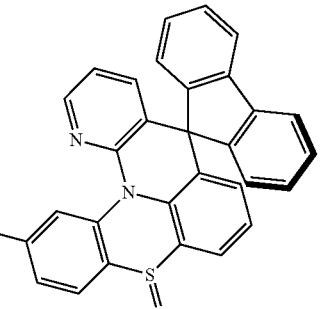
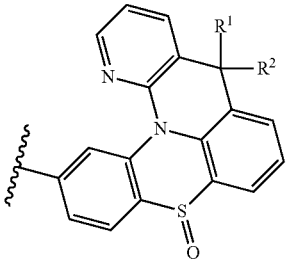

59
-continued
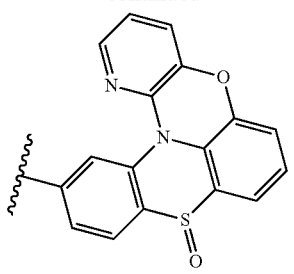
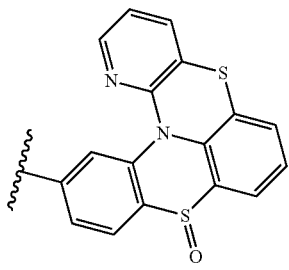
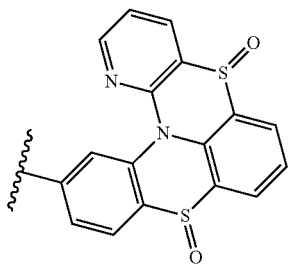
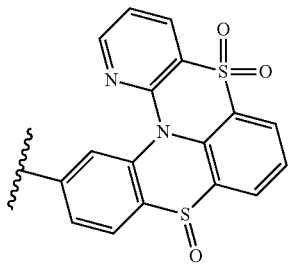
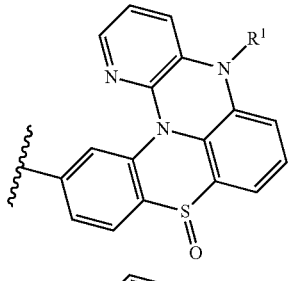
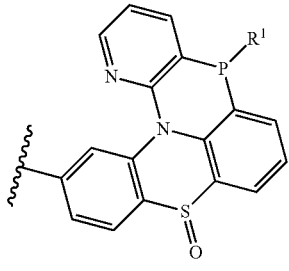
60
-continued
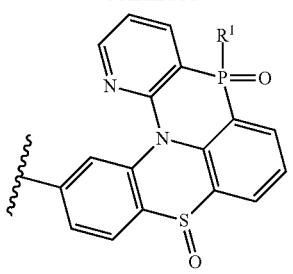
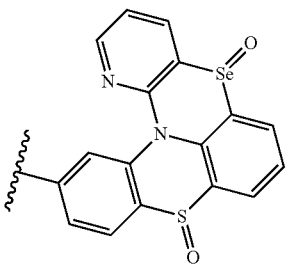
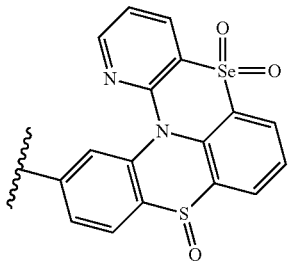
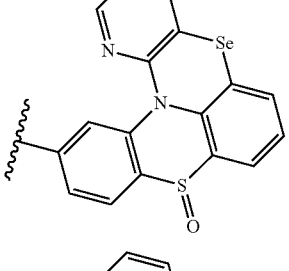
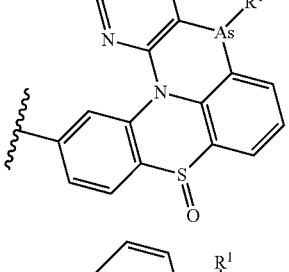
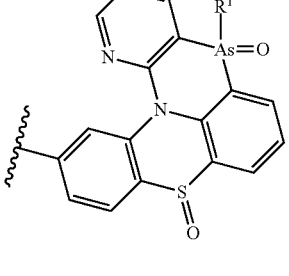

61
-continued
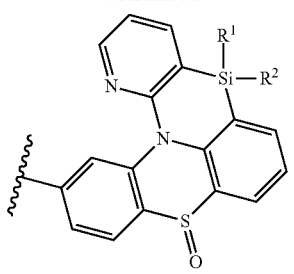
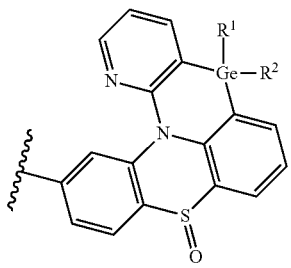
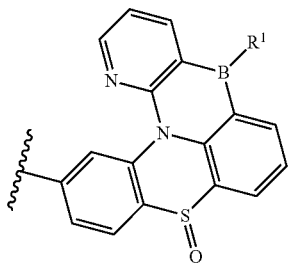
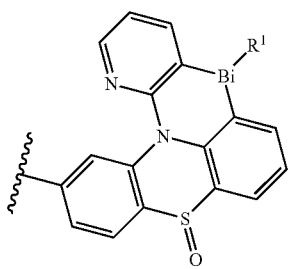
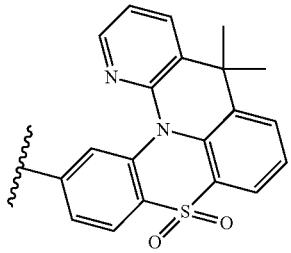
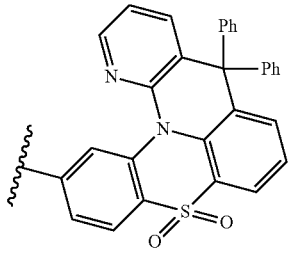
62
-continued
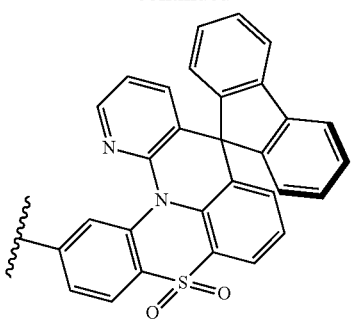
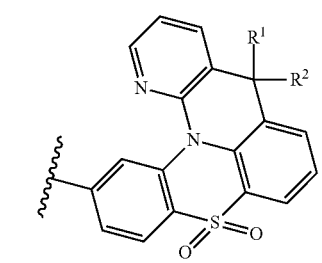
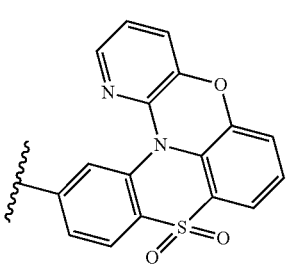
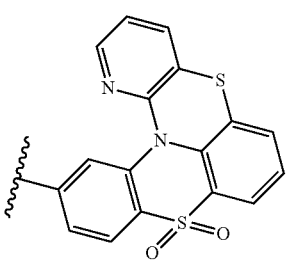
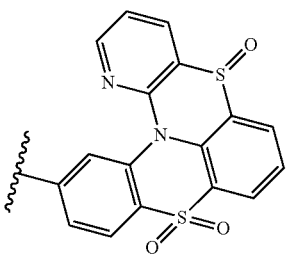
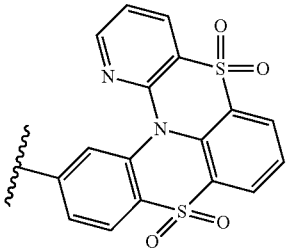

-continued
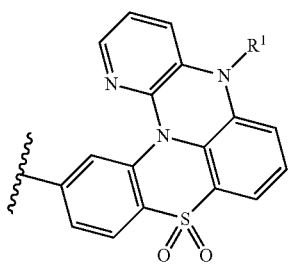
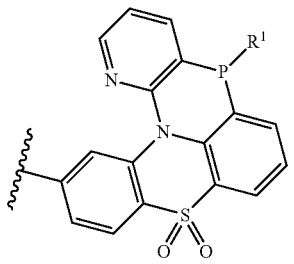
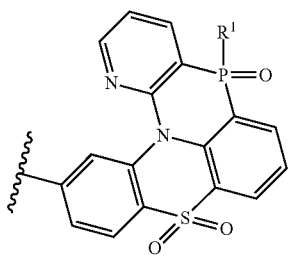
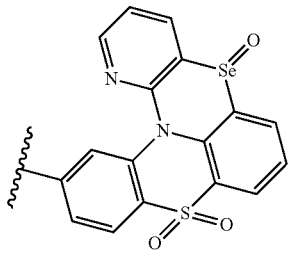
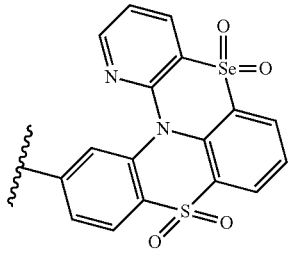
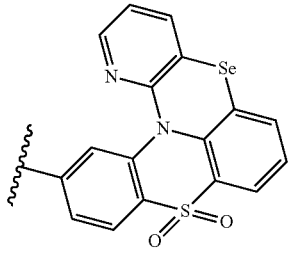
-continued
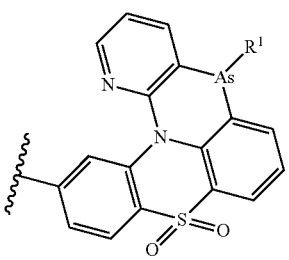
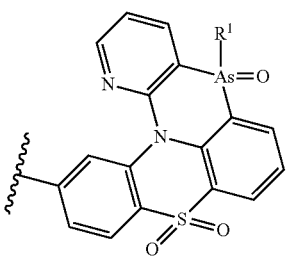
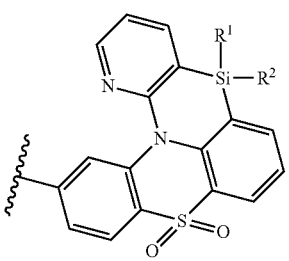
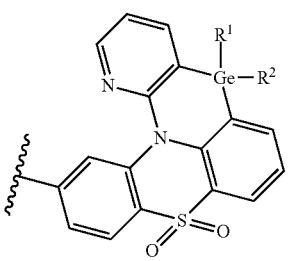
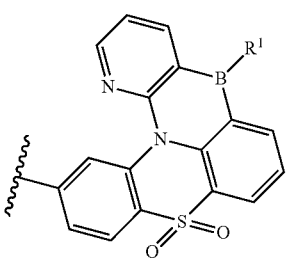
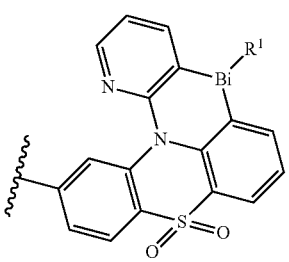

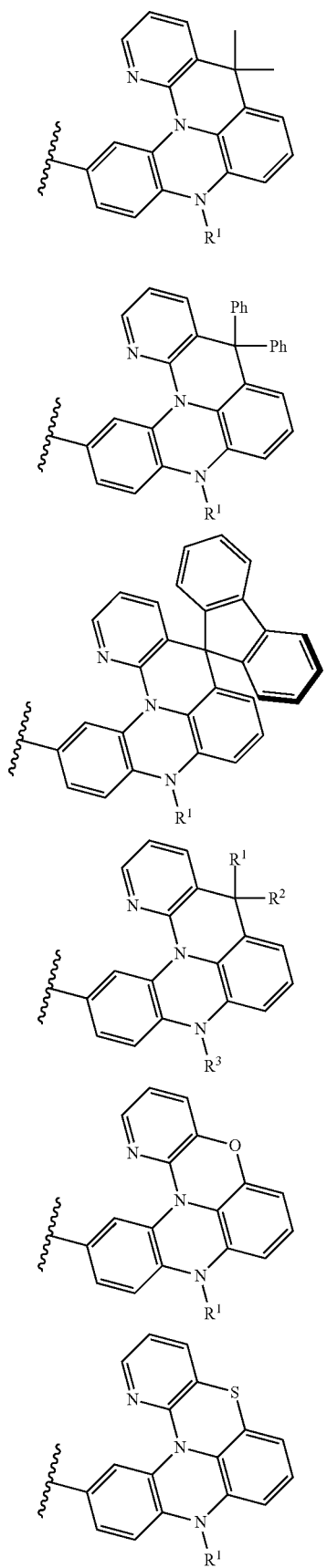
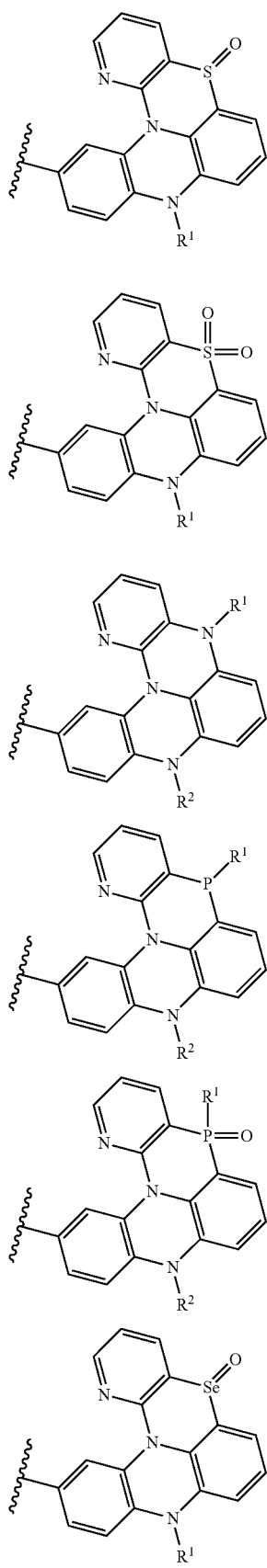

67
-continued
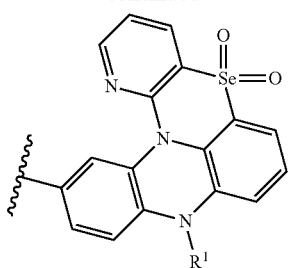
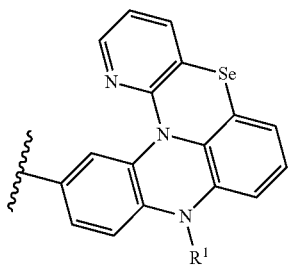
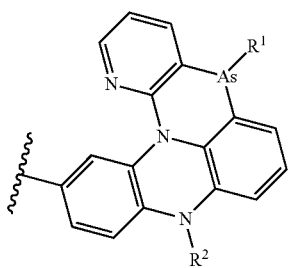
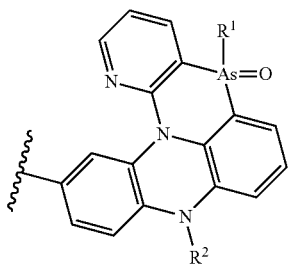
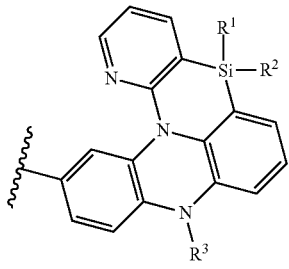
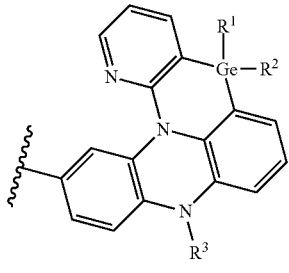
68
-continued
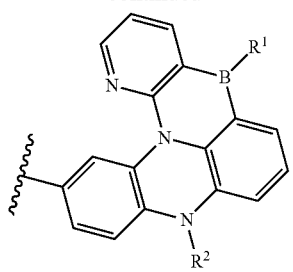
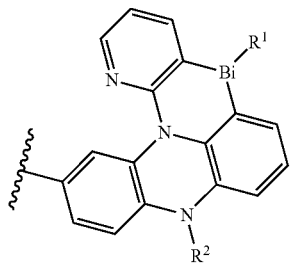
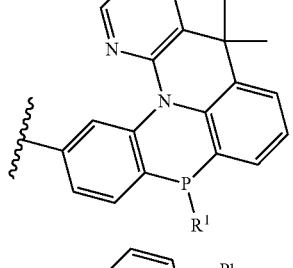
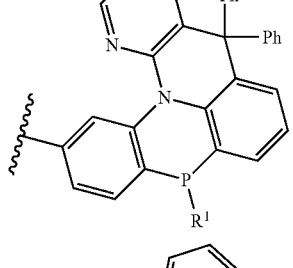
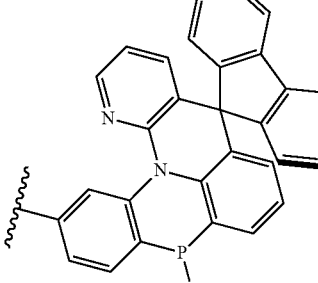
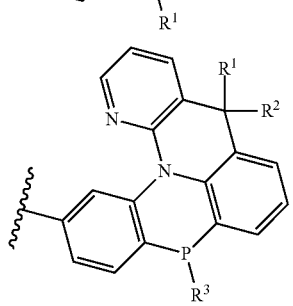

-continued
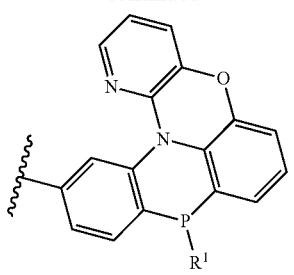
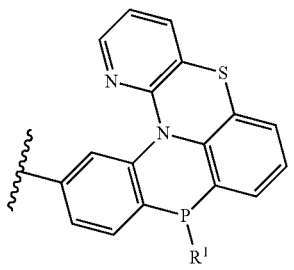
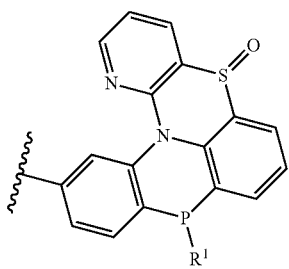
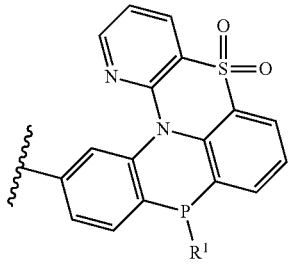
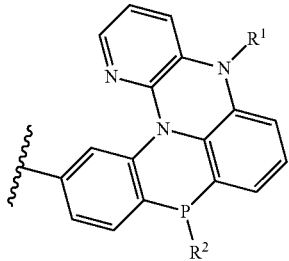
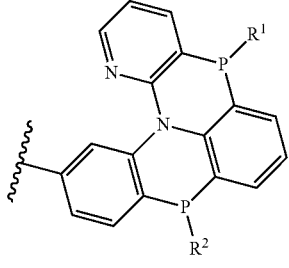
-continued
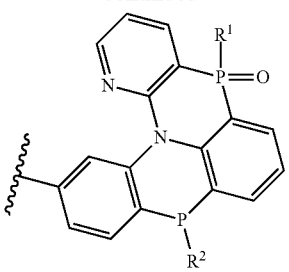
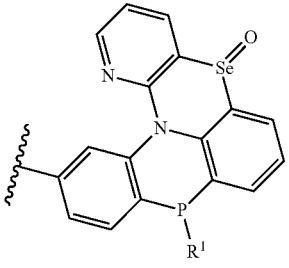
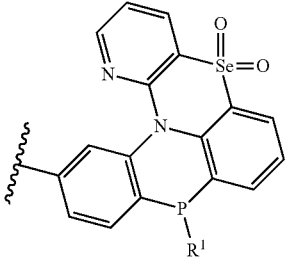
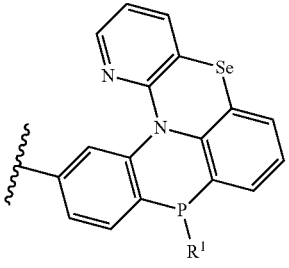
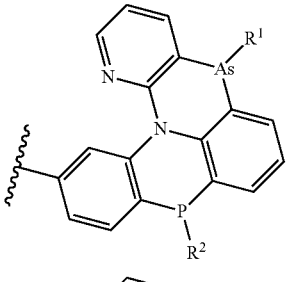
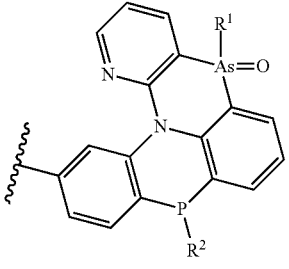

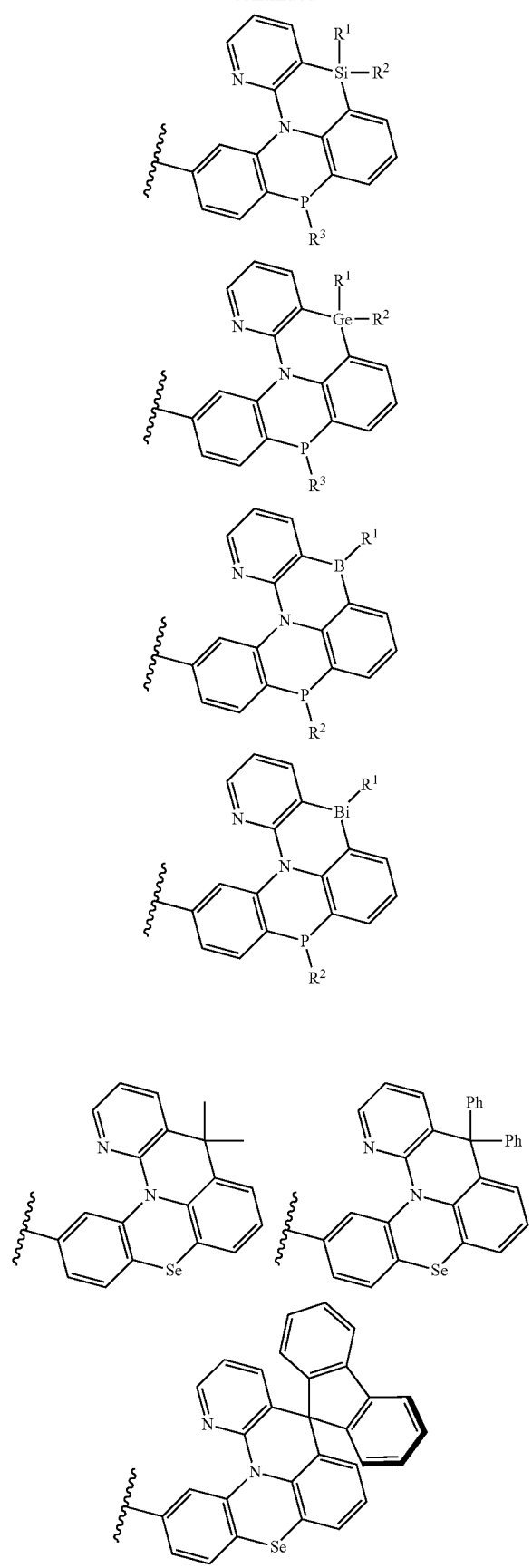
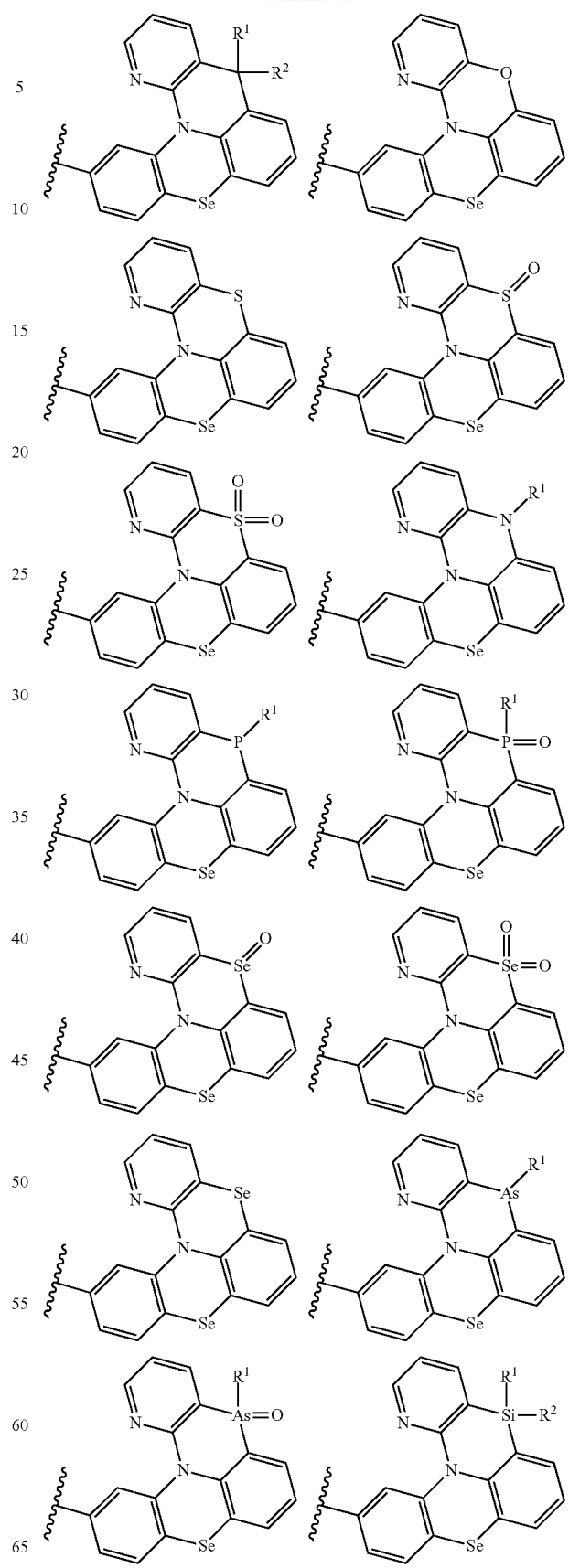

73
-continued
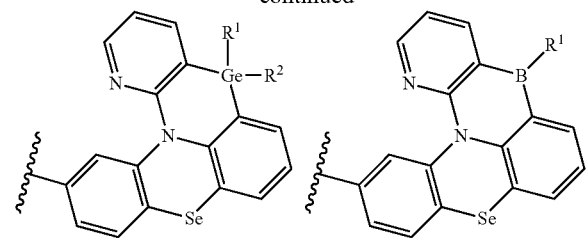
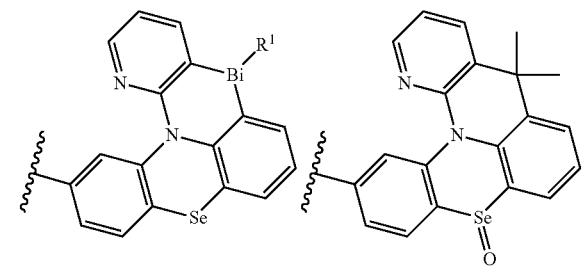
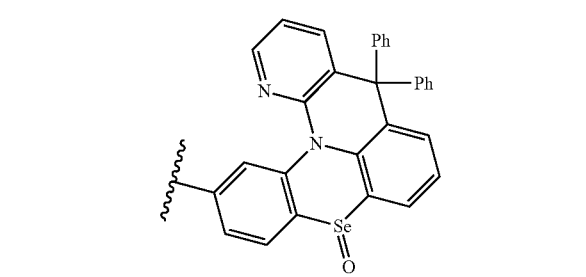
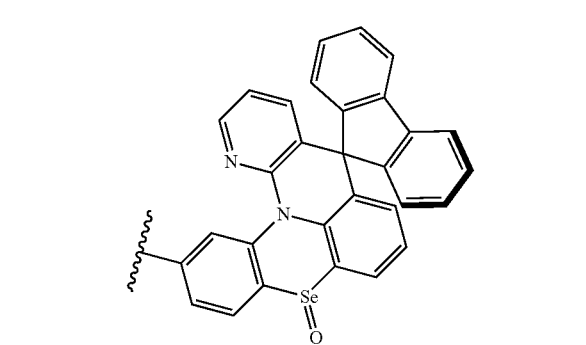
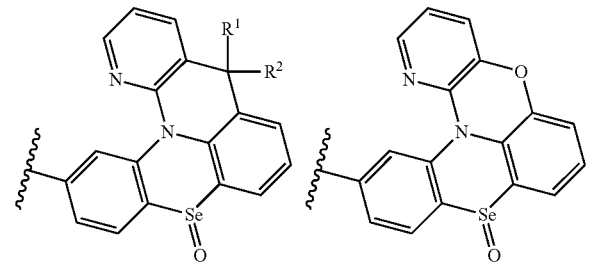
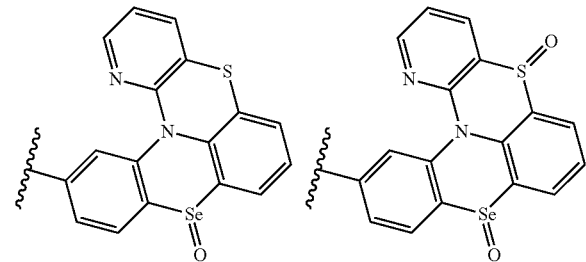
74
-continued
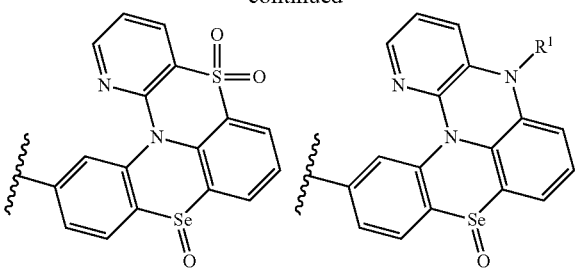
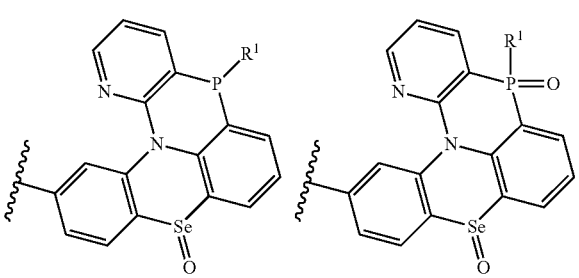
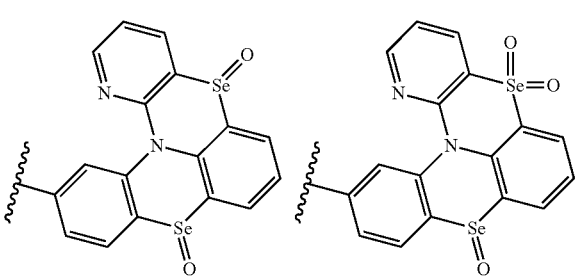
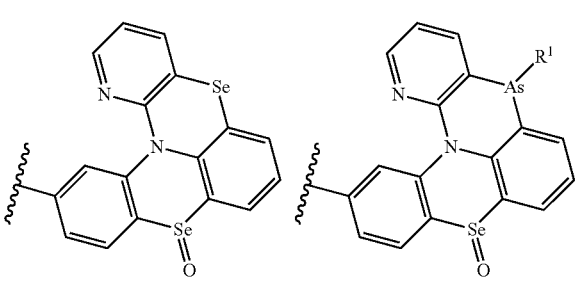
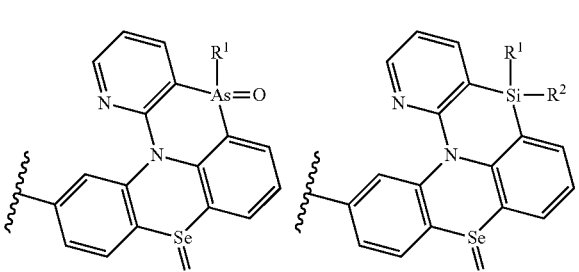
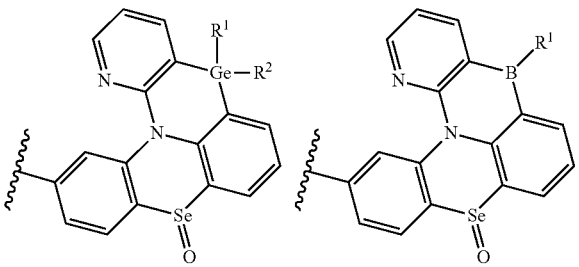

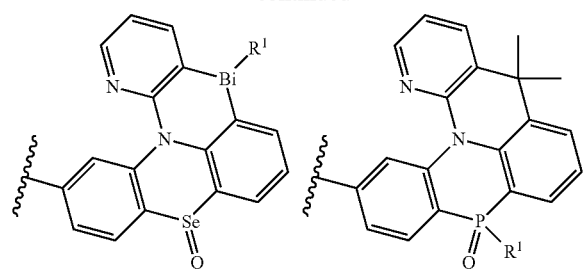
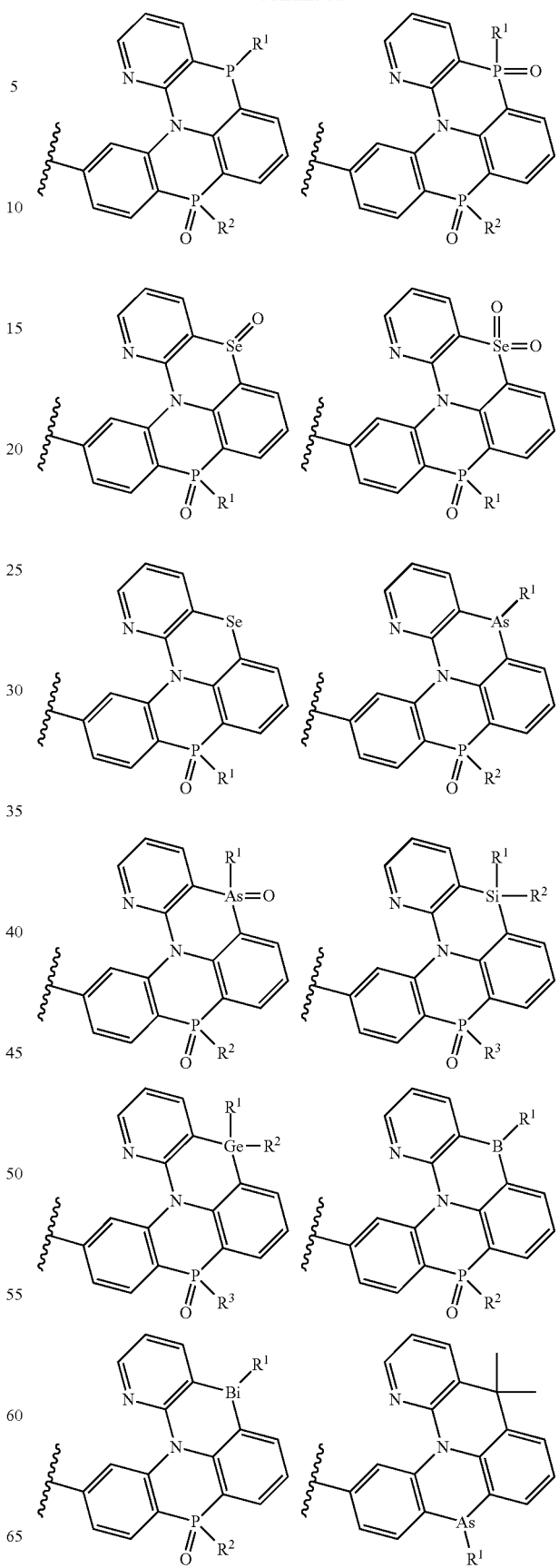

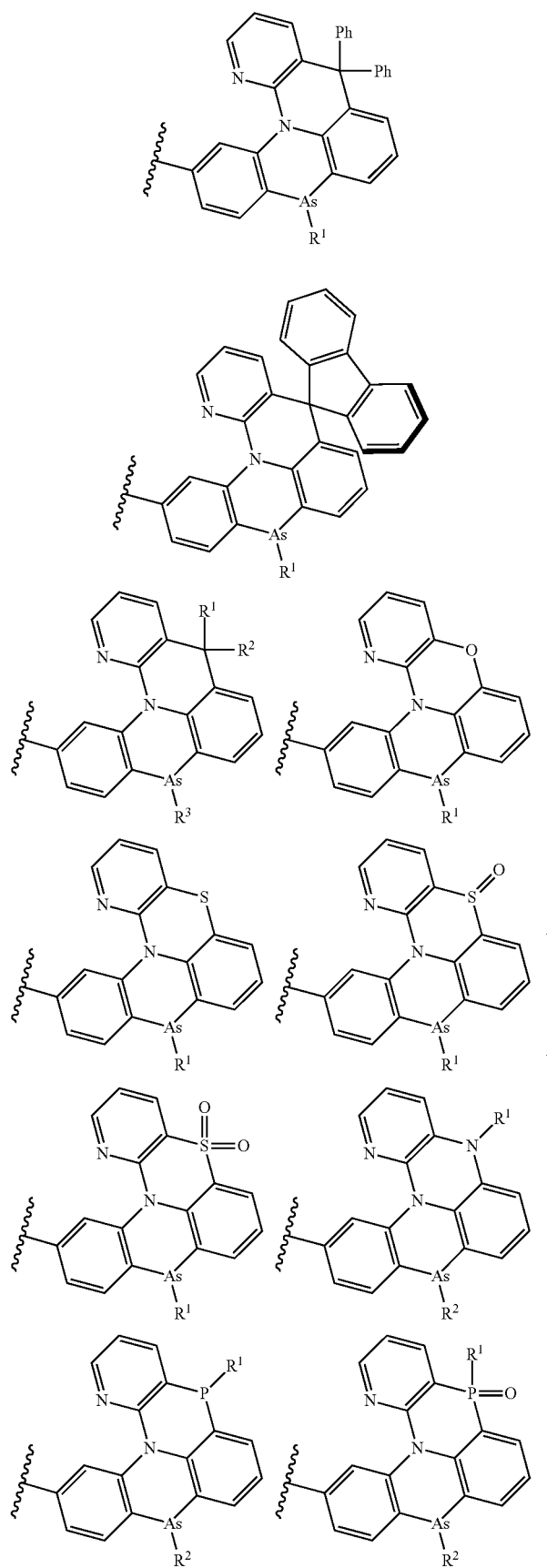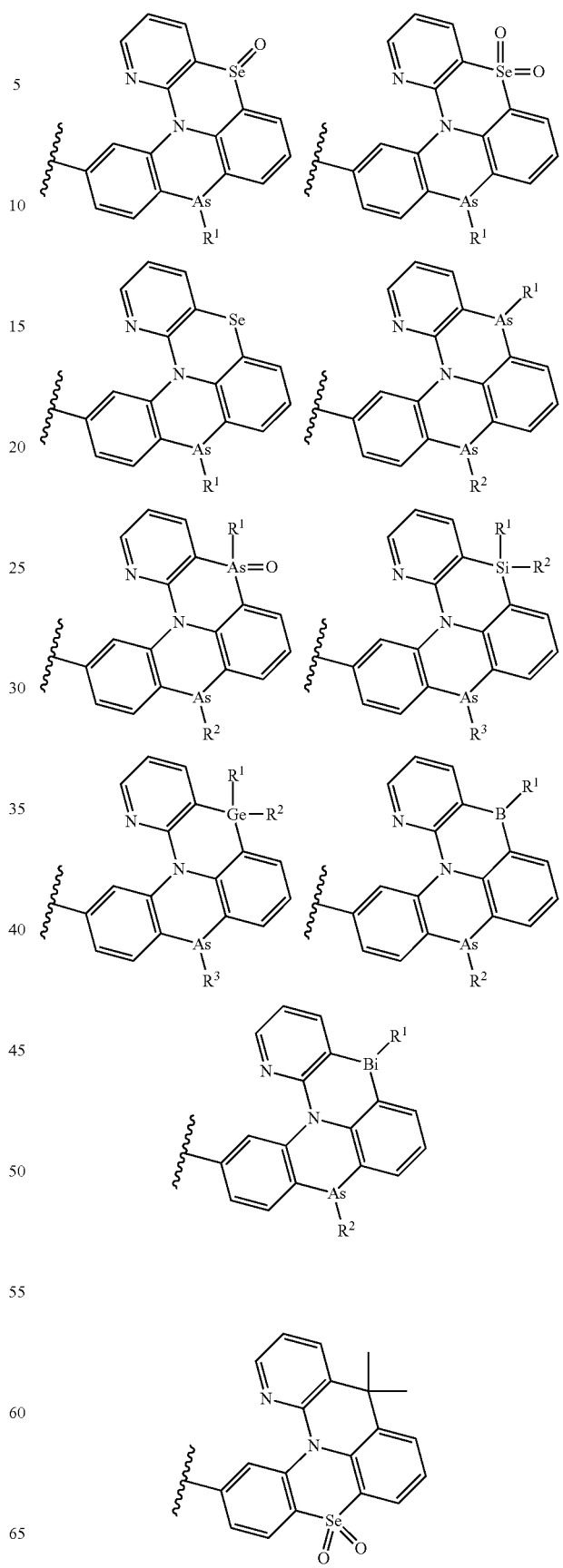

79
-continued
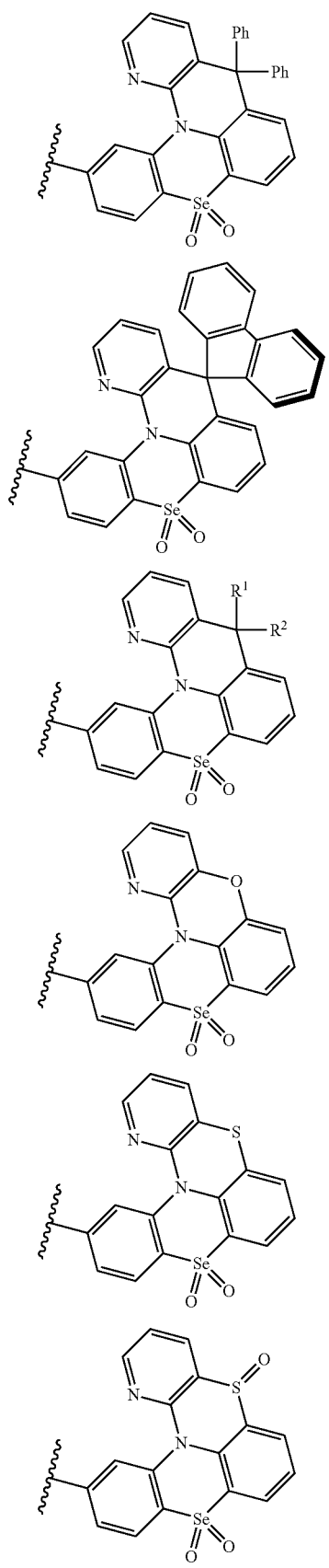
80
-continued
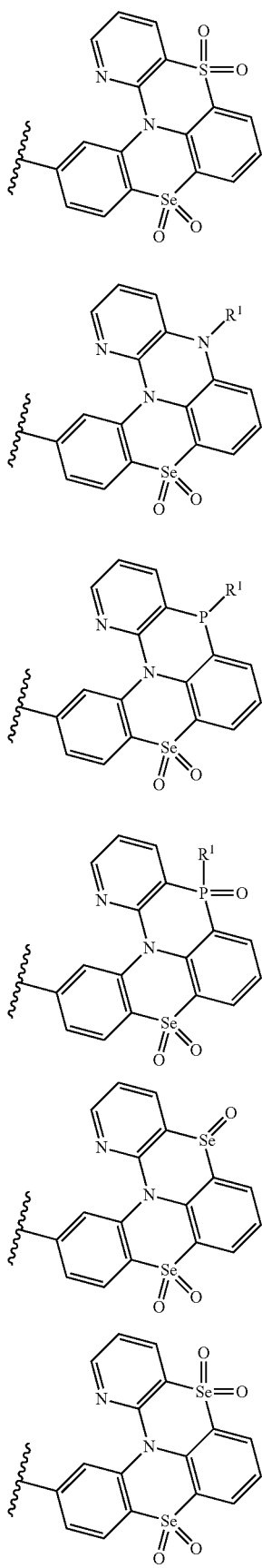

-continued
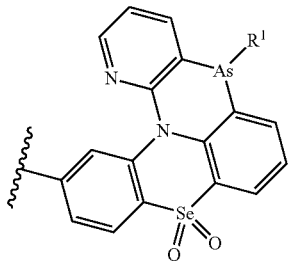
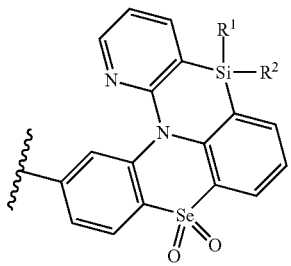
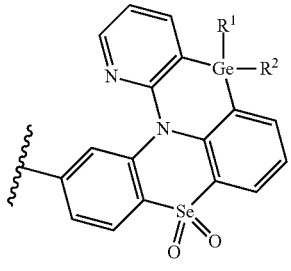
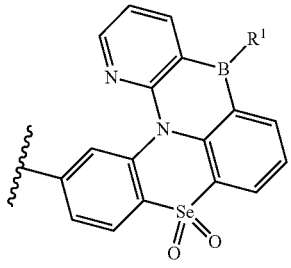
-continued
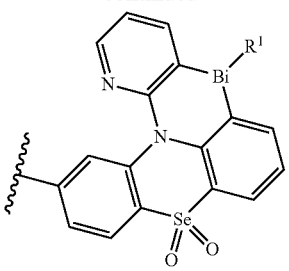
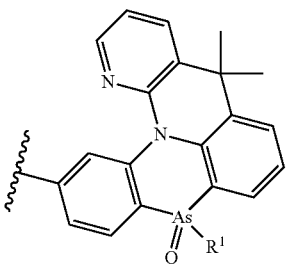

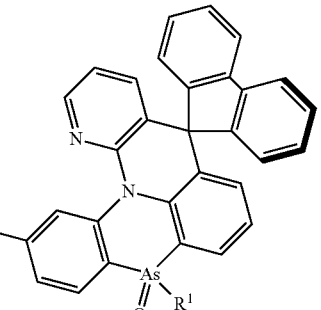
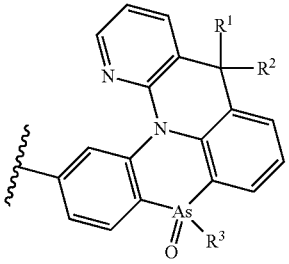
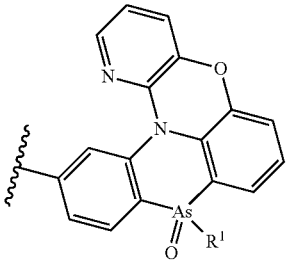

-continued
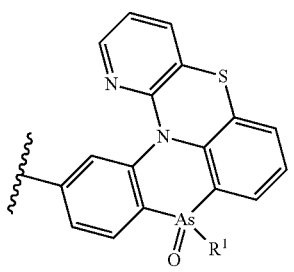
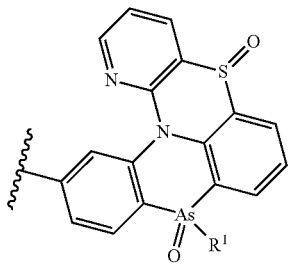
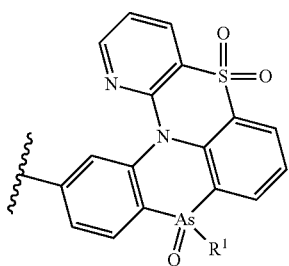
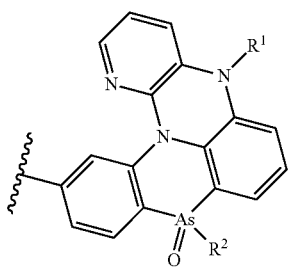
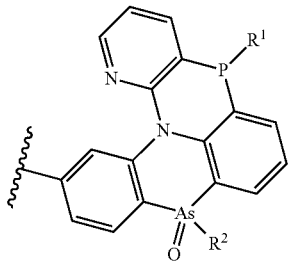
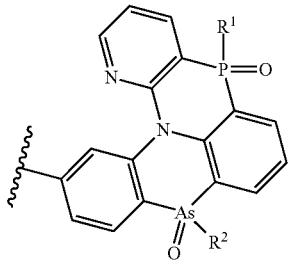
-continued
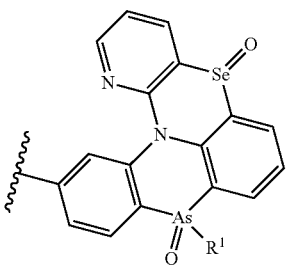
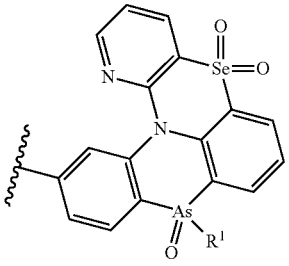
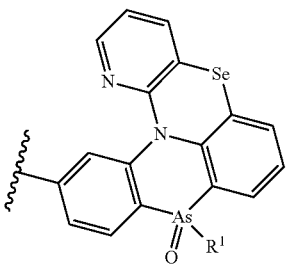
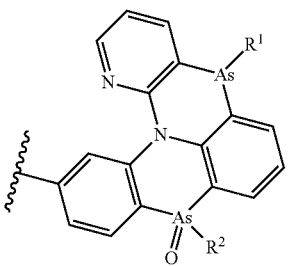
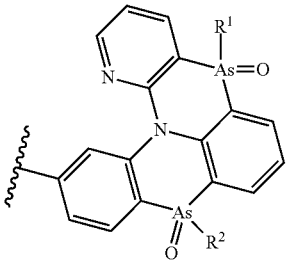
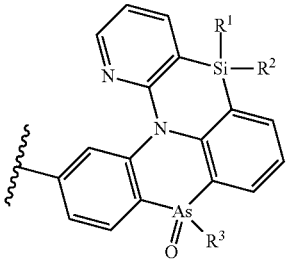

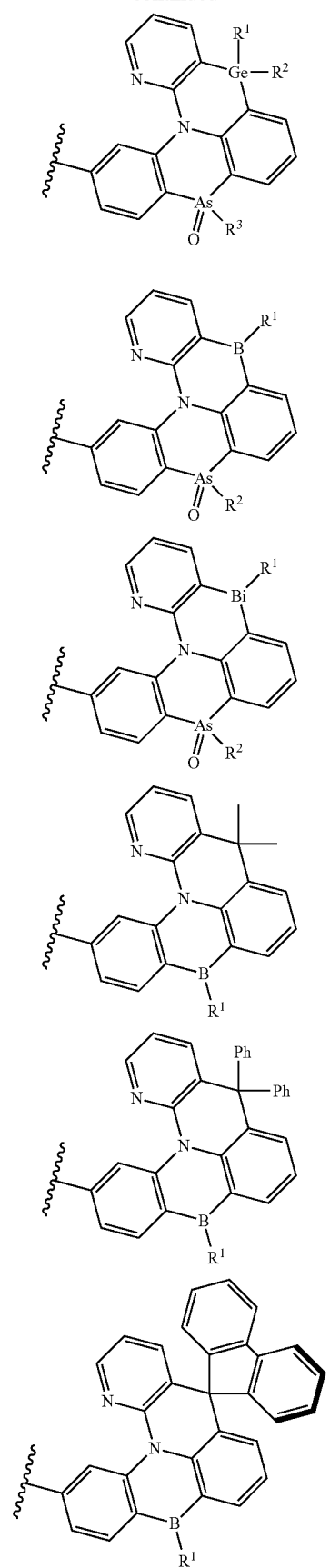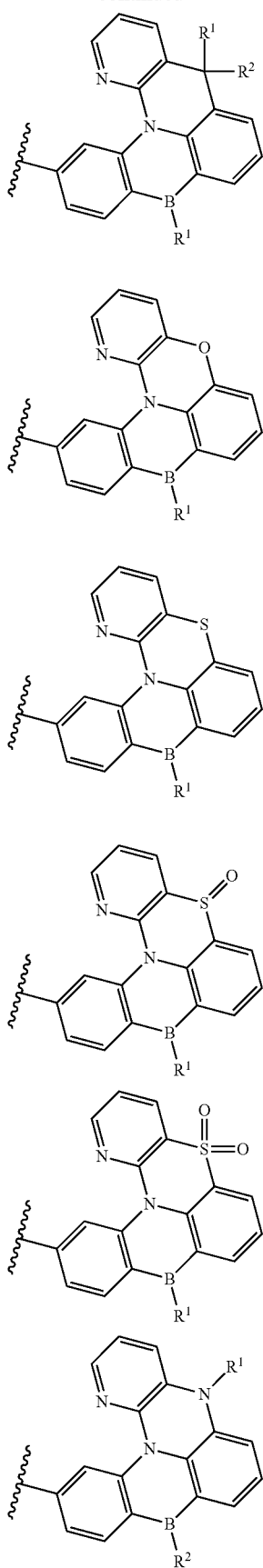

87
-continued
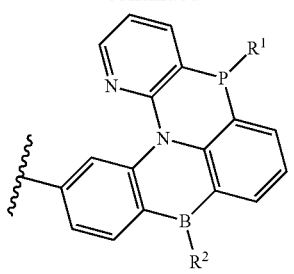
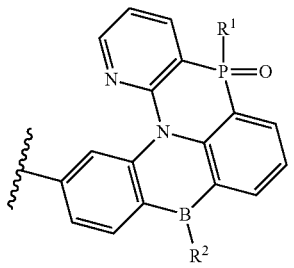
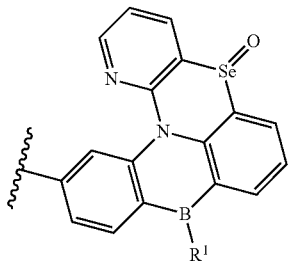
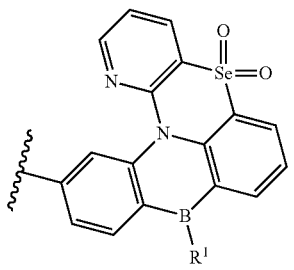
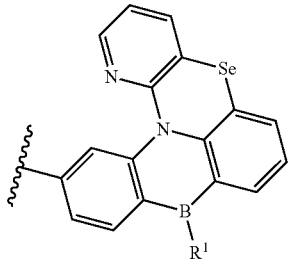
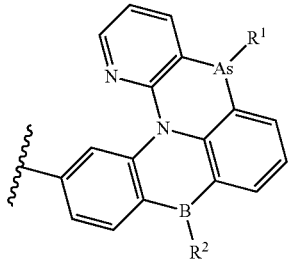
88
-continued
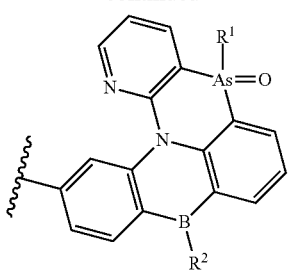
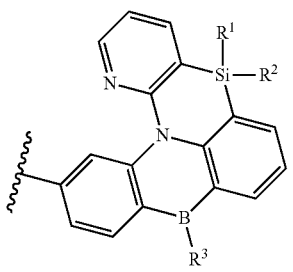
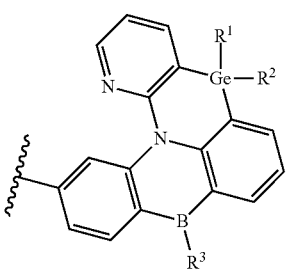
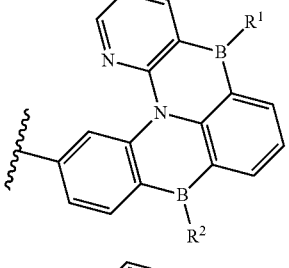
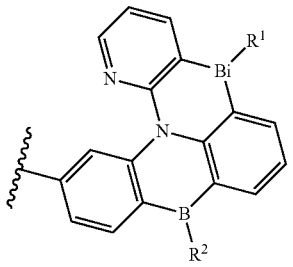
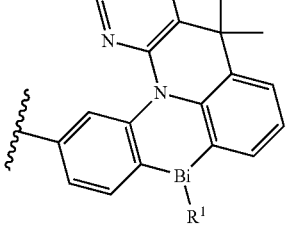

-continued
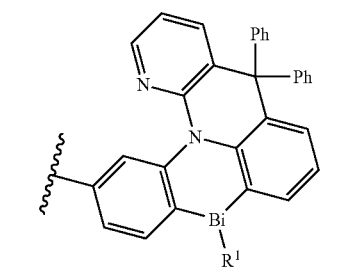
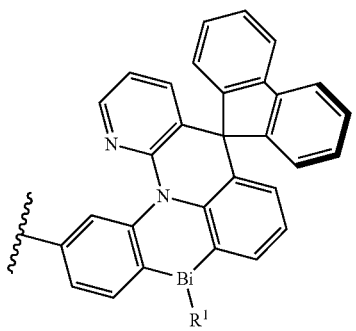
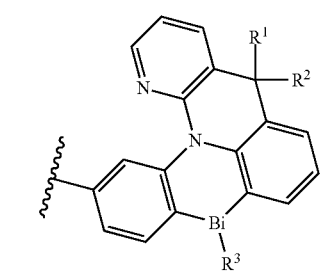
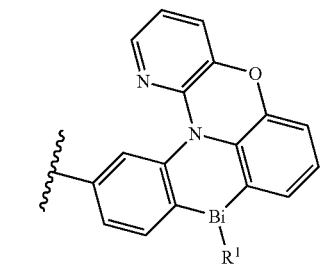
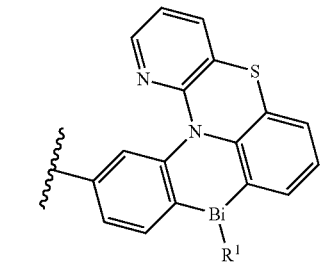
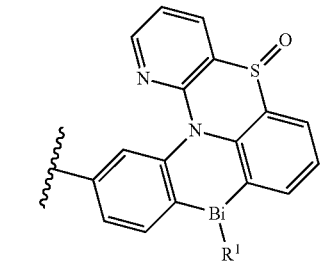
-continued
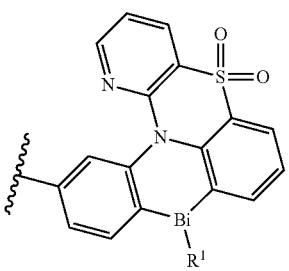
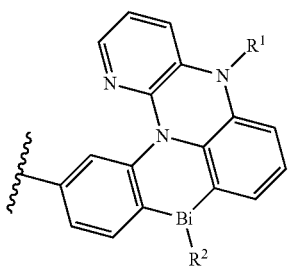
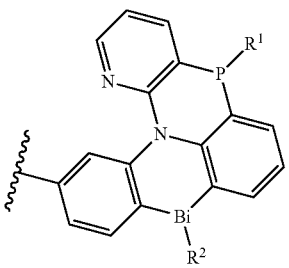
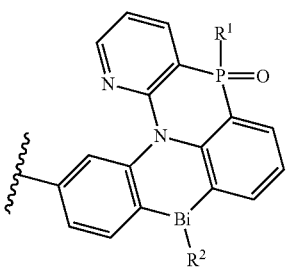
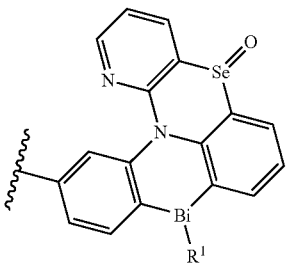
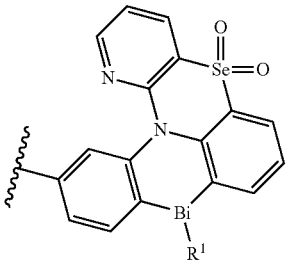

-continued
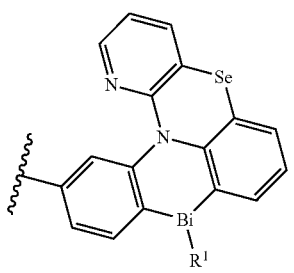
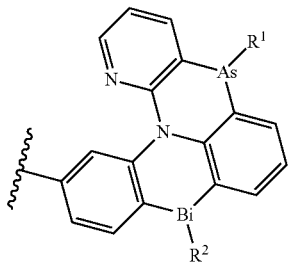
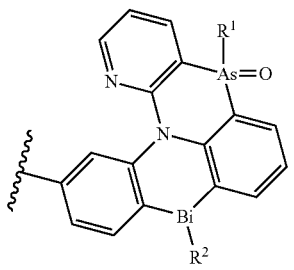
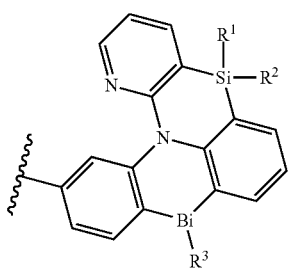
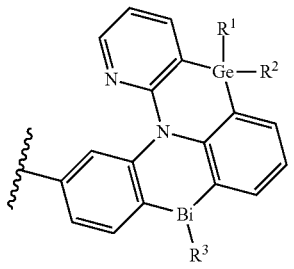
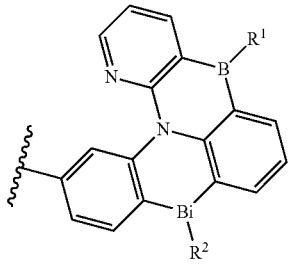
-continued
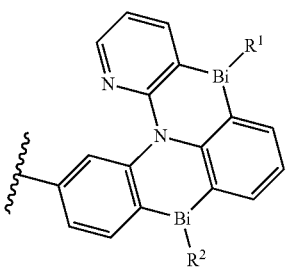
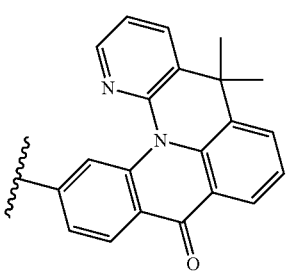
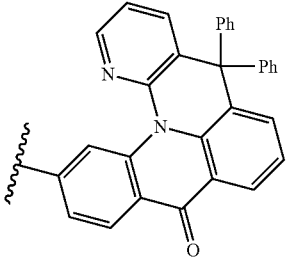
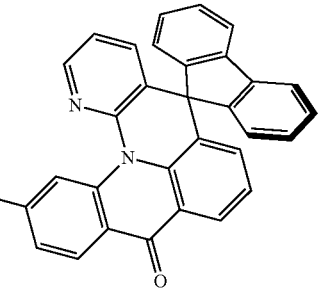
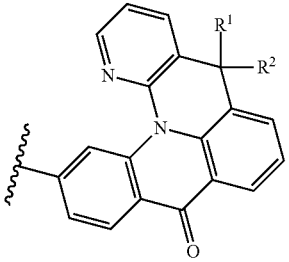
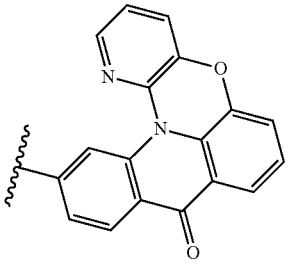

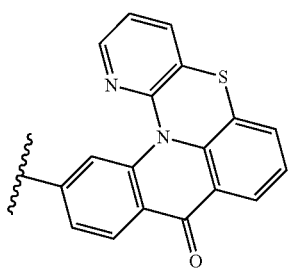
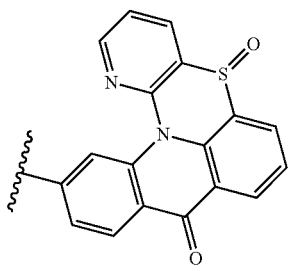
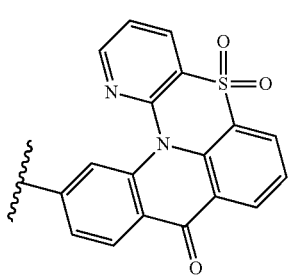
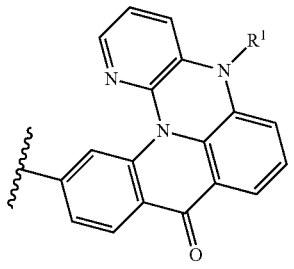
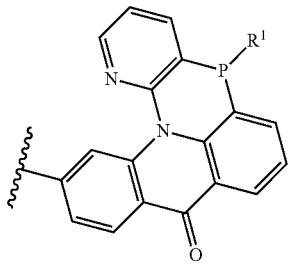
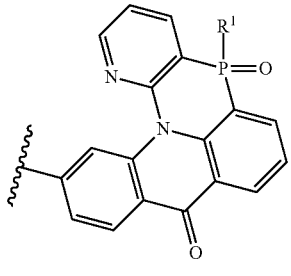
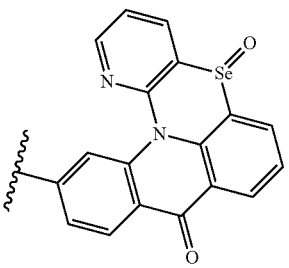
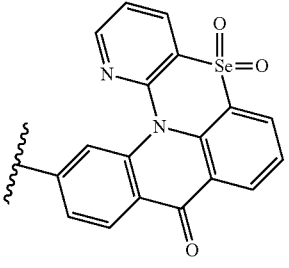
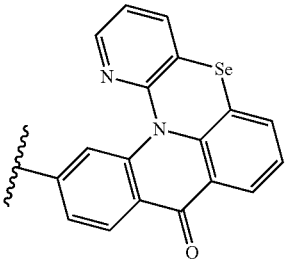
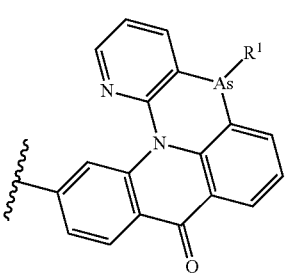
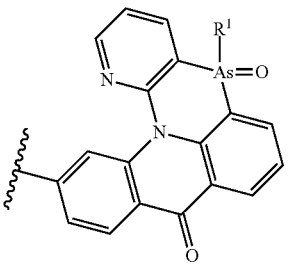
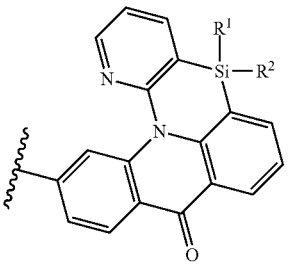

95
-continued
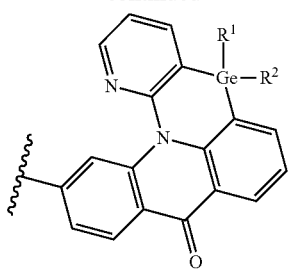
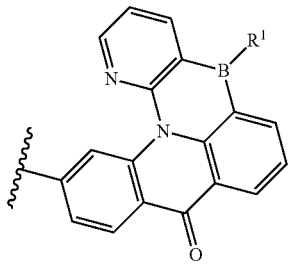
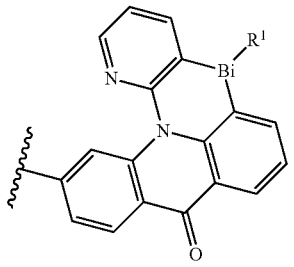
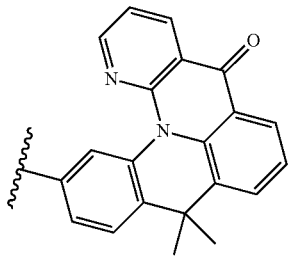
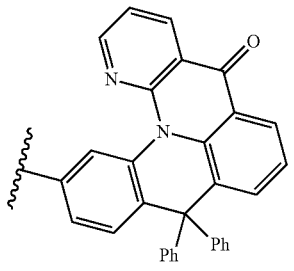
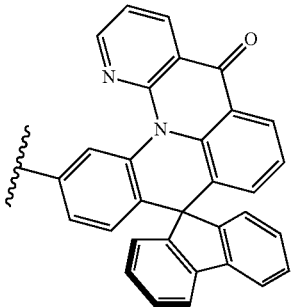
96
-continued
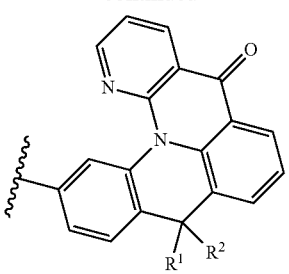
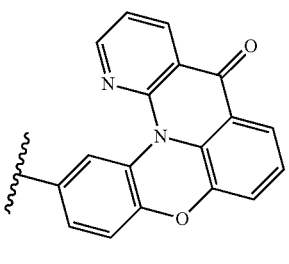
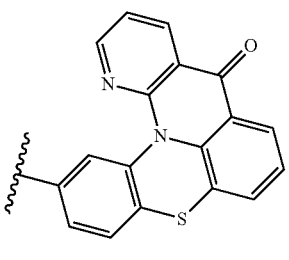
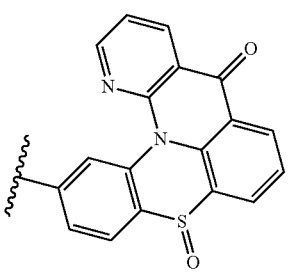
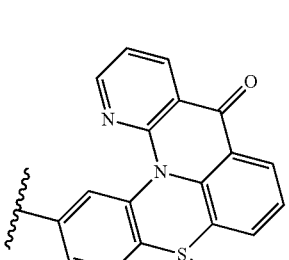
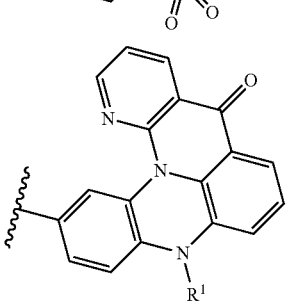

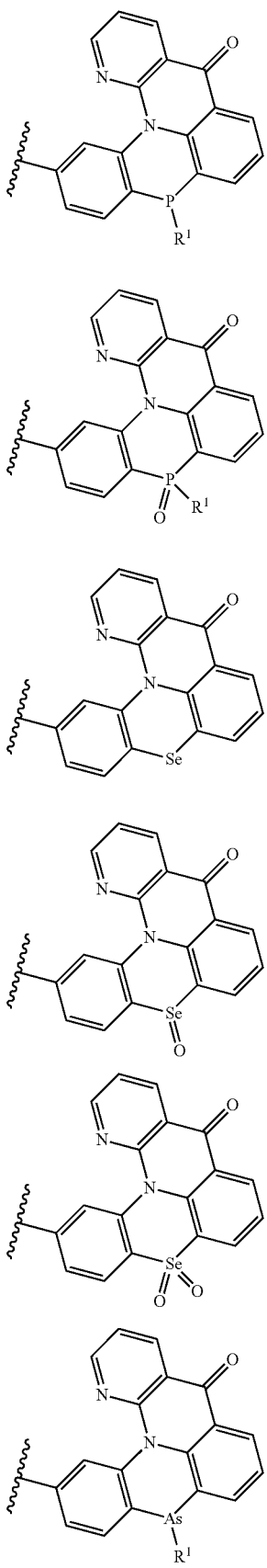
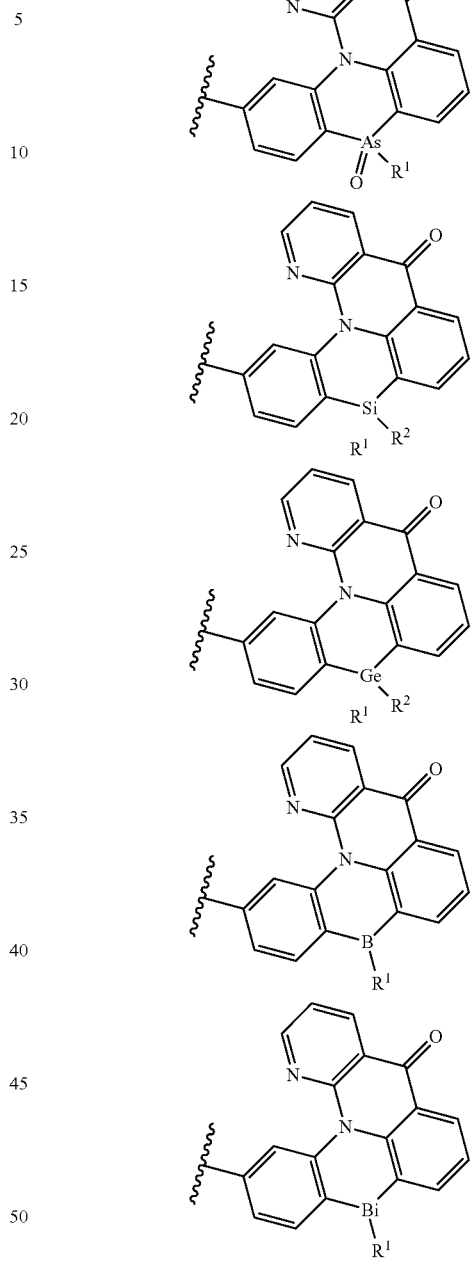

wherein each of $R^1$, $R^2$, $R^3$ and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

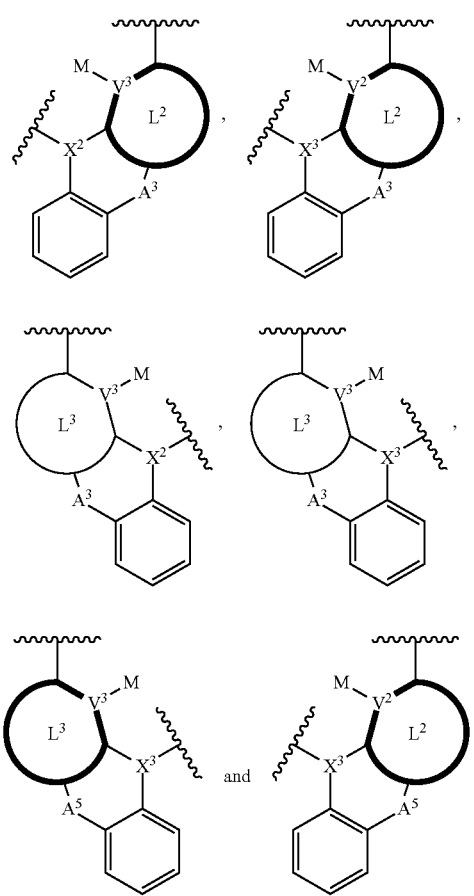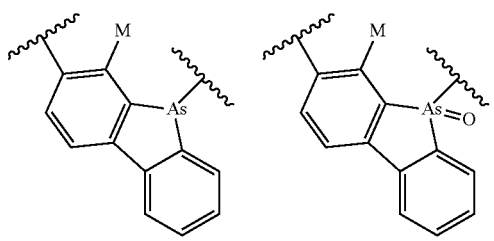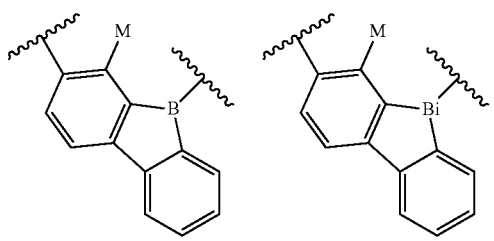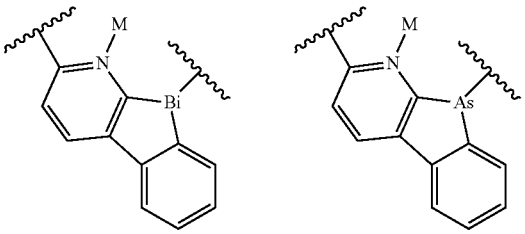
is independently one of the following structures:
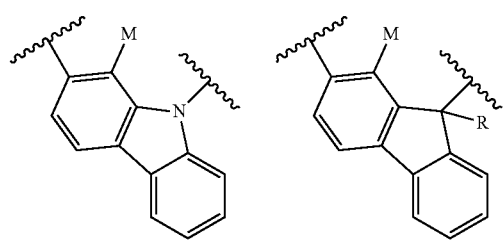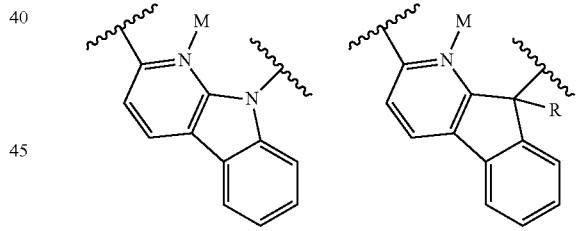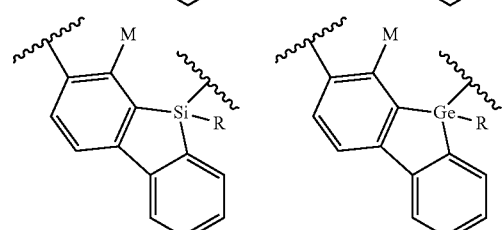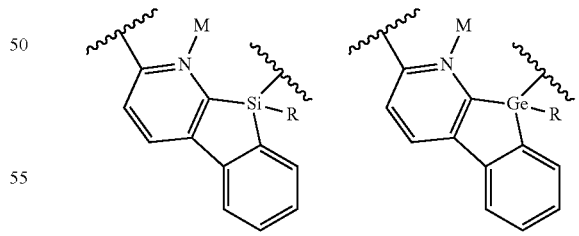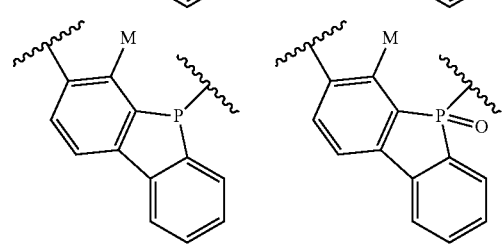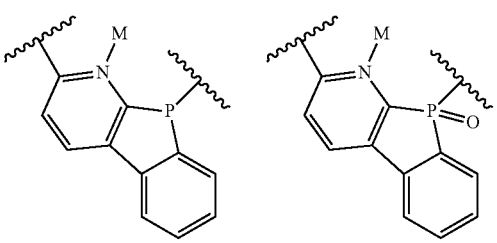

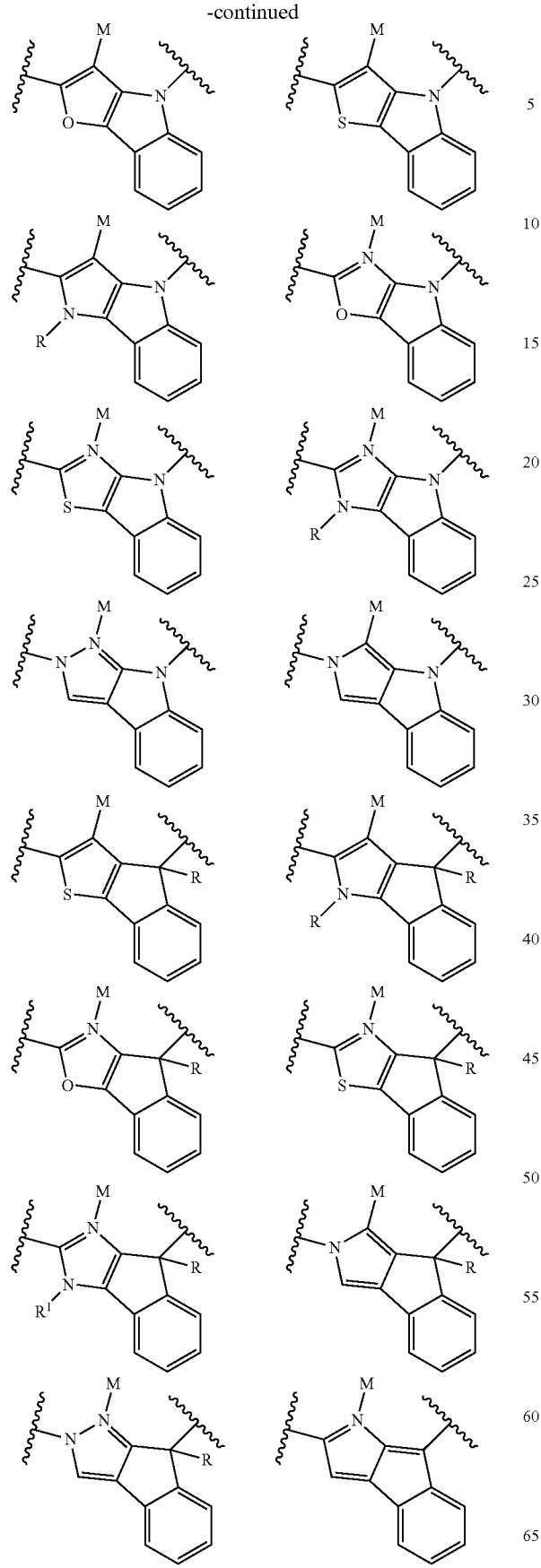
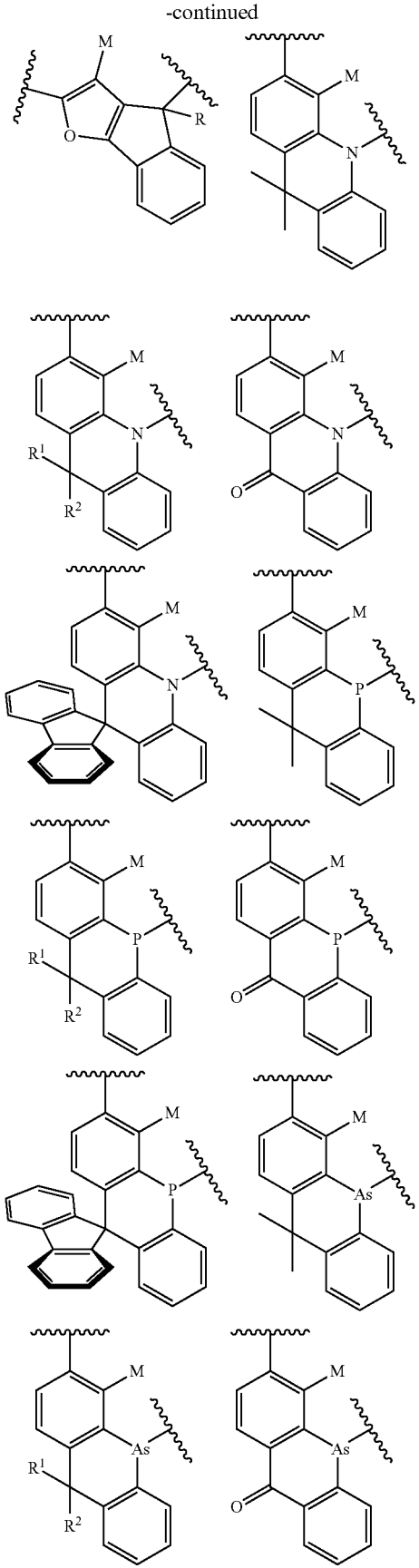

103
-continued
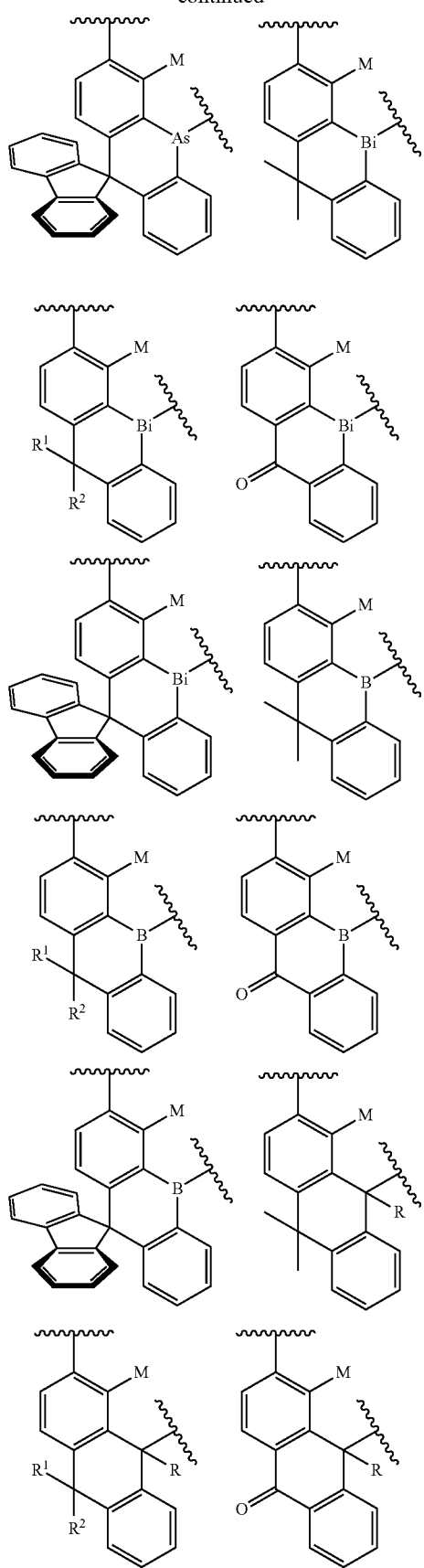
104
-continued
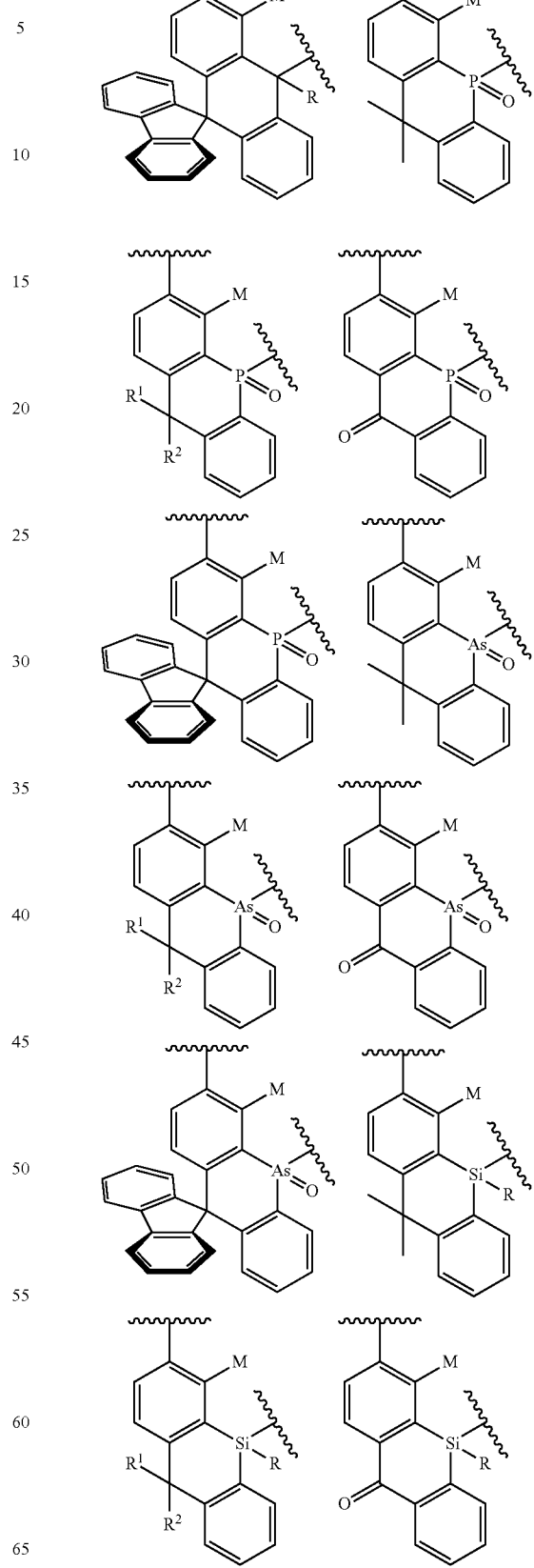

-continued
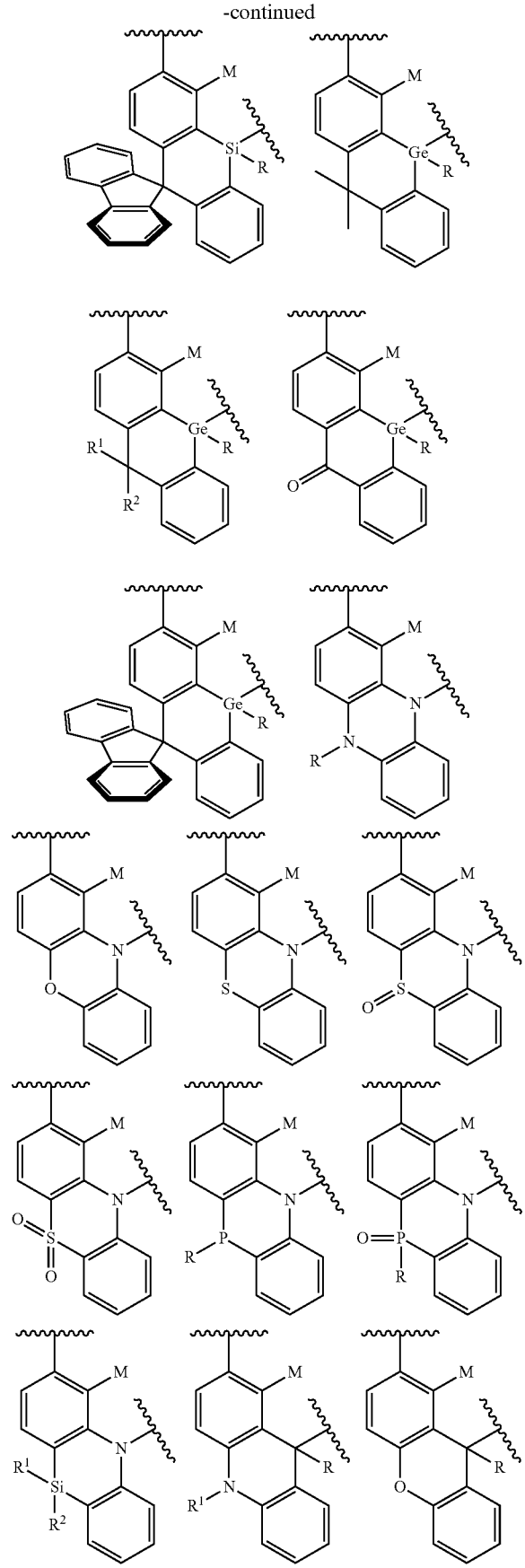
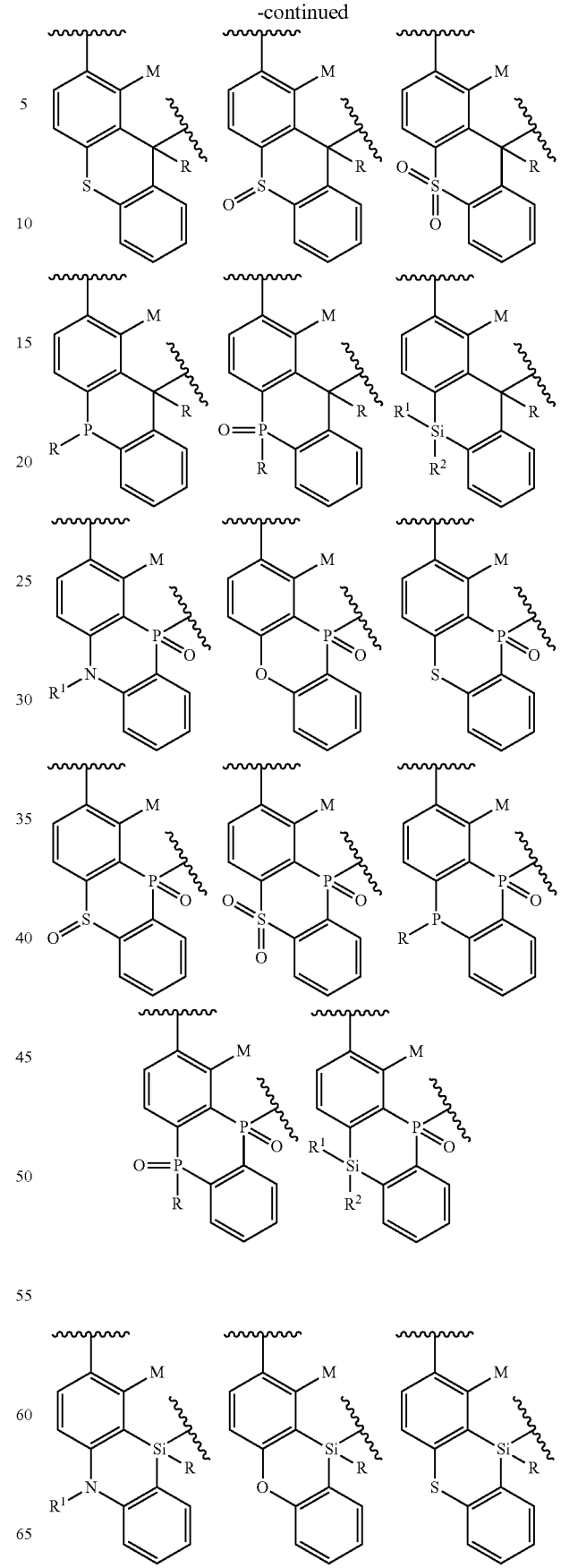

107
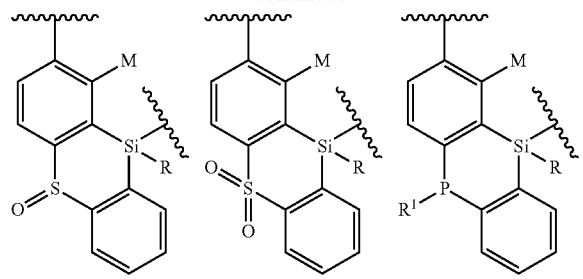
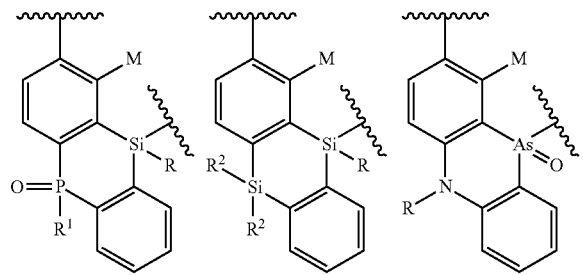
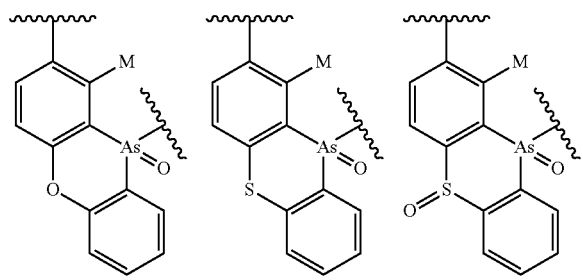
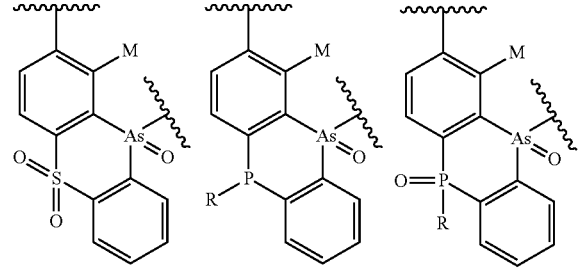
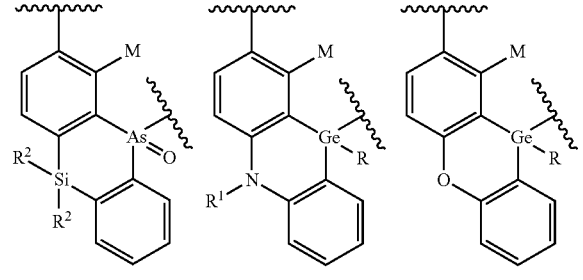
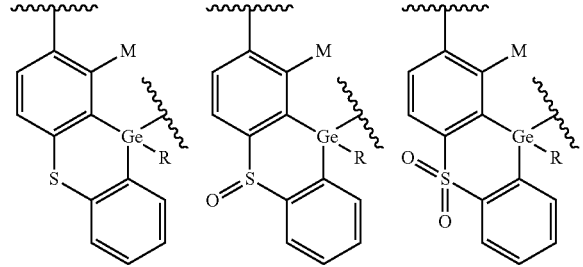
108
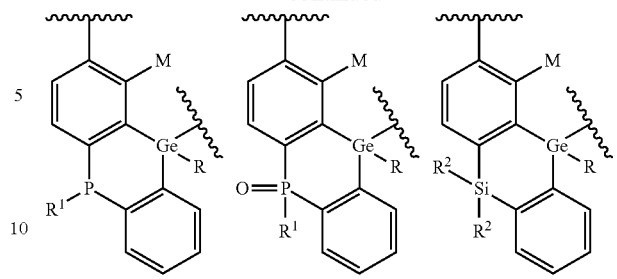
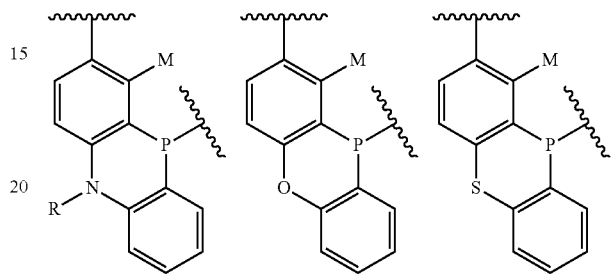
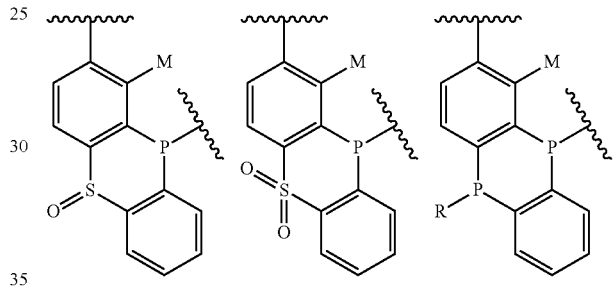
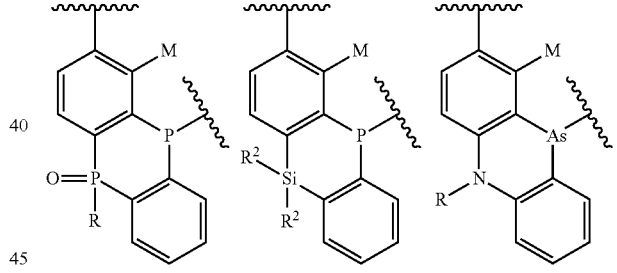
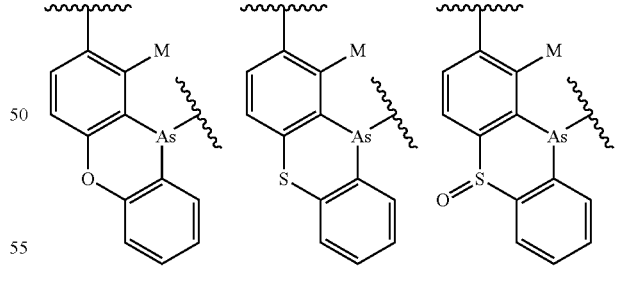
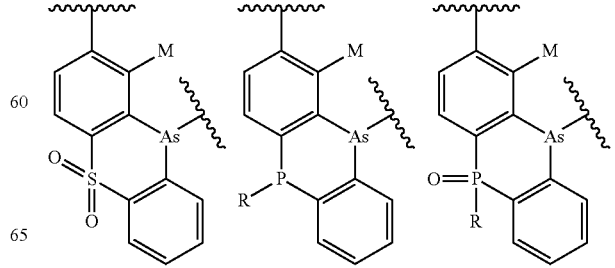

-continued

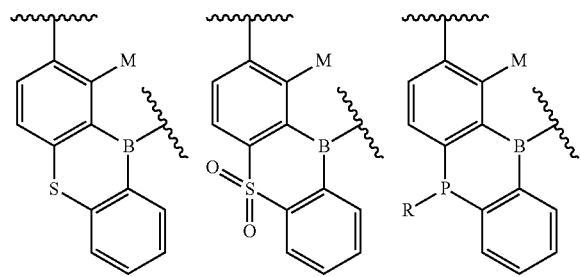
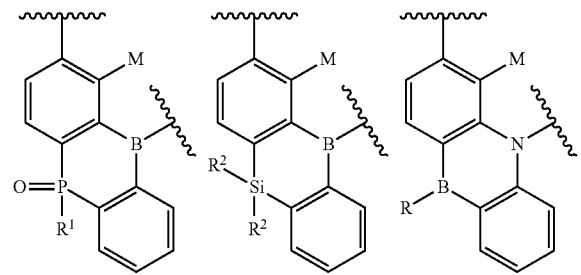
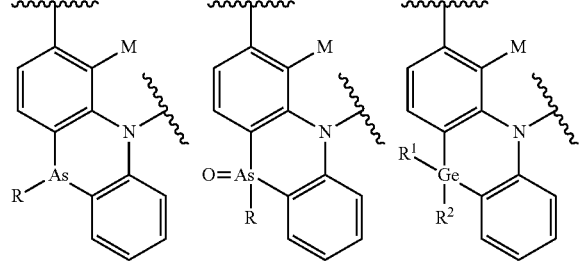
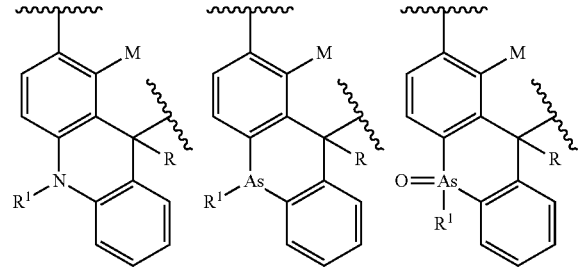
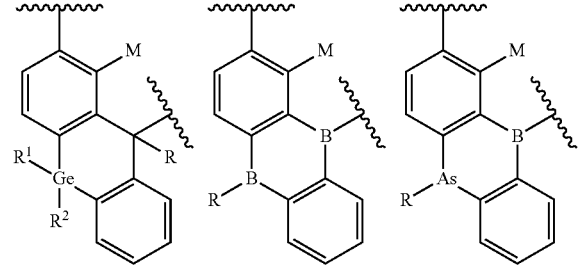
-continued

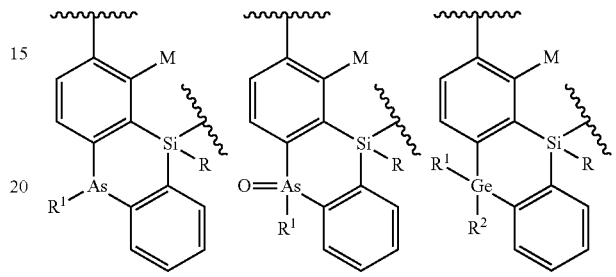
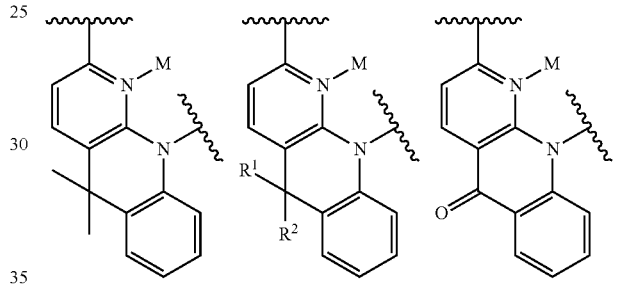
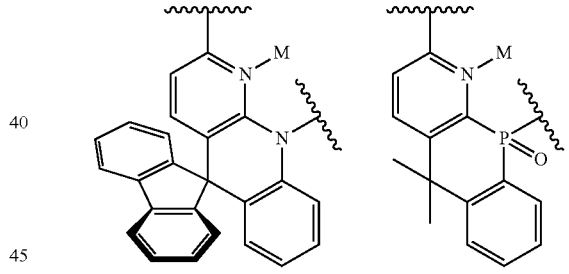
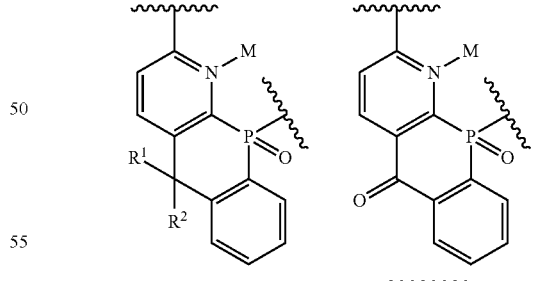
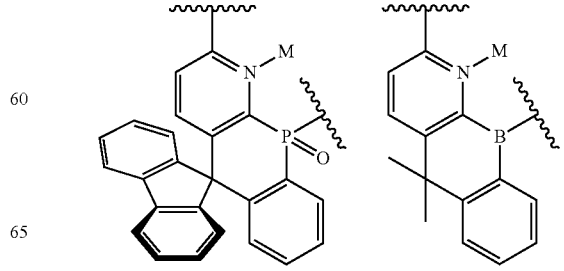

111
-continued
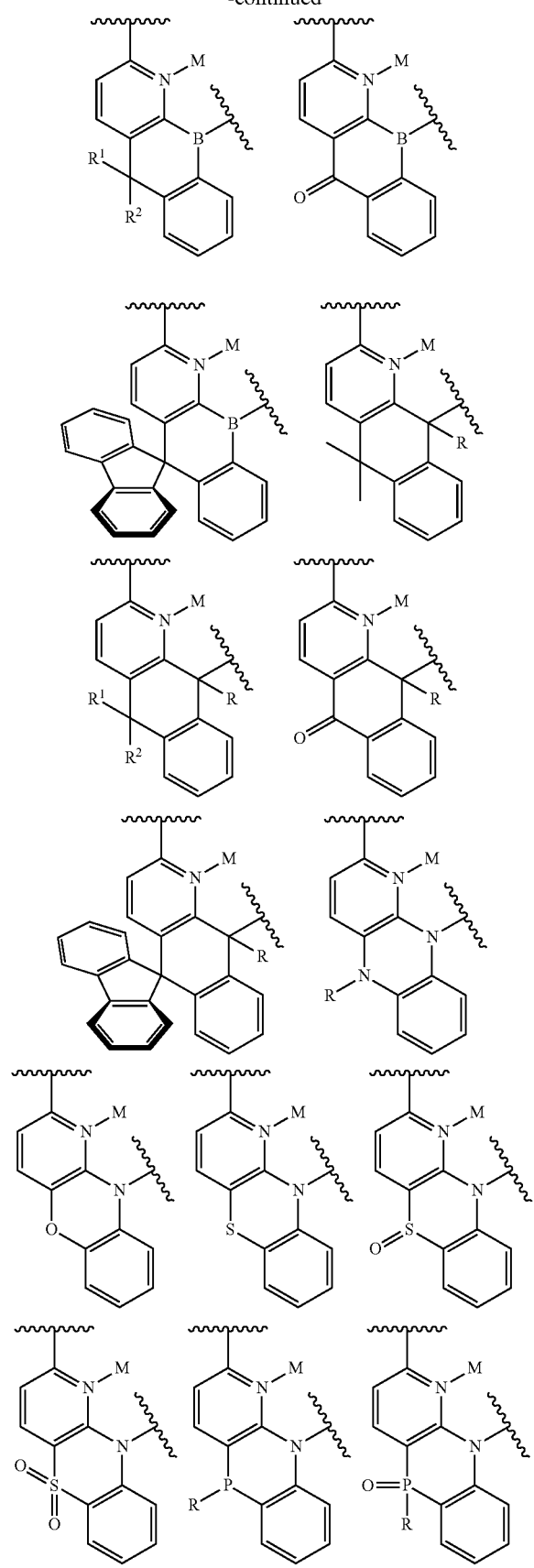
112
-continued
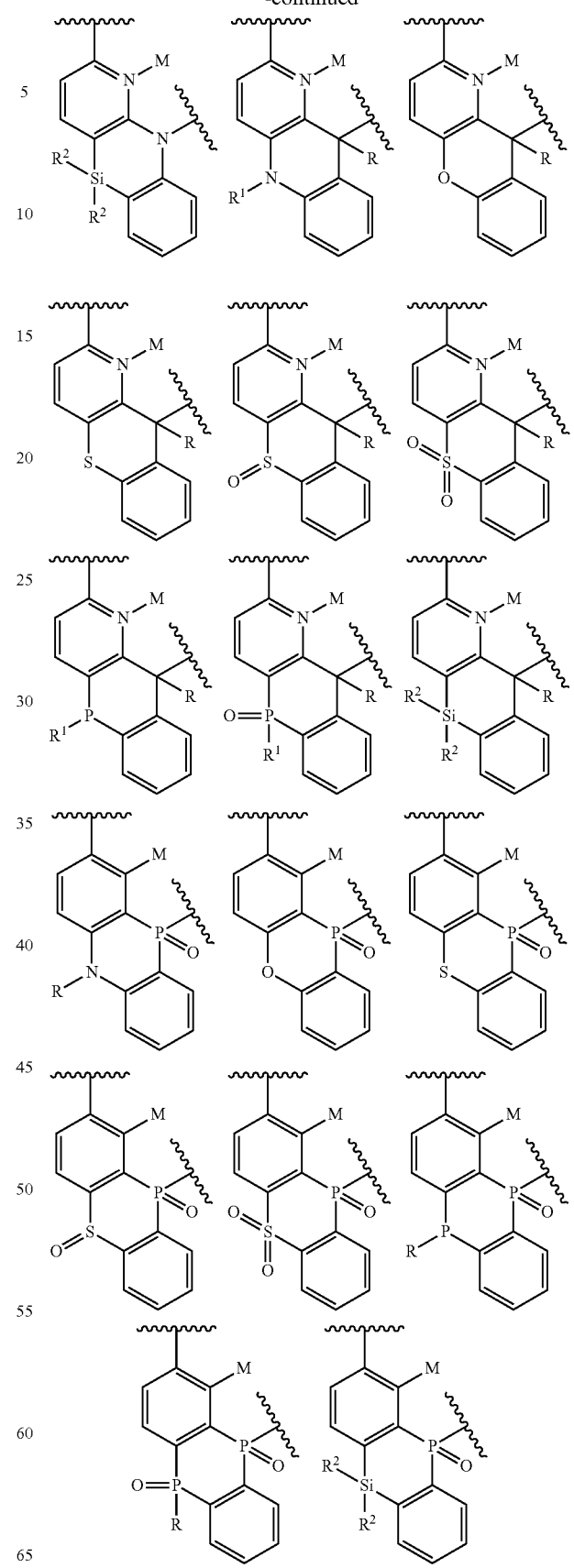

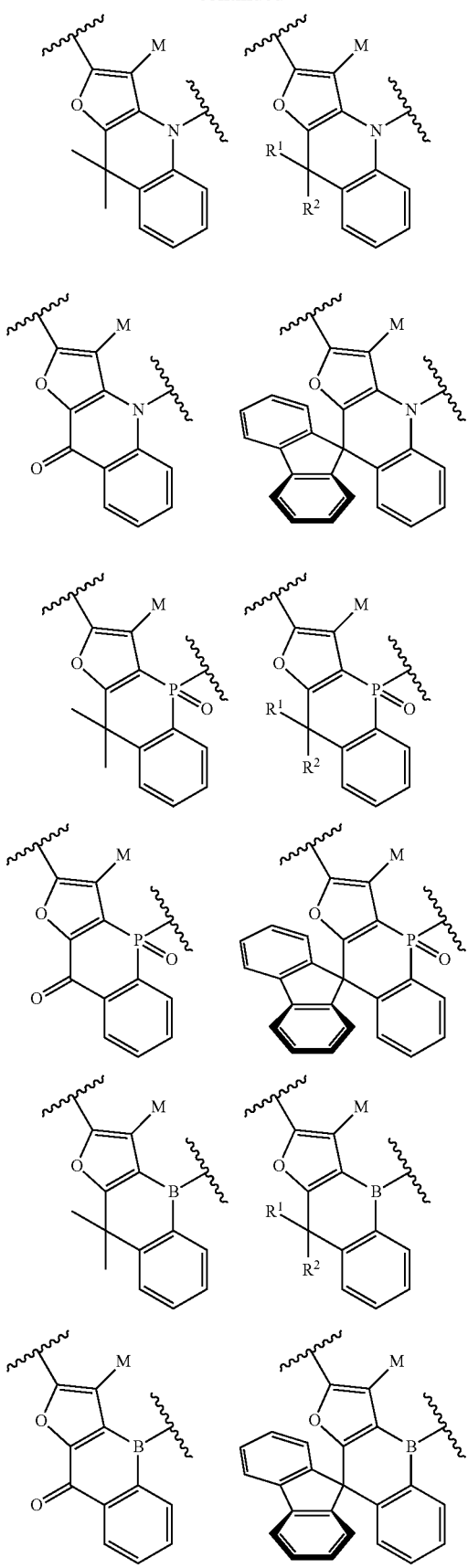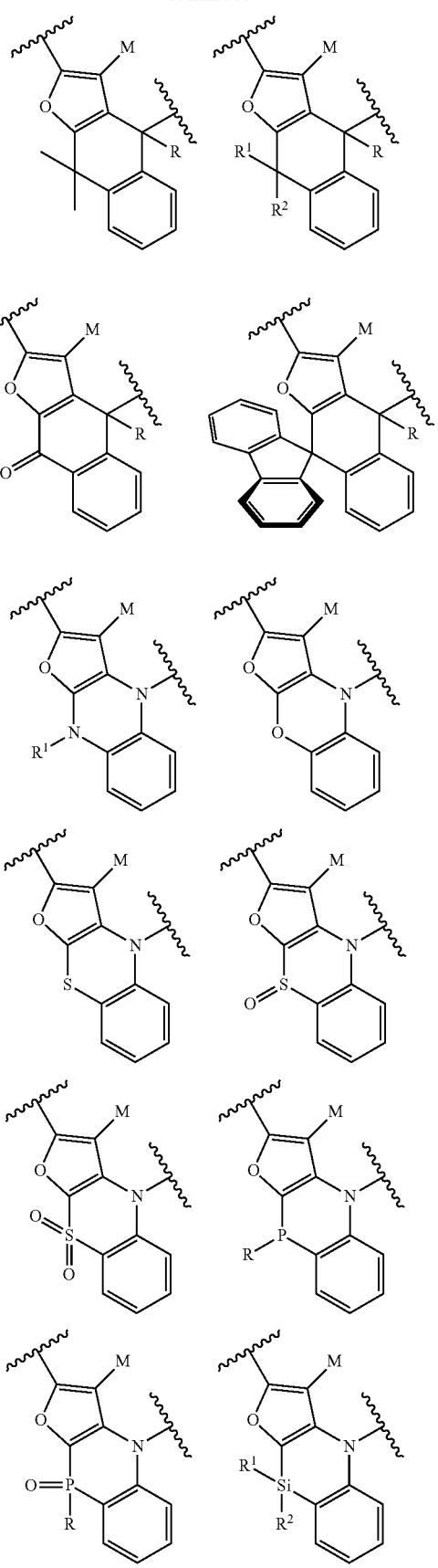

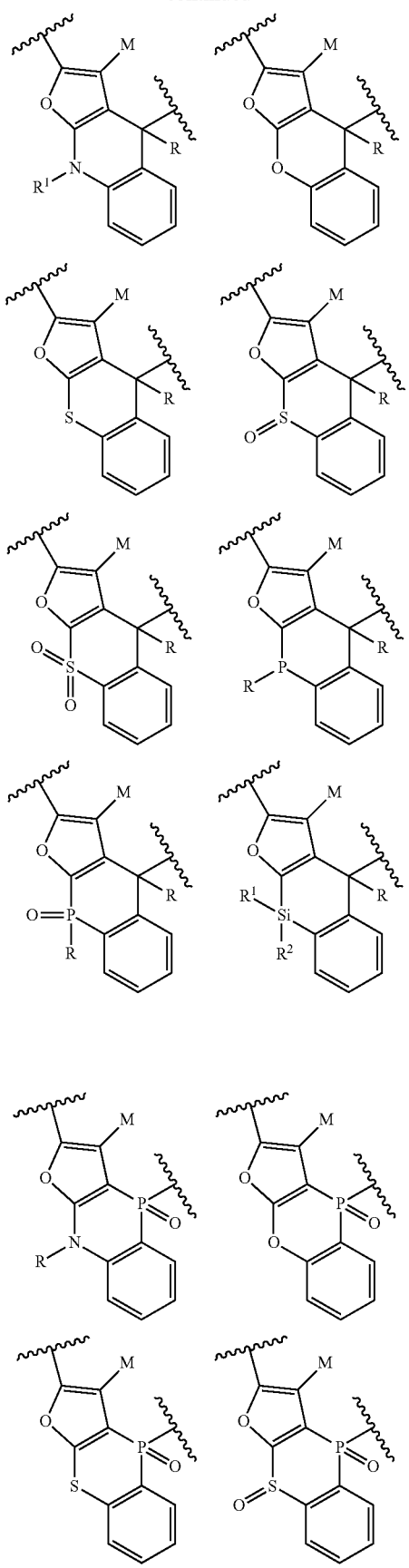
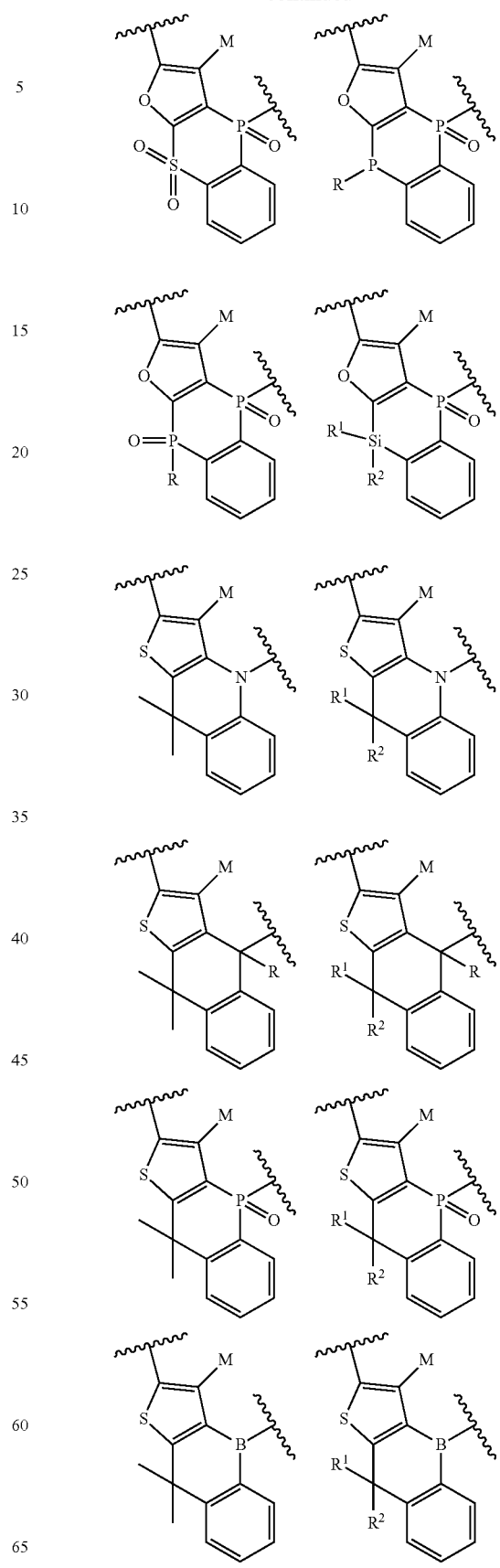

-continued
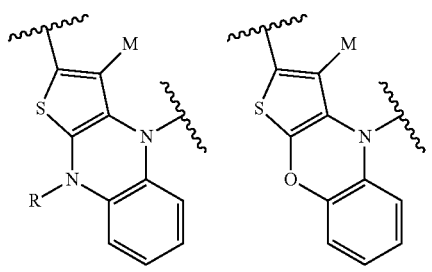
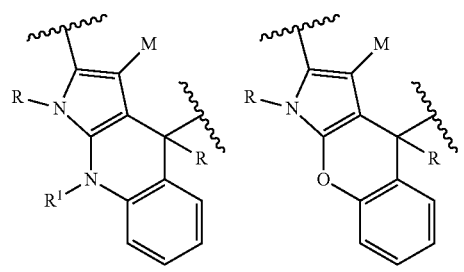
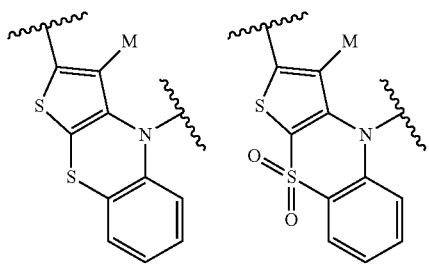
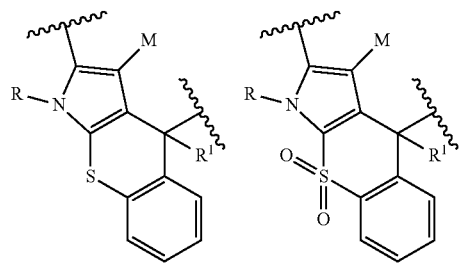
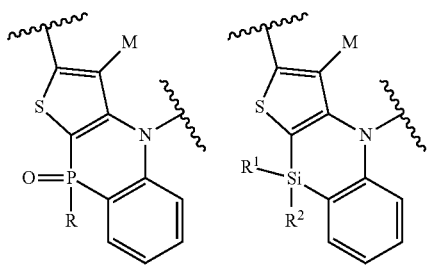
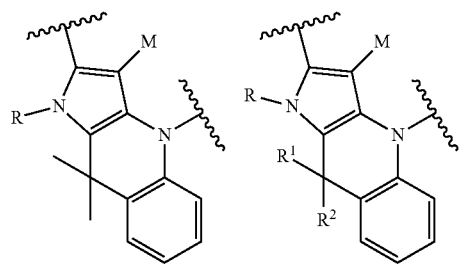
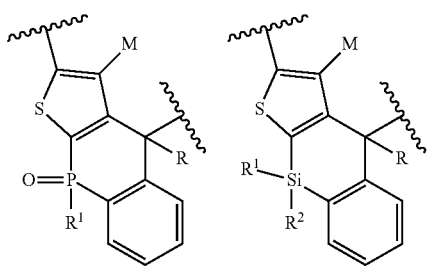
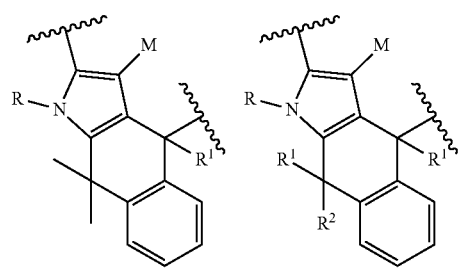
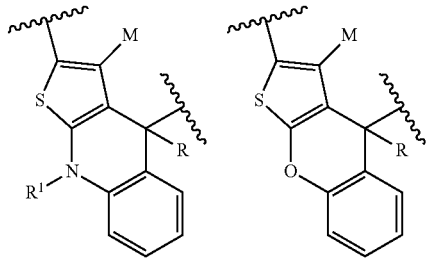
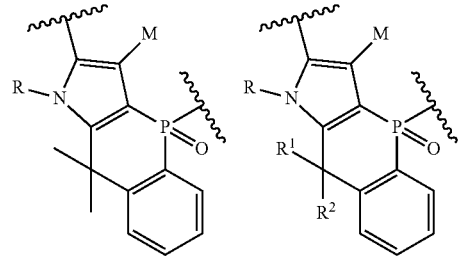
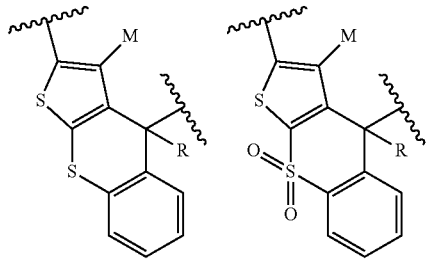
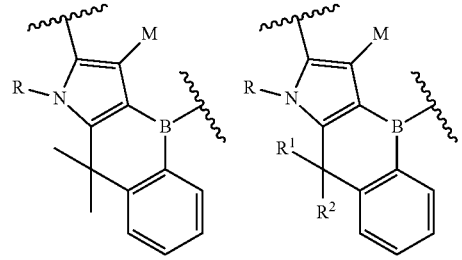

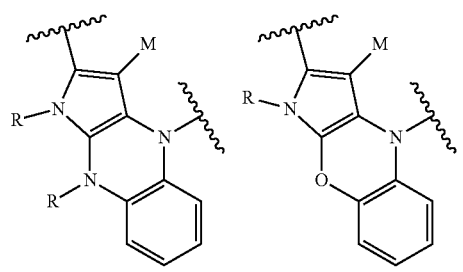
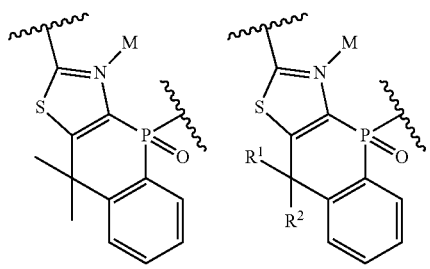
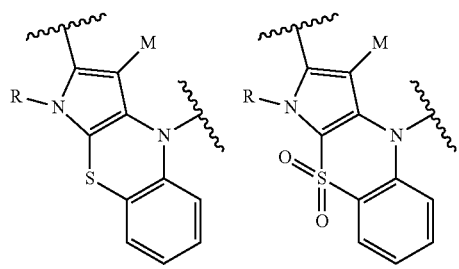
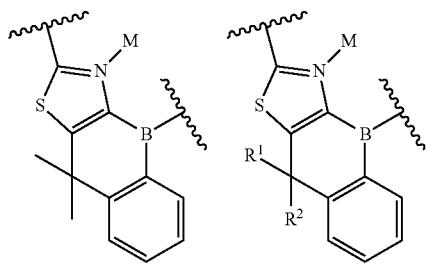
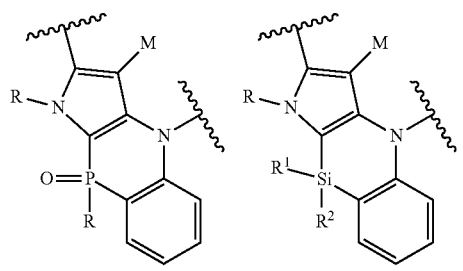
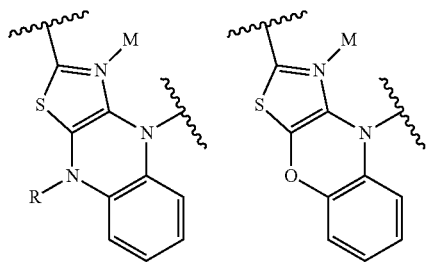
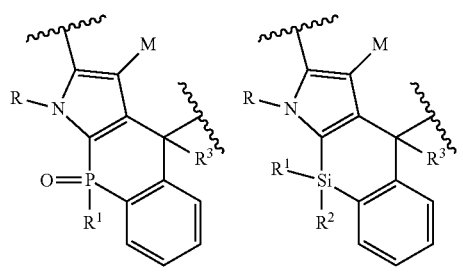
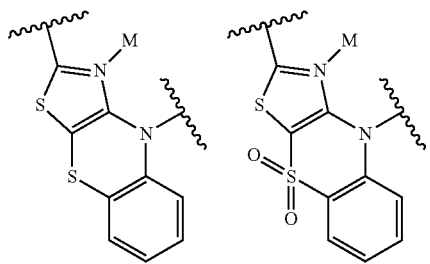
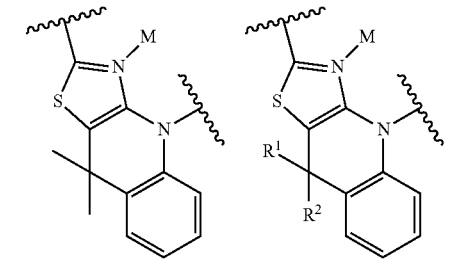
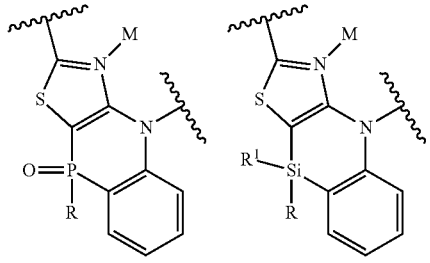
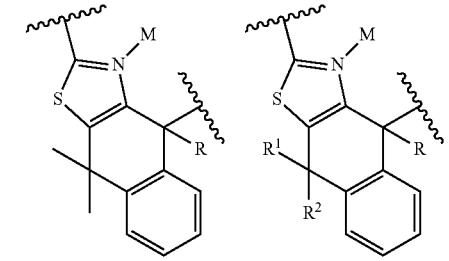
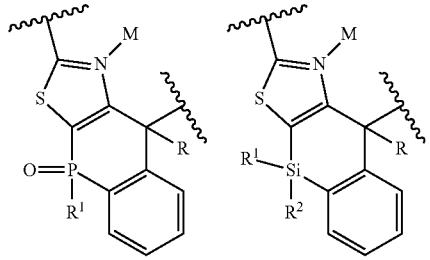

121
-continued
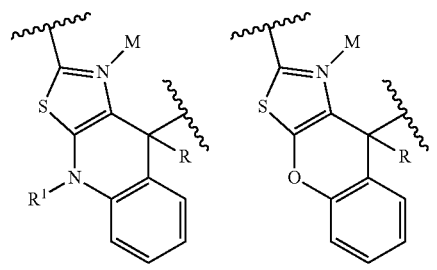
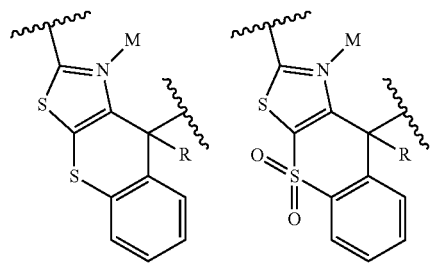
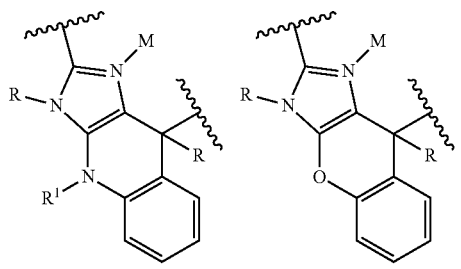
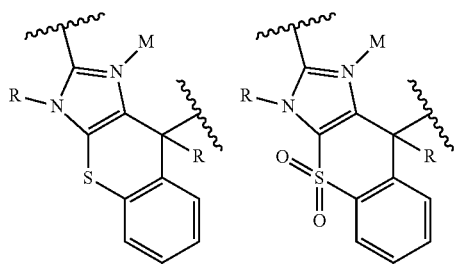
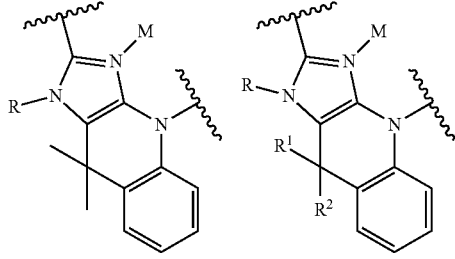
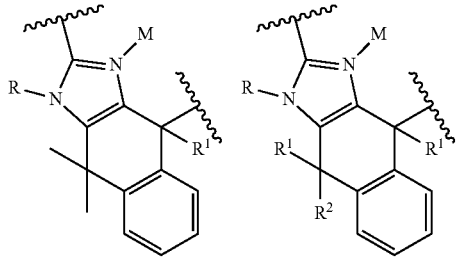
122
-continued
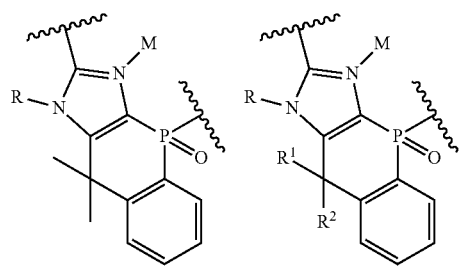
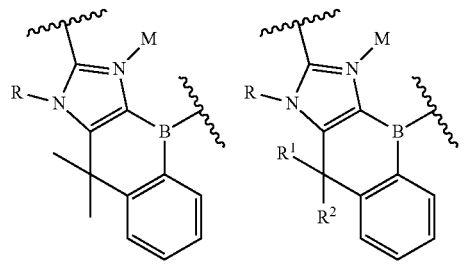
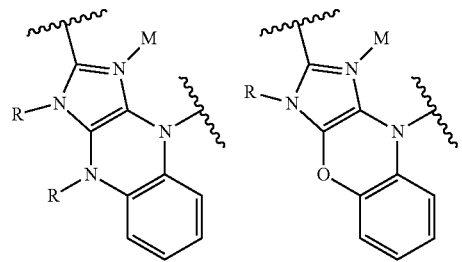
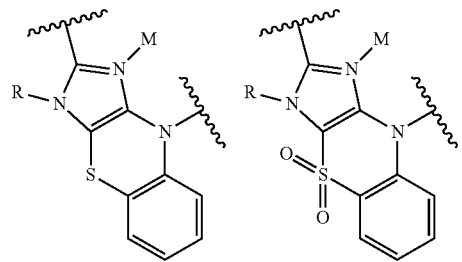
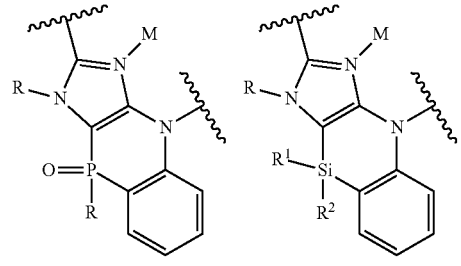
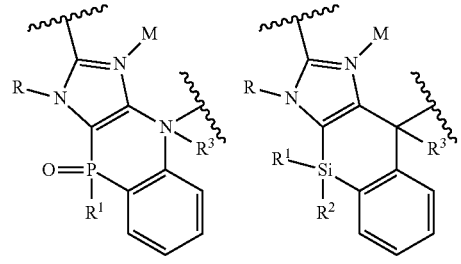

123
-continued
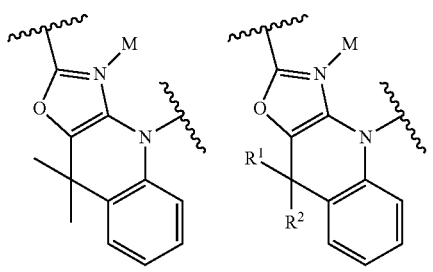
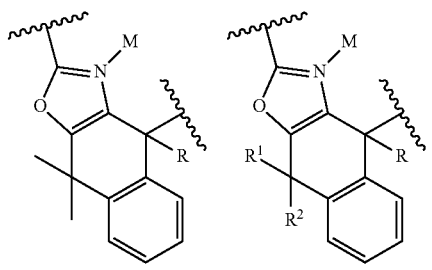
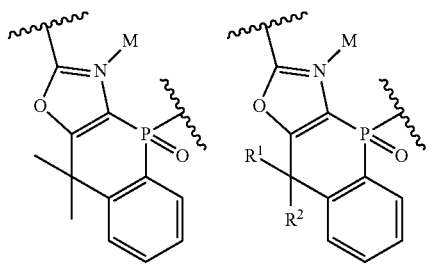
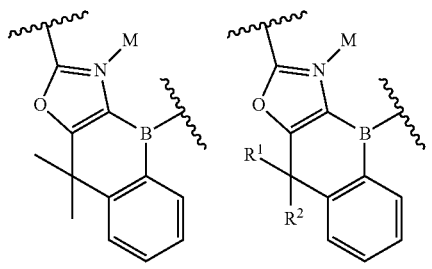
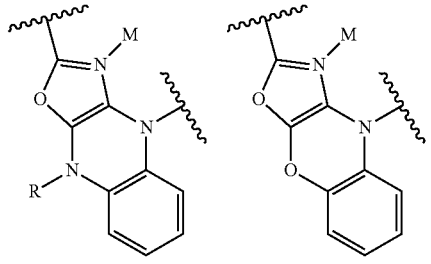
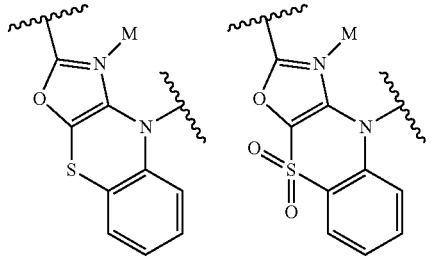
124
-continued
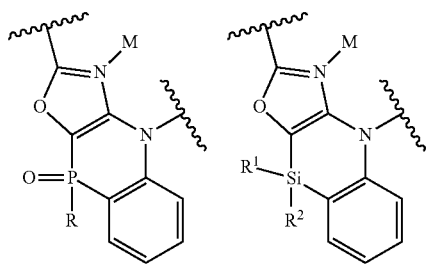
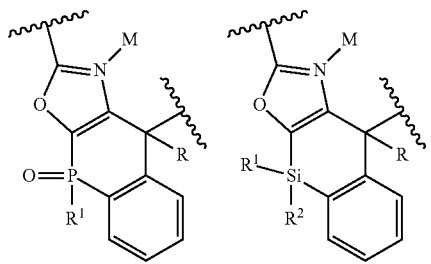
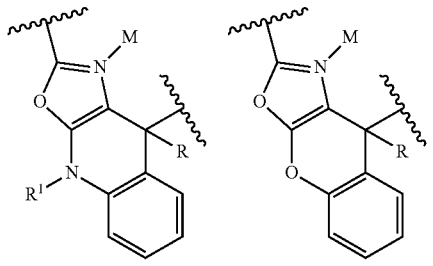
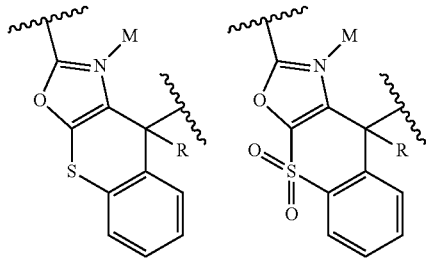
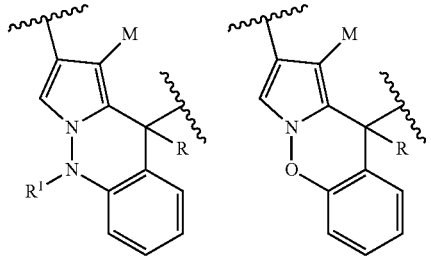
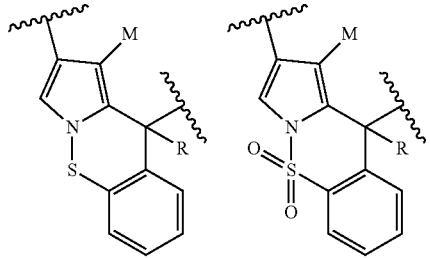

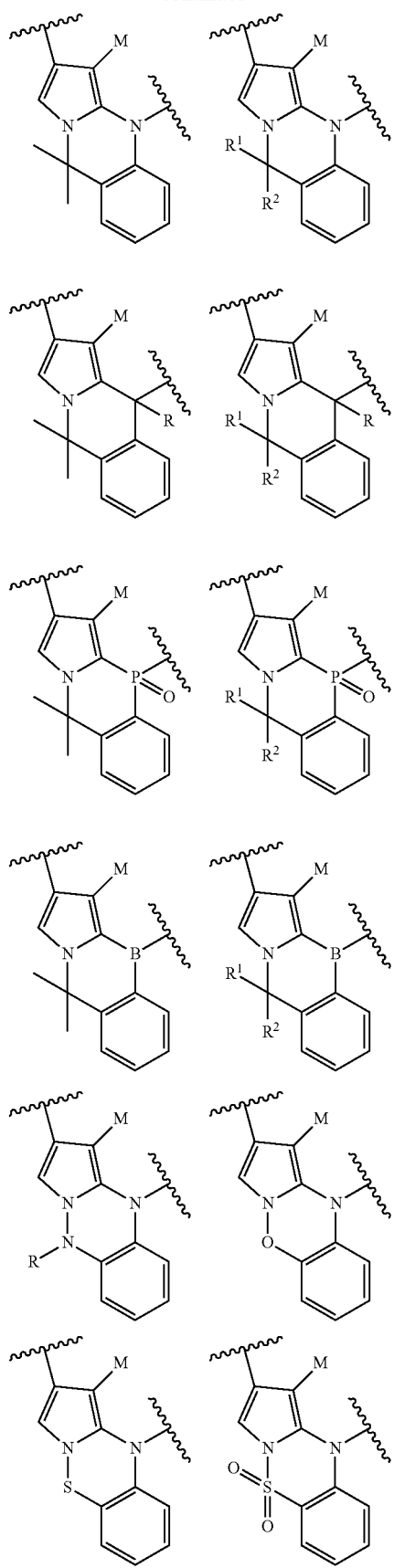
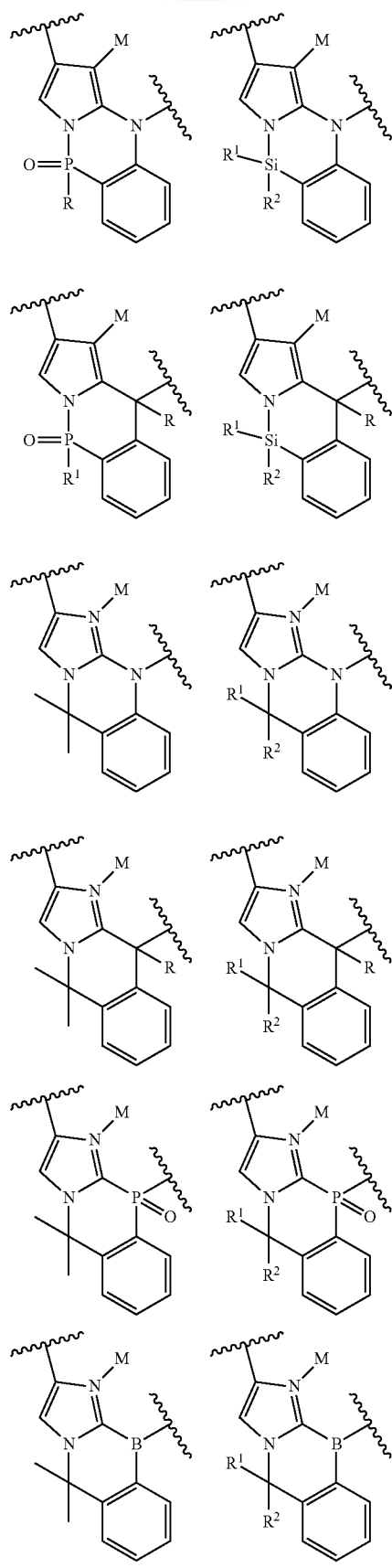

-continued

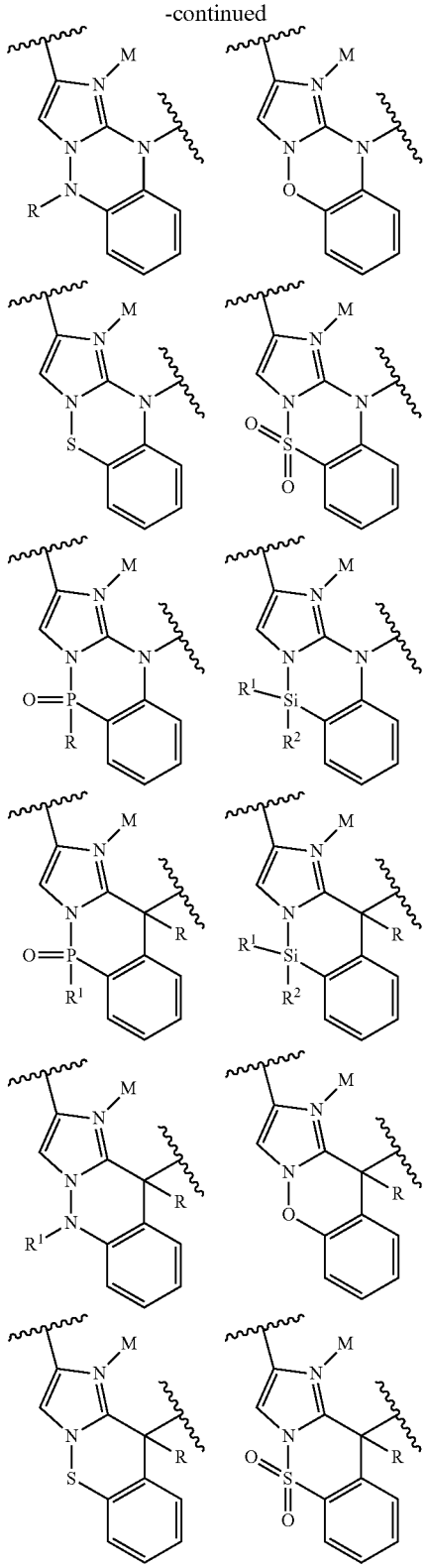

wherein each of R, R$^1$, R$^2$, and R$^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, metal complexes illustrated in this disclosure can comprise one or more of the following structures. In another aspect, metal complexes illustrated in this disclosure can also comprise other structures or portions thereof not specifically recited herein, and the present disclosure is not intended to be limited to those structures or portions thereof specifically recited.

Structure 1 (M = Pt or Pd)

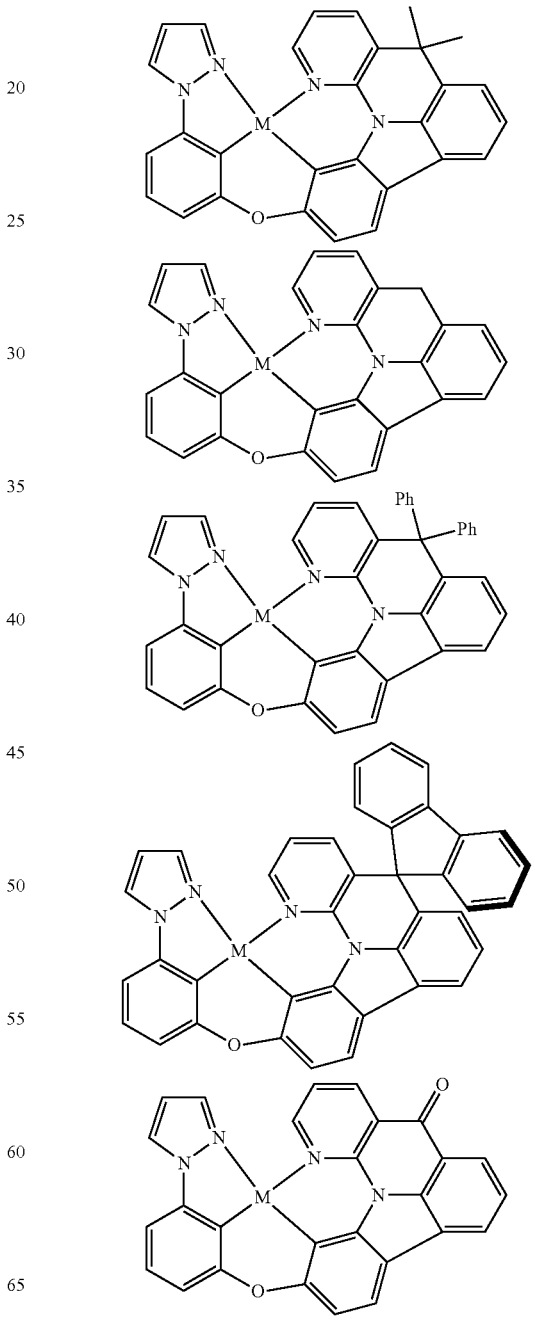

-continued

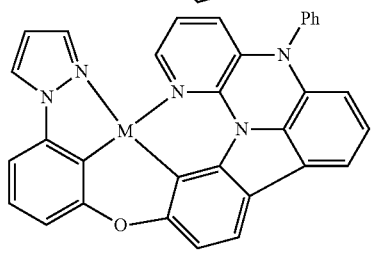
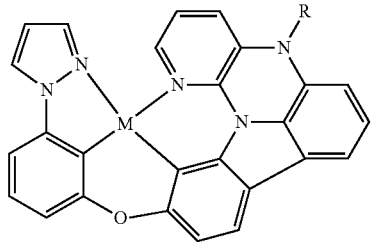
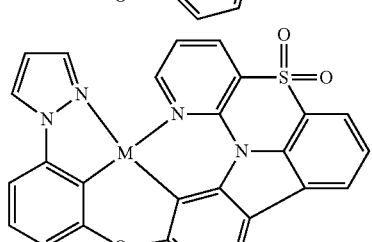
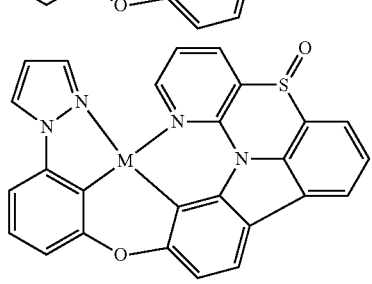
-continued
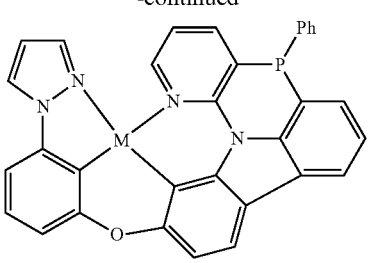
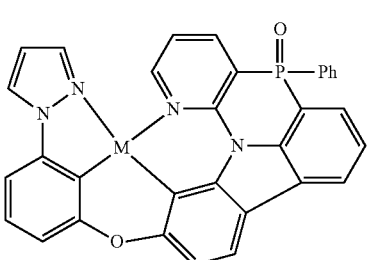
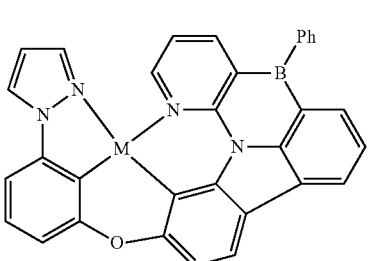
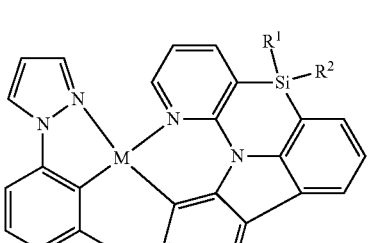
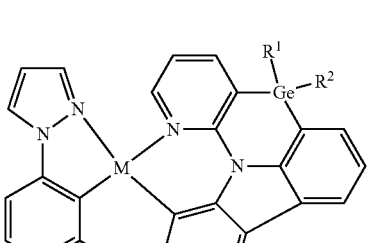
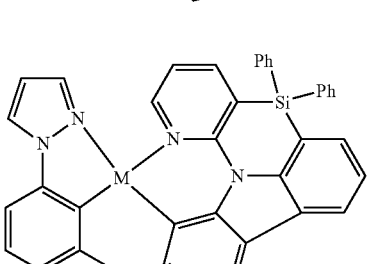

131
-continued
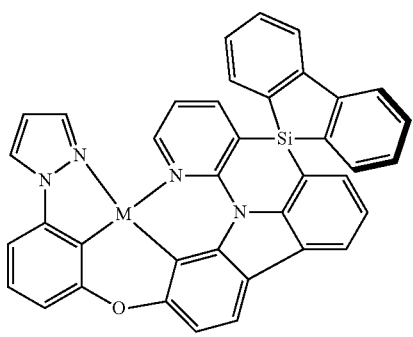
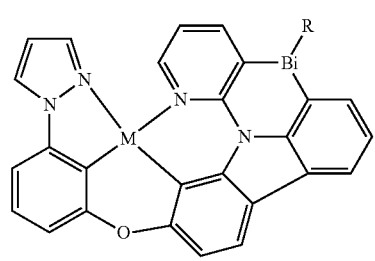
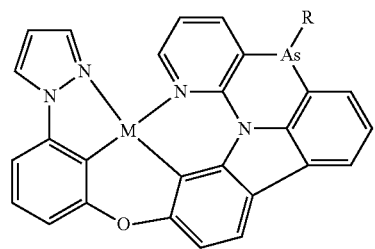
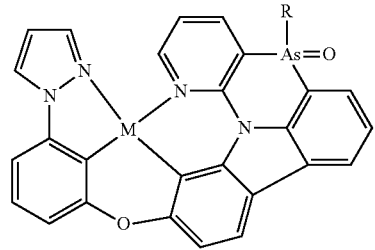
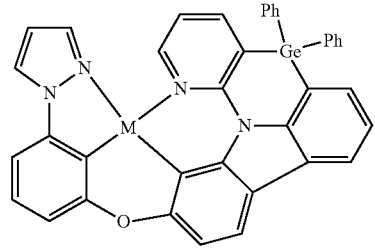
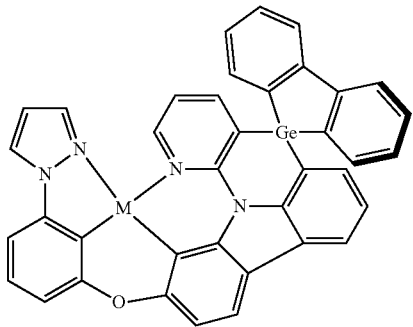
132
-continued
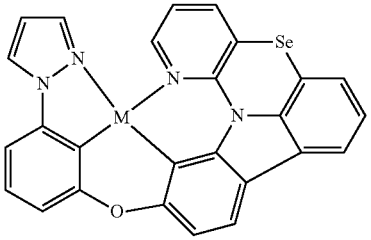
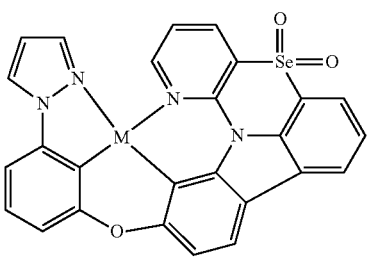
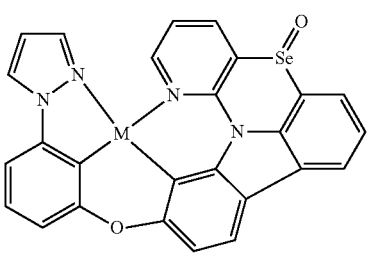
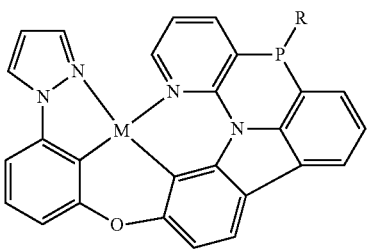
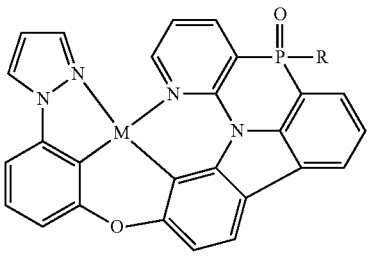
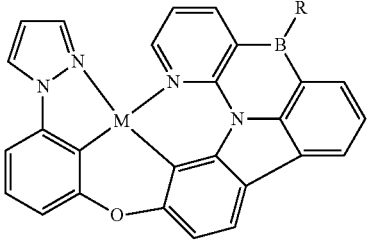

133
-continued
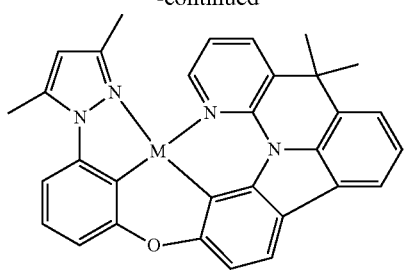
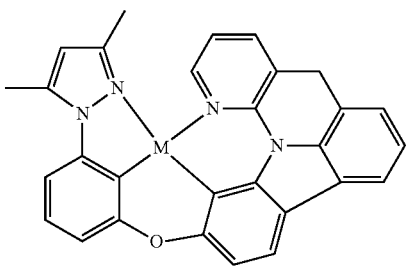
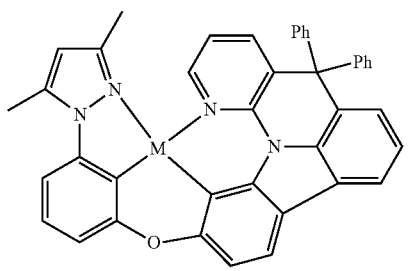
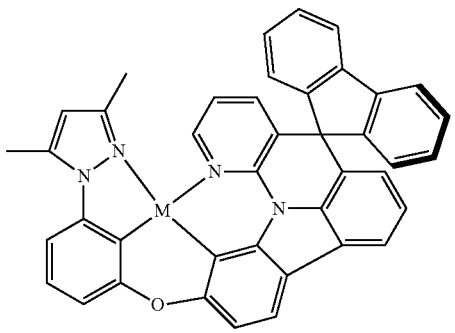
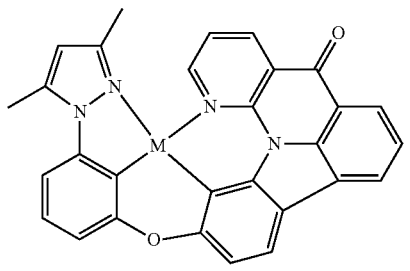
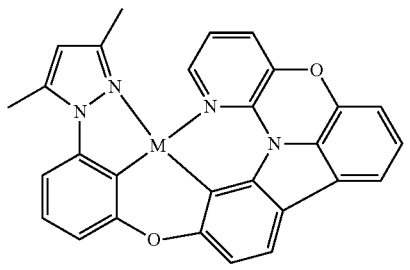
134
-continued
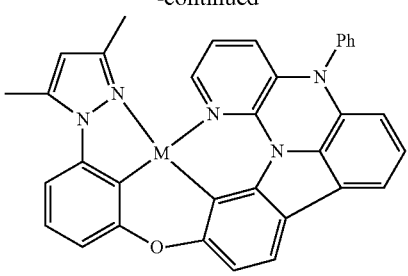
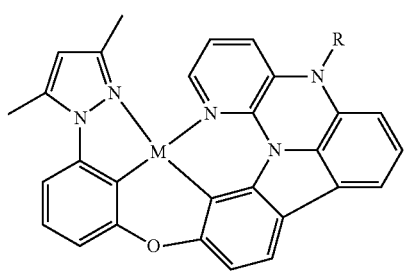
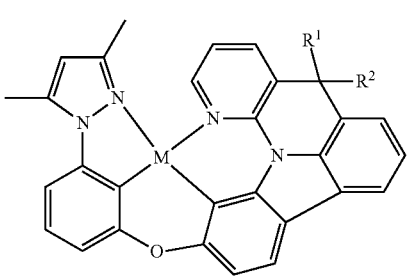
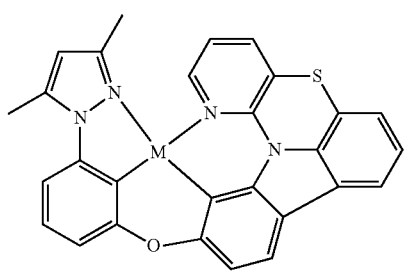
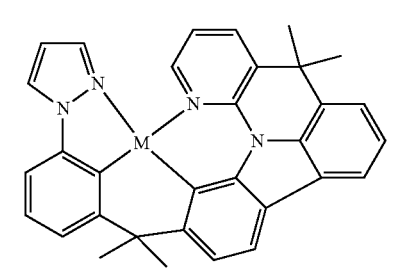
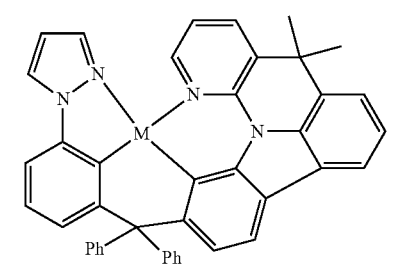

135
-continued
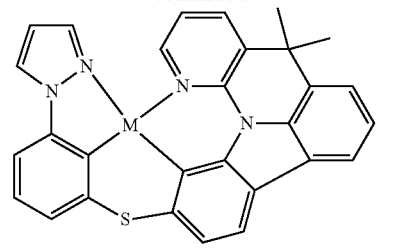
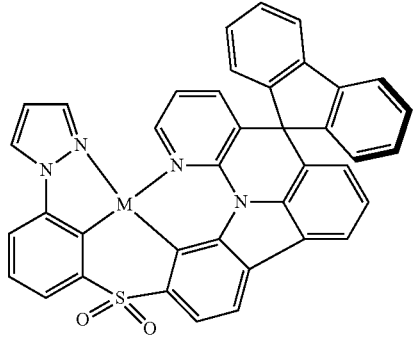
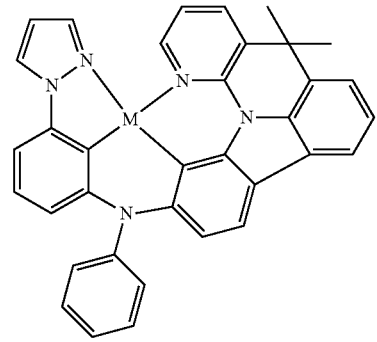
Structure 2 (M = Pt or Pd)
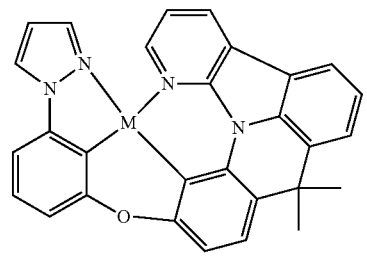
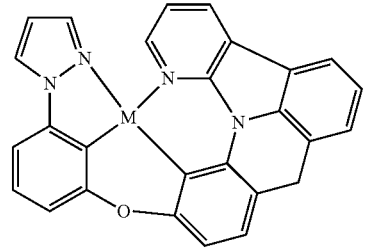
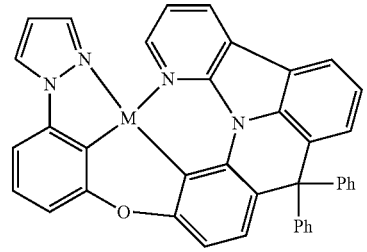
136
-continued
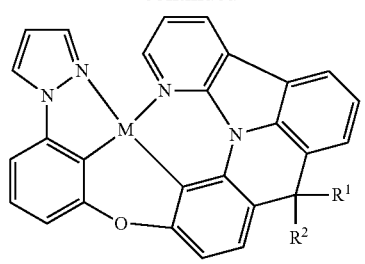
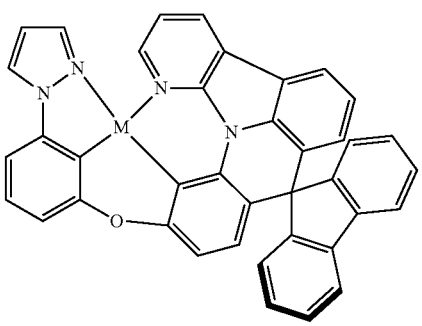
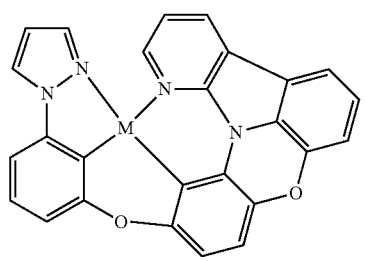
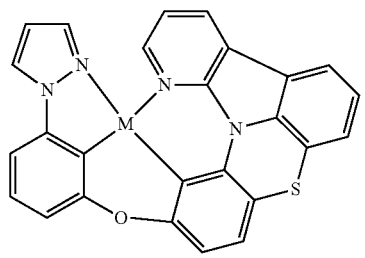
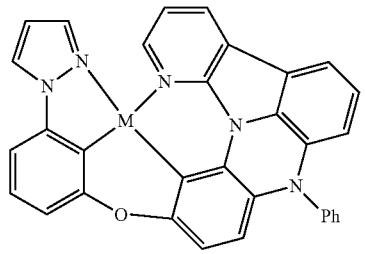
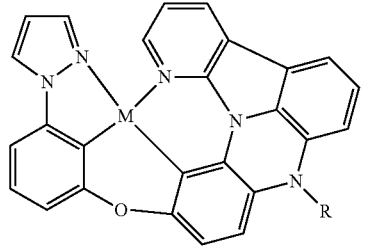

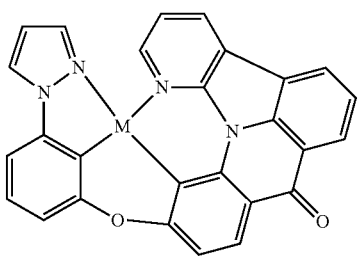
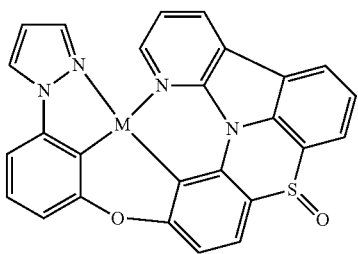
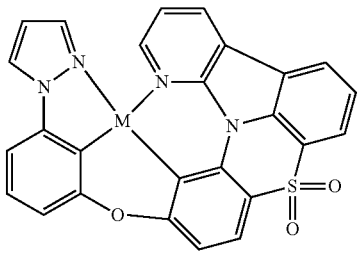
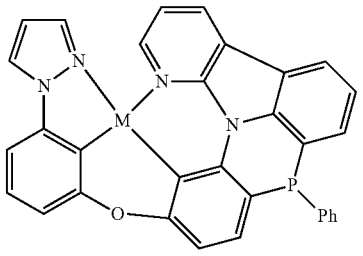
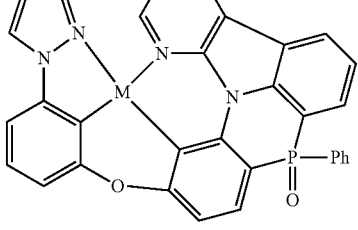
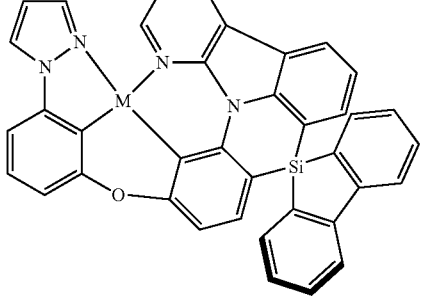
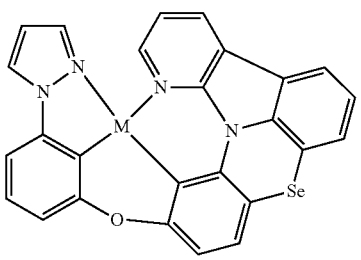
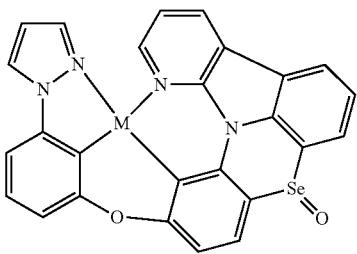
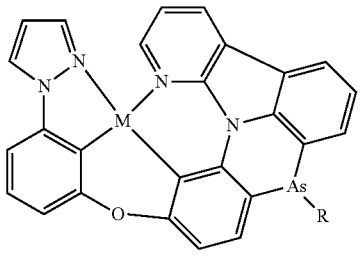
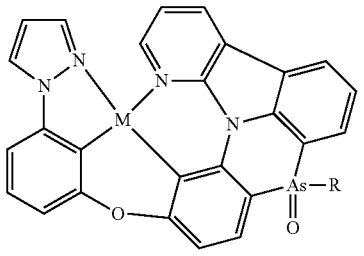
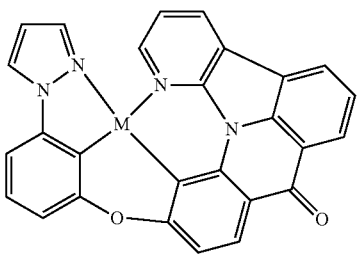
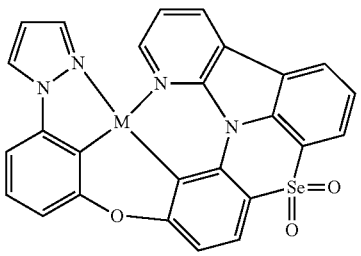

139
-continued
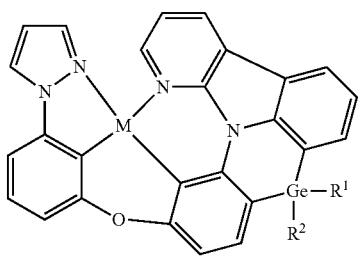
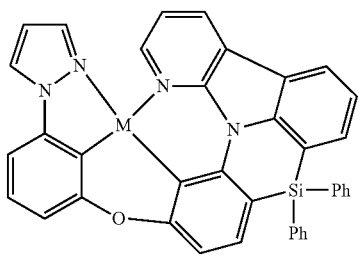
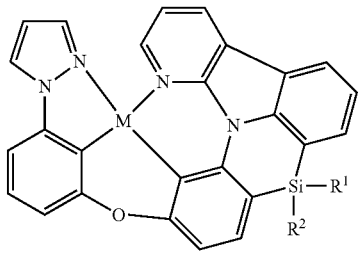
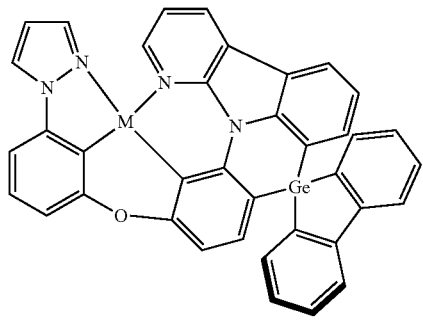
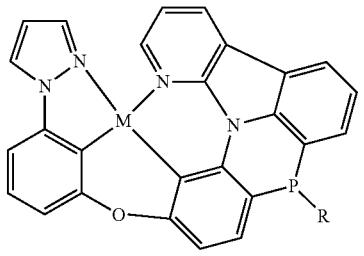
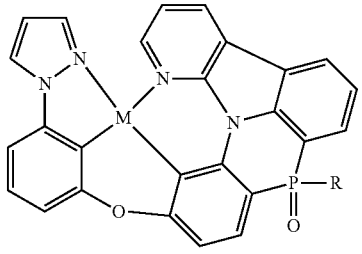
140
-continued
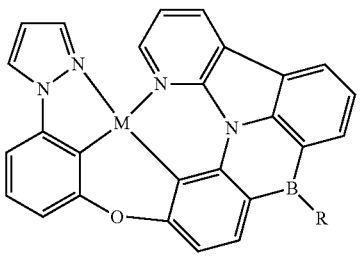
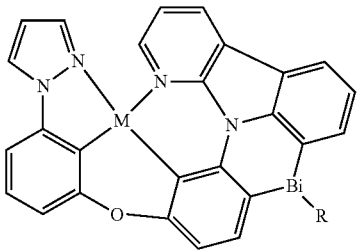
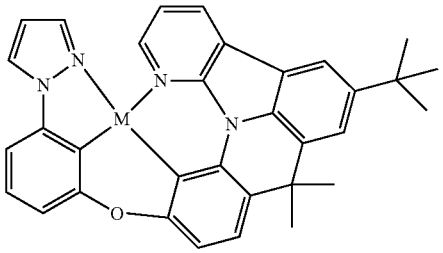
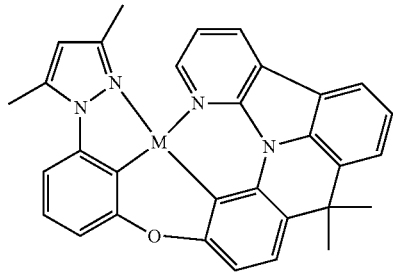
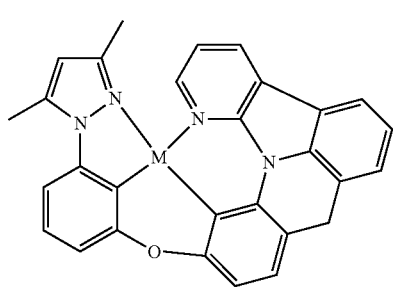
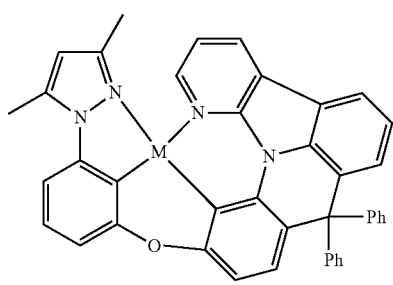

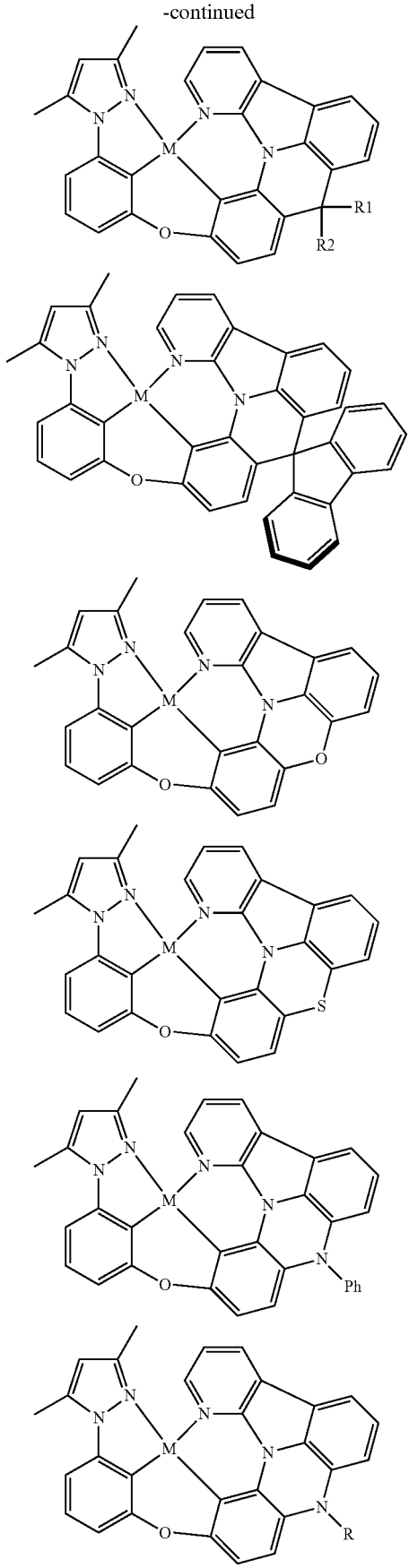
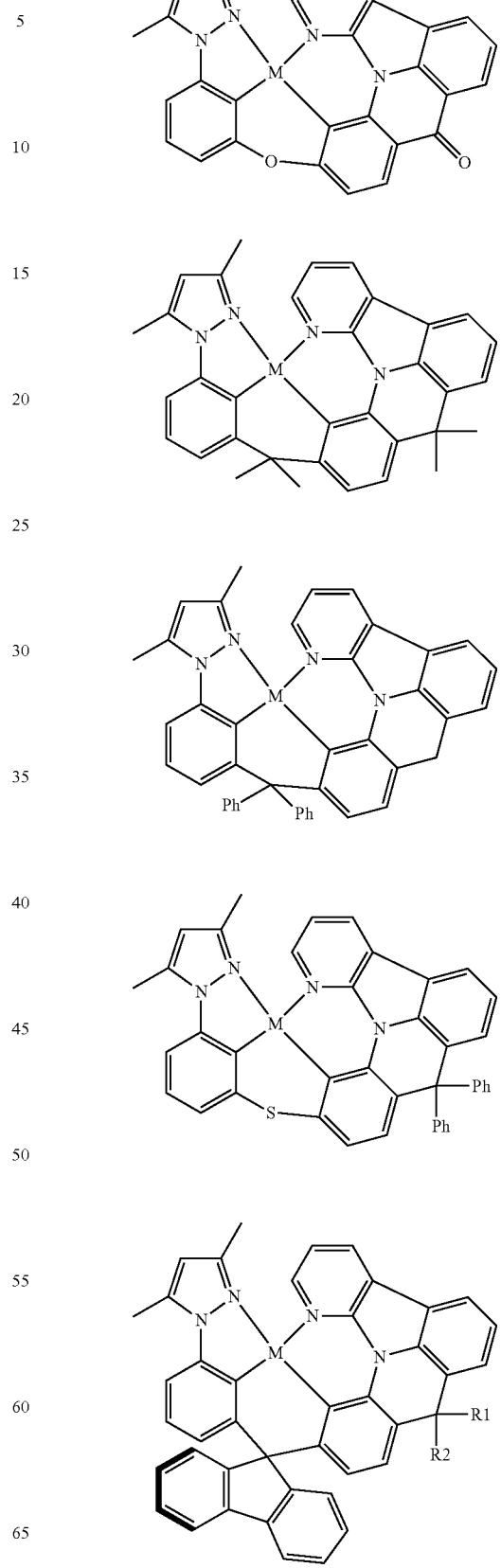

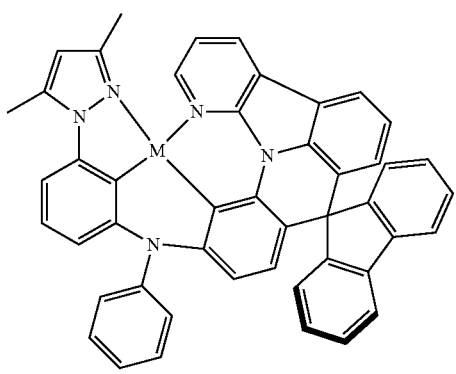
Structure 3 (M = Pt or Pd)
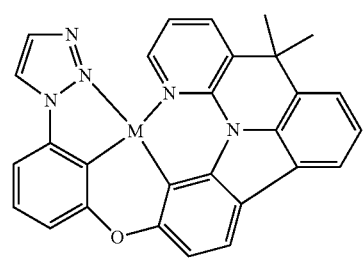
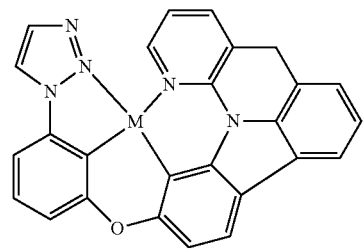
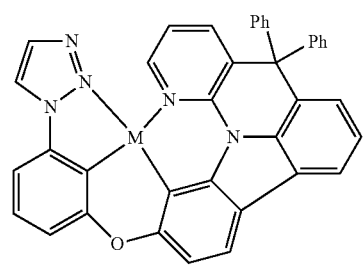
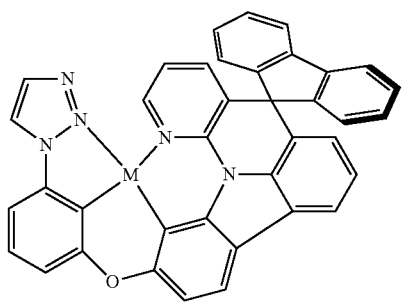
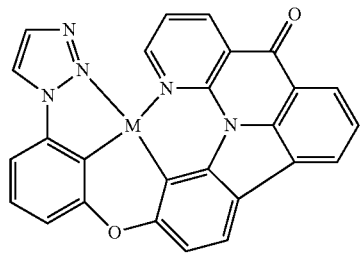
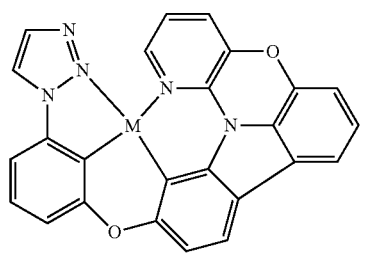
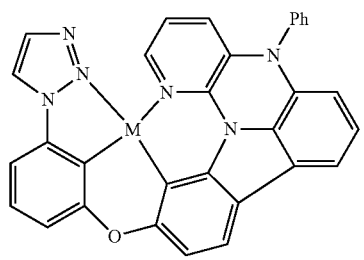
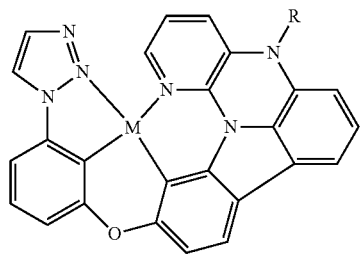
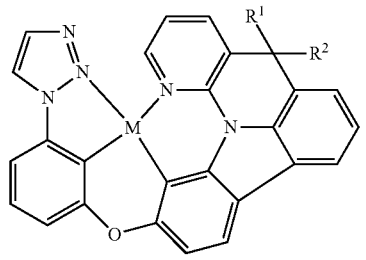
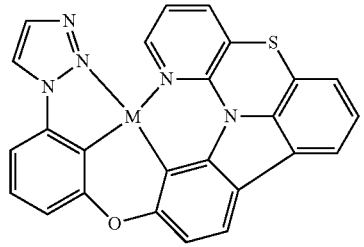

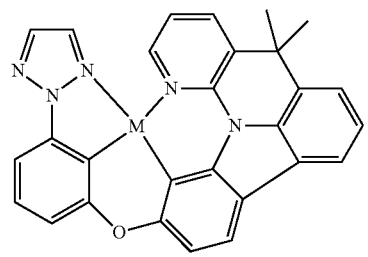
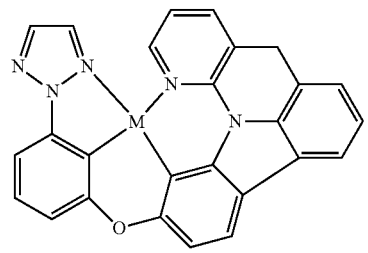
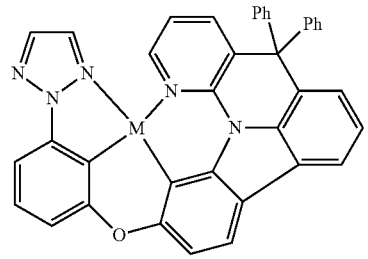
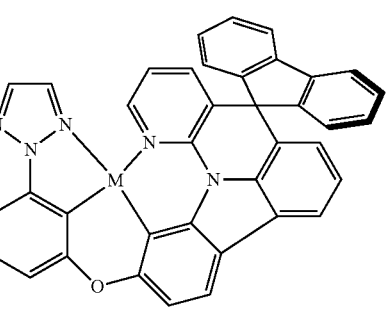
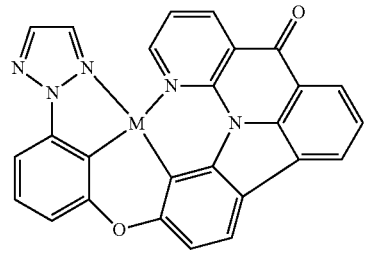
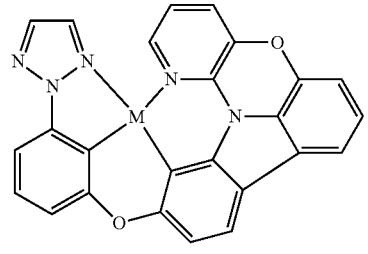
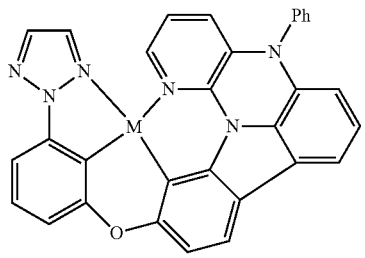
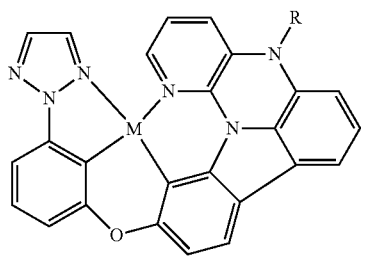
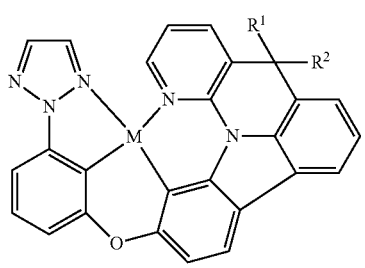
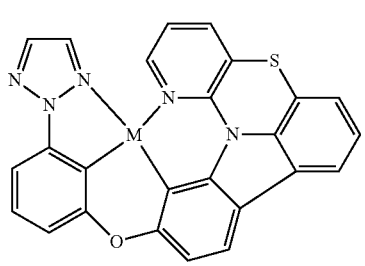
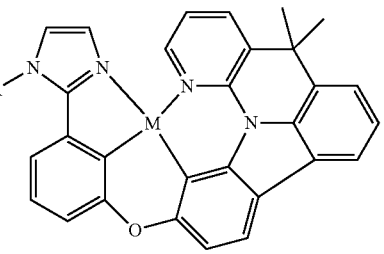
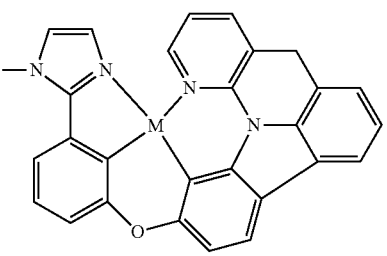

147
-continued
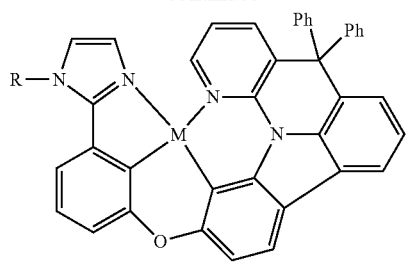
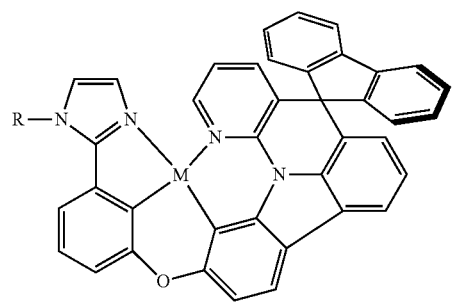
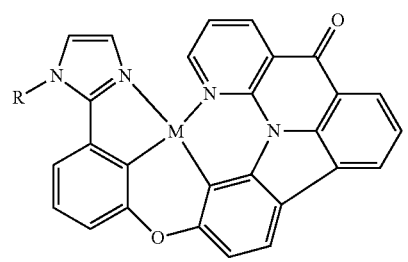
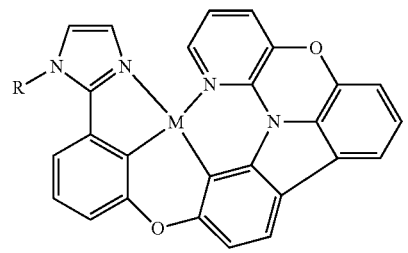
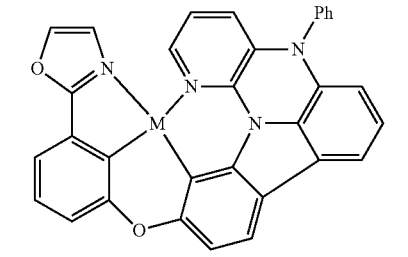
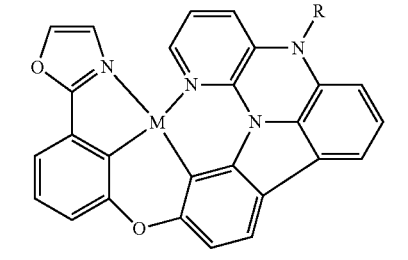
148
-continued
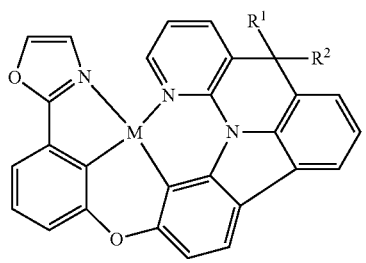
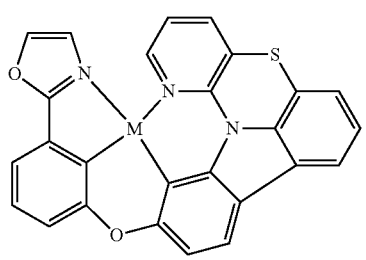
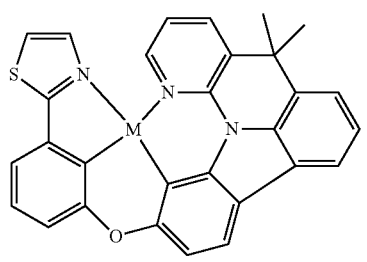
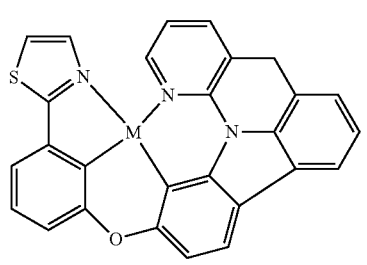
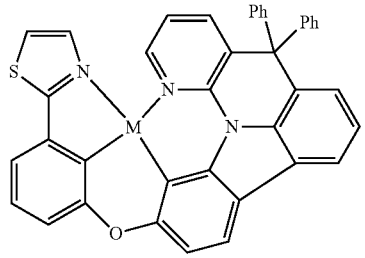
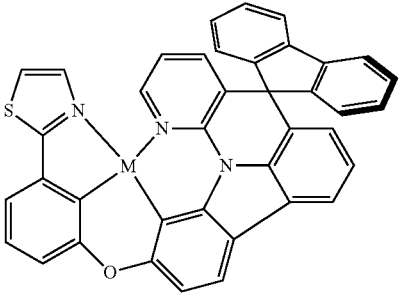

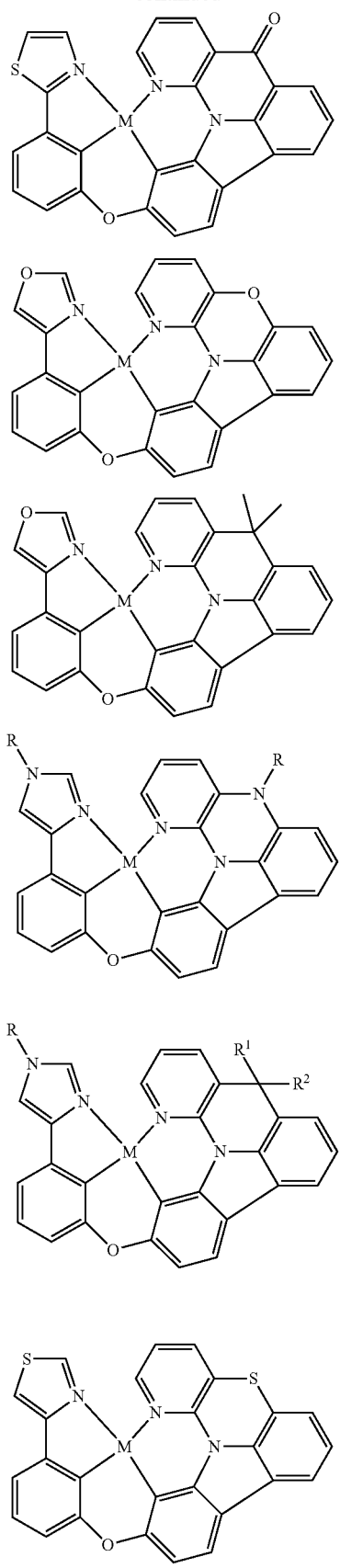
Structure 4 (M = Pt or Pd)
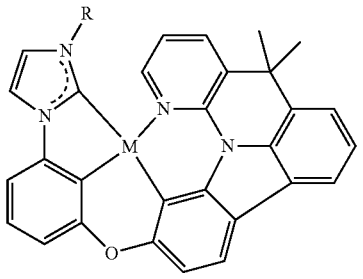
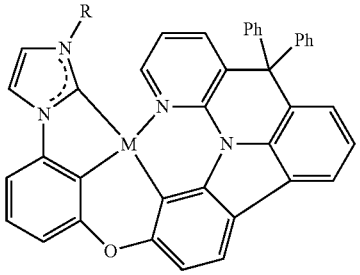
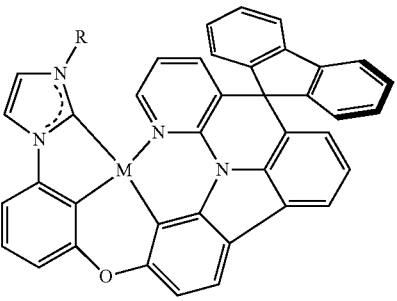
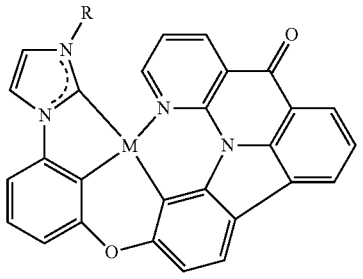
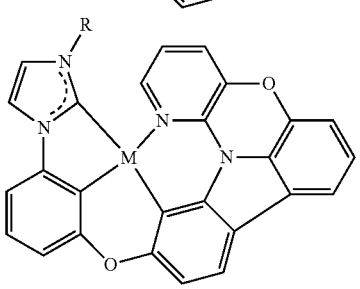

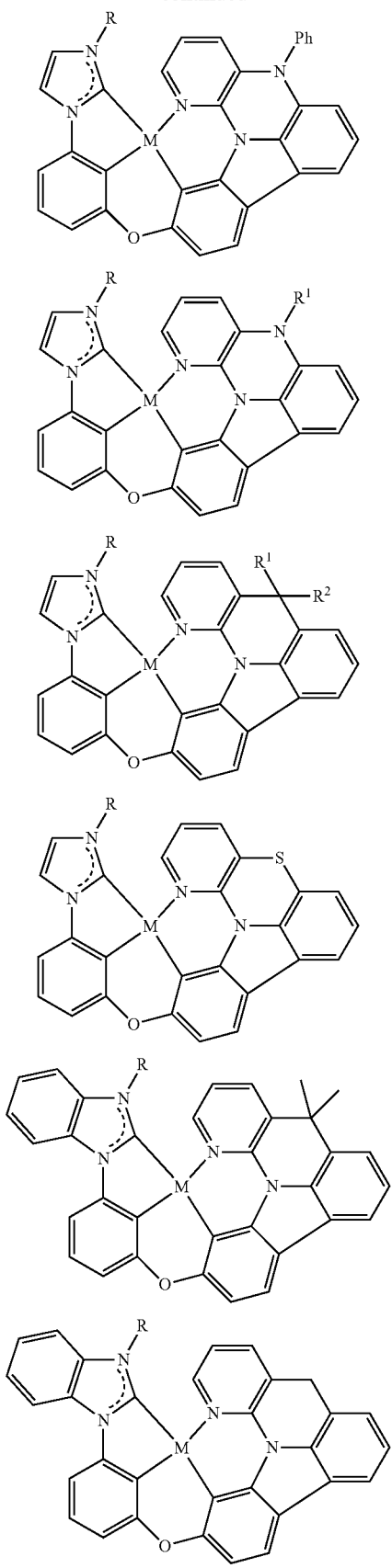
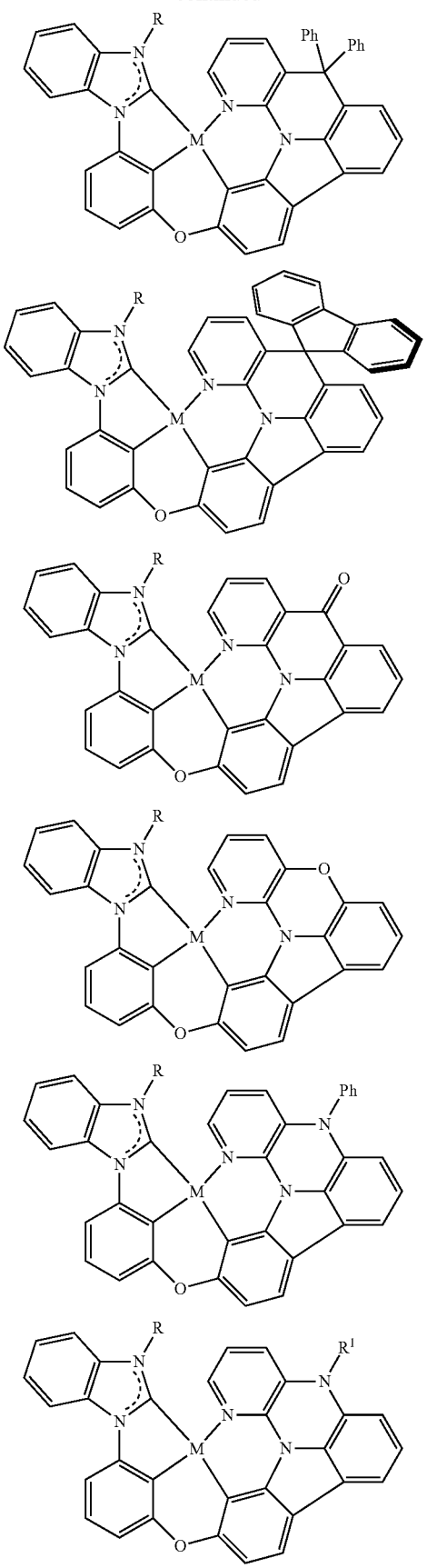

153
-continued
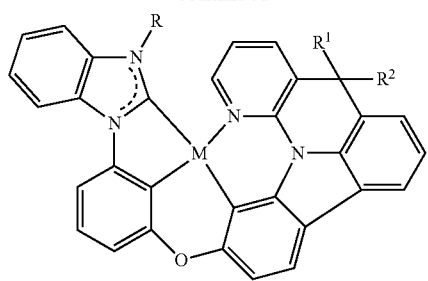
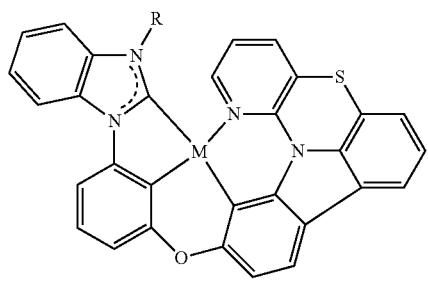
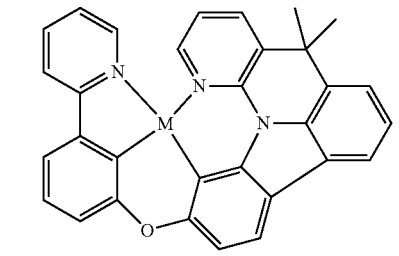
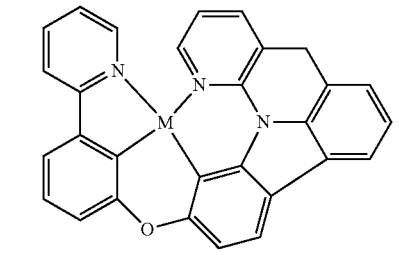
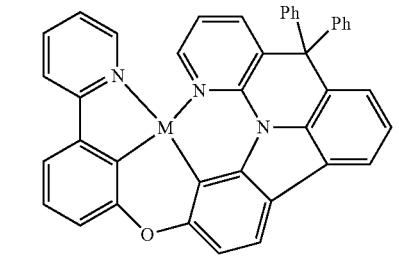
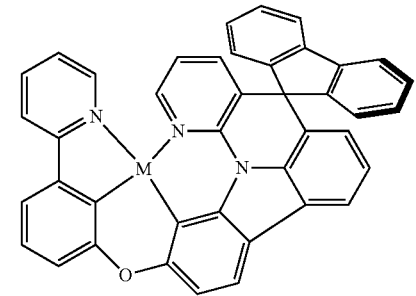
154
-continued
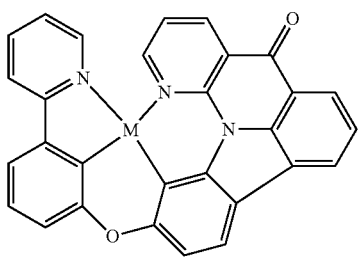
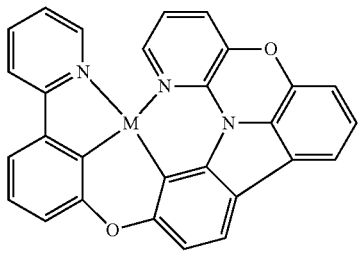
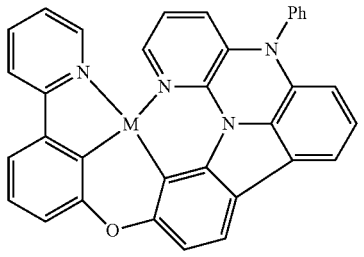
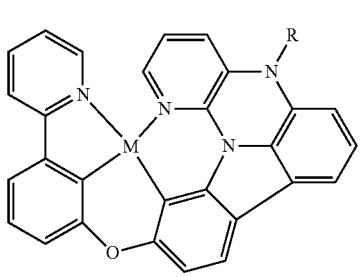
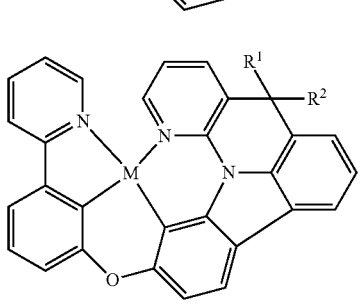
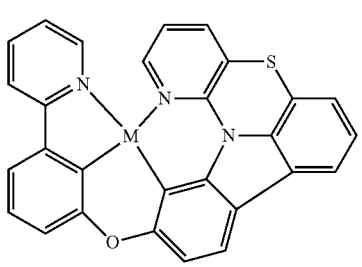

155
-continued
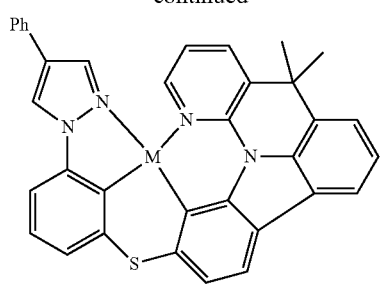
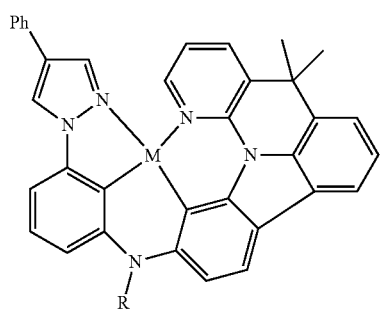
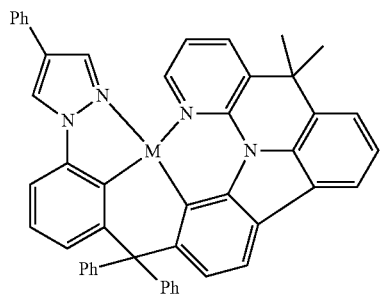
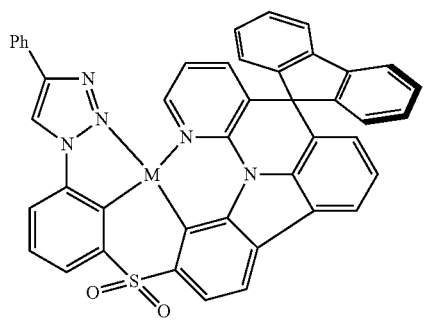
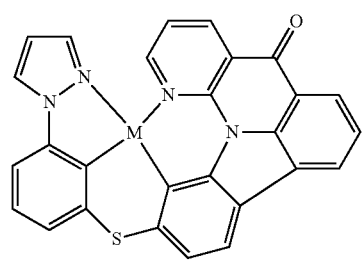
156
-continued
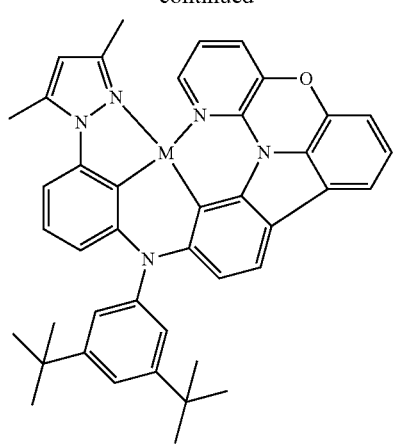
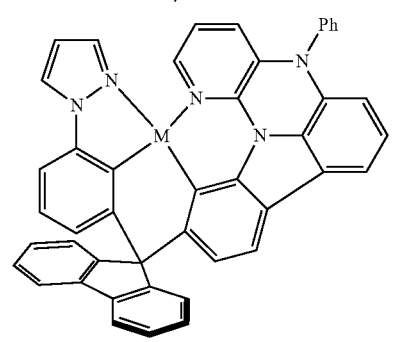
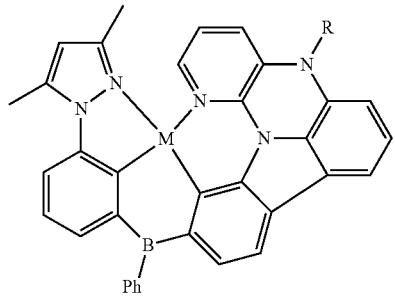
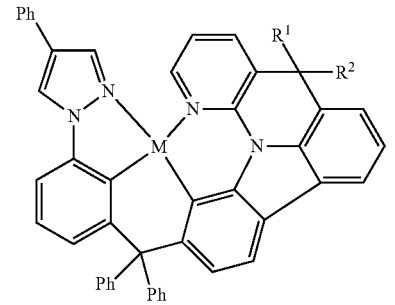
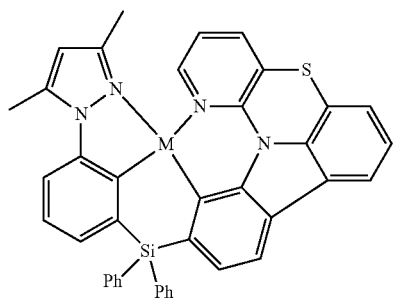

Structure 5 (M = Pt or Pd)
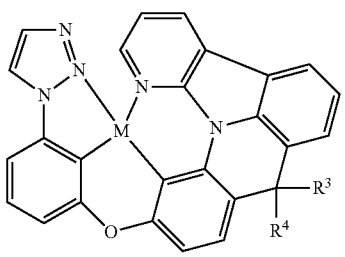
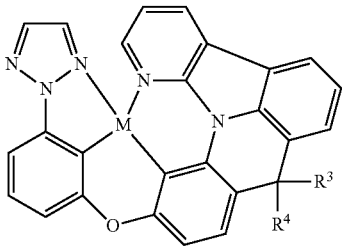
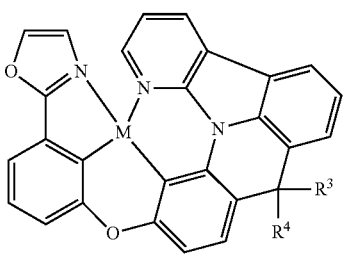
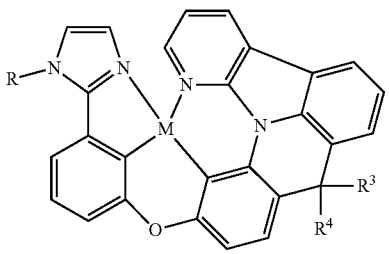
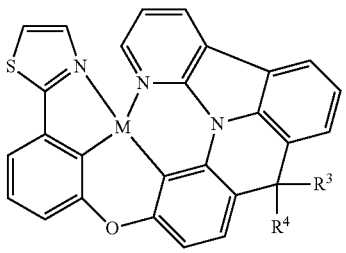
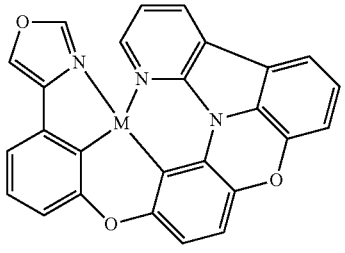
-continued
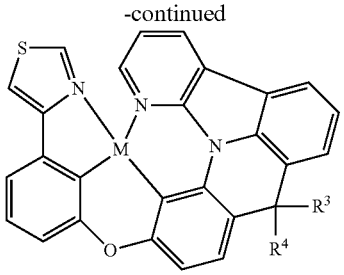
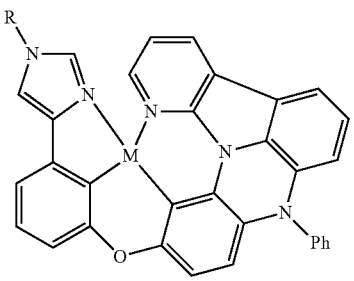
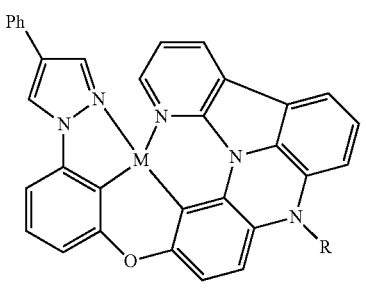
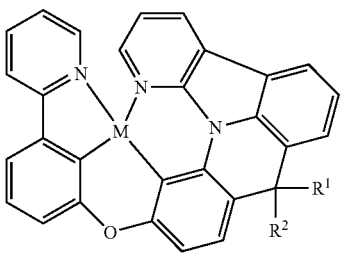
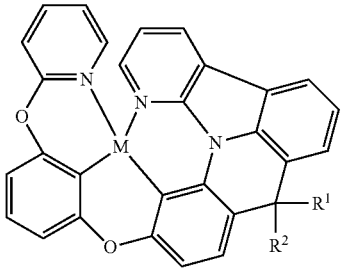
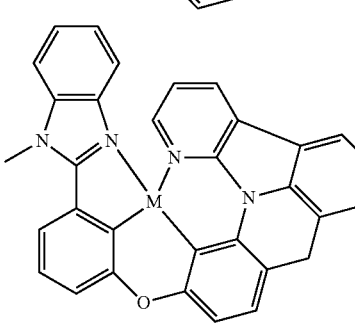

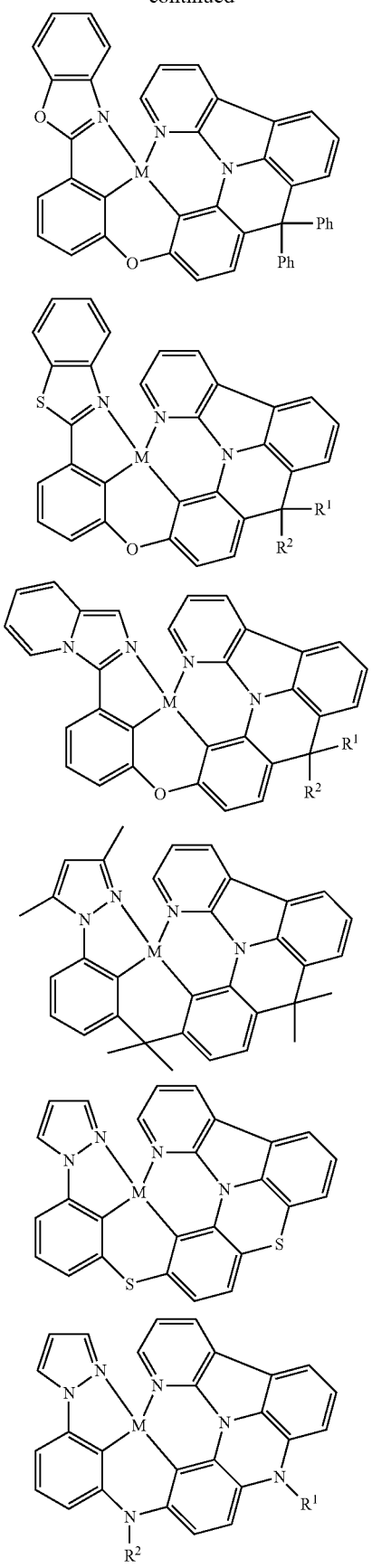
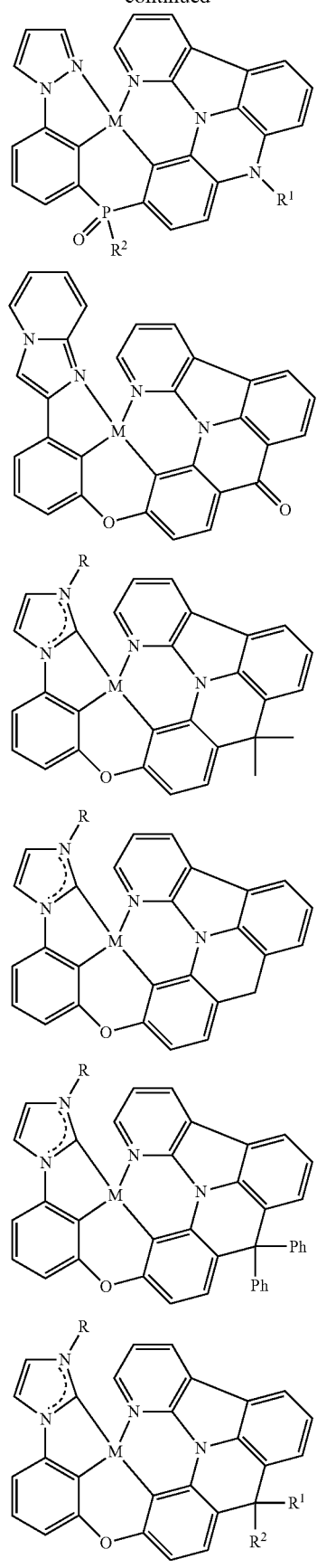

161
-continued
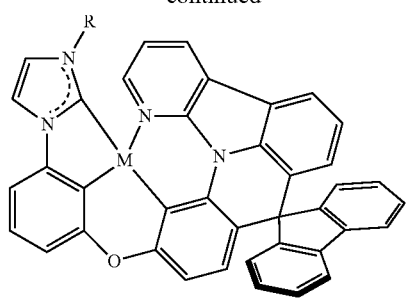
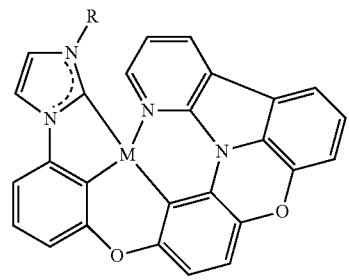
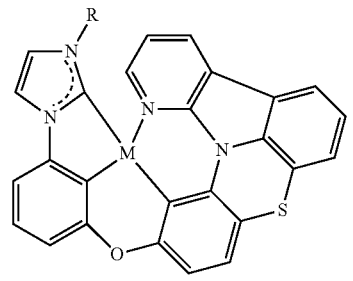
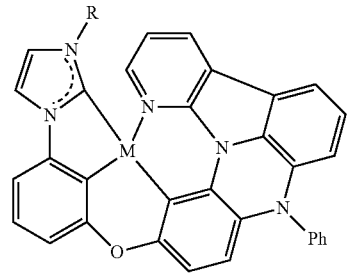
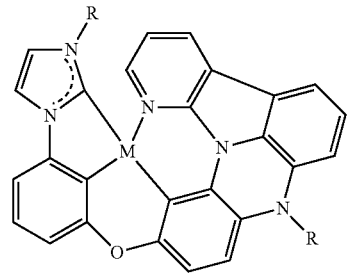
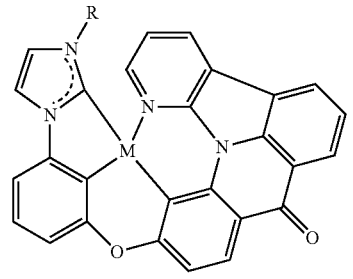
162
-continued
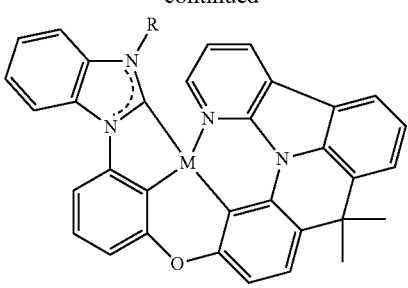
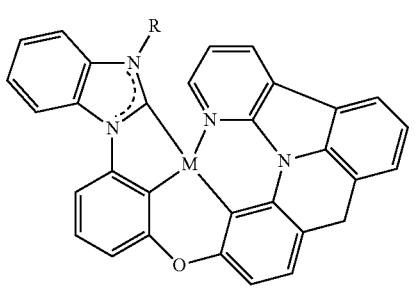
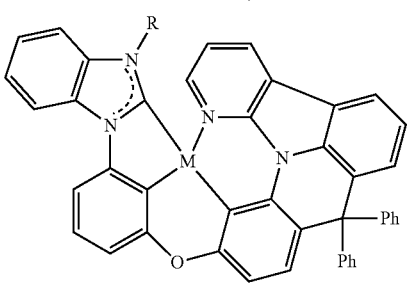
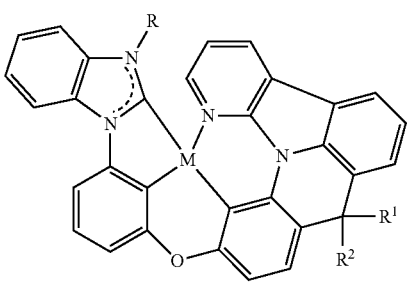
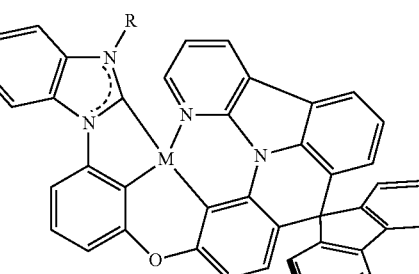
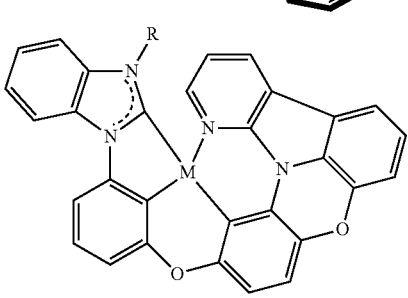

163
-continued
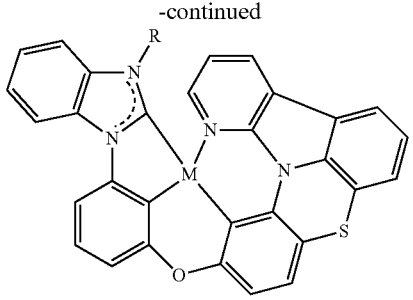
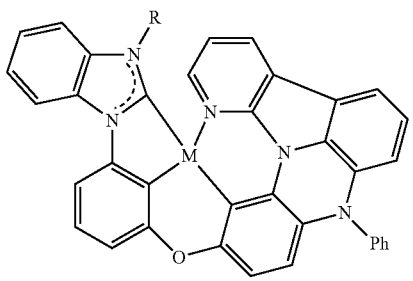
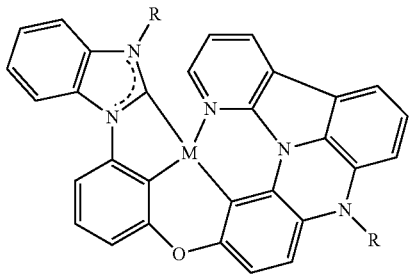
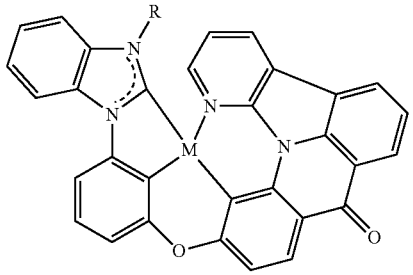
Structure 6 (M = Pt or Pd)
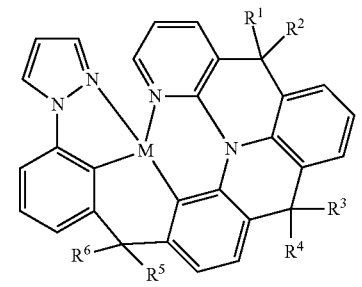
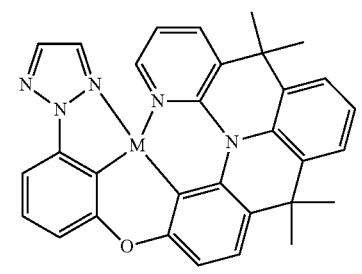
164
-continued
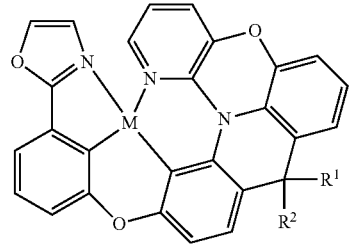
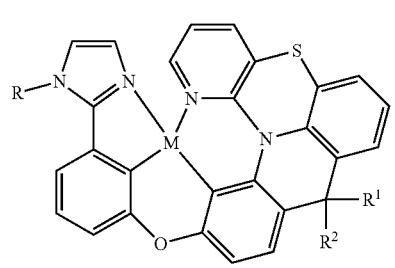
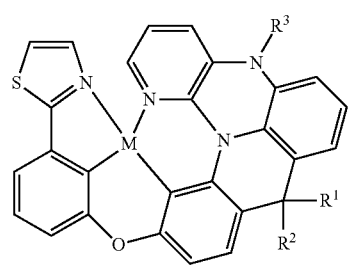
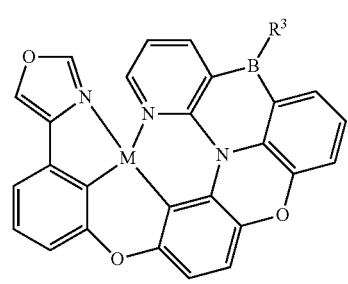
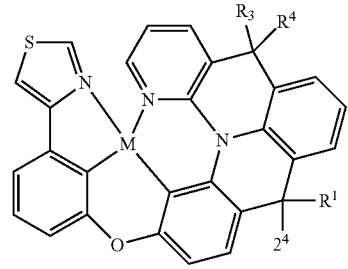
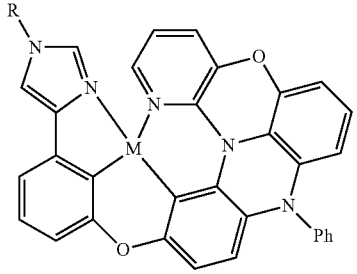

165
-continued
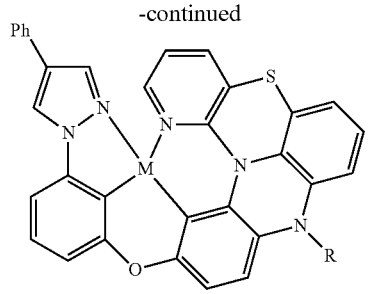
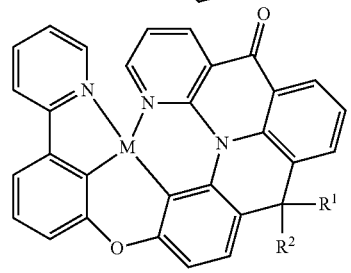
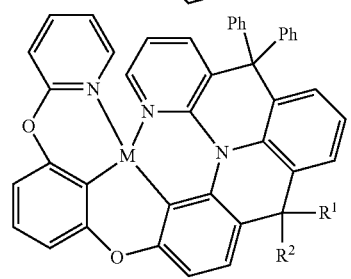
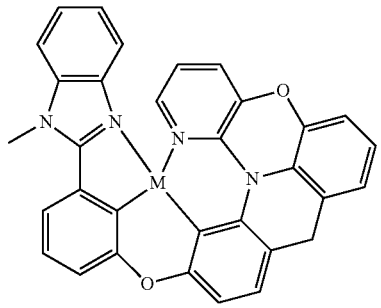
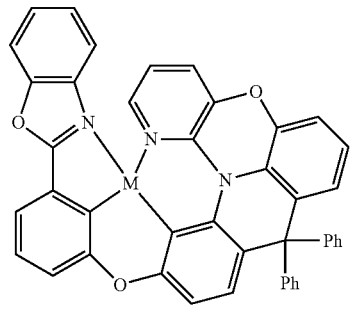
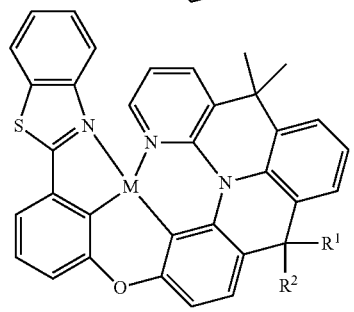
166
-continued
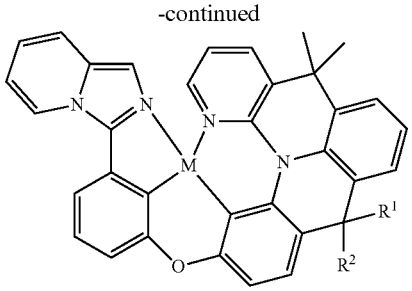
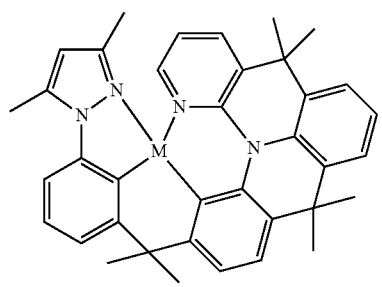
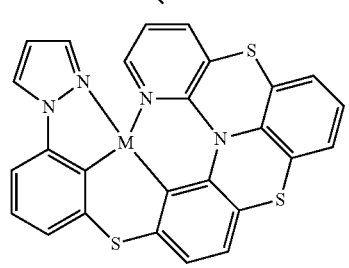
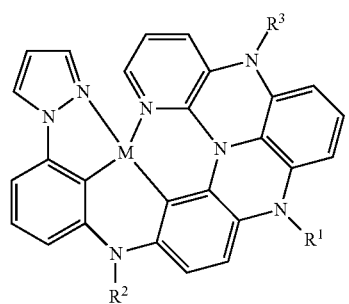
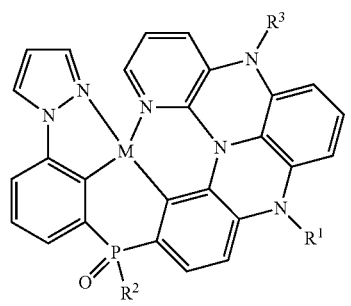
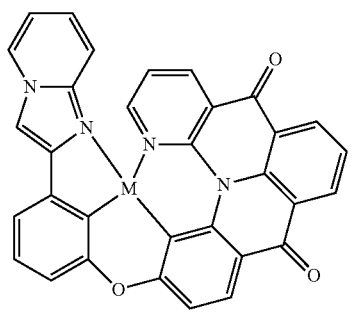

167
-continued
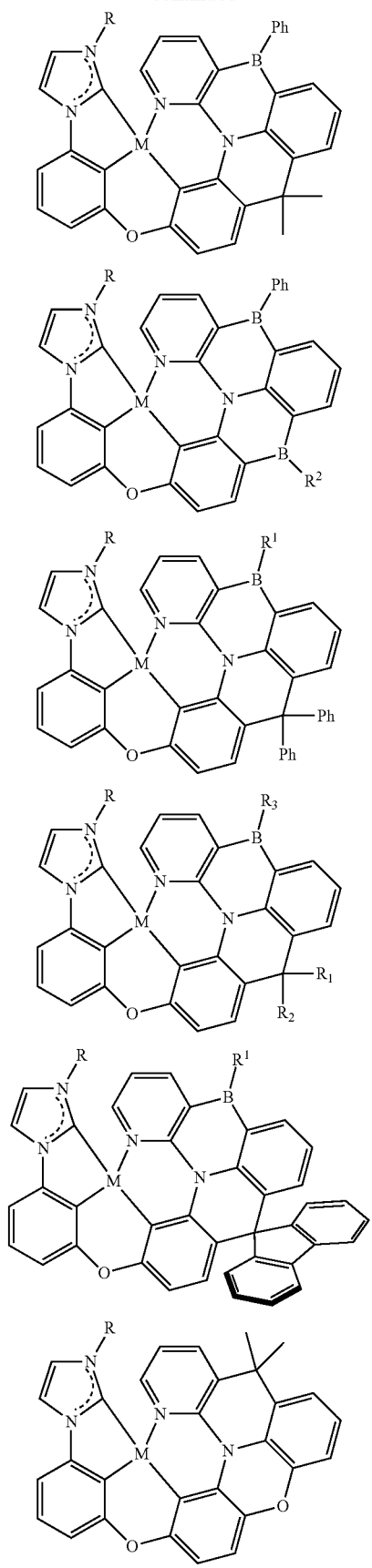
168
-continued
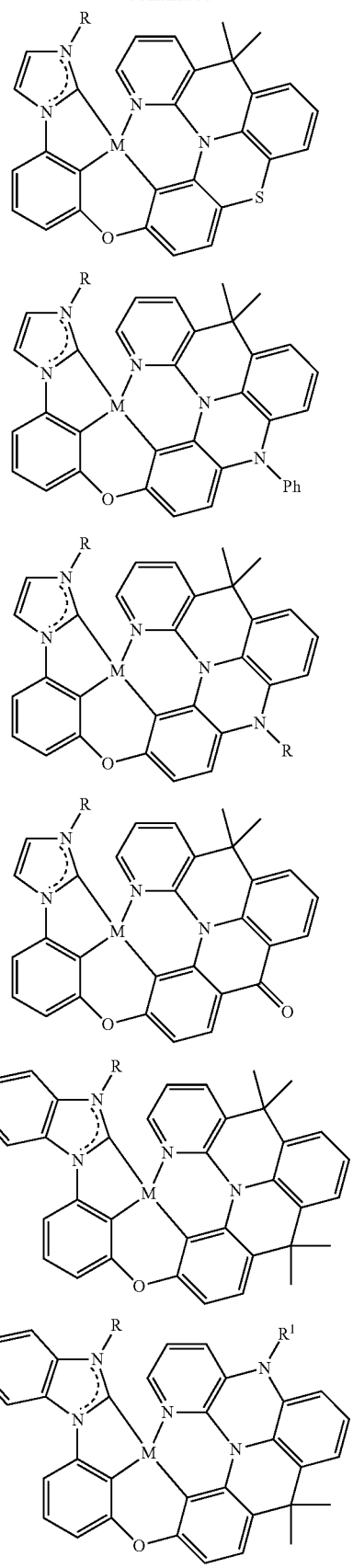

169
-continued
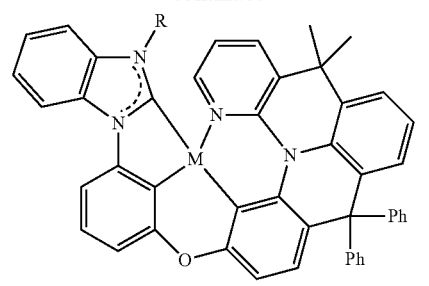
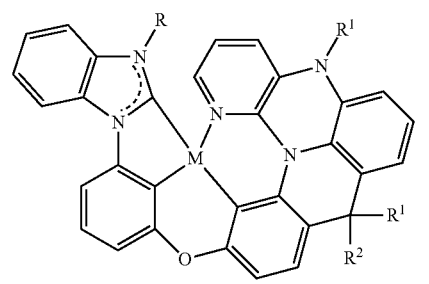
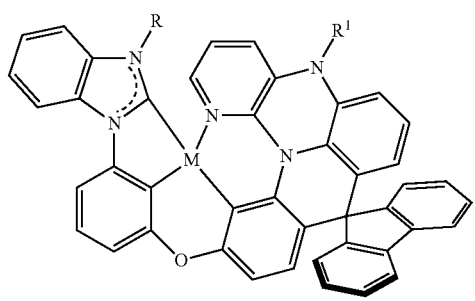
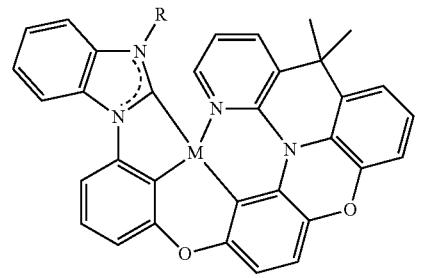
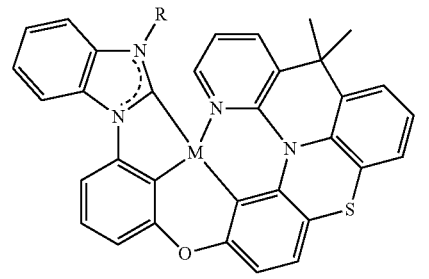
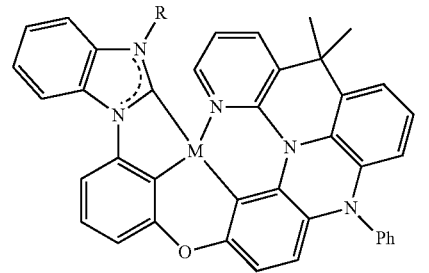
170
-continued
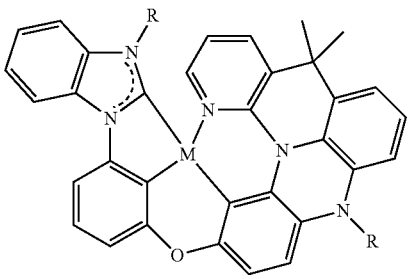
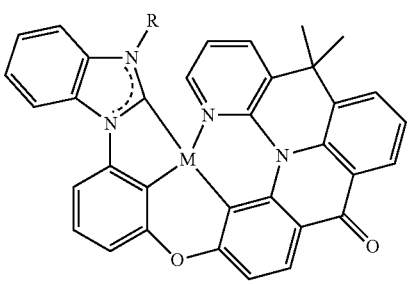
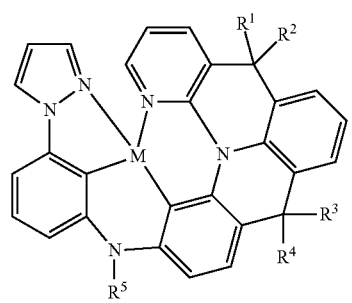
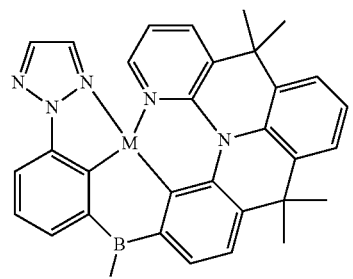
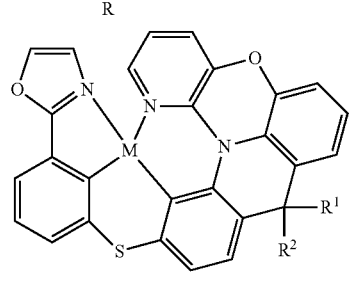
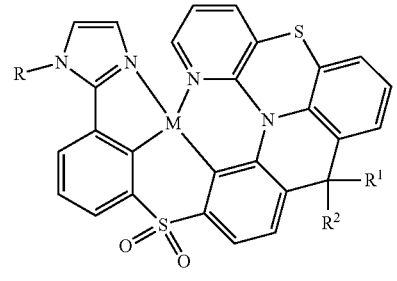

171
-continued
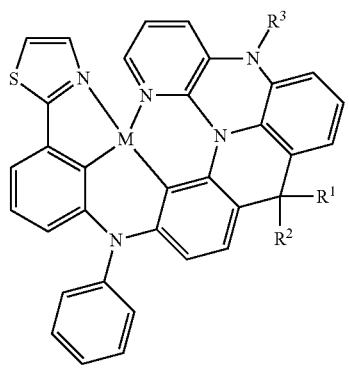
Structure 7 (M = Pt or Pd)
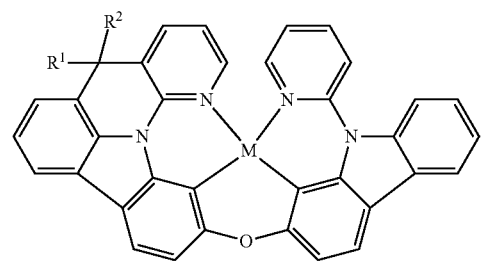
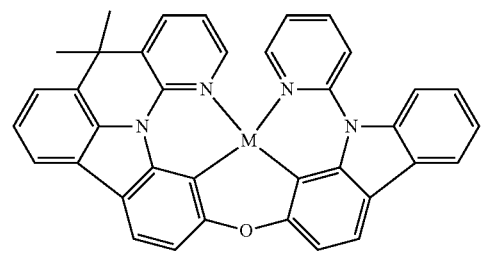
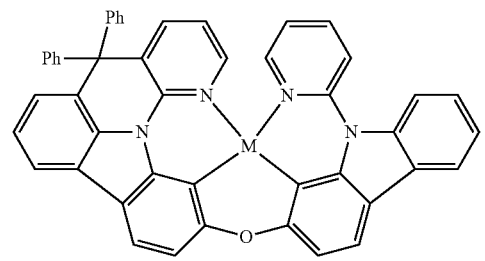
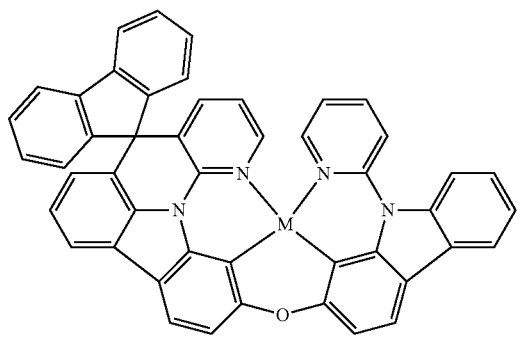
172
-continued

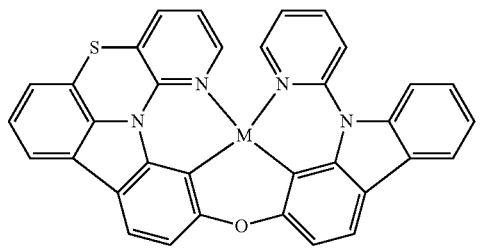
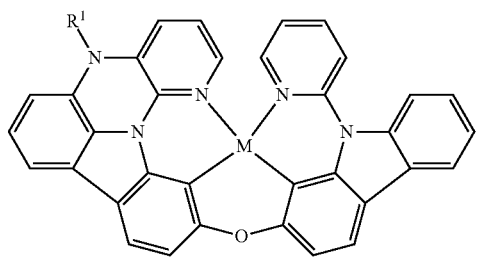
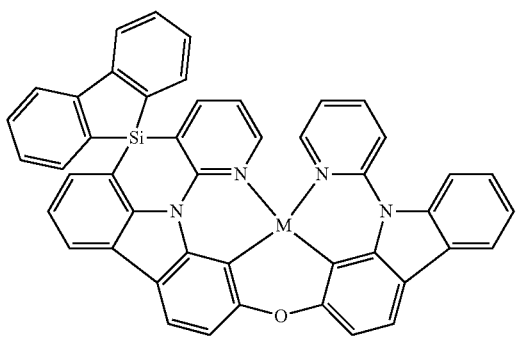
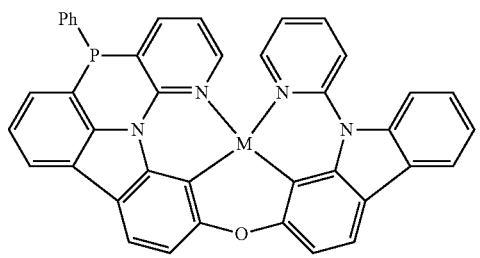
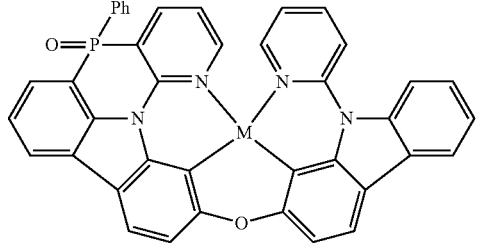

173
-continued
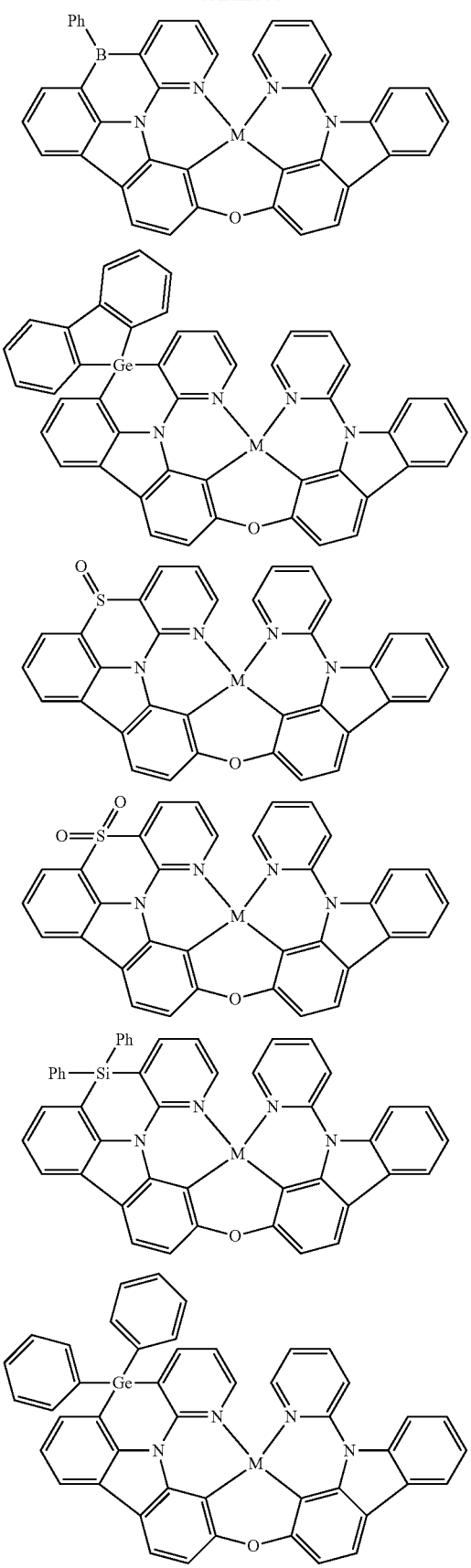
174
-continued
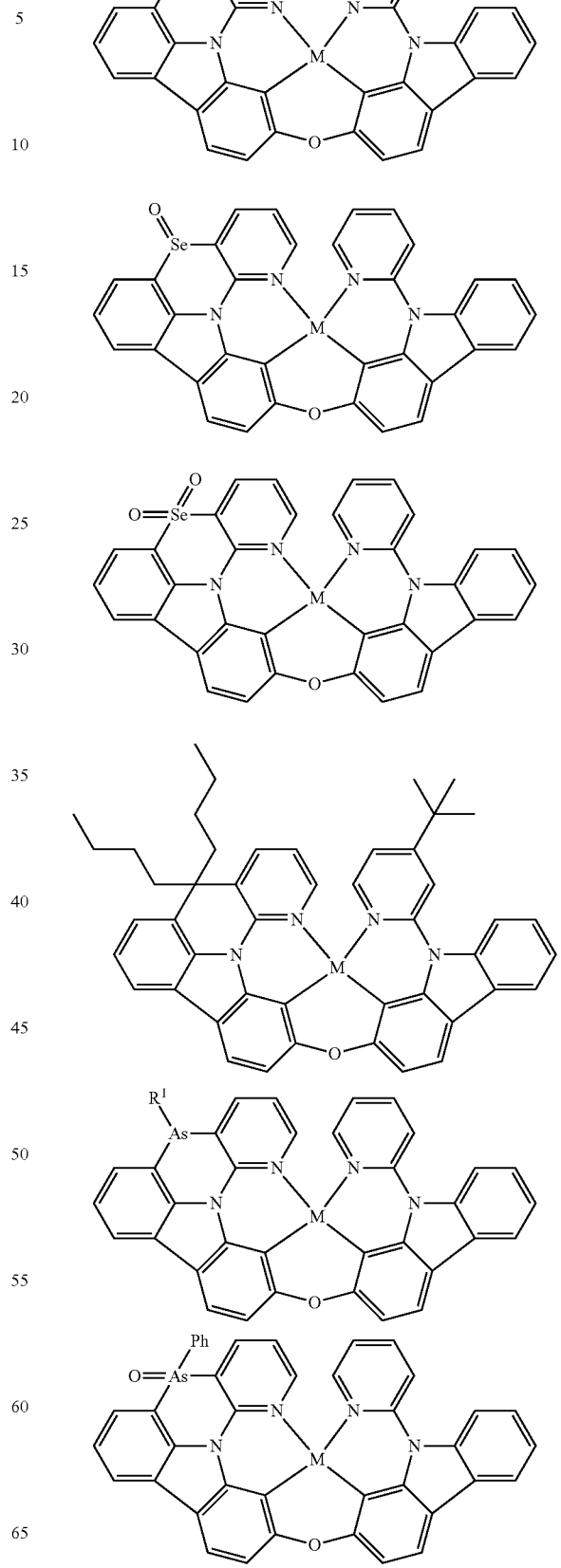

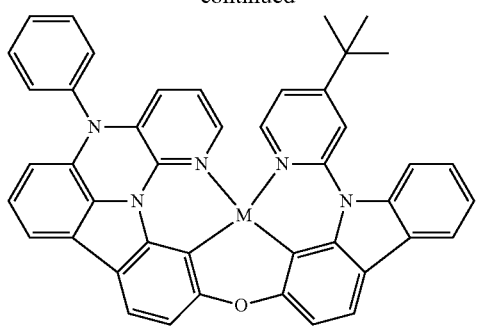
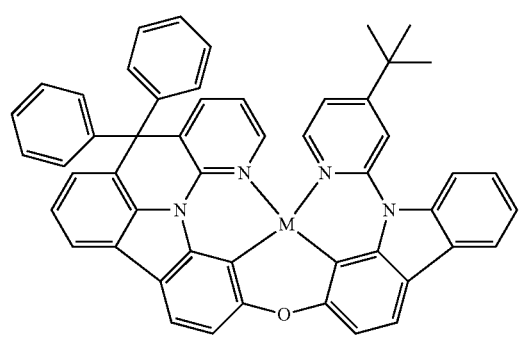
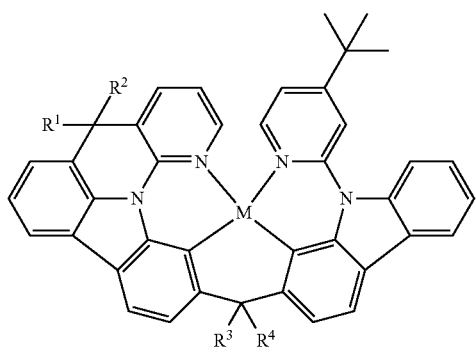
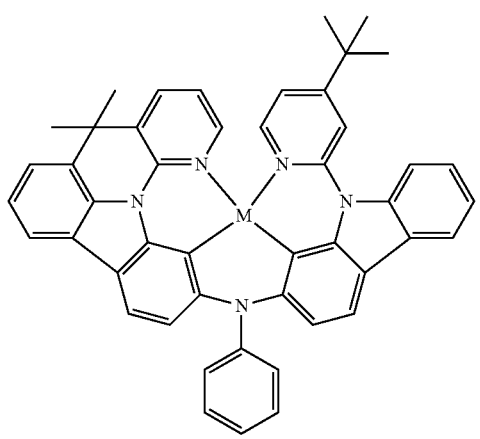
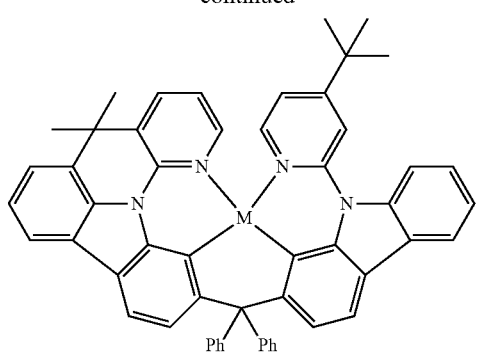
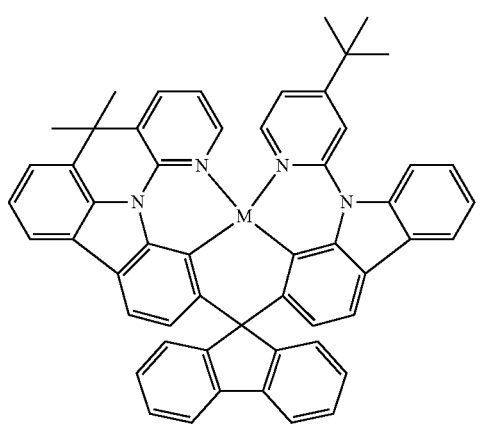
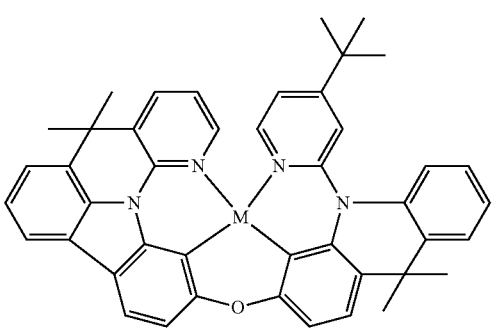
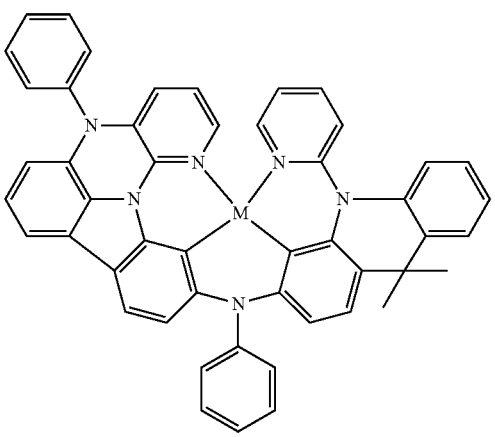

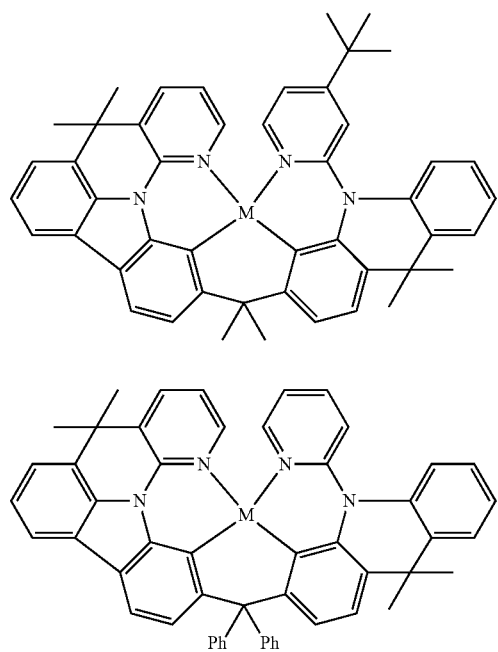
Structure 8 (M = Pt or Pd)
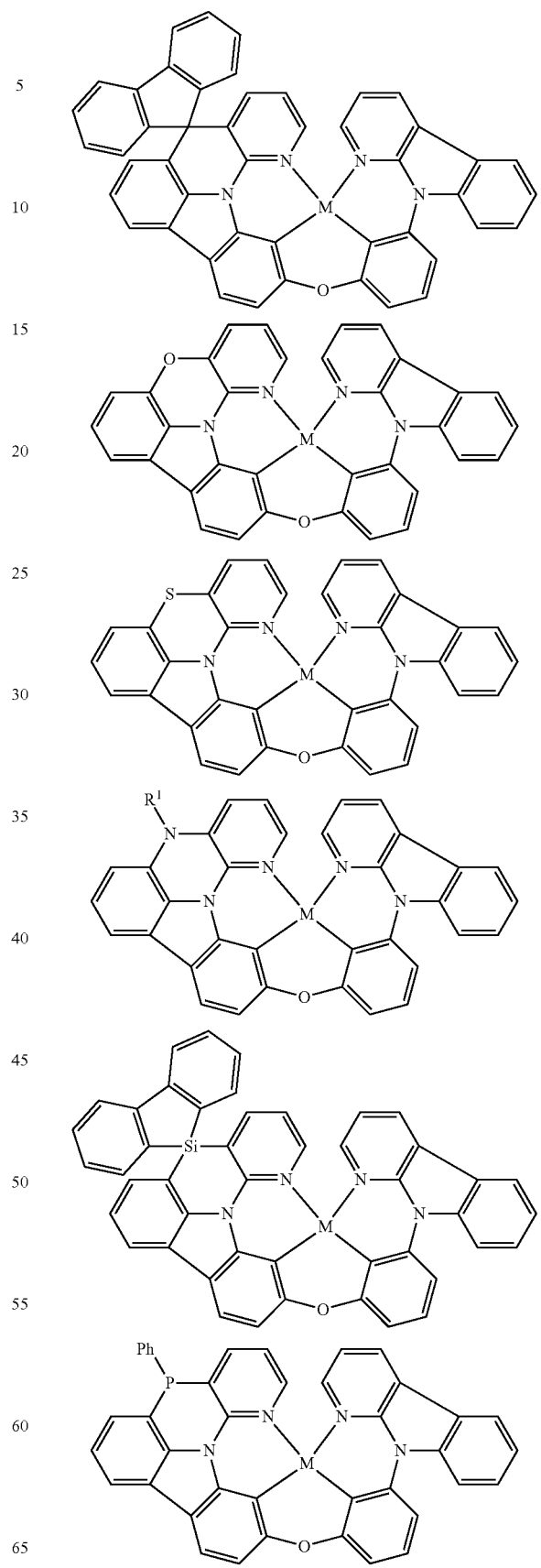

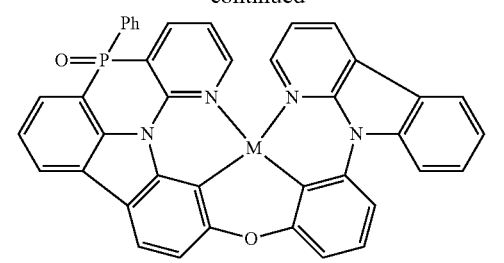
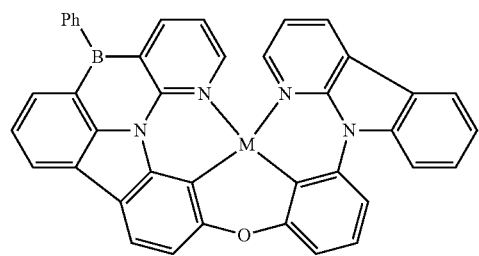
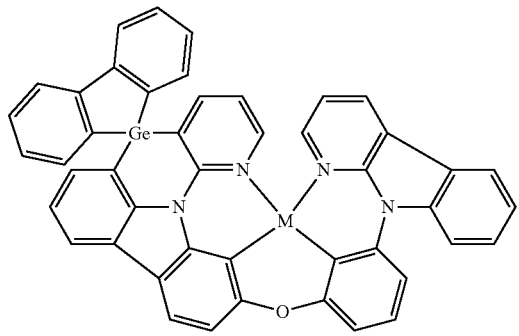
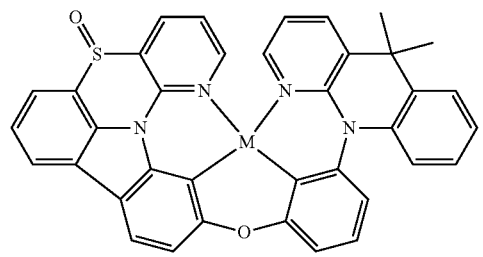
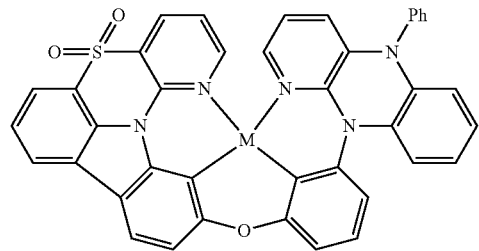
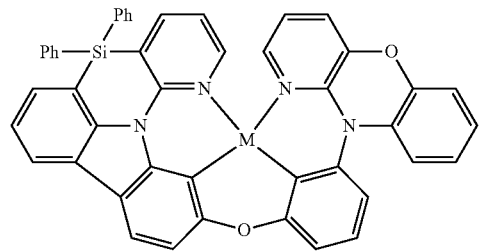
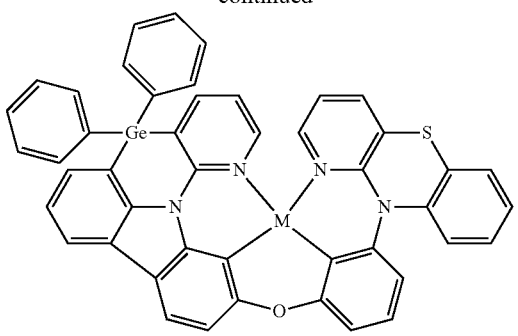
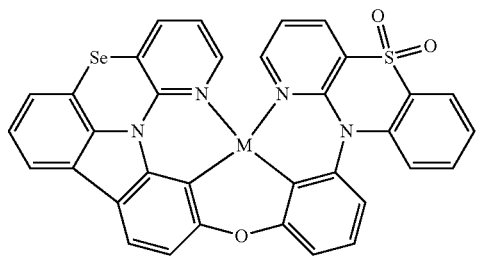
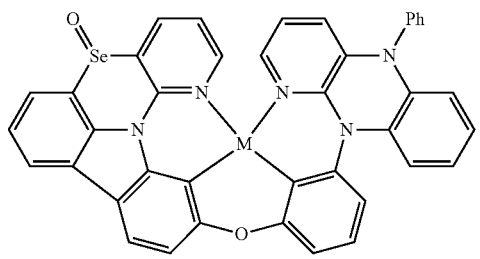
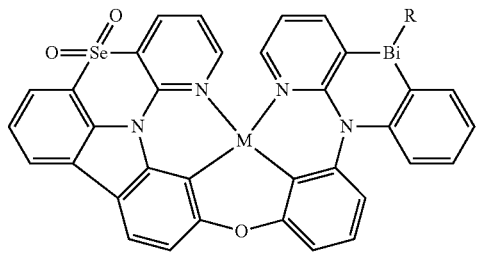
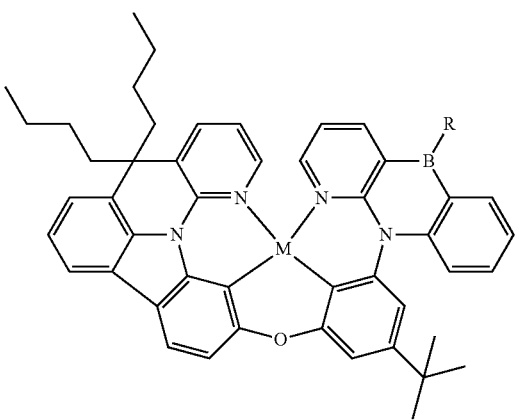

181
-continued
182
-continued
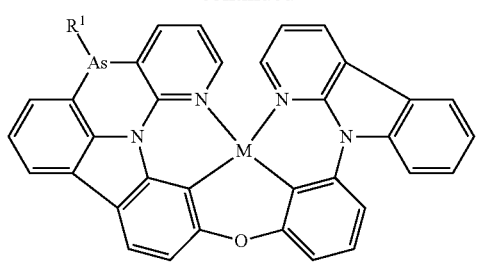
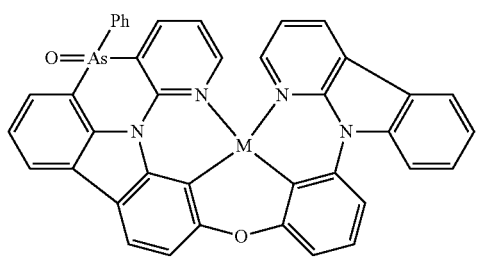
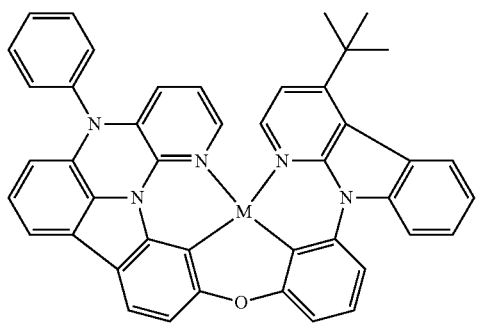
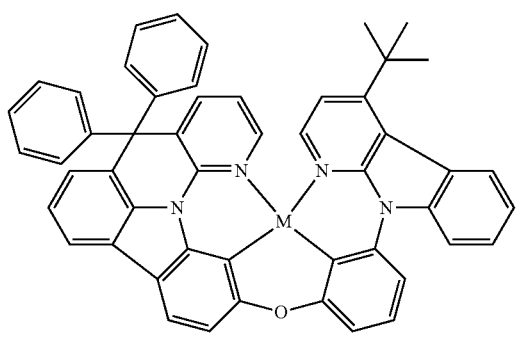
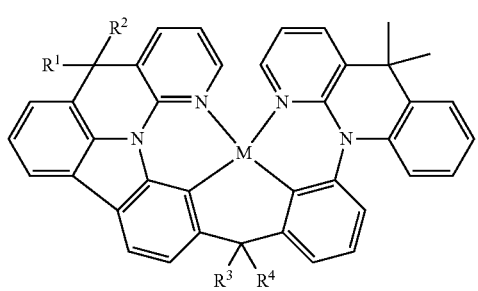
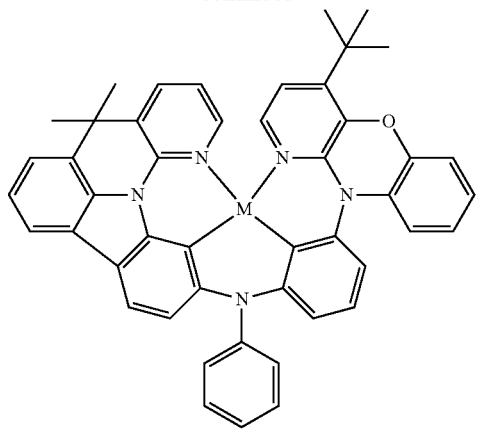
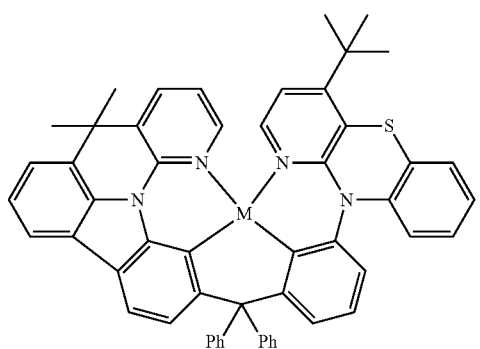

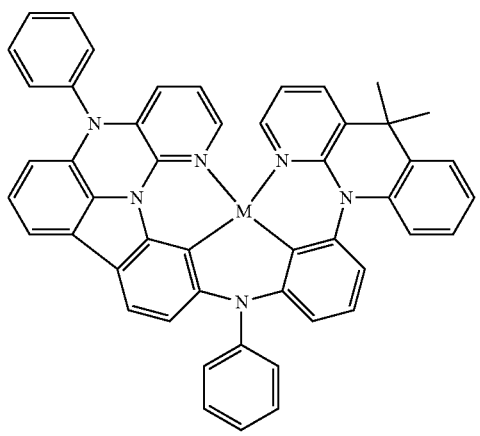
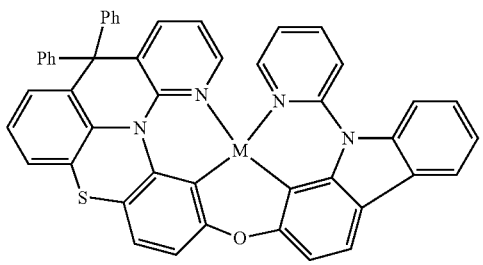
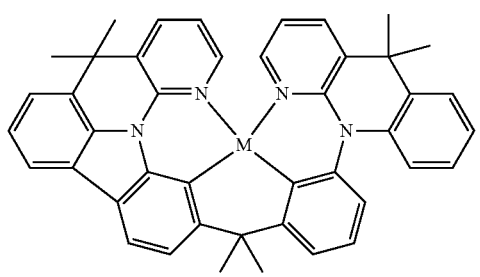
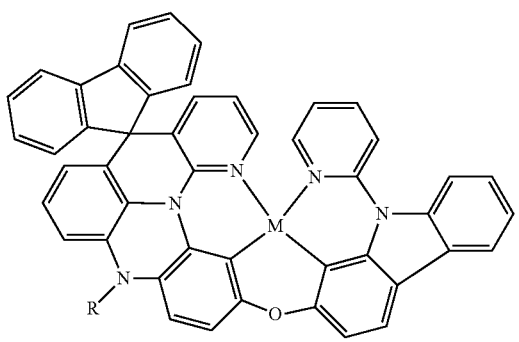
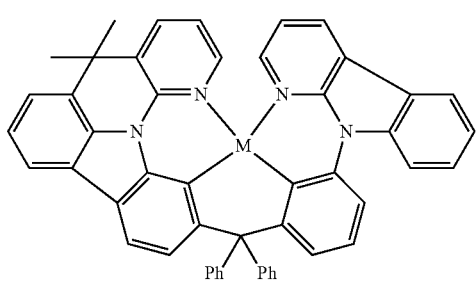
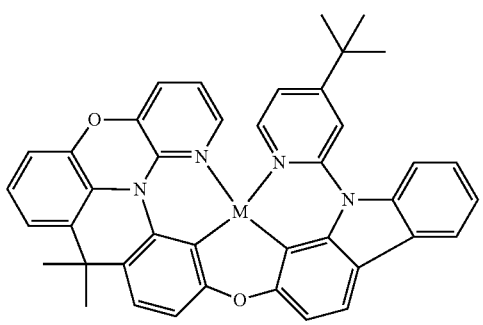
Structure 9 (M = Pt or Pd)
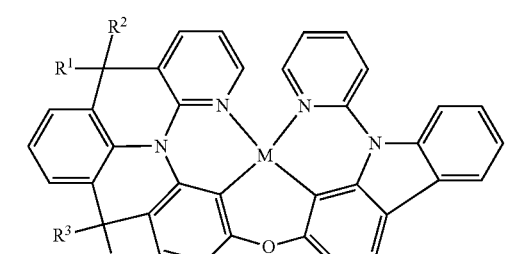
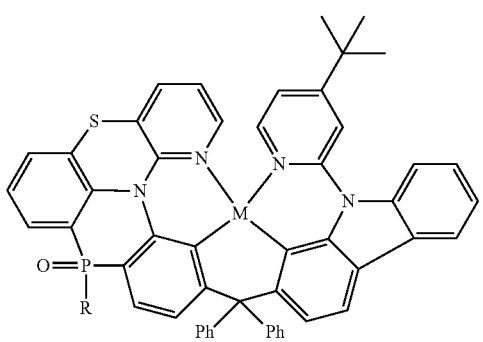
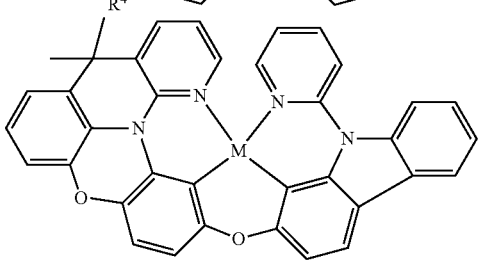
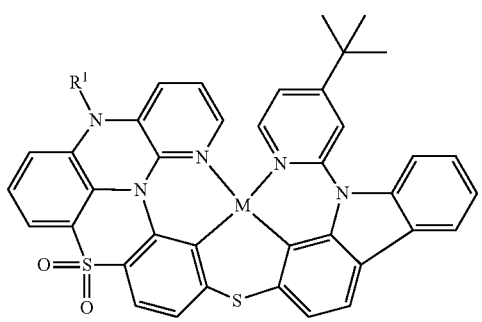

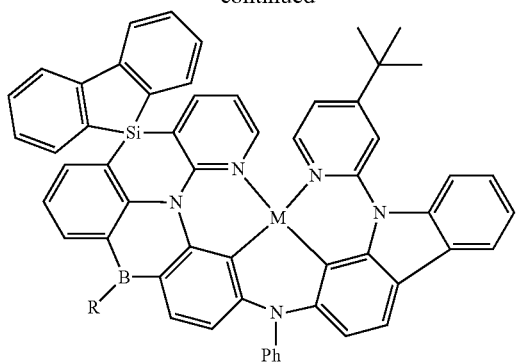
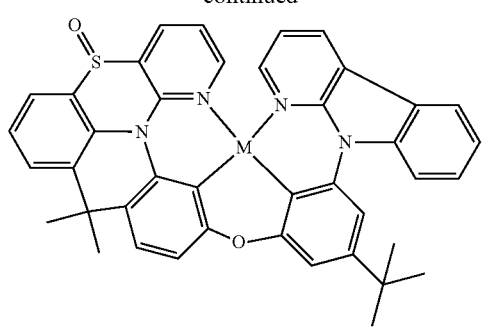
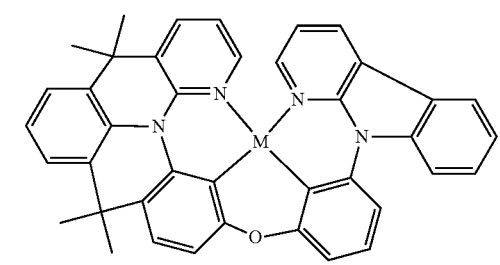
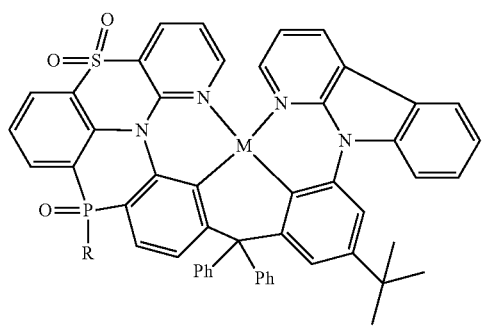
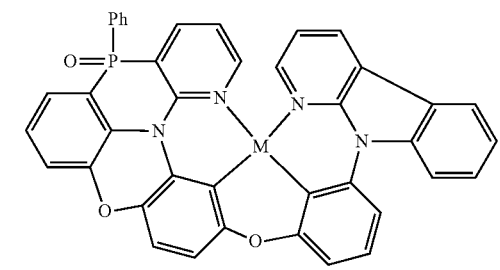
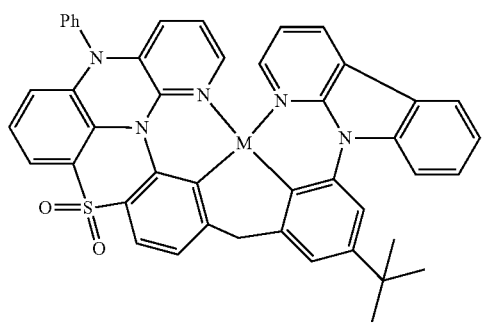
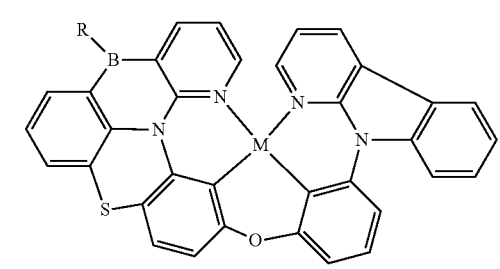
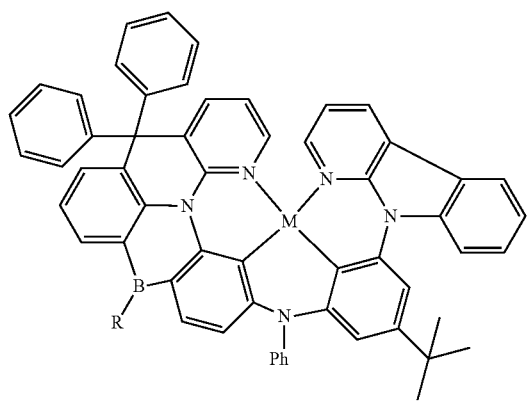
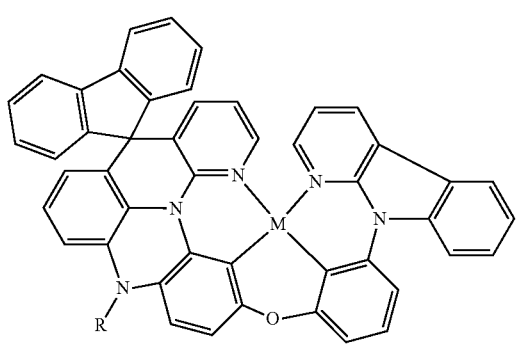
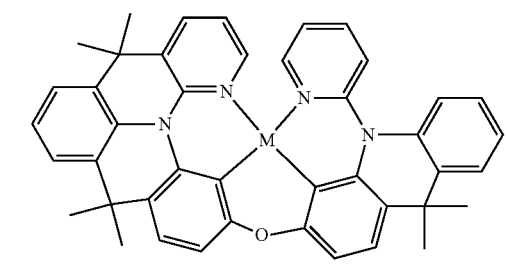

187
-continued
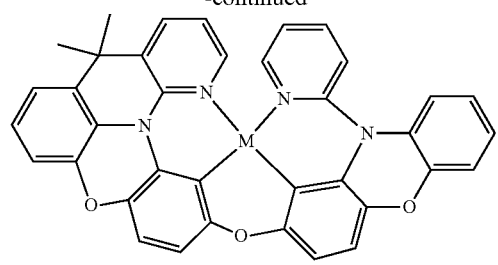
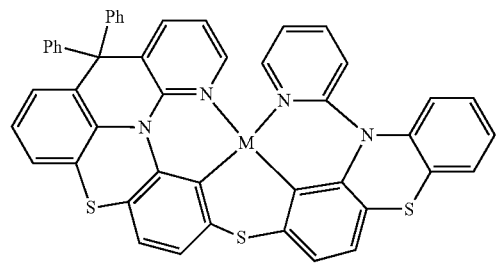
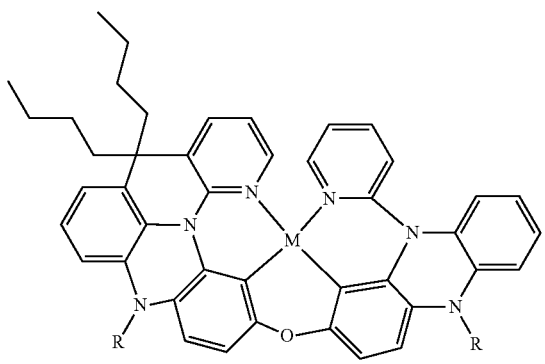
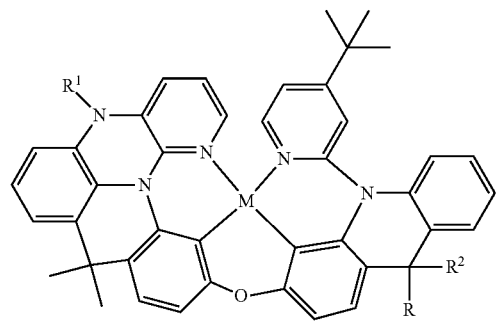
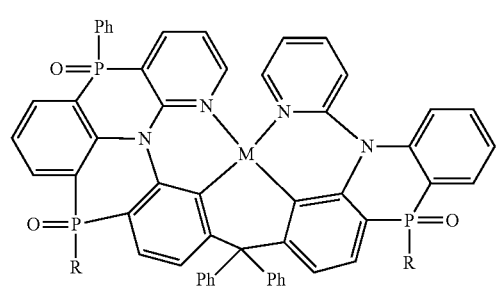
188
-continued
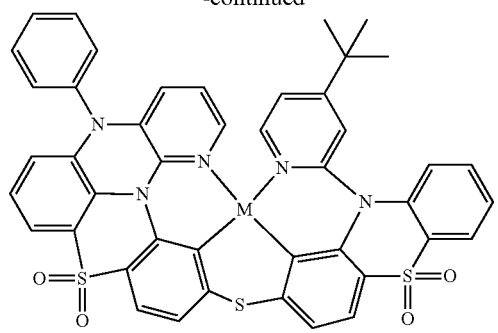
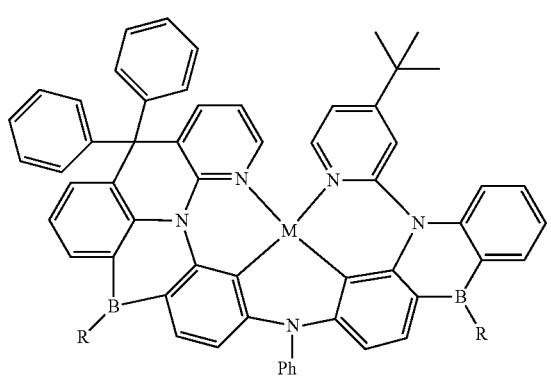
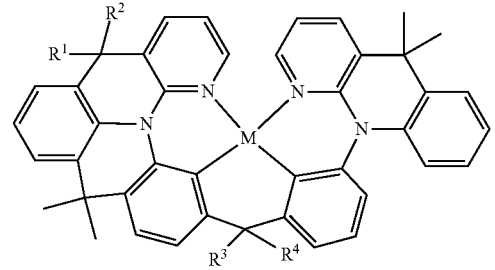
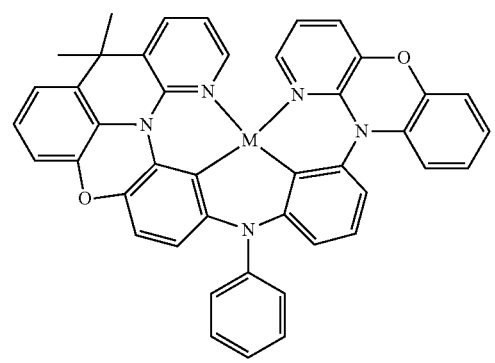
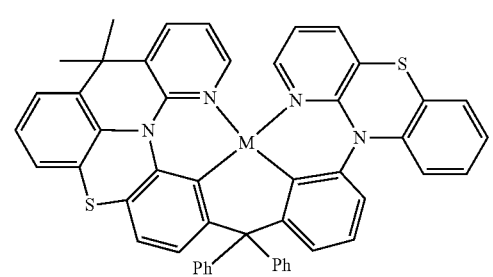

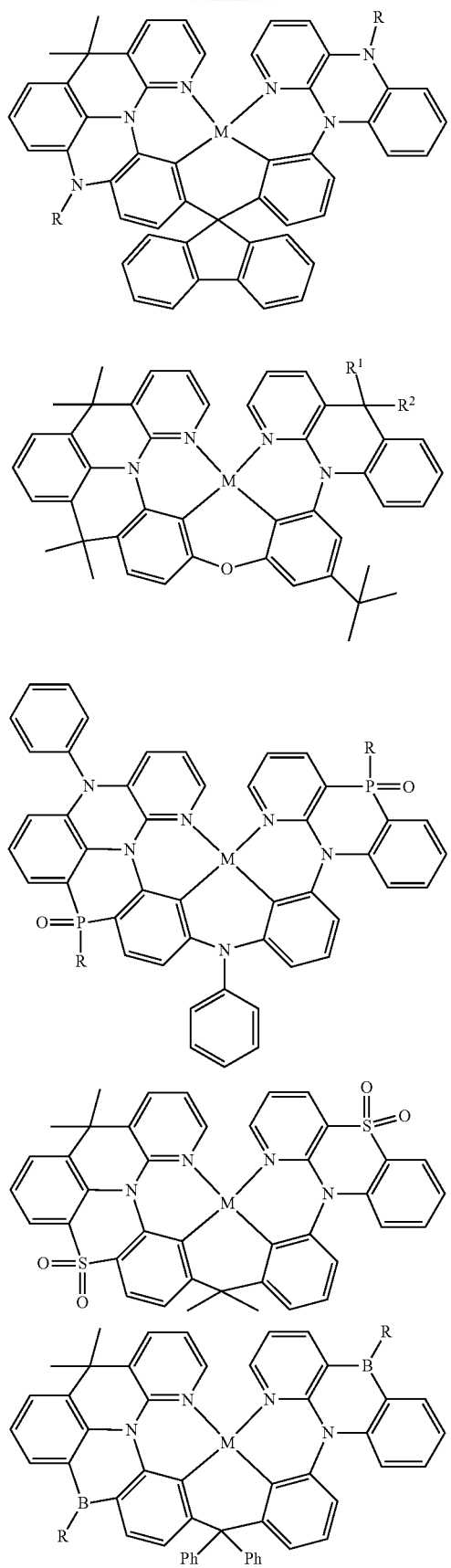
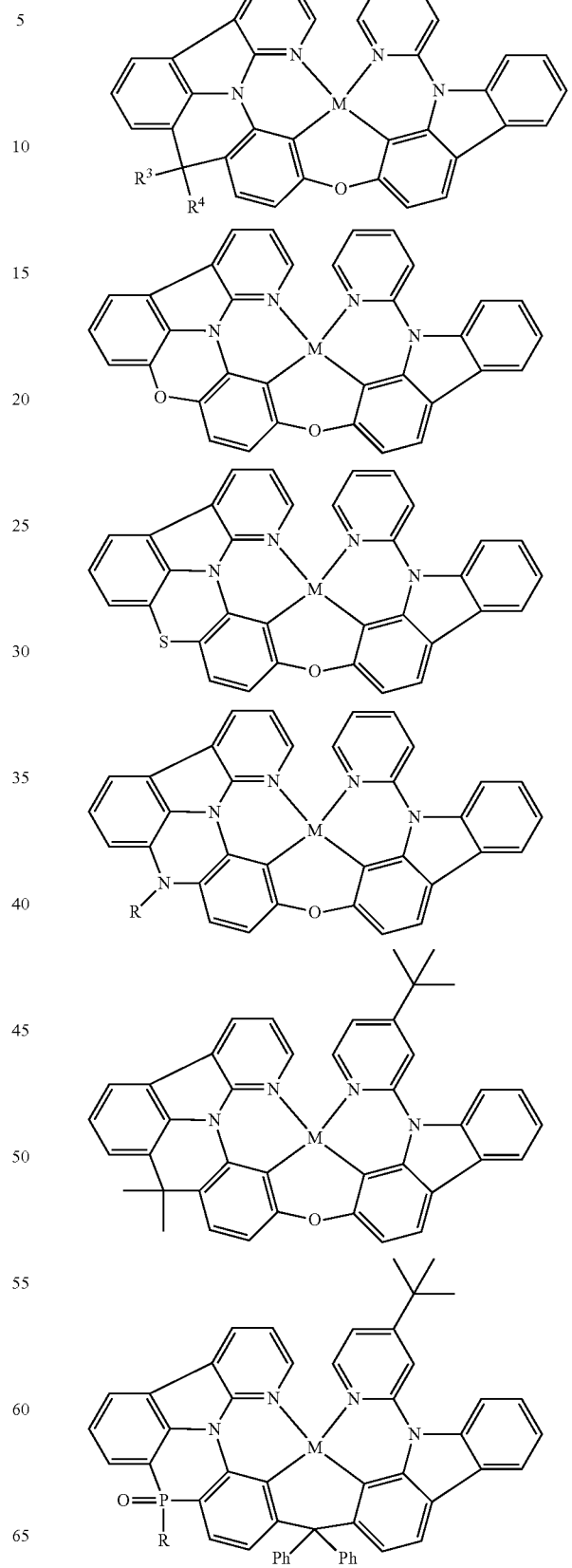
Structure 10 (M = Pt or Pd)

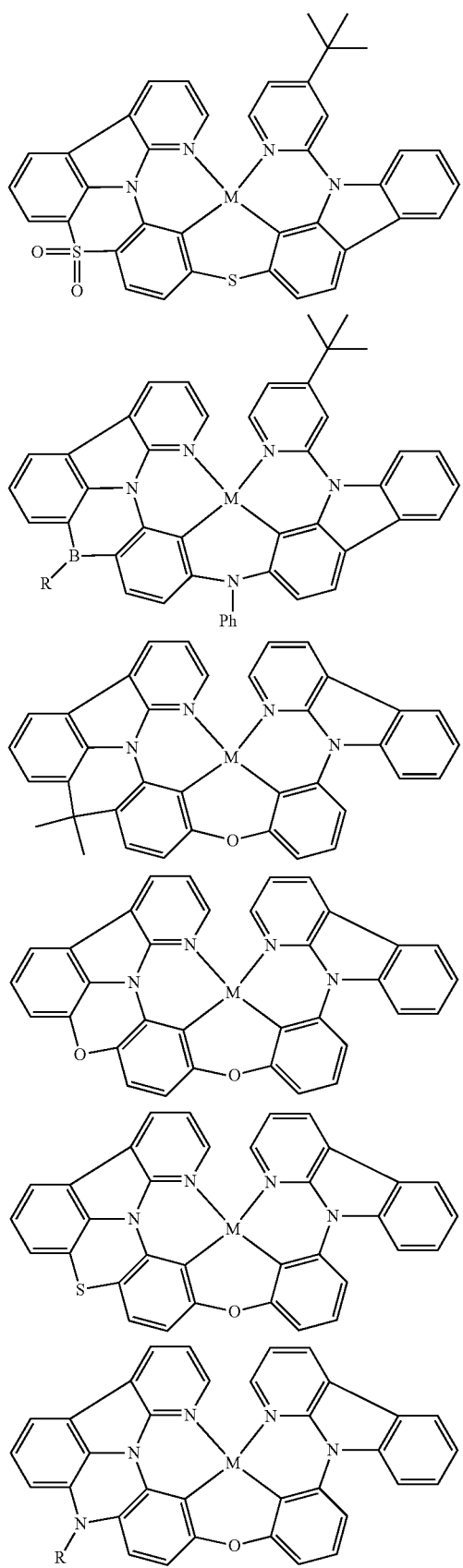
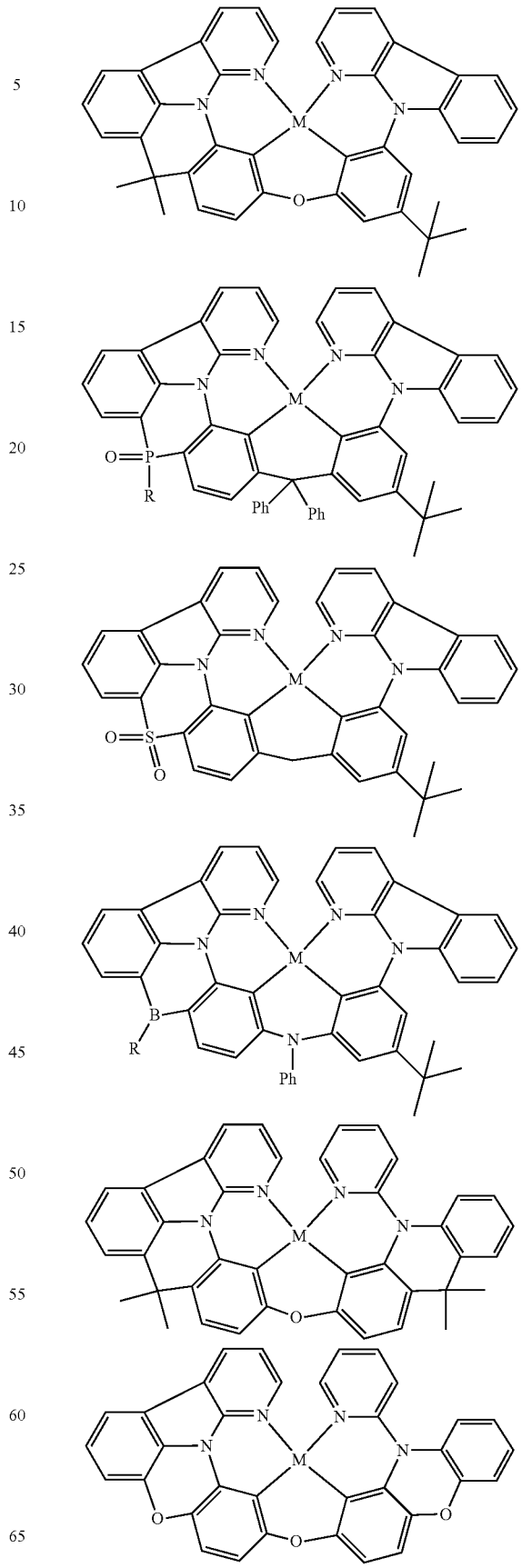

193
-continued
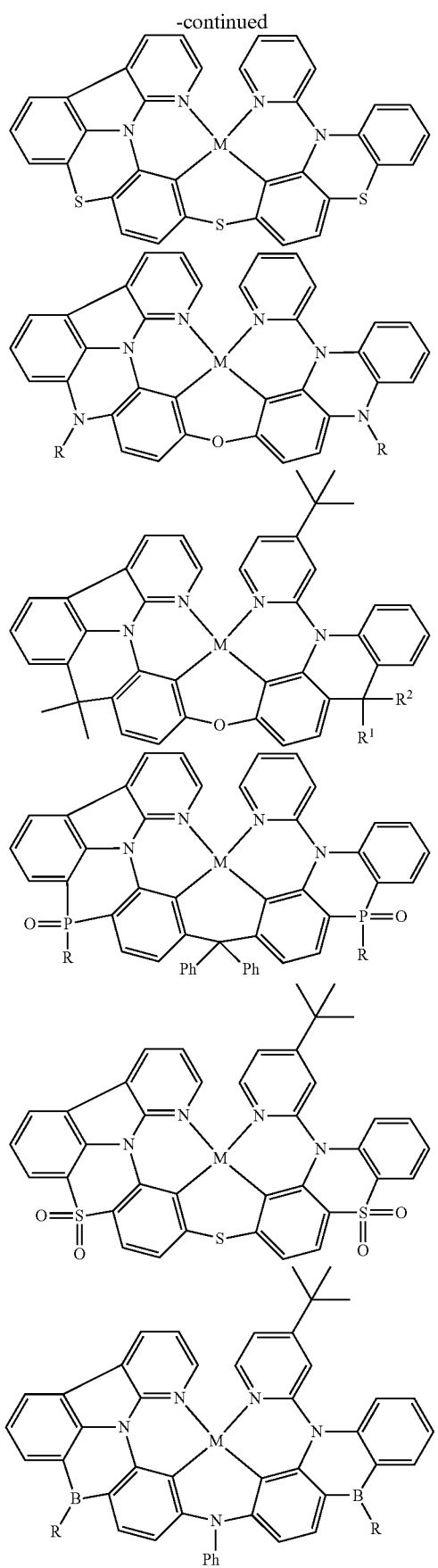
194
-continued
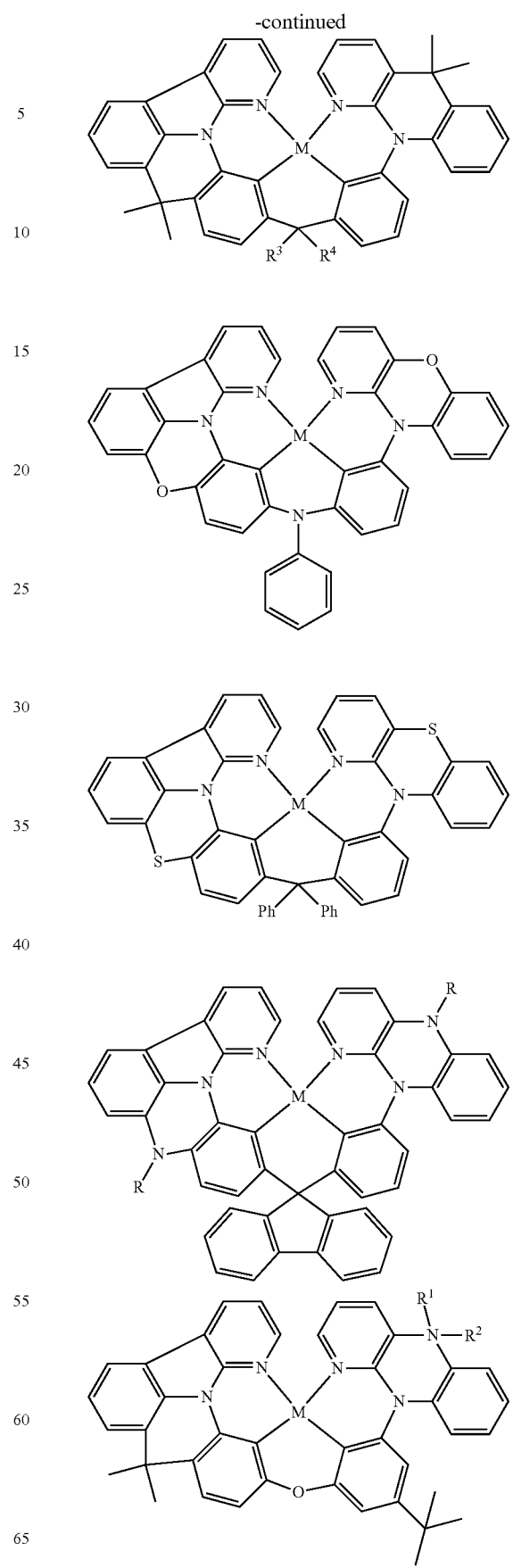

195
-continued
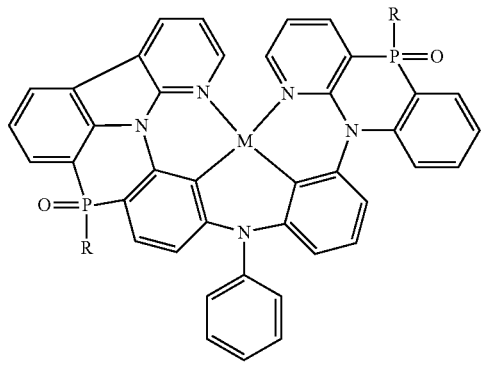
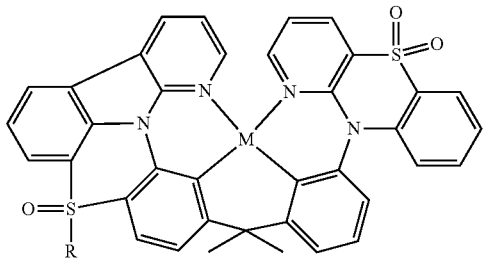
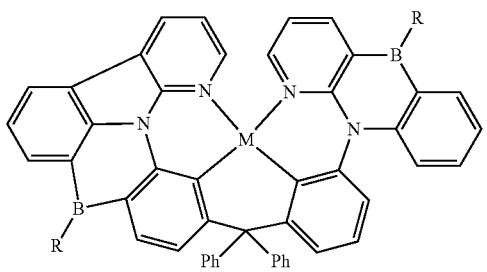
Structure 11 (M = Pt or Pd)
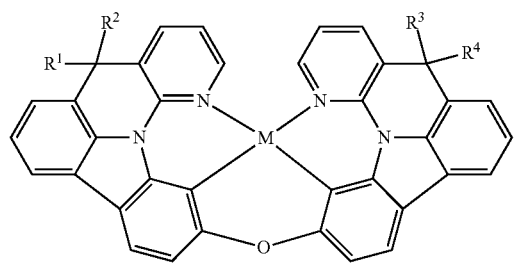
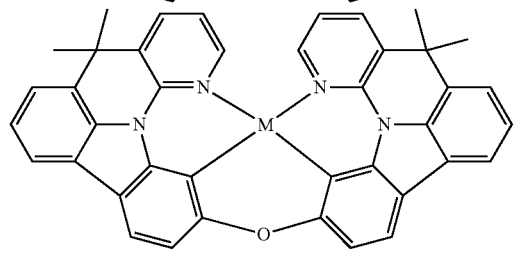
196
-continued
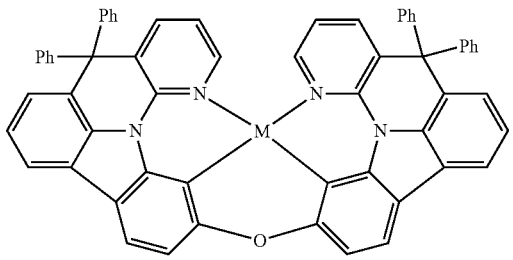
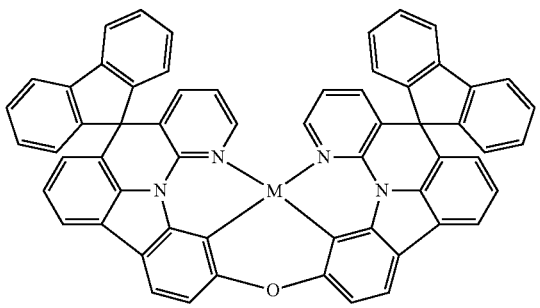
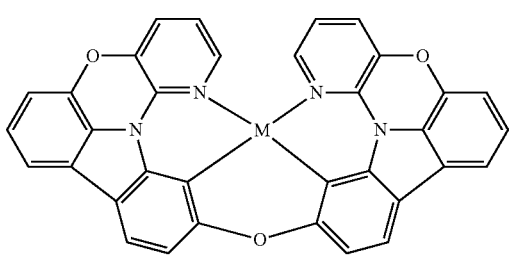
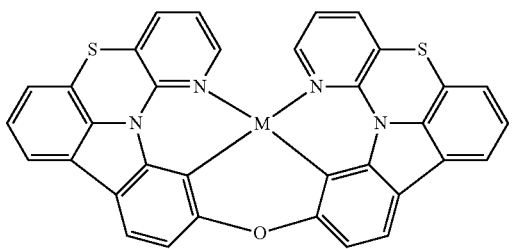
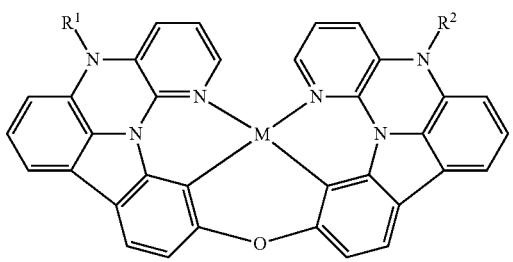
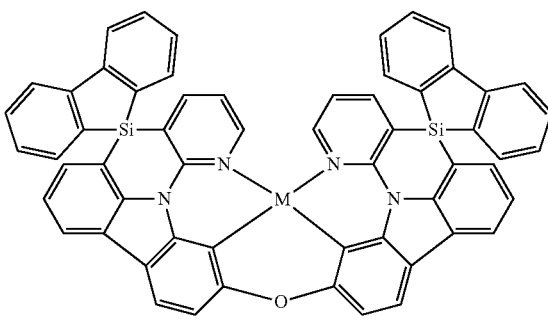

197
-continued
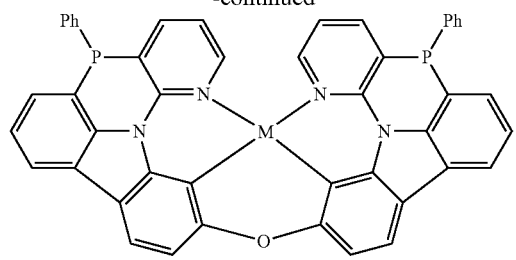
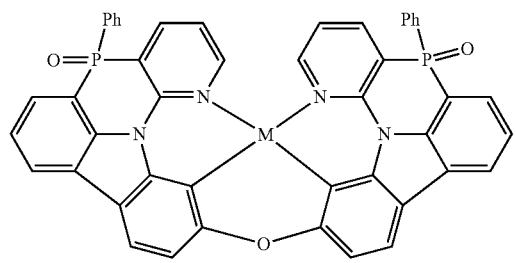
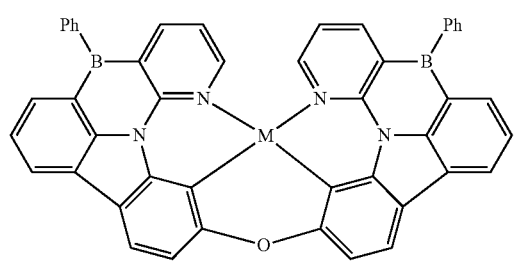
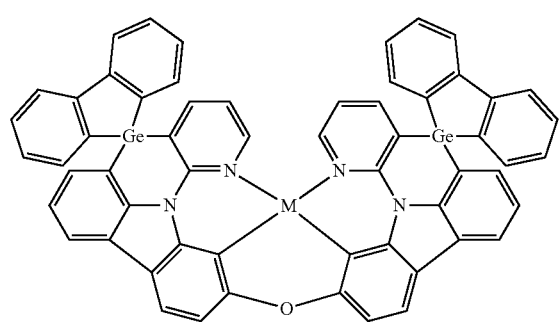
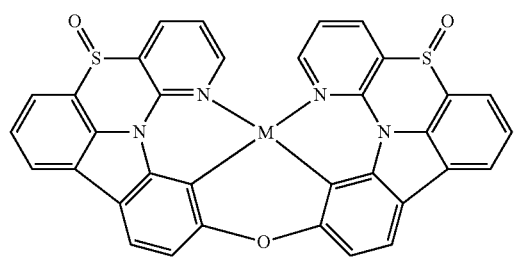
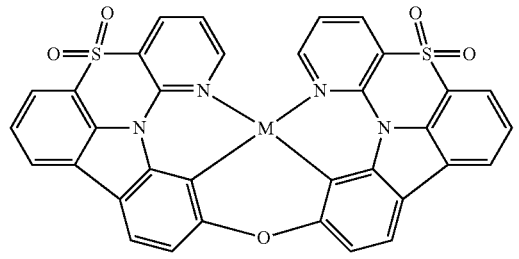
198
-continued
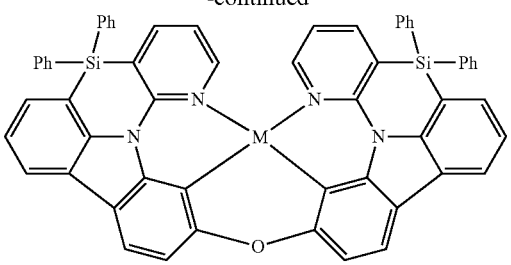
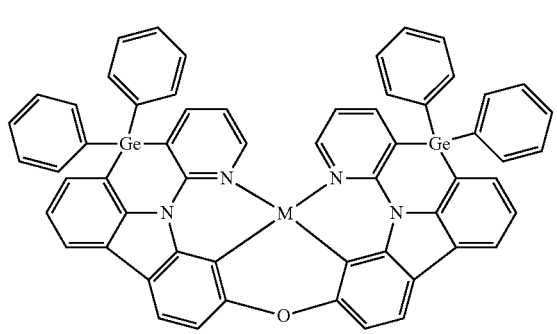
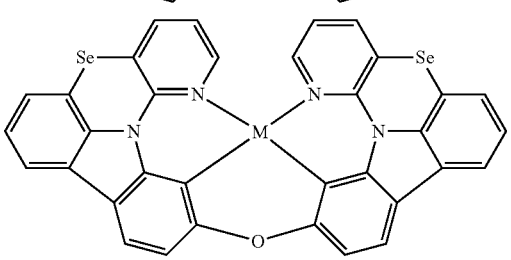
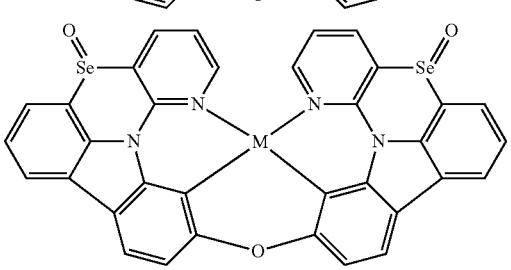
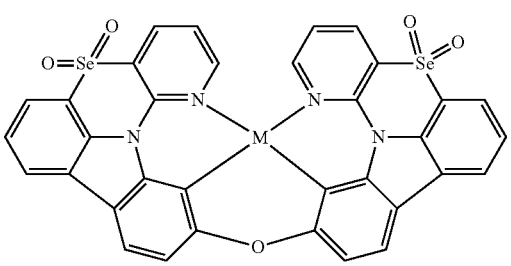
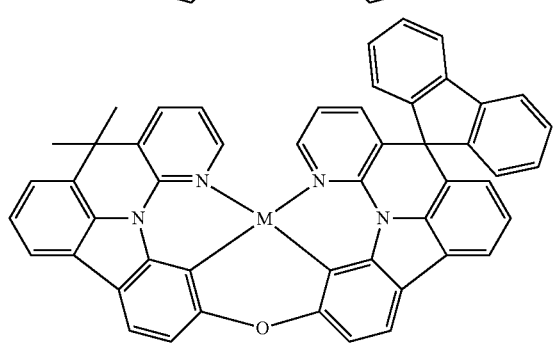

199
-continued
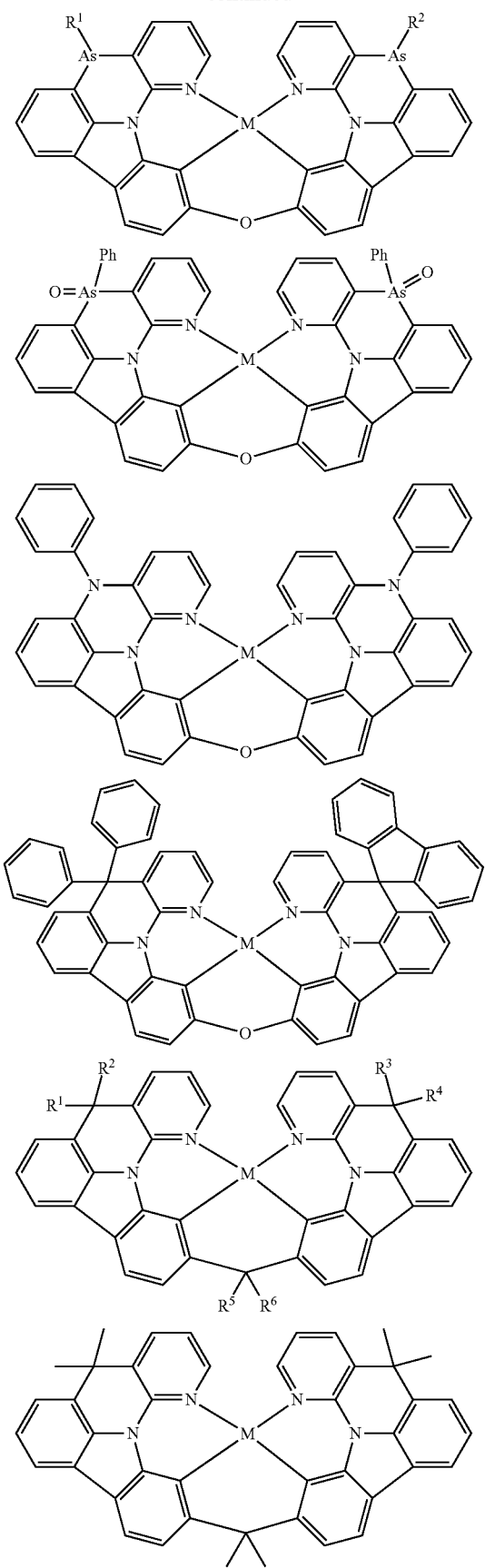
200
-continued
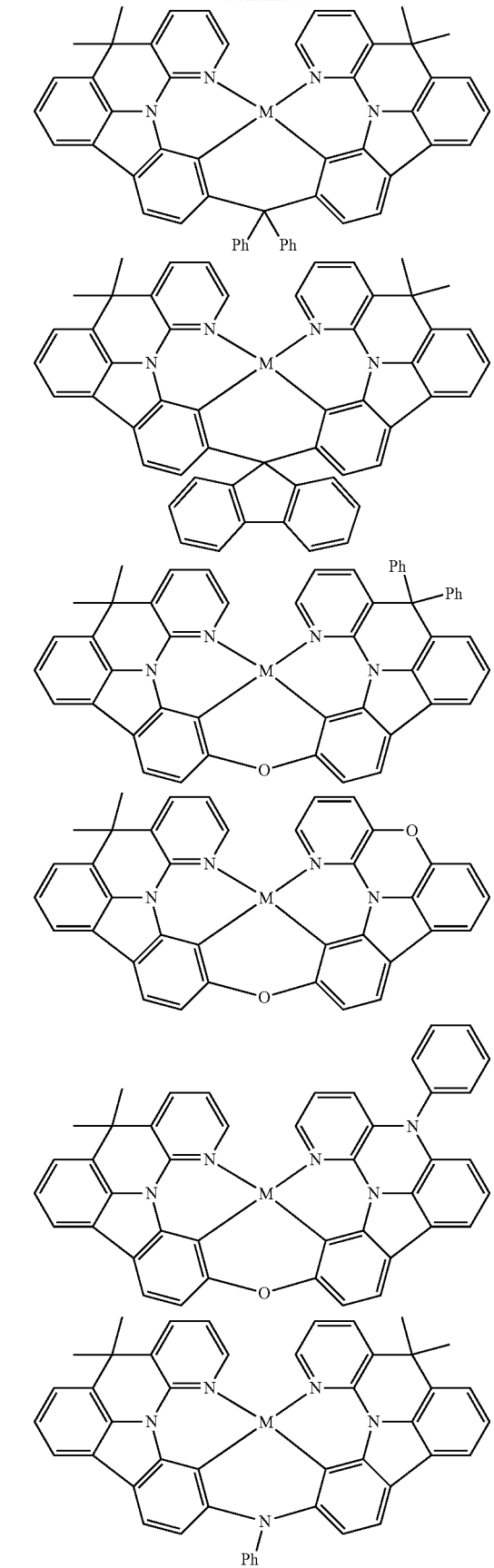

Structure 12 (M = Pt or Pd)
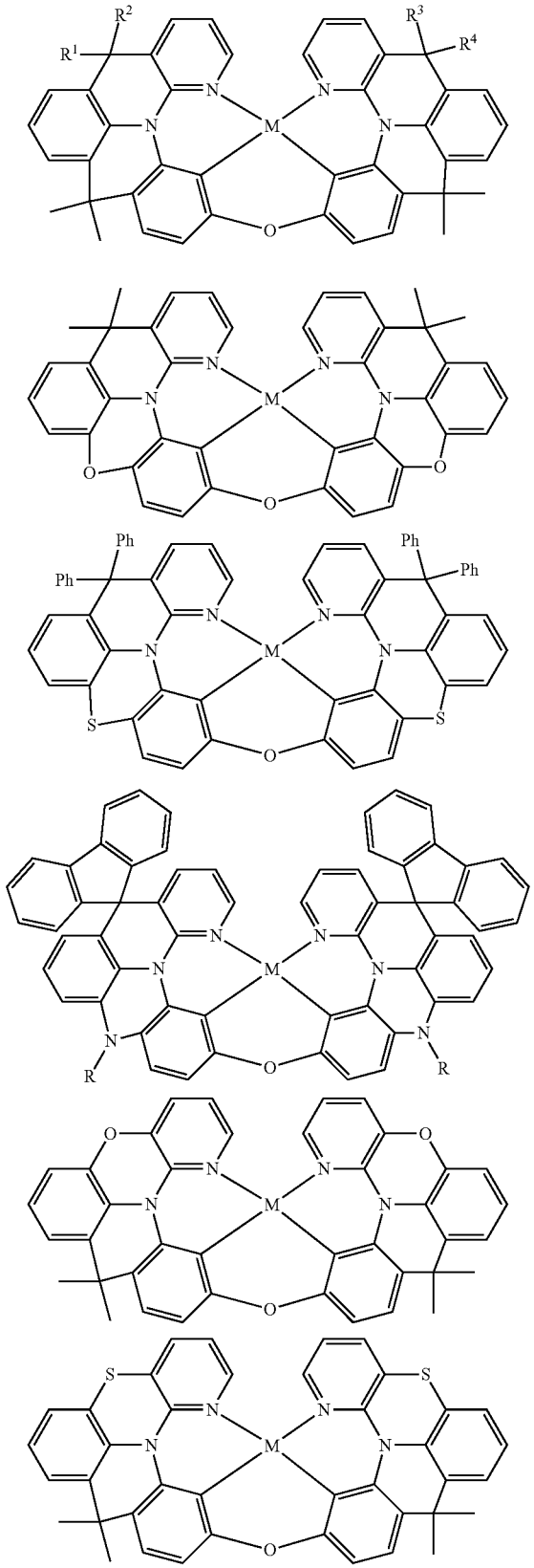
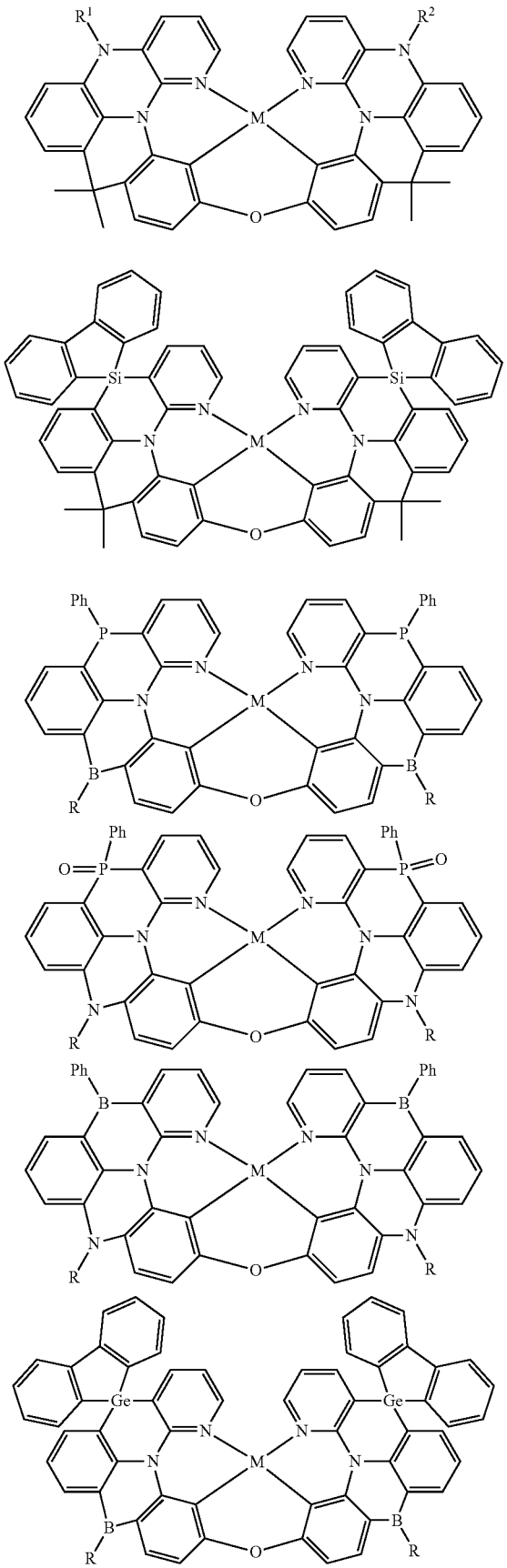

203
-continued
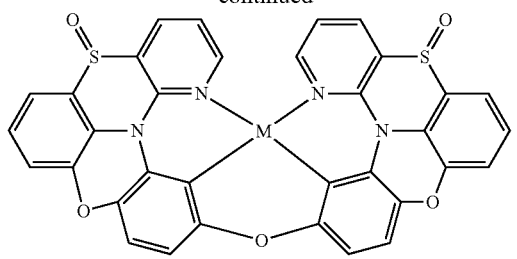
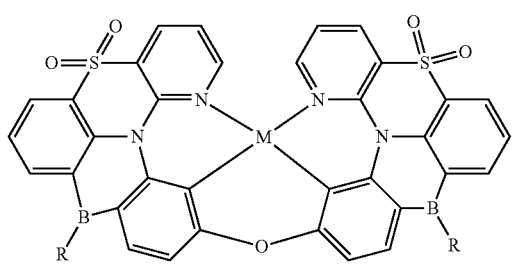
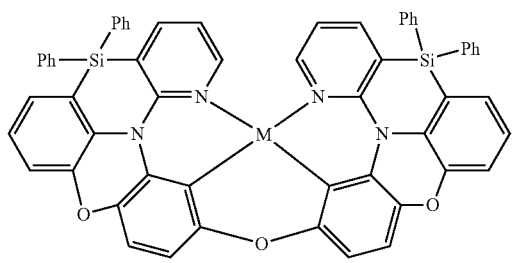
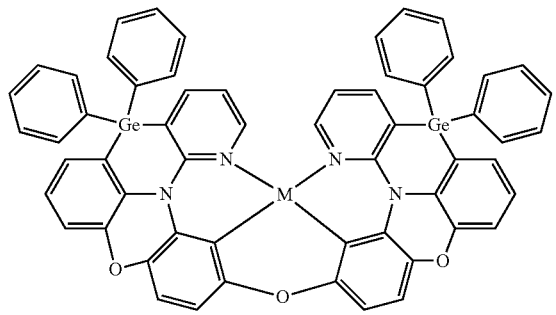
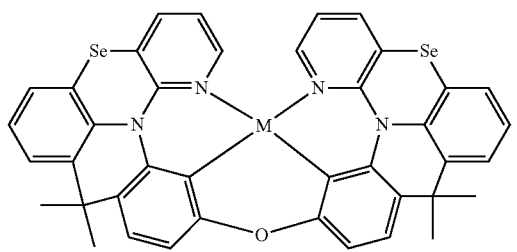
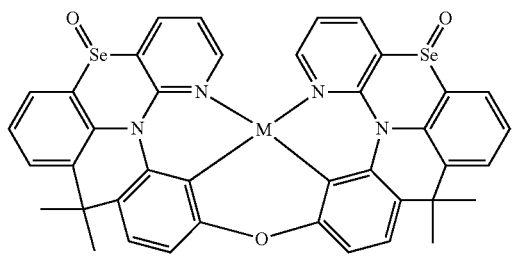
204
-continued
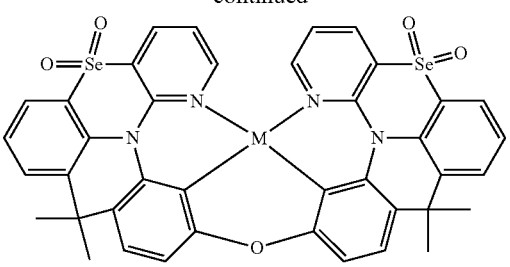
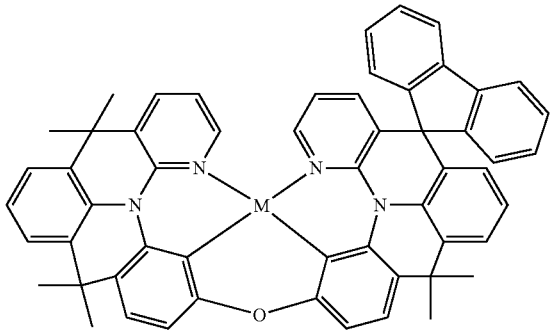
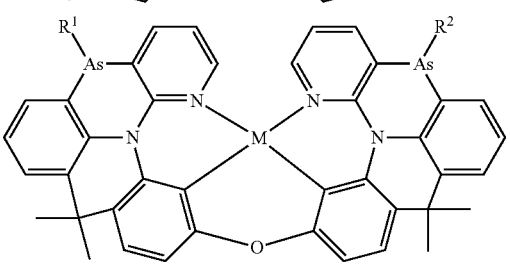
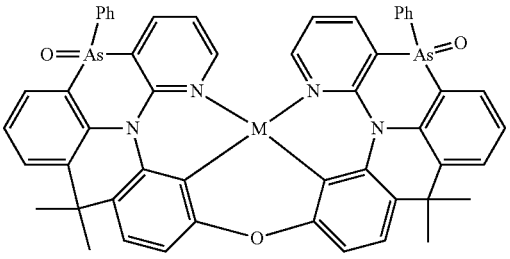
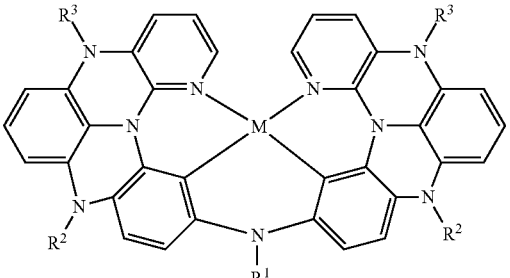
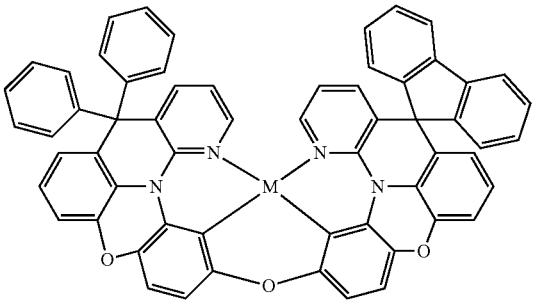

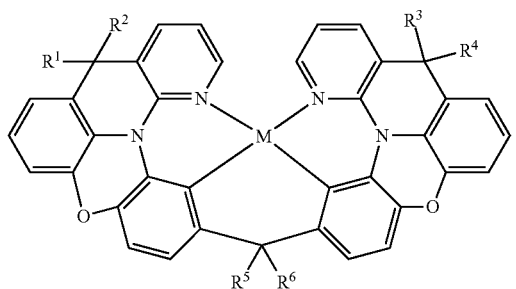
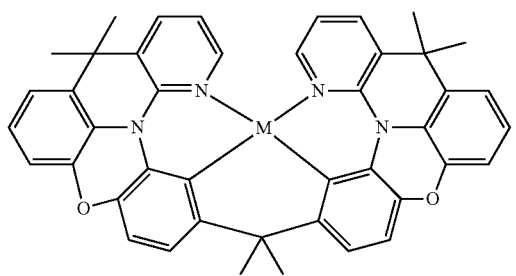
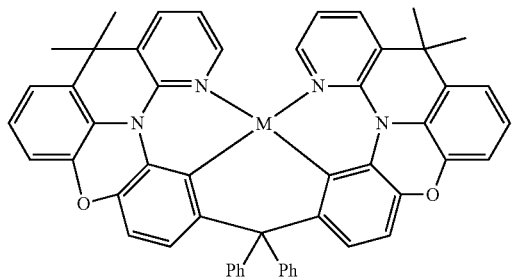
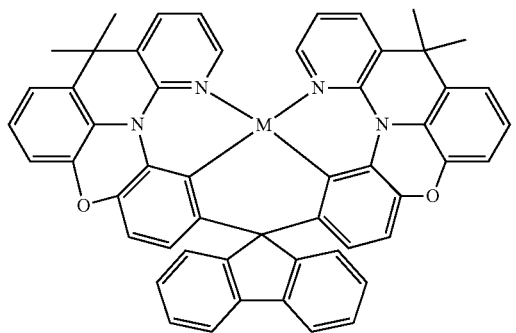
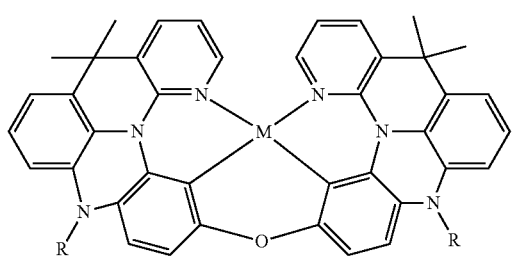
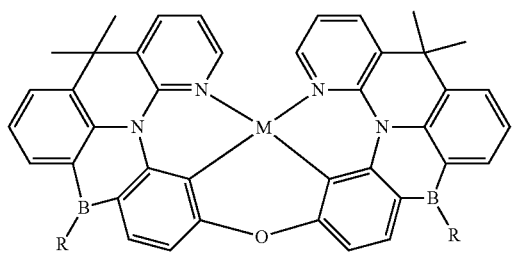
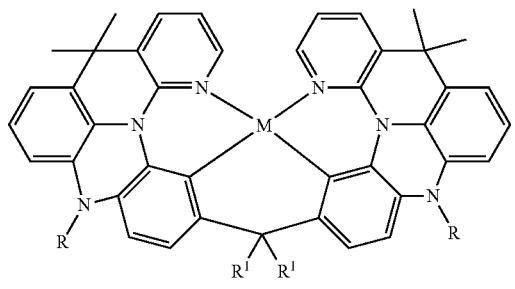
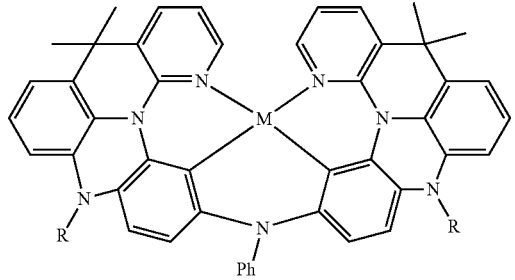
Structure 13 (M = Pt or Pd)
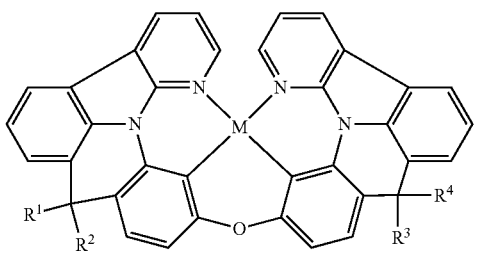
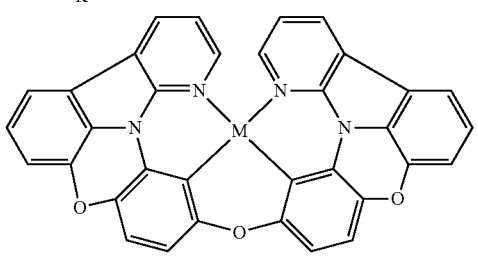
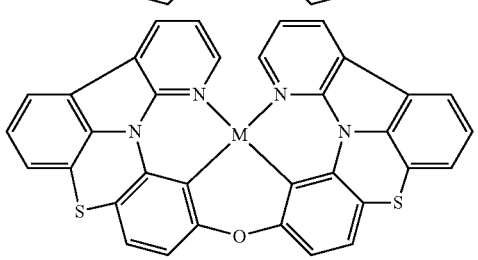
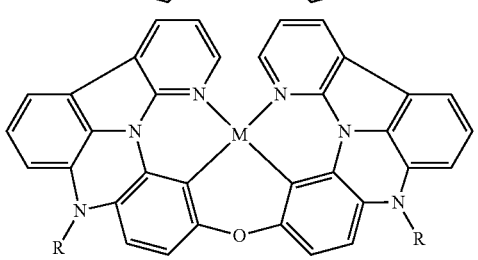

207
-continued
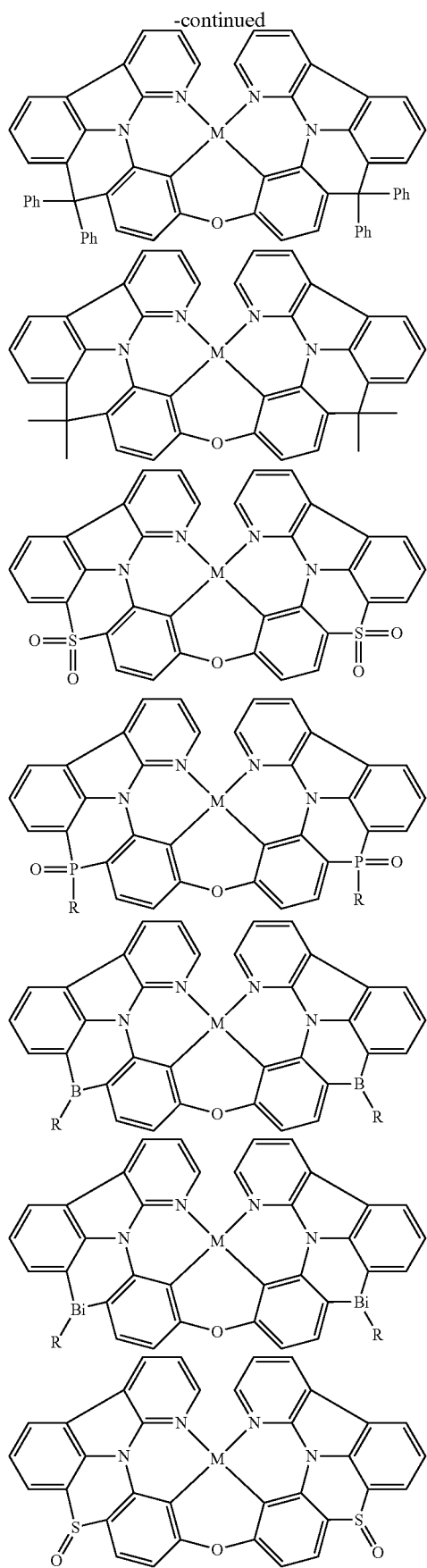
208
-continued
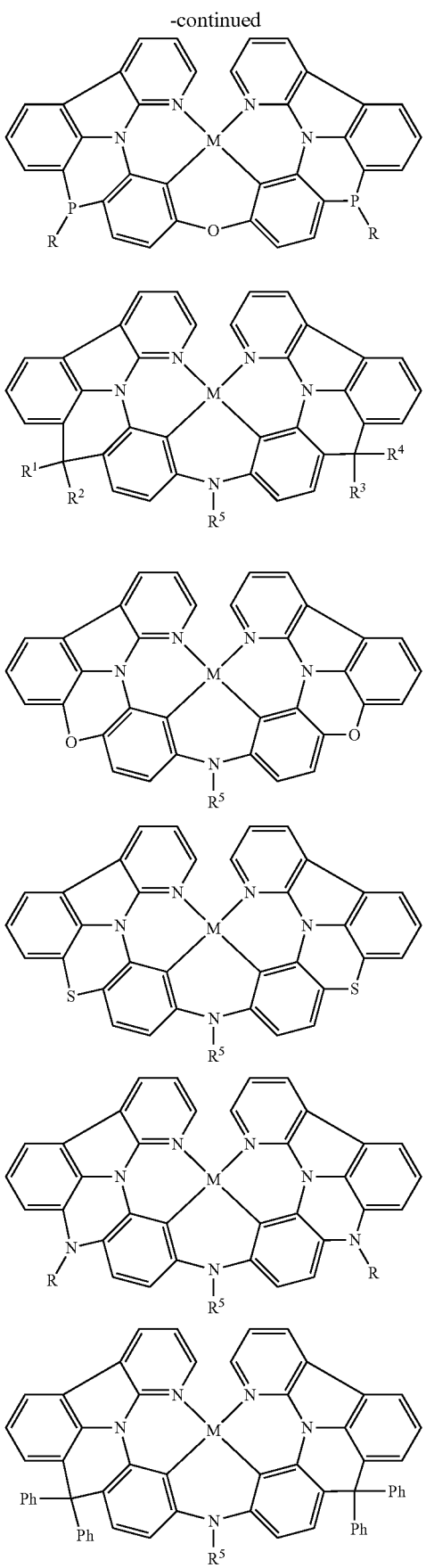

209
-continued
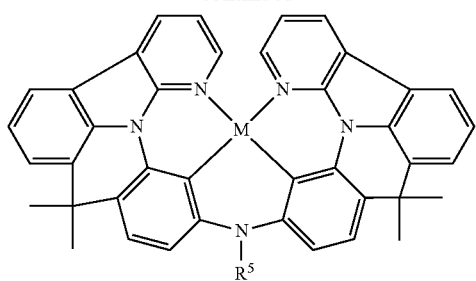
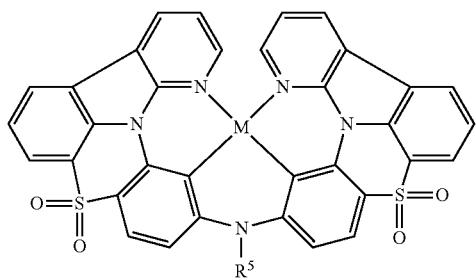
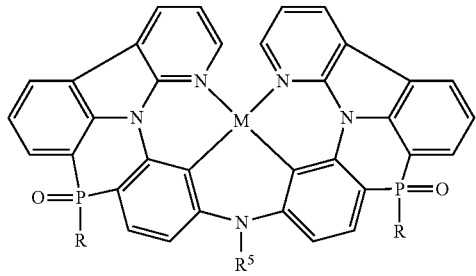
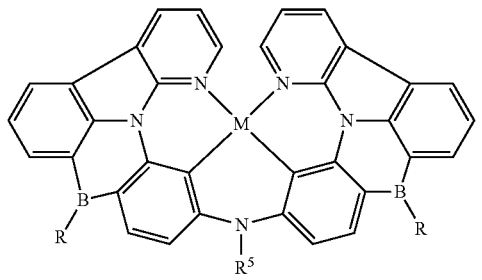
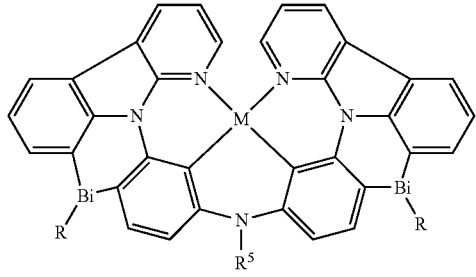
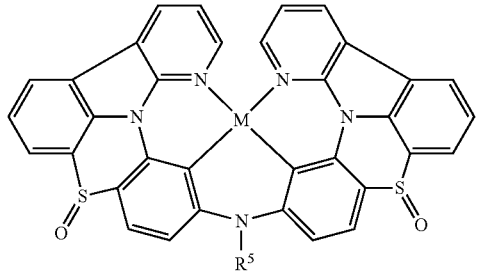
210
-continued
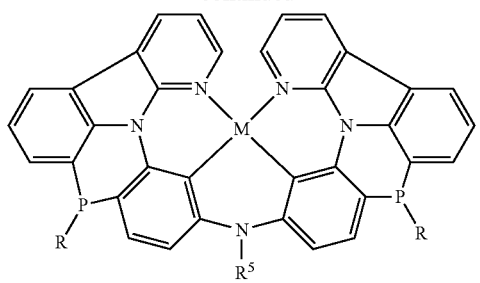
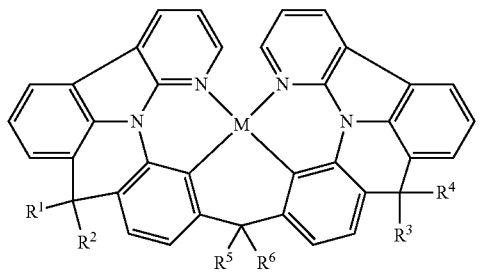
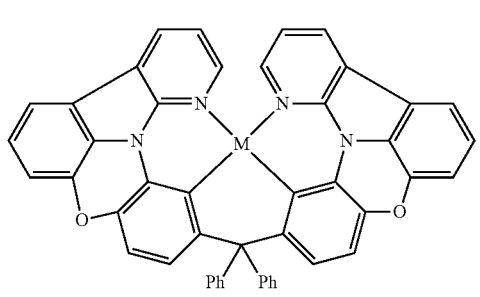
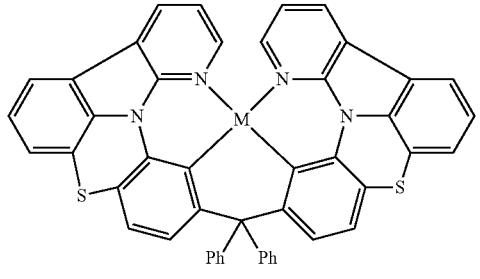
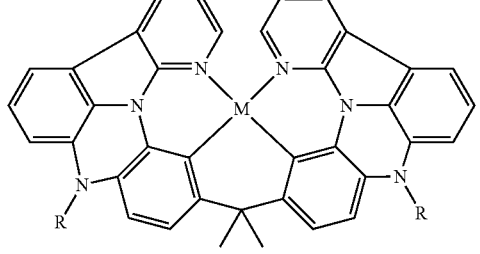
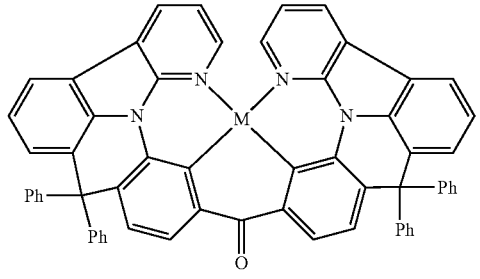

211
-continued
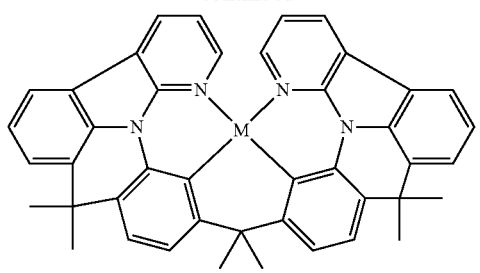
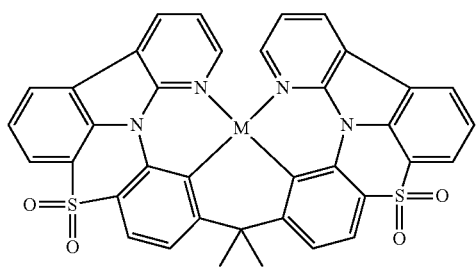
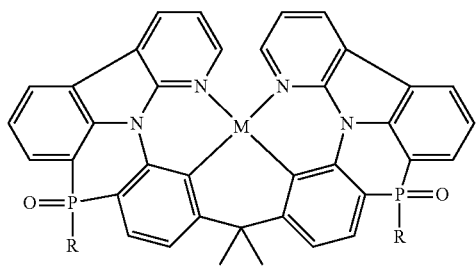
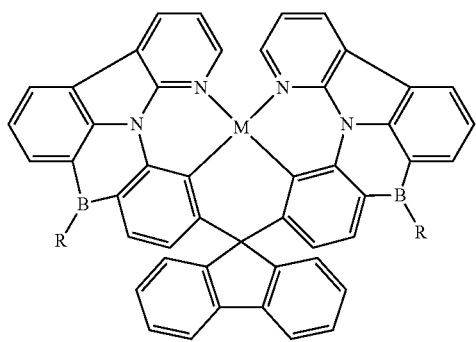
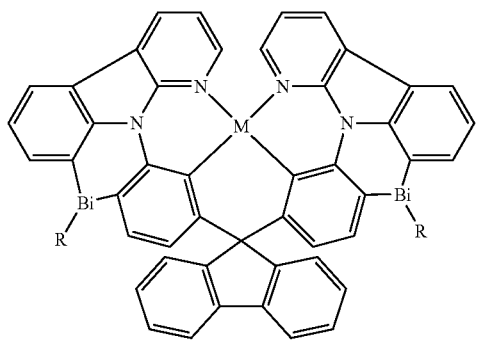
212
-continued
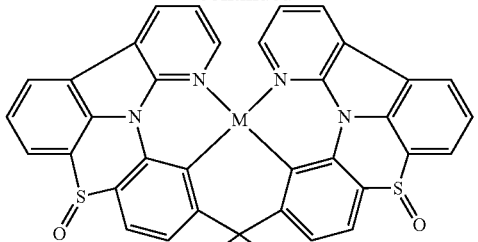
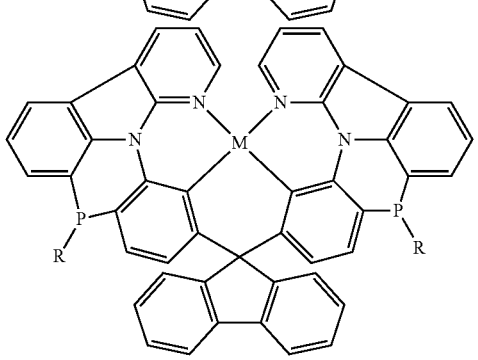
Structure 14 (M = Pt or Pd)
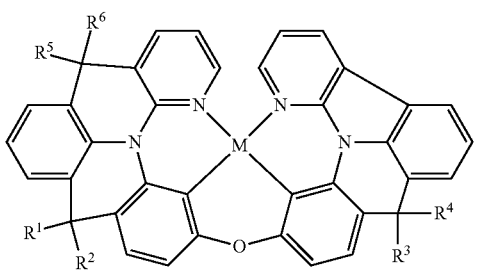
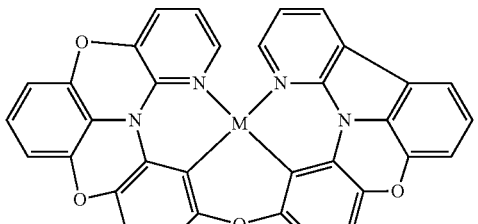
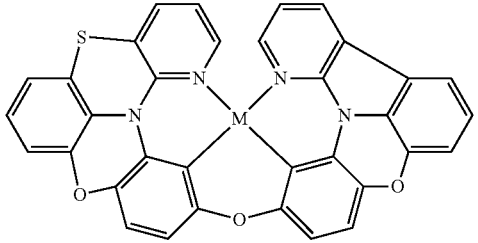
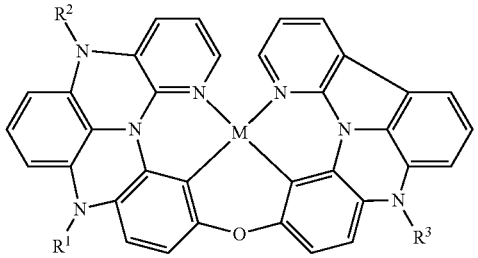

213
-continued
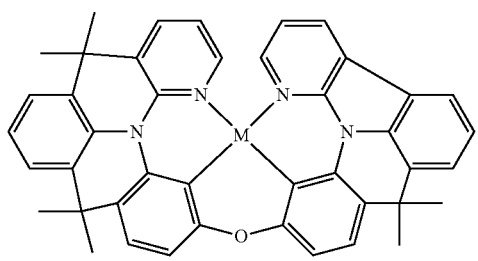
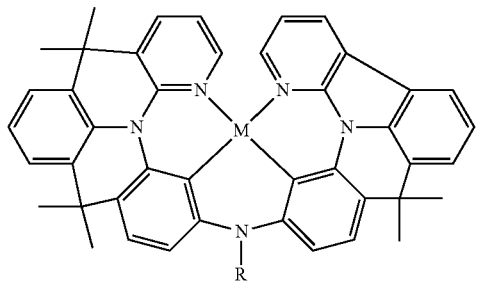
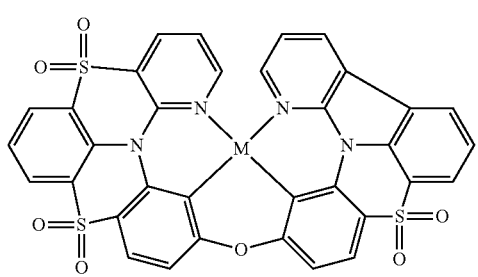
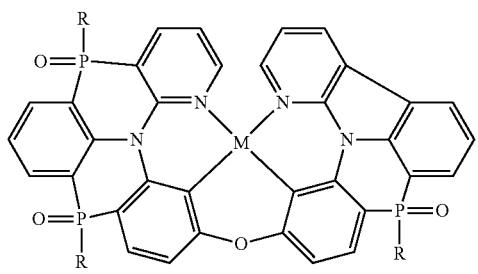
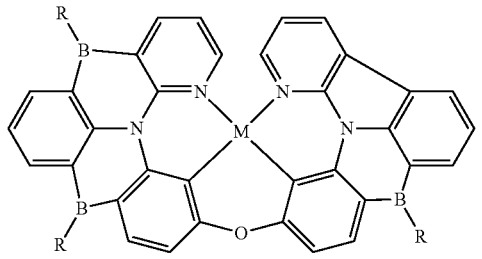
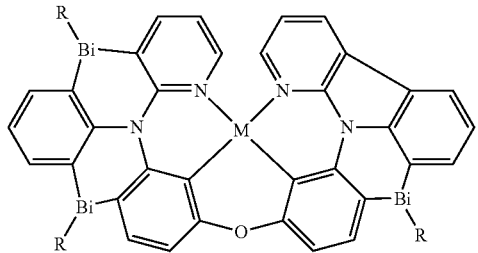
214
-continued
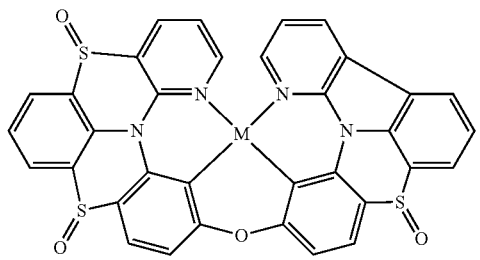
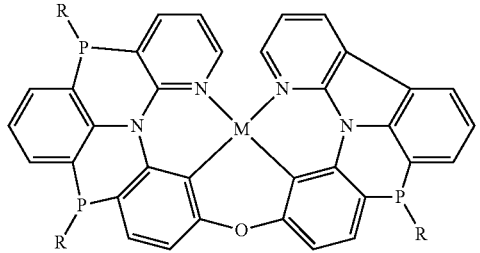
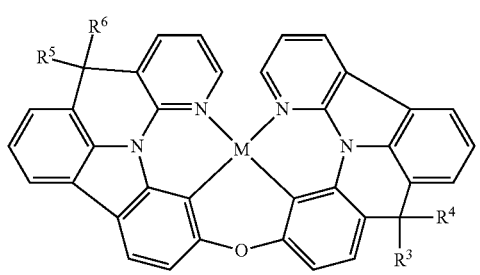
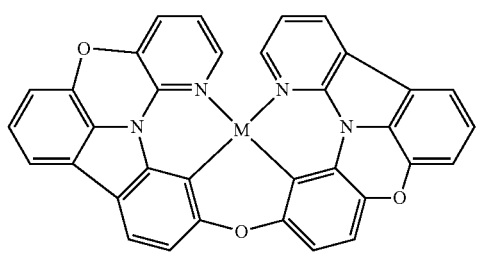
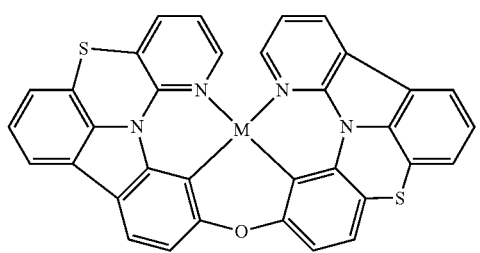
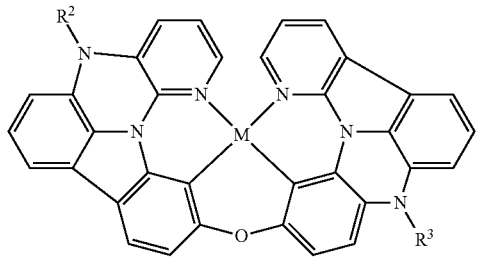

215
-continued
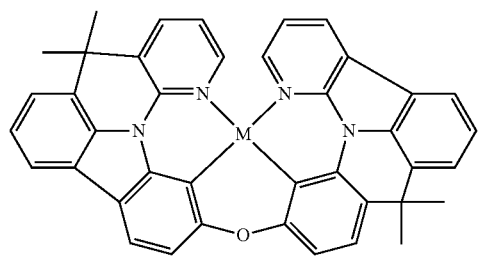
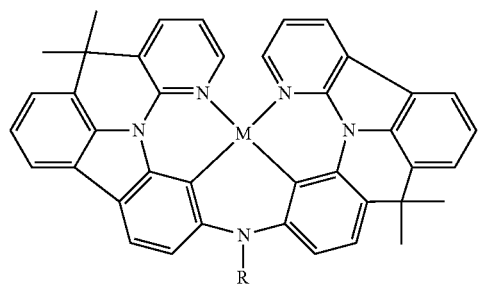
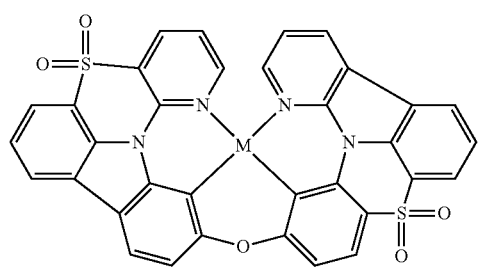
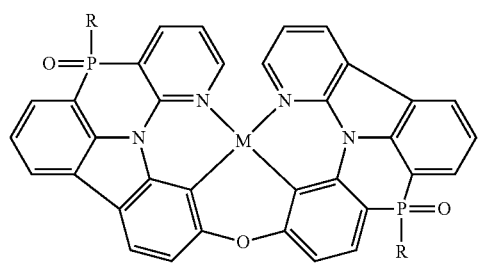
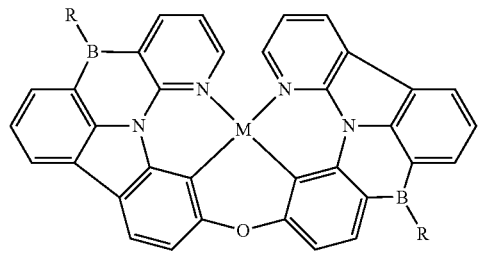
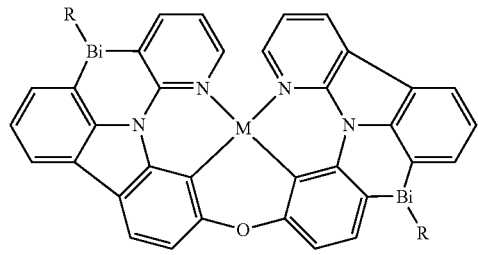
216
-continued
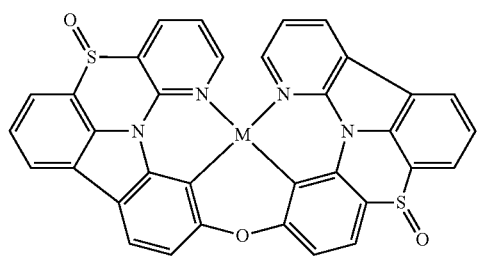
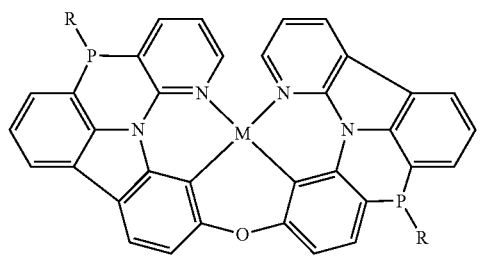
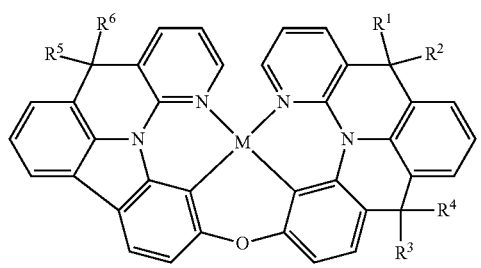
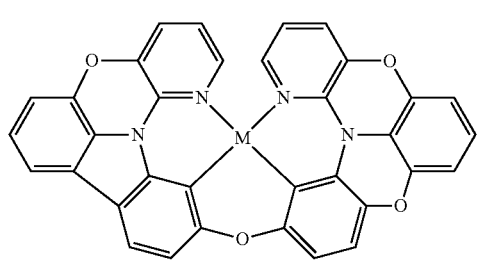
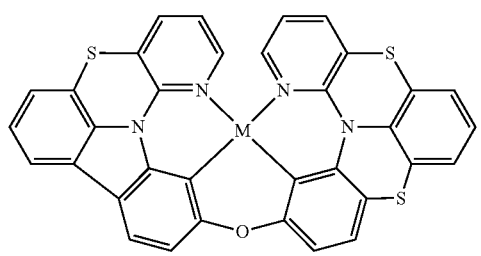
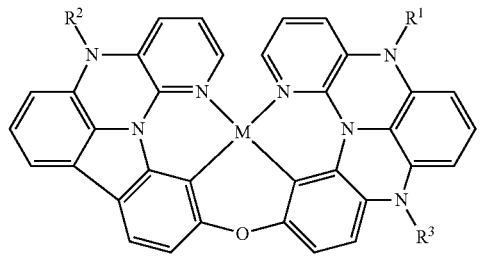

217
-continued
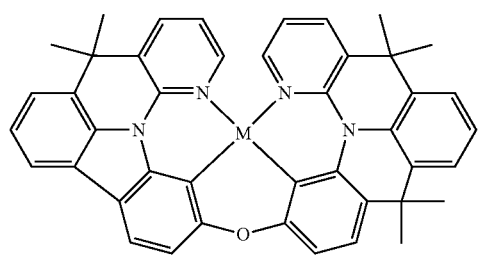
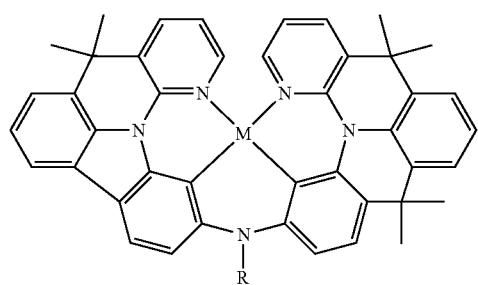
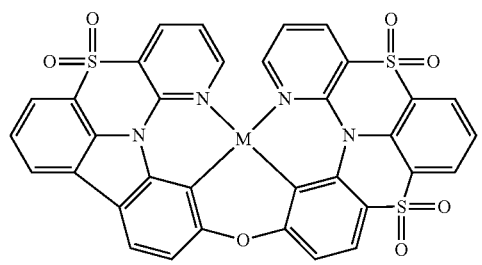
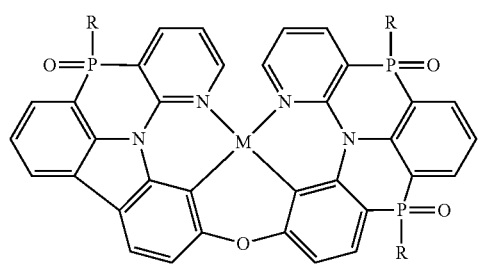
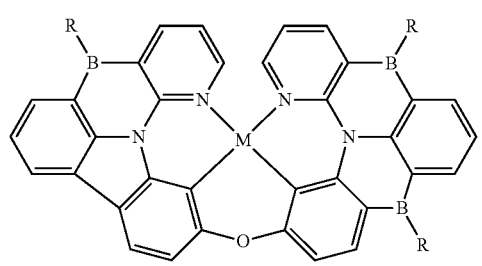
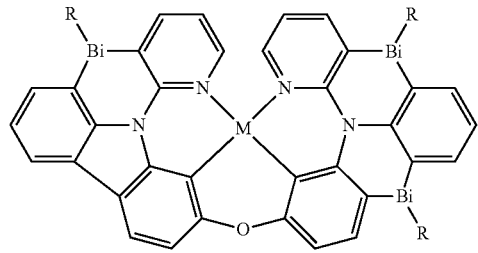
218
-continued
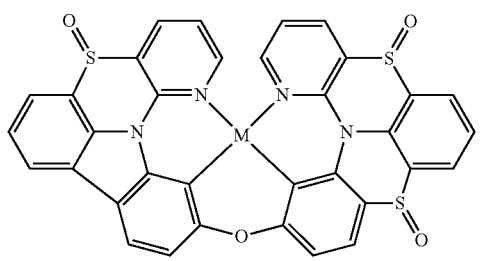
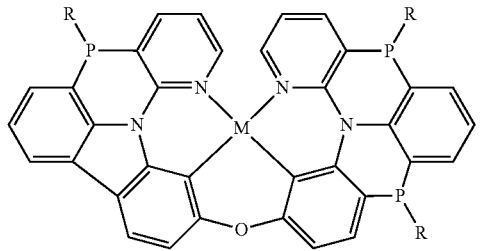
Structure 15 (M = Pt or Pd)
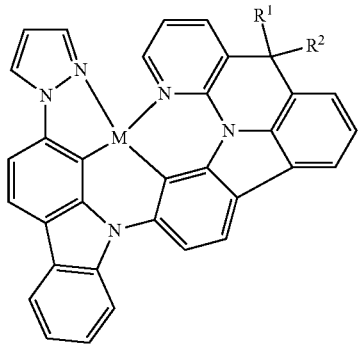
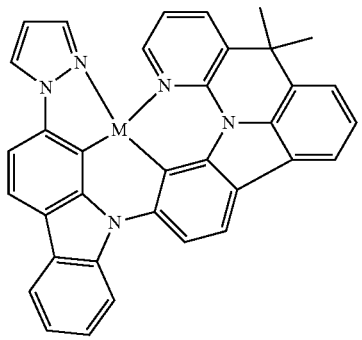
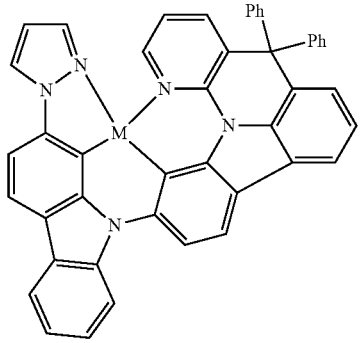

219
-continued
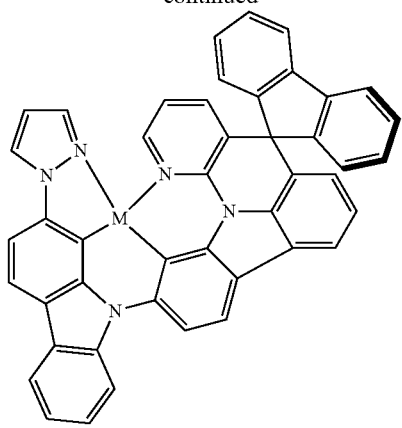
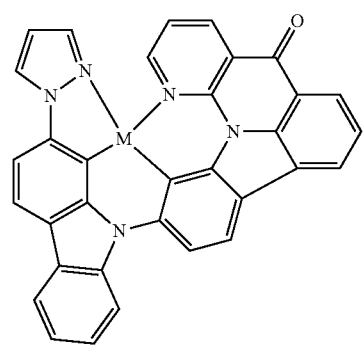
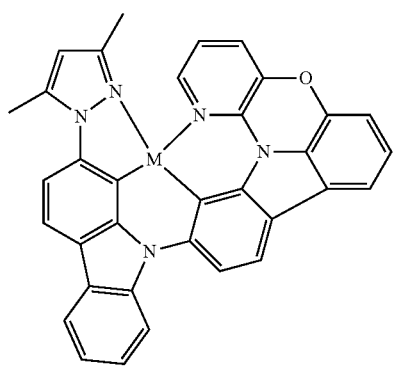
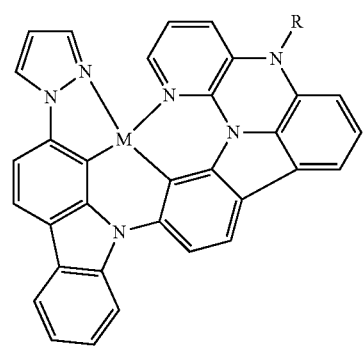
220
-continued
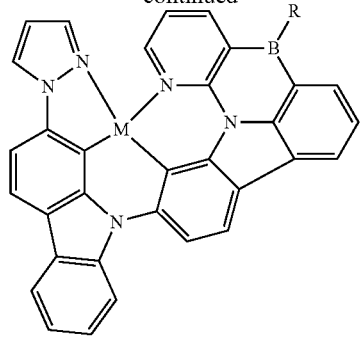
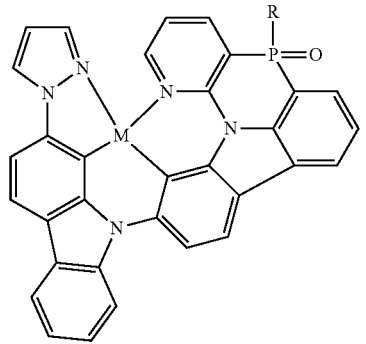
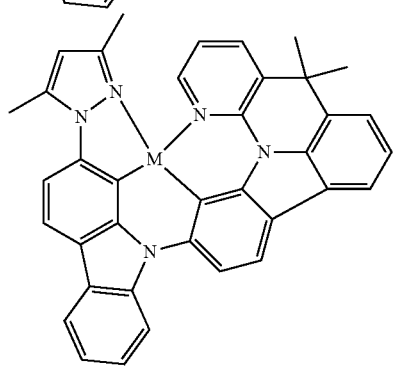
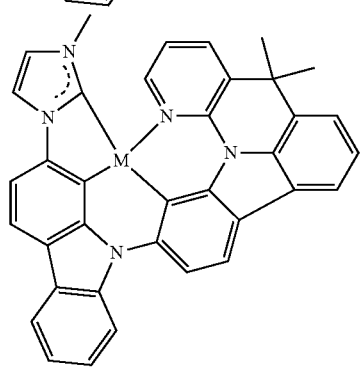

221
-continued
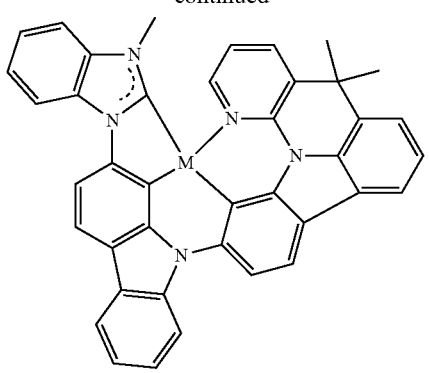
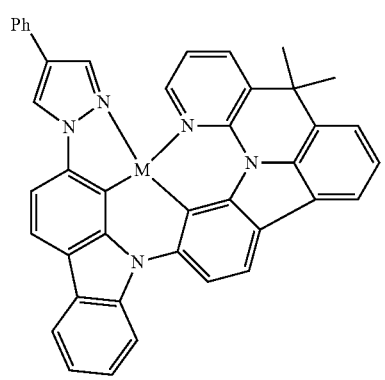
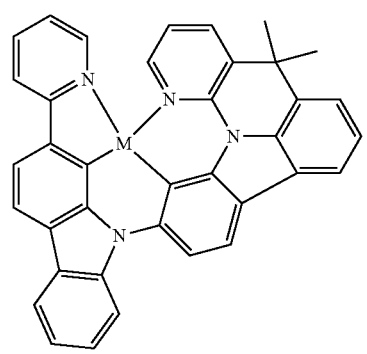
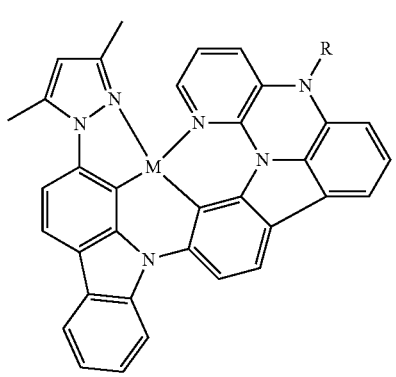
222
-continued
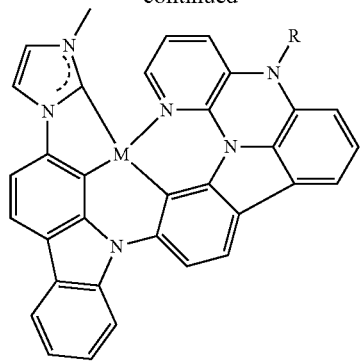
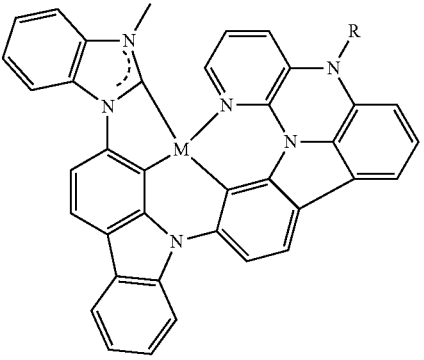
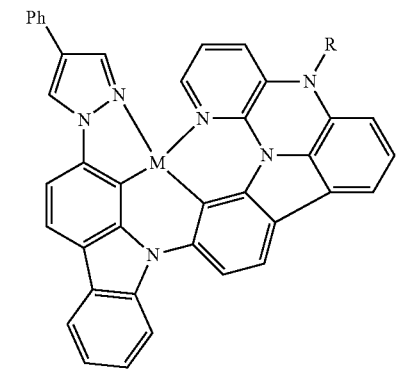
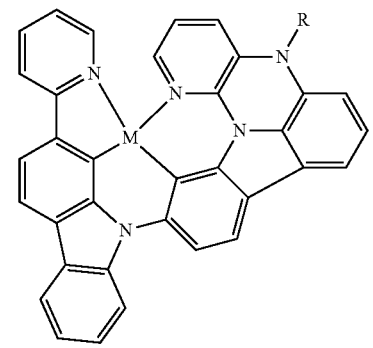

223
-continued
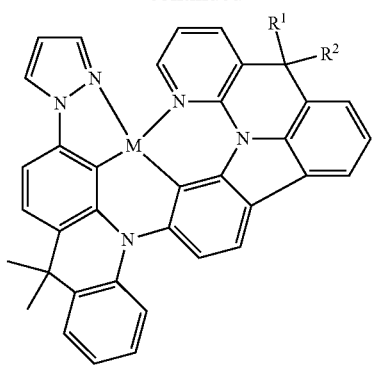
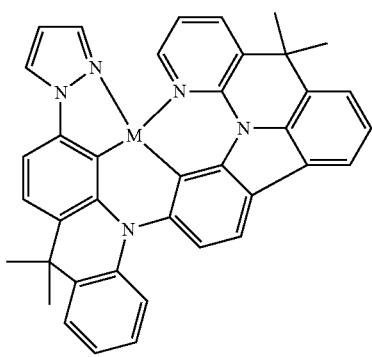
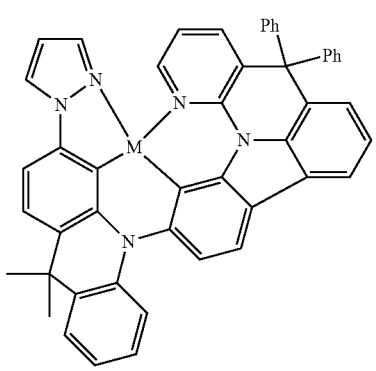
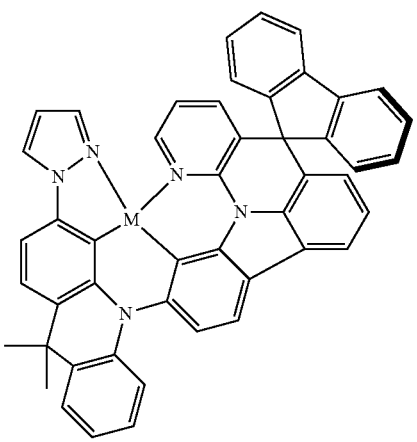
224
-continued
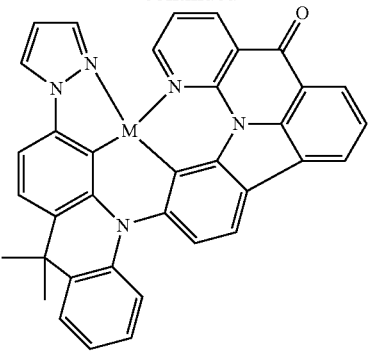
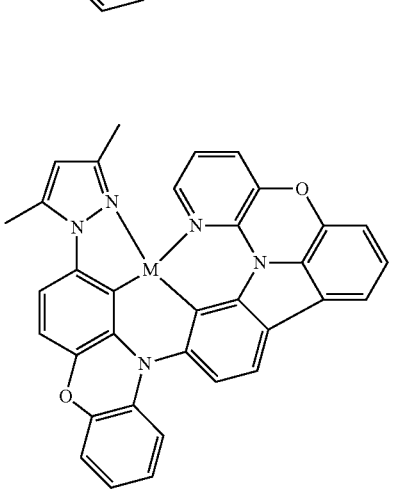
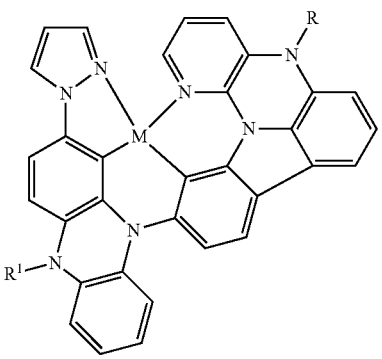
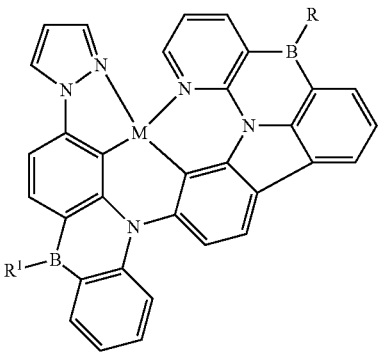

225
-continued
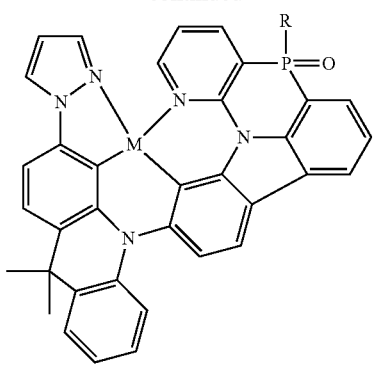
226
-continued
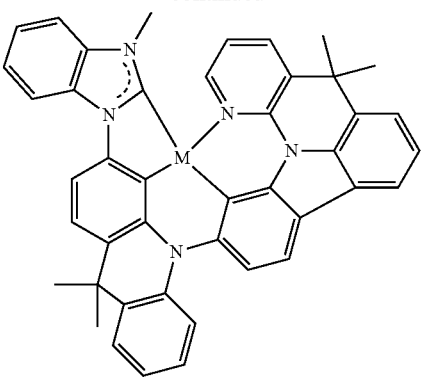
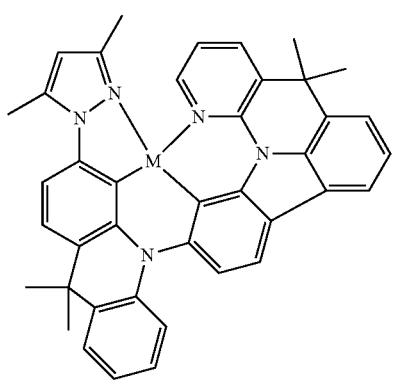
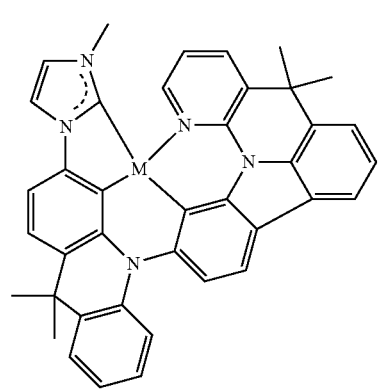
Structure 16 (M = Pt or Pd)

| 227 -continued | 228 -continued |
|---|---|
| 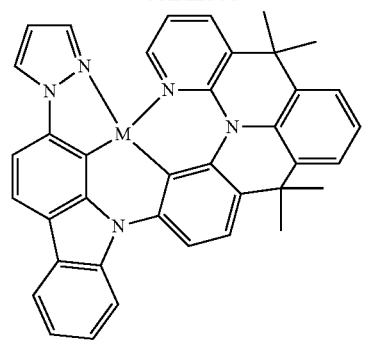 | 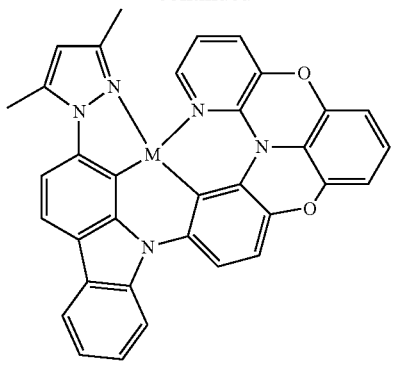 |
| 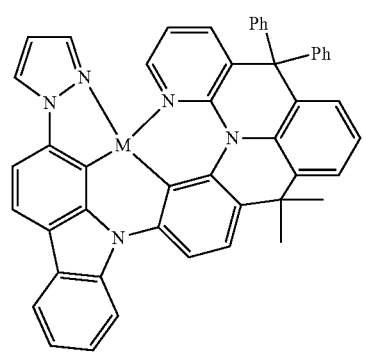 | 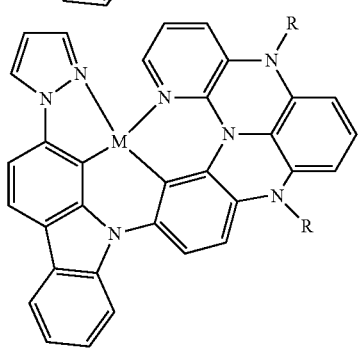 |
| 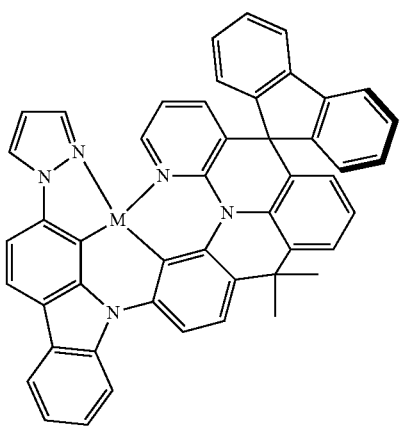 | 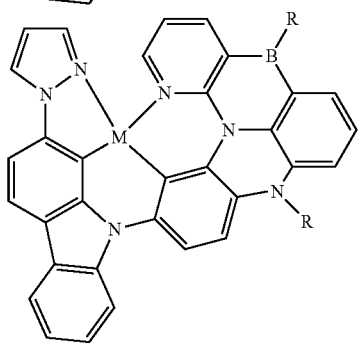 |
| | 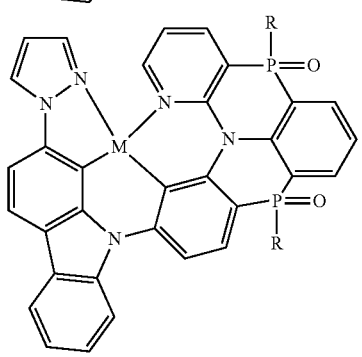 |
| 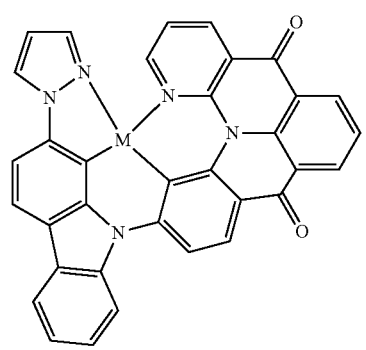 | 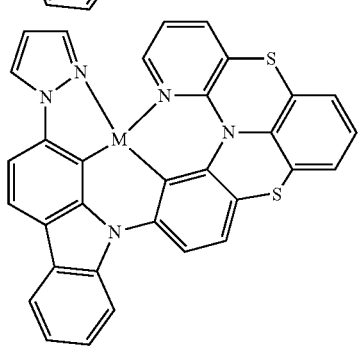 |

229
-continued
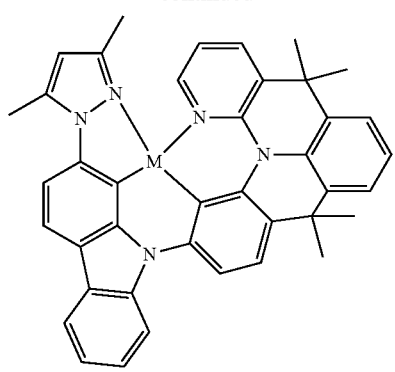
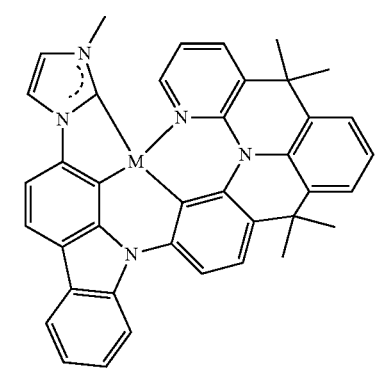
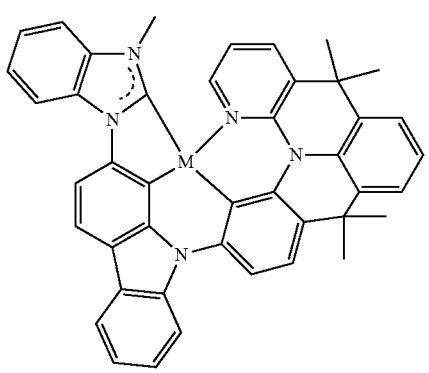
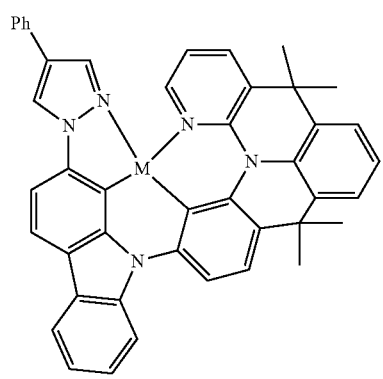
230
-continued
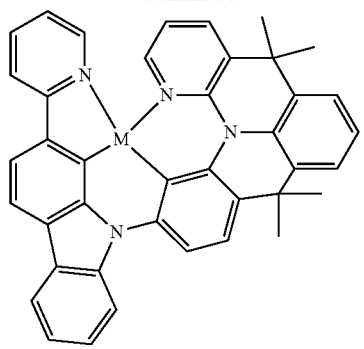
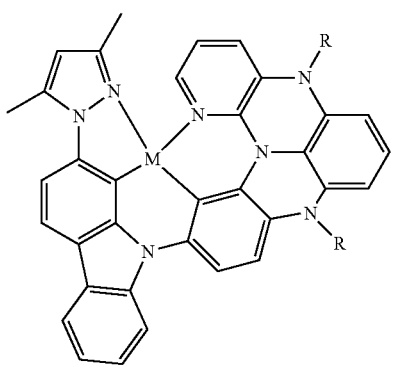
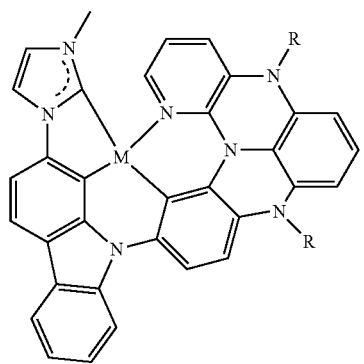
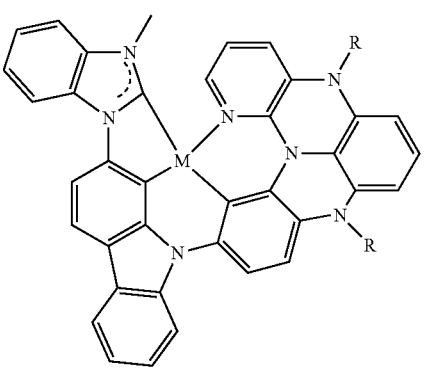

231
-continued
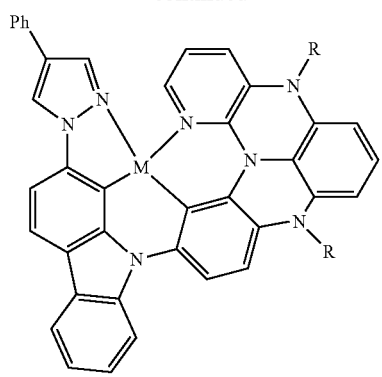
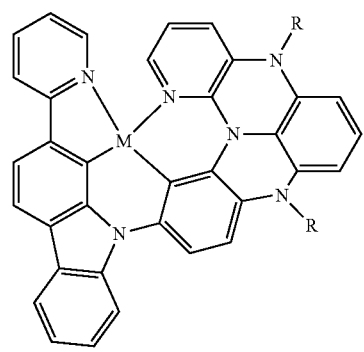
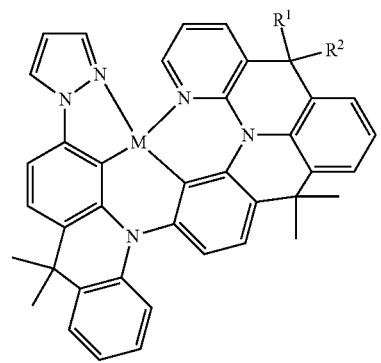
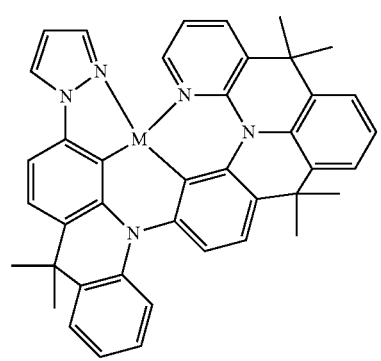
232
-continued
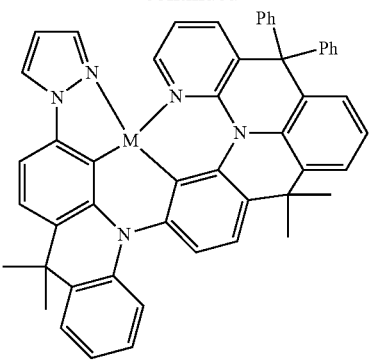
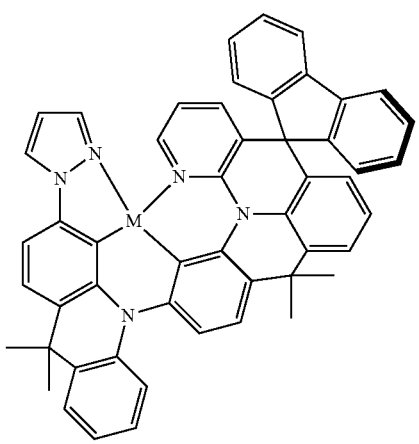
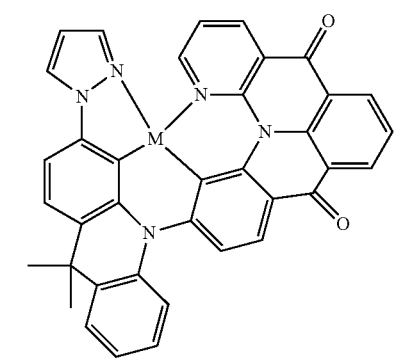
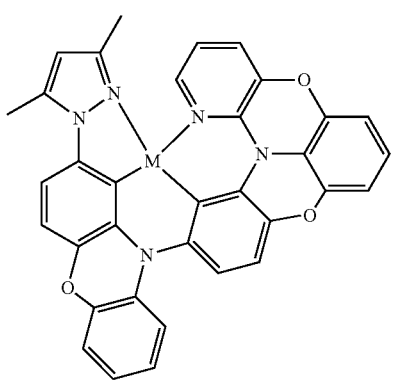

233
-continued
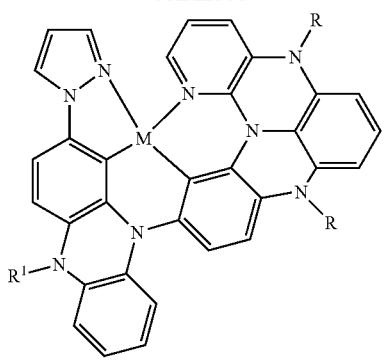
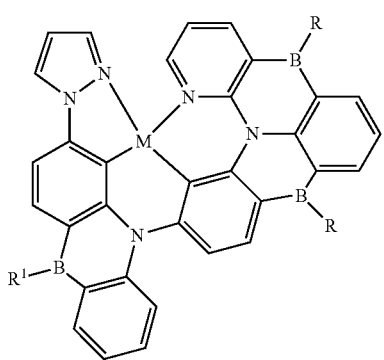
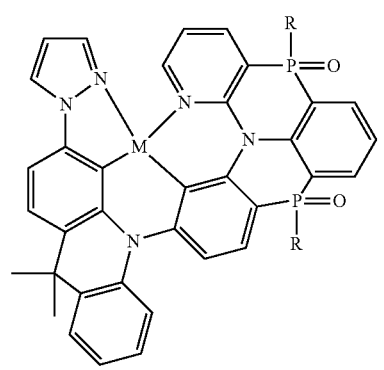
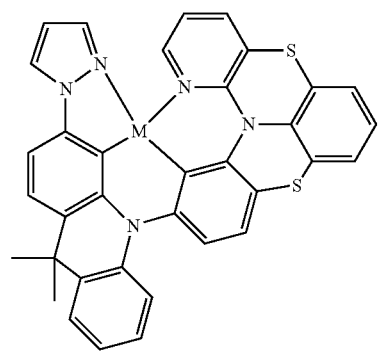
234
-continued
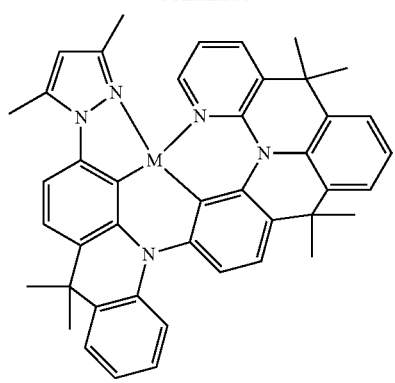
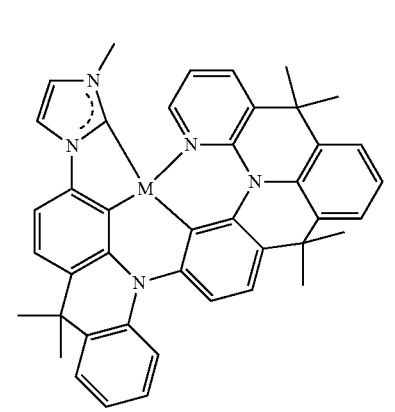
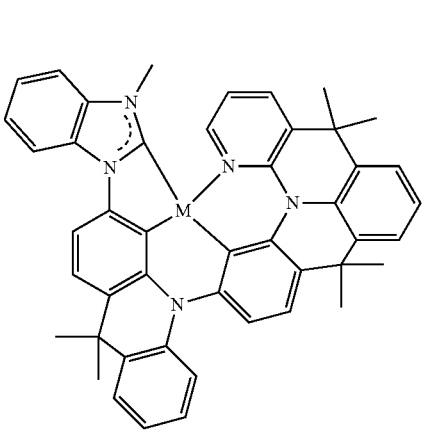
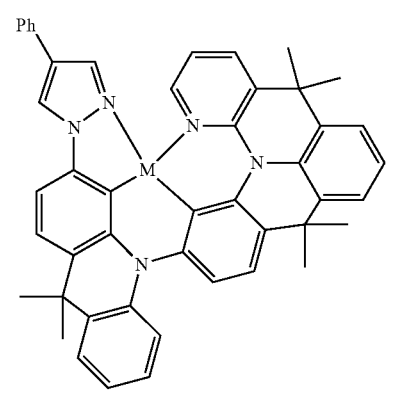

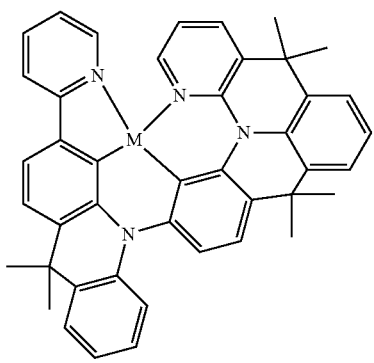
Structure 17 (M = Pt or Pd)
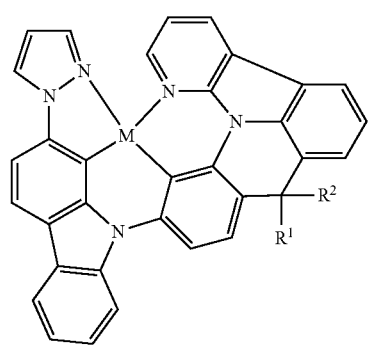
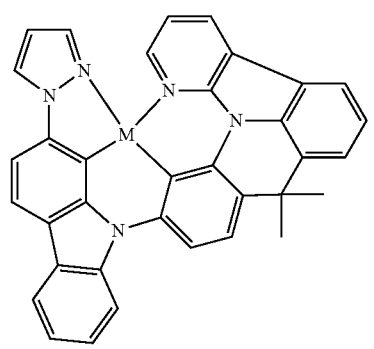
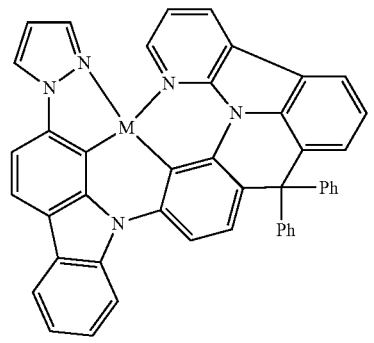
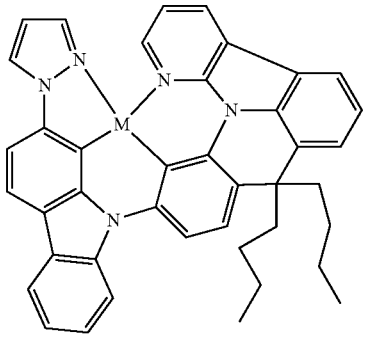
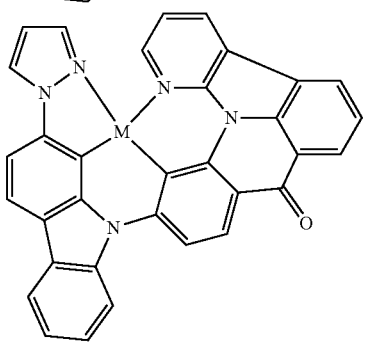
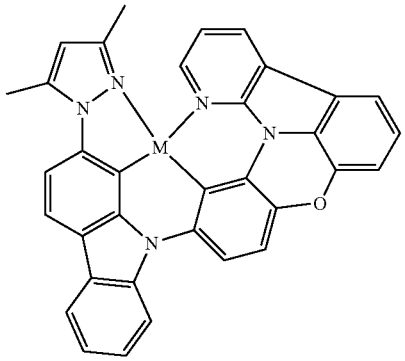
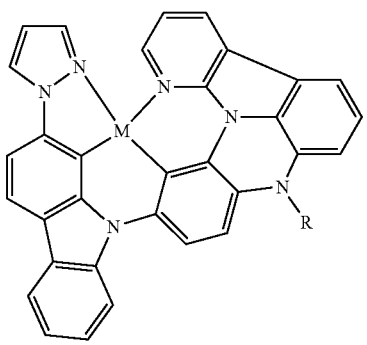
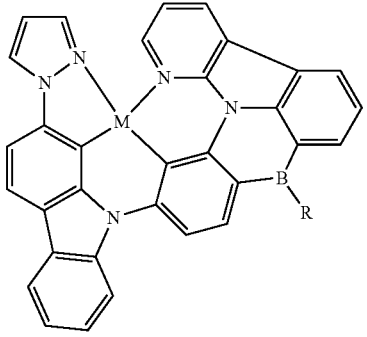

237
-continued
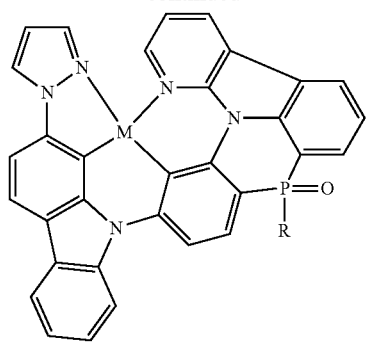
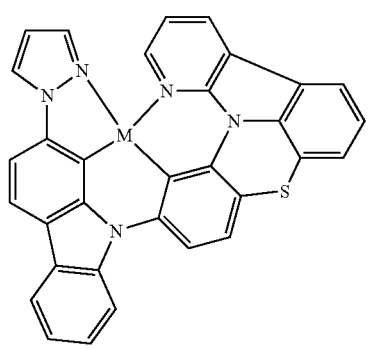
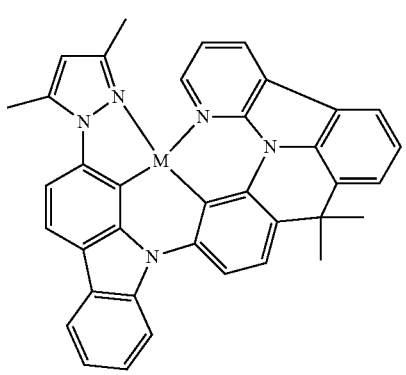
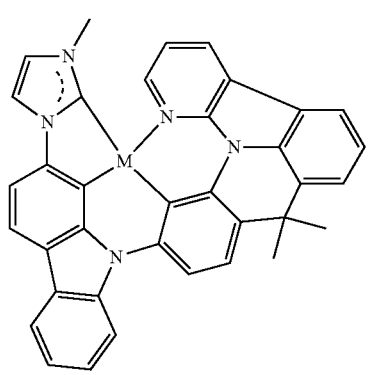
238
-continued
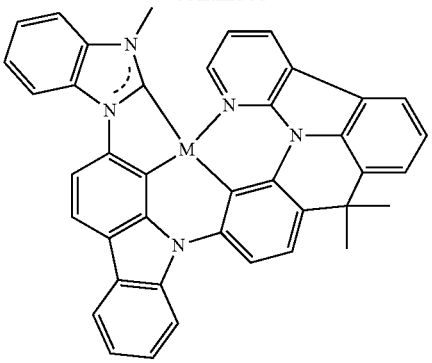
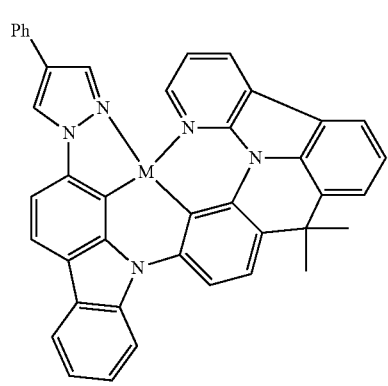
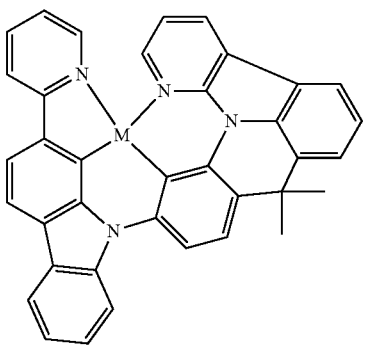
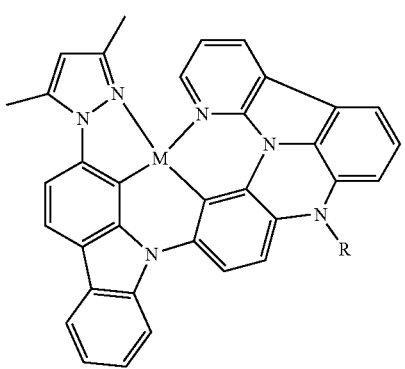

239
-continued
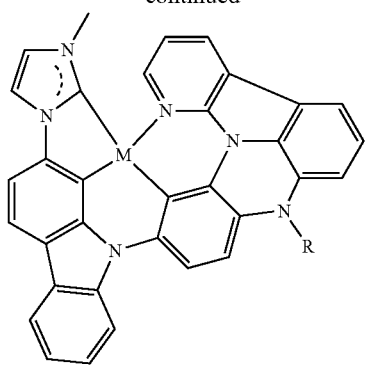
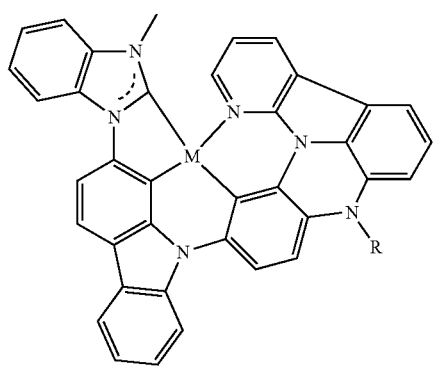
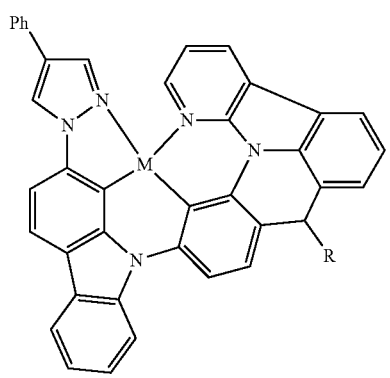
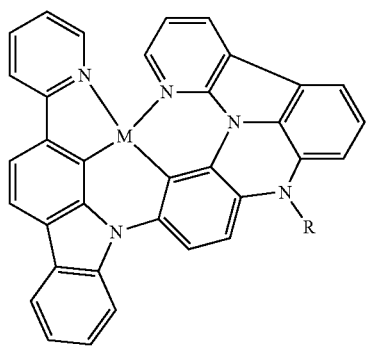
240
-continued
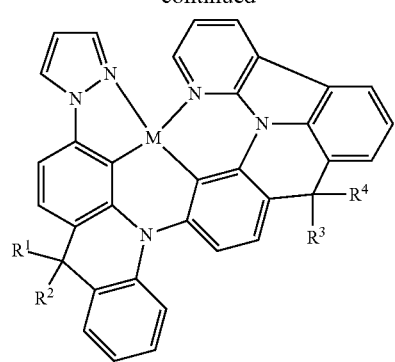
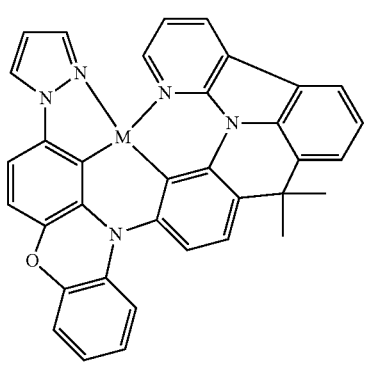
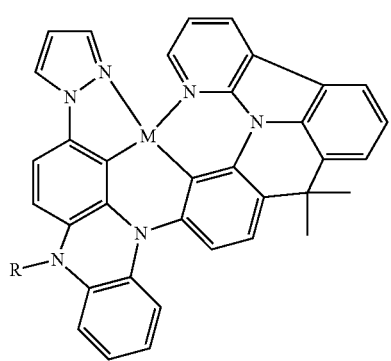
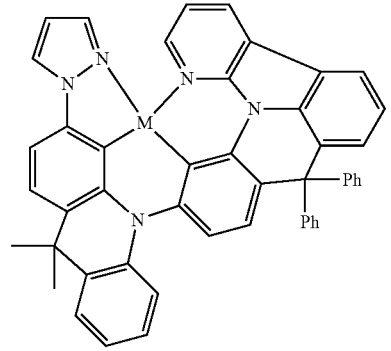

241
-continued
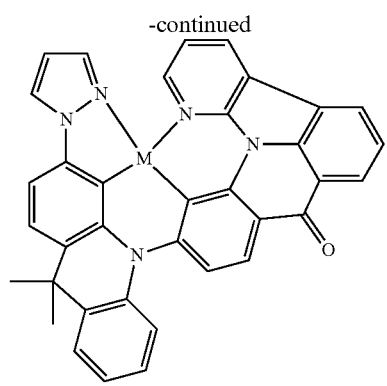
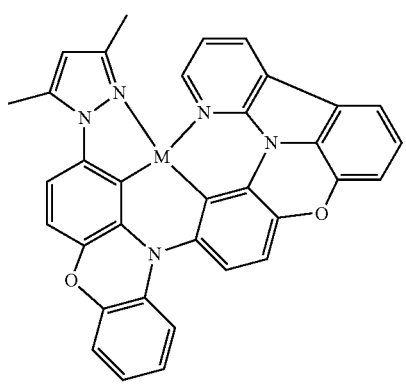
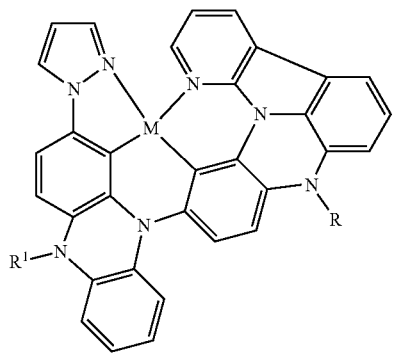
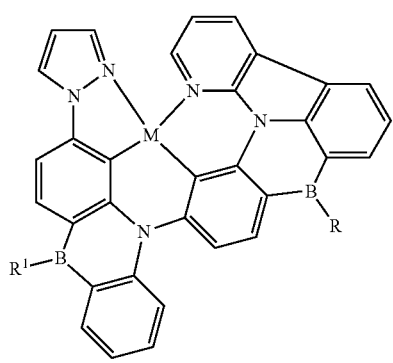
242
-continued
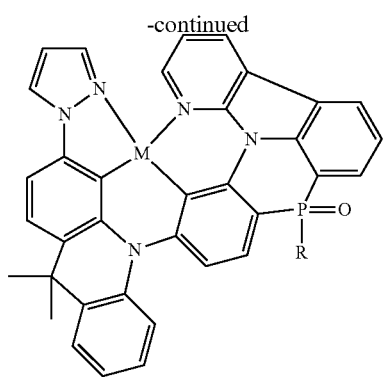
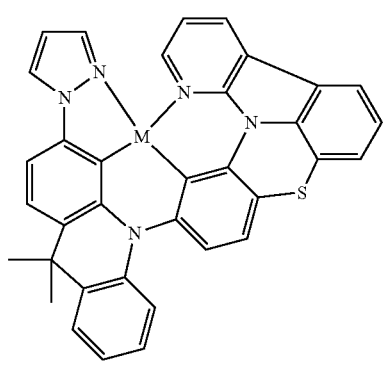
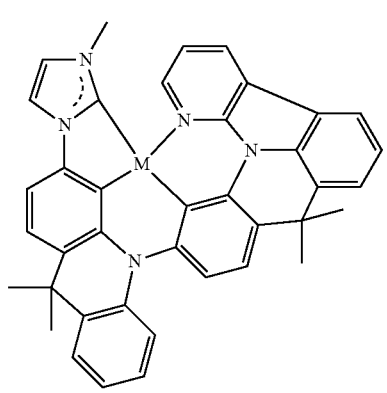

243
-continued
244
-continued
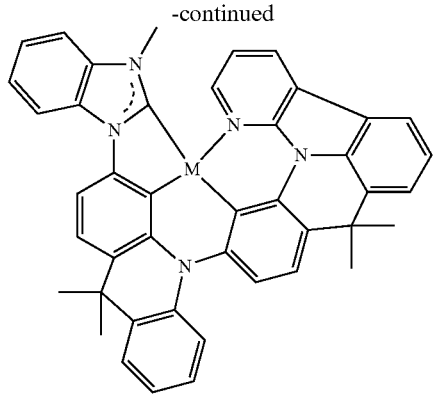
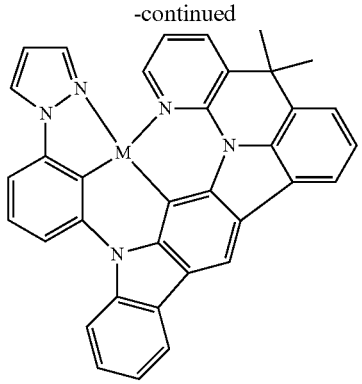
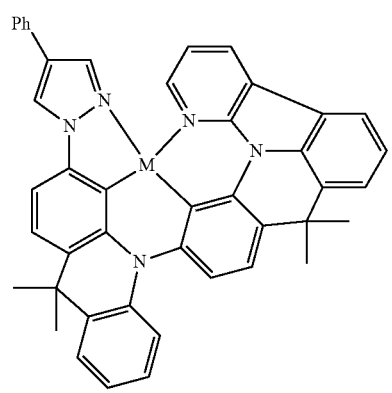
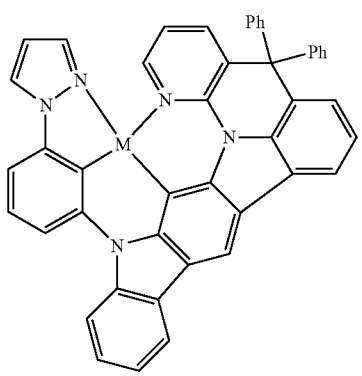
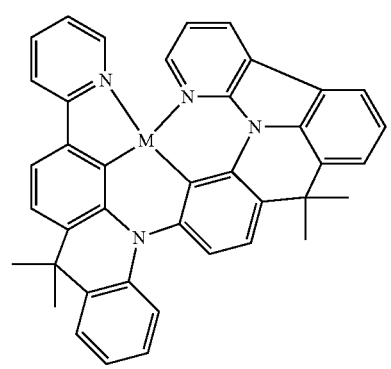
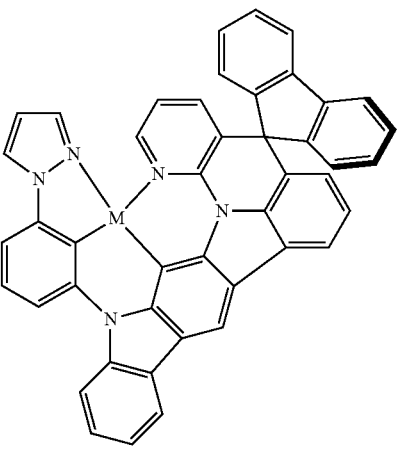
Structure 18 (M = Pt or Pd)
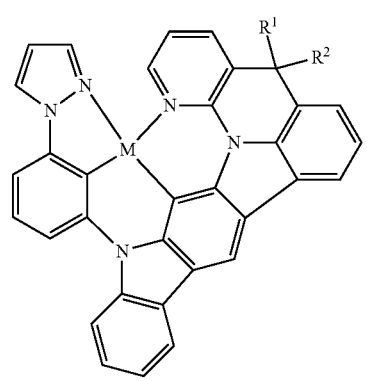
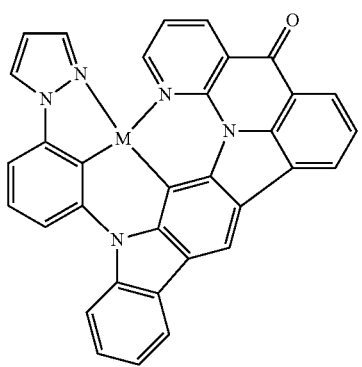

245
-continued
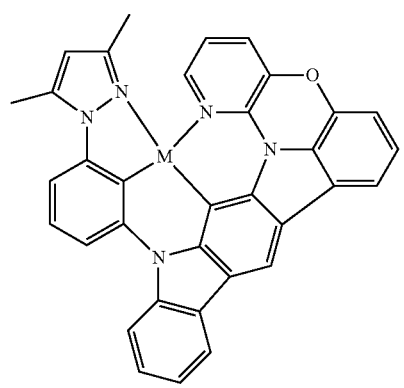
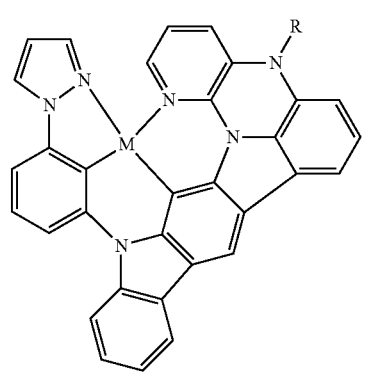
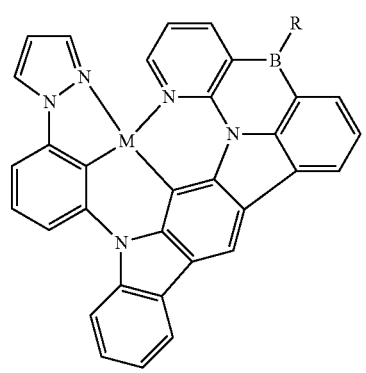
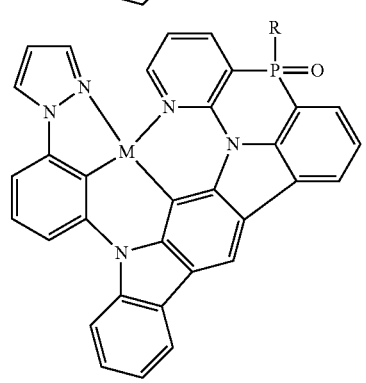
246
-continued
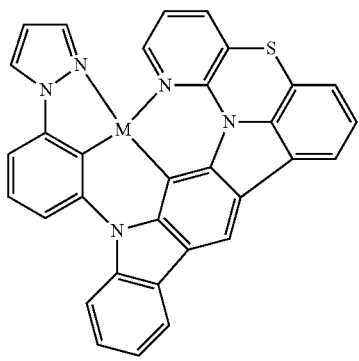
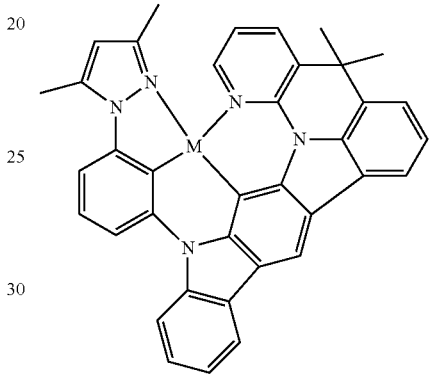
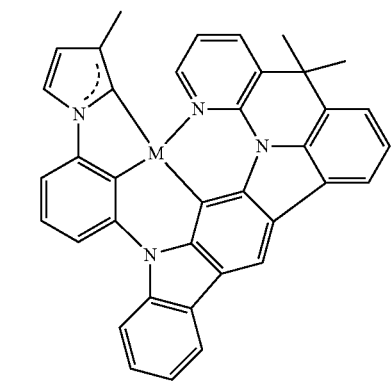
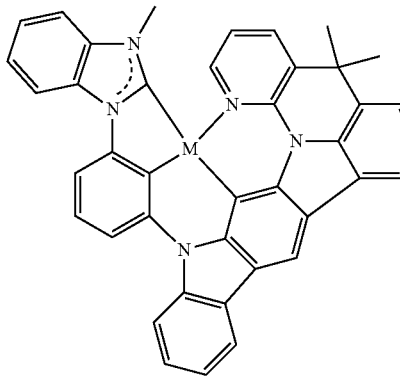

247
-continued
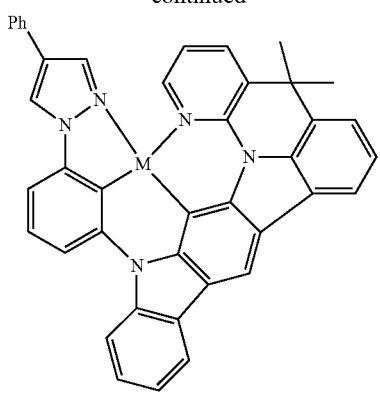
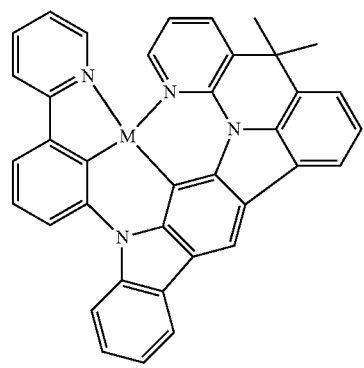
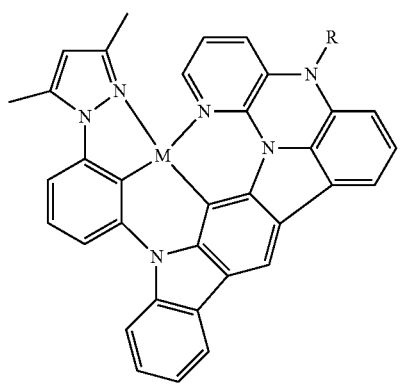
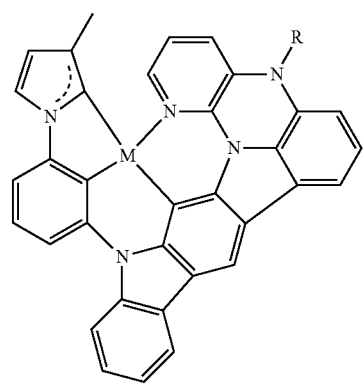
248
-continued
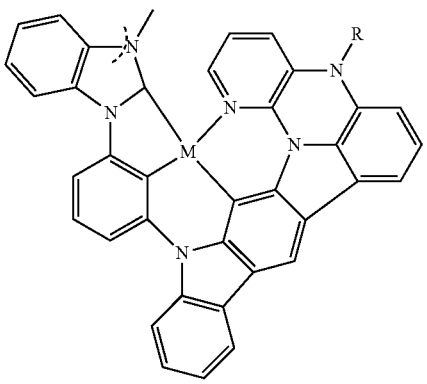
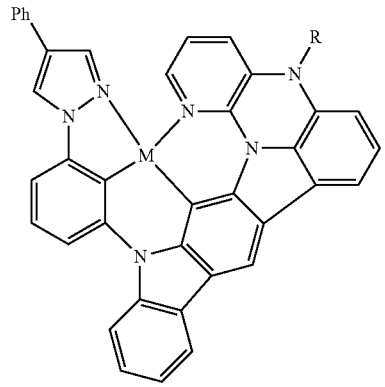
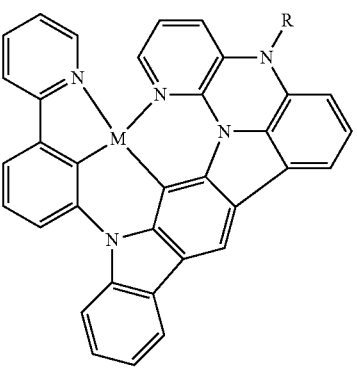
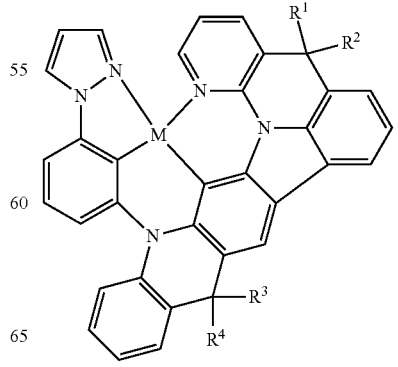

249
-continued
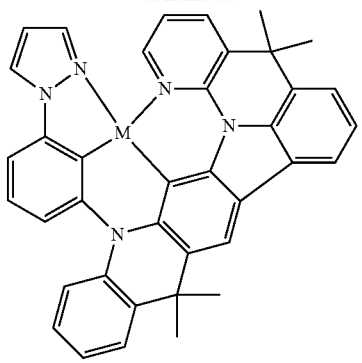
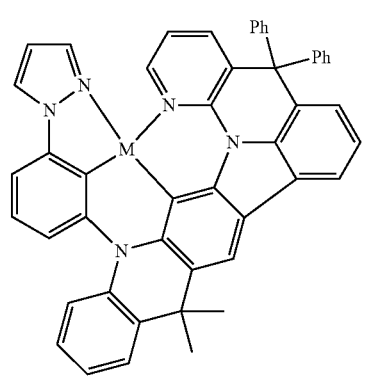
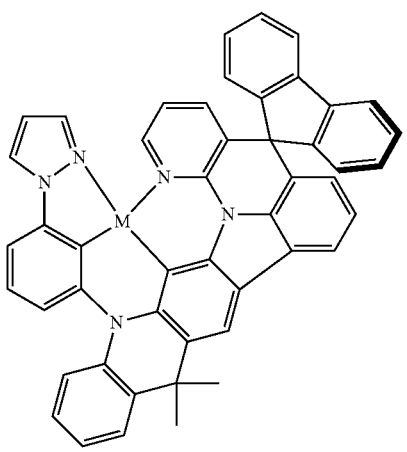
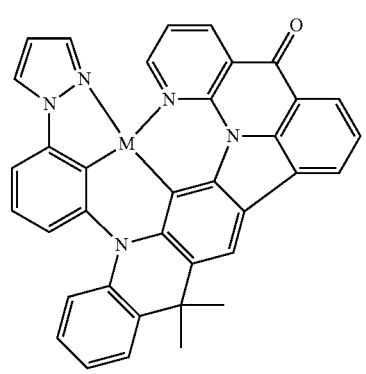
250
-continued
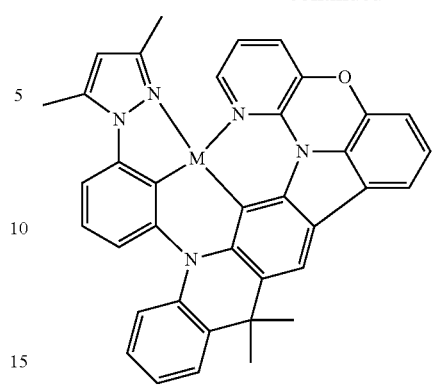
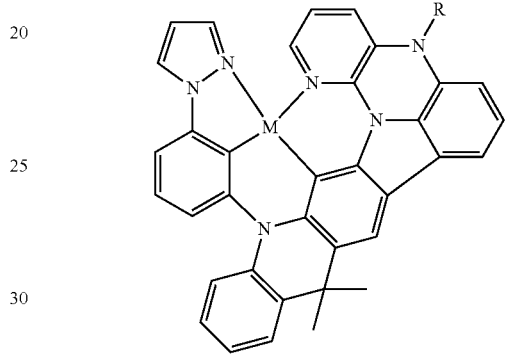
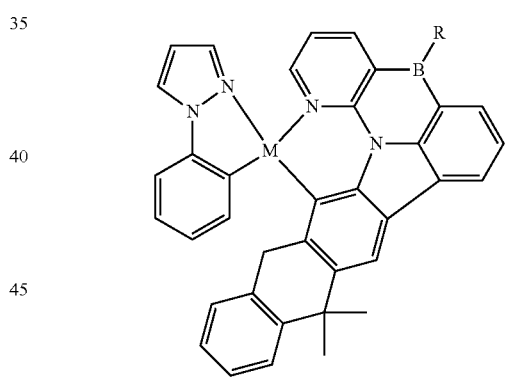
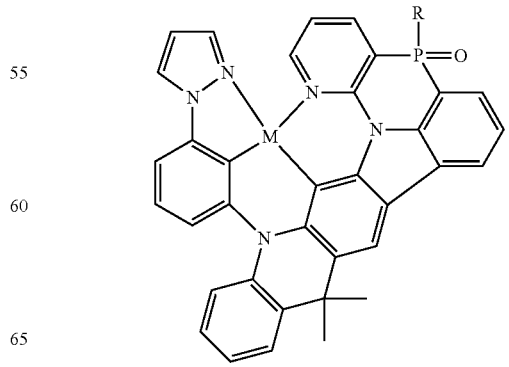

251
-continued
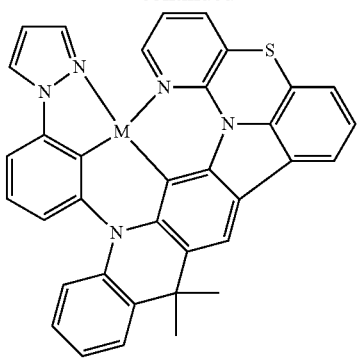
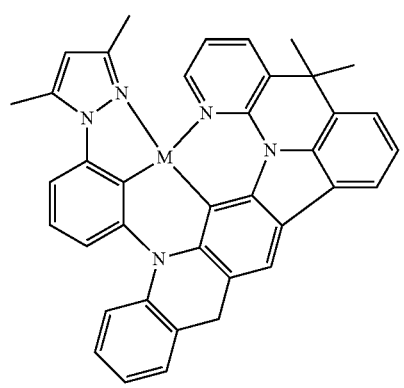
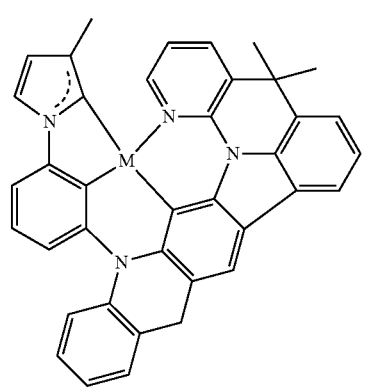
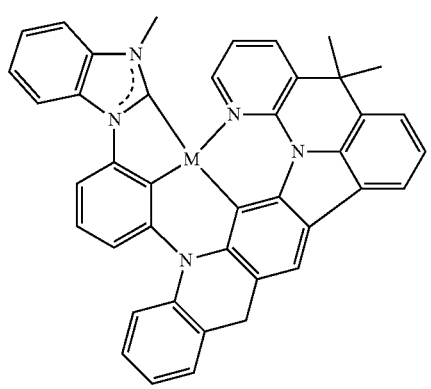
252
-continued
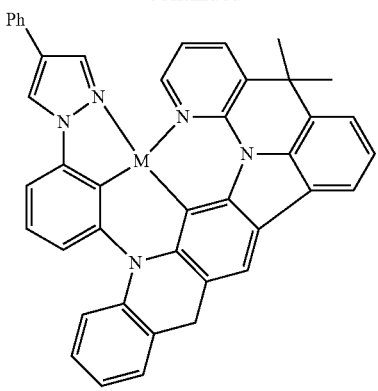
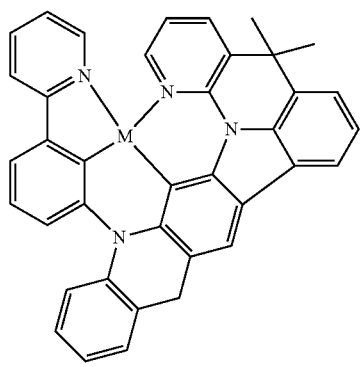
Structure 19 (M = Pt or Pd)
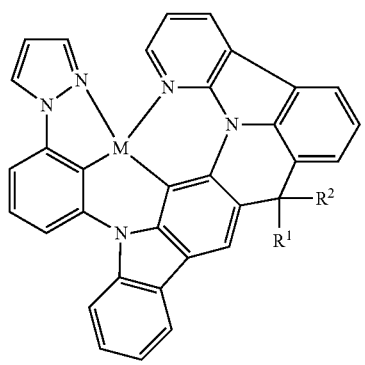
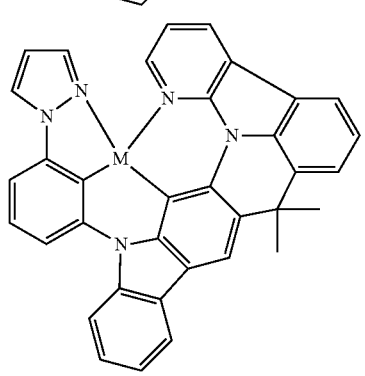

253
-continued
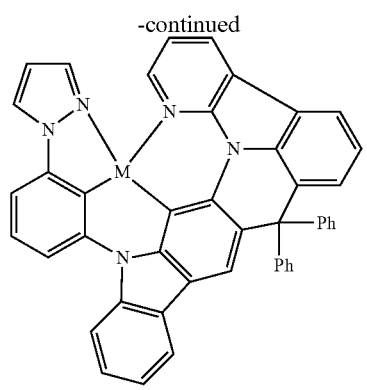
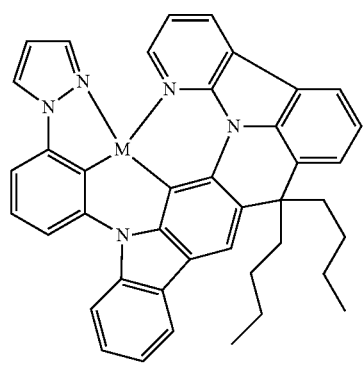
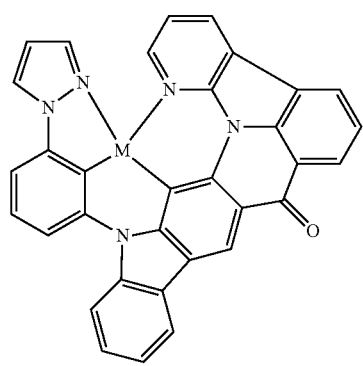
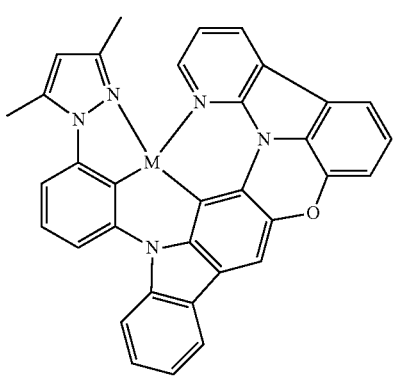
254
-continued
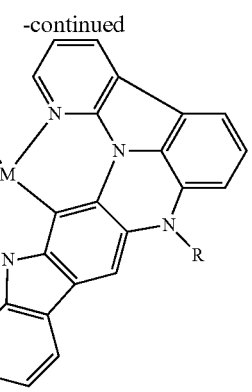
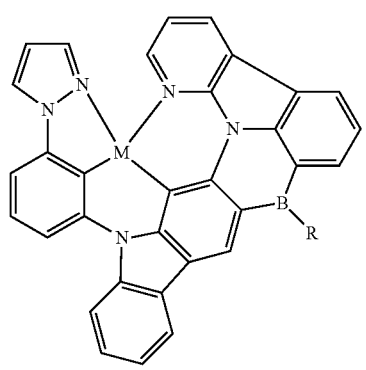
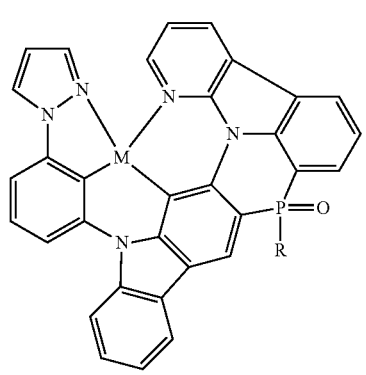
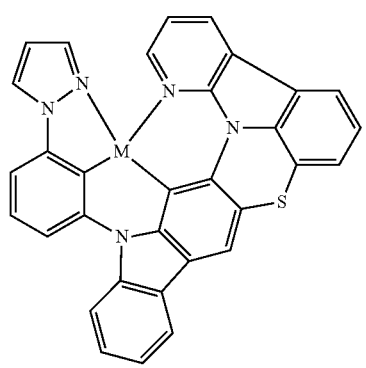

255
-continued
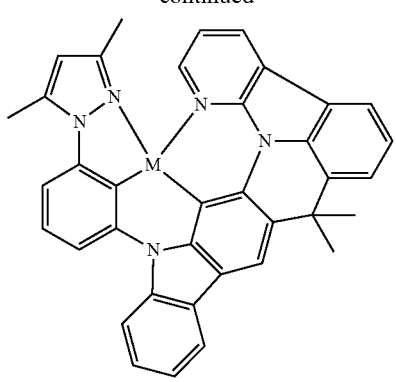
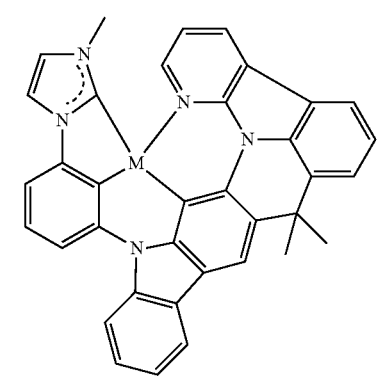
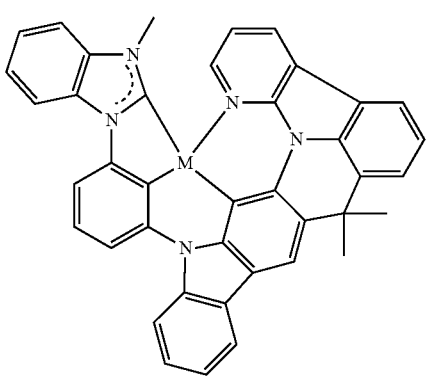
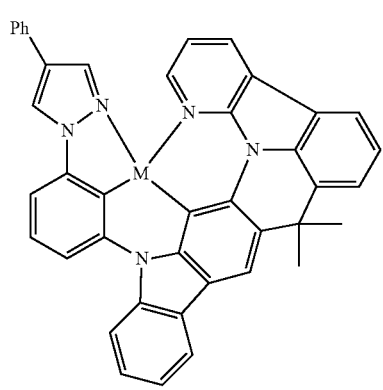
256
-continued
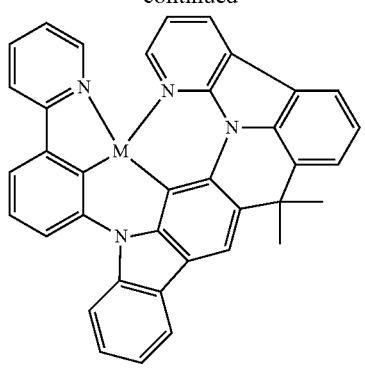
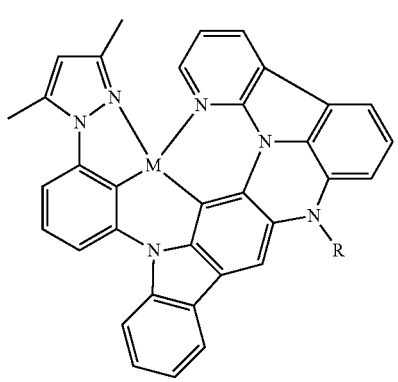
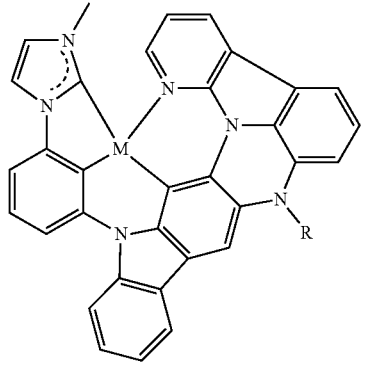
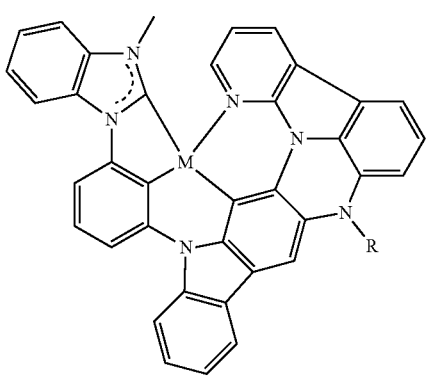

257
-continued
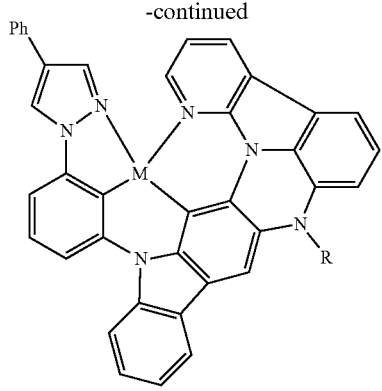
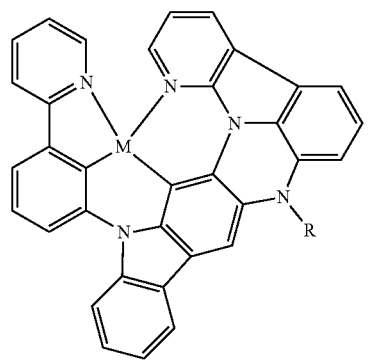
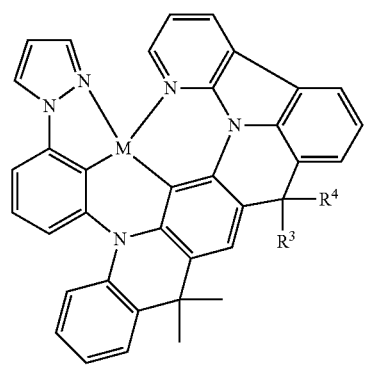
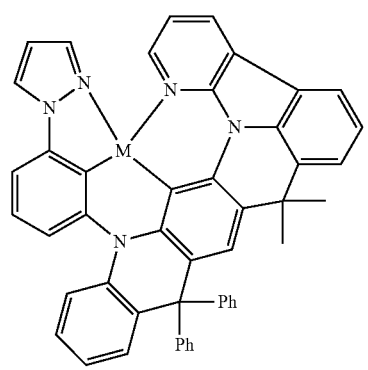
258
-continued
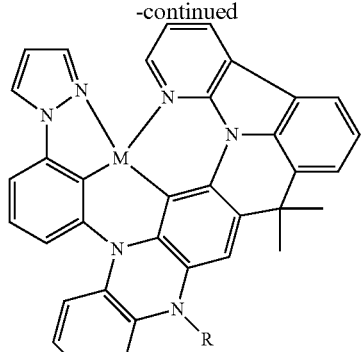
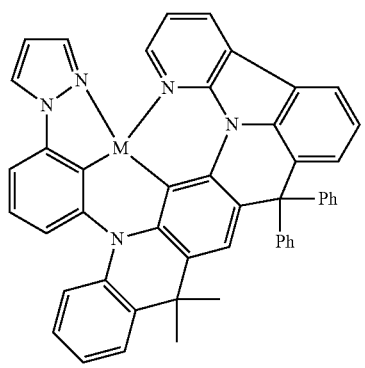
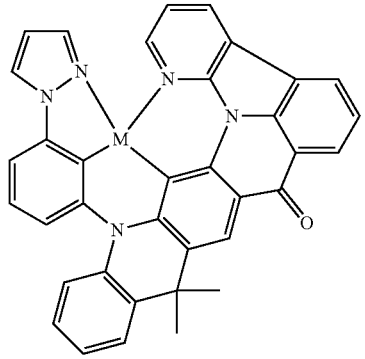
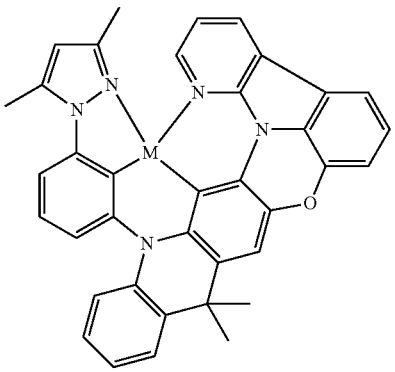

259
-continued

260
-continued

261
-continued
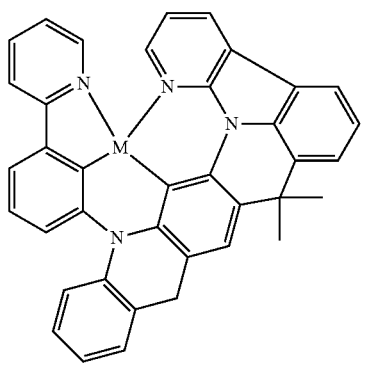
Structure 20 (M = Pt or Pd)
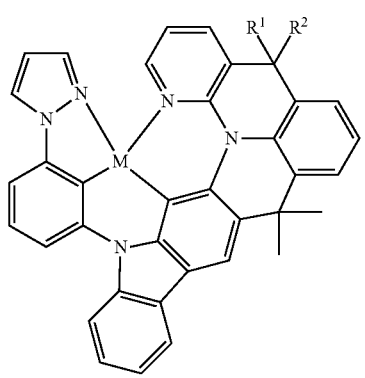
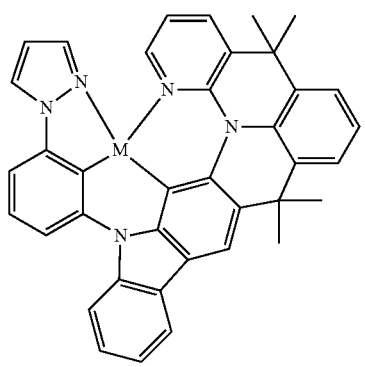
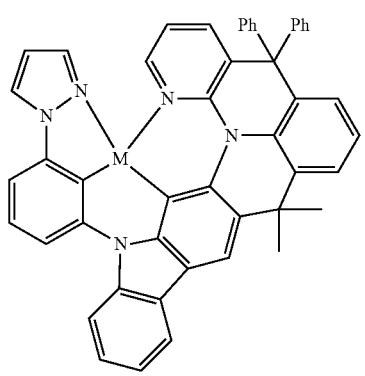
262
-continued
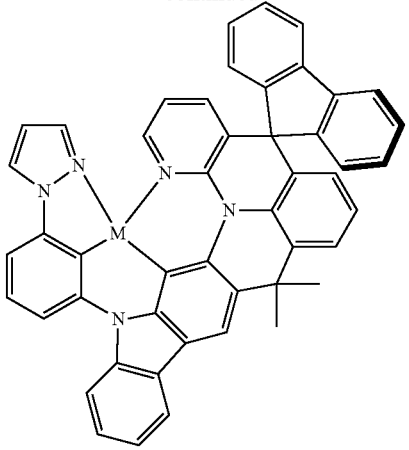
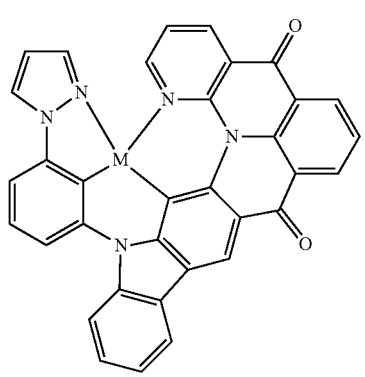
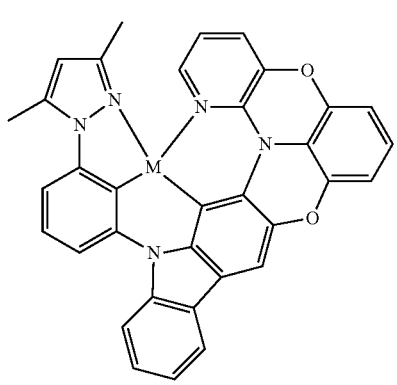
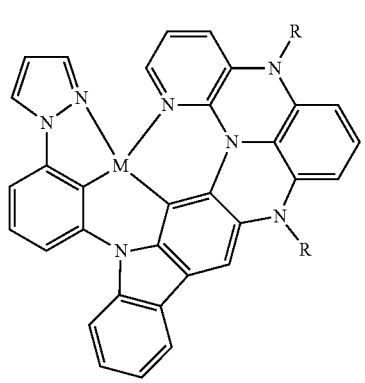

263
-continued
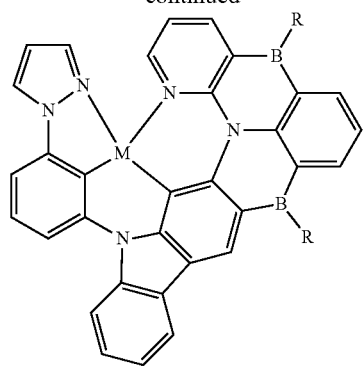
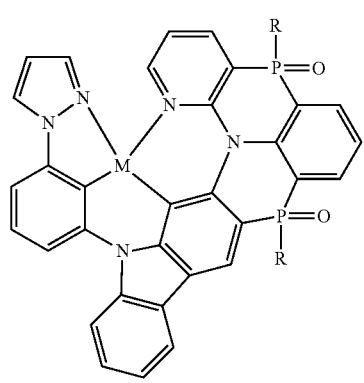
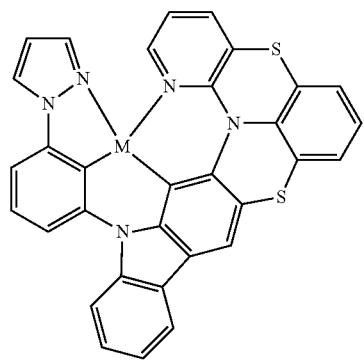
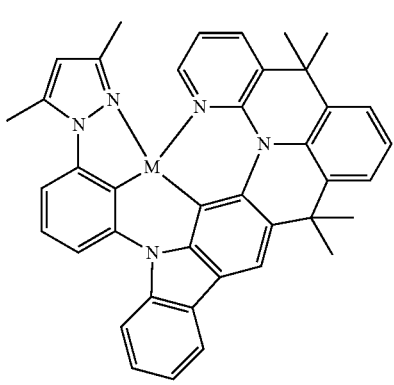
264
-continued
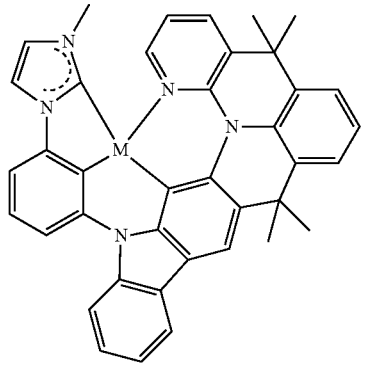
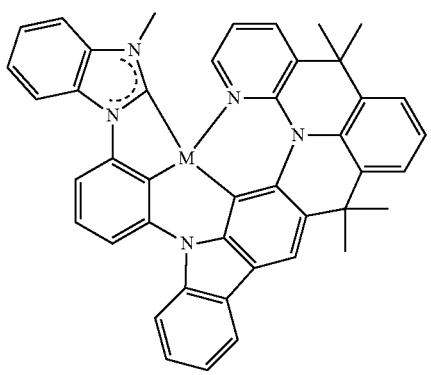
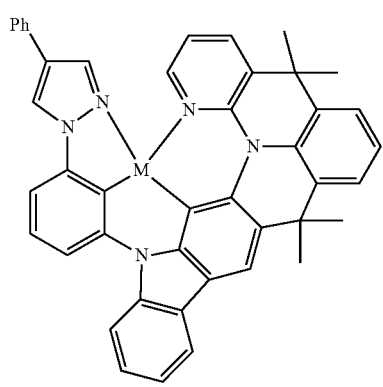
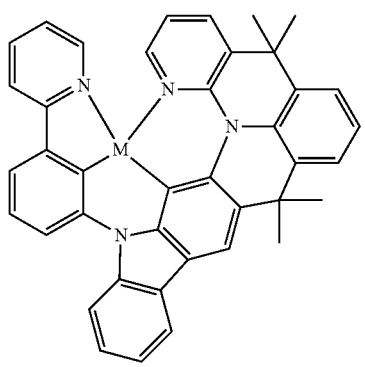

265
-continued
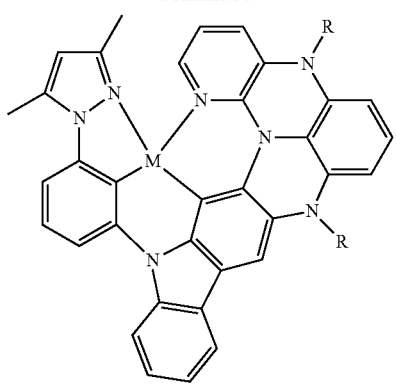
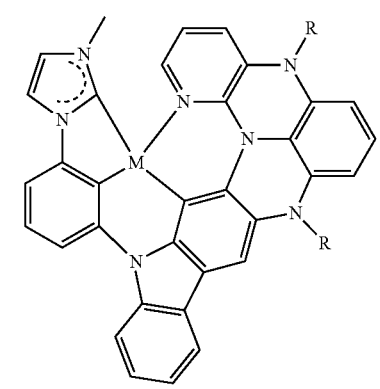
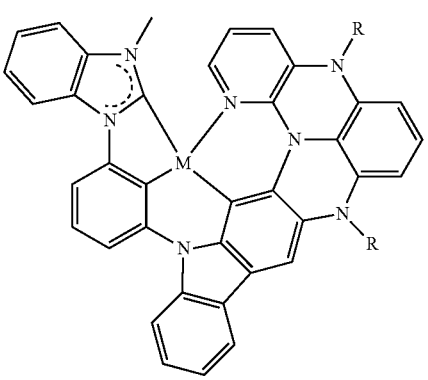
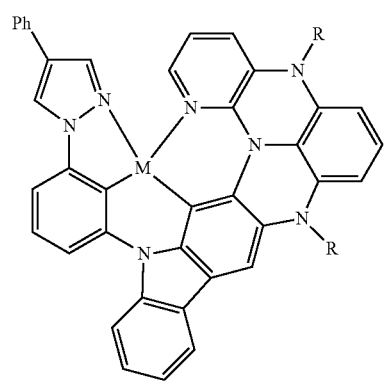
266
-continued
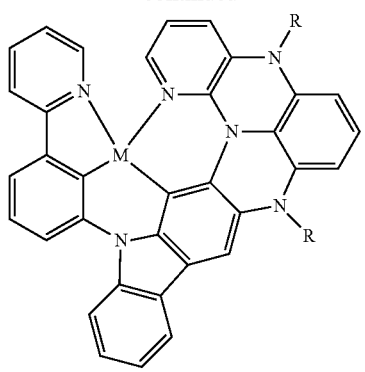
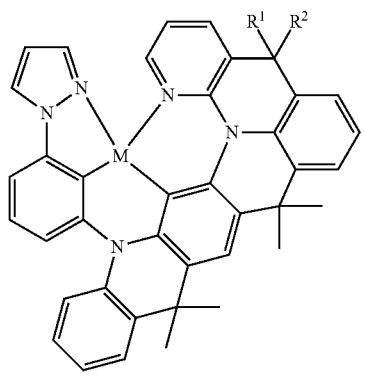
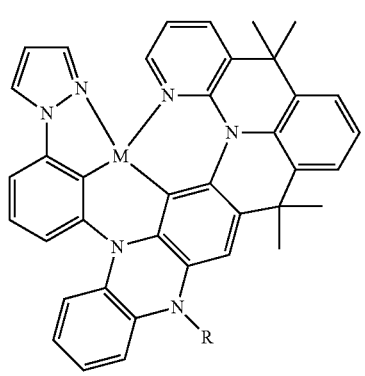
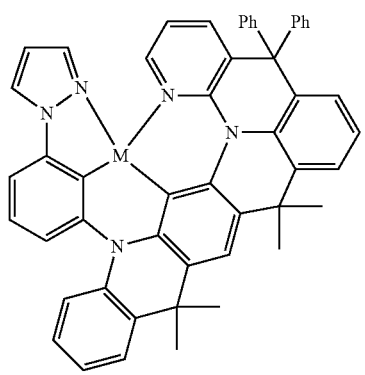

267
-continued
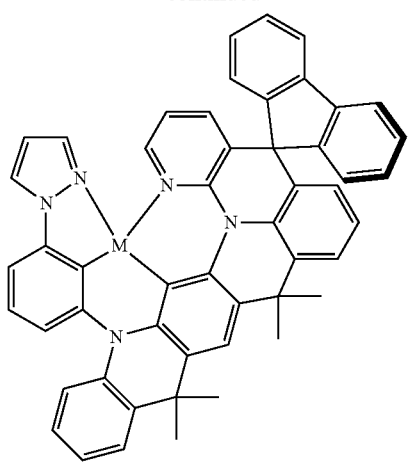
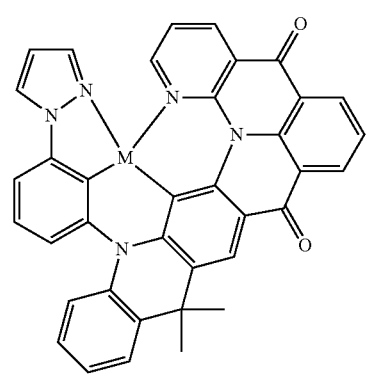
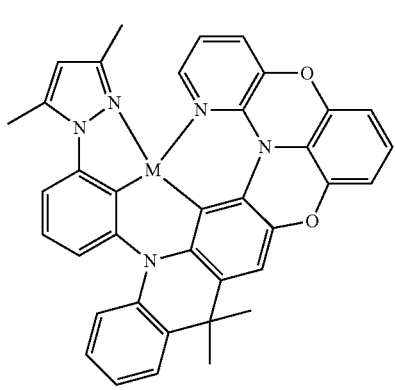
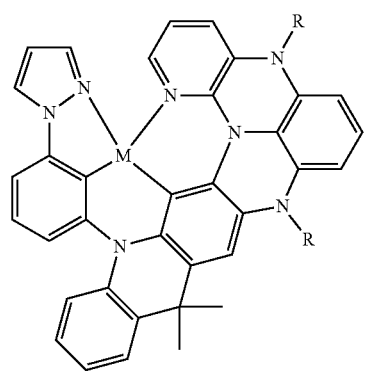
268
-continued
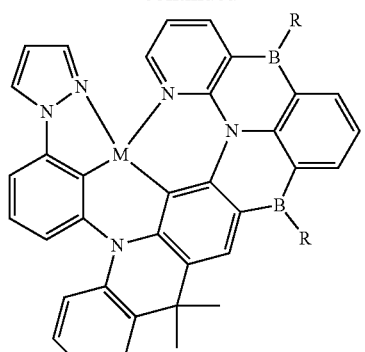
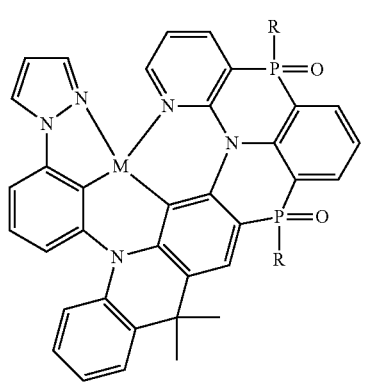
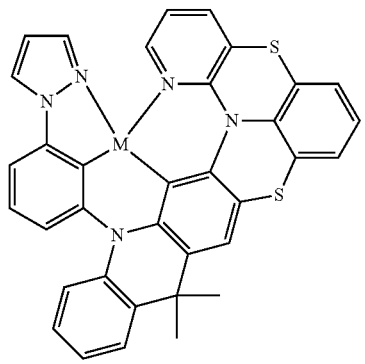
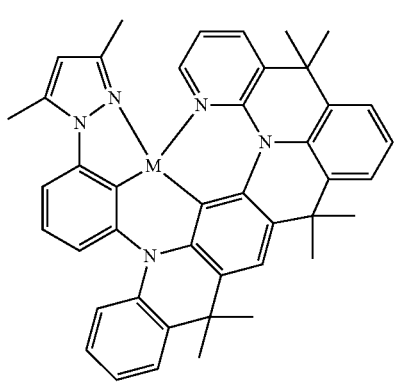

-continued
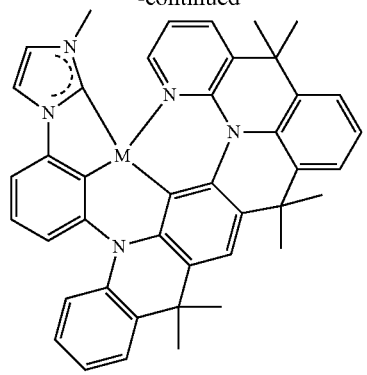
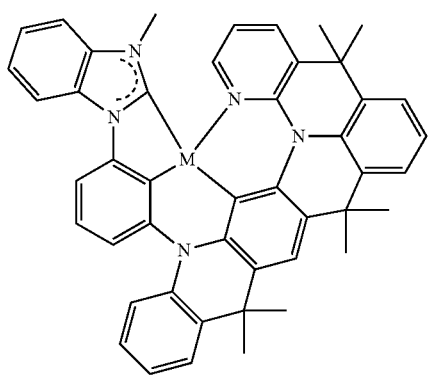
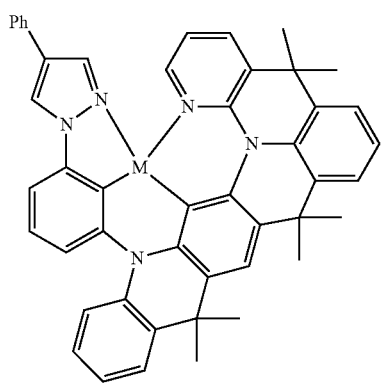
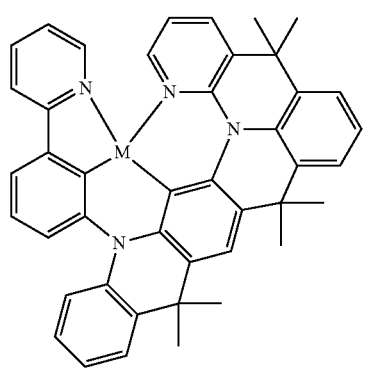
Structure 21 (M = Pt or Pd)
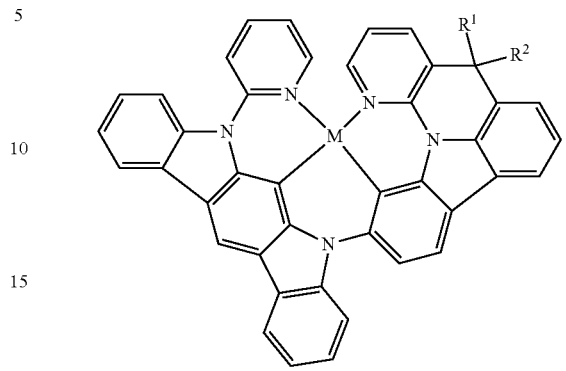
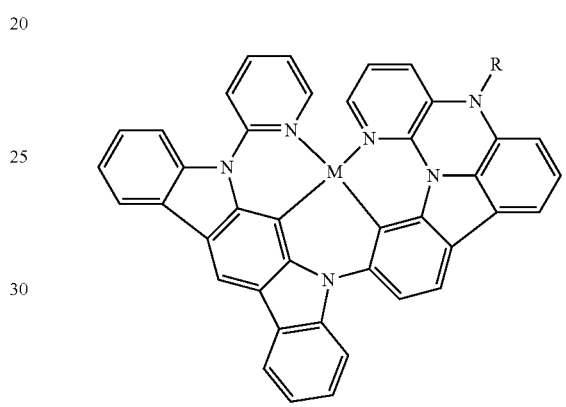
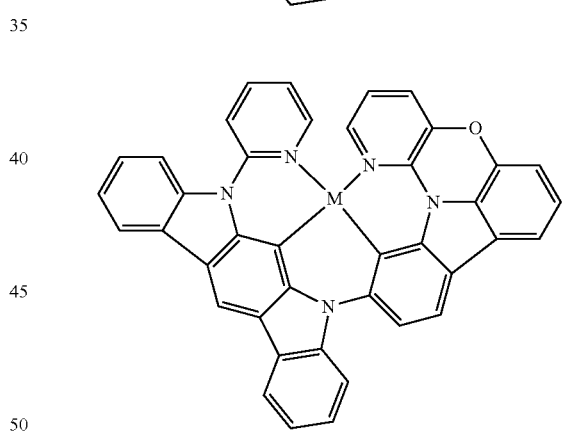
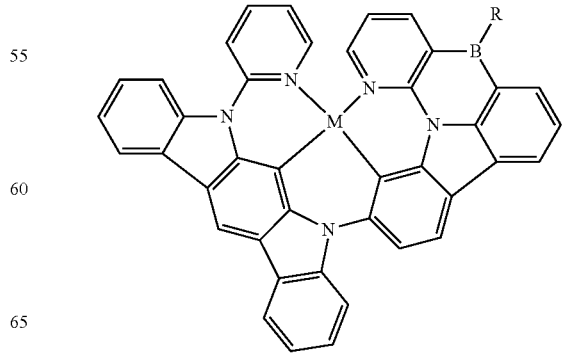

271
-continued
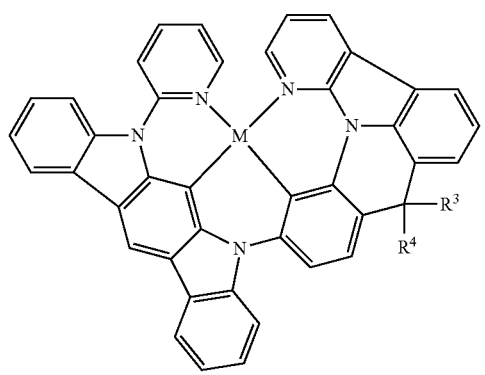
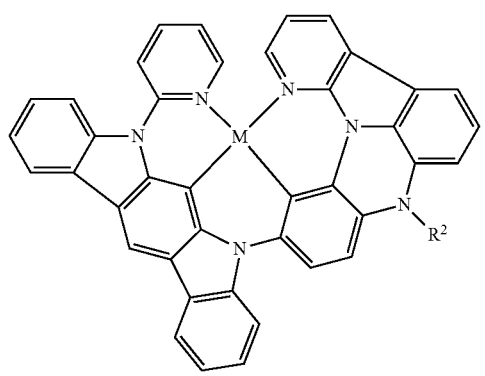
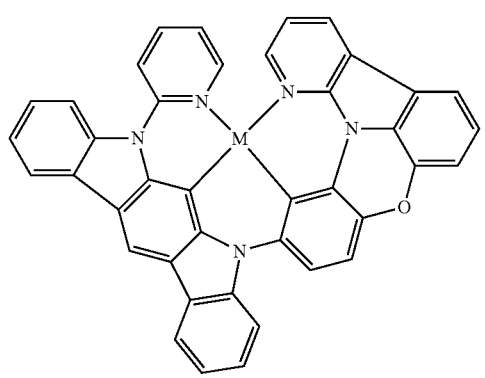
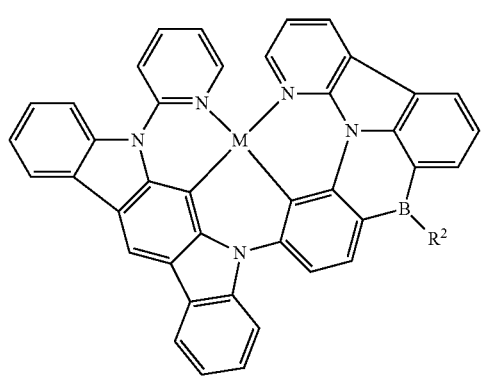
272
-continued
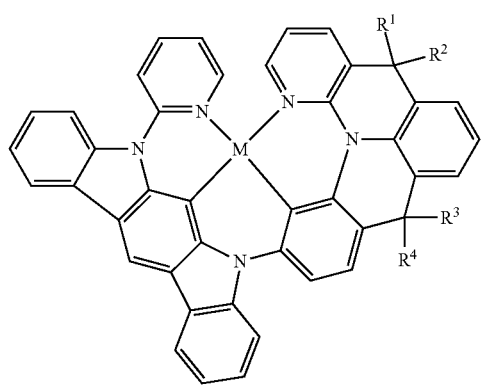
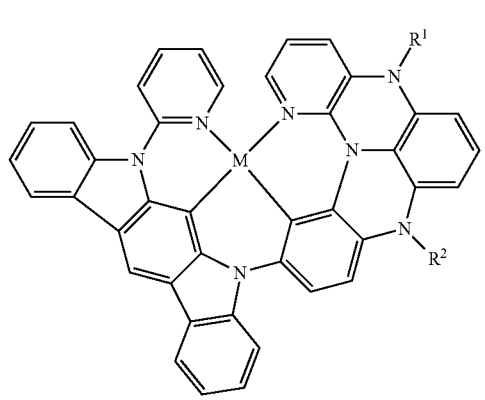
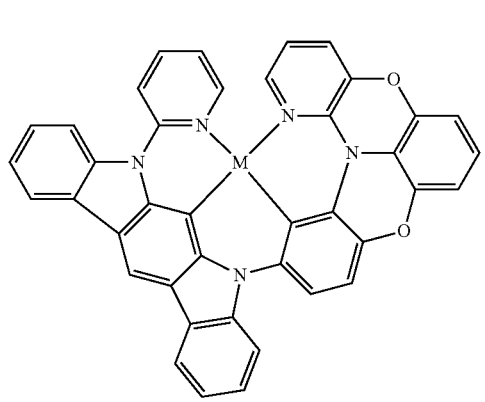
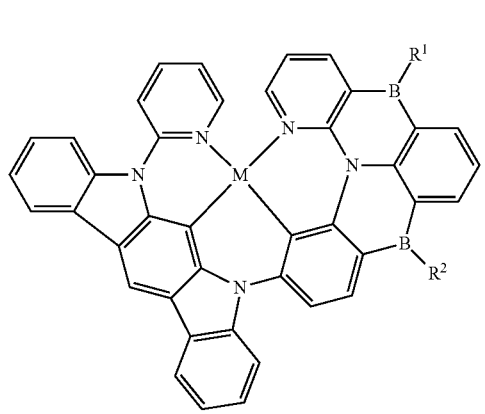

273
-continued
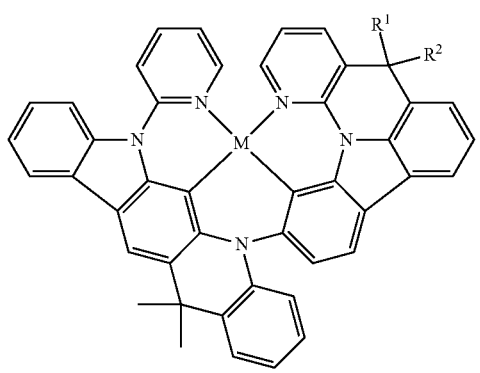
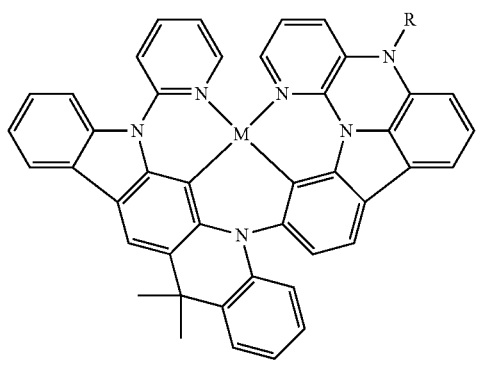
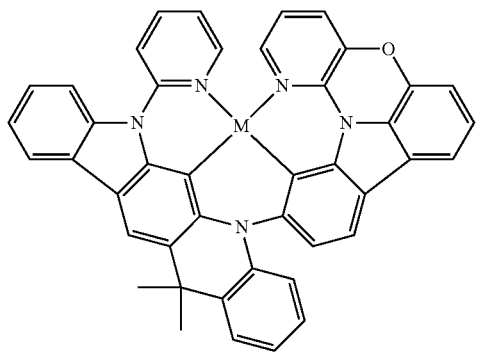
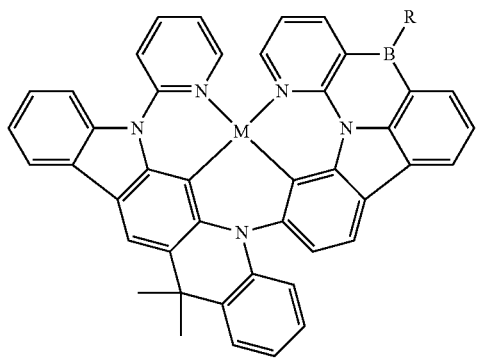
274
-continued
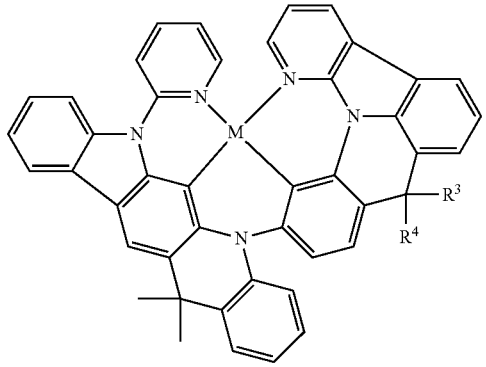
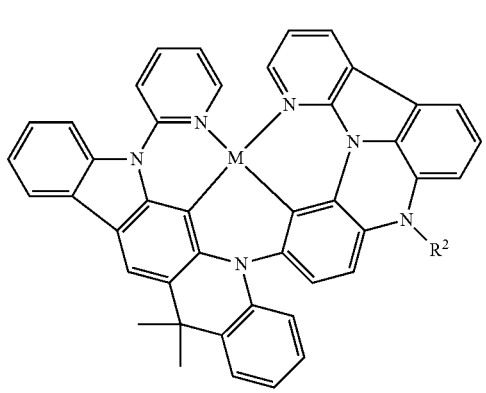
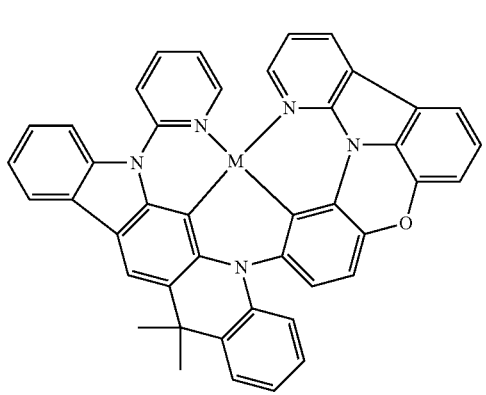
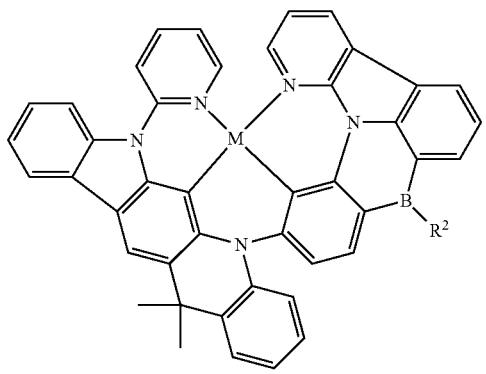

275
-continued
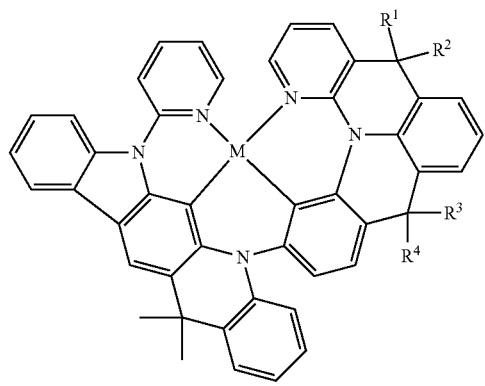
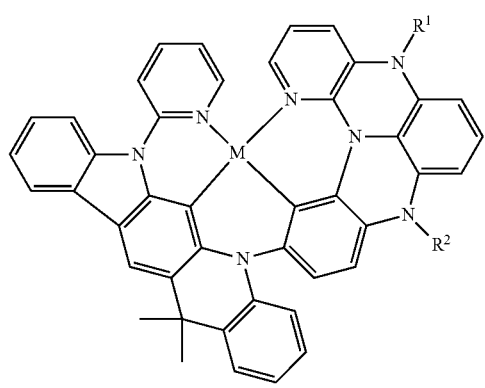
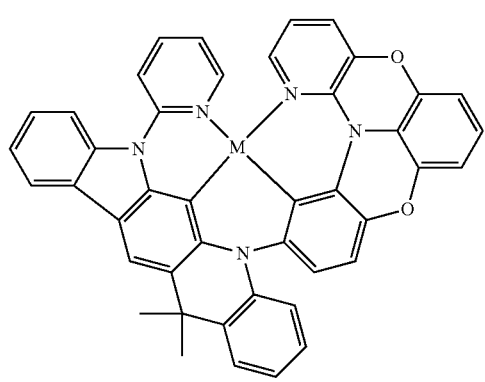
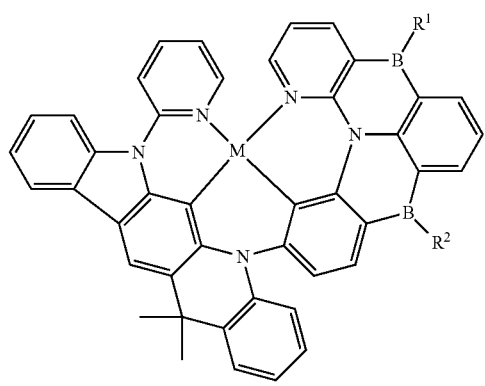
276
-continued
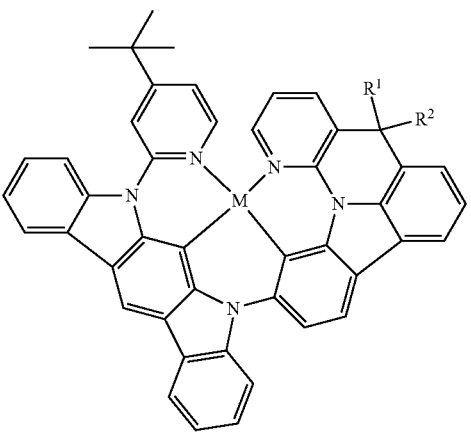
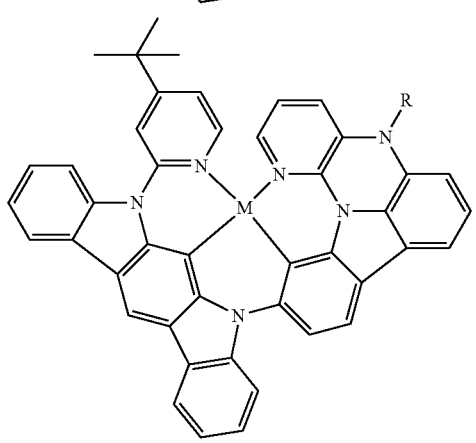
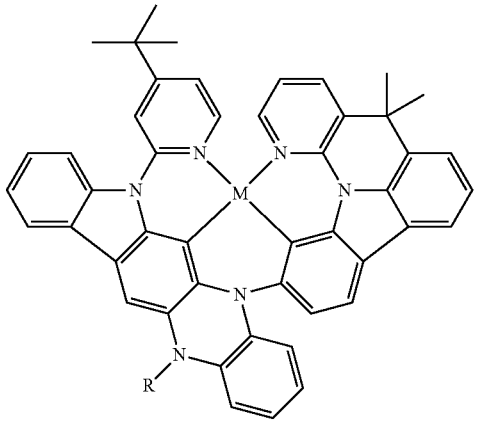
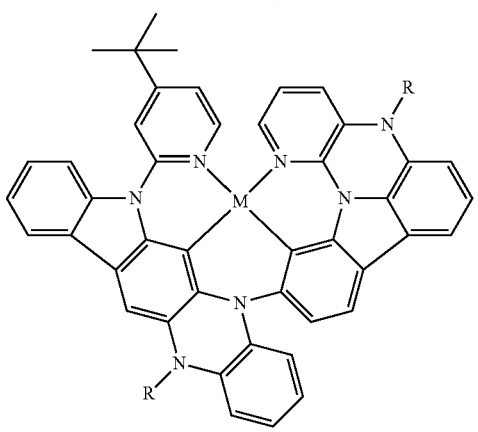

Structure 22 (M = Pt or Pd)
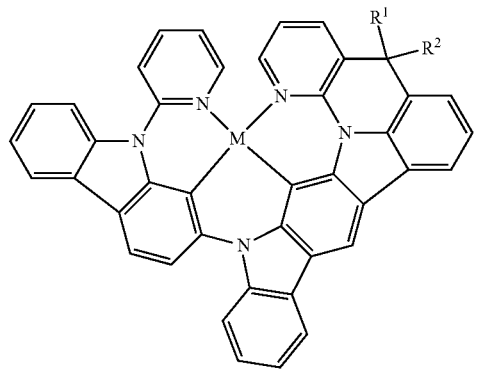
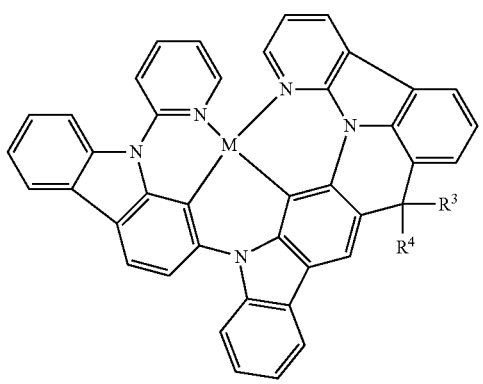
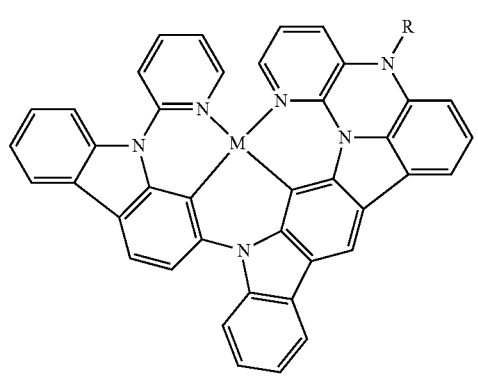
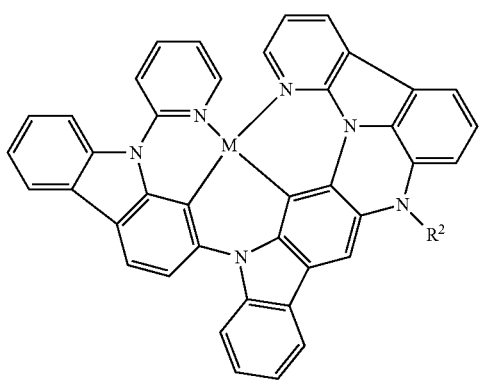
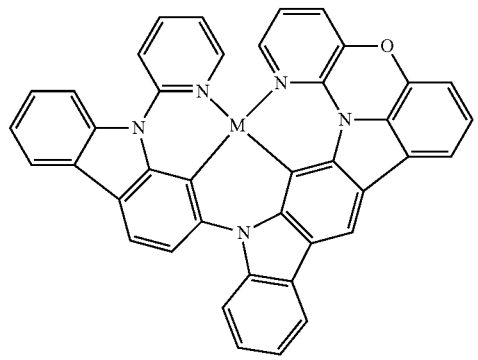
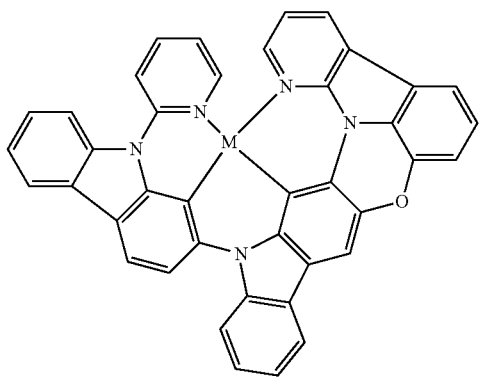
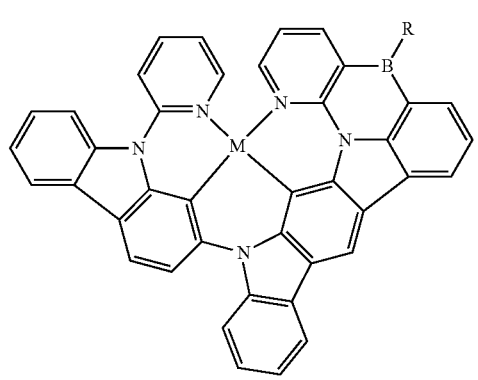
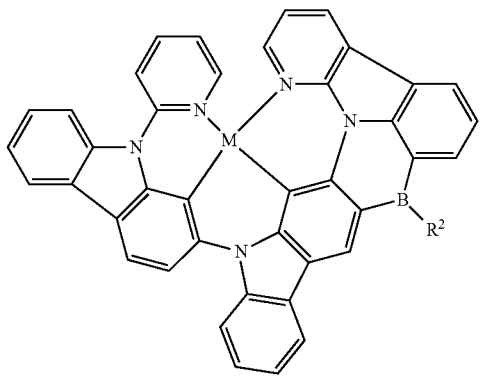

279
-continued
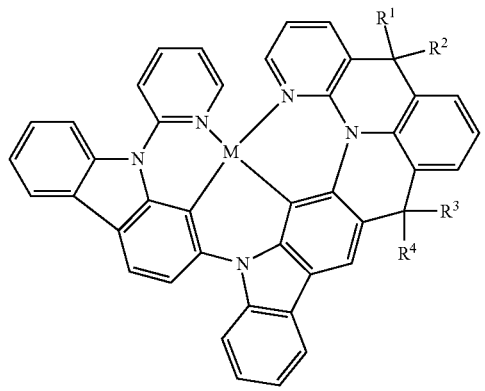
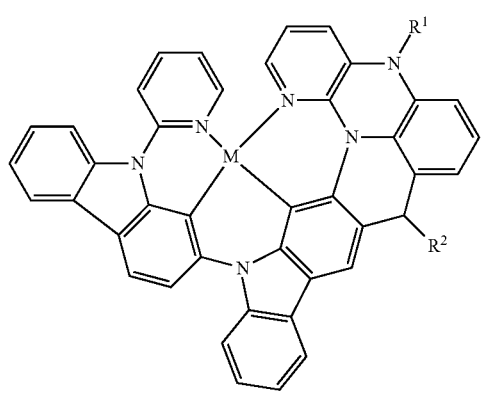
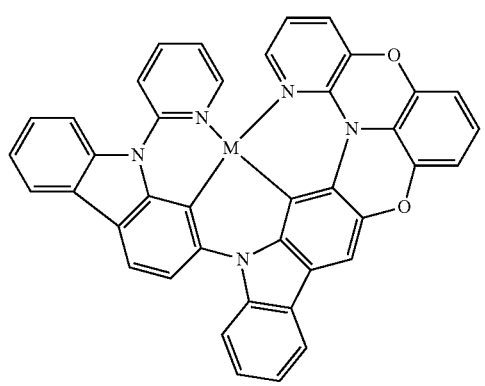
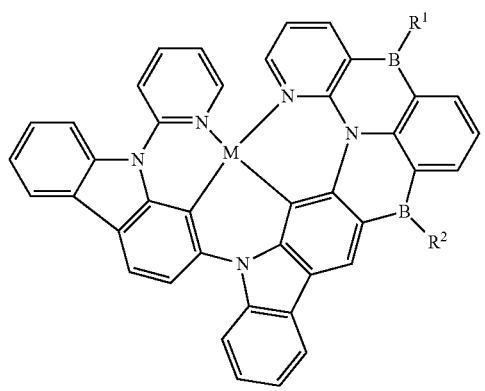
280
-continued
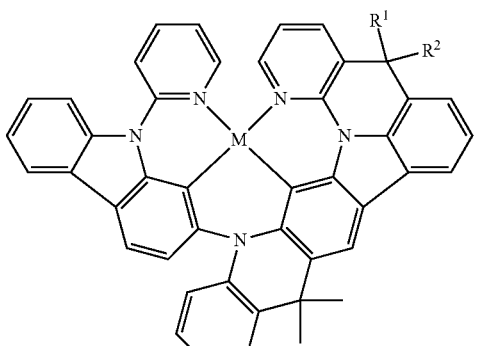
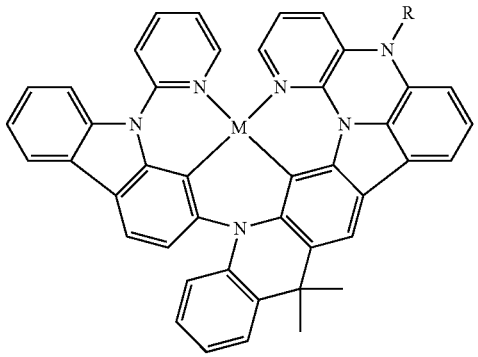
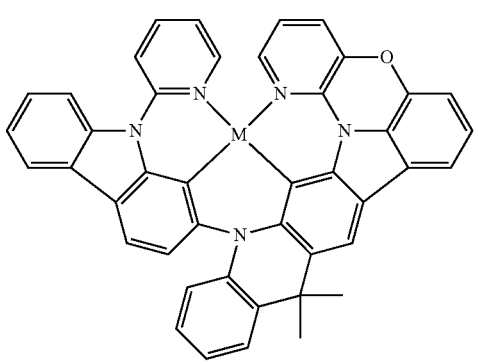
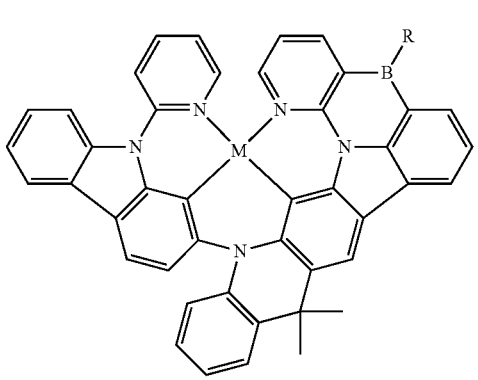

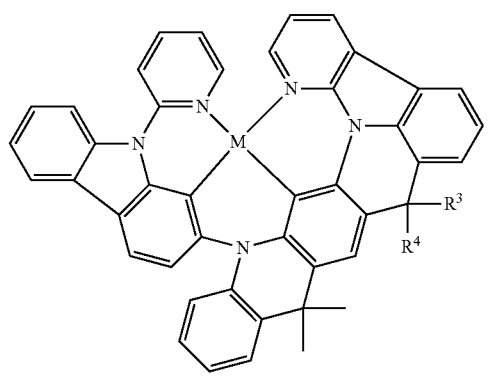
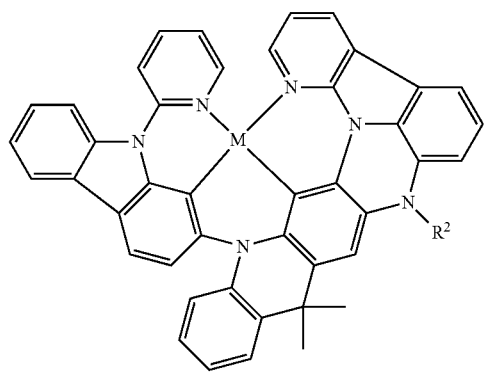
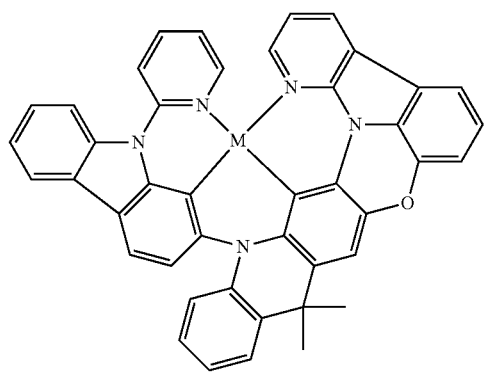
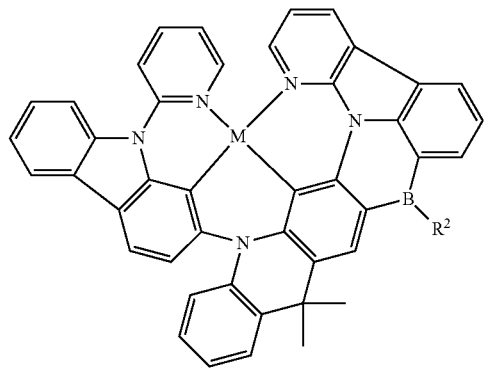
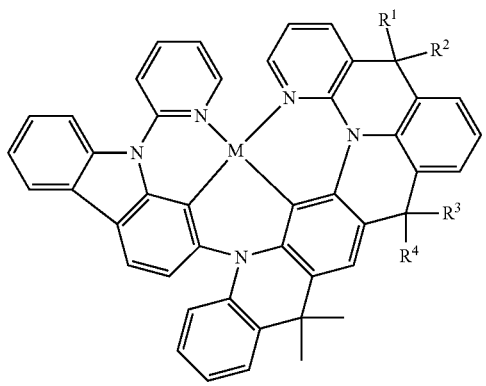
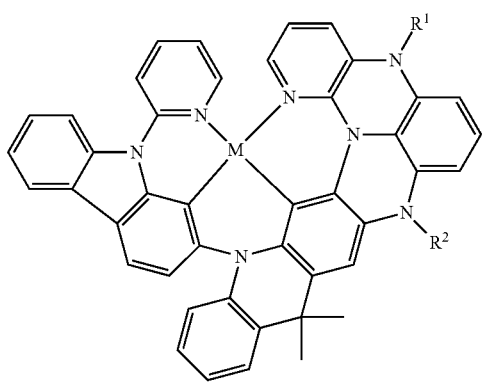
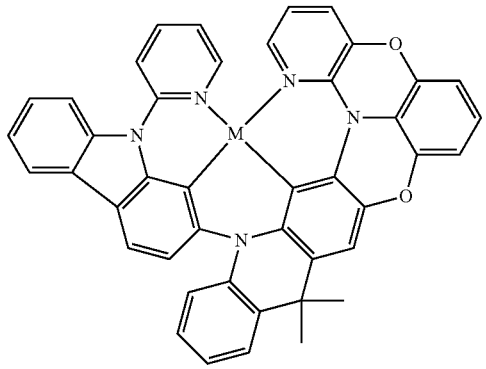
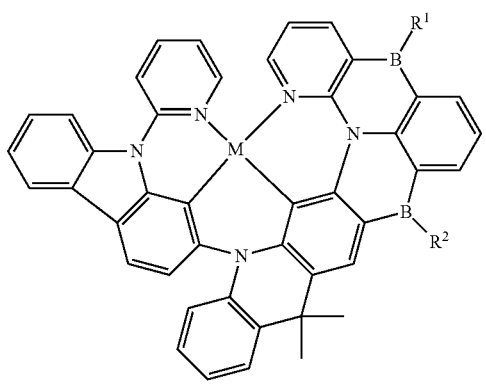

-continued
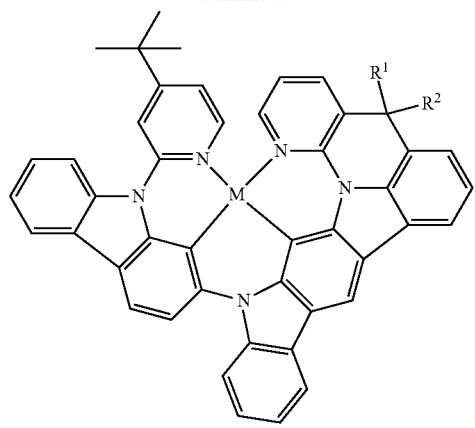
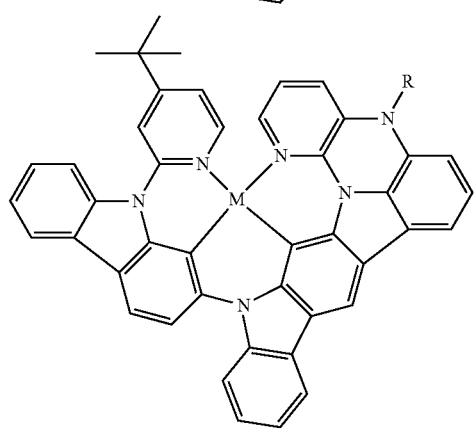
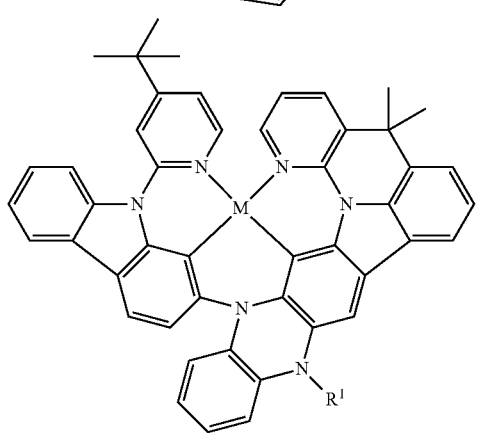
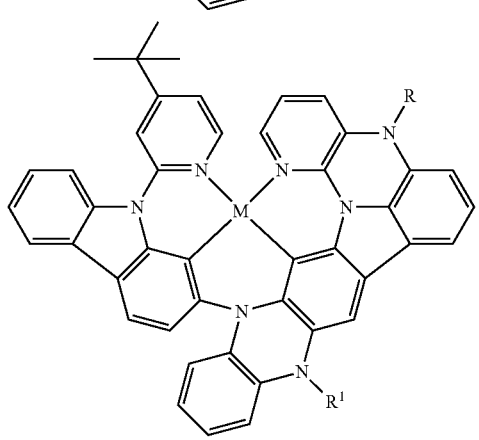
Structure 23 (M = Pt or Pd)
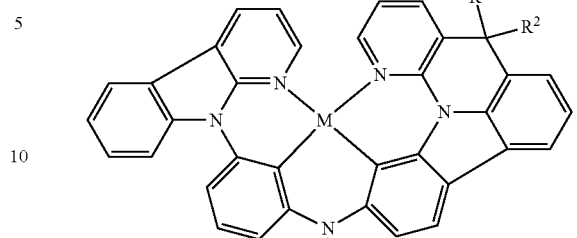
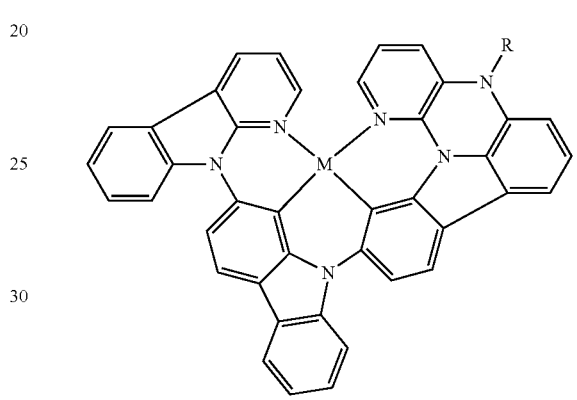
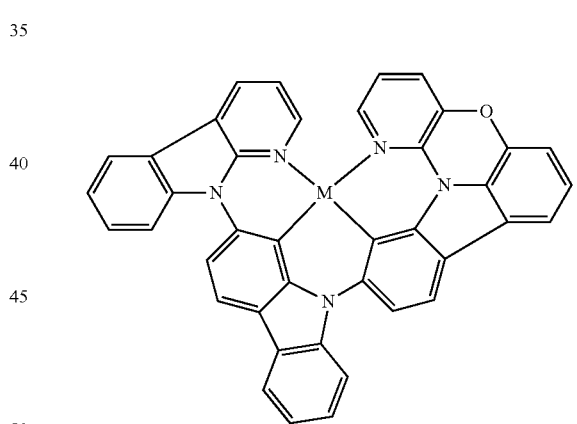
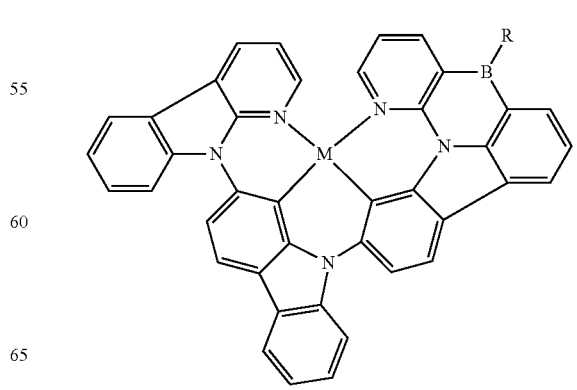

285
-continued
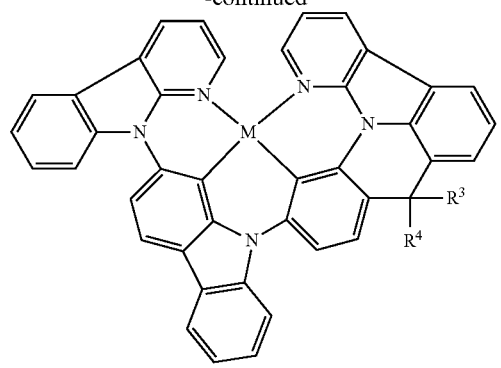
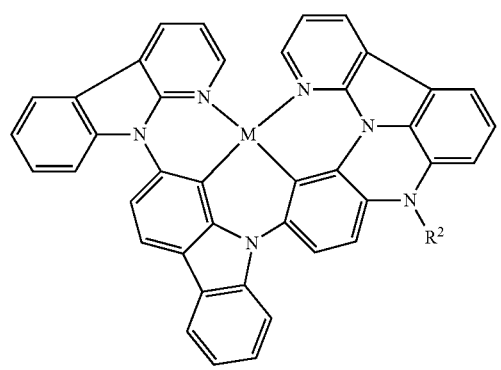
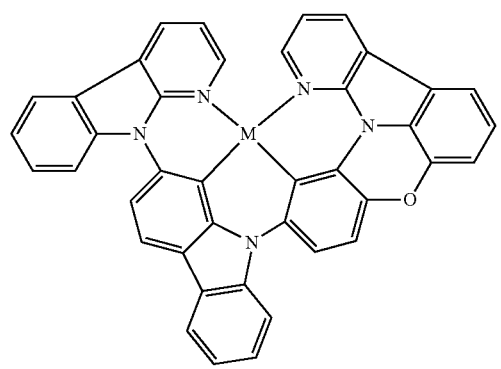
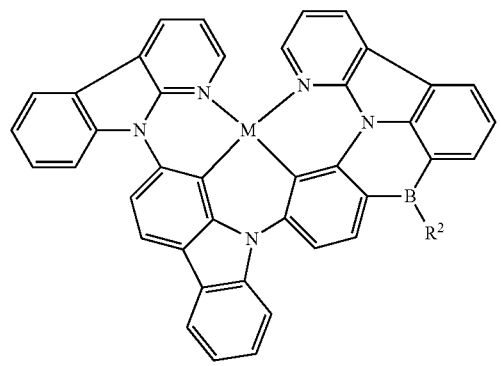
286
-continued
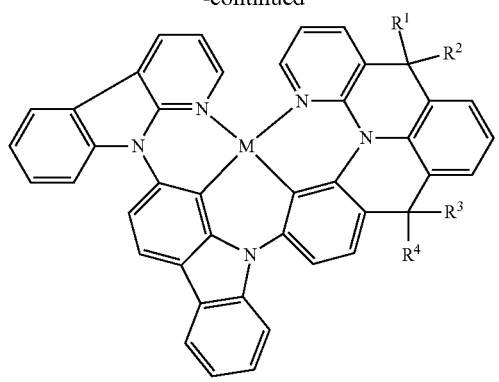
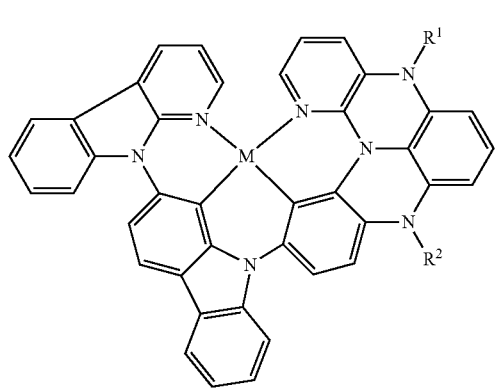
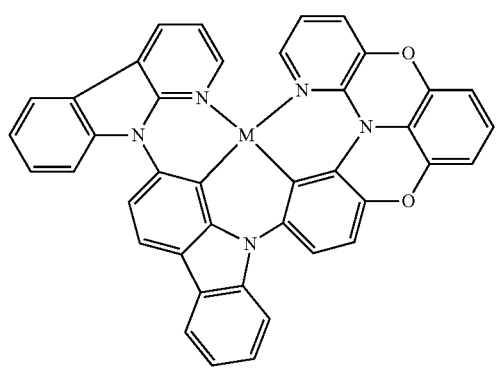
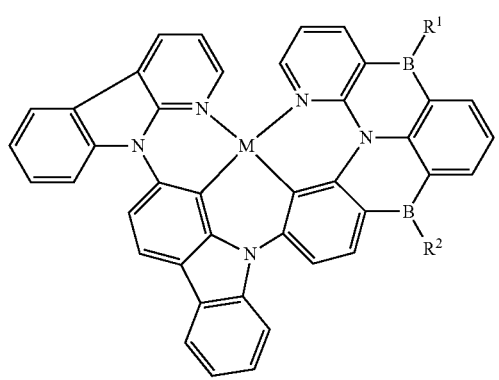

287
-continued
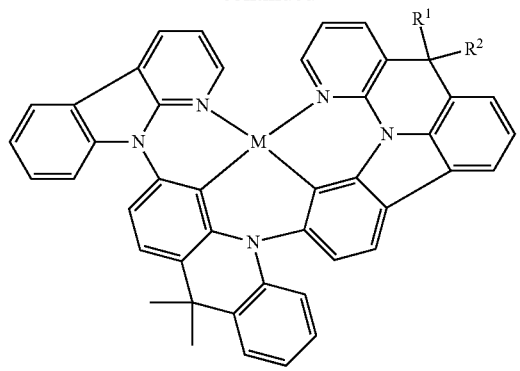
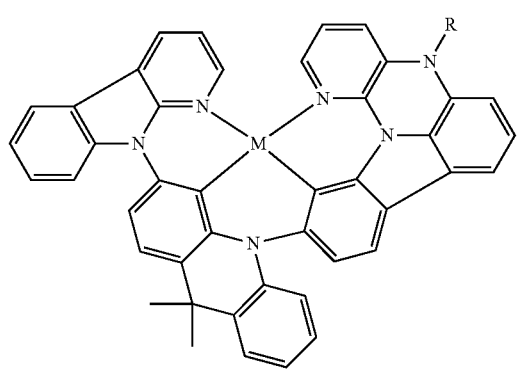
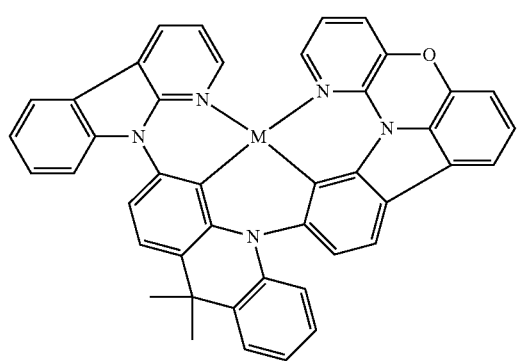
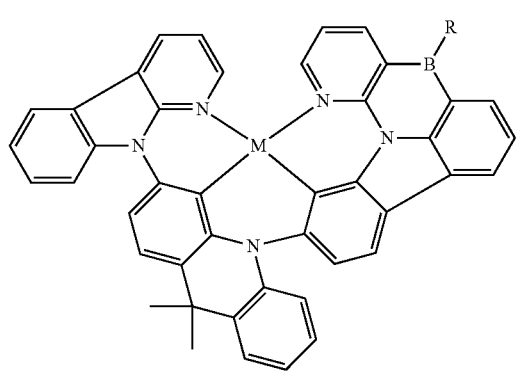
288
-continued
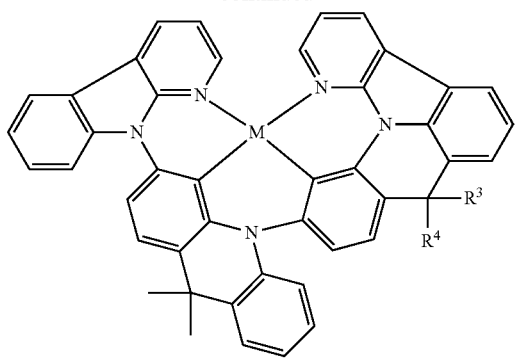
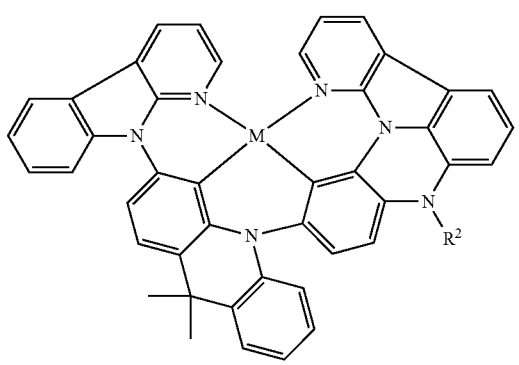
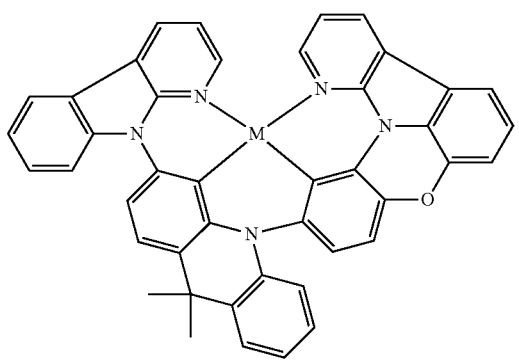
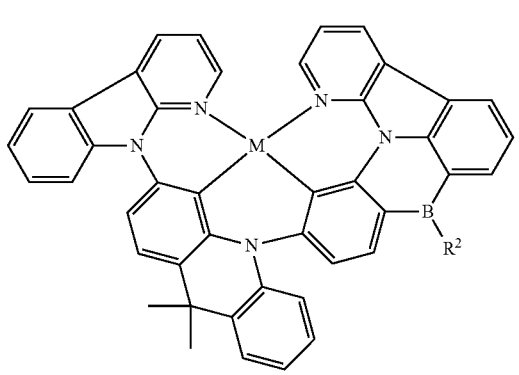

289
-continued
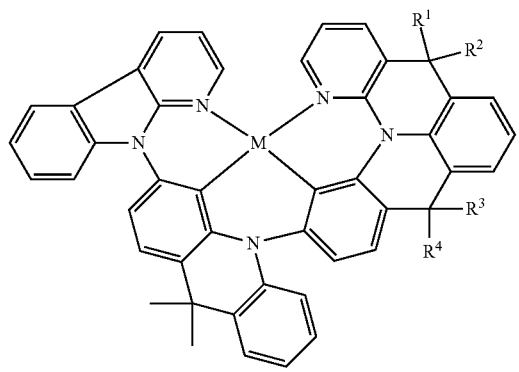
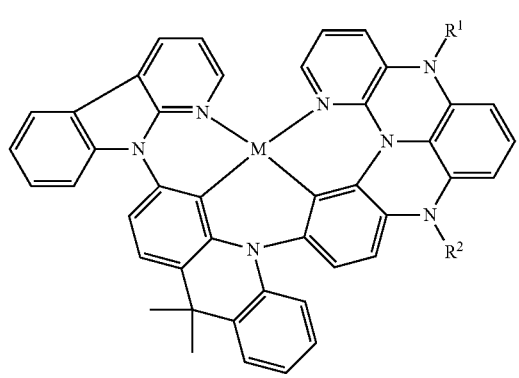
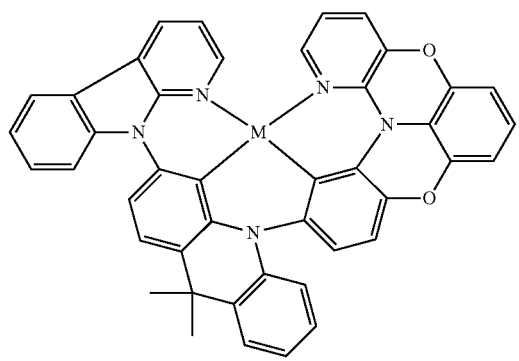
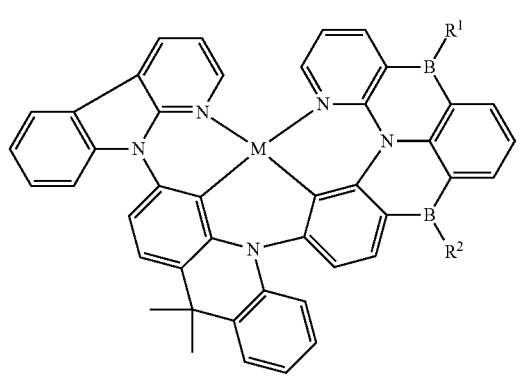
290
-continued
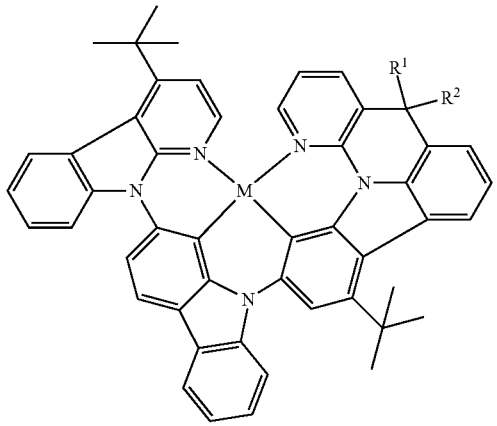
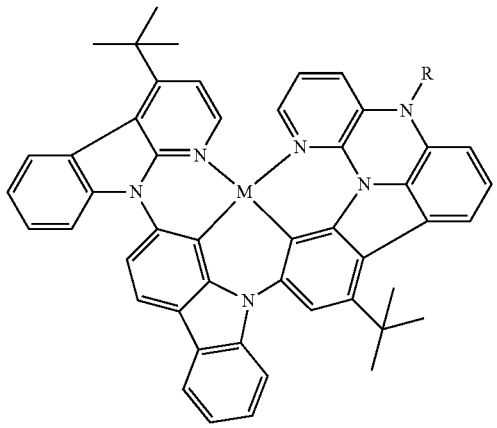
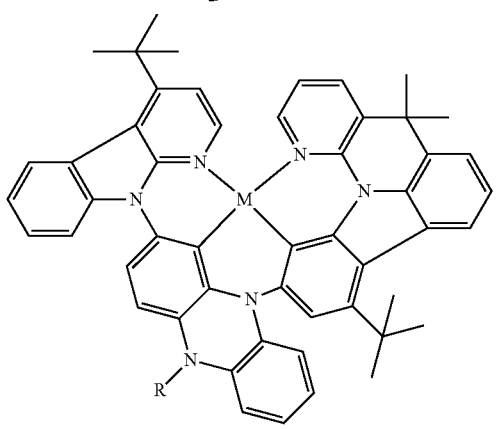
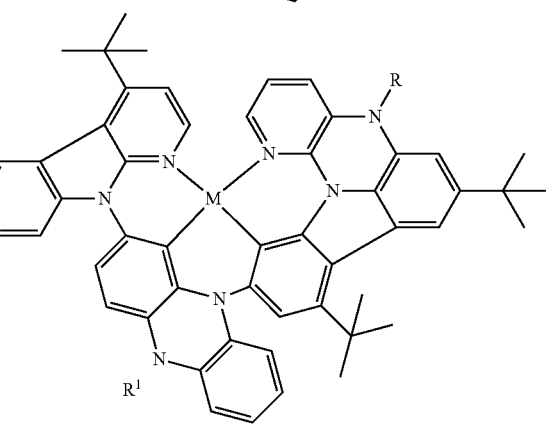

-continued
Structure 24 (M = Pt or Pd)
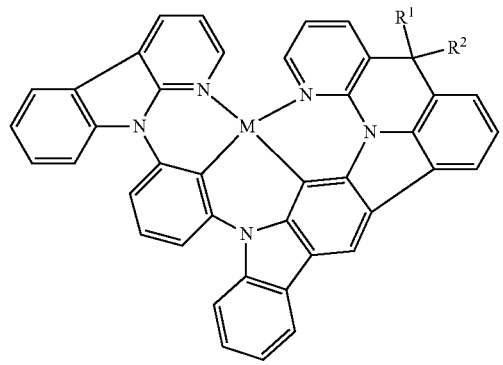
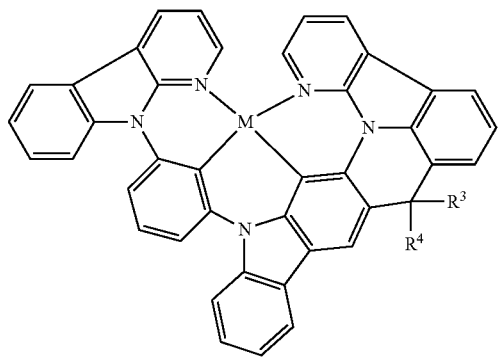
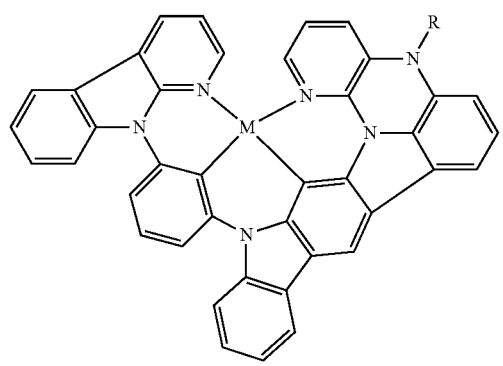
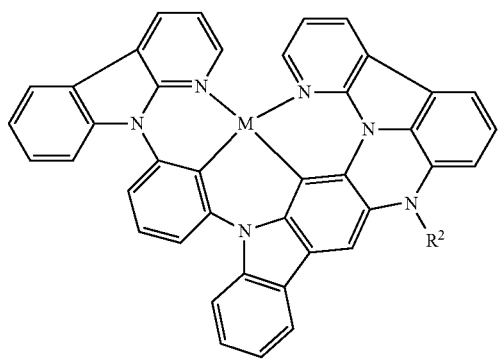
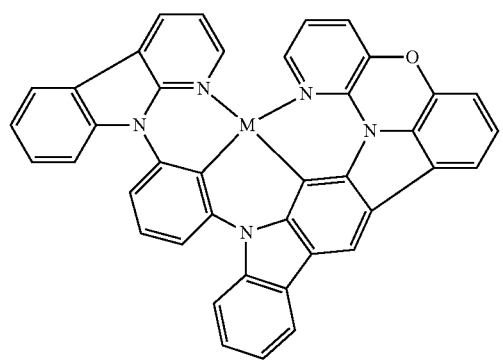
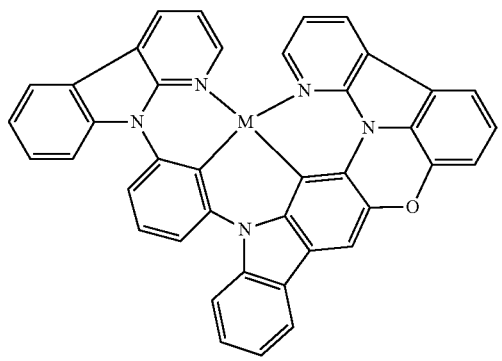
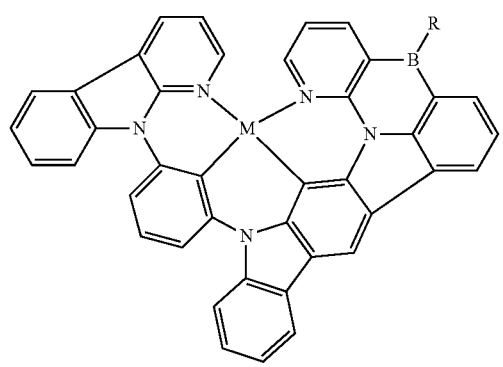
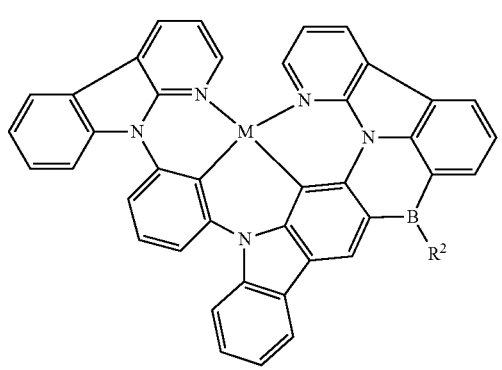

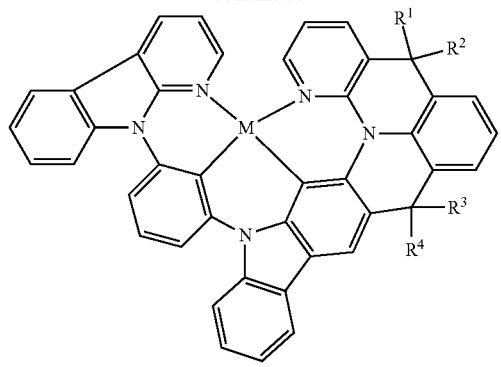
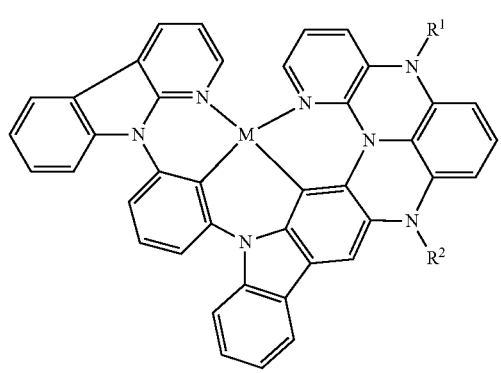
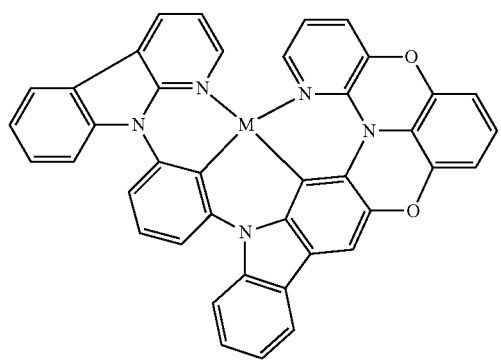
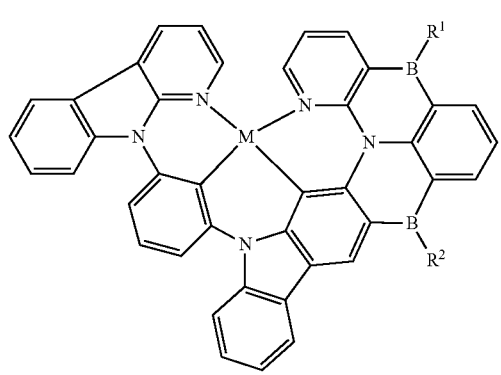
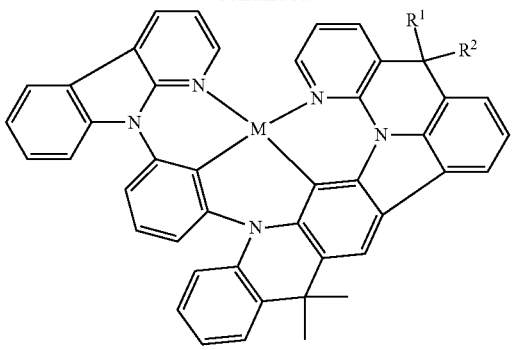
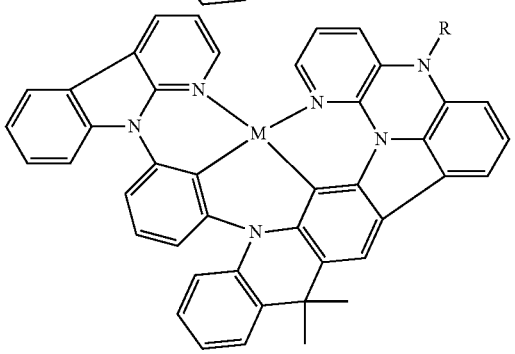
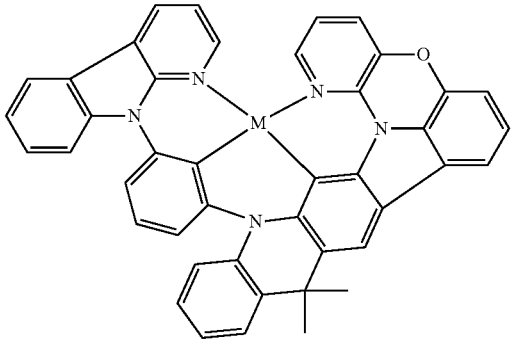
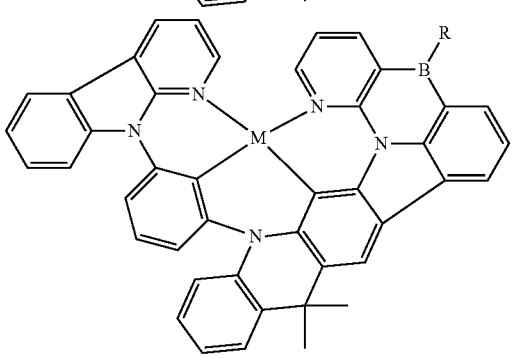
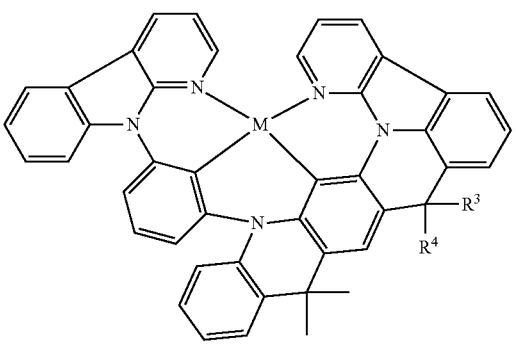

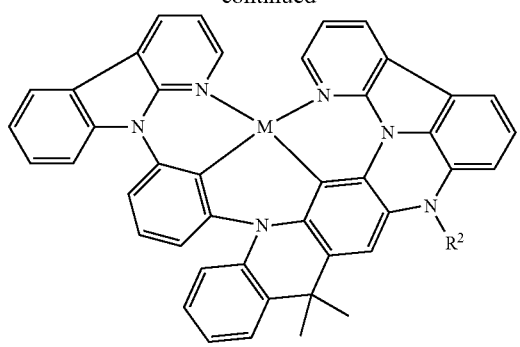
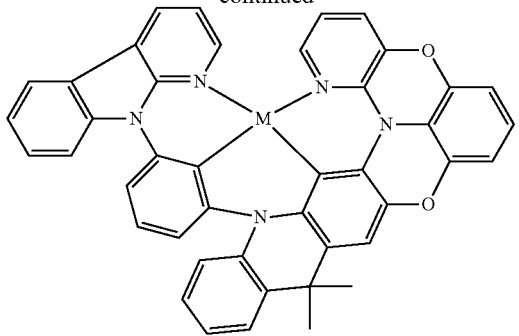
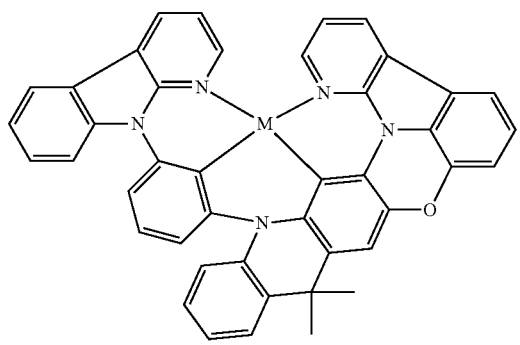
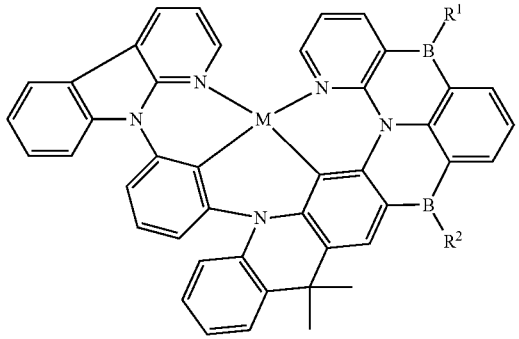
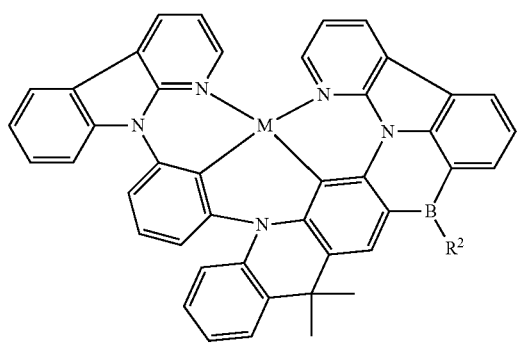
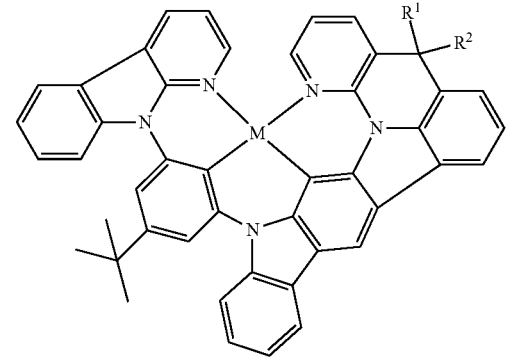
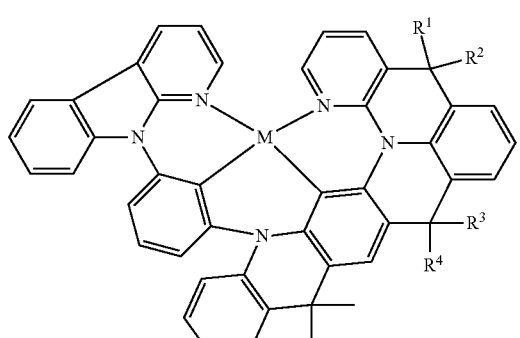
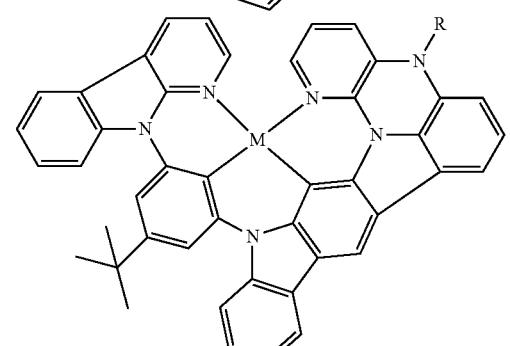
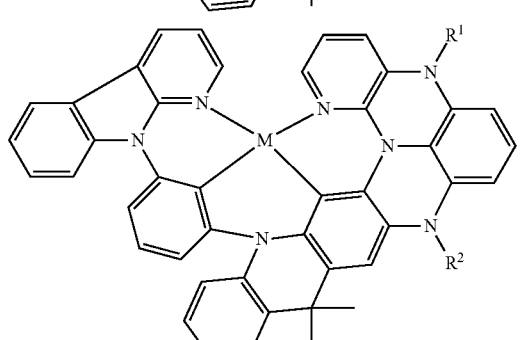
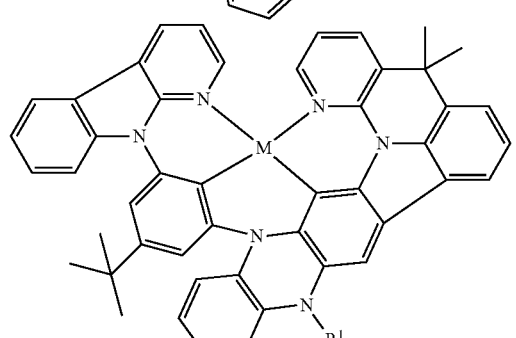

297
-continued
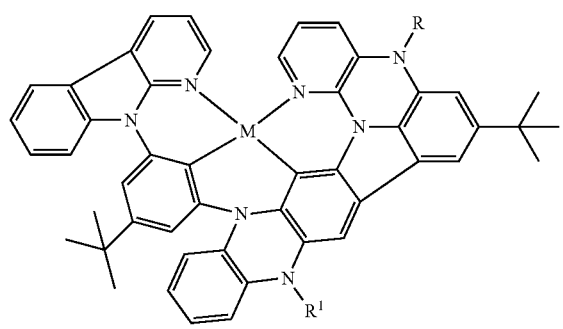
Structure 25 (M = Pt or Pd)
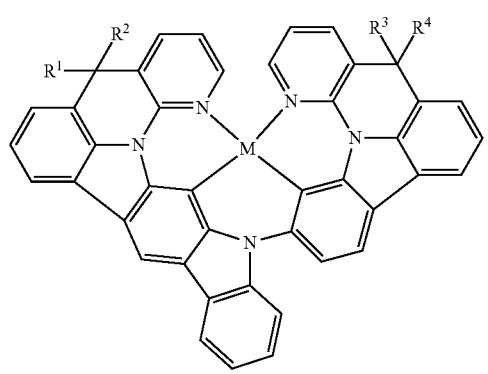
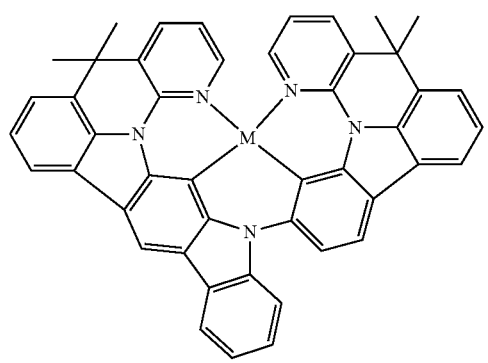
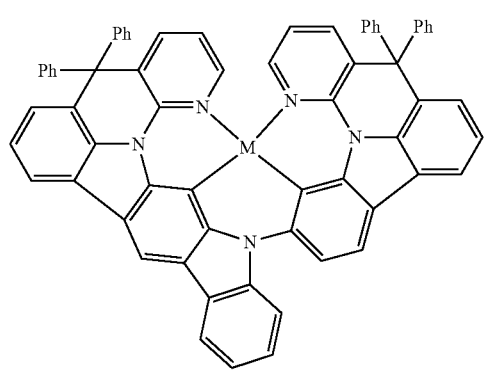
298
-continued
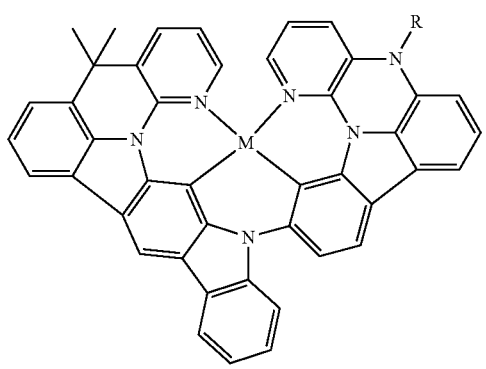
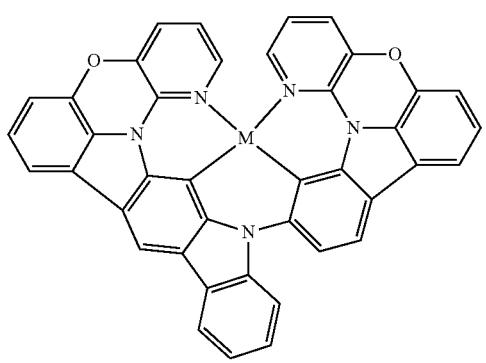
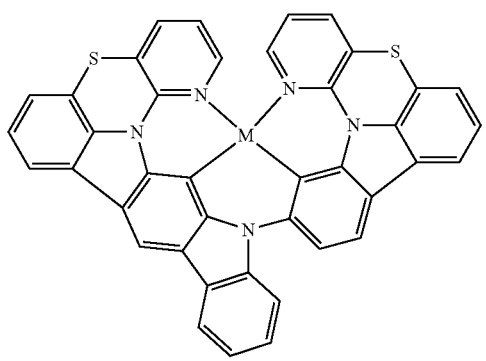
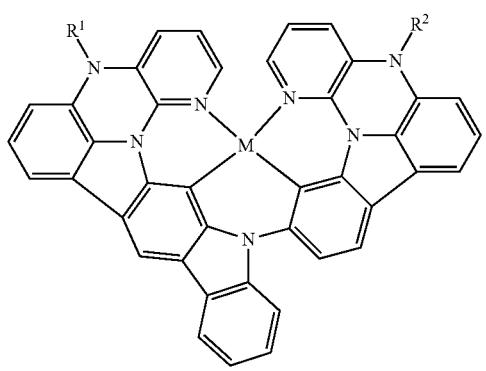

299
-continued
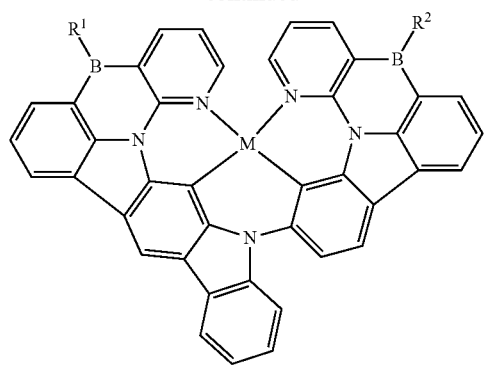
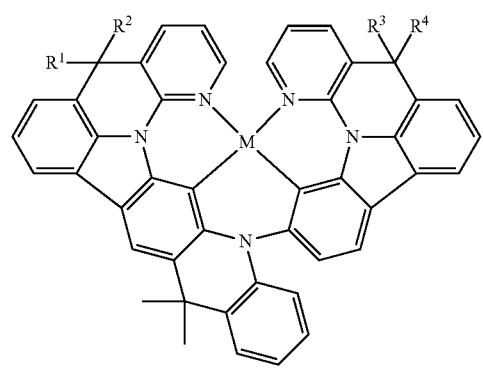
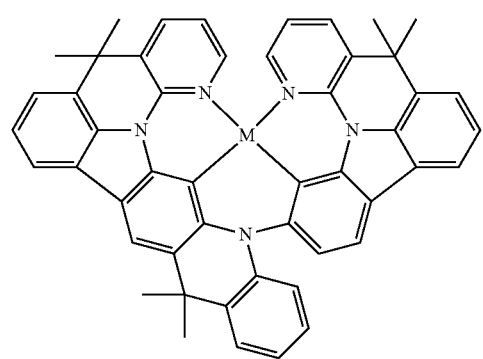
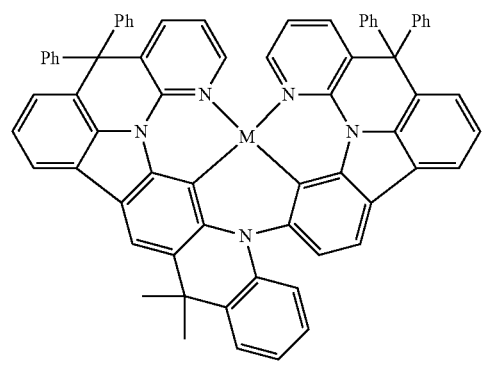
300
-continued
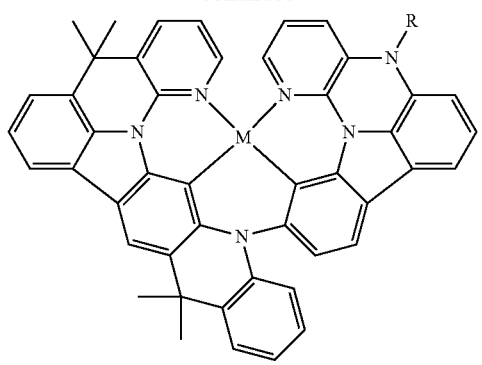
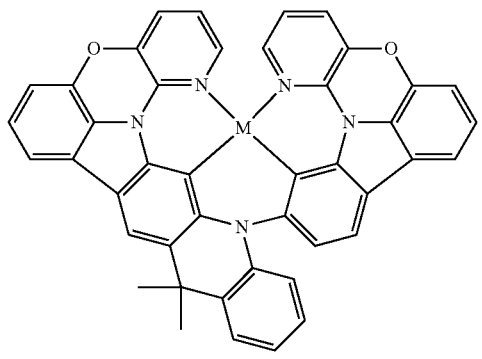
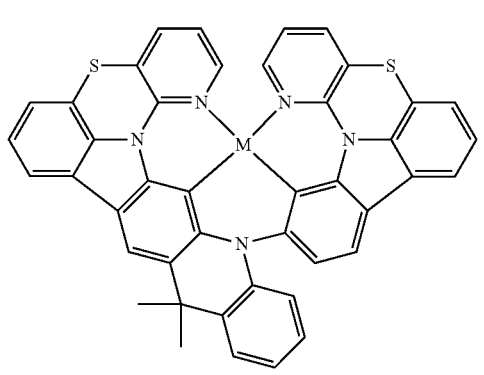
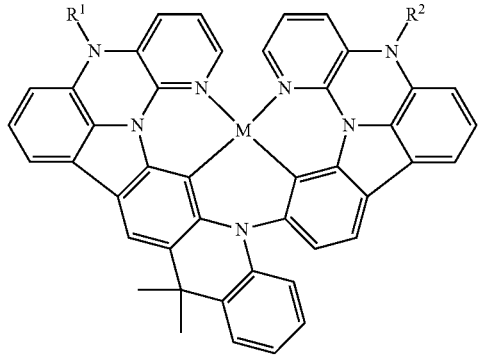

301
-continued
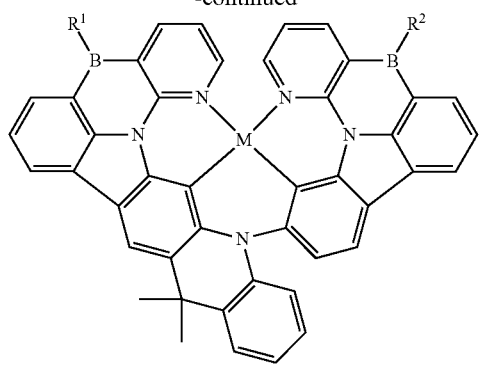
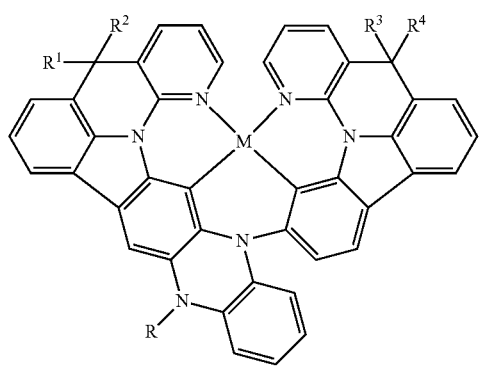
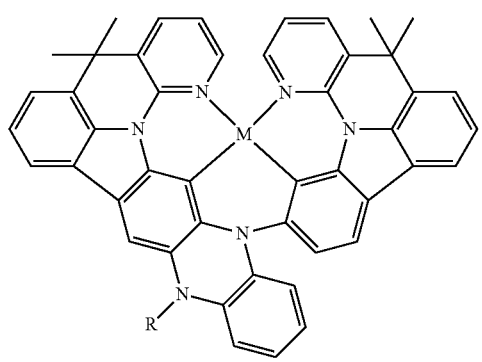
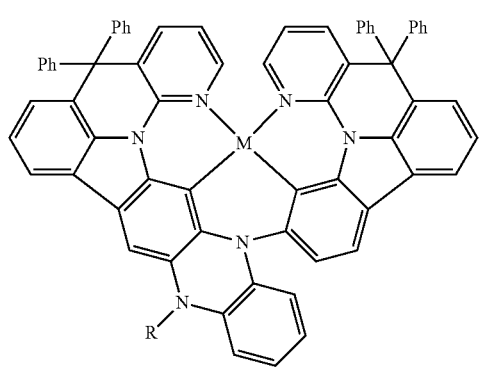
302
-continued
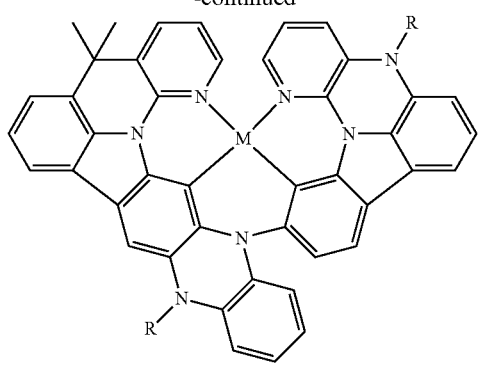
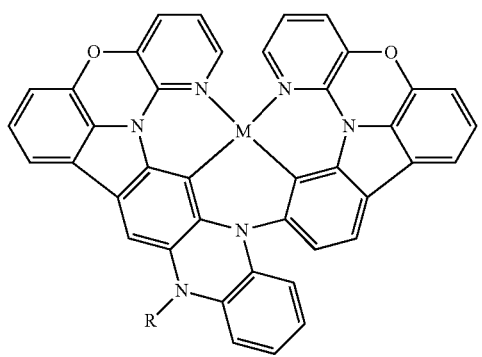
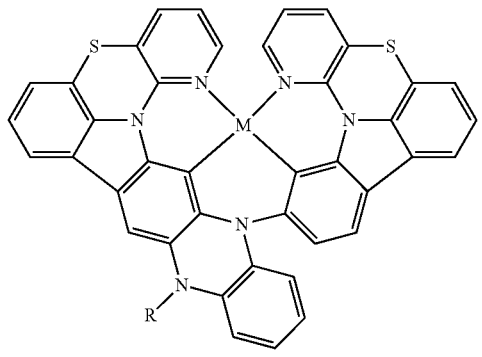
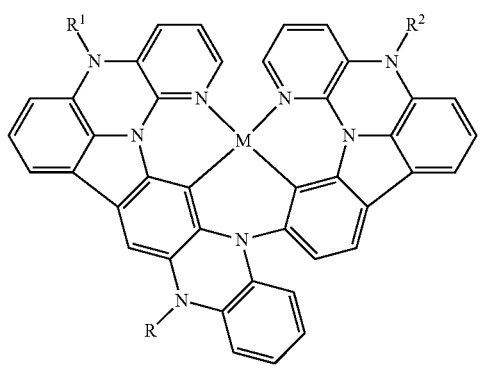

303
-continued
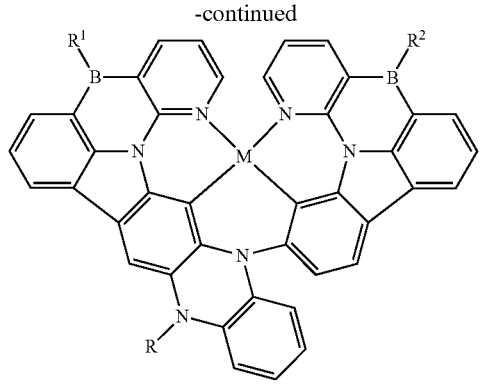
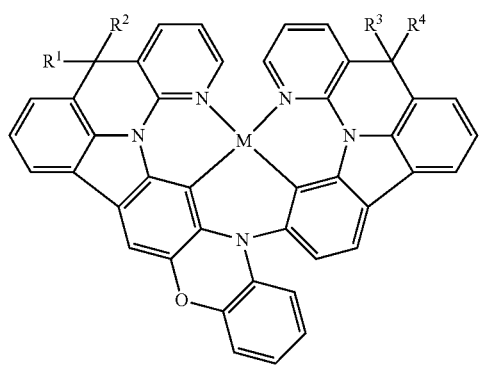
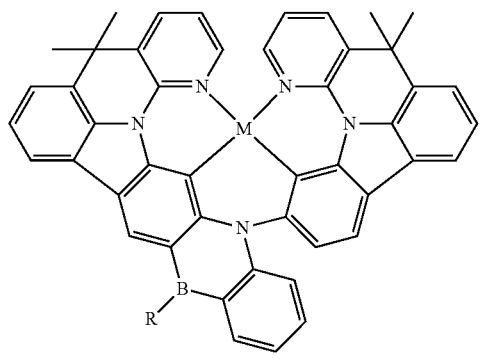
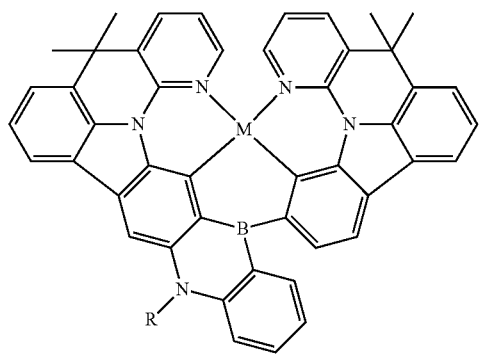
304
-continued
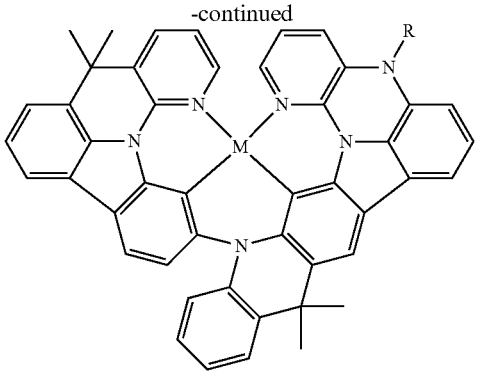
Structure 26 (M = Pt or Pd)
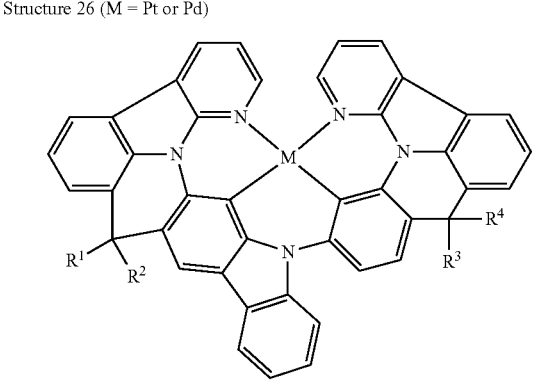
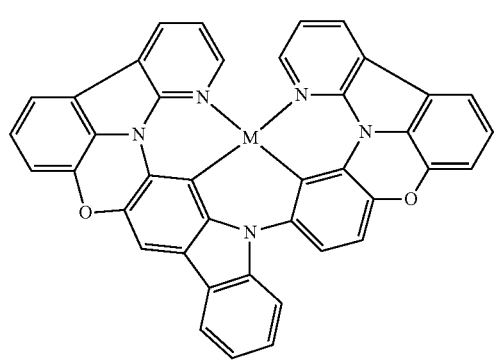
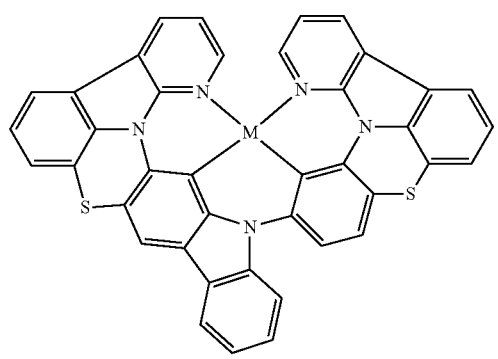

305
-continued
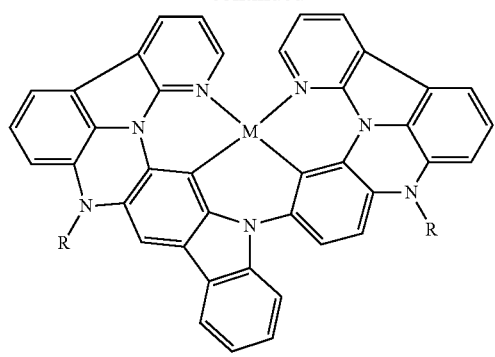
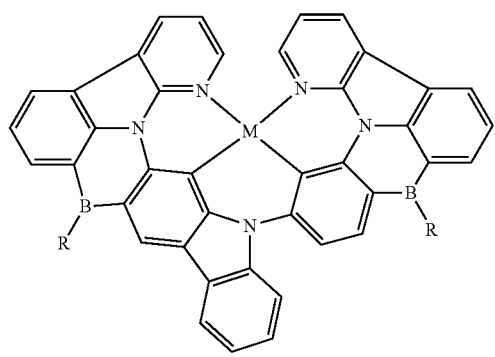
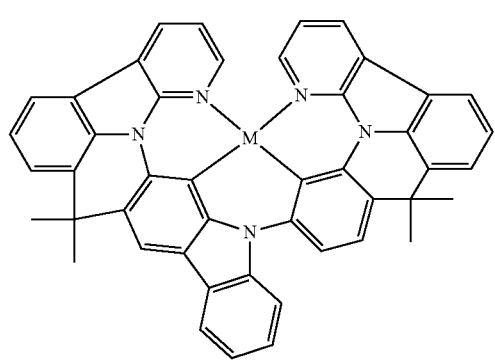
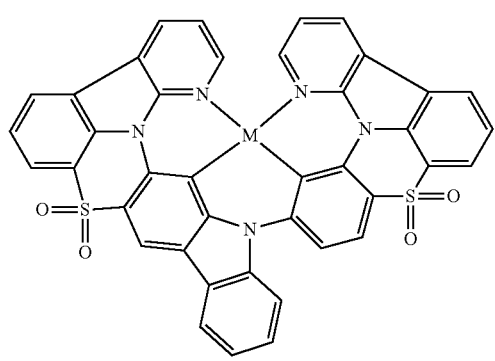
306
-continued
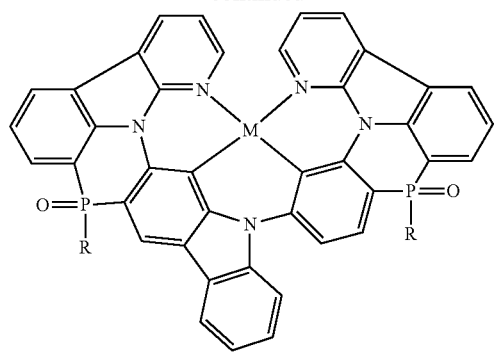
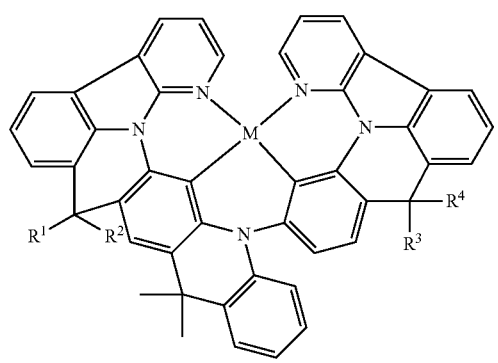
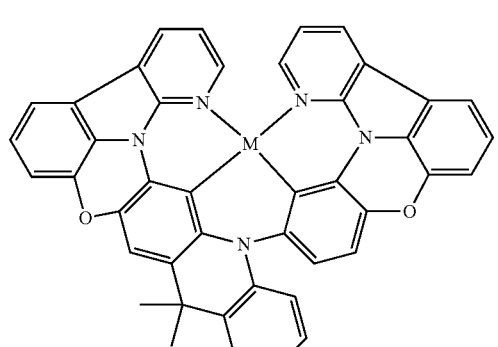
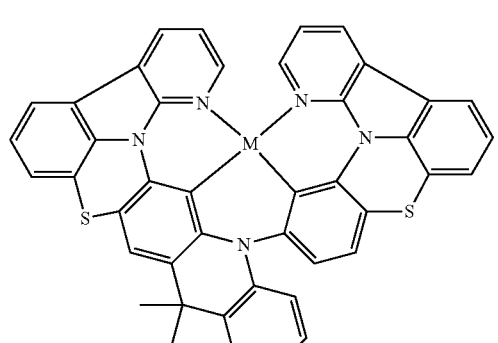

307
-continued
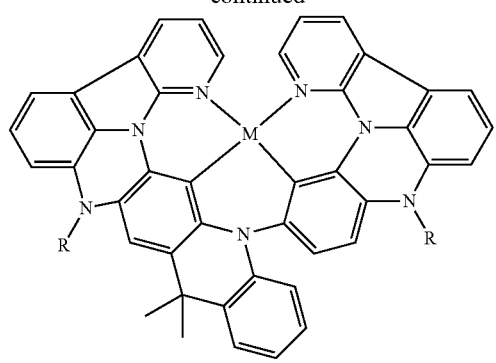
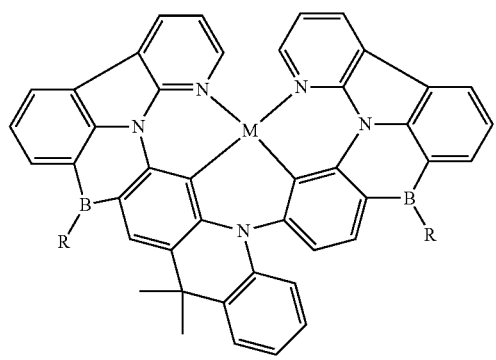
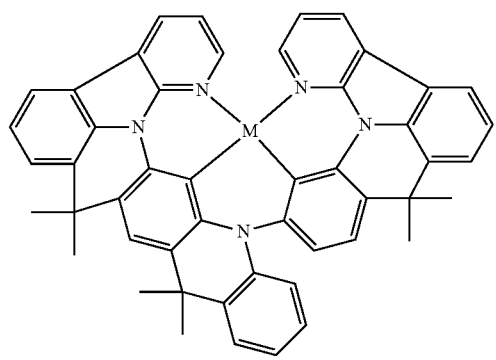
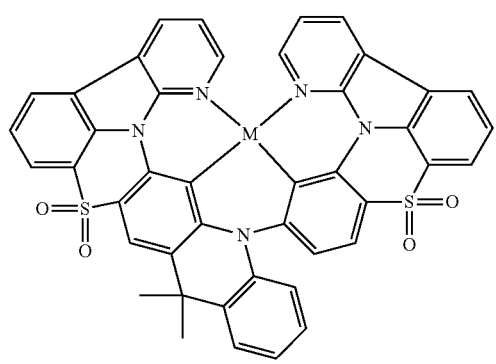
308
-continued
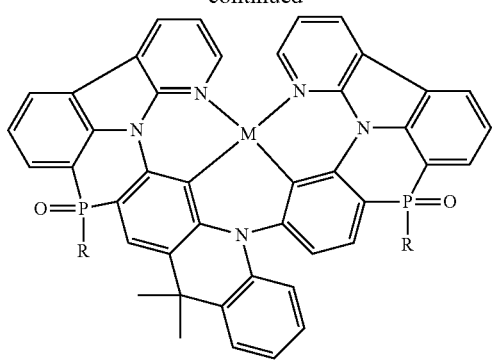
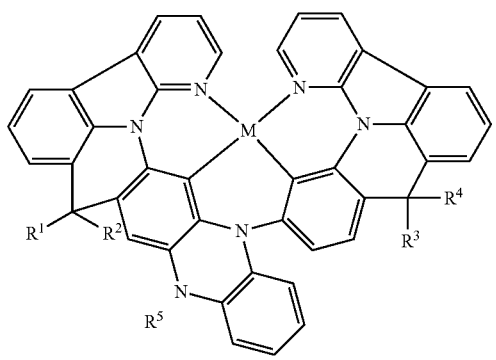
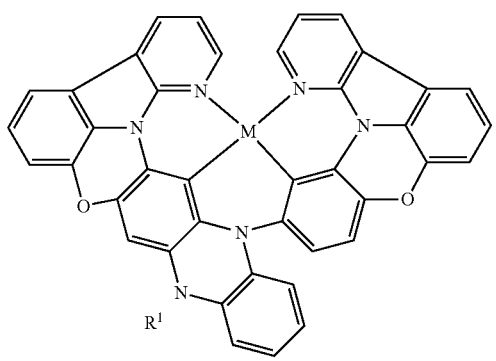
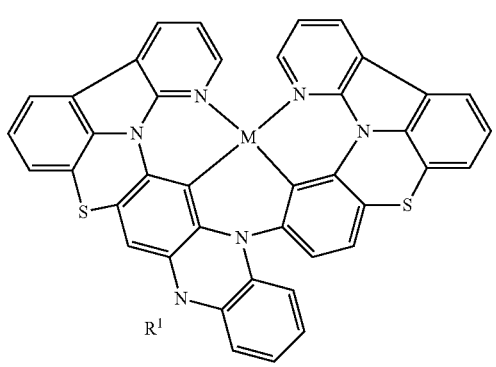

309
-continued
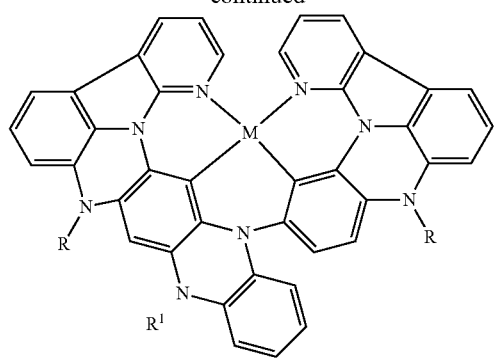
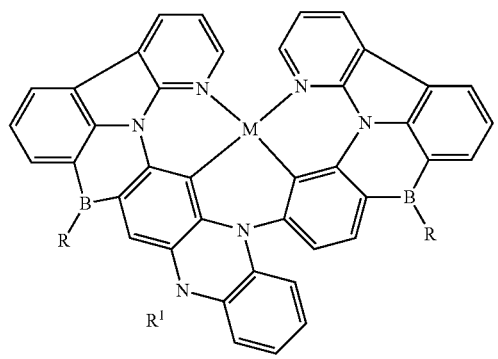
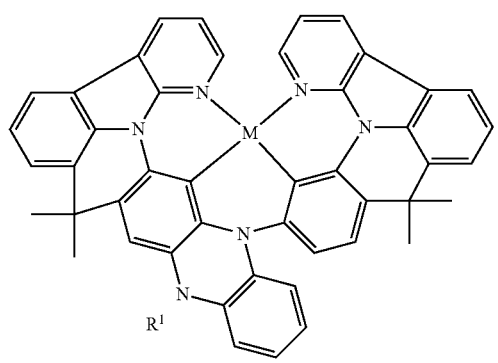
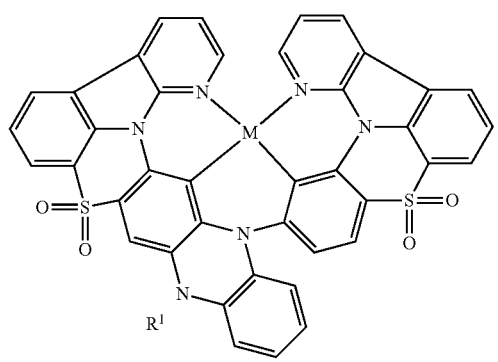
310
-continued
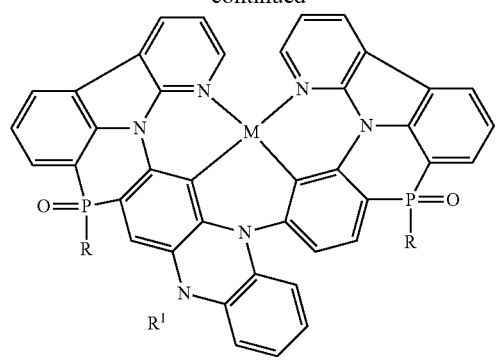
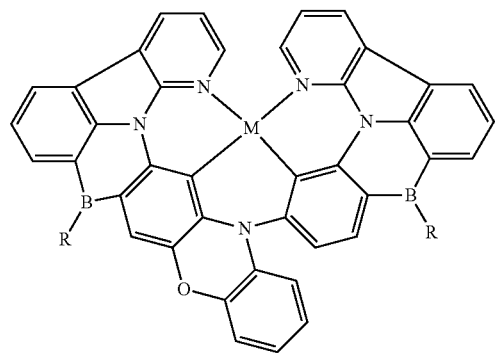
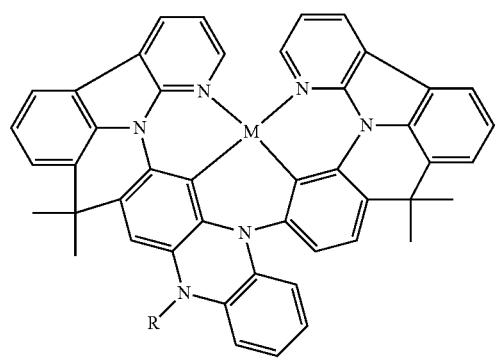
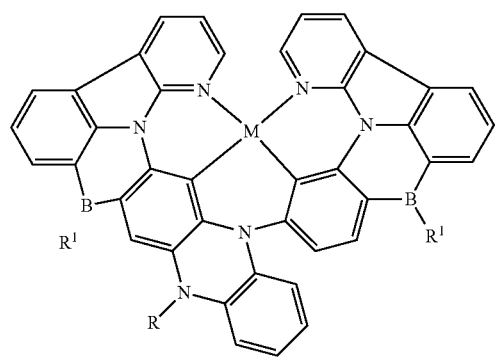

311
-continued
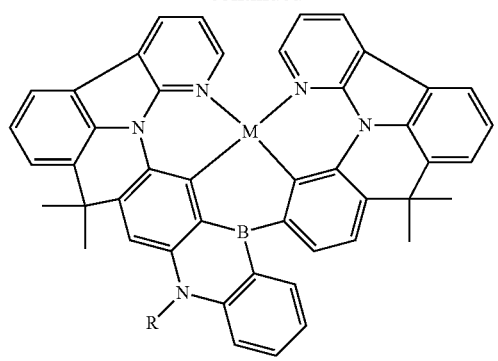
Structure 27 (M = Pt or Pd)
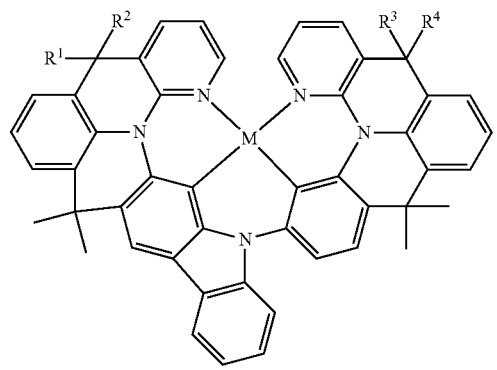
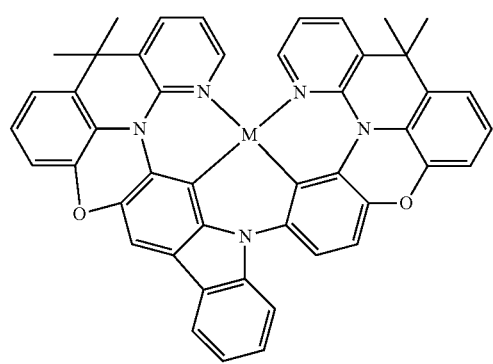
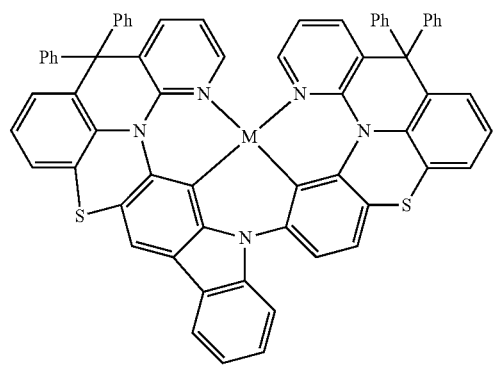
312
-continued
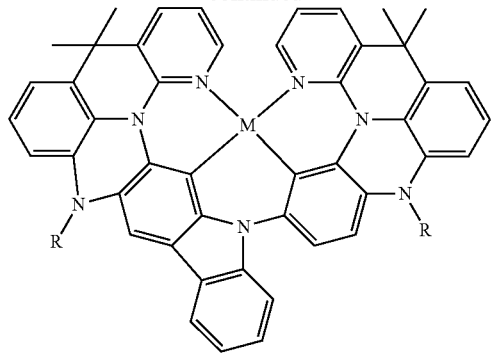
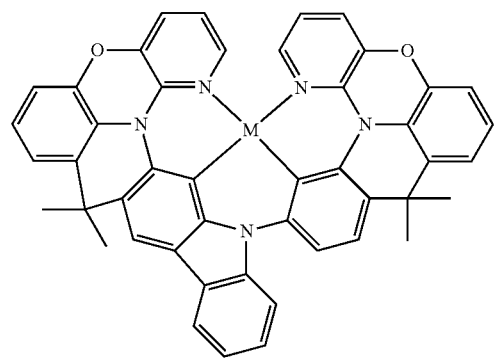
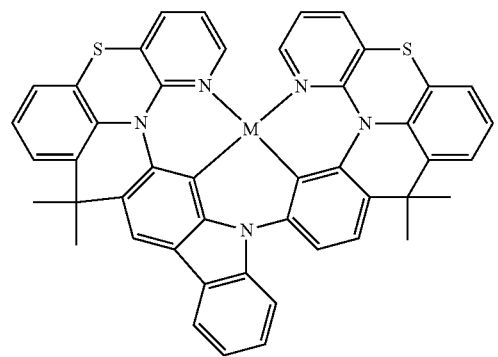
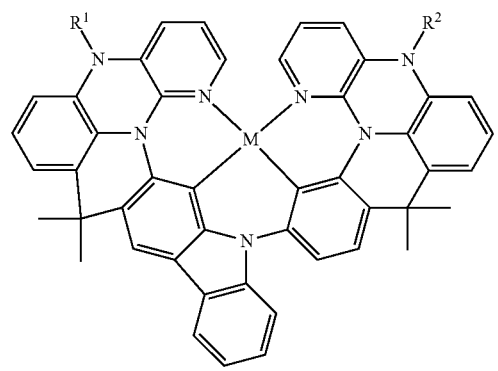

313
-continued
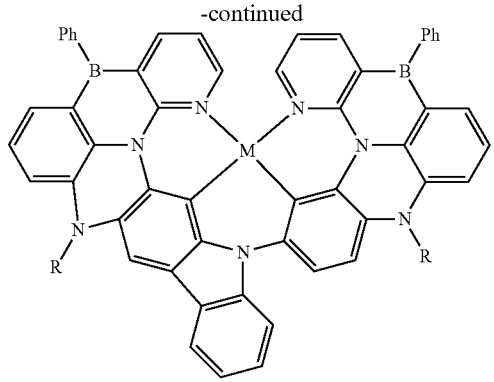
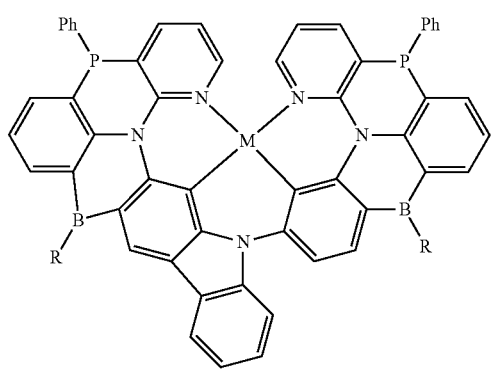
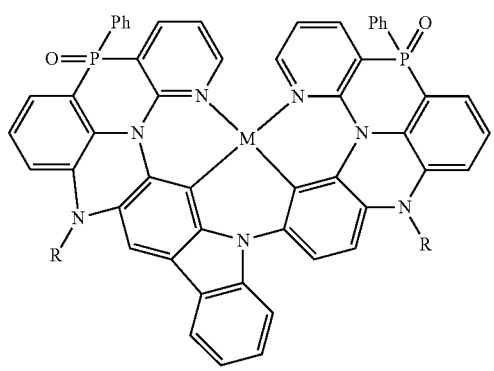
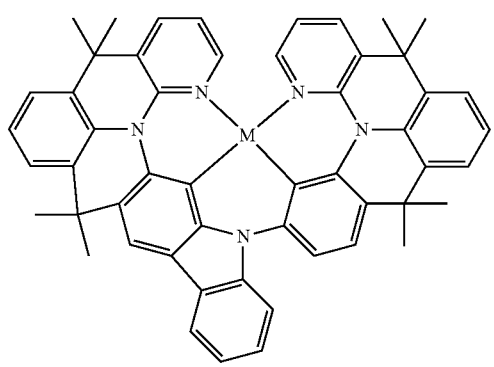
314
-continued
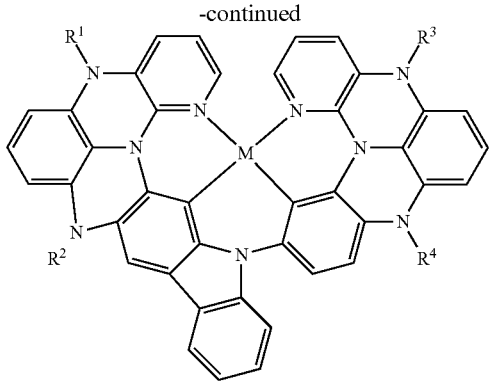
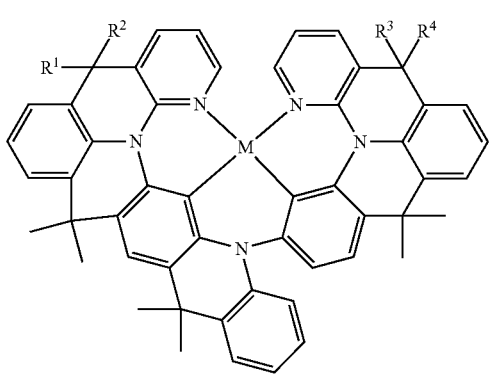
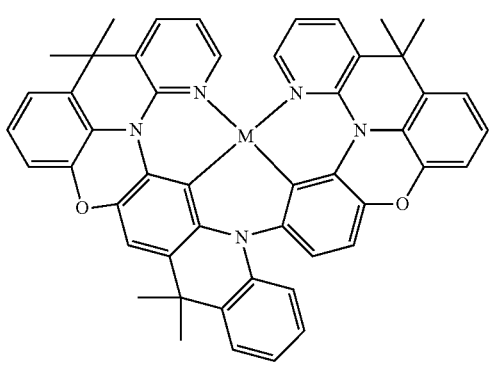
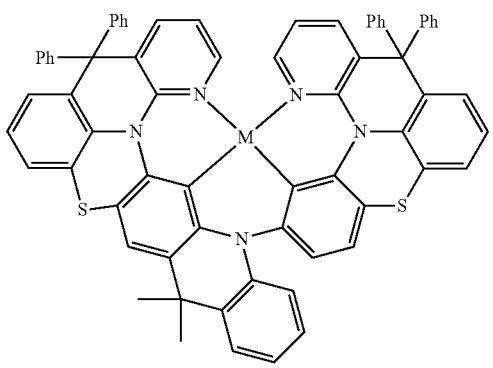

315
-continued
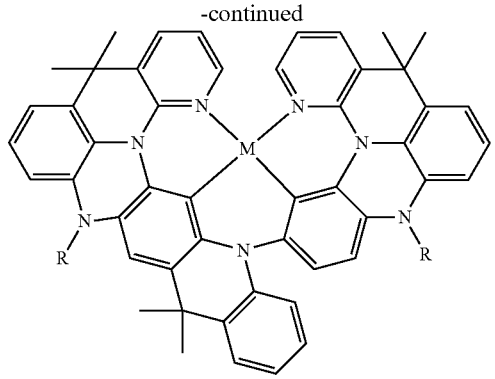
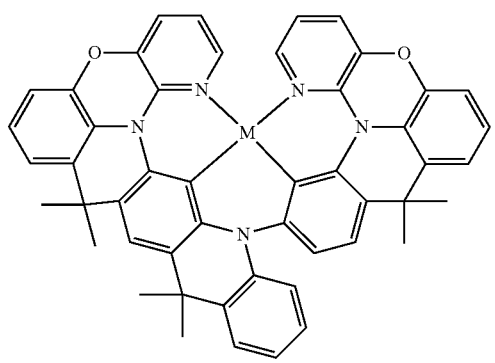
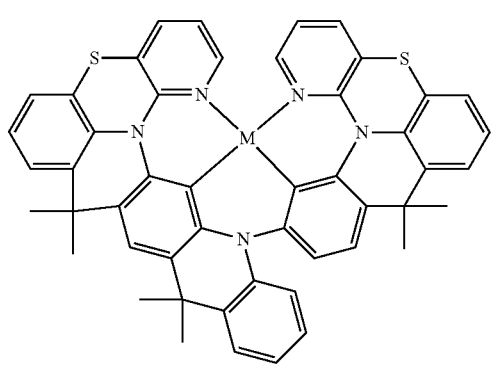
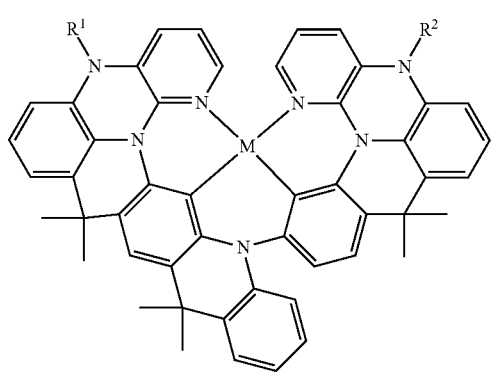
316
-continued
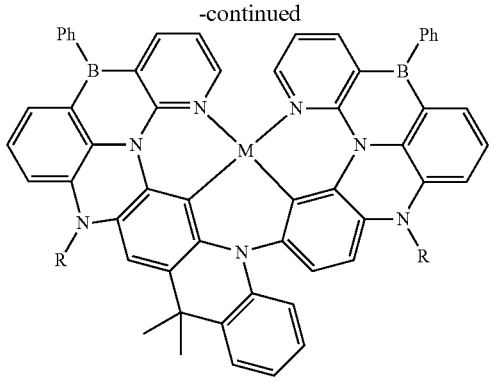
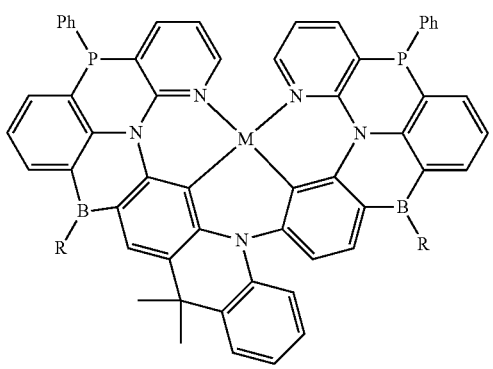
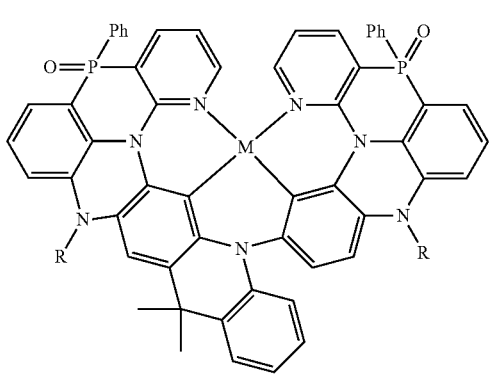
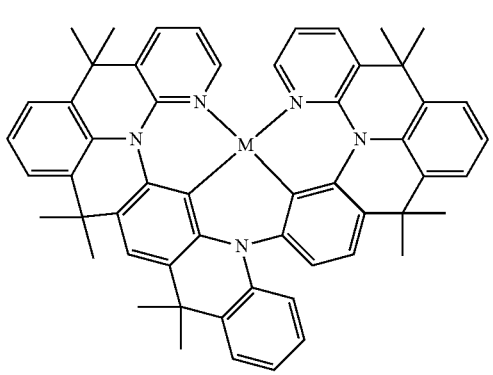

317
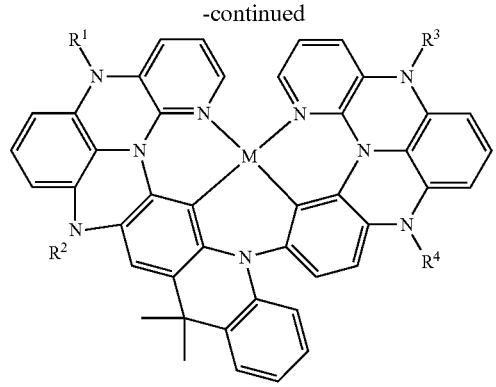
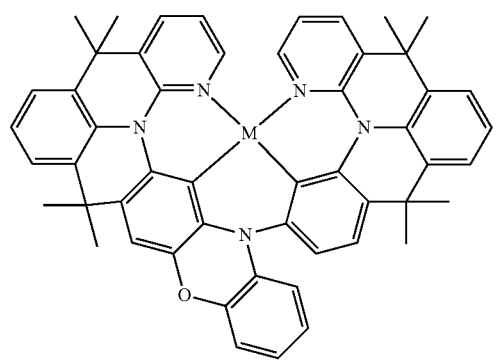
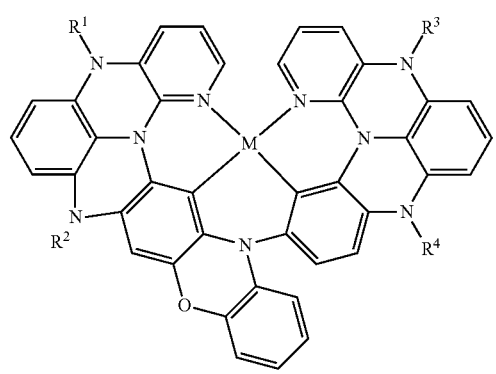
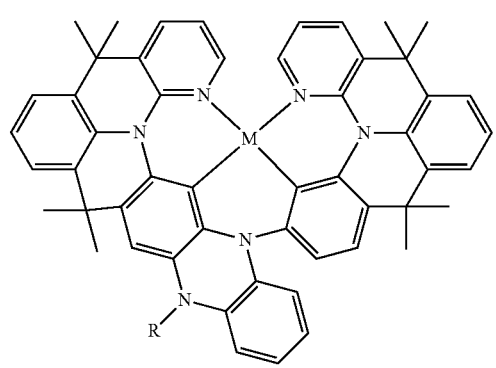
318
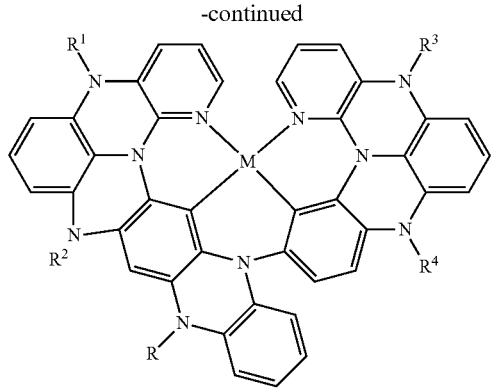
Structure 28 (M = Pt or Pd)
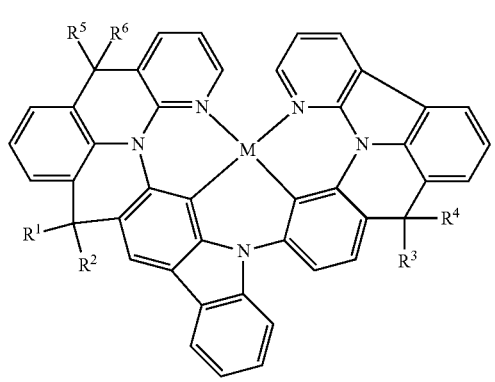
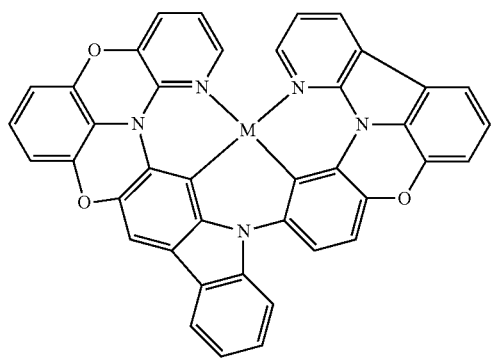
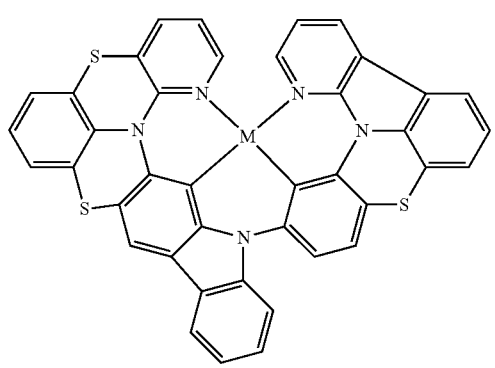

319
-continued
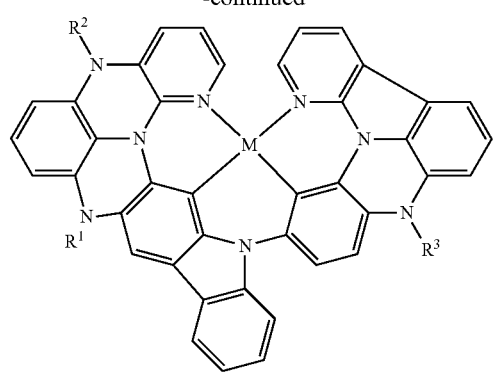
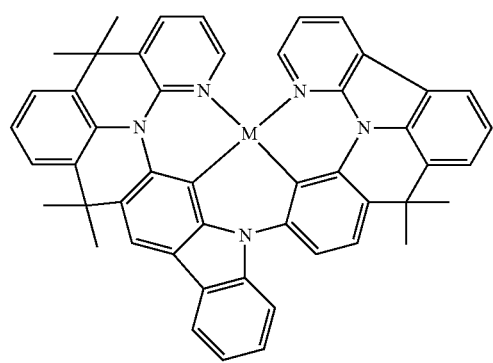
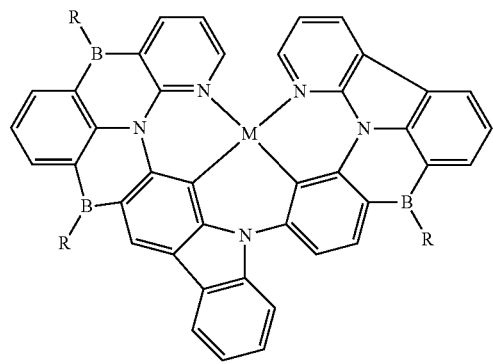
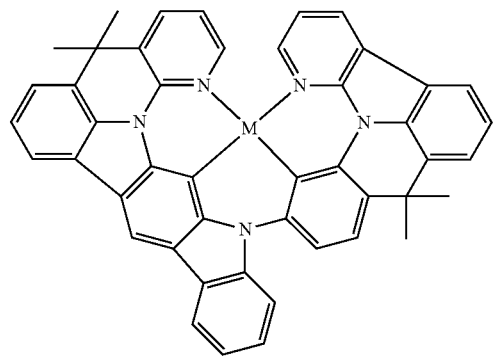
320
-continued
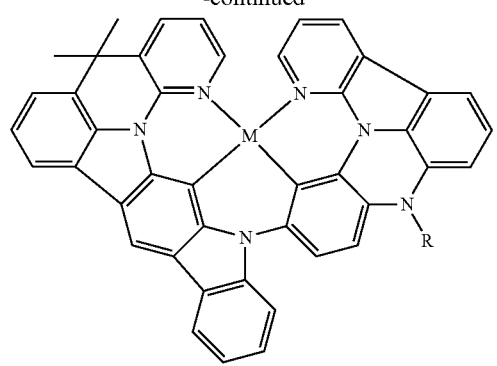
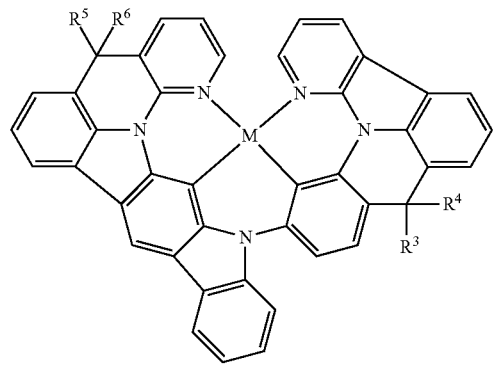
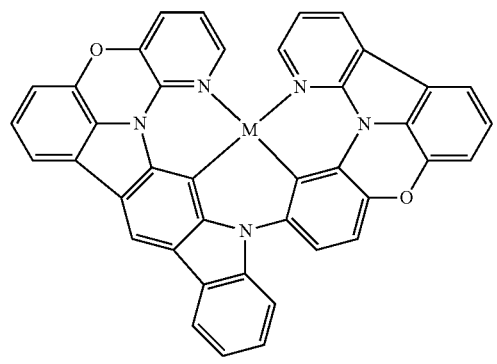
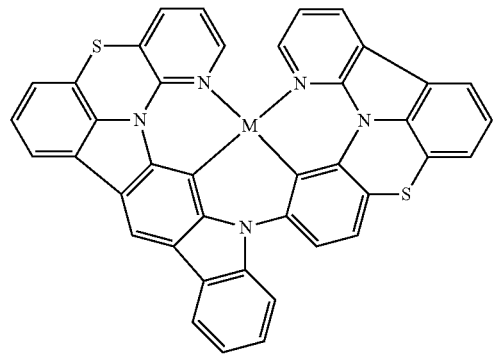

321
-continued
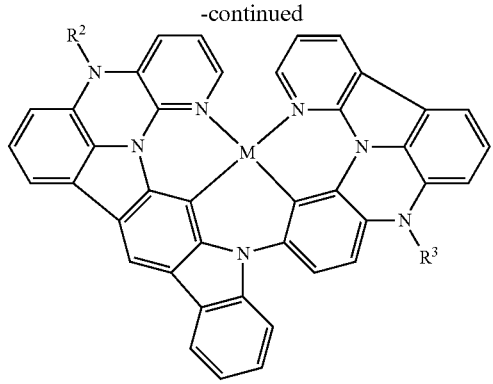
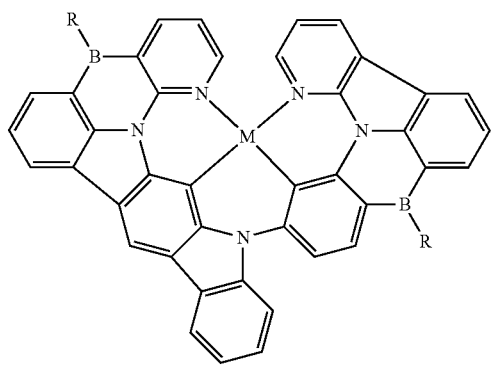
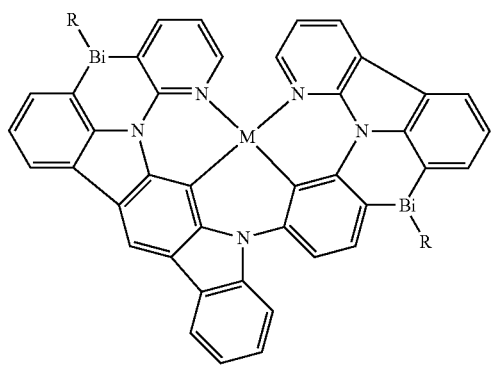
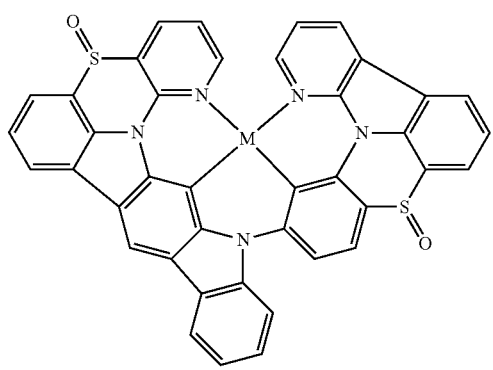
322
-continued
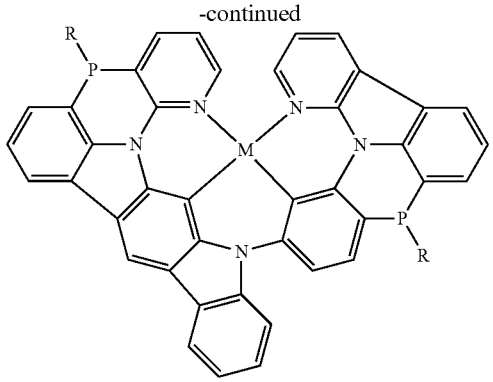
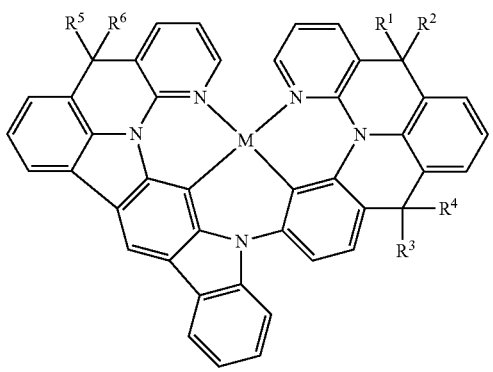
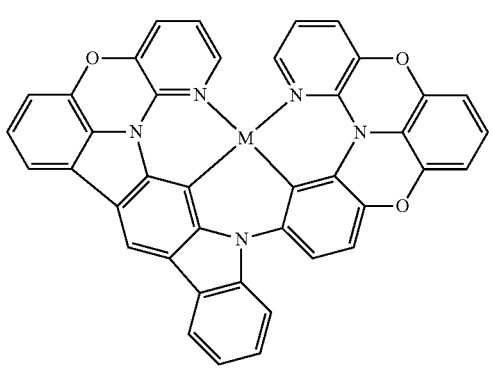
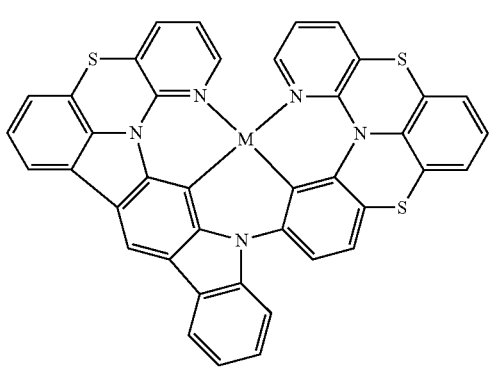

323
-continued
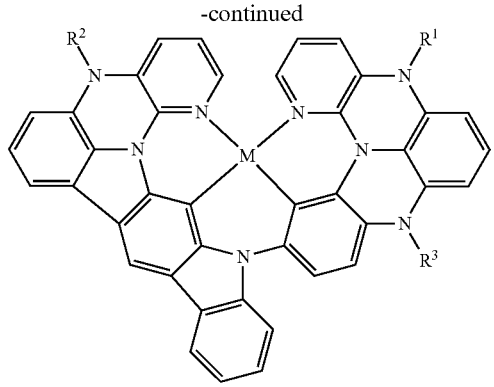
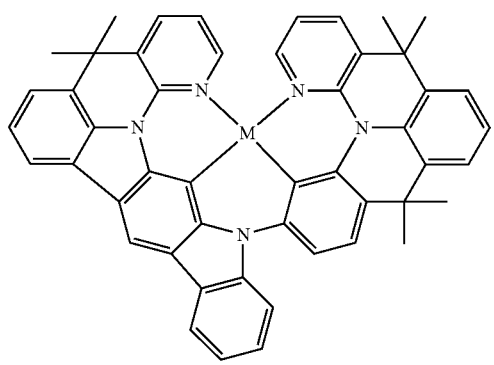
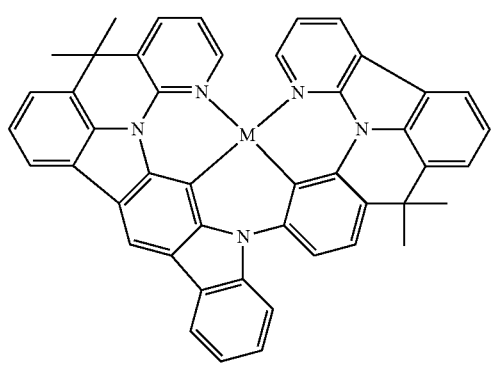
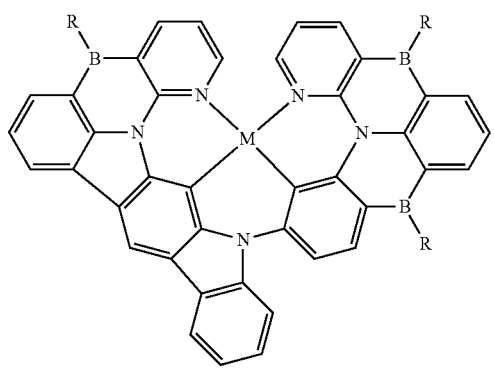
324
-continued
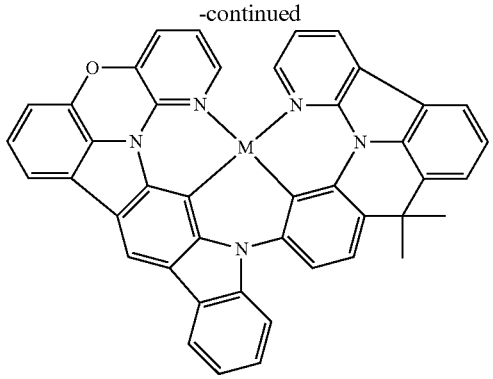
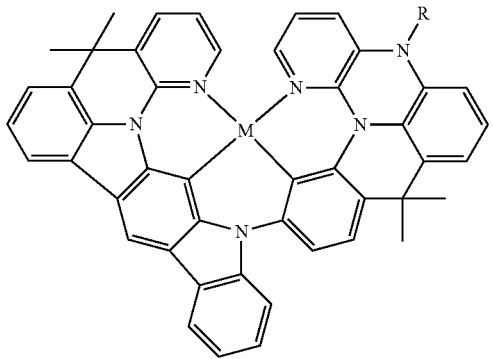
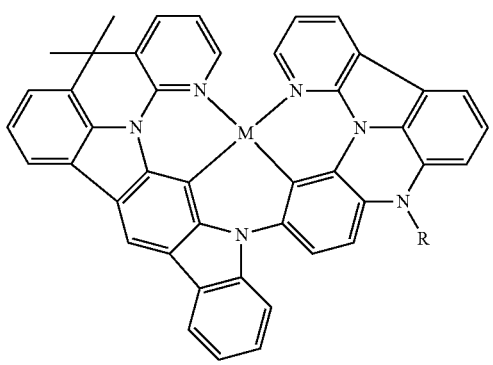
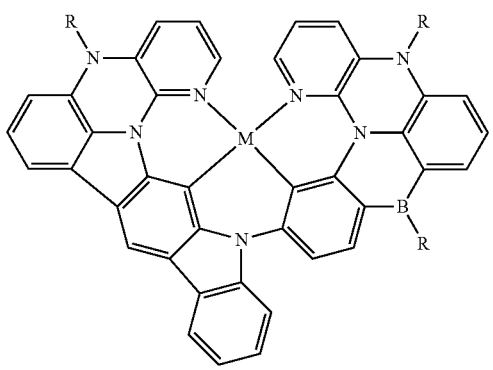

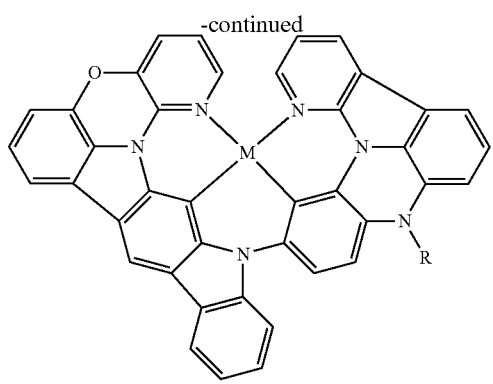
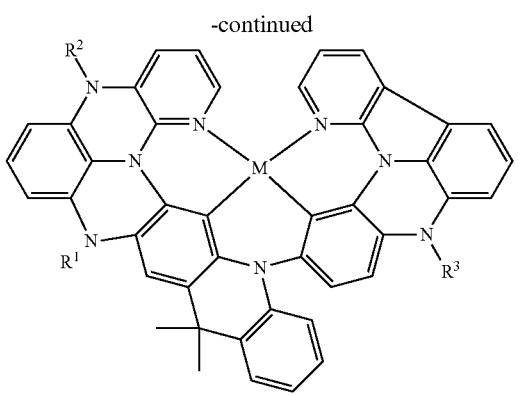
Structure 29 (M = Pt or Pd)
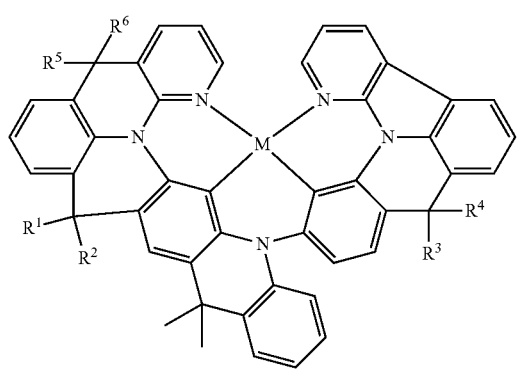
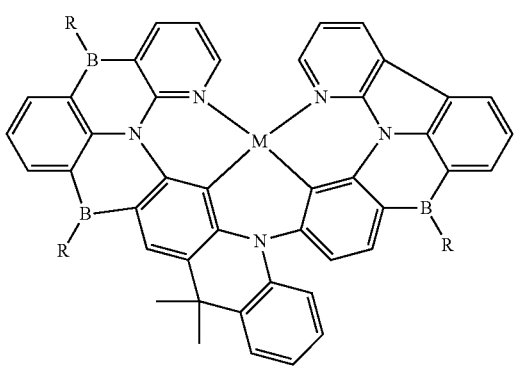
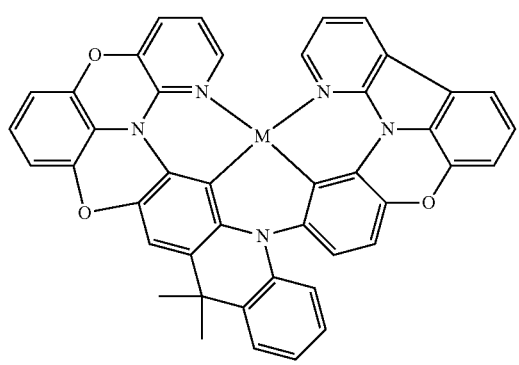
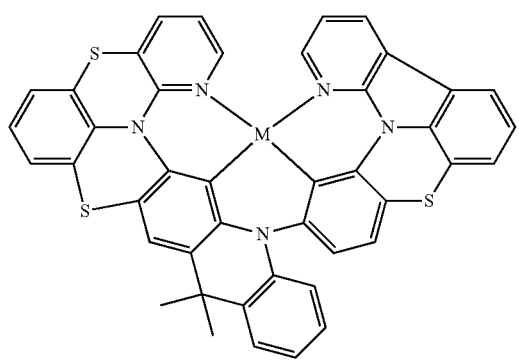
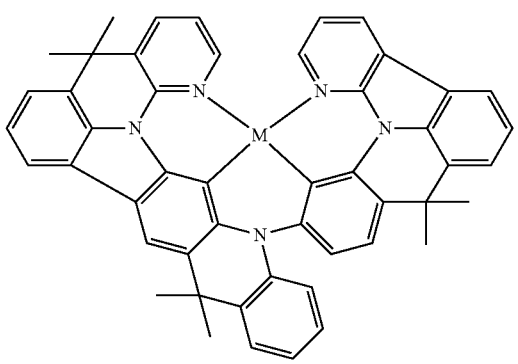

327
-continued
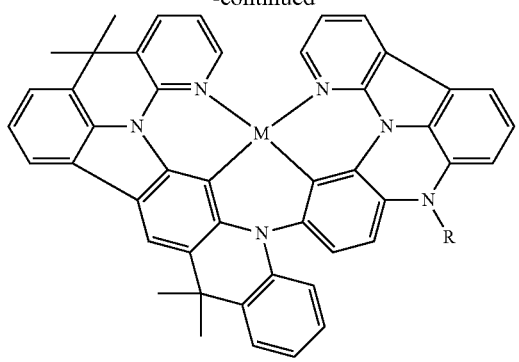
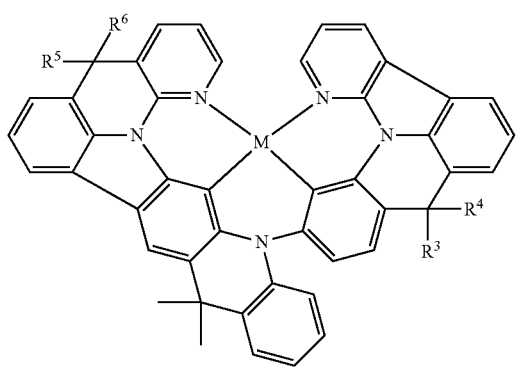
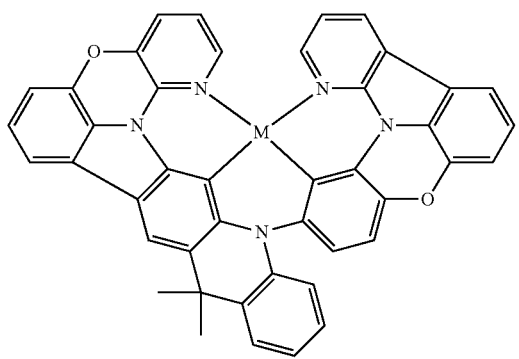
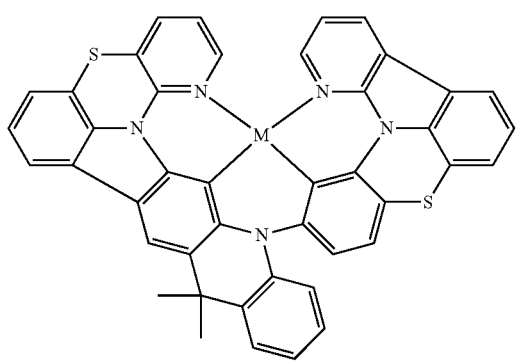
328
-continued
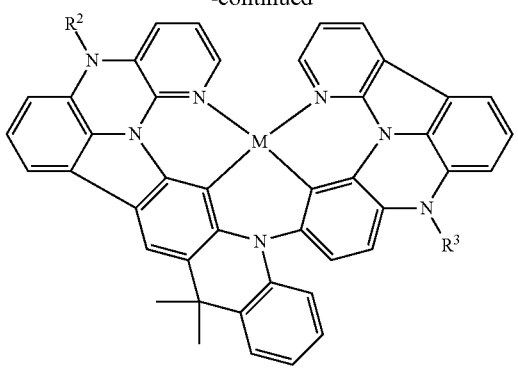
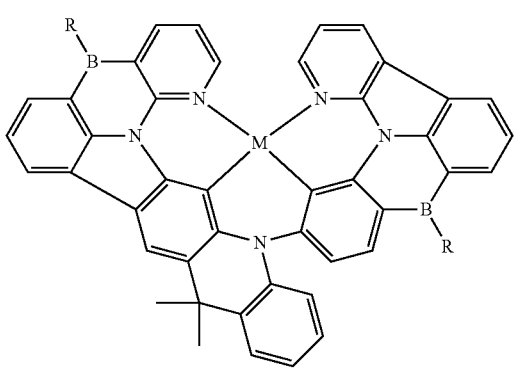
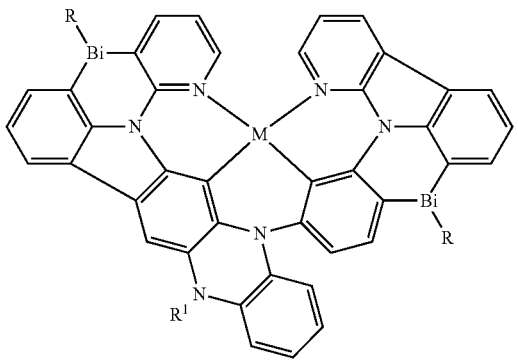
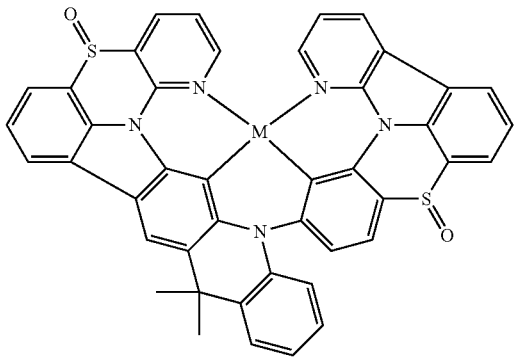

329
-continued
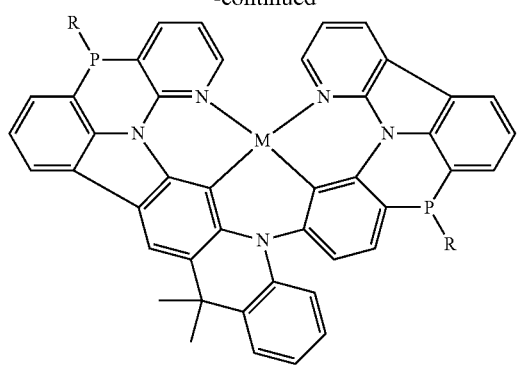
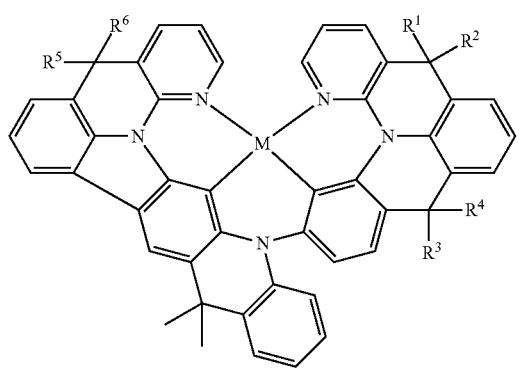
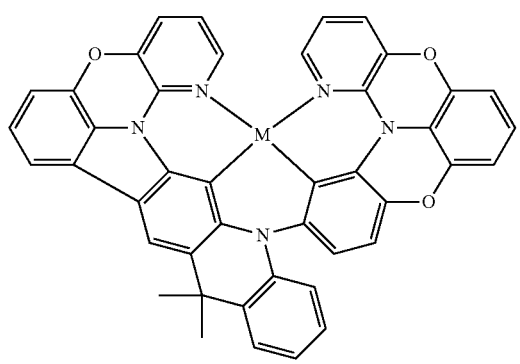
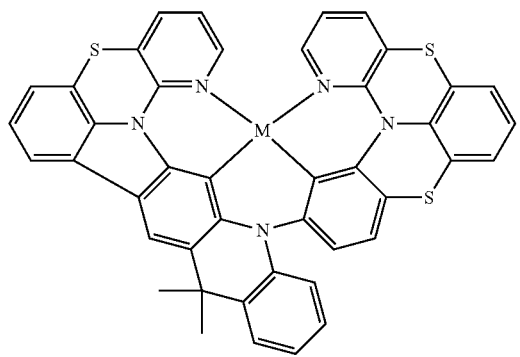
330
-continued
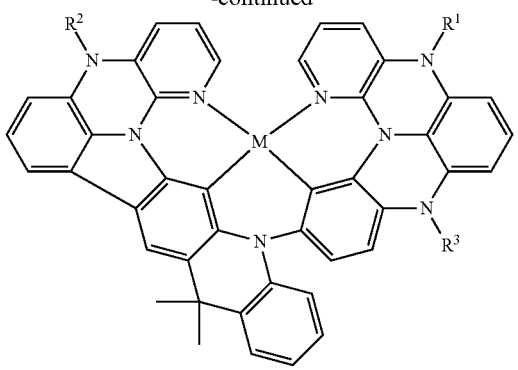
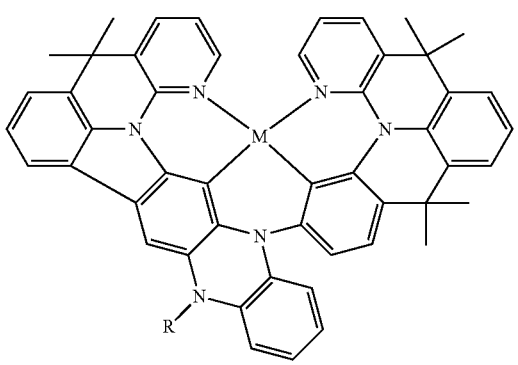
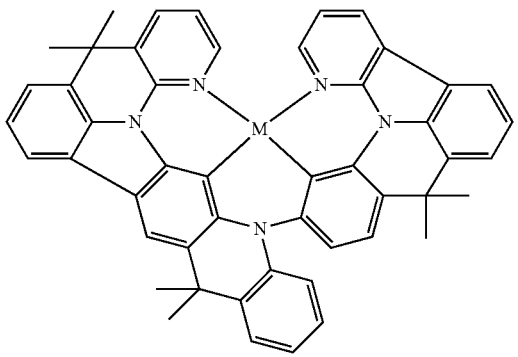
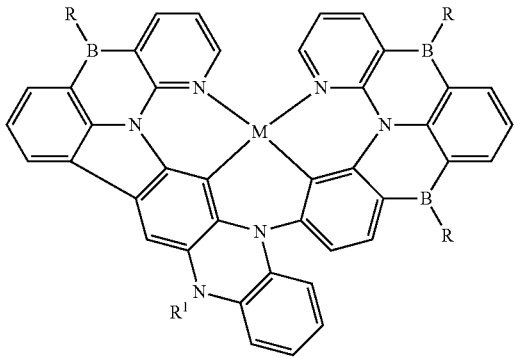

331
-continued
332
-continued
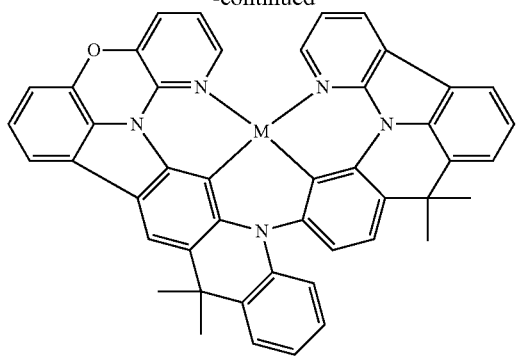
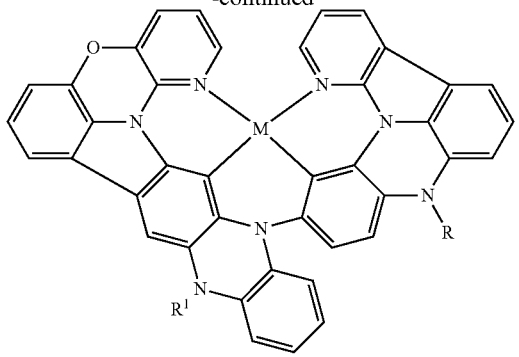
Structure 30 (M = Pt or Pd)
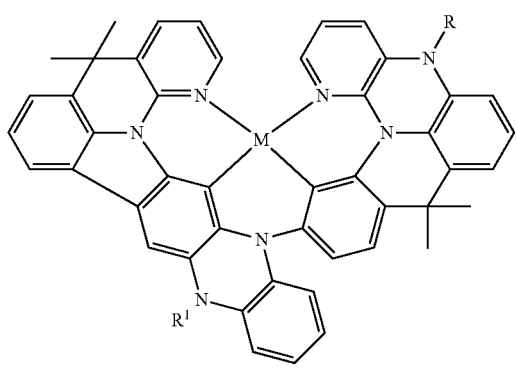
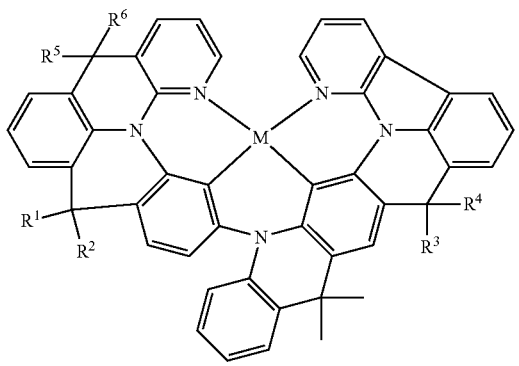
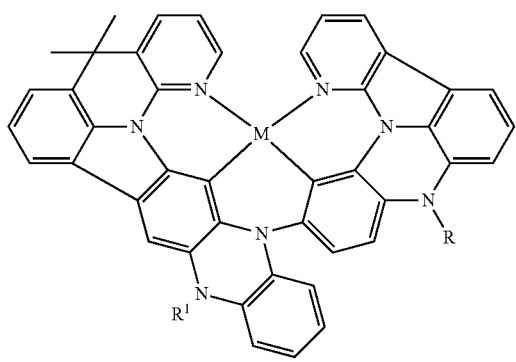
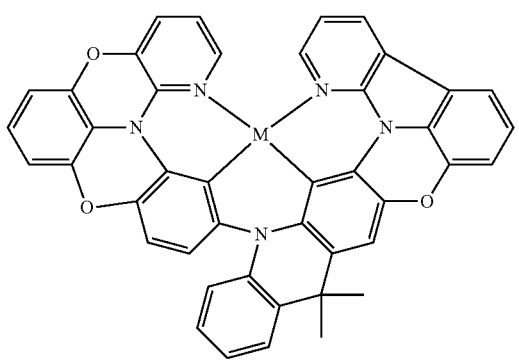
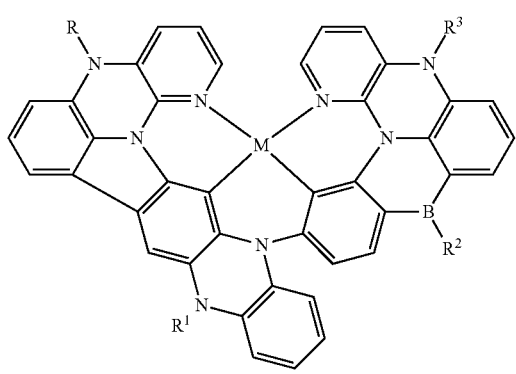
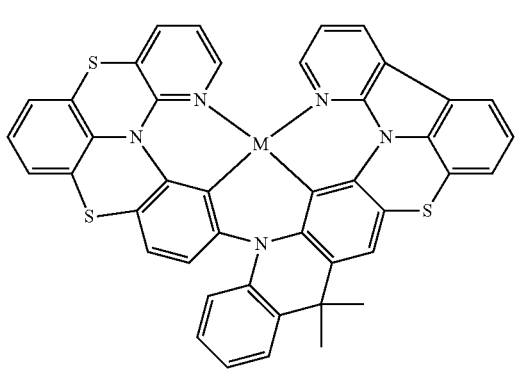

333
-continued
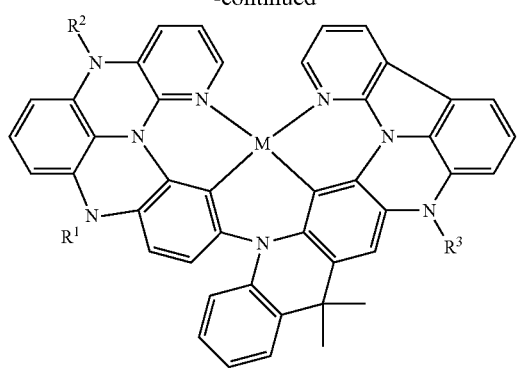
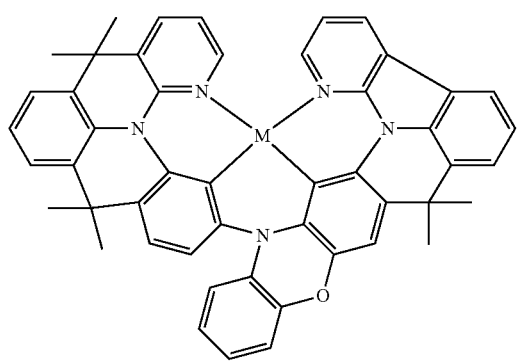
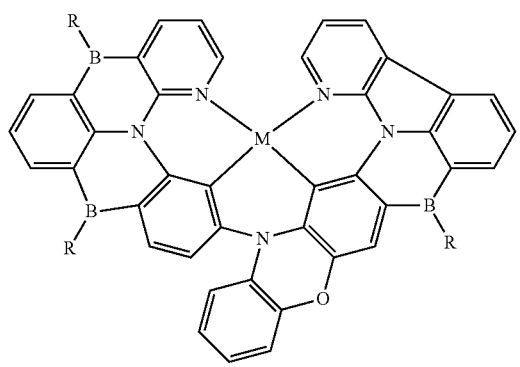
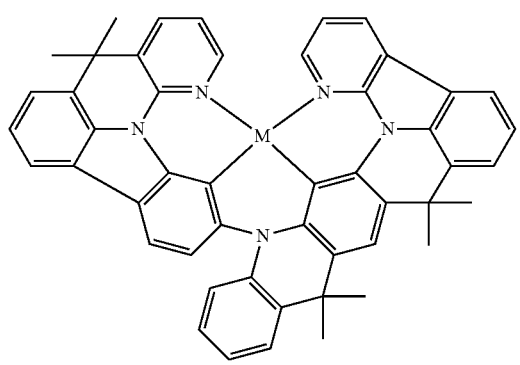
334
-continued
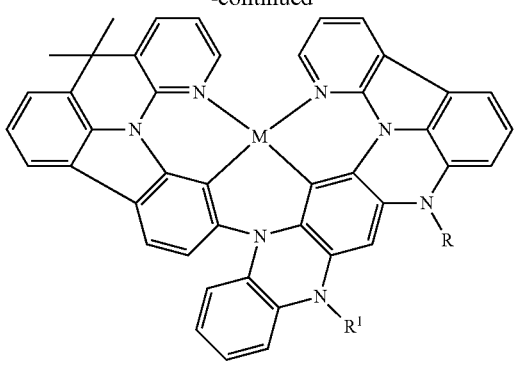
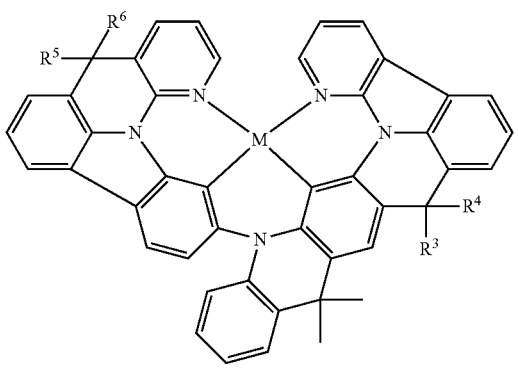
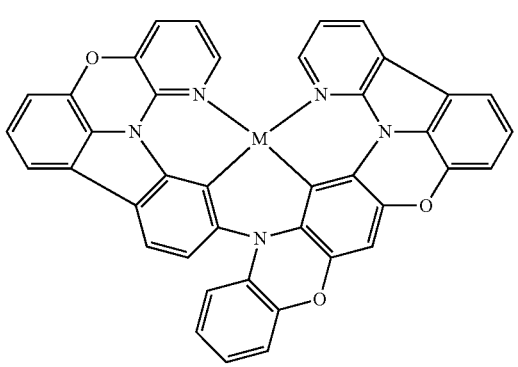
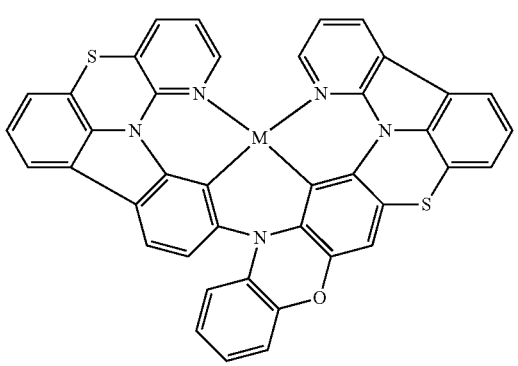

335
-continued
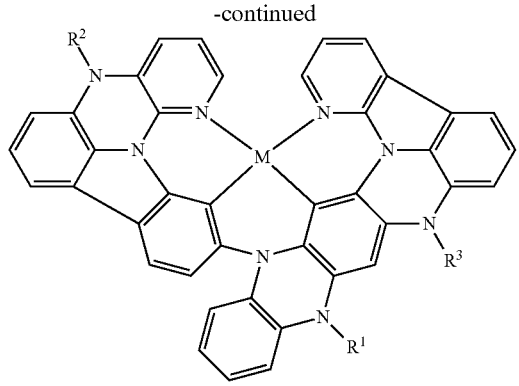
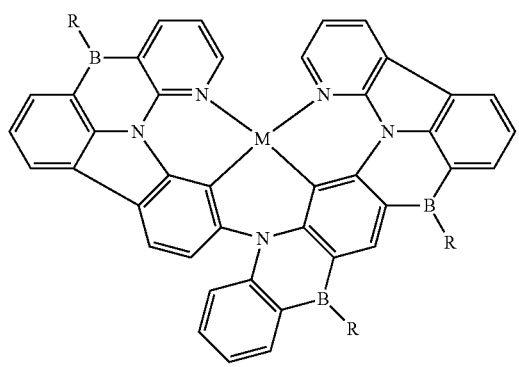
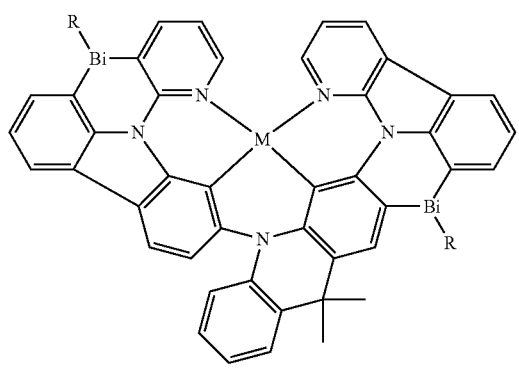
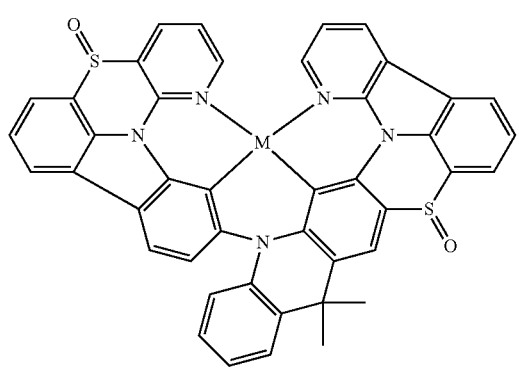
336
-continued
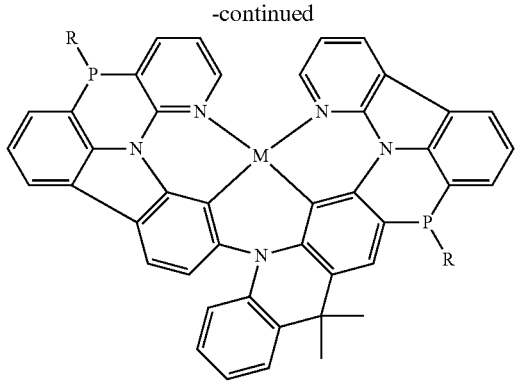
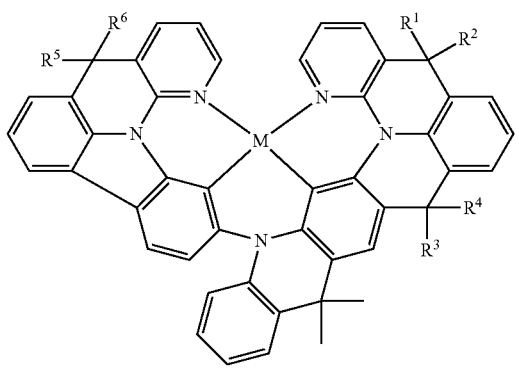
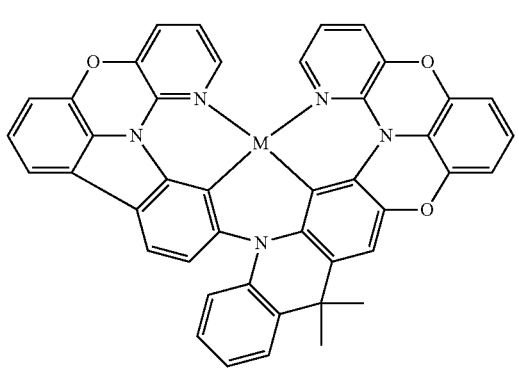
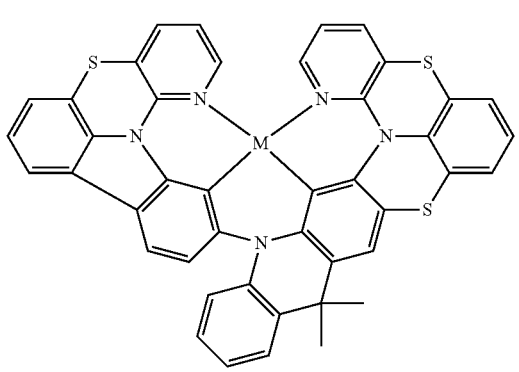

337
-continued
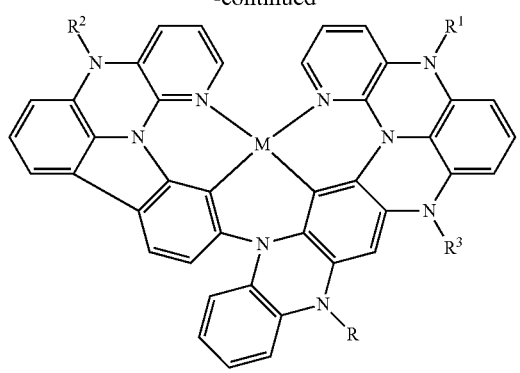
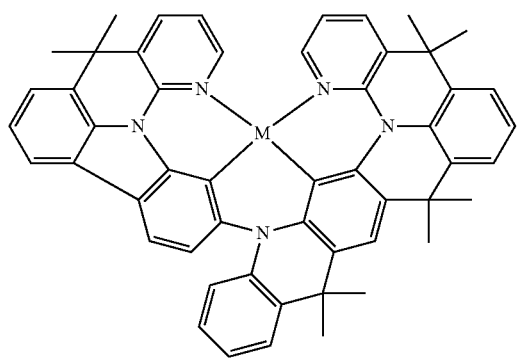
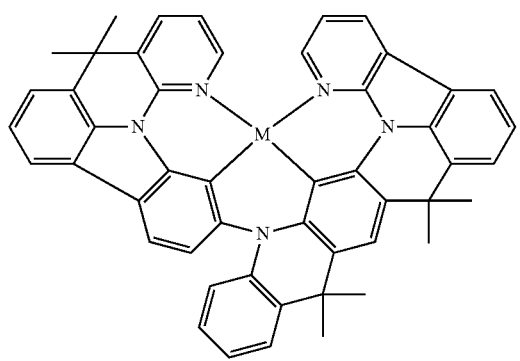
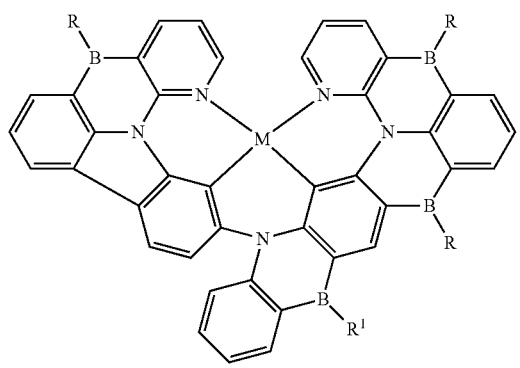
338
-continued
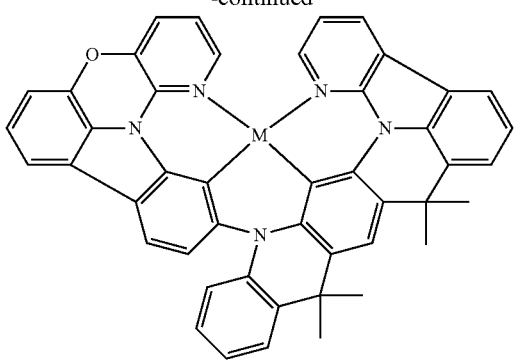
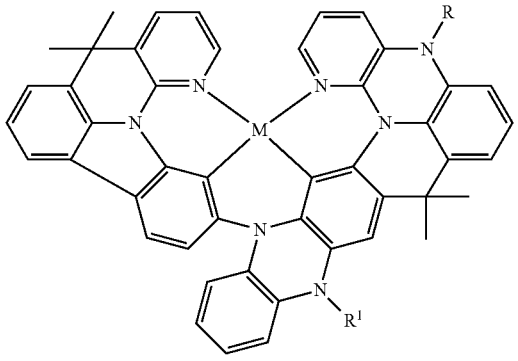
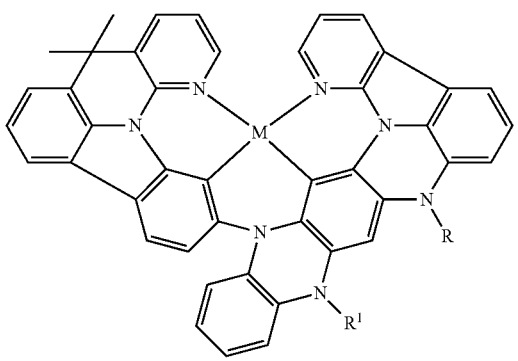
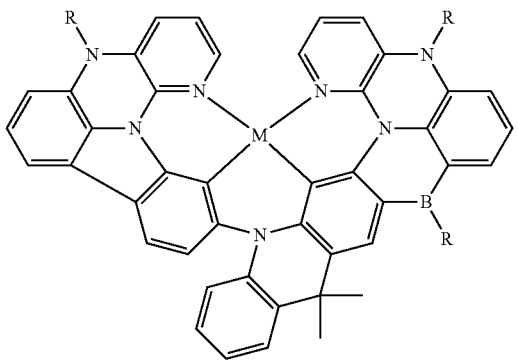

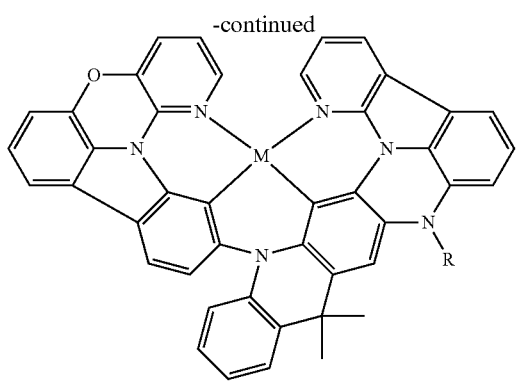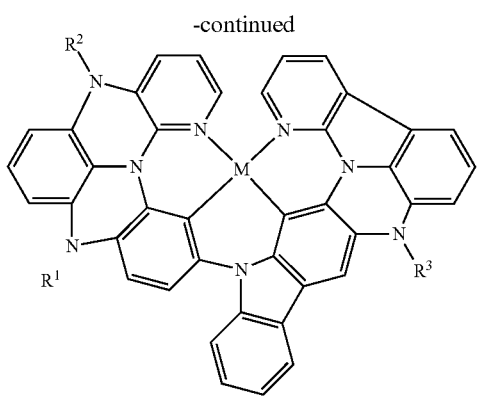
Structure 31 (M=Pt or Pd)
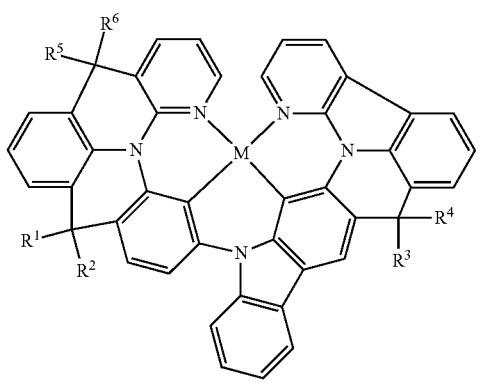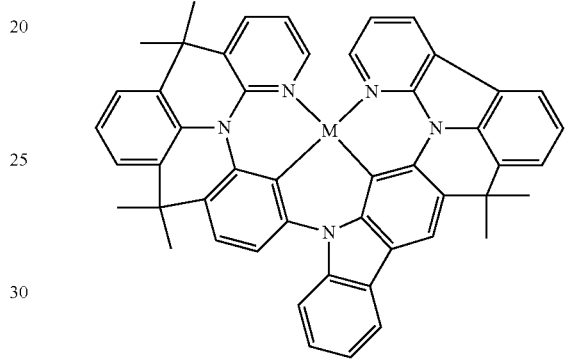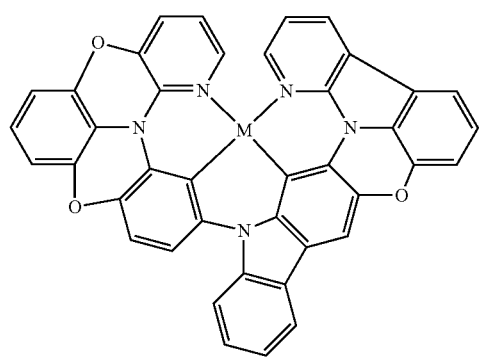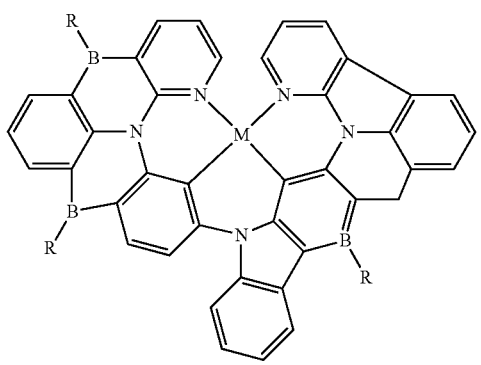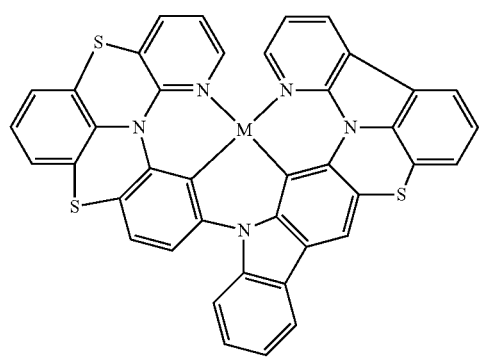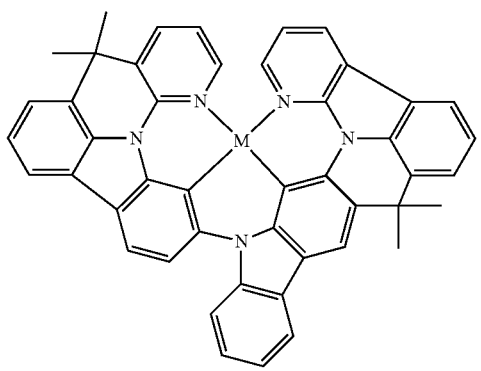

341
-continued
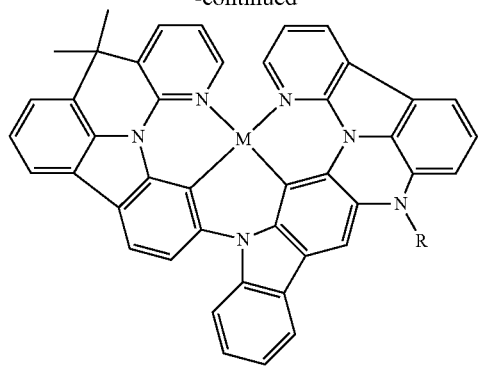
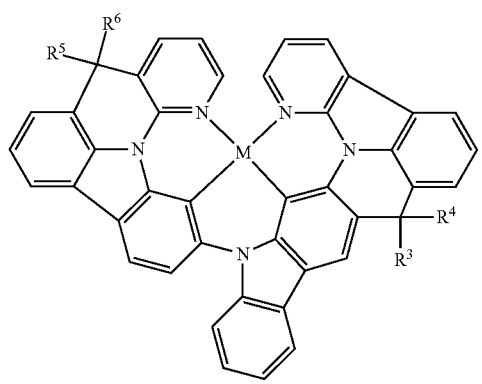
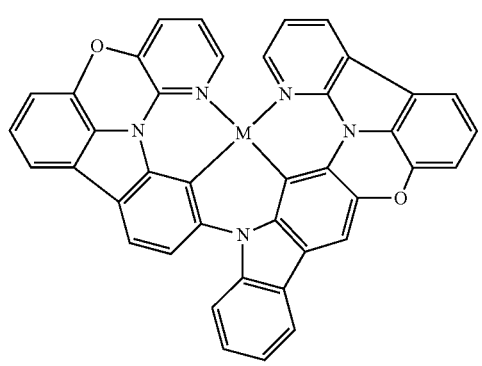
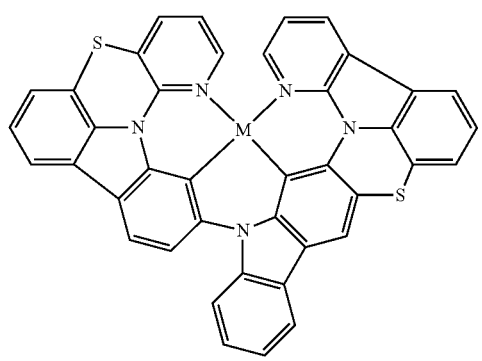
342
-continued
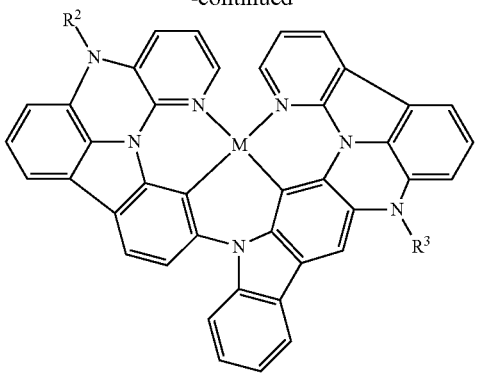
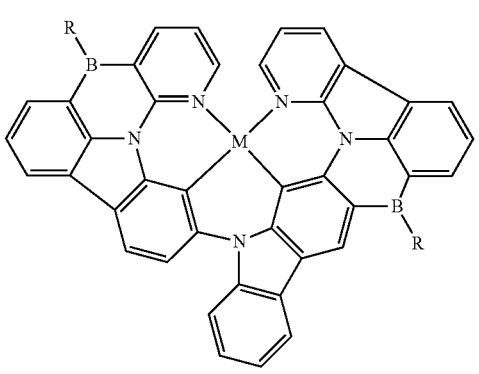
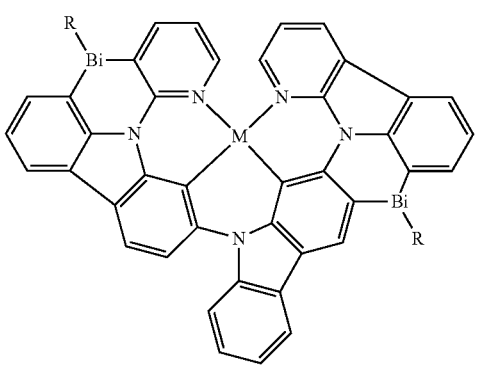
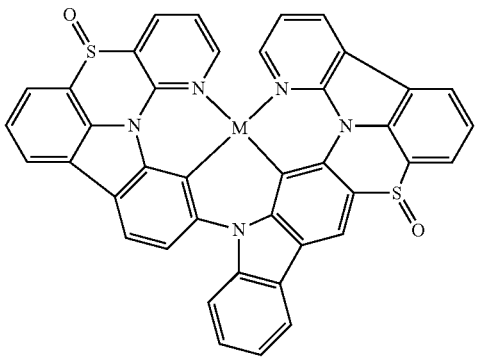

343
-continued
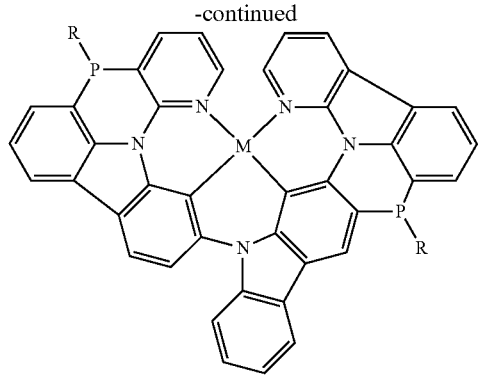
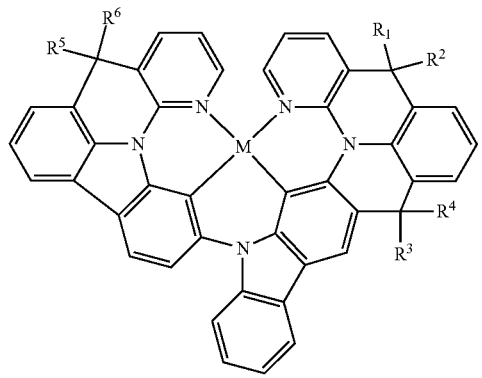
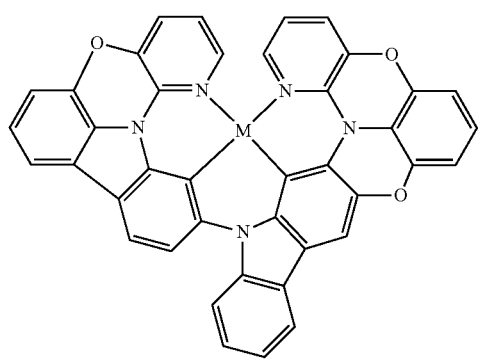
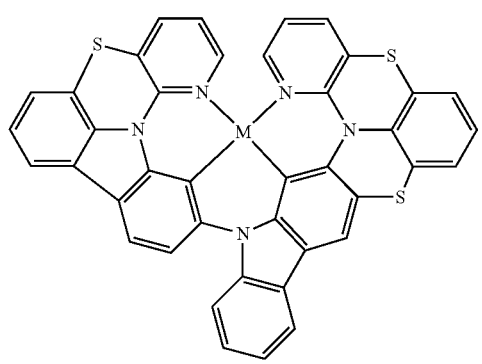
344
-continued
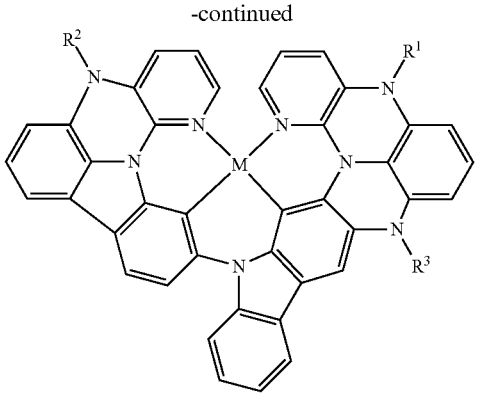
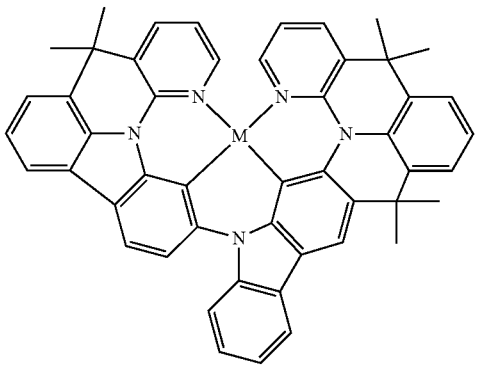
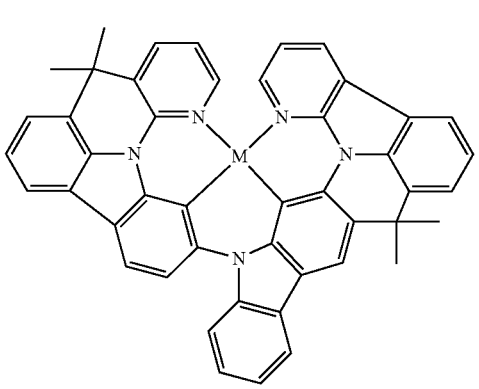
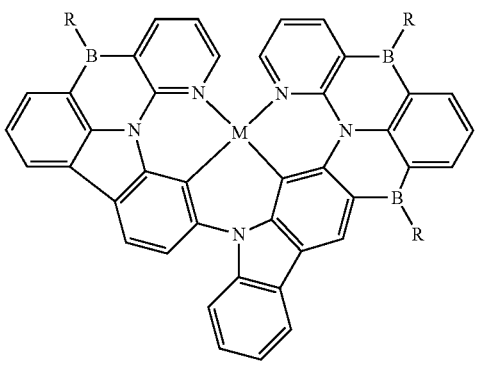

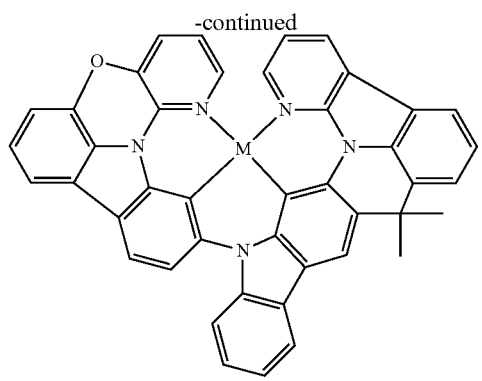
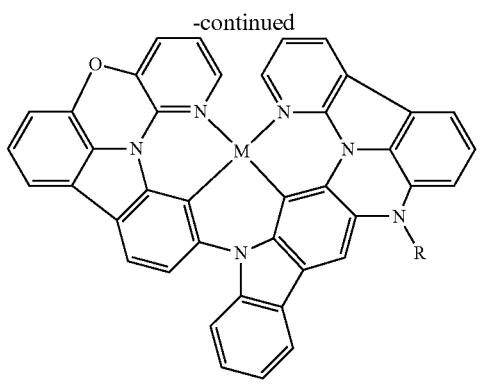
Structure 32
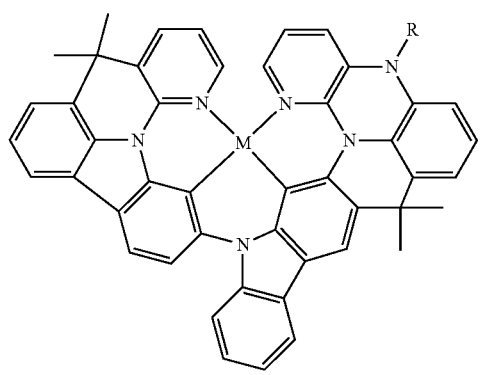
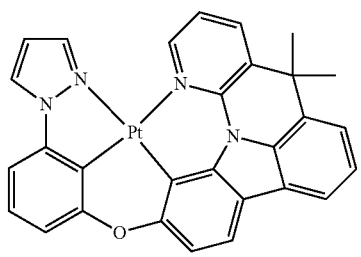
PtON$^c$1
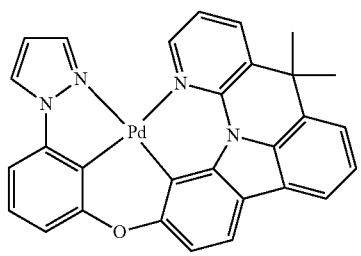
PdON$^c$1
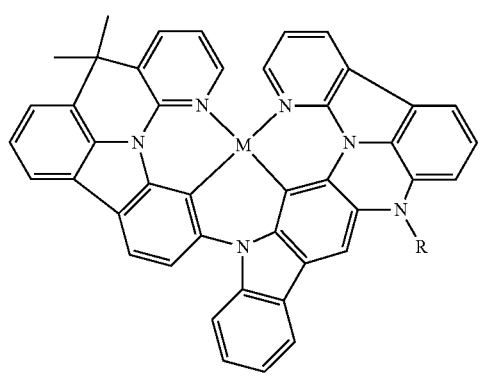
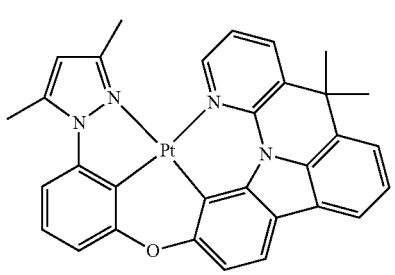
PtON$^c$1-DM
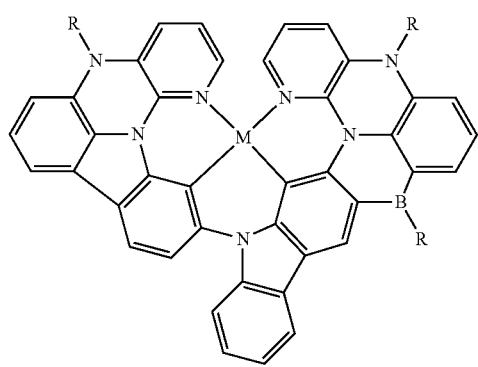
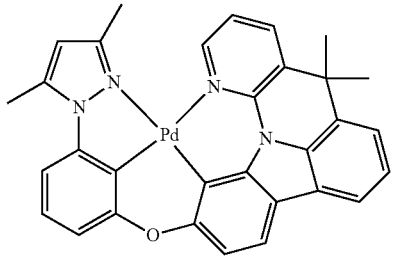
PdON$^c$1-DM -continued
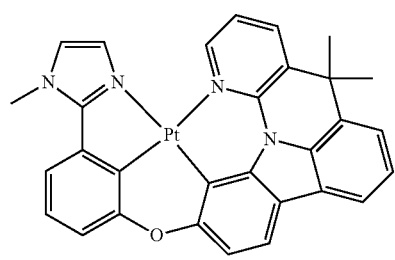
PtON<sup>c</sup>2
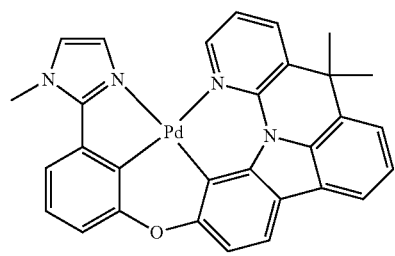
PdON<sup>c</sup>2
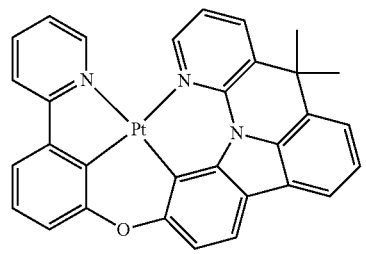
PtON<sup>c</sup>3
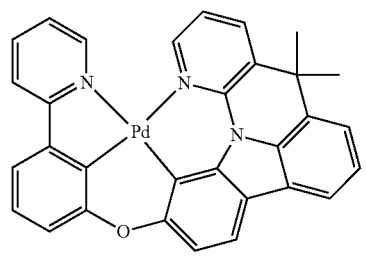
PdON<sup>c</sup>3
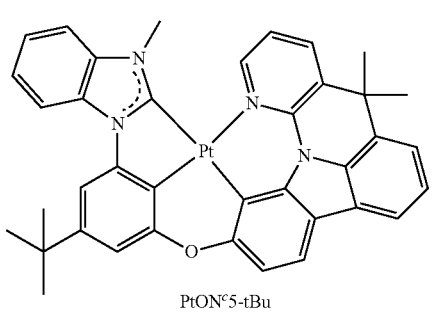
PtON<sup>c</sup>5-tBu
-continued
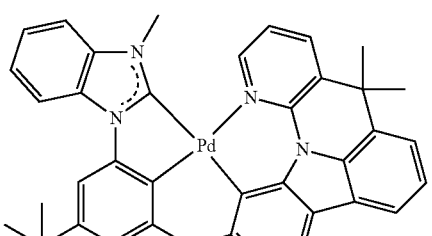
PdON<sup>c</sup>5-tBu
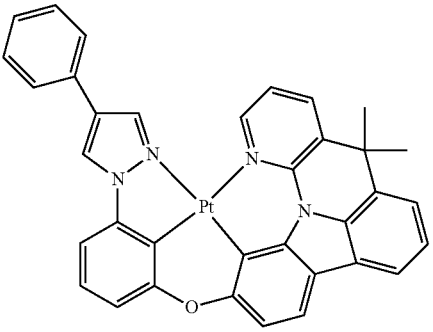
PtON<sup>c</sup>6
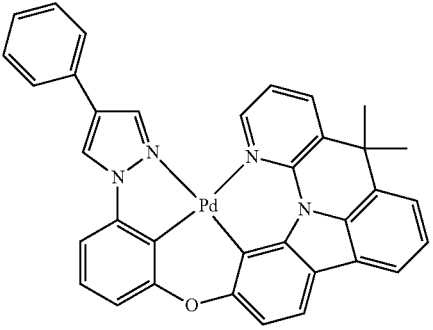
PdON<sup>c</sup>6
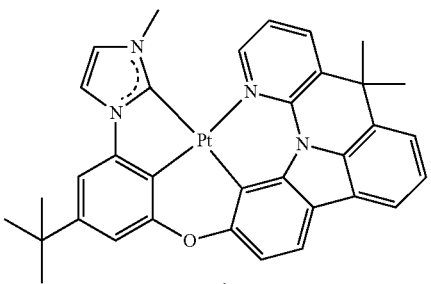
PtON<sup>c</sup>7-tBu
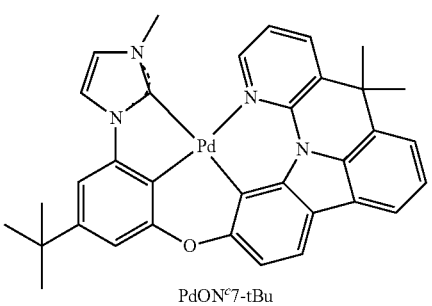
PdON<sup>c</sup>7-tBu -continued
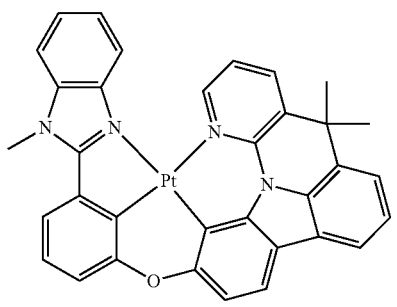
PtON^c8
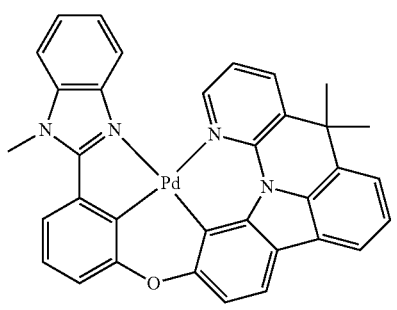
PdON^c8
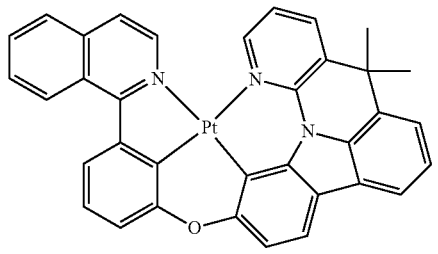
PtON^c10
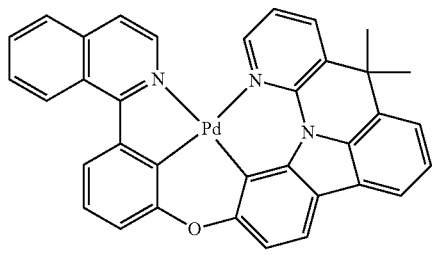
PdON^c10
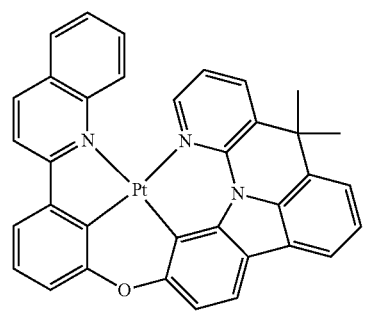
PtON^c11
-continued
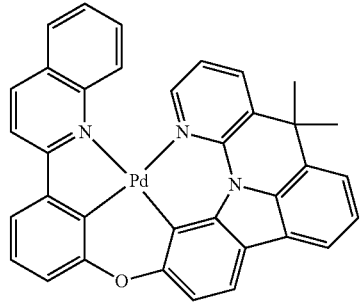
PdON^c11
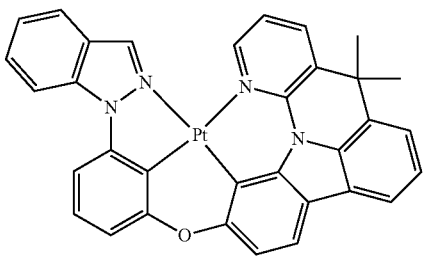
PtON^c12
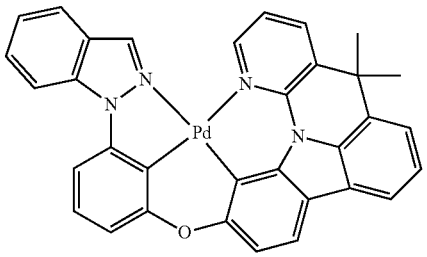
PdON^c12
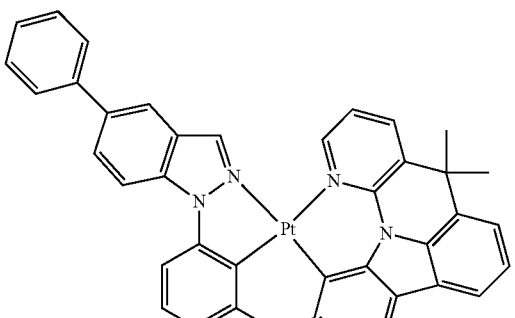
PtON^c12Ph
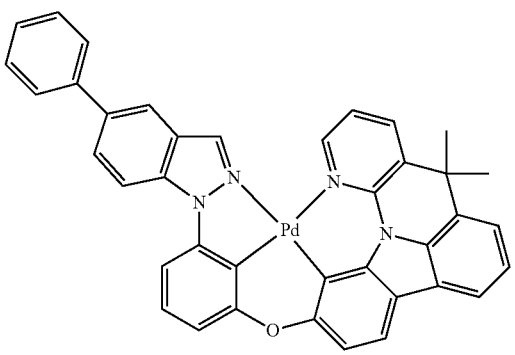
PdON^c12Ph -continued
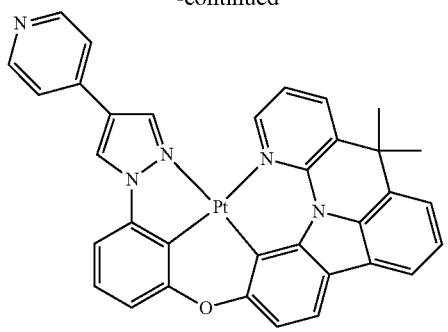
PtON^c1c
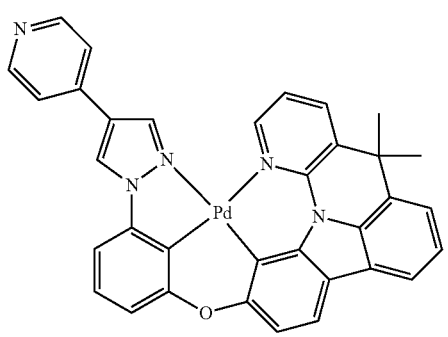
PdON^c1c
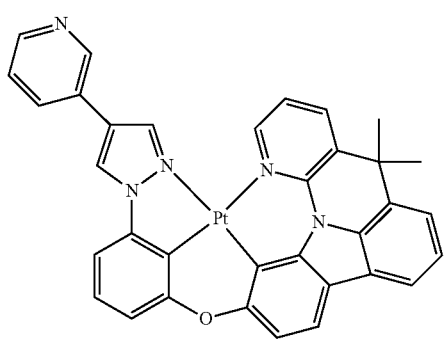
PtON^c1d
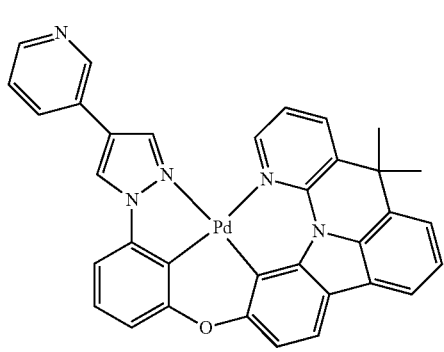
PdON^c1d
Structure 33
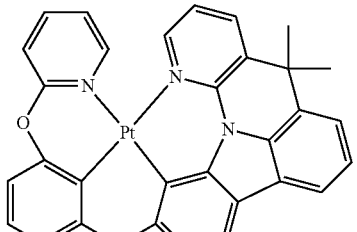
PtOON^C3
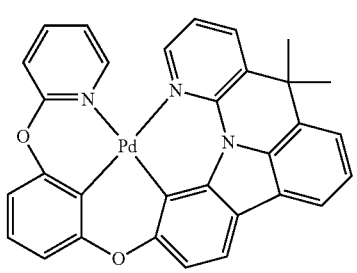
PdOON^C3
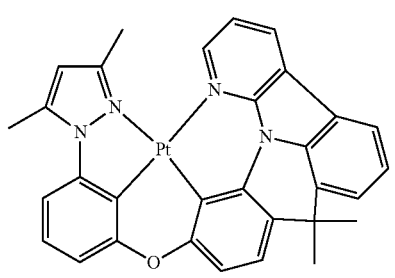
PtON^C1-DM
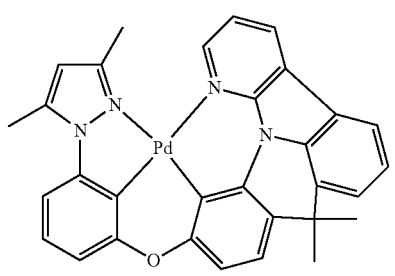
PdON^C1-DM
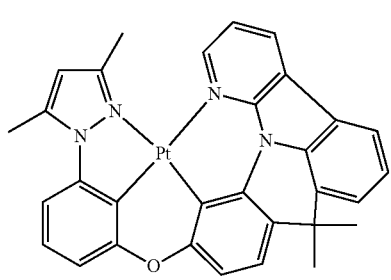
PtON^C1-DM -continued
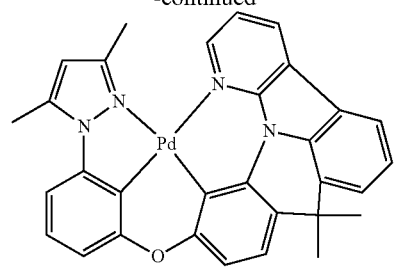
PdON<sup>C</sup>1-DM
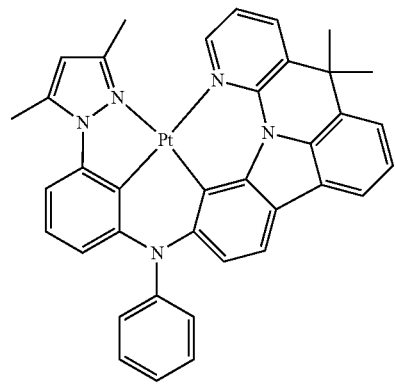
PtN<sup>C</sup>N-DM
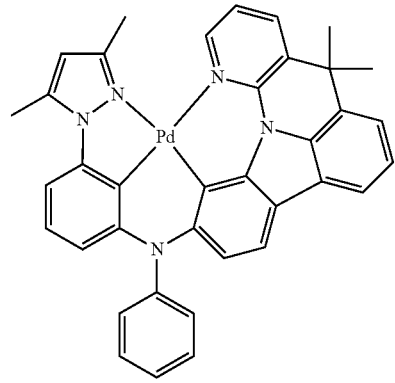
PdN<sup>C</sup>N-DM
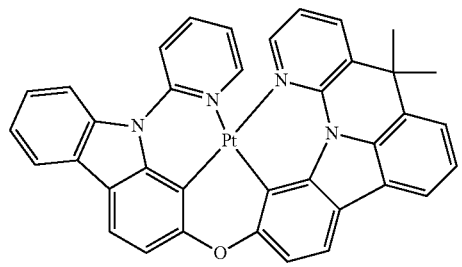
PtNON<sup>C</sup>
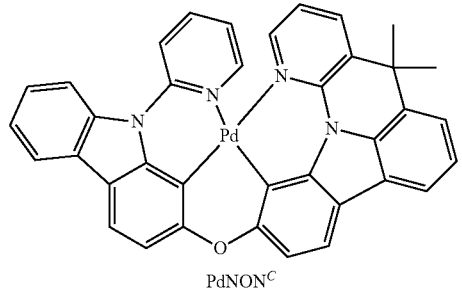
PdNON<sup>C</sup>
-continued
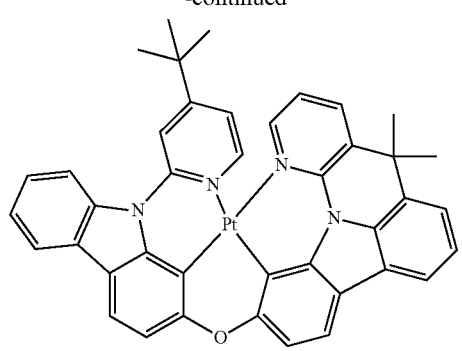
PtNON<sup>C</sup>-tBu
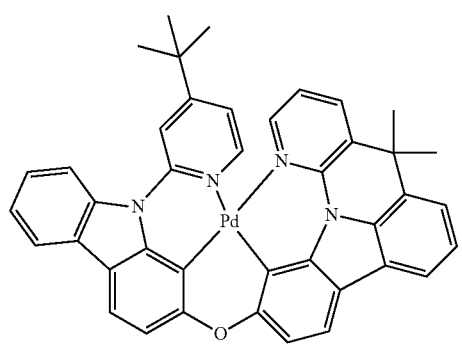
PdNON<sup>C</sup>-tBu
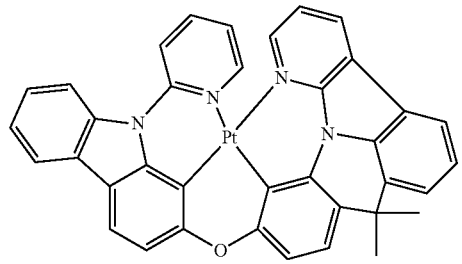
PtNON<sup>C'</sup>
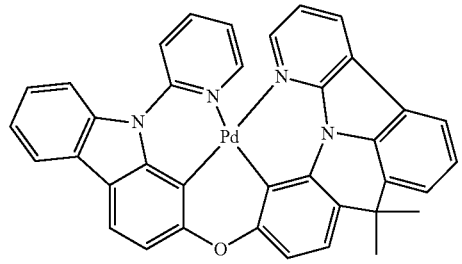
PdNON<sup>C'</sup>
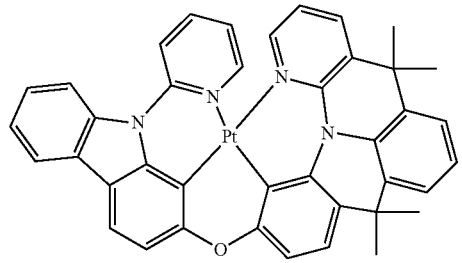
PtNON<sup>CC</sup>

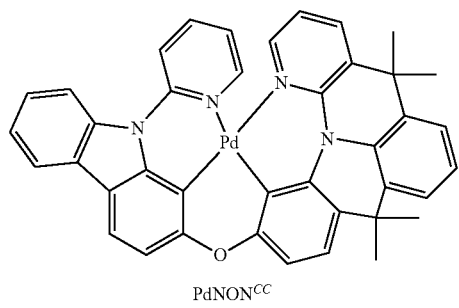
PdNON^{CC}
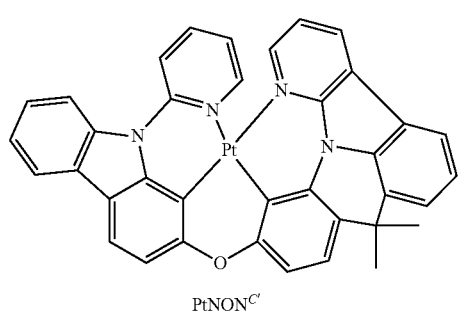
PtNON^{C'}
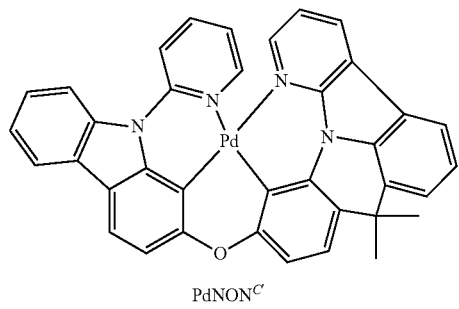
PdNON^{C'}
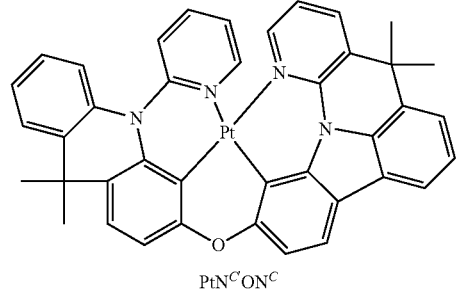
PtN^{C}ON^{C}
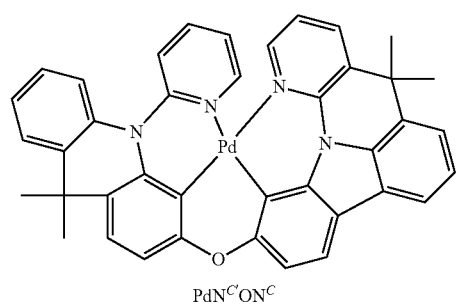
PdN^{C}ON^{C}
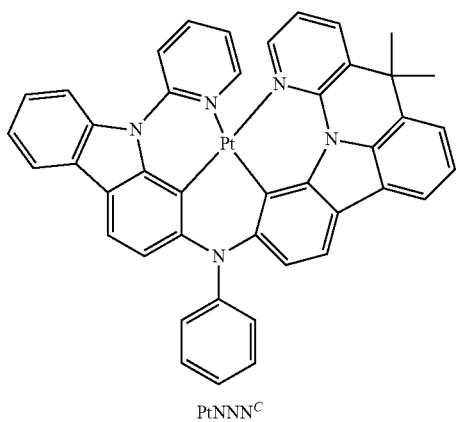
PtNNN^{C}
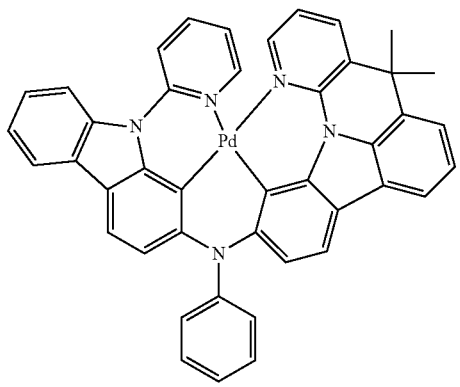
PdNNN^{C}
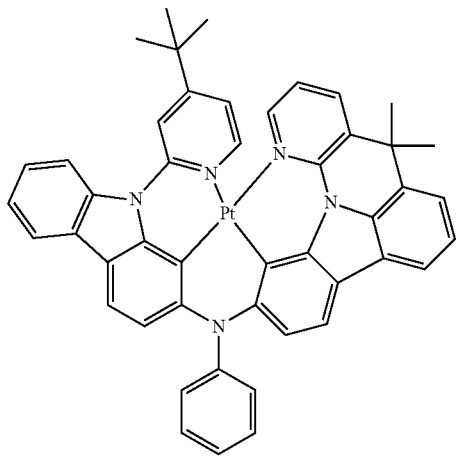
PtNNN^{C}-tBu 357
-continued
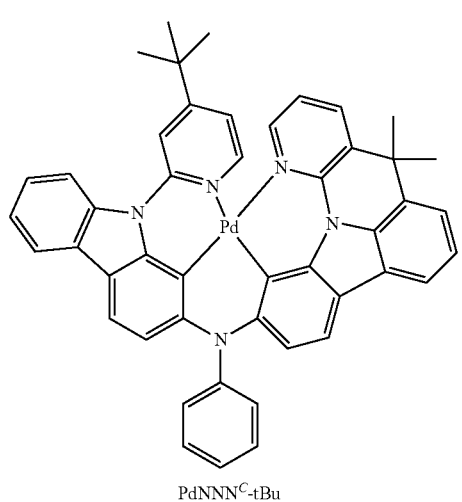
PdNNN<sup>C</sup>-tBu
Structure 34
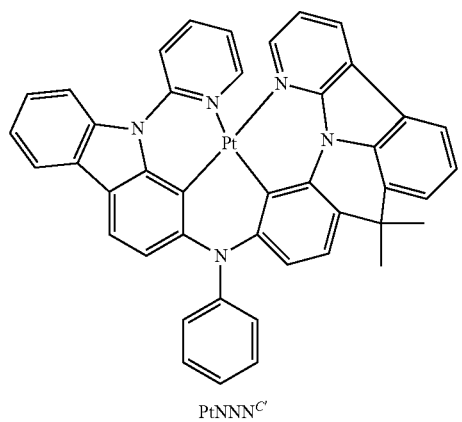
PtNNN<sup>C'</sup>
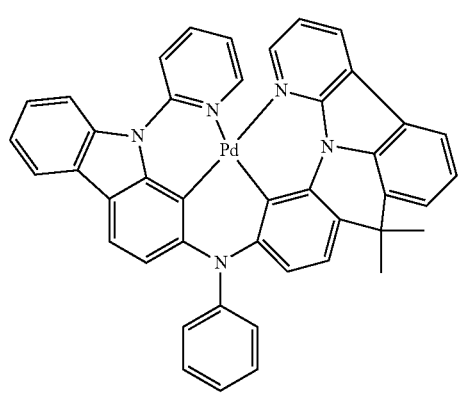
PdNNN<sup>C'</sup>
358
-continued
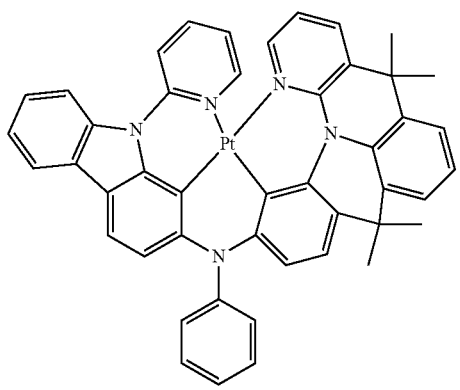
PtNNN<sup>CC</sup>
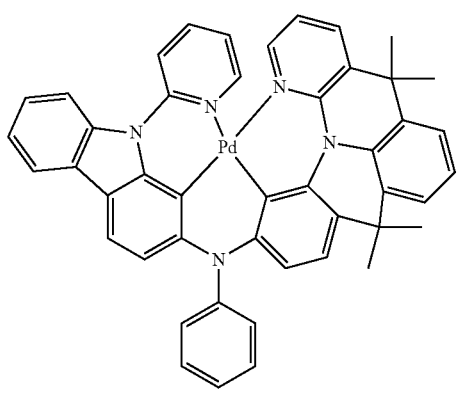
PdNNN<sup>CC</sup>
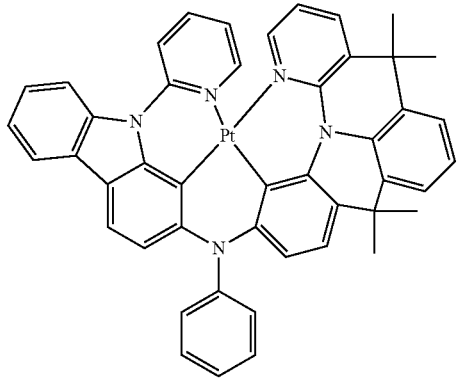
PtNNN<sup>CC</sup>
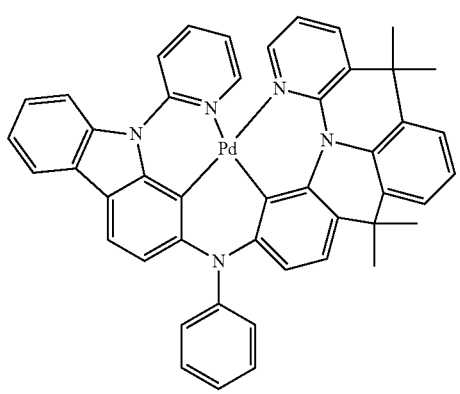
PdNNN<sup>CC</sup>

359
-continued
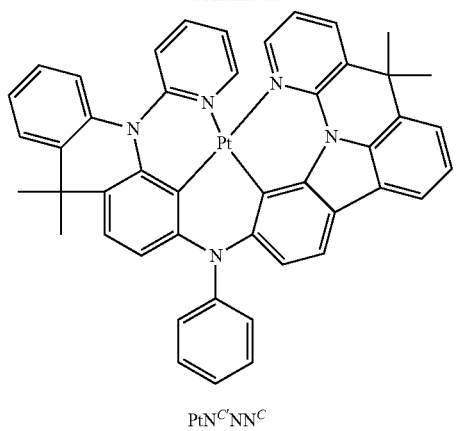
PtN<sup>C'</sup>NN<sup>C</sup>
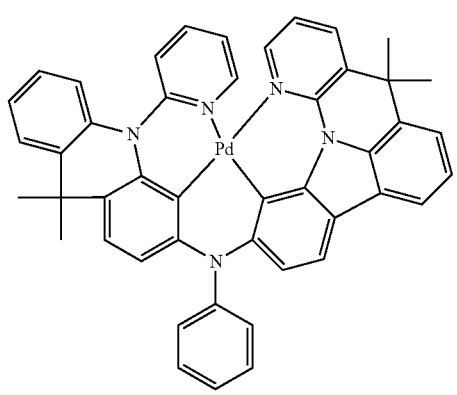
PdN<sup>C'</sup>NN<sup>C</sup>
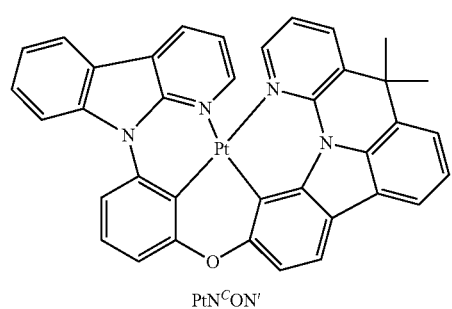
PtN<sup>C</sup>ON'
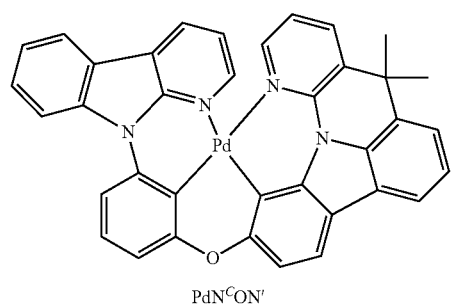
PdN<sup>C</sup>ON'
360
-continued
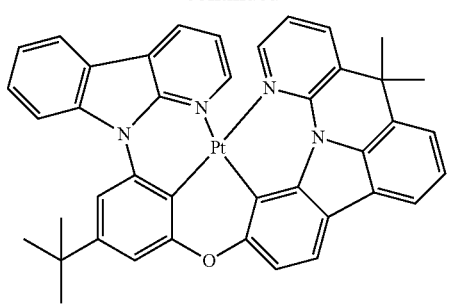
PtN<sup>C</sup>ON'-tBu
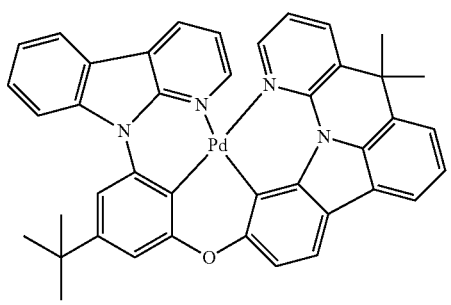
PdN<sup>C</sup>ON'-tBu
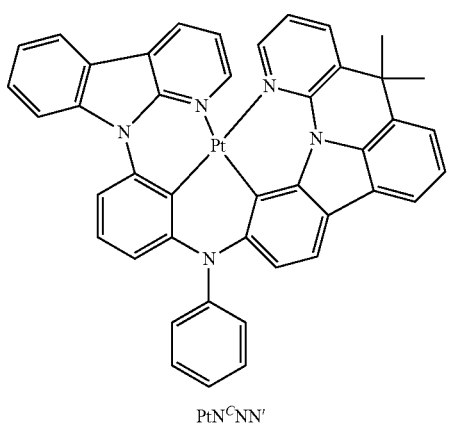
PtN<sup>C</sup>NN'
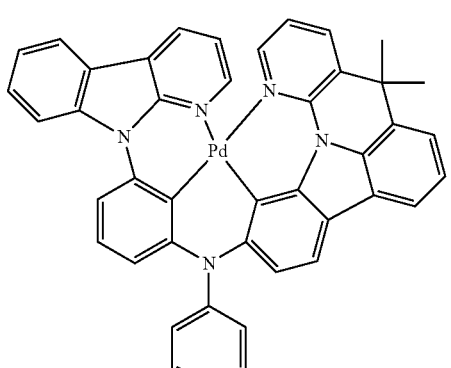
PdN<sup>C</sup>NN'

361
-continued
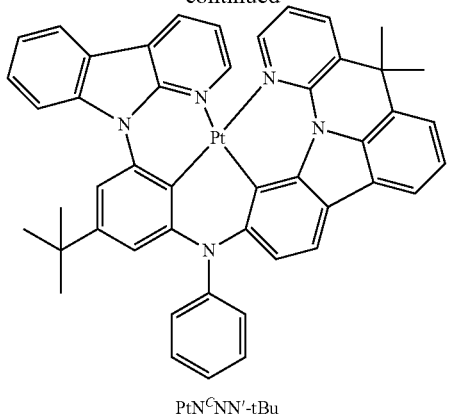
PtN^C NN'-tBu
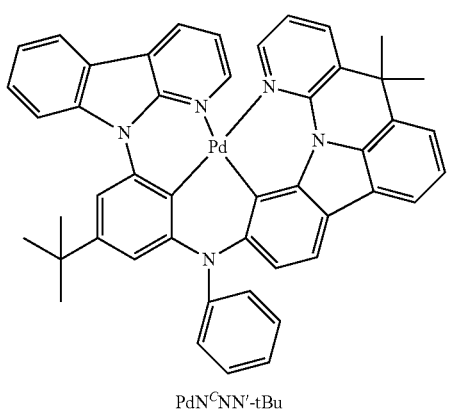
PdN^C NN'-tBu
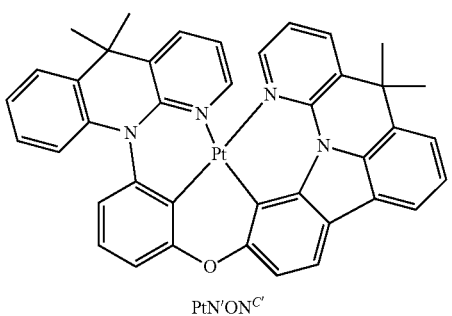
PtN'ON^C'
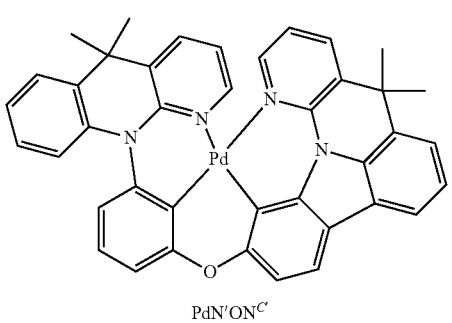
PdN'ON^C'
362
-continued
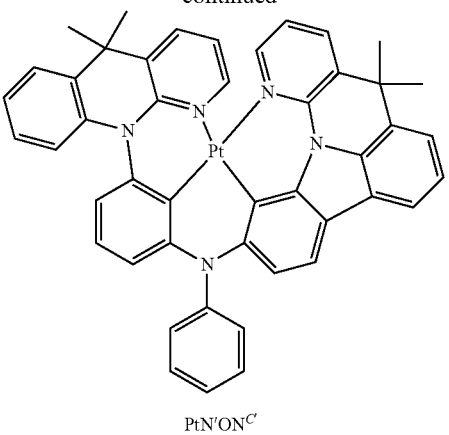
PtN'ON^C'
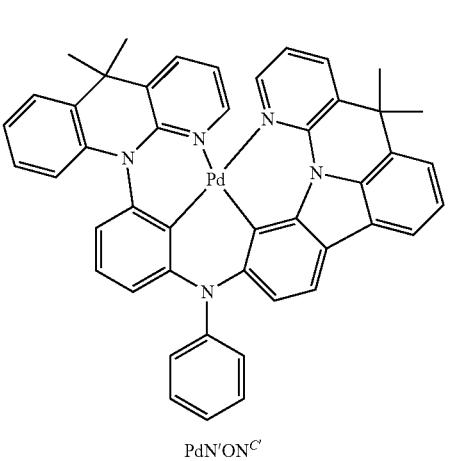
PdN'ON^C'
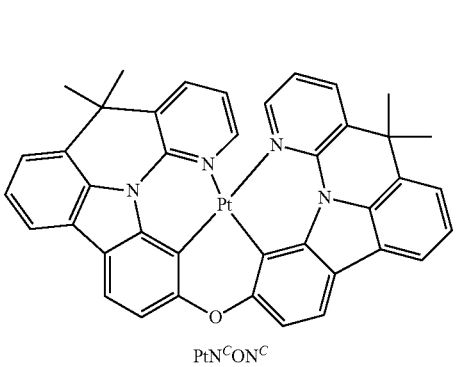
PtN^C ON^C
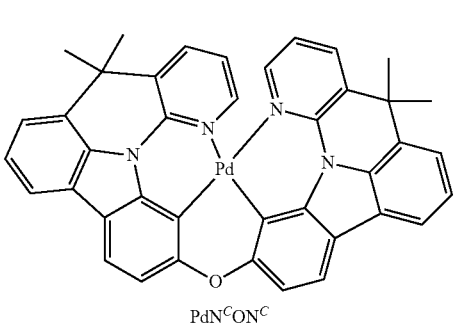
PdN^C ON^C

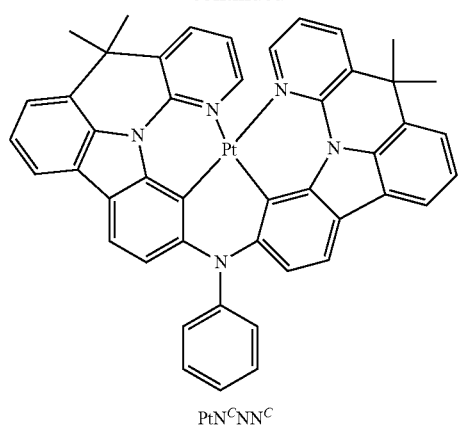
PtN$^C$NN$^C$
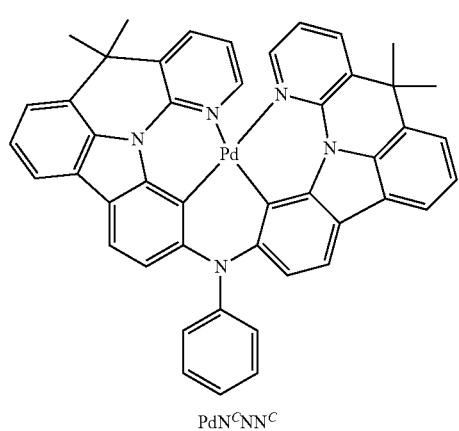
PdN$^C$NN$^C$
Structure 35
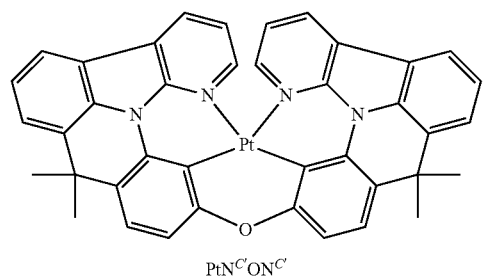
PtN$^{C'}$ON$^{C'}$
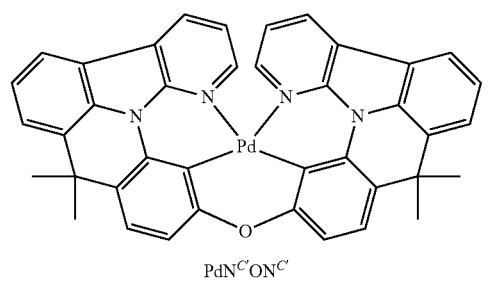
PdN$^{C'}$ON$^{C'}$
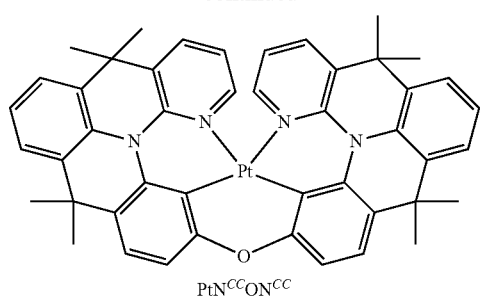
PtN$^{CC}$ON$^{CC}$
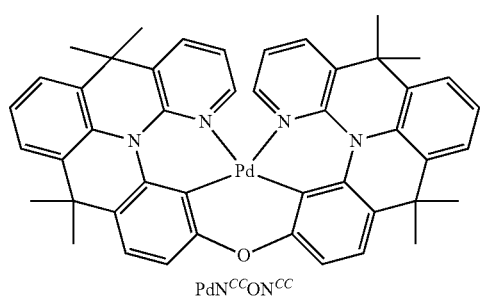
PdN$^{CC}$ON$^{CC}$
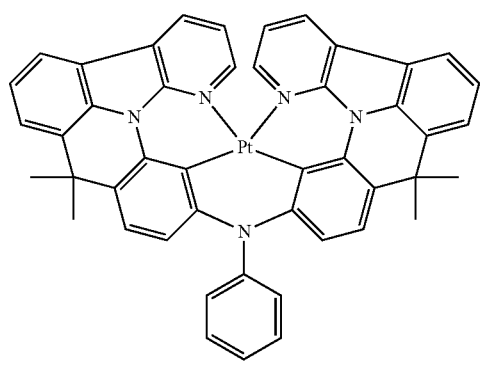
PtN$^{C'}$NN$^{C'}$
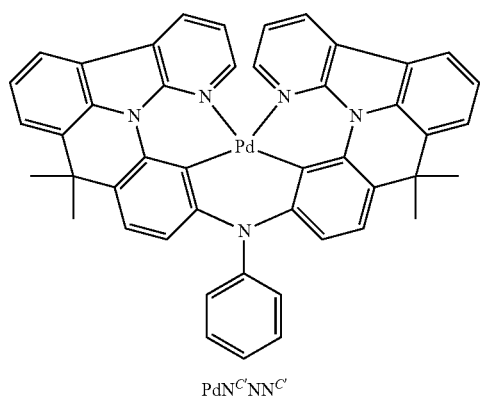
PdN$^{C'}$NN$^{C'}$ 365
-continued
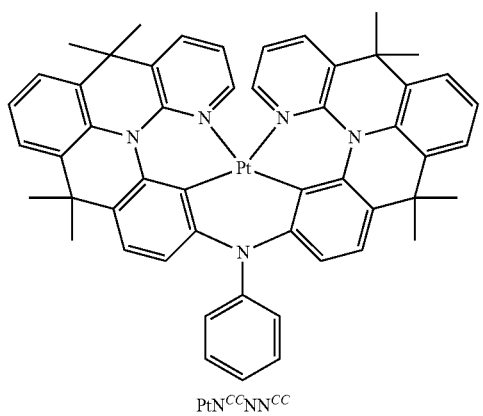
PtN^{CC}NN^{CC}
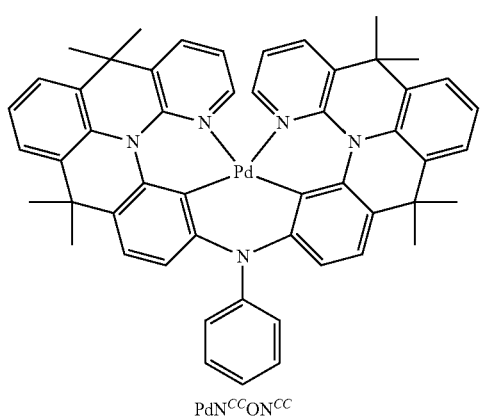
PdN^{CC}ON^{CC}
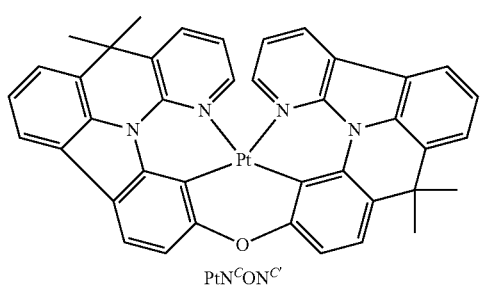
PtN^{C}ON^{C'}
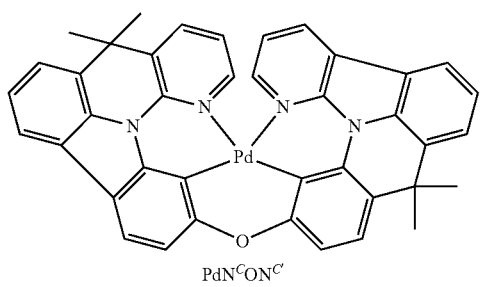
PdN^{C}ON^{C'}
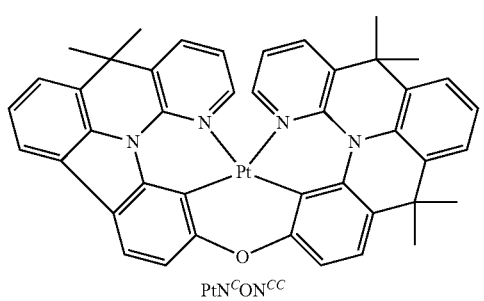
PtN^{C}ON^{CC}
366
-continued
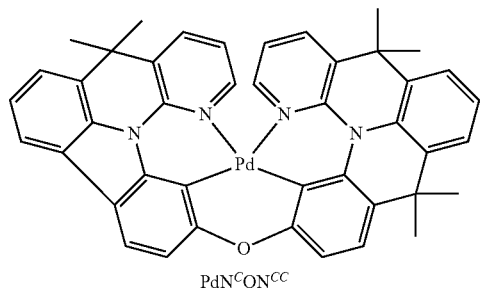
PdN^{C}ON^{CC}
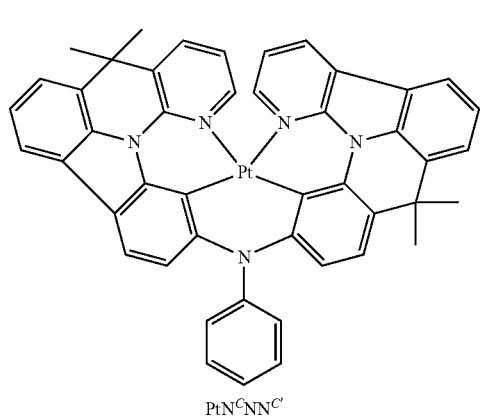
PtN^{C}NN^{C'}
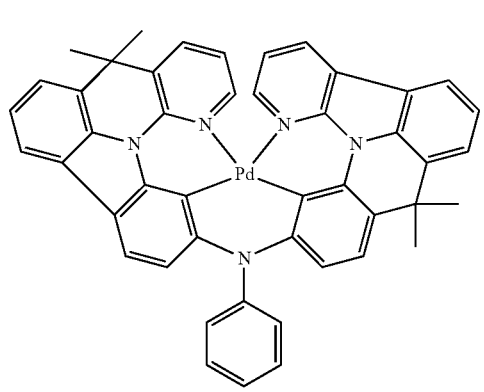
PdN^{C}NN^{C'}
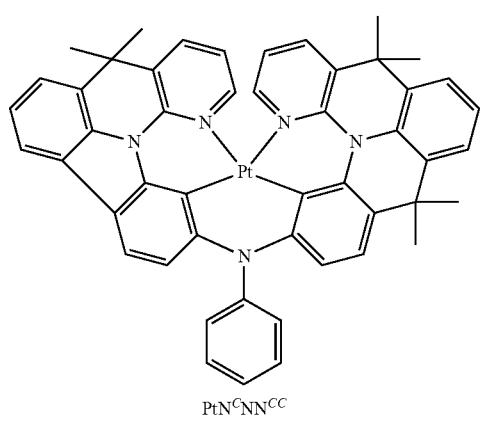
PtN^{C}NN^{CC}

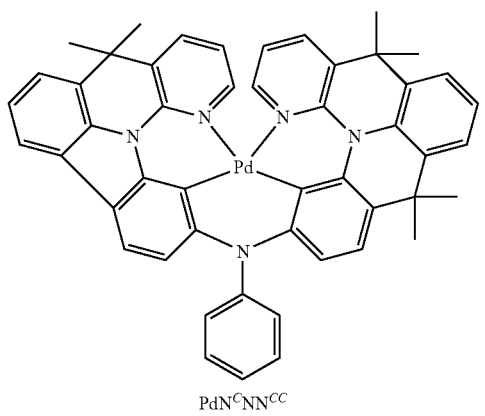
PdN^C NN^{CC}
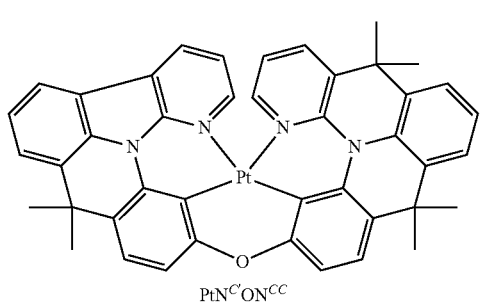
PtN^{C'}ON^{CC}
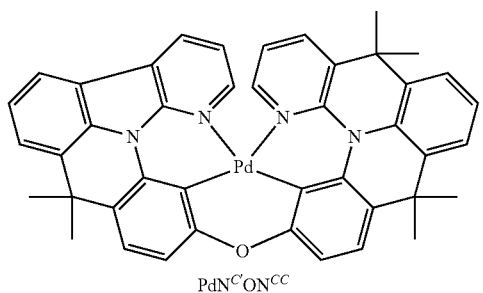
PdN^{C'}ON^{CC}
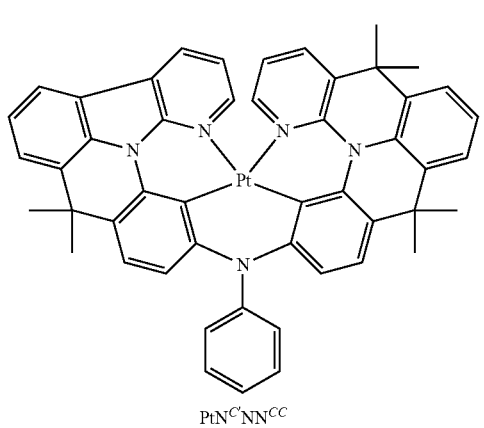
PtN^{C'}NN^{CC}
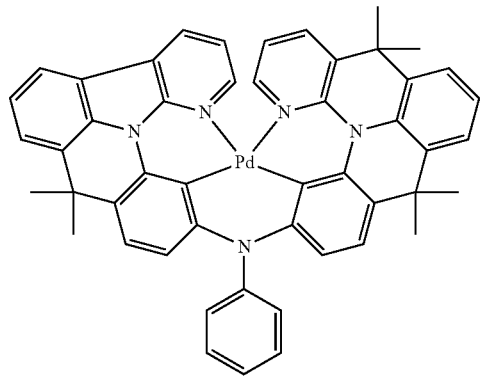
PdN^{C'}NN^{CC}
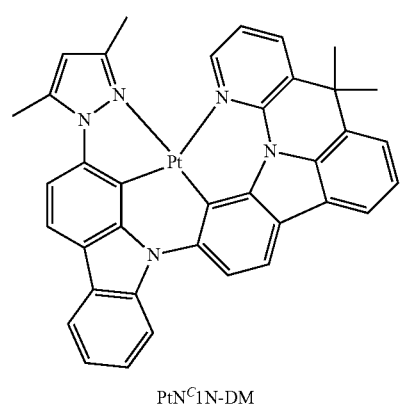
PtN^C 1N-DM
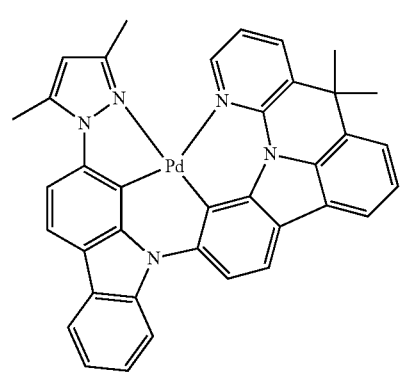
PdN^C 1N-DM
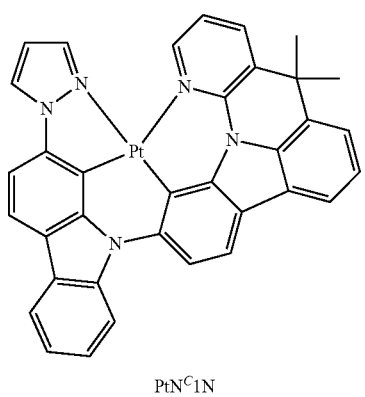
PtN^C 1N -continued
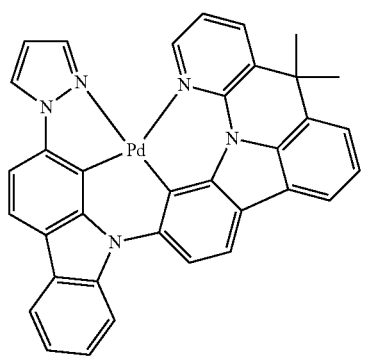
PdN^C1N
Structure 36
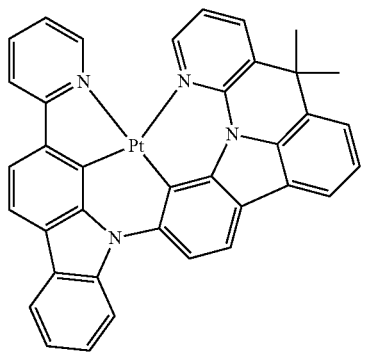
PtN3^CN
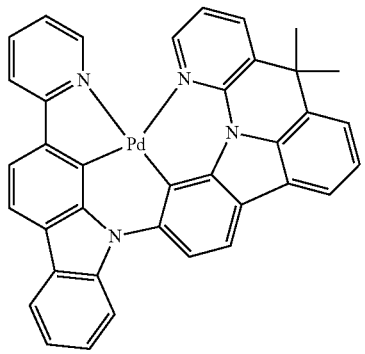
PdN3^CN
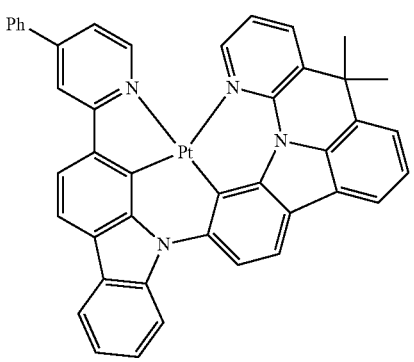
PtN^C3N-Ph
-continued
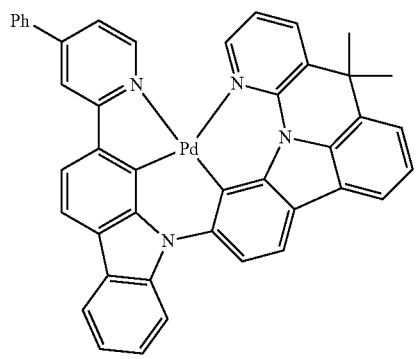
PdN^C3N-Ph
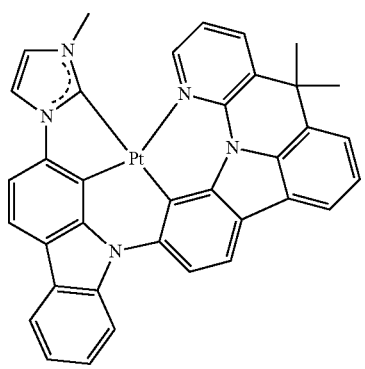
PtN^C7N
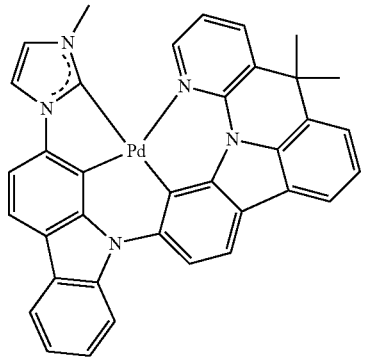
PdN^C7N
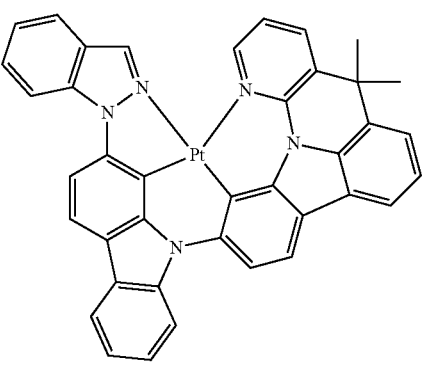
PtN^C12N -continued
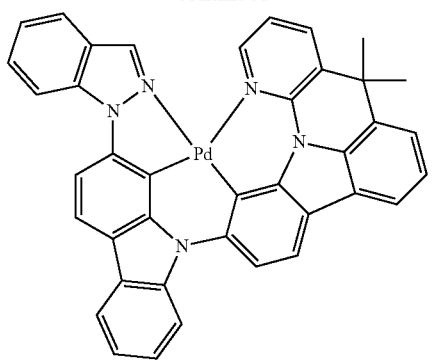
PdN^C12N
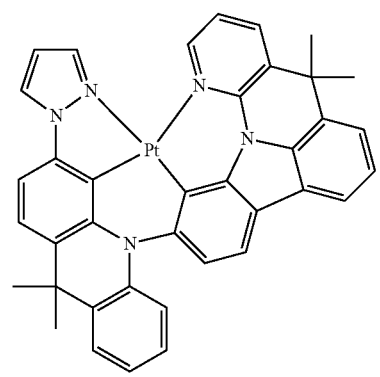
PtN^C1N'
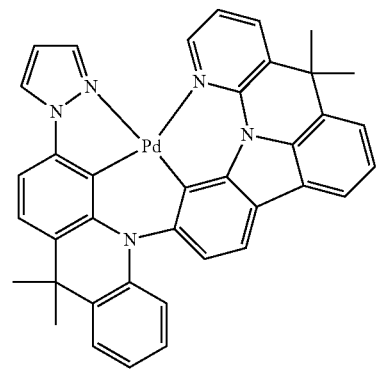
PdN^C1N'
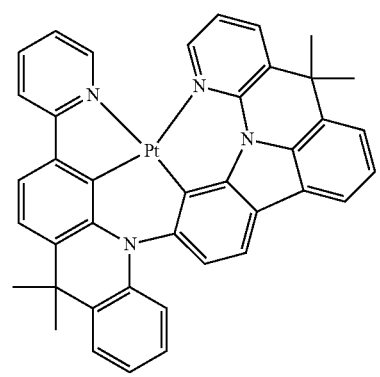
PtN^C3N'
-continued
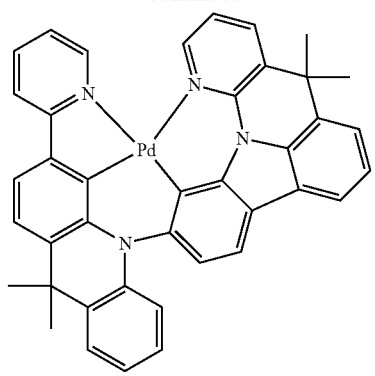
PdN^C3N'
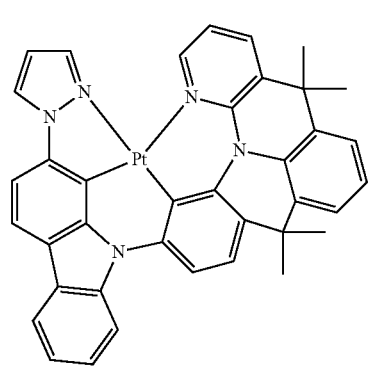
PtN^CC1N
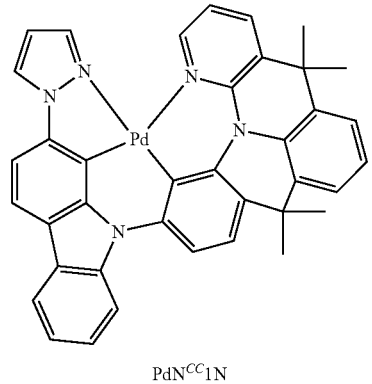
PdN^CC1N
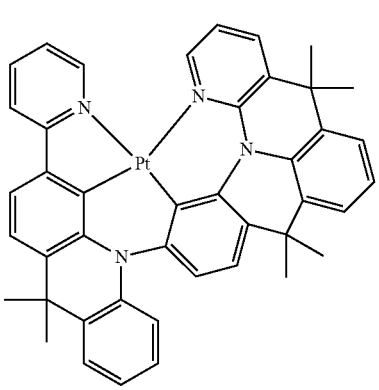
PtN^CC3N'

373
-continued
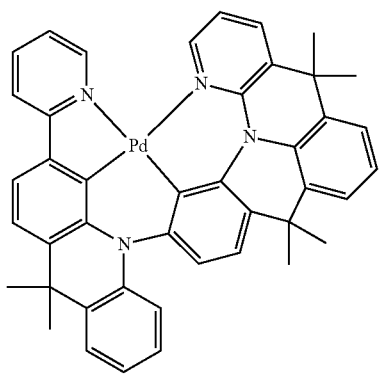
PdN^{CC}3N'
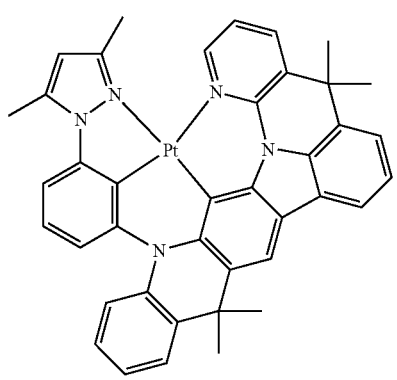
PtN-N^{C}1-DM
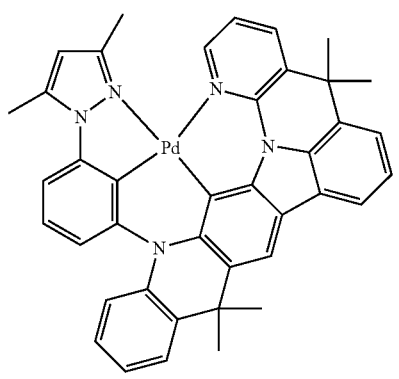
PdN-N^{C}1-DM
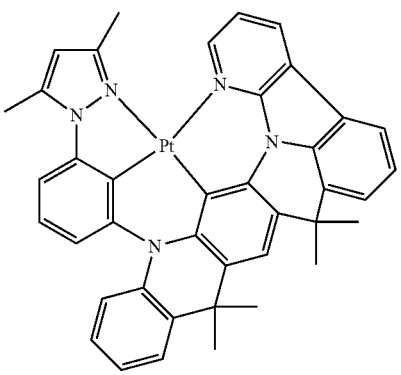
PtN-N^{C'}1-DM
374
-continued
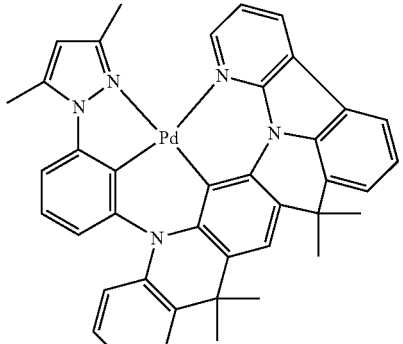
PdN-N^{C'}1-DM
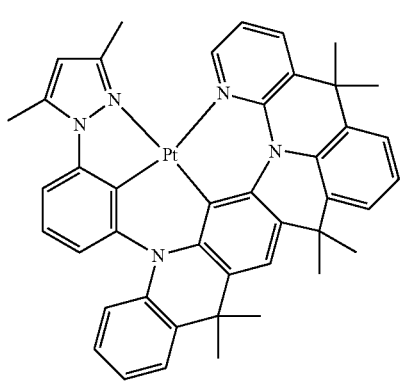
PtN-N^{CC}1-DM
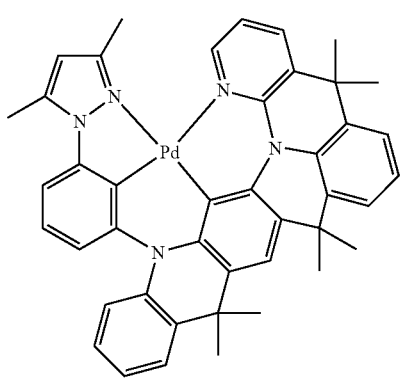
PdN-N^{CC}1-DM
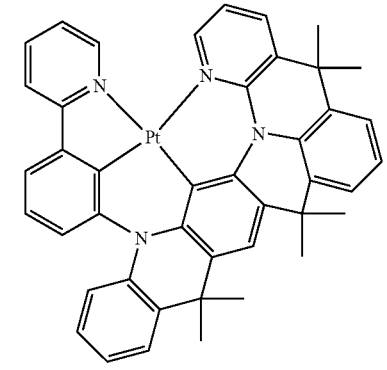
PtN-N^{CC}3

375
-continued
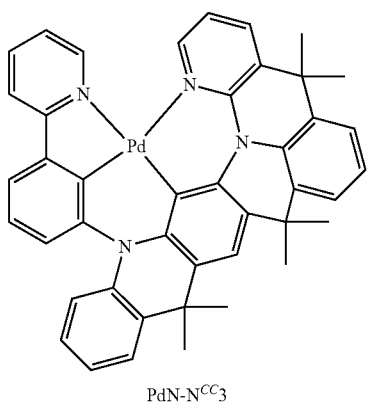
PdN-N$^{CC}$3
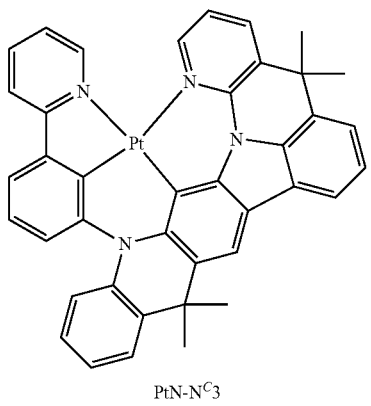
PtN-N$^{C}$3
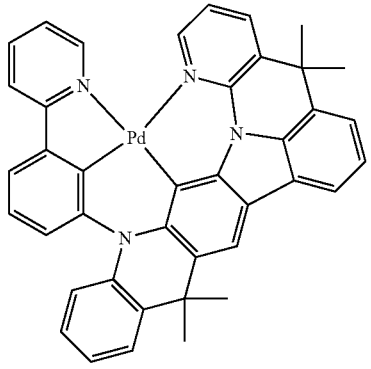
PdN-N$^{C}$3
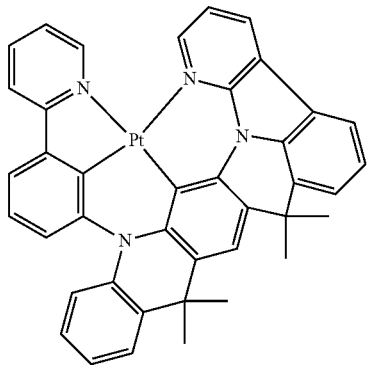
PtN-N$^{C'}$3
376
-continued
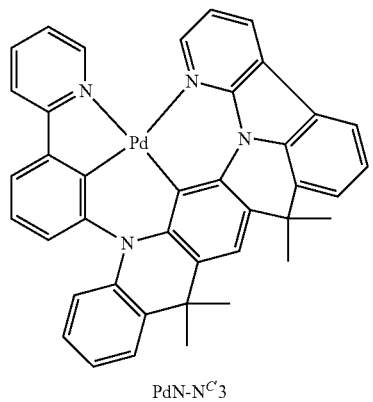
PdN-N$^{C}$3
Structure 37
PdN-N$^{c}$N$^{c}$
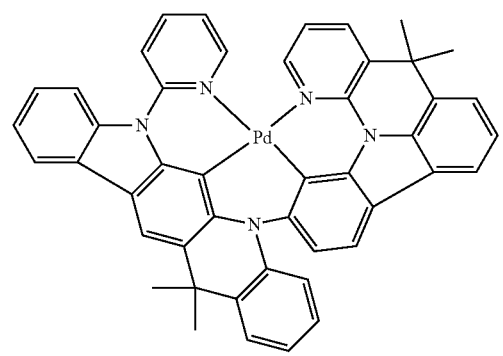
PtN-N$^{c}$N$^{c}$
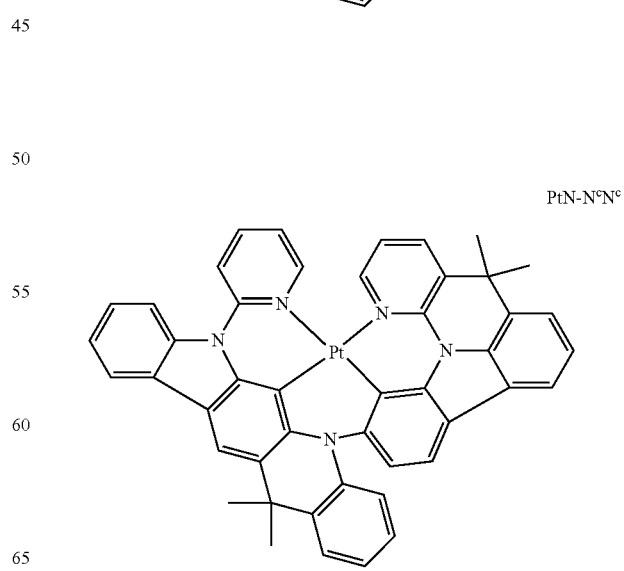

PdN-N<sup>c</sup>N<sup>c'</sup>-tBu
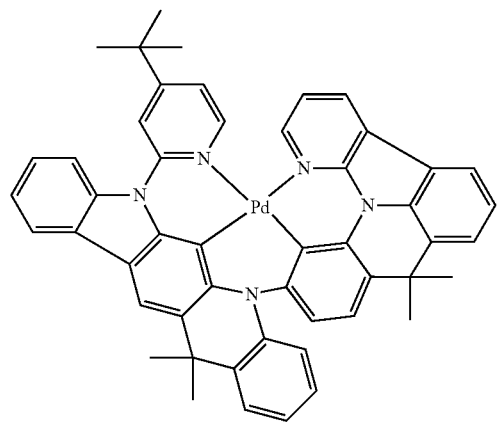
PtN-N<sup>c</sup>N<sup>c'</sup>-tBu
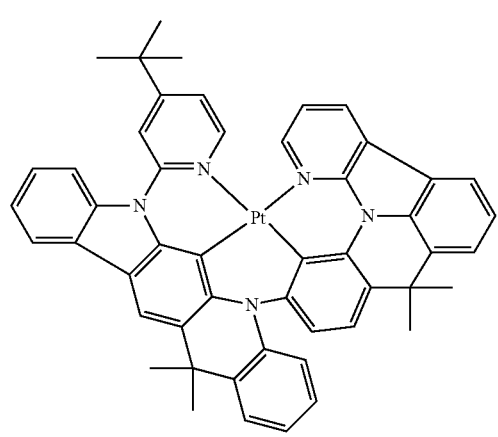
PdN-N<sup>c</sup>N<sup>cc</sup>
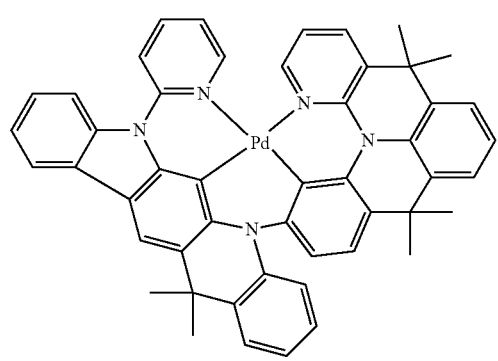
PtN-N<sup>c</sup>N<sup>cc</sup>
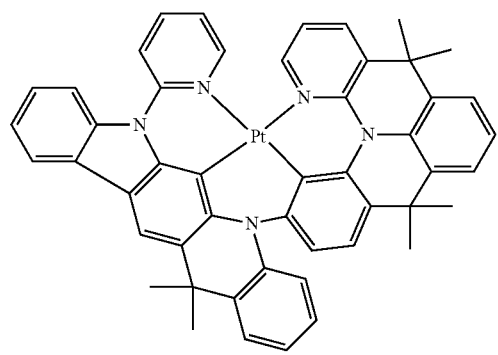
PdN<sup>c</sup>-N<sup>c</sup>N<sup>cc</sup>
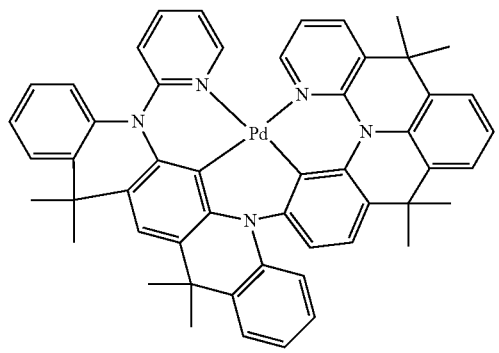
PtN<sup>c</sup>-N<sup>c</sup>N<sup>cc</sup>
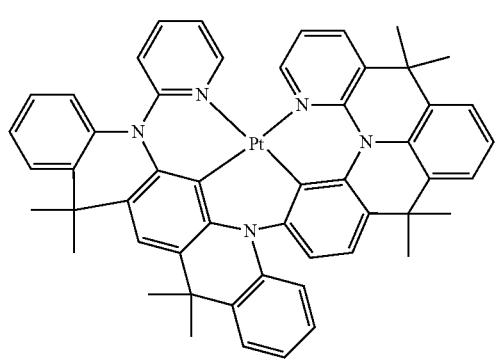
PdN<sup>c</sup>-N<sup>c</sup>N<sup>c</sup>-tBu
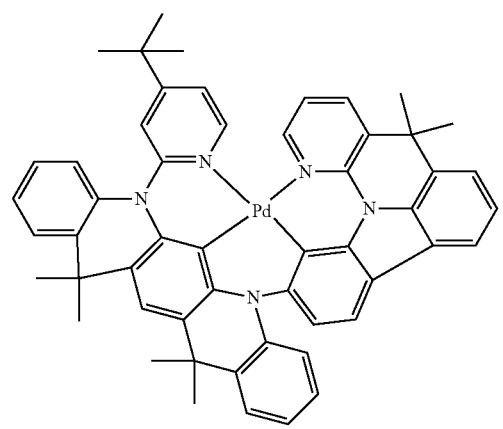
PtN<sup>c</sup>-N<sup>c</sup>N<sup>c</sup>-tBu
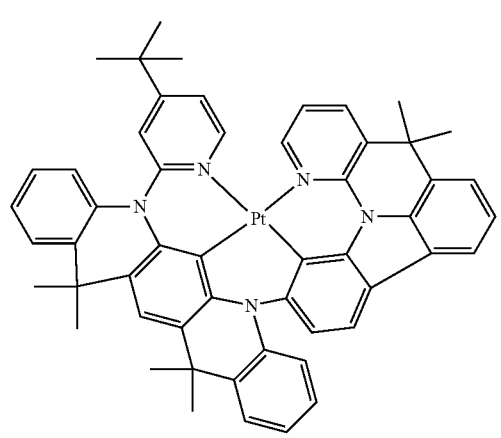

PdNc-NcNc'-tBu
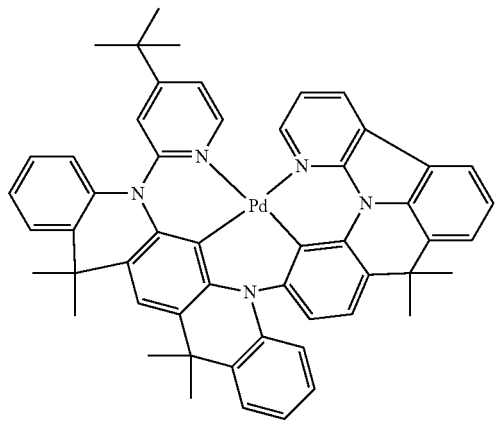
PtNc-NcNc'-tBu
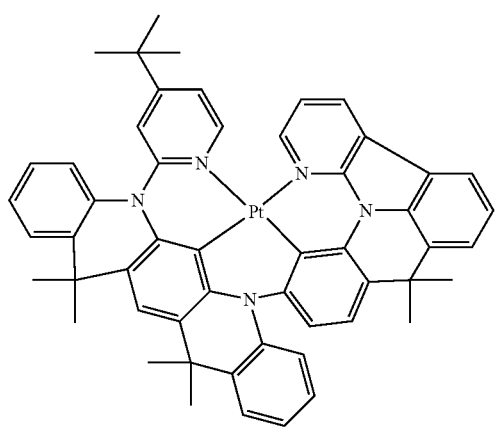
PdNNc-Nc
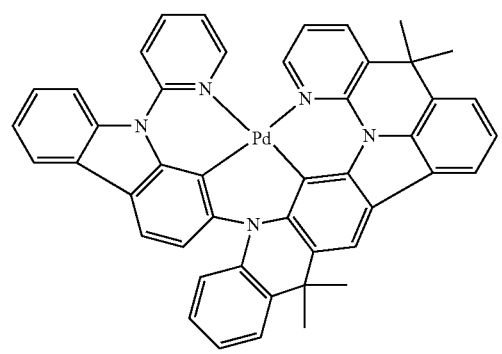
PtNNc-Nc
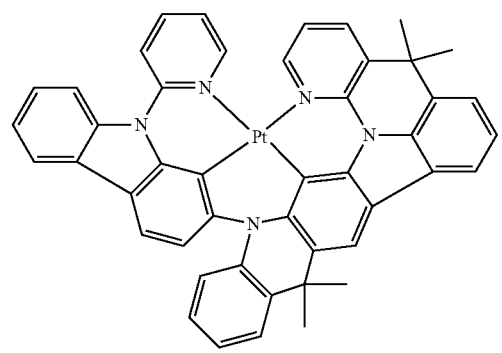
PdNNc-Nc'
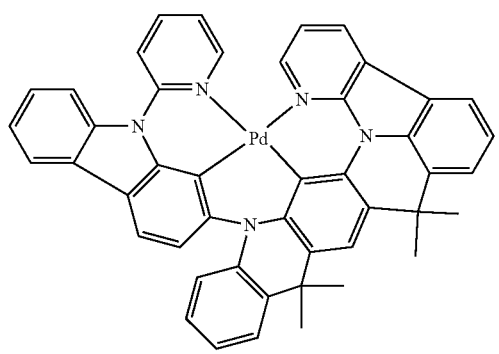
PtNNc-Nc'
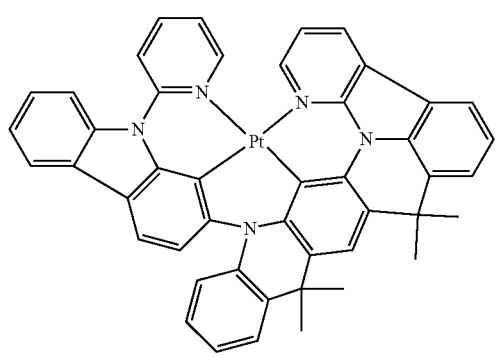
PdNNc-Ncc
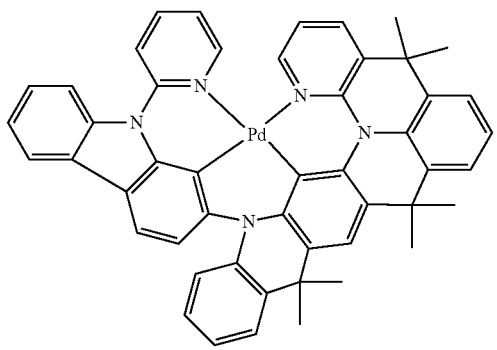
PtNNc-Ncc
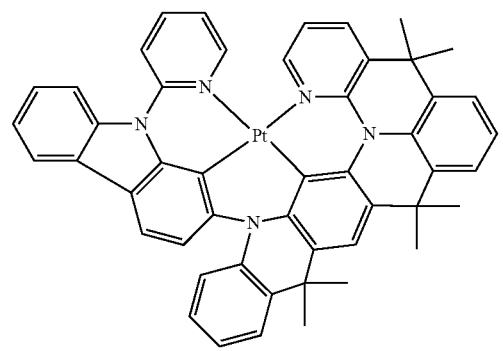

381
-continued
PdN<sup>c</sup>N<sup>c</sup>-N<sup>cc</sup>
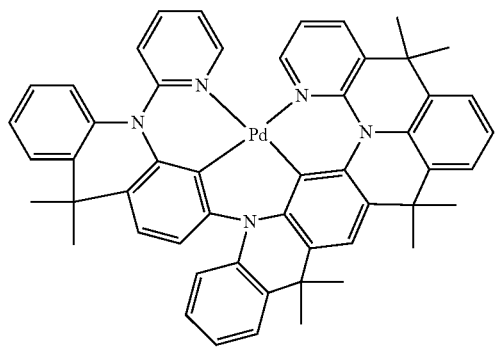
PtN<sup>c</sup>N<sup>c</sup>-N<sup>cc</sup>
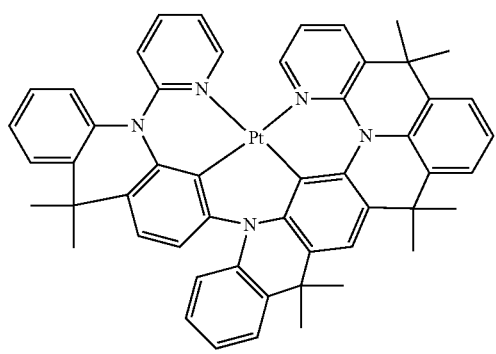
PdN<sup>c</sup>N<sup>c</sup>-N<sup>c</sup>
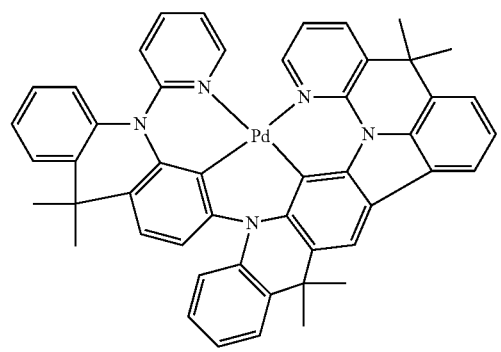
PtN<sup>c</sup>N<sup>c</sup>-N<sup>c</sup>
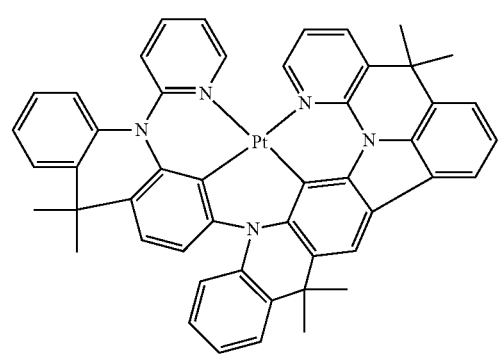
382
-continued
PdN<sup>c</sup>N<sup>c</sup>-N<sup>c'</sup>
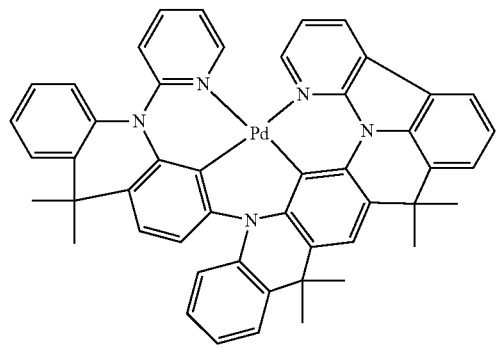
PtN<sup>c</sup>N<sup>c</sup>-N<sup>c'</sup>
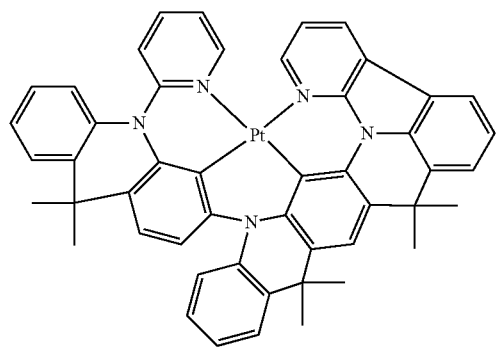
Structure 38
PtN'NN<sup>c</sup>
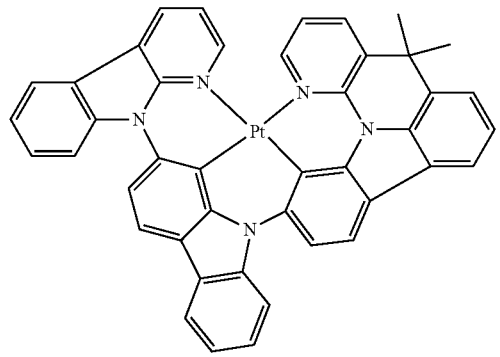
PdN'NN<sup>c</sup>
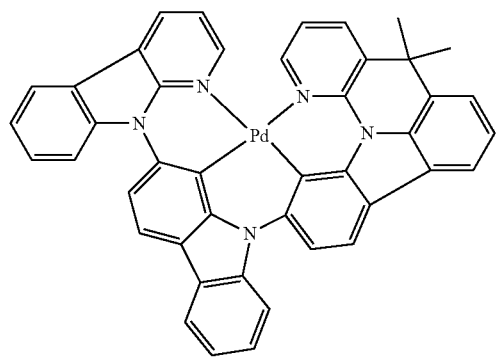

PtN'NN^{c'}
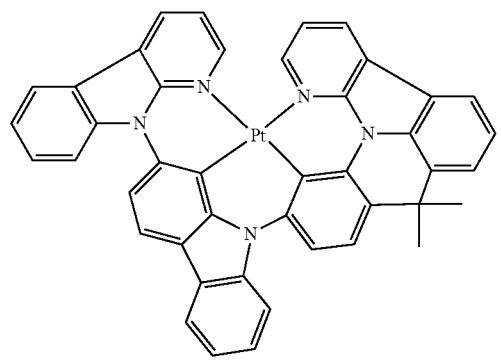
PtN^cNN^{cc}
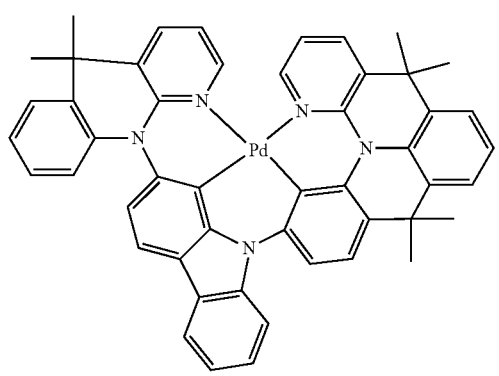
PdN'NN^{c'}
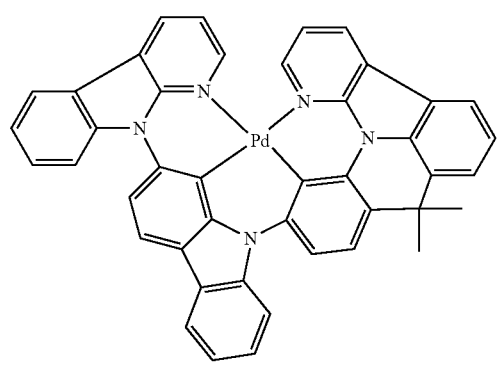
PtN^cNN^{cc}
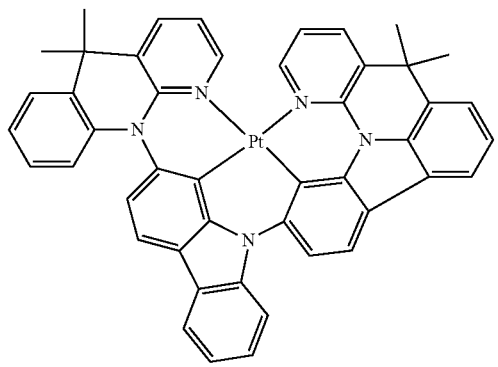
PtN'NN^{cc}
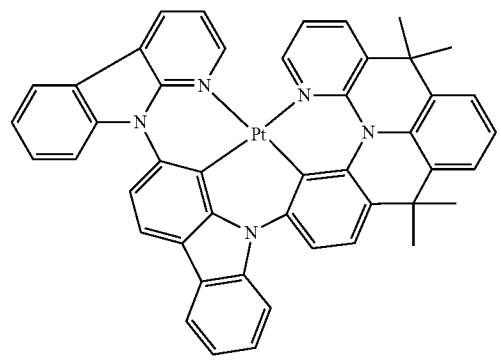
PtN^cNN^c
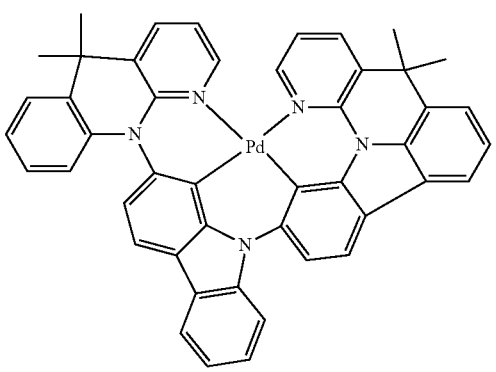
PdN'NN^{cc}
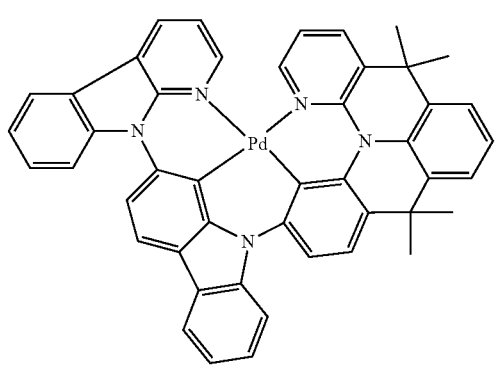
PdN^cNN^c 385
-continued
PtN$^c$NN$^{c\prime}$
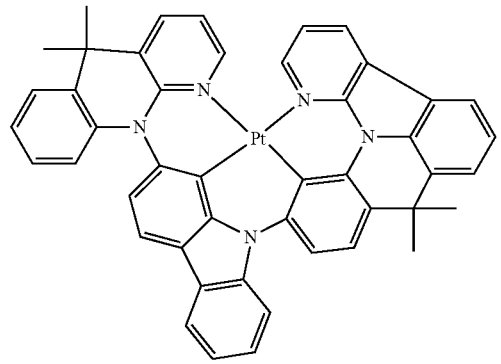
PdN$^c$NN$^{c\prime}$
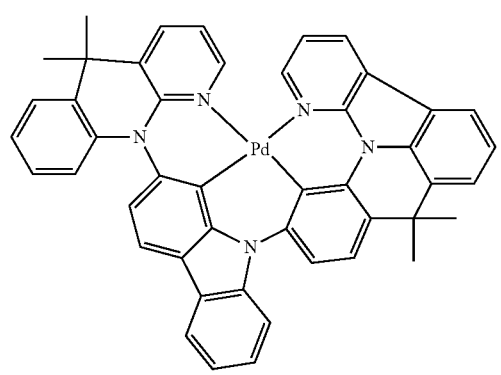
PtN$^c$N$^c$N$^c$
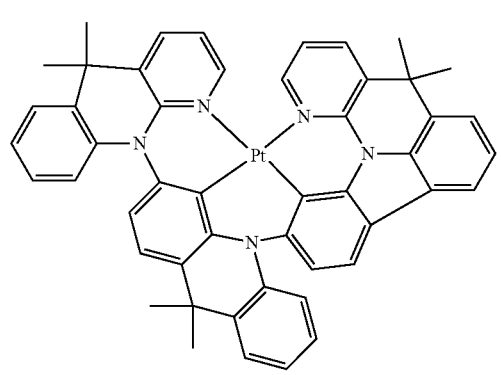
PdN$^c$N$^c$N$^c$
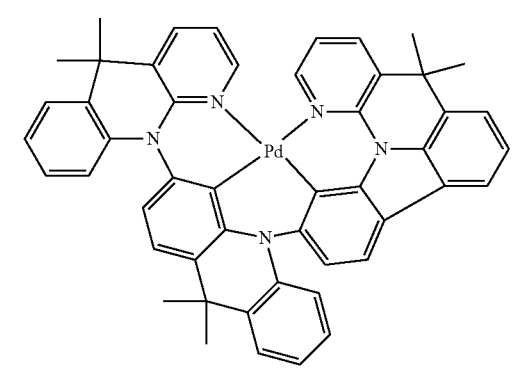
386
-continued
PtN$^c$N$^c$N$^{c\prime}$
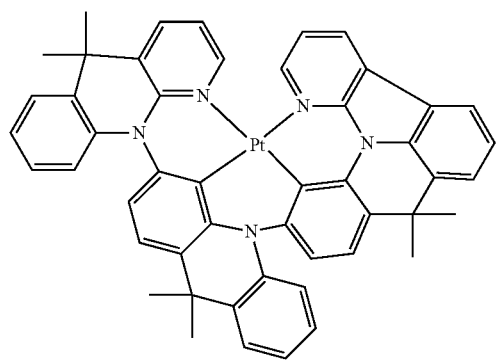
PdN$^c$N$^c$N$^{c\prime}$
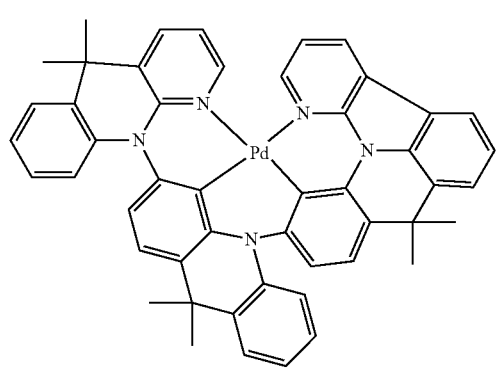
PtN$^\prime$N$^c$N$^{cc}$
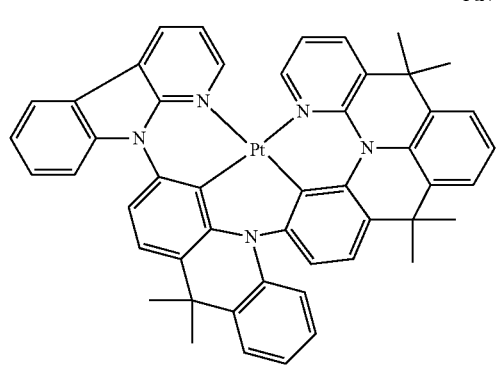
PdN$^\prime$N$^c$N$^{cc}$
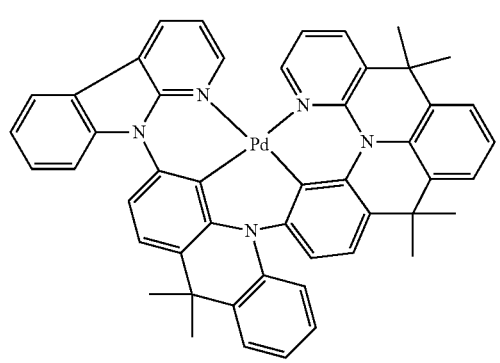

PtN^cN^cN^cc
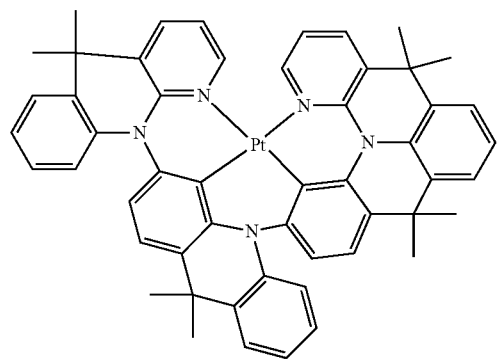
PtN'N-N^c'
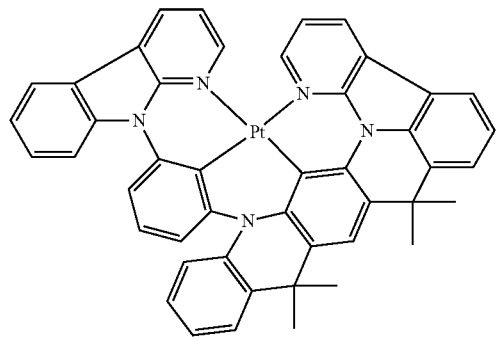
PdN^cN^cN^cc
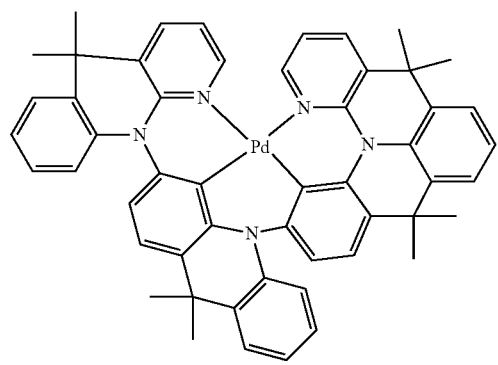
PdN'N-N^c'
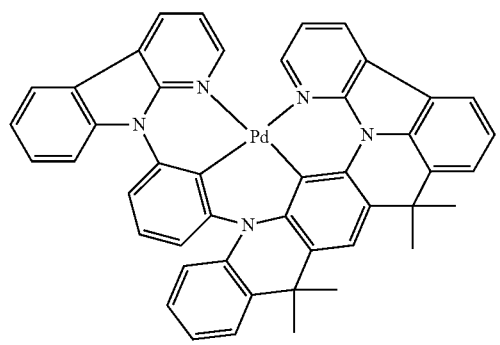
Structure 39
PtN'N-N^c
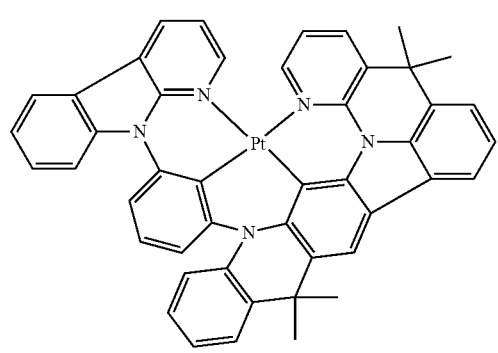
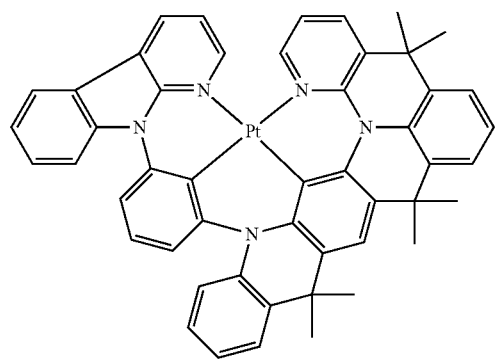
PdN'N-N^c
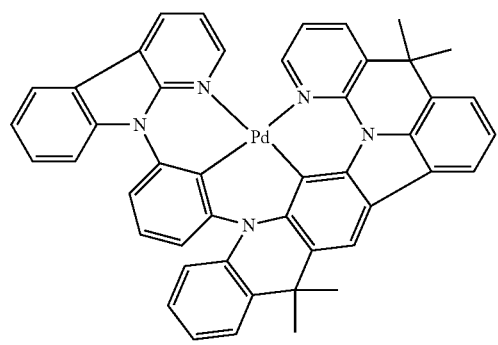
PtN'N-N^{CC}
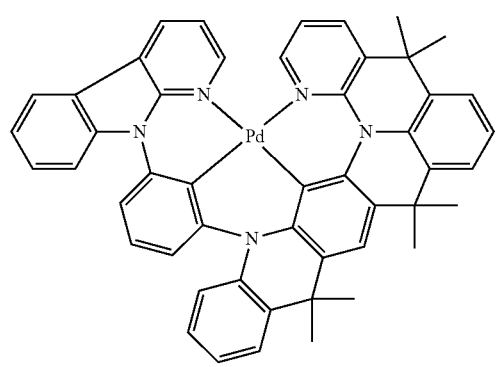
PdN'N-N^{CC}

389
-continued
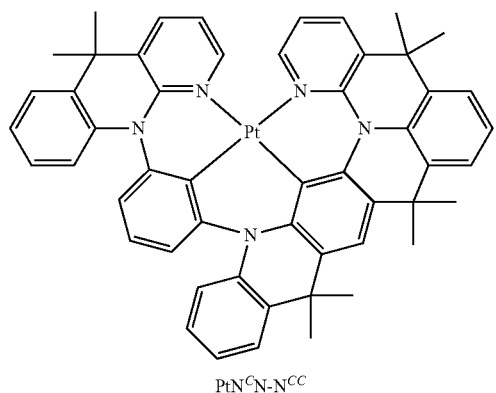
PtN^CN-N^{CC}
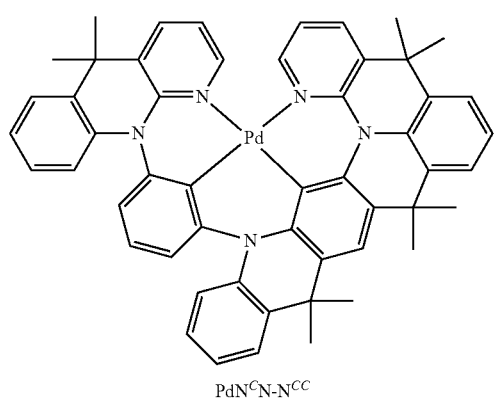
PdN^CN-N^{CC}
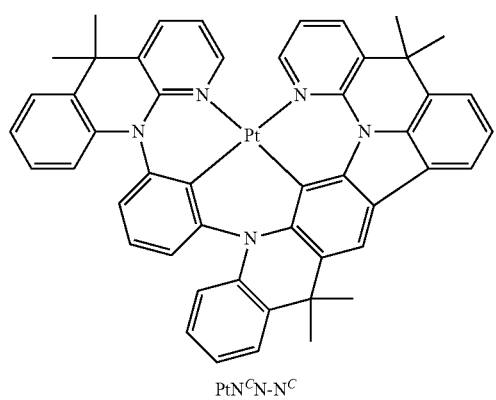
PtN^CN-N^C
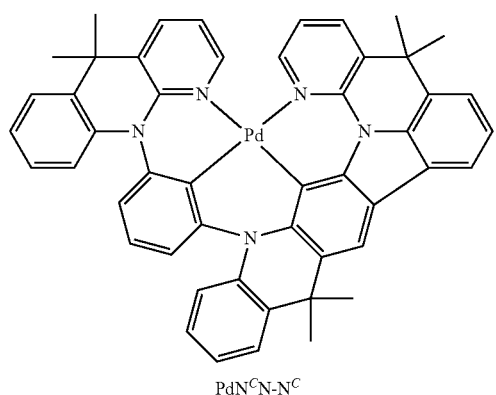
PdN^CN-N^C
390
-continued
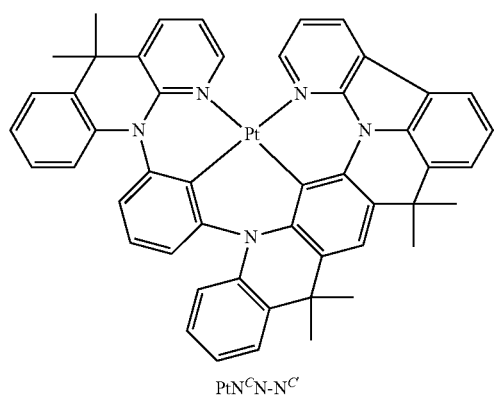
PtN^CN-N^{C'}
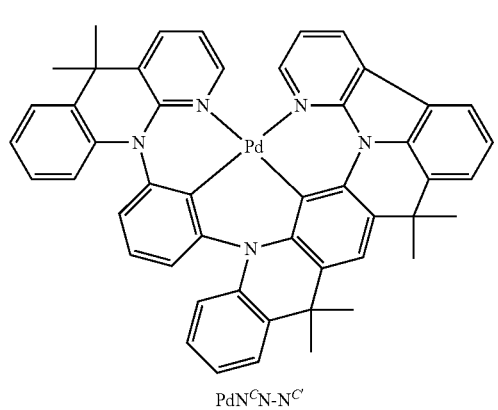
PdN^CN-N^{C'}
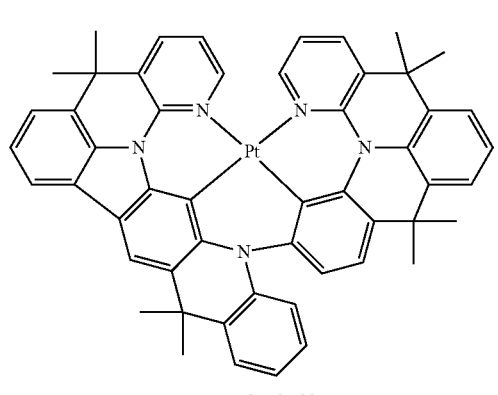
PtN^C-N^CN^{CC}
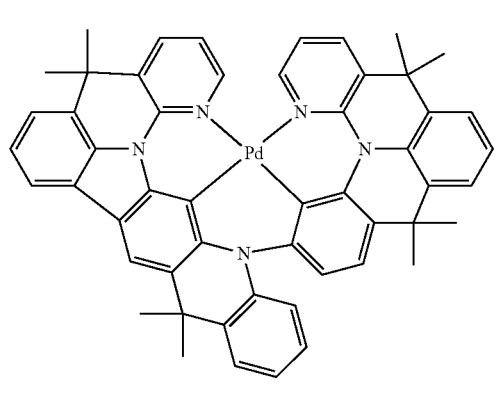
PdN^C-N^CN^{CC}

391
-continued
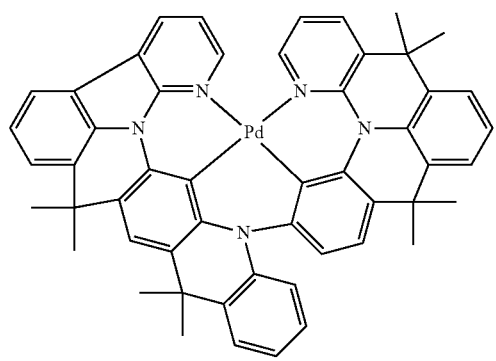
PdN^{C'}-N^{C}N^{CC}
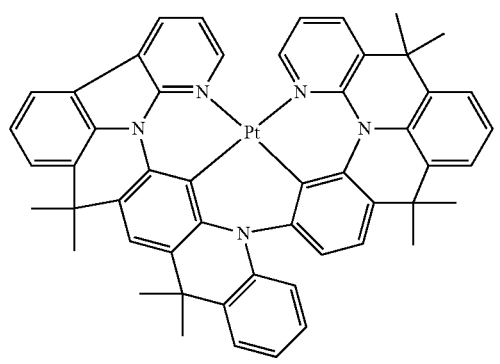
PtN^{C'}-N^{C}N^{CC}
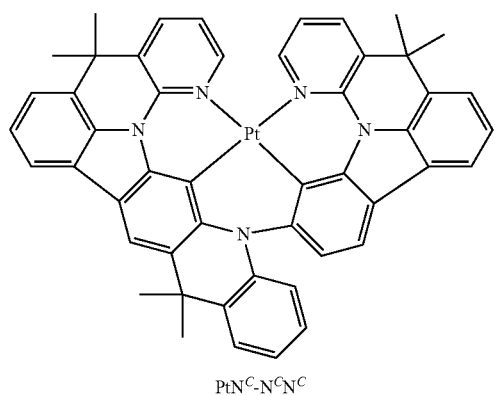
PtN^{C}-N^{C}N^{C}
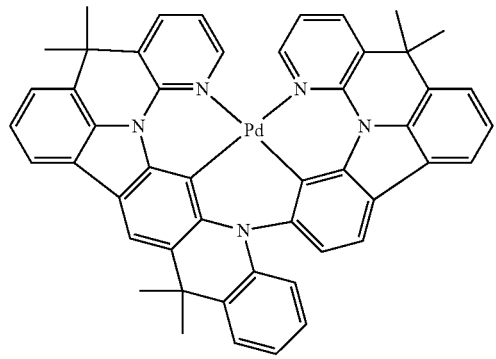
PdN^{C}-N^{C}N^{C}
392
-continued
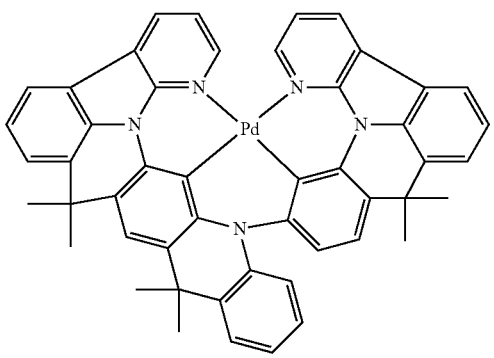
PdN^{C'}-N^{C}N^{C'}
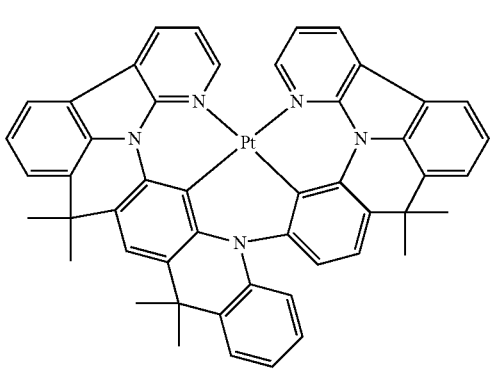
PtN^{C'}-N^{C}N^{C'}
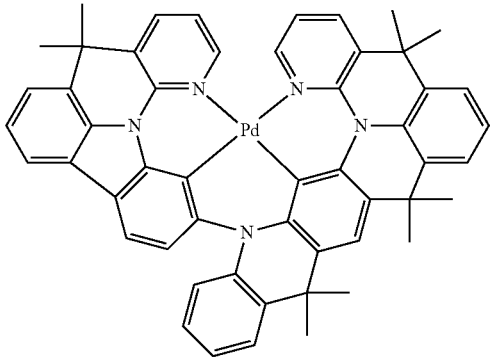
PdN^{C}N^{C}-N^{CC}
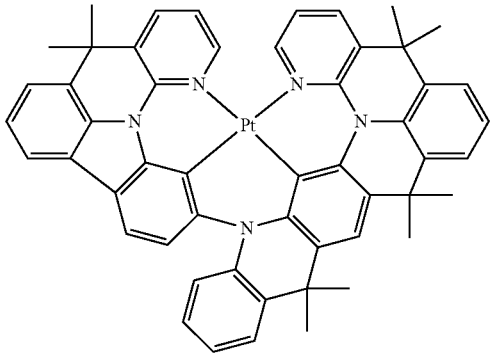
PtN^{C}N^{C}-N^{CC}

-continued
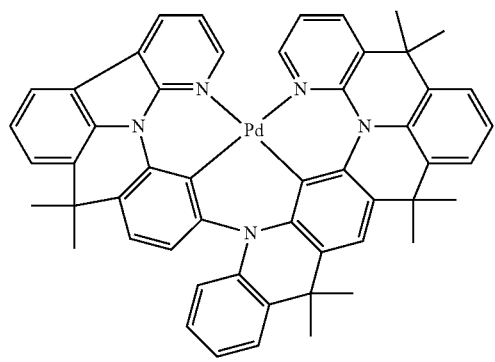
PdN^C N^C-N^CC
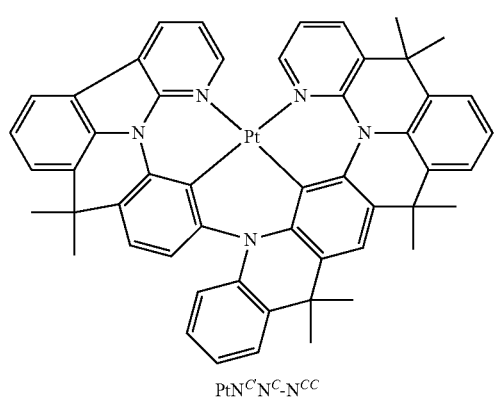
PtN^C N^C-N^CC
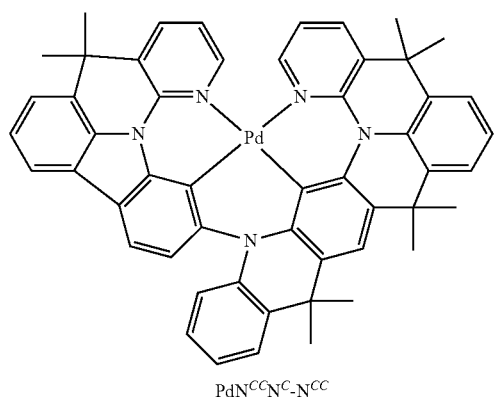
PdN^CC N^C-N^CC
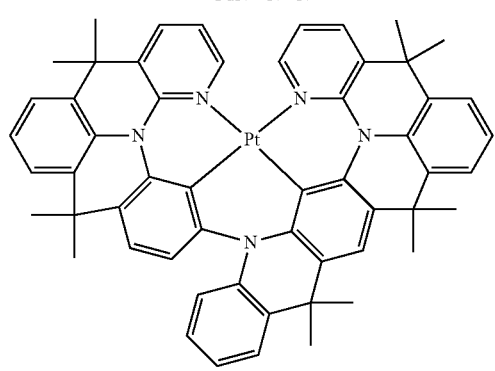
PtN^CC N^C-N^CC
-continued
Structure 40
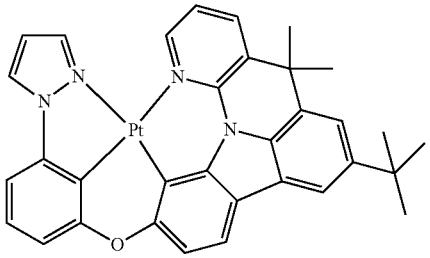
PtON^C1-tBu
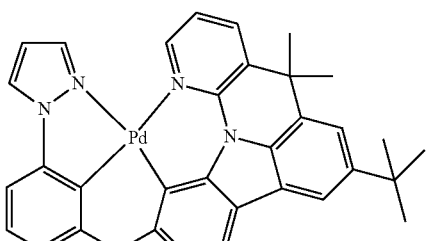
PdON^C1-tBu
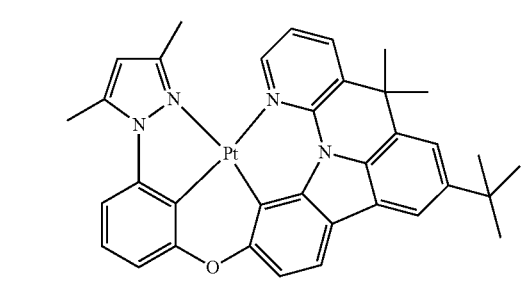
PtON^C1-DM-tBu
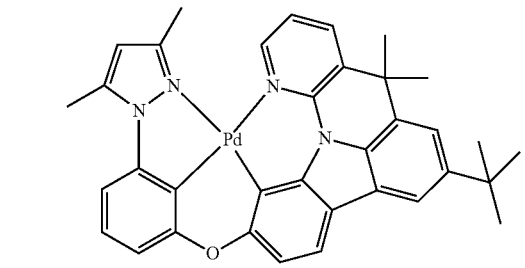
PdON^C1-DM-tBu
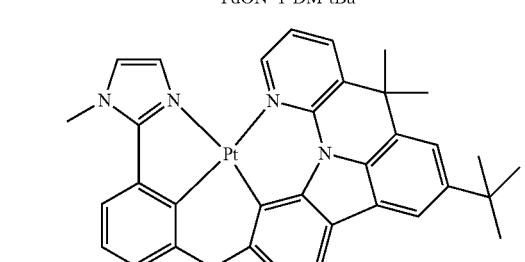
PtON^C2-tBu

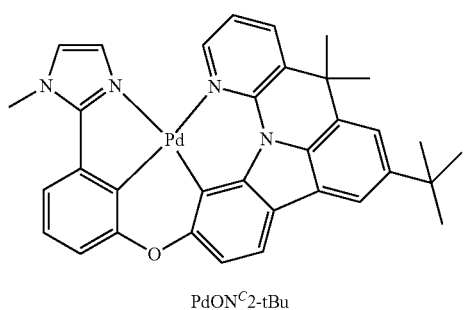
PdON^C2-tBu
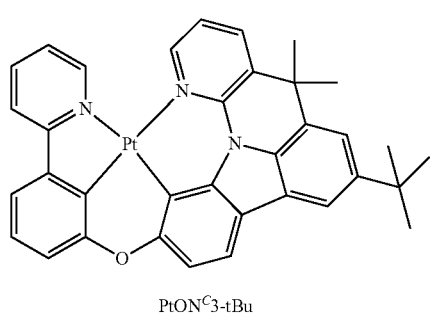
PtON^C3-tBu
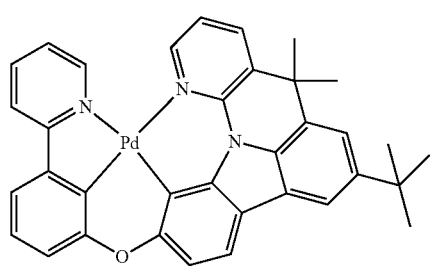
PdON^C3-tBu
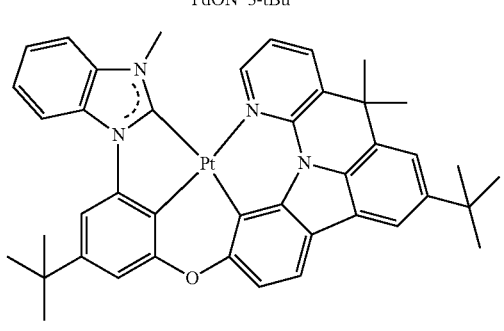
PtON^C5-dtb
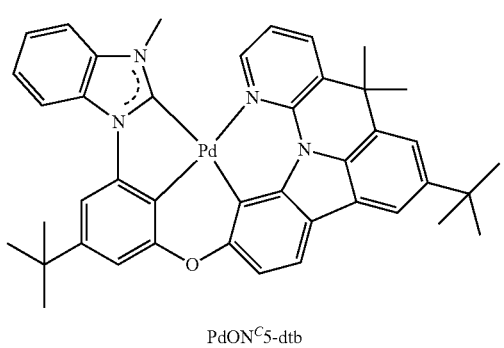
PdON^C5-dtb
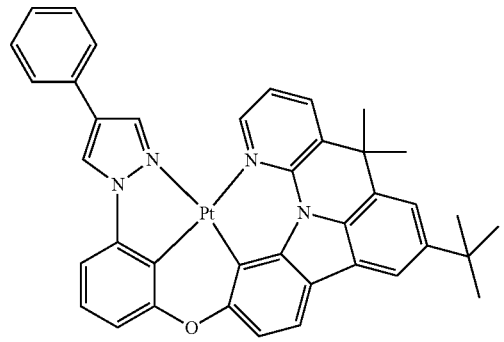
PtON^C6-tBu
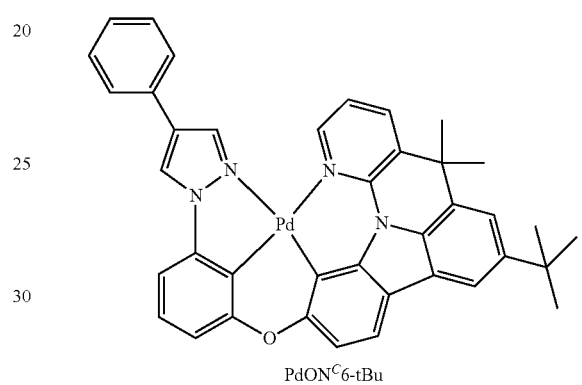
PdON^C6-tBu
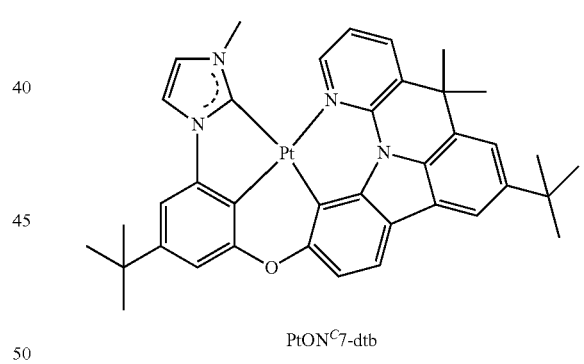
PtON^C7-dtb
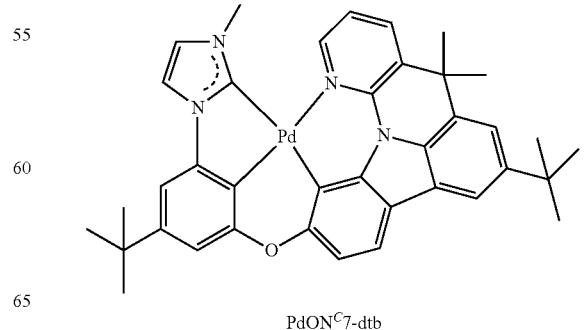
PdON^C7-dtb 397
-continued
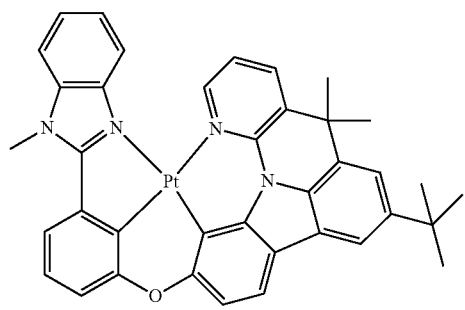
PtON^C8-tBu
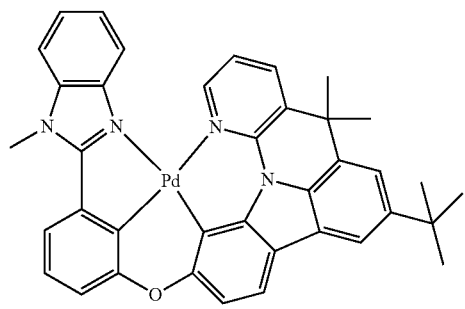
PdON^C8-tBu
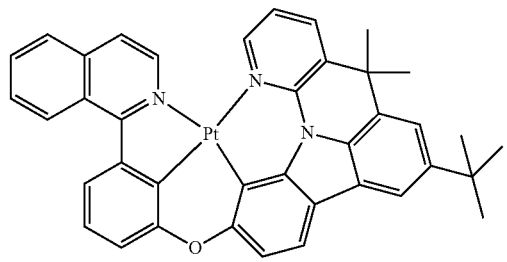
PtON^C10-tBu
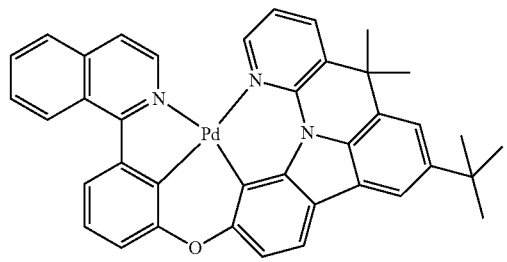
PdON^C10-tBu
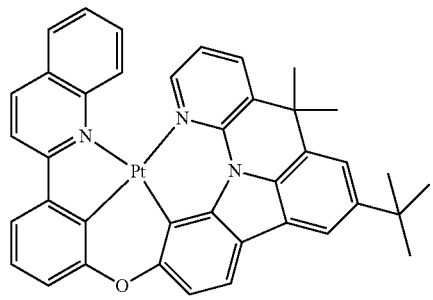
PtON^C11-tBu
398
-continued
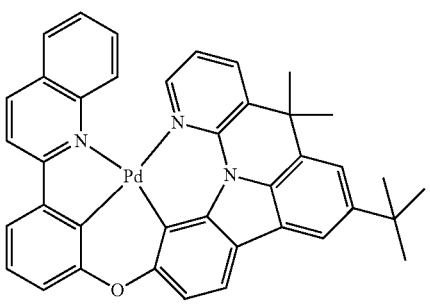
PdON^C11-tBu
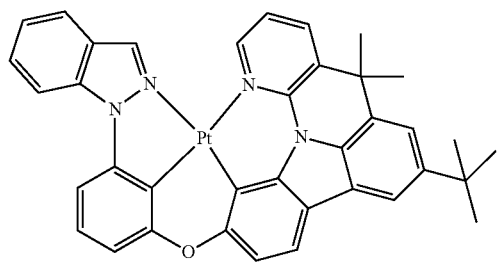
PtON^C12-tBu
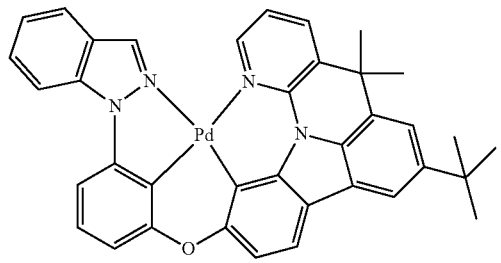
PdON^C12-tBu
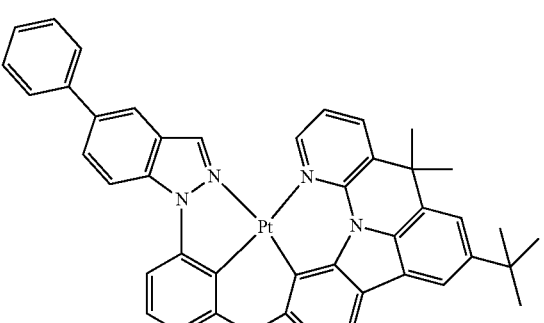
PtON^C12Ph-tBu -continued
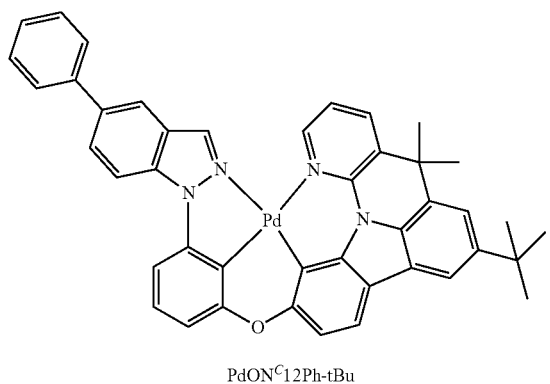
PdON^C12Ph-tBu
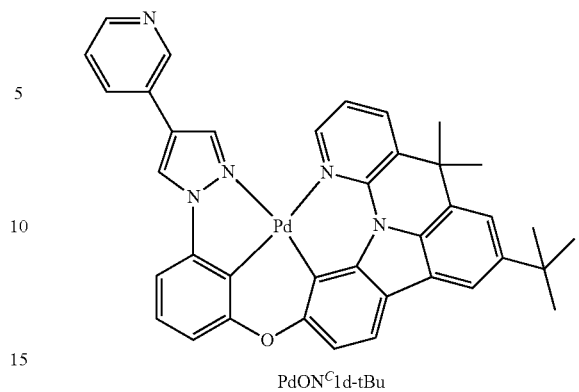
PdON^C1d-tBu
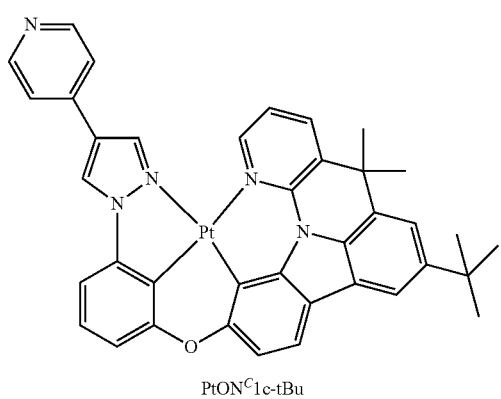
PtON^C1c-tBu
Structure 41
PtOON^C3-tBu
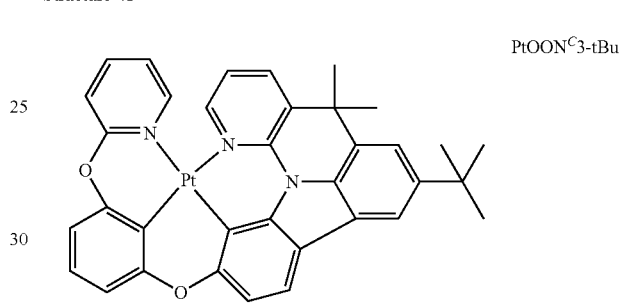
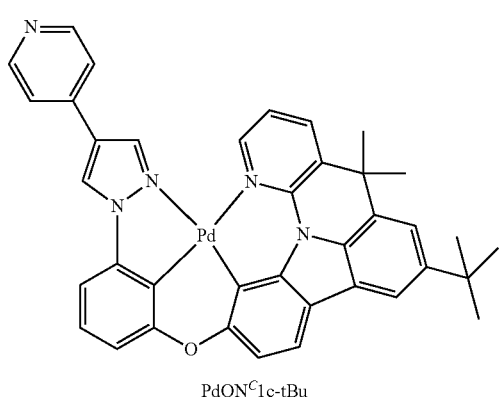
PdON^C1c-tBu
PdOON^C3-tBu
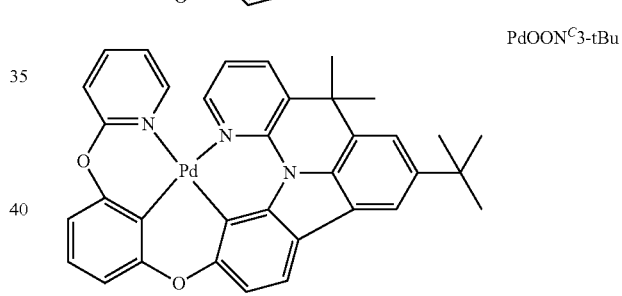
PtON^C1-DM-tBU
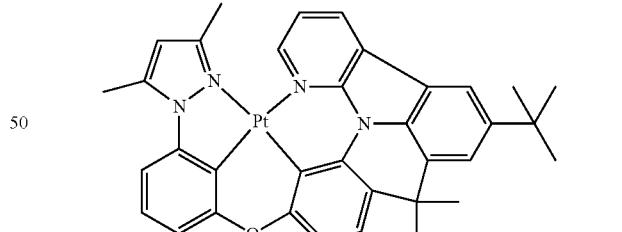
PdON^C1-DM-tBu
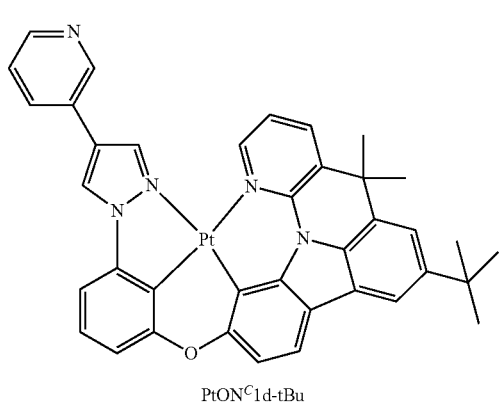
PtON^C1d-tBu
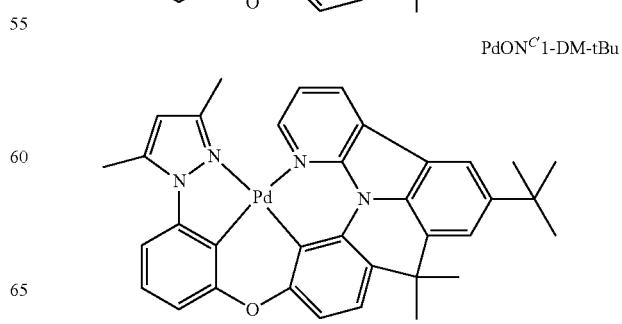

401
-continued
PtON$^C$1-DM-tBu
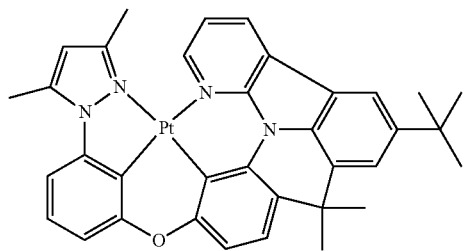
PdONC¢1-DM-tBu
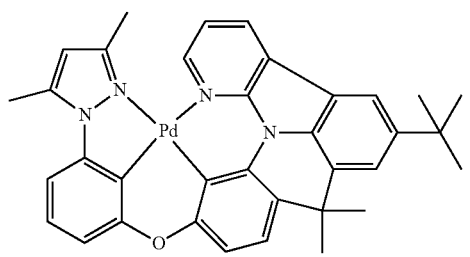
PdON$^C$1-DM-tBu
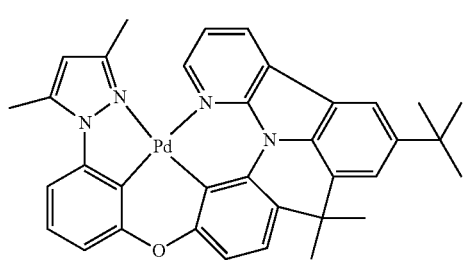
PtN$^C$N-DM-tBu
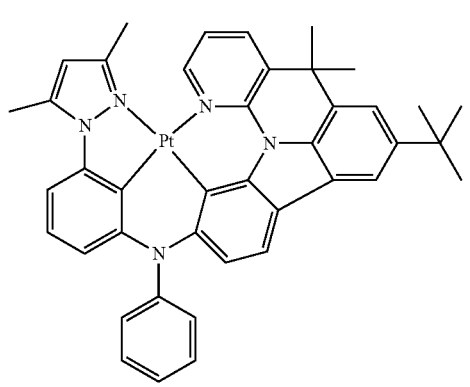
PdN$^C$N-DM-tBu
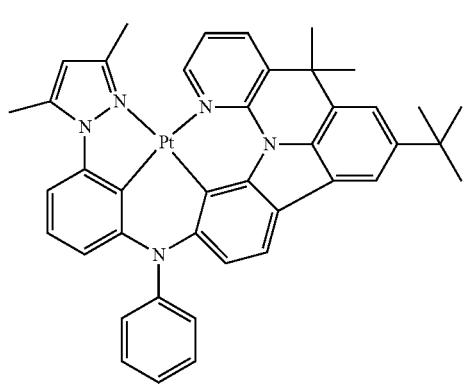
402
-continued
PtNON$^C$-tBu
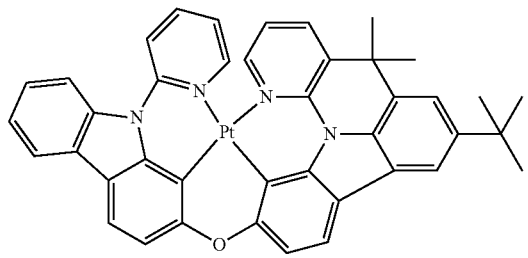
PdNON$^C$-tBu
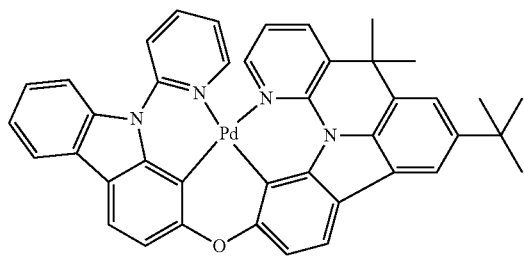
PtNON$^C$-dtb
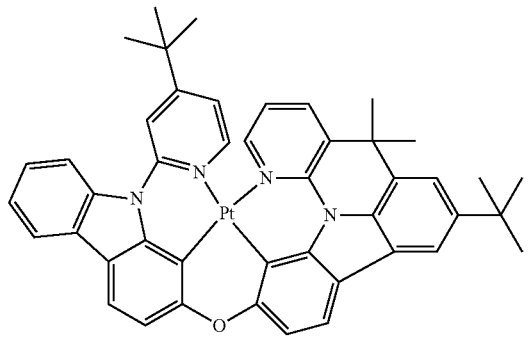
PdNON$^C$-dtb
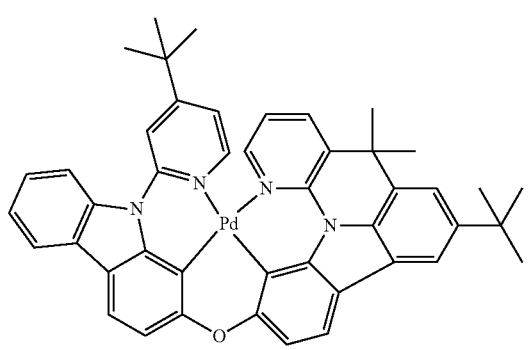
PtNON$^C$-tBu
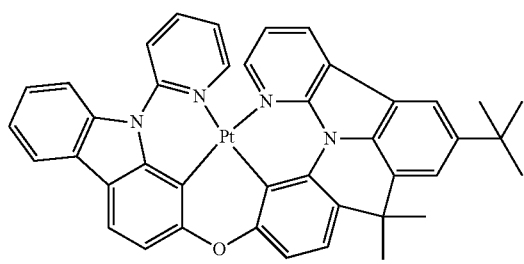

403
-continued
PdNON^C'-tBu
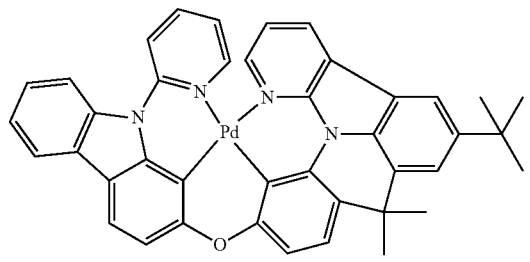
PtNON^{CC}-tBu
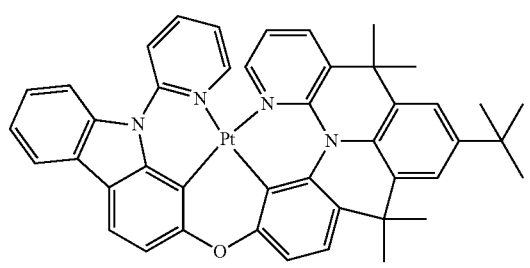
PdNON^{CC}-tBu
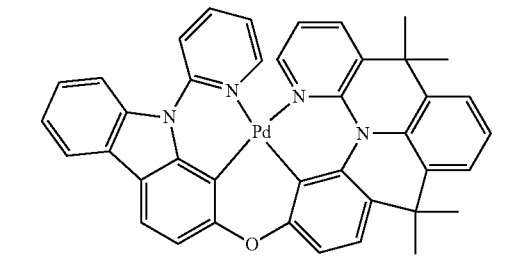
PtNON^{C'}-tBu
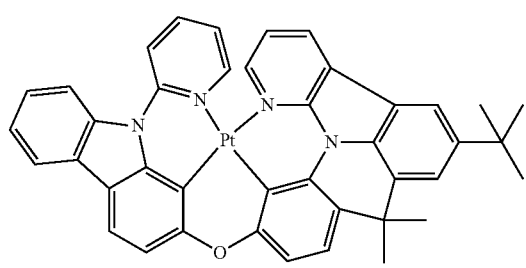
PdNON^{C'}-tBu
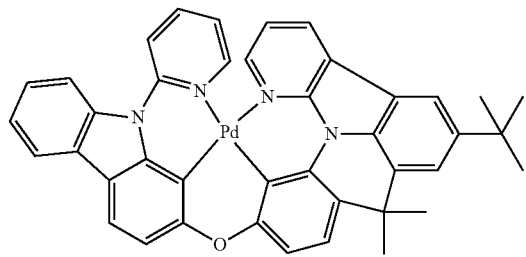
404
-continued
PtN^C ON^C-tBu
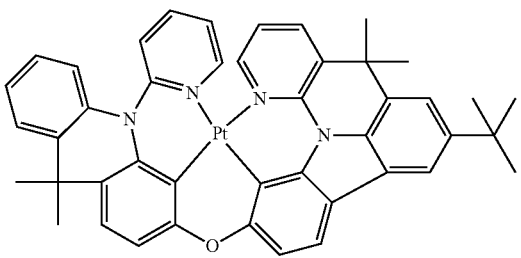
PdN^C ON^C-tBu
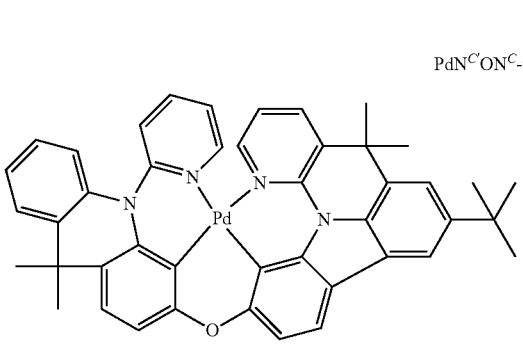
PtNNN^C-tBu
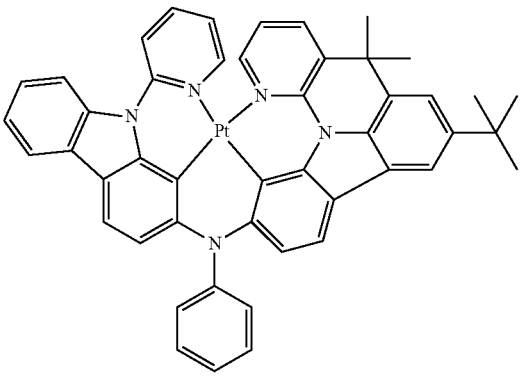
PdNNN^C-tBu
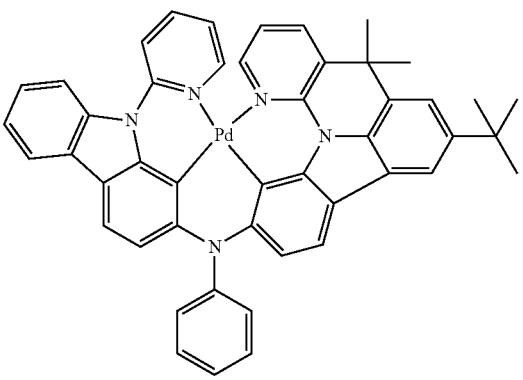

PtNNN<sup>C</sup>-dtb
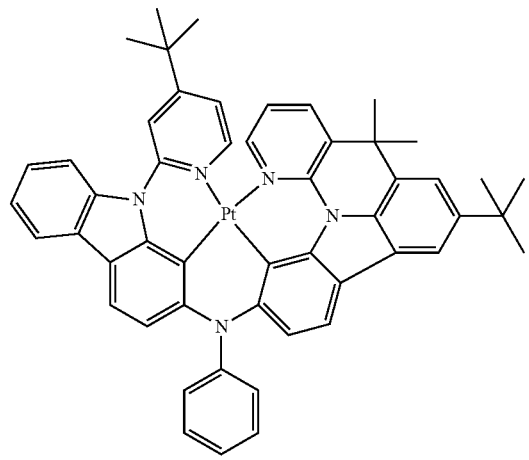
Structure 42
PdNNN<sup>C</sup>-dtb
PtNNN<sup>C'</sup>-tBu
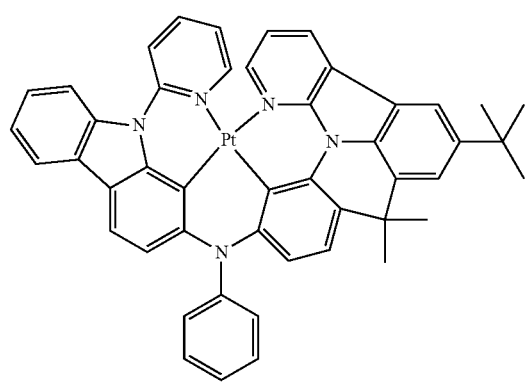
PdNNN<sup>C'</sup>-tBu
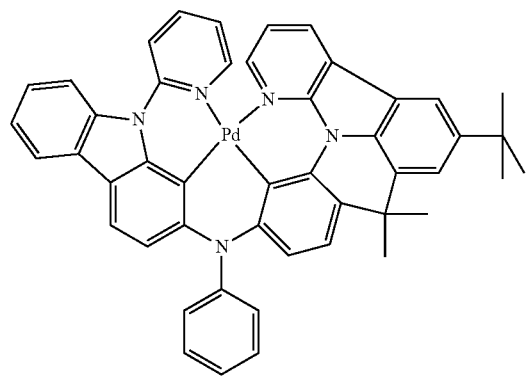
PtNNN<sup>CC</sup>-tBu
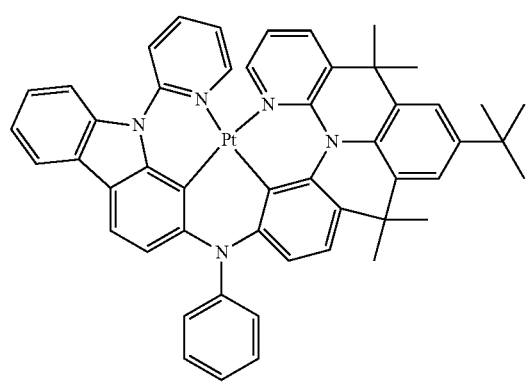
PdNNN<sup>CC</sup>-tBu
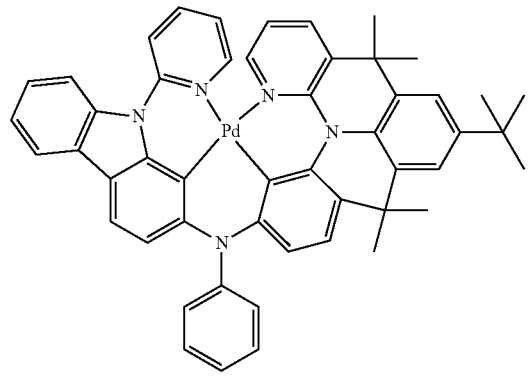
PtNNN<sup>CC</sup>-tBu
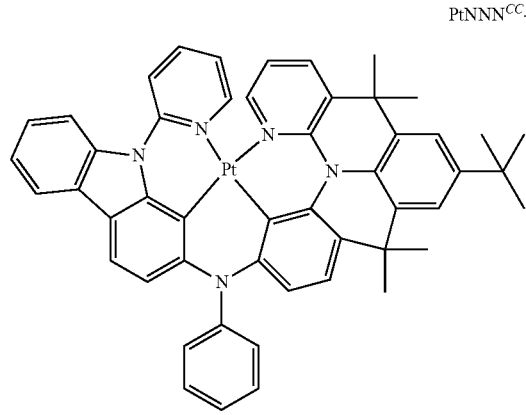

PdNNN^{CC}-tBu
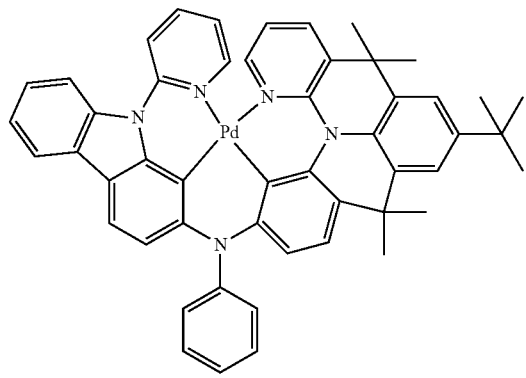
PtN^{C'}NN^C-tBu
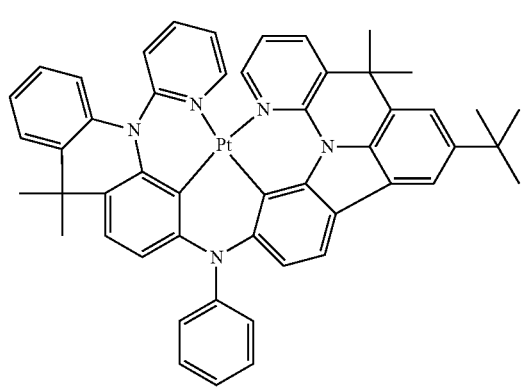
PdN^{C'}NN^C-tBu
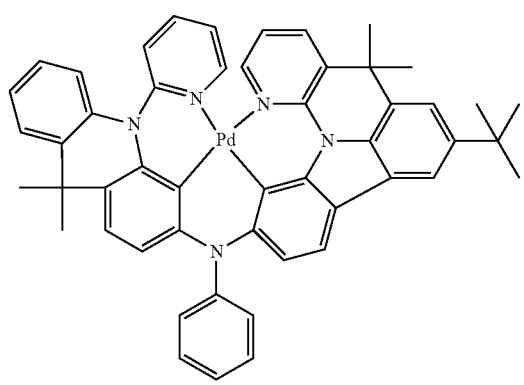
PtN^CON'-tBu
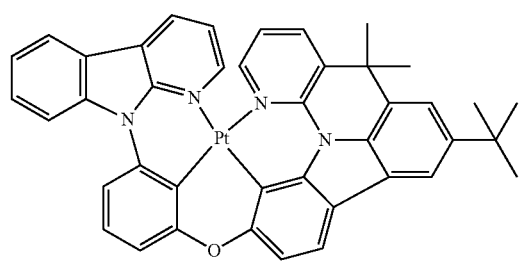
PdN^CON'-tBu
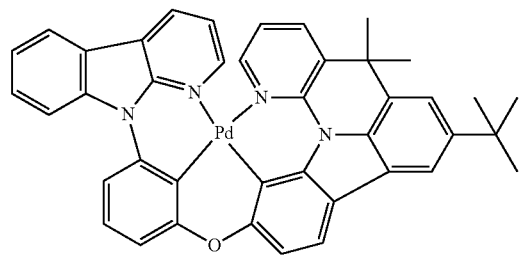
PtN^CON'-dtb
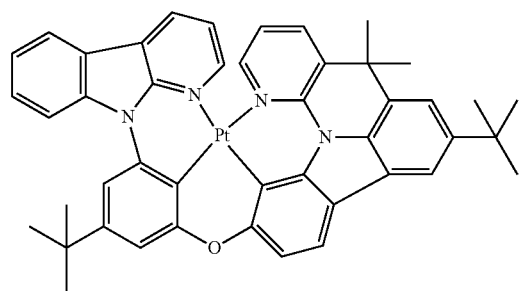
PdN^CON'-dtb
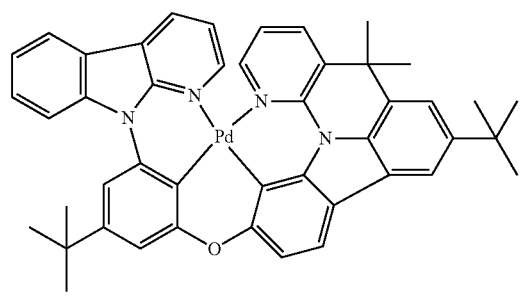
PtN^CNN'-tBu
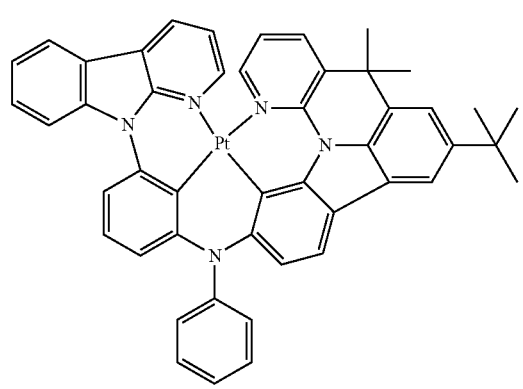

409
-continued
PdN<sup>C</sup>NN'-tBu
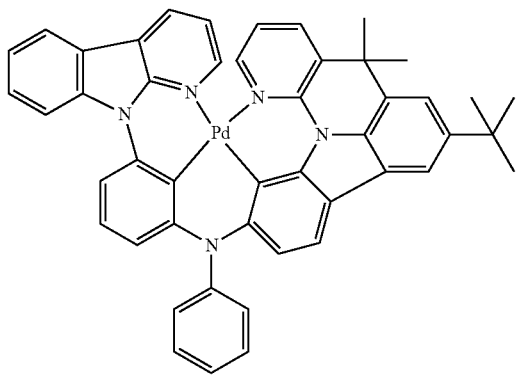
PtN<sup>C</sup>NN'-dtb
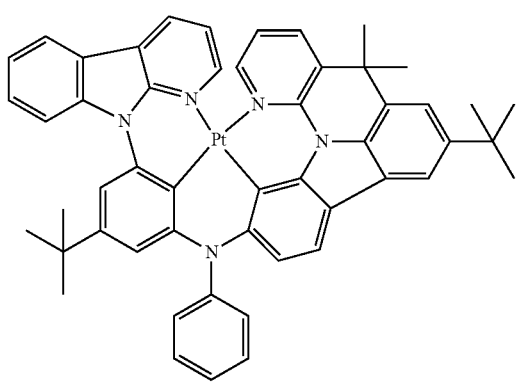
PdN<sup>C</sup>NN'-dtb
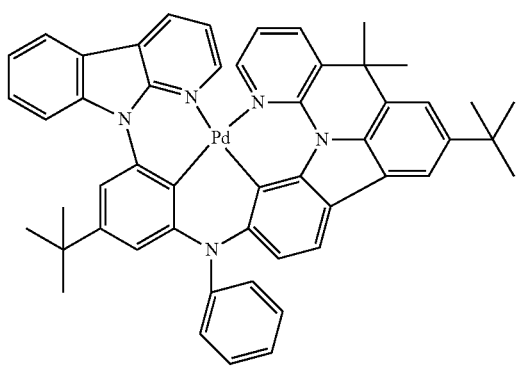
PtN'ON<sup>C'</sup>-tBu
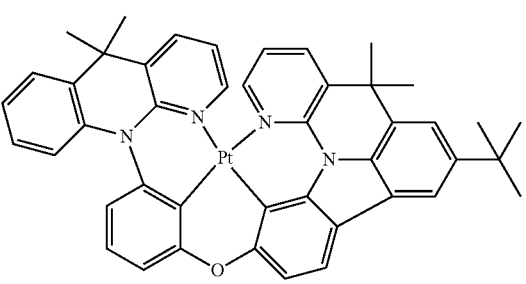
410
-continued
PdN'ON<sup>C'</sup>-tBu
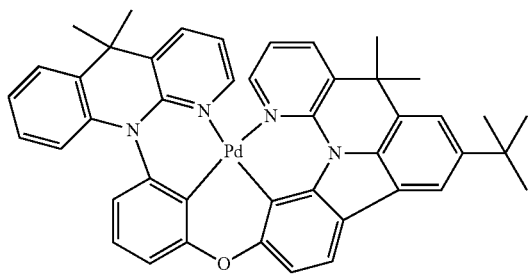
PtN'ON<sup>C'</sup>-tBu
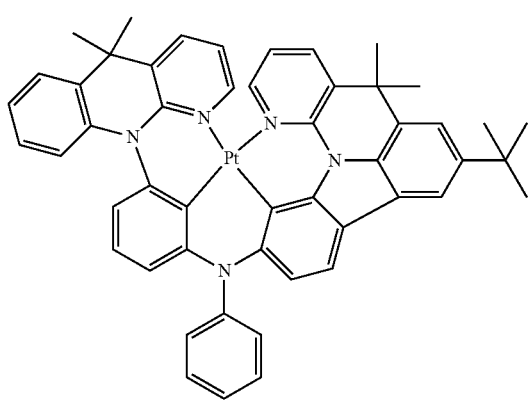
PdN'ON<sup>C'</sup>-tBu
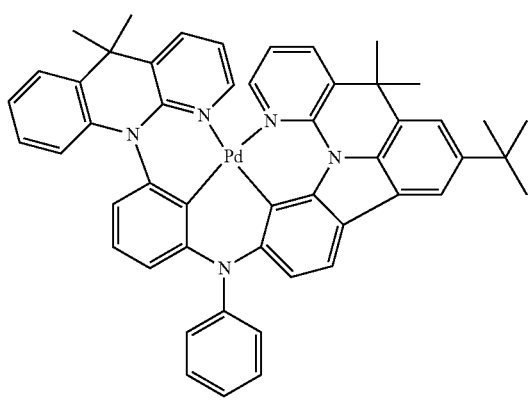
PtN<sup>C</sup>ON<sup>C</sup>-dtb
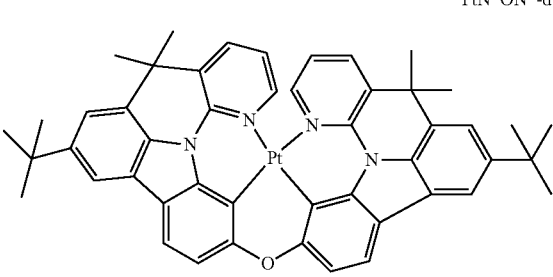

-continued
PdN^CON^C-dtb
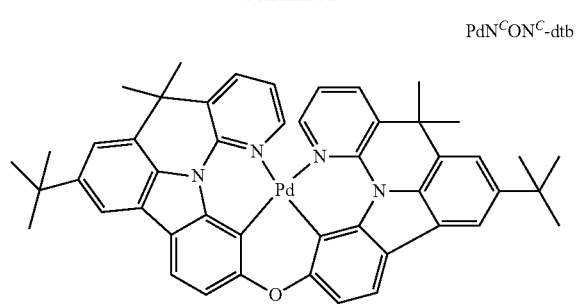
PtN^CNN^C-dtb
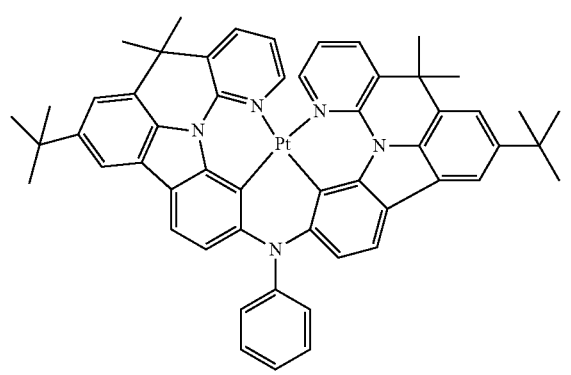
PdN^CNN^C-dtb
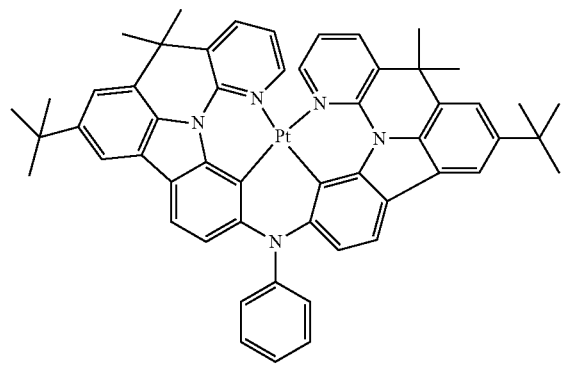
Structure 43
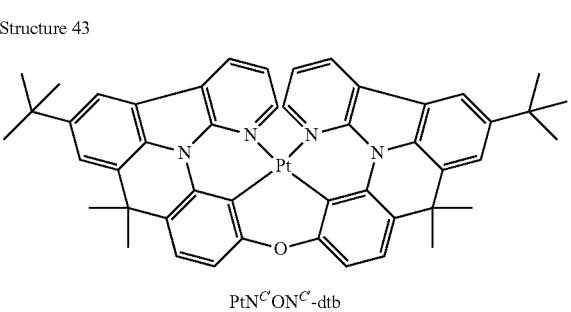
PtN^CON^C-dtb
-continued
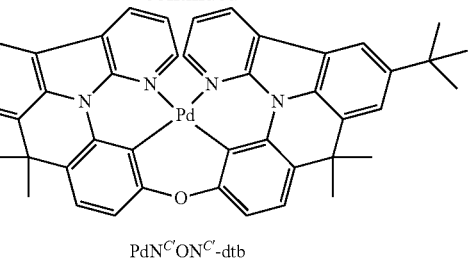
PdN^{C'}ON^{C'}-dtb
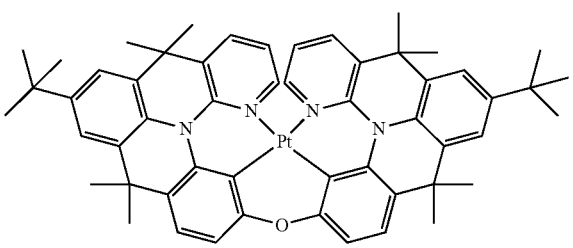
PtN^{CC}ON^{CC}-dtb
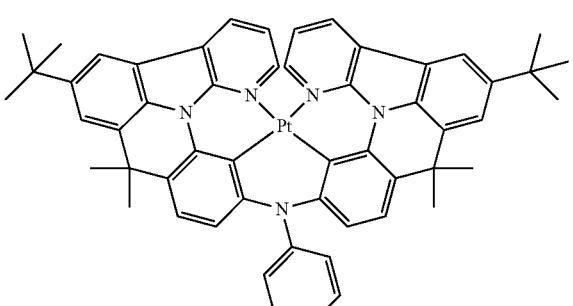
PtN^{C'}NN^{C'}-dtb
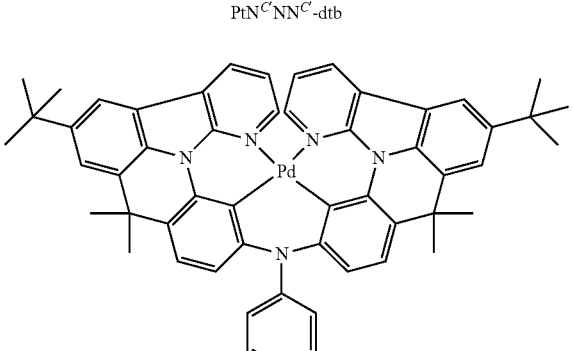
PdN^{C'}NN^{C'}-dtb
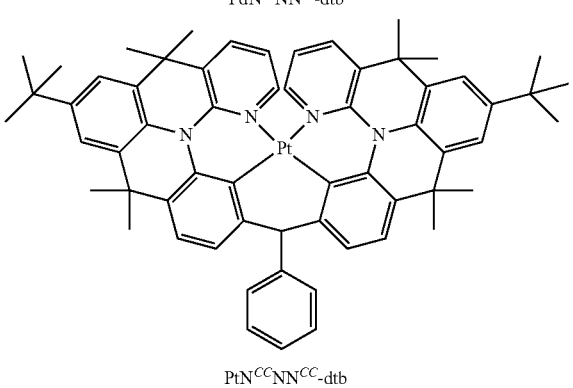
PtN^{CC}NN^{CC}-dtb

413
-continued
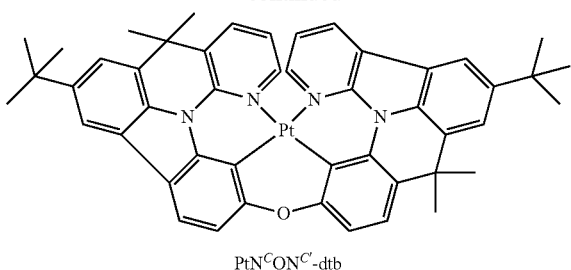
PtN^C ON^C'-dtb
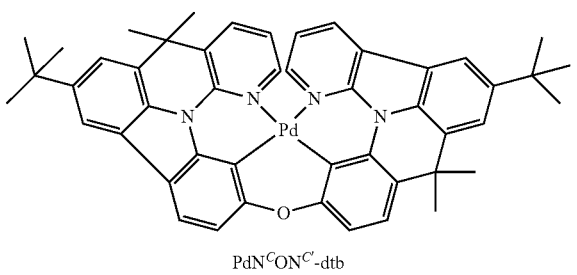
PdN^C ON^C'-dtb
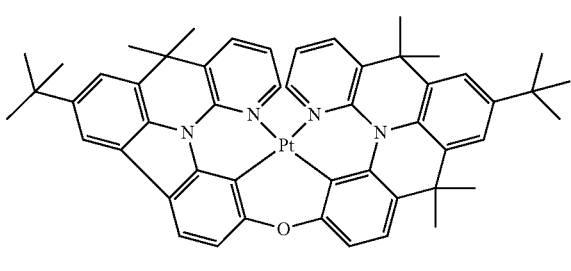
PtN^C ON^{CC}-dtb
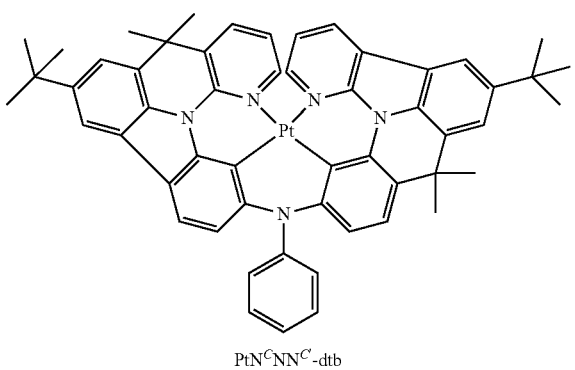
PtN^C NN^C'-dtb
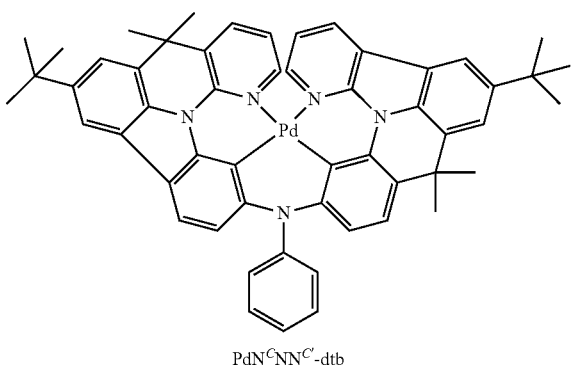
PdN^C NN^C'-dtb
414
-continued
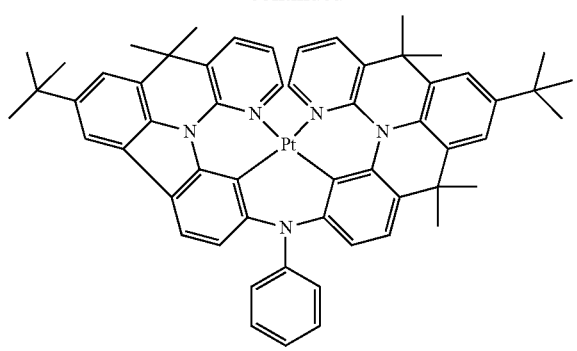
PtN^C NN^{CC}-dtb
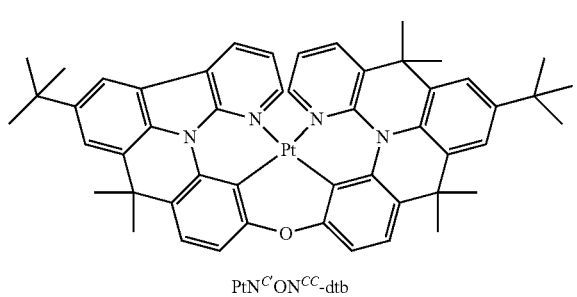
PtN^{C'} ON^{CC}-dtb
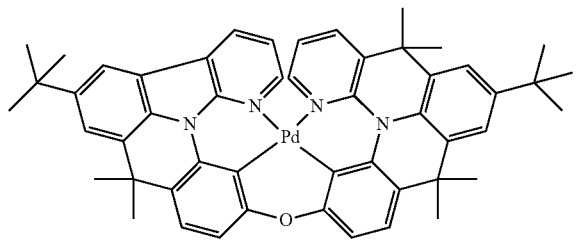
PdN^{C'} ON^{CC}-dtb
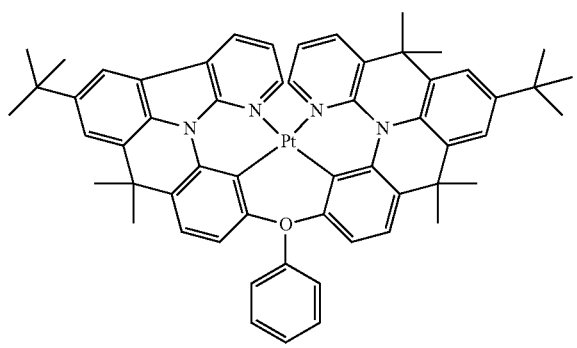
PtN^{C'} NN^{CC}-dtb

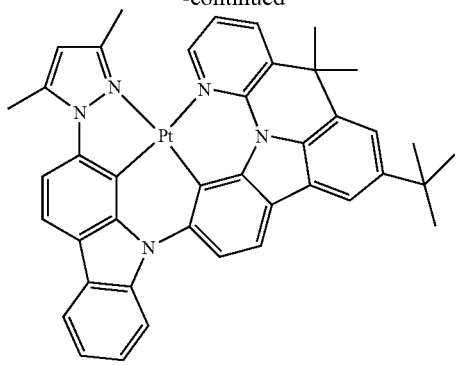
PtN$^C$1N-DM-tBu
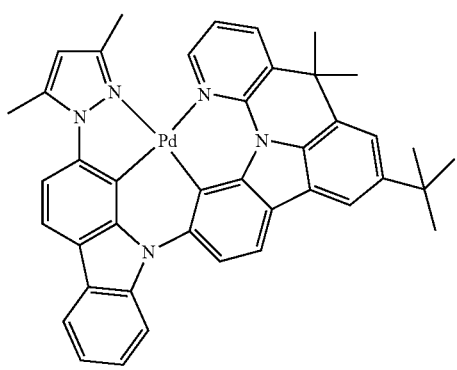
PdN$^C$1N-DM-tBu
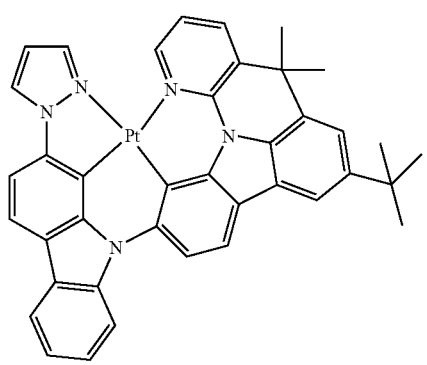
PtN$^C$1N-tBu
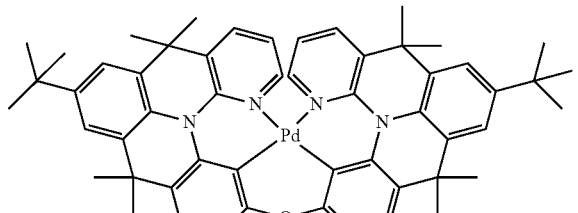
PdN$^{CC}$ON$^{CC}$-dtb
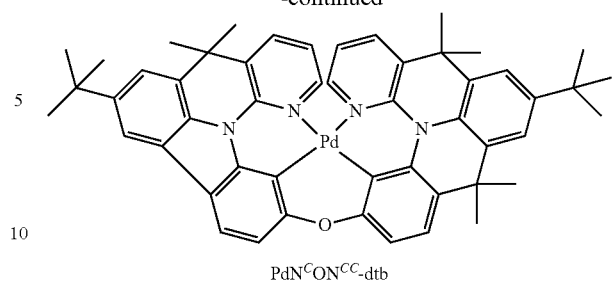
PdN$^C$ON$^{CC}$-dtb
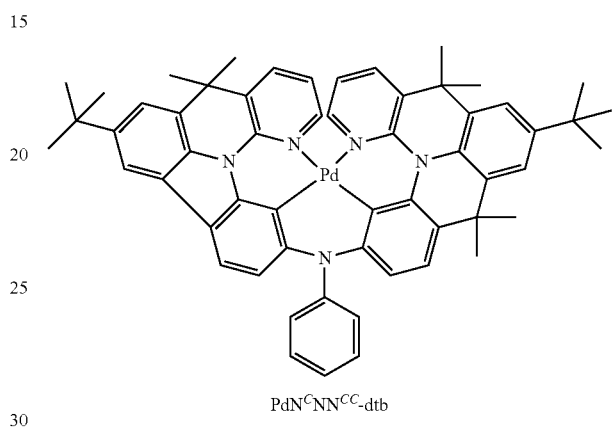
PdN$^C$NN$^{CC}$-dtb
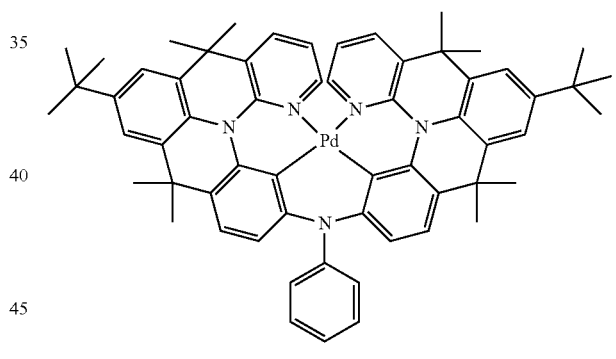
PdN$^{CC}$NN$^{CC}$-dtb
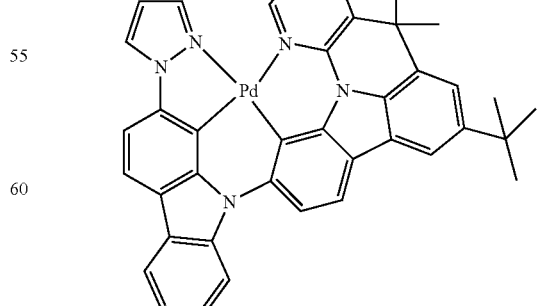
PdN$^C$1N-tBu -continued
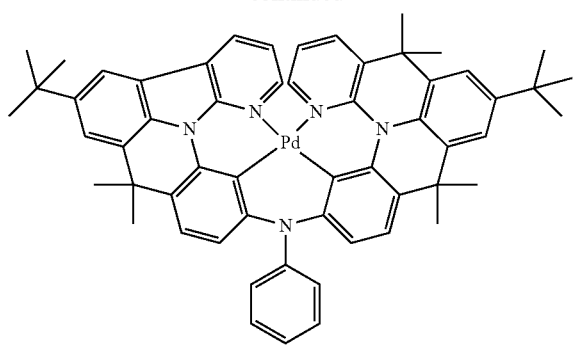
PdN^C NN^CC-dtb
Structure 44
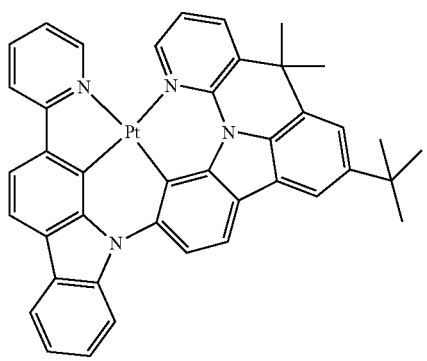
PtN3^C N-tBu
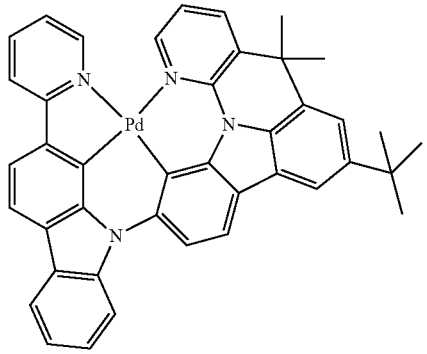
PdN^C 3N-tBu
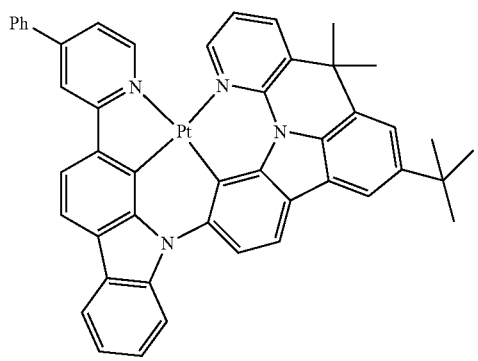
PtN^C 3N-Ph-tBu
-continued
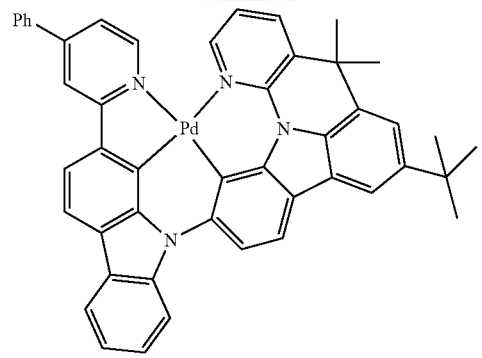
PdN^C 3N-Ph-tBu
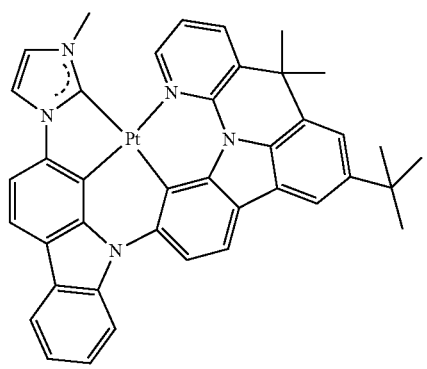
PtN^C 7N-tBu
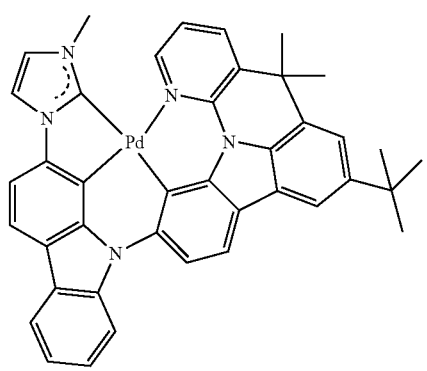
PdN^C 7N-tBu
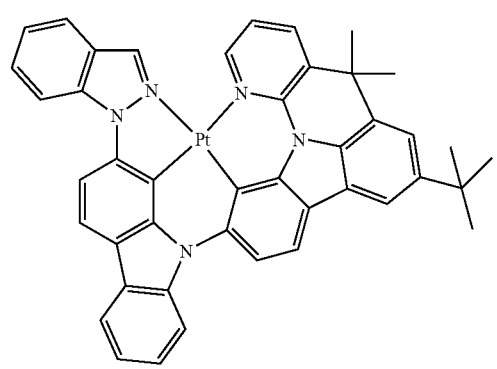
PtN^C 12N-tBu

419
-continued
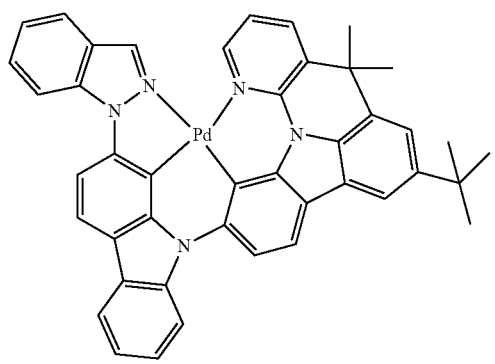
PdN^C12N-tBu
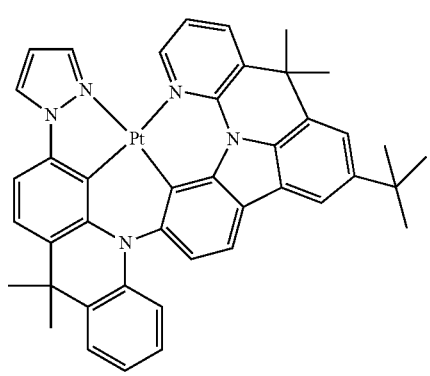
PtN^C1N'-tBu
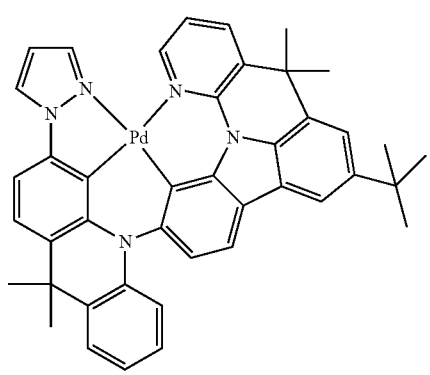
PdN^C1N'-tBu
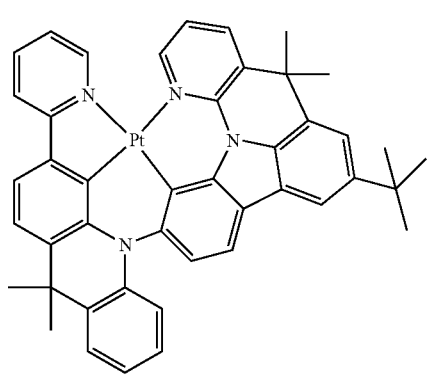
PtN^C3N'-tBu
420
-continued
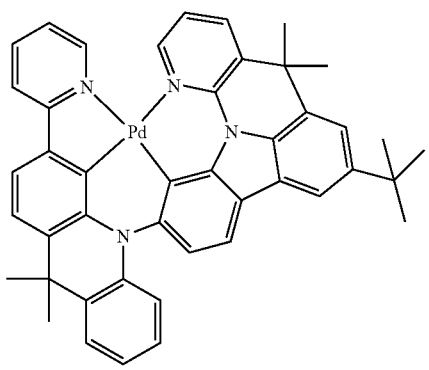
PdN^C3N'-tBu
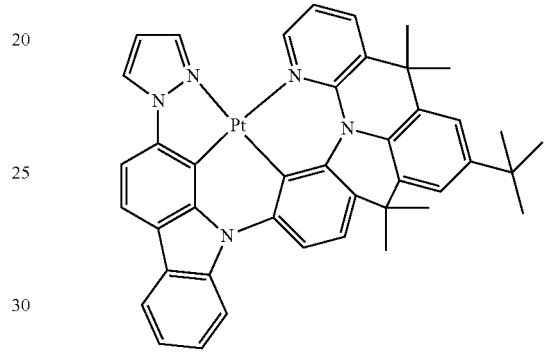
PtN^{CC}1N-tBu
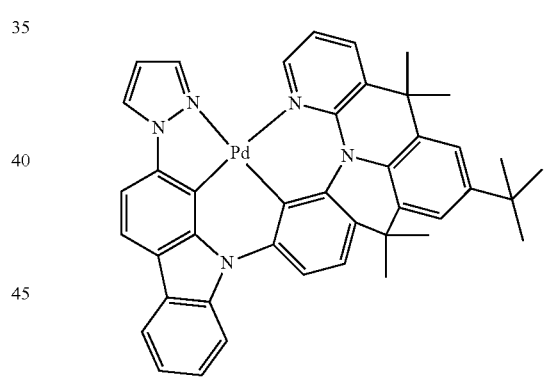
PdN^{CC}1N-tBu
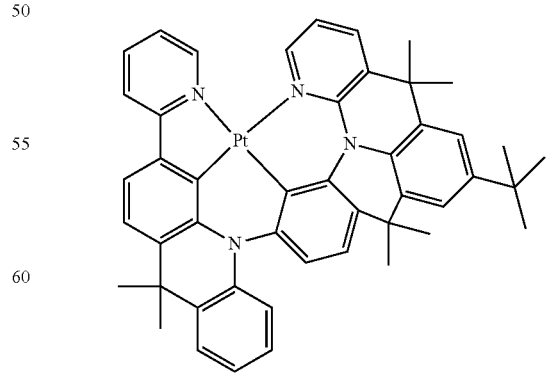
PtN^{CC}3N'-tBu 421
-continued
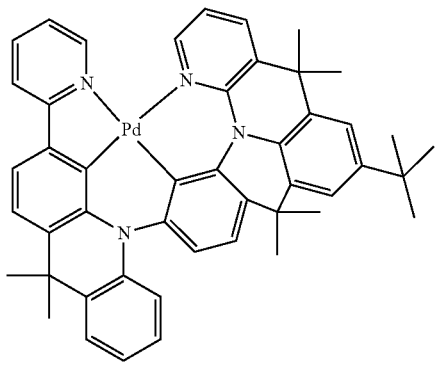
PdN<sup>CC</sup>3N'-tBu
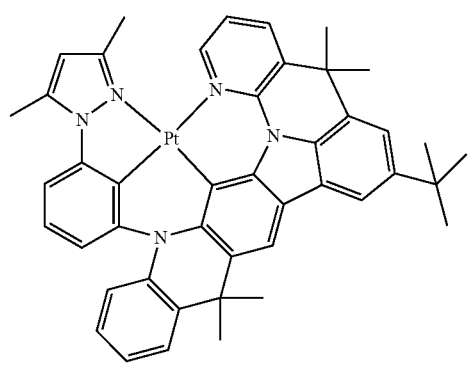
PtN-N<sup>C</sup>1-DM-tBu
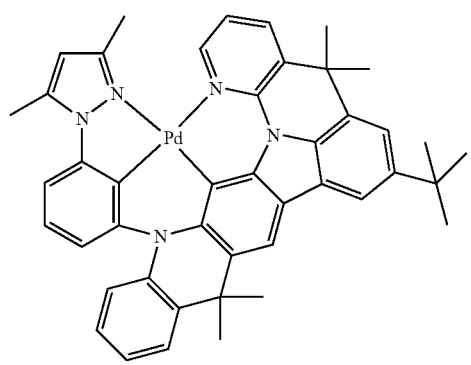
PdN-N<sup>C</sup>1-DM-tBu
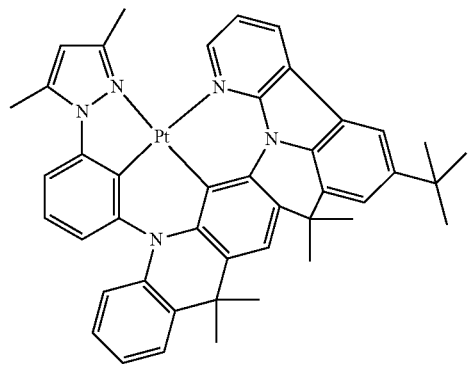
PtN-N<sup>C</sup>1-DM-tBu
422
-continued
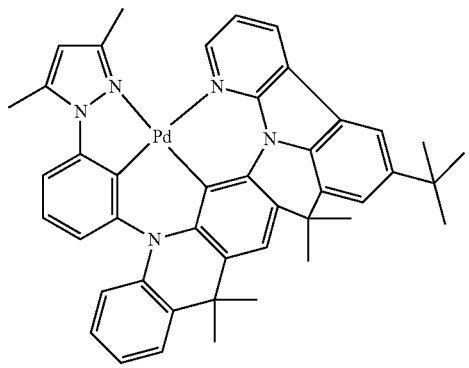
PdN-N<sup>C'</sup>1-DM-tBu
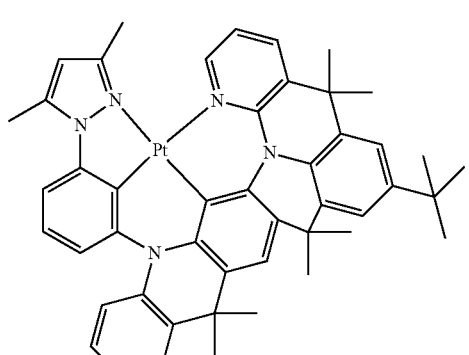
PtN-N<sup>CC</sup>1-DM-tBu
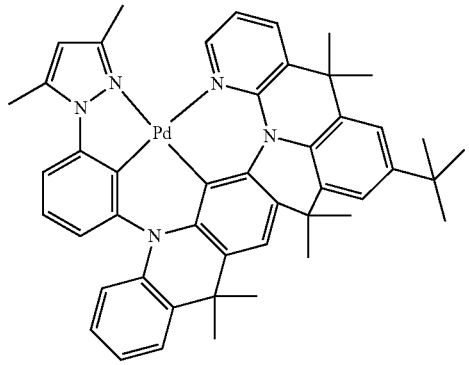
PdN-N<sup>CC</sup>1-DM-tBu
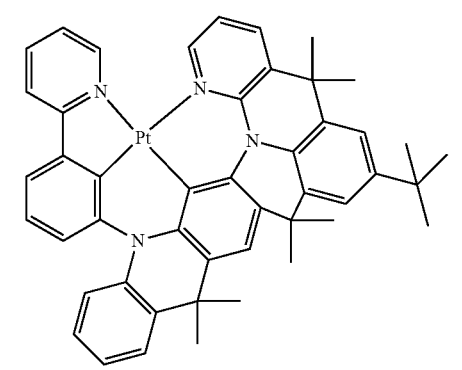
PtN-N<sup>CC</sup>3-tBu 423
-continued
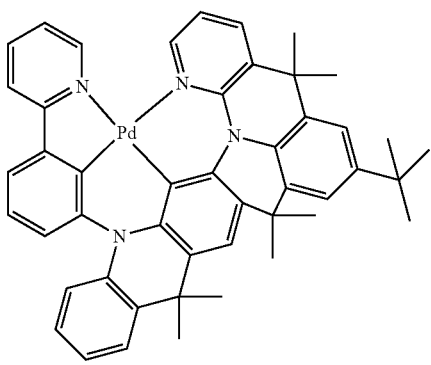
PdN-N<sup>CC</sup>3-tBu
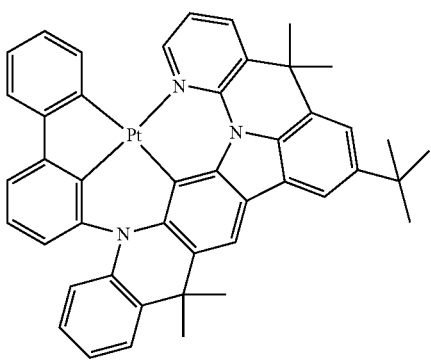
PtN-N<sup>C</sup>3-tBu
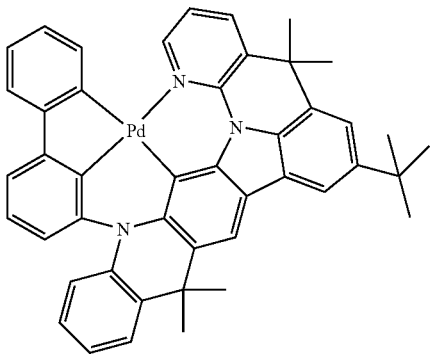
PdN-N<sup>C</sup>3-tBu
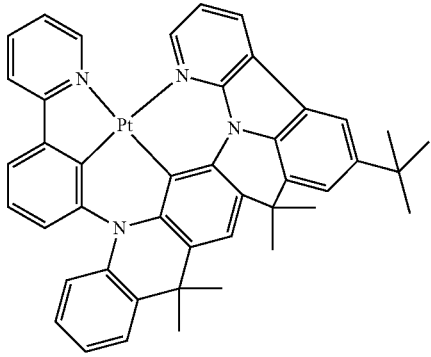
PtN-N<sup>C</sup>3-tBu
424
-continued
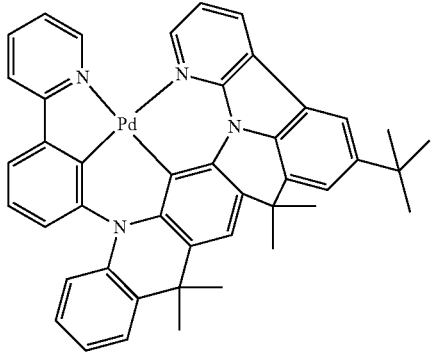
PdN-N<sup>C</sup>3-tBu
Structure 45
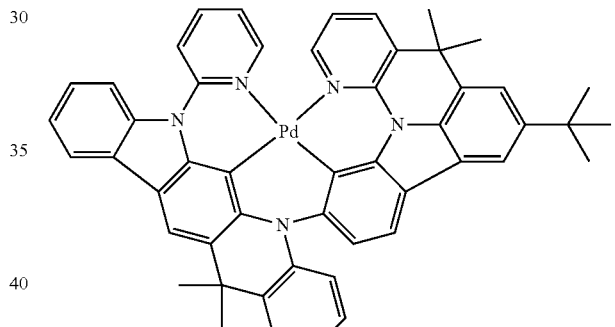
PdN-N<sup>C</sup>N<sup>C</sup>-tBu
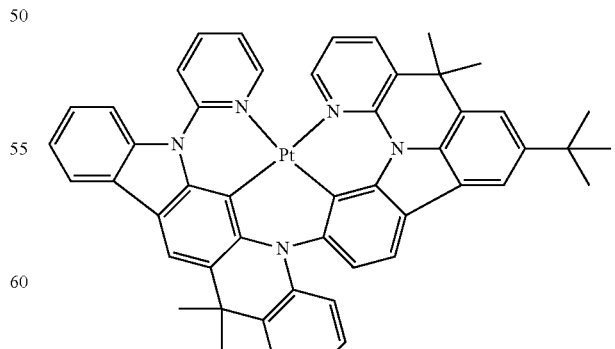
PtN-N<sup>C</sup>N<sup>C</sup>-tBu

425
-continued
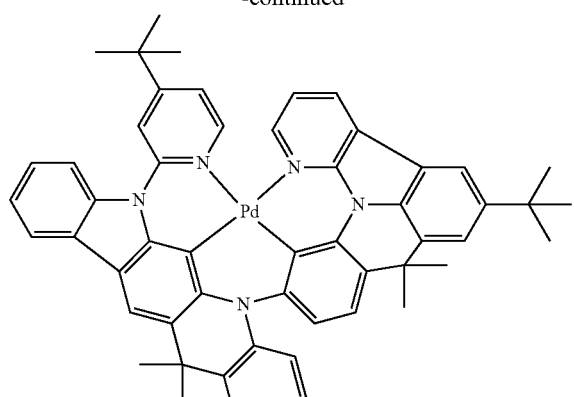
PdN-N$^C$N$^{C'}$-dtb
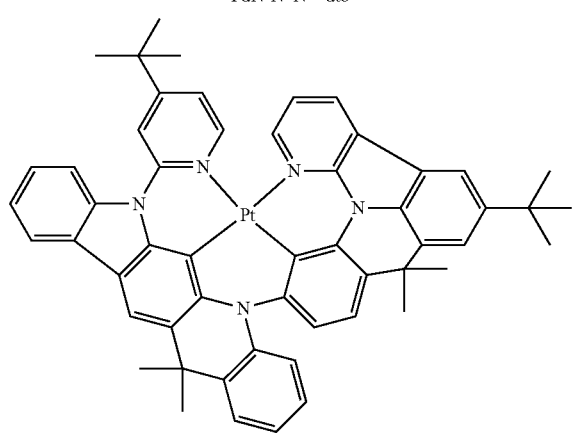
PtN-N$^C$N$^{C'}$-dtb
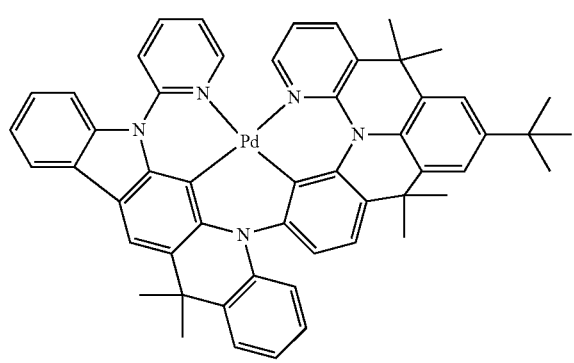
PdN-N$^C$N$^{CC}$-tBu
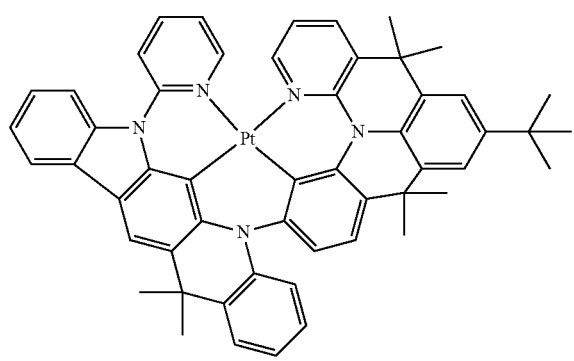
PtN-N$^C$N$^{CC}$-tBu
426
-continued
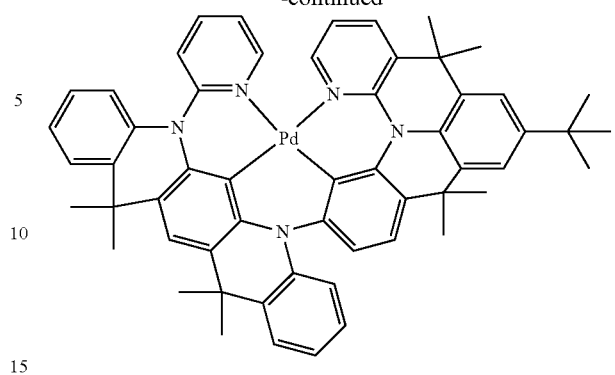
PdN$^C$-N$^C$N$^{CC}$-tBu
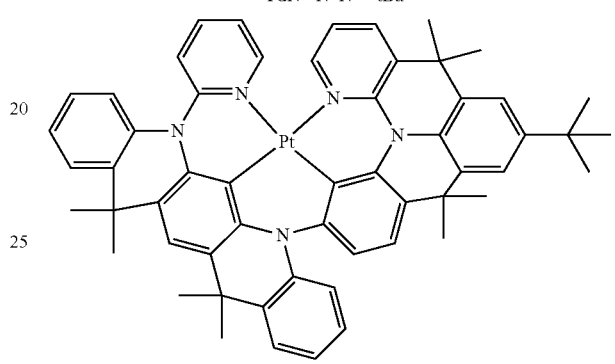
PtN$^C$-N$^C$N$^{CC}$-tBu
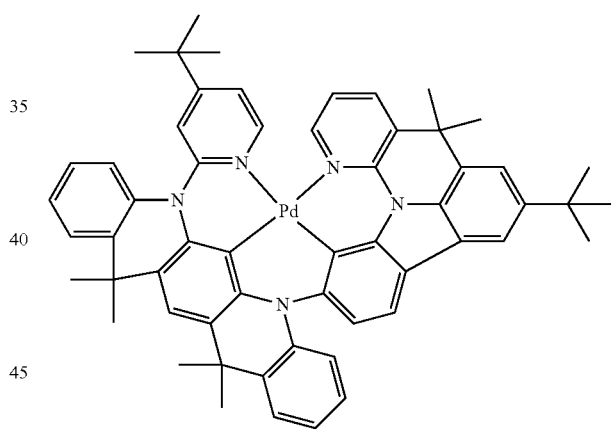
PdN$^C$-N$^C$N$^C$-dtb
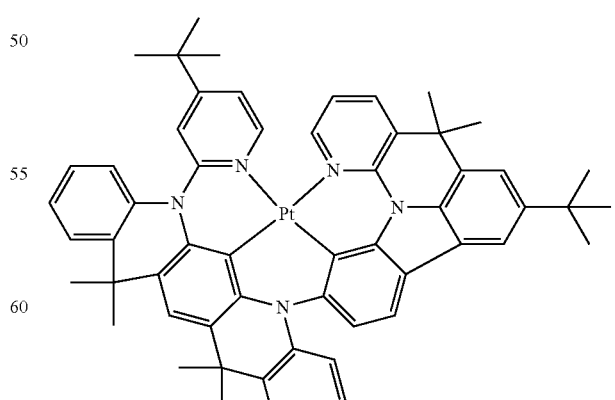
PtN$^C$-N$^C$N$^C$-dtb 427
-continued
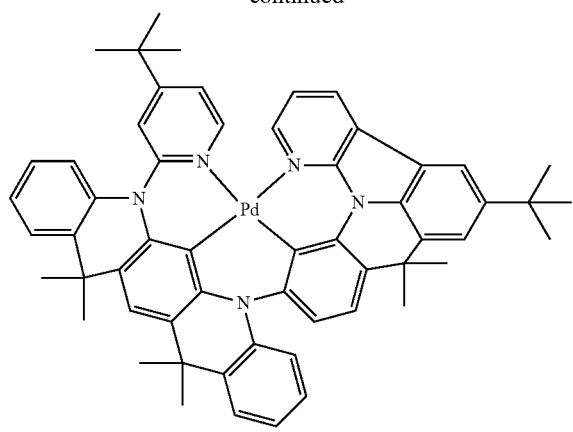
PdN$^C$-N$^C$N$^{C'}$-dtb
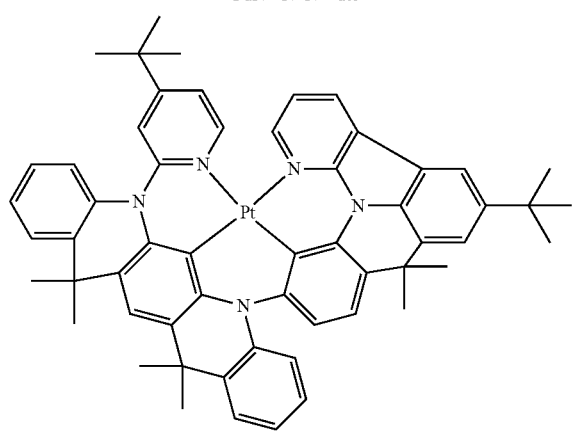
PtN$^C$-N$^C$N$^{CC}$-dtb
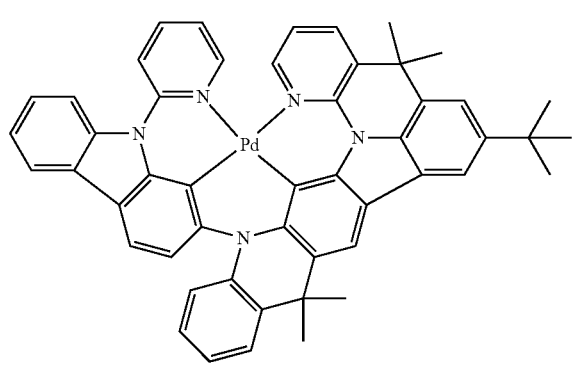
PdNN$^C$-N$^C$-tBu
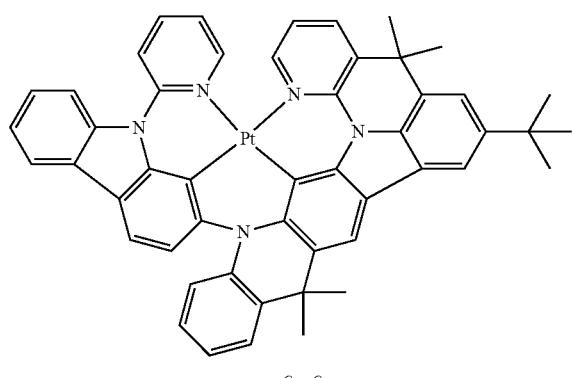
PtNN$^C$-N$^C$-tBu
428
-continued
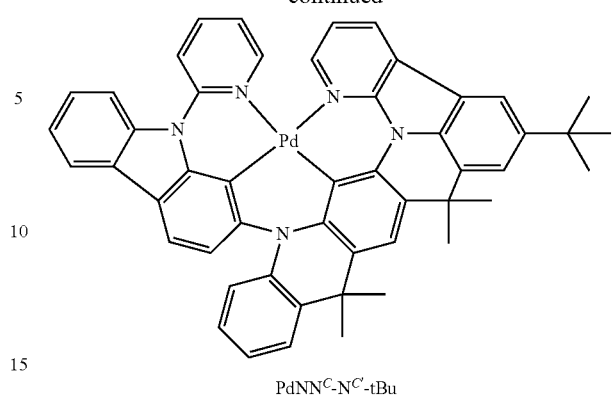
PdNN$^C$-N$^{C'}$-tBu
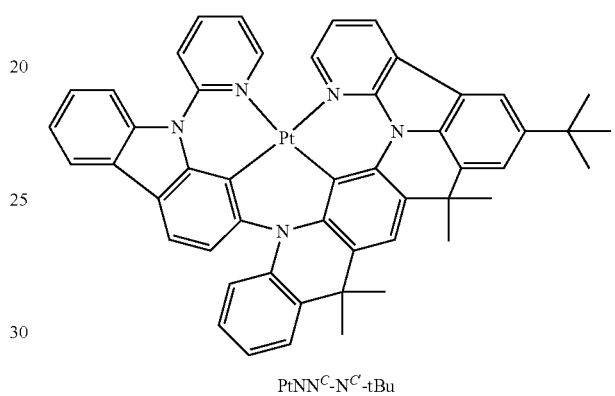
PtNN$^C$-N$^{C'}$-tBu
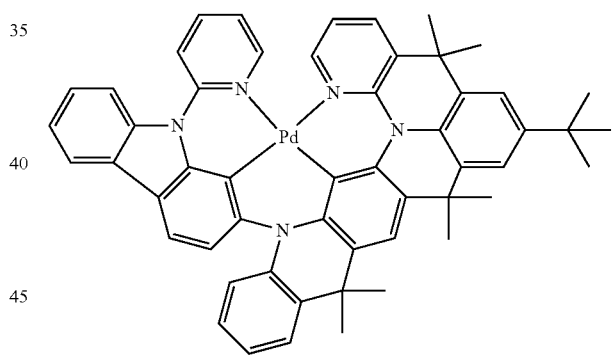
PdNN$^C$-N$^{CC}$-tBu
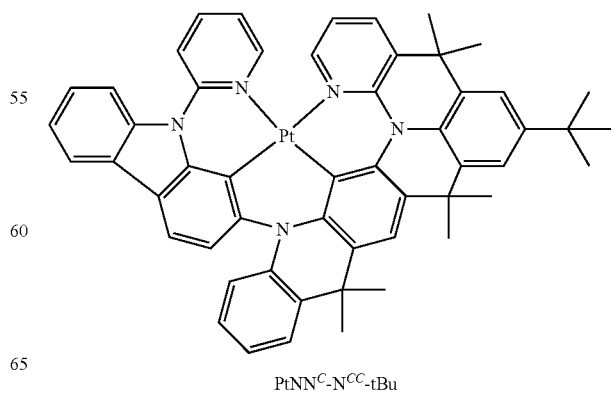
PtNN$^C$-N$^{CC}$-tBu

429
-continued
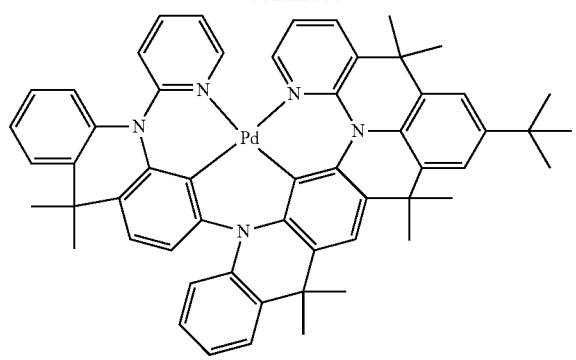
PdN$^C$N$^C$-N$^{CC}$-tBu
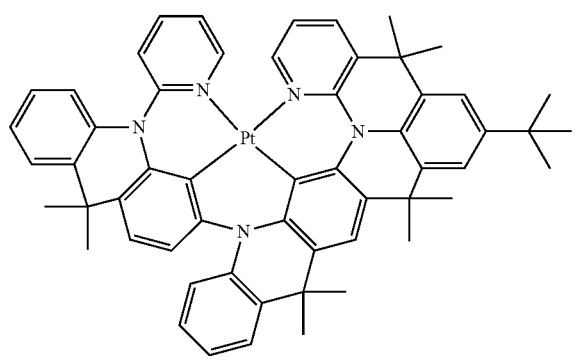
PtN$^C$N$^C$-N$^{CC}$-tBu
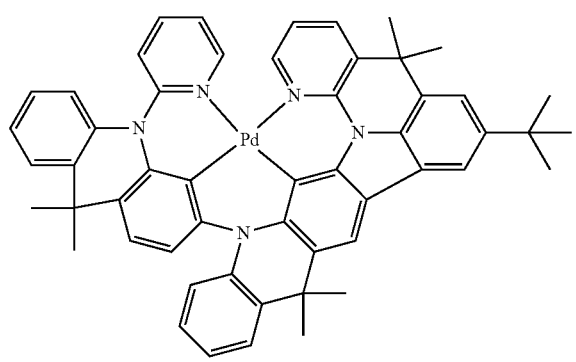
PdN$^C$N$^C$-N$^C$-tBu
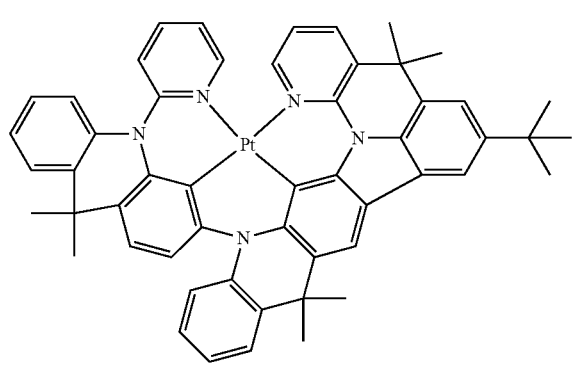
PtN$^C$N$^C$-N$^C$-tBu
430
-continued
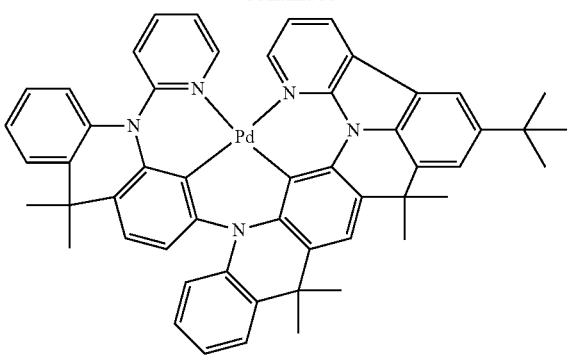
PdN$^C$N$^C$-N$^{C'}$-tBu
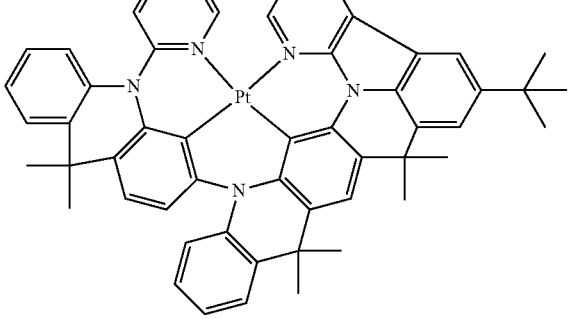
PtN$^C$N$^C$-N$^{C'}$-tBu
Structure 46
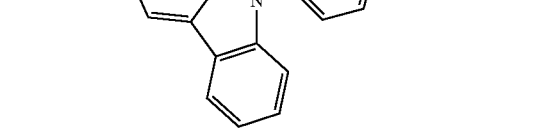
PtN'NN$^C$-tBu
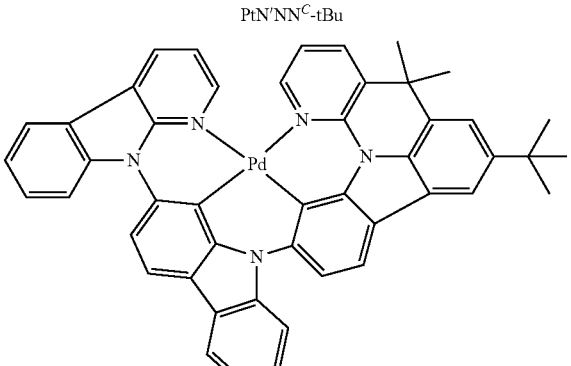
PdN'NN$^C$-tBu

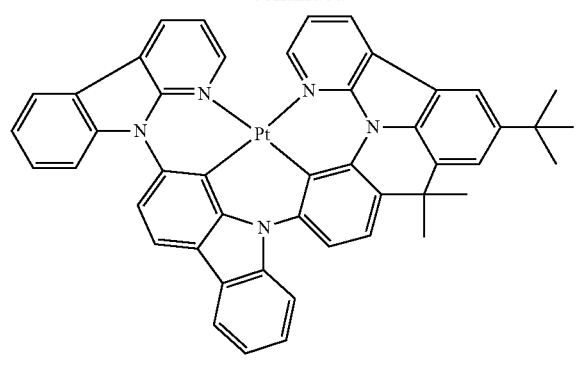
PtN'NN$^{C'}$-tBu
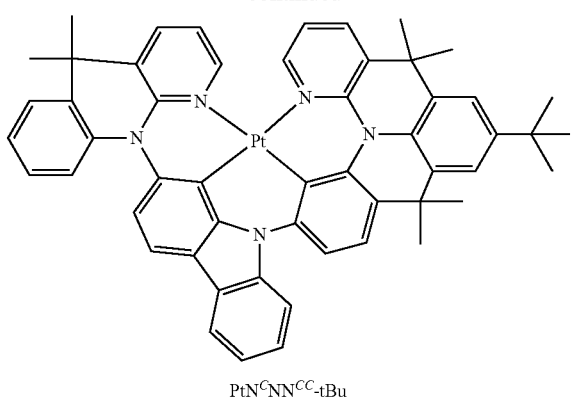
PtN$^C$NN$^{CC}$-tBu
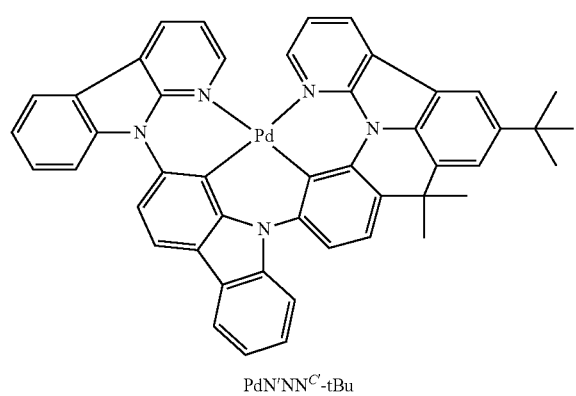
PdN'NN$^{C'}$-tBu
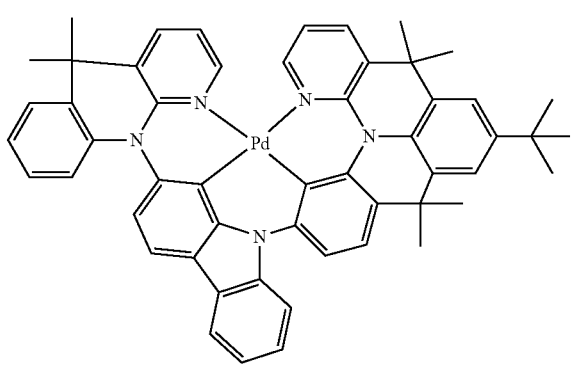
PdN$^C$NN$^{CC}$-tBu
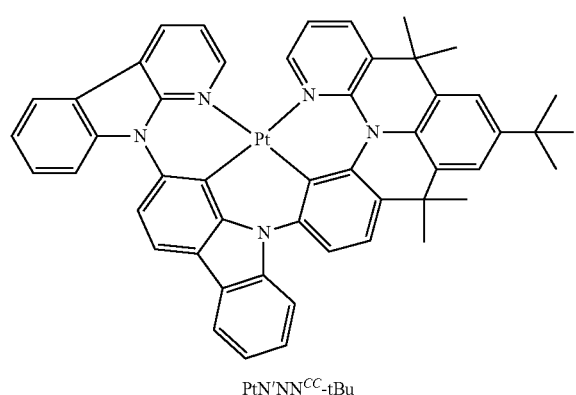
PtN'NN$^{CC}$-tBu
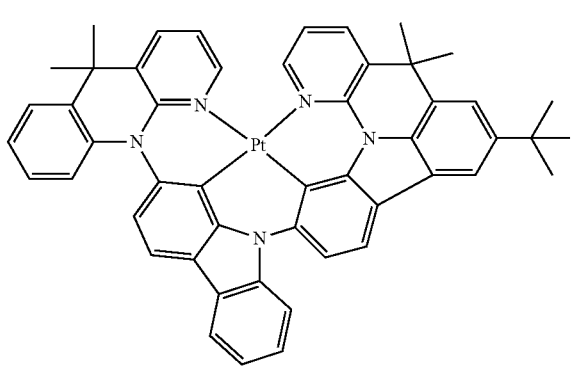
PtN$^C$NN$^C$-tBu
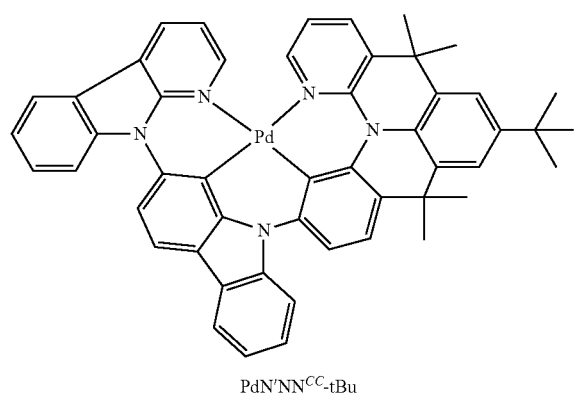
PdN'NN$^{CC}$-tBu
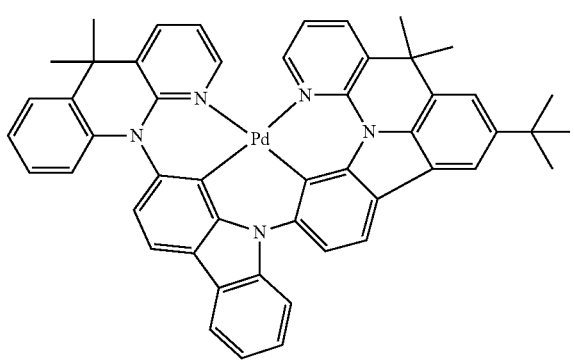
PdN$^C$NN$^C$-tBu

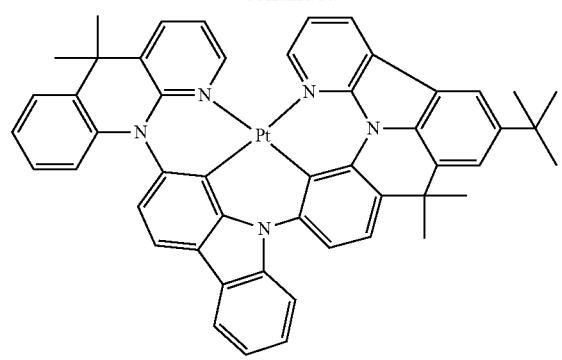
PtN$^C$NN$^{C'}$-tBu
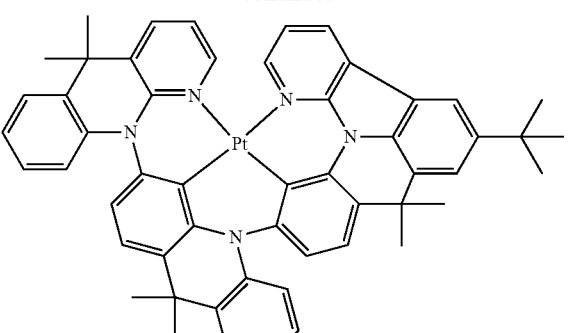
PtN$^C$N$^C$N$^{C'}$-tBu
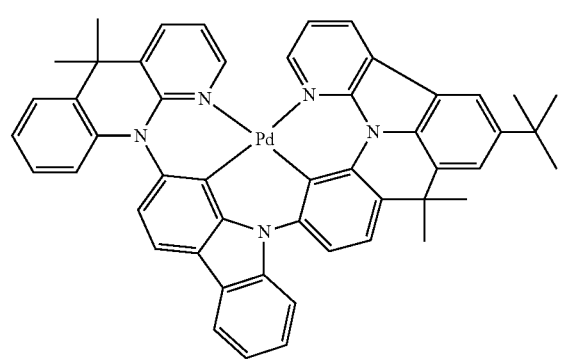
PdN$^C$NN$^{C'}$-tBu
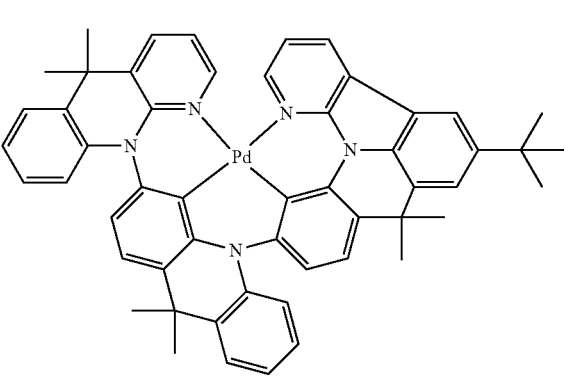
PdN$^C$N$^C$N$^{C'}$-tBu
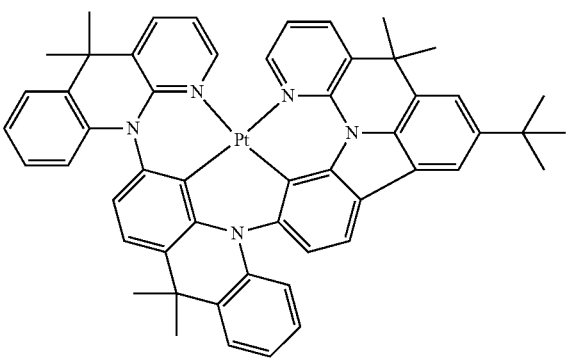
PtN$^C$N$^C$N$^C$-tBu
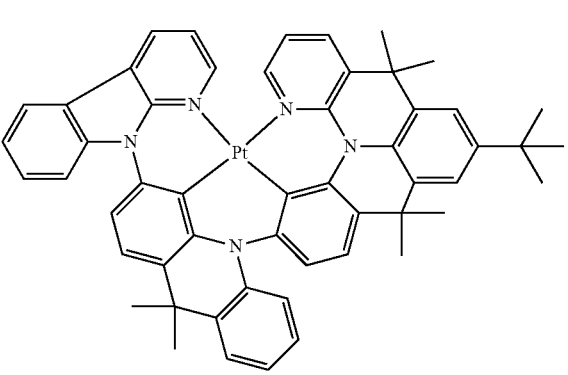
PtN'N$^C$N$^C$N$^{CC}$-tBu
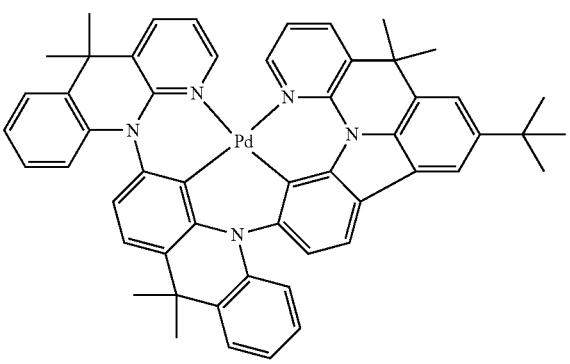
PdN$^C$N$^C$N$^C$-tBu
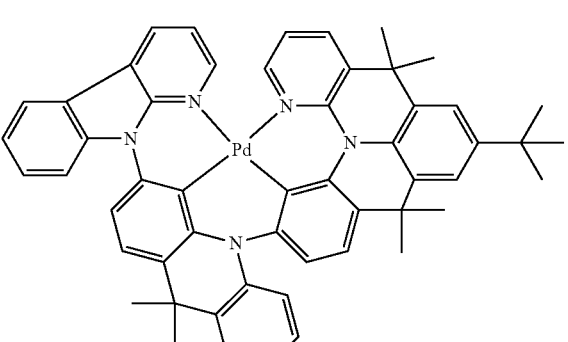
PdN'N$^C$N$^C$N$^{CC}$-tBu

435
-continued
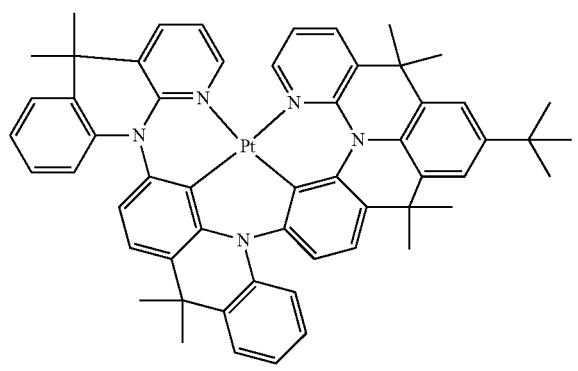
PtN$^C$N$^C$N$^{CC}$-tBu
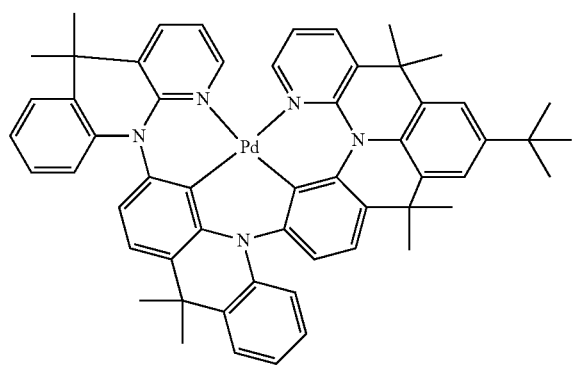
PdN$^C$N$^C$N$^{CC}$-tBu
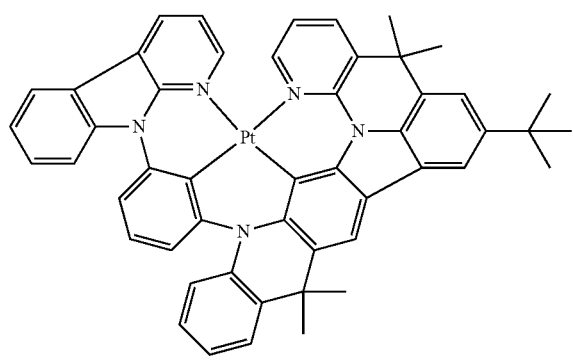
PtN'N-N$^C$-tBu
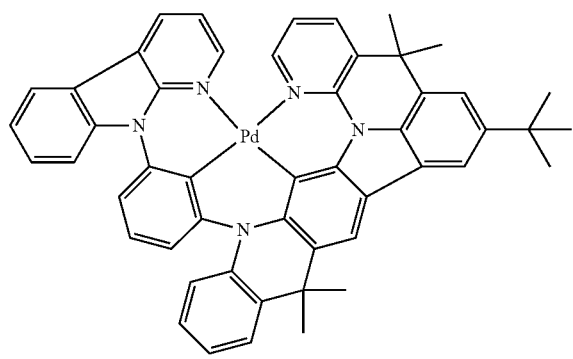
PdN'N-N$^C$-tBu
436
-continued
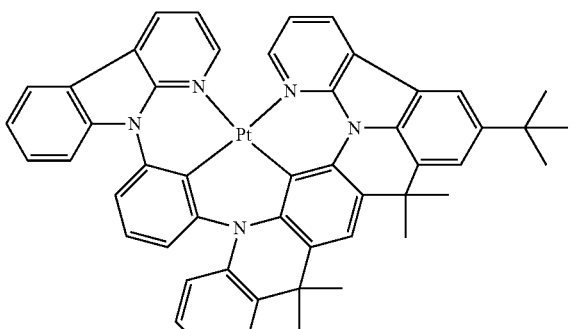
PtN'N-N$^{C'}$-tBu
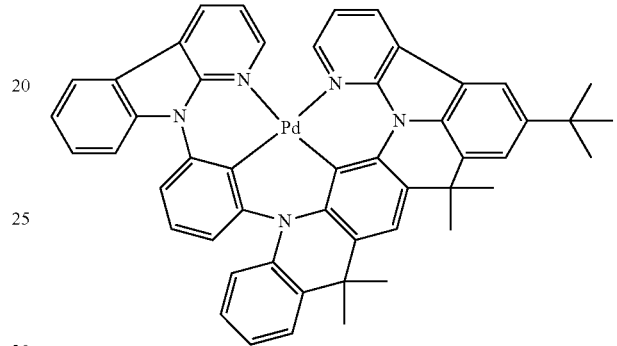
PdN'N-N$^{C'}$-tBu
Structure 47
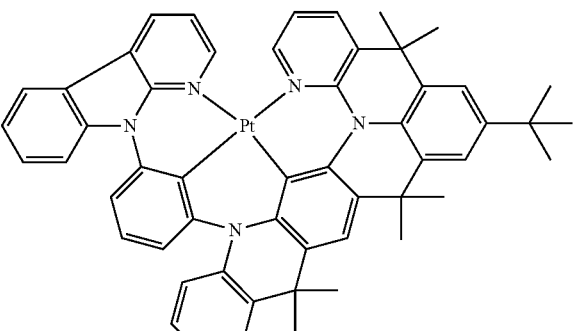
PtN'N-N$^{cc}$-tBu
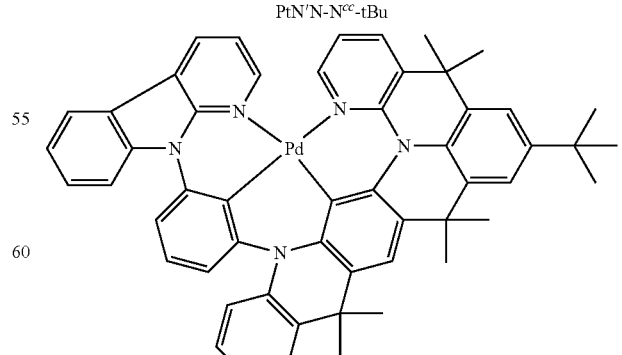
PdN'N-N$^{cc}$-tBu 437
-continued
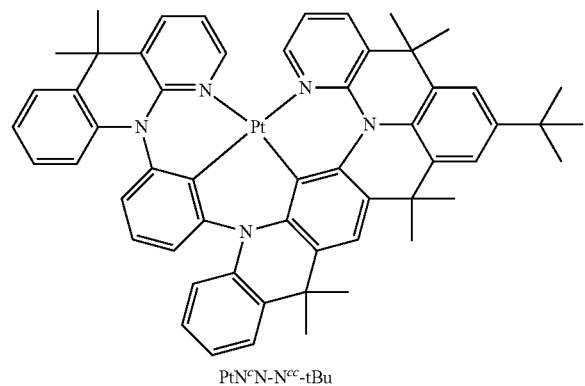
PtN^cN-N^{cc}-tBu
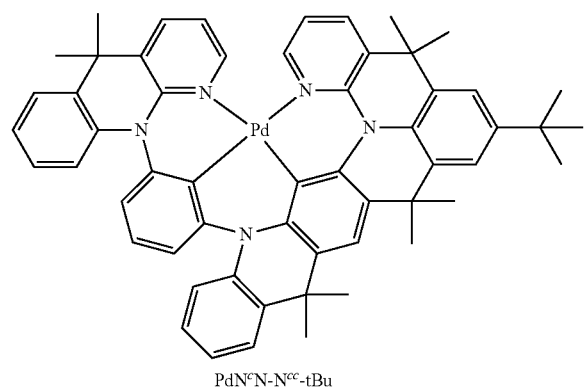
PdN^cN-N^{cc}-tBu
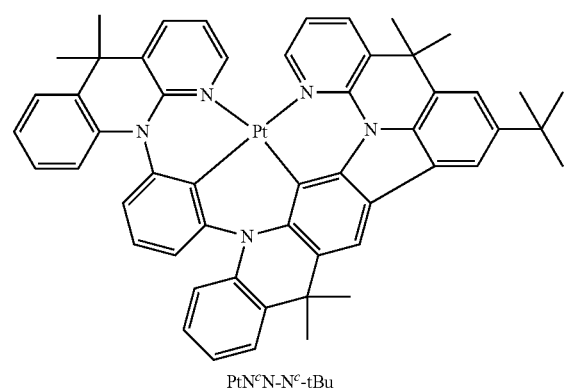
PtN^cN-N^c-tBu
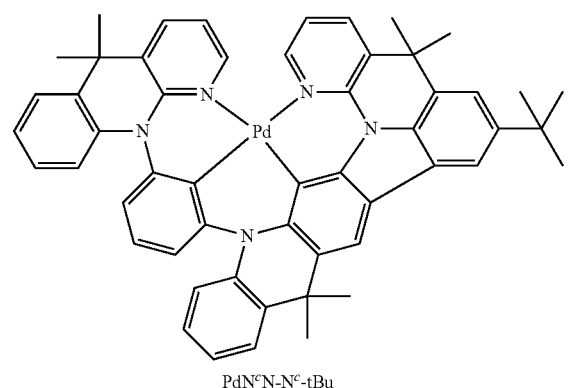
PdN^cN-N^c-tBu
438
-continued
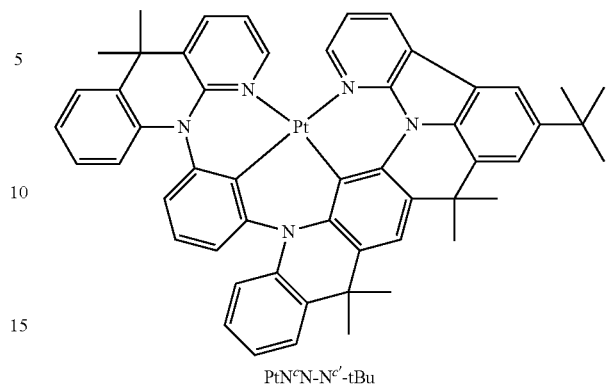
PtN^cN-N^{c'}-tBu
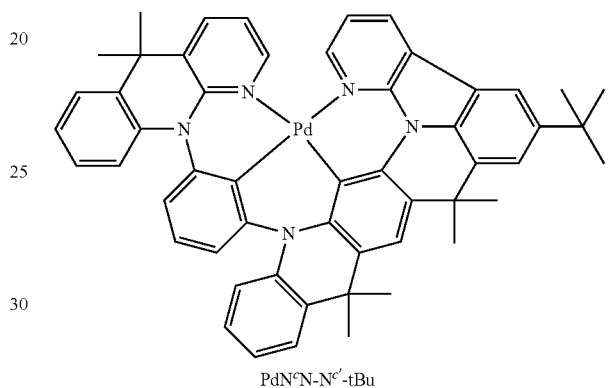
PdN^cN-N^{c'}-tBu
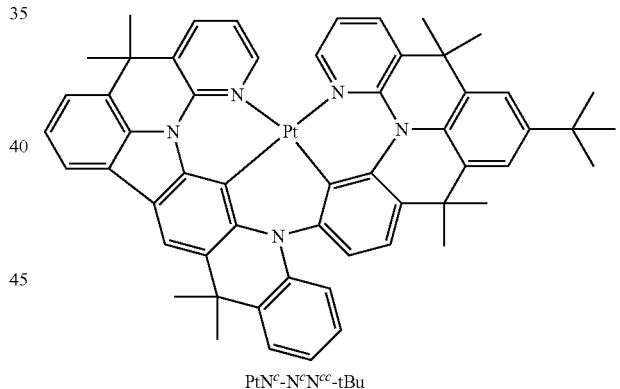
PtN^c-N^cN^{cc}-tBu
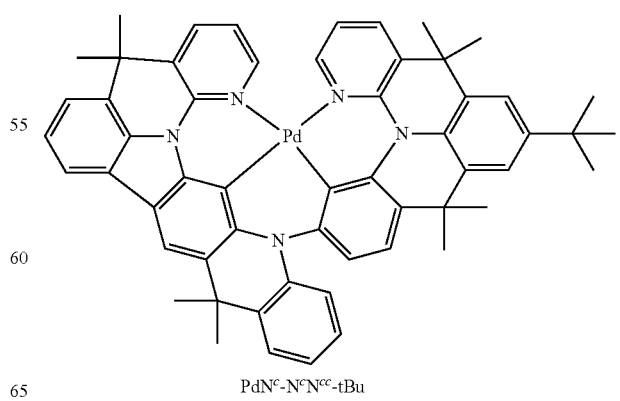
PdN^c-N^cN^{cc}-tBu

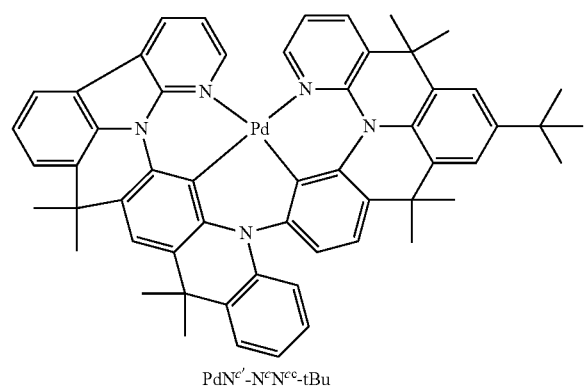
PdN^{c'}-N^cN^{cc}-tBu
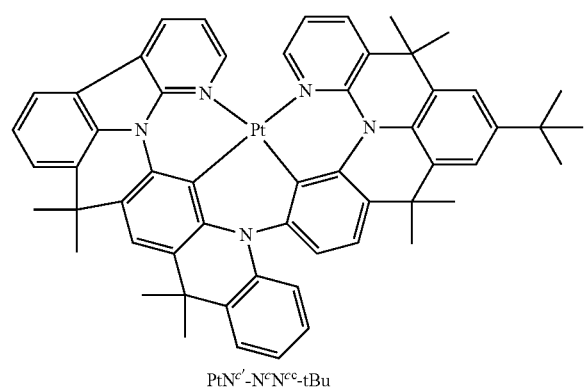
PtN^{c'}-N^cN^{cc}-tBu
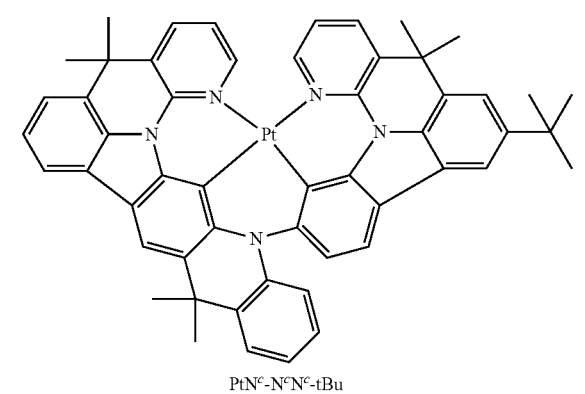
PtN^c-N^cN^c-tBu
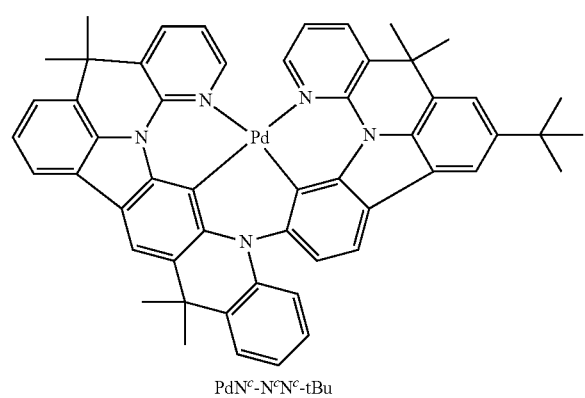
PdN^c-N^cN^c-tBu
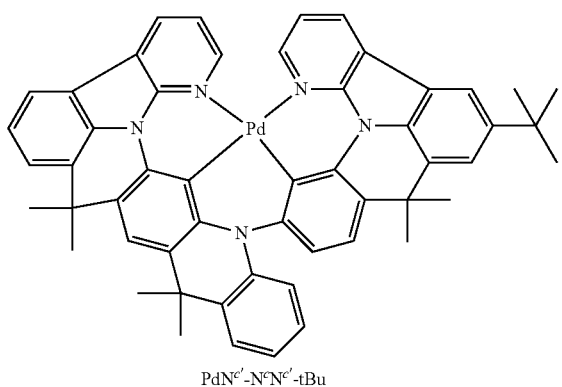
PdN^{c'}-N^cN^{c'}-tBu
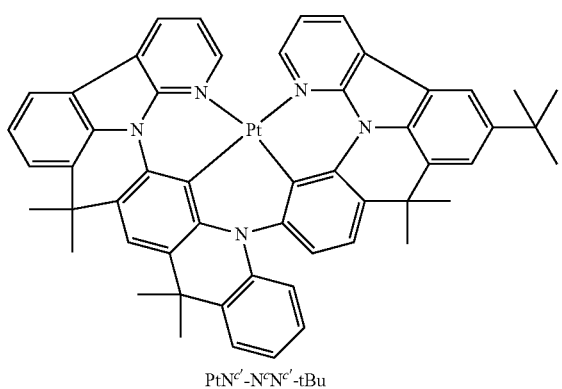
PtN^{c'}-N^cN^{c'}-tBu
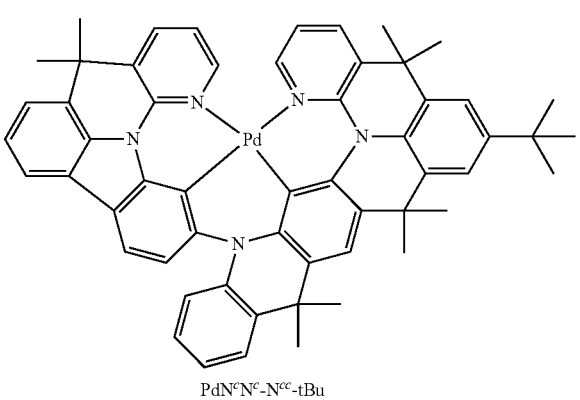
PdN^cN^c-N^{cc}-tBu
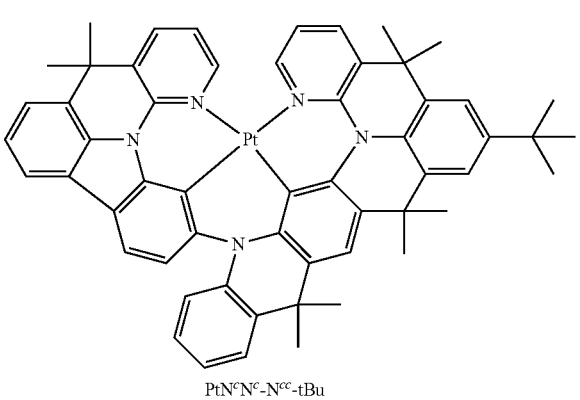
PtN^cN^c-N^{cc}-tBu

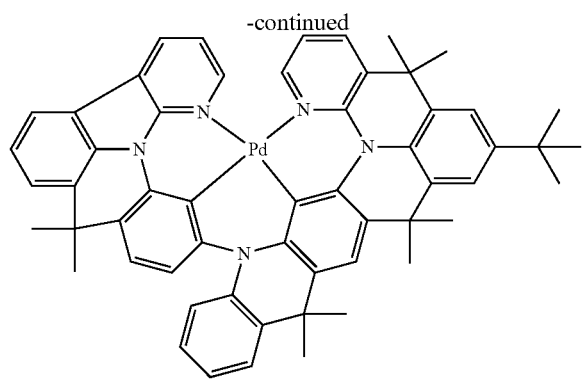

PdN$^{c'}$N$^{c}$-N$^{cc}$-tBu


PtN$^{c'}$N$^{c}$-N$^{cc}$-tBu

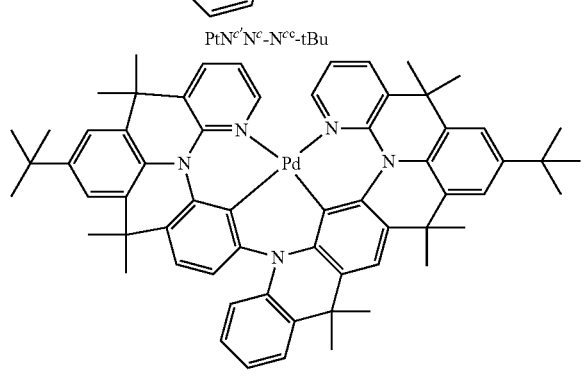

PdN$^{cc}$N$^{c}$-N$^{cc}$-dtb

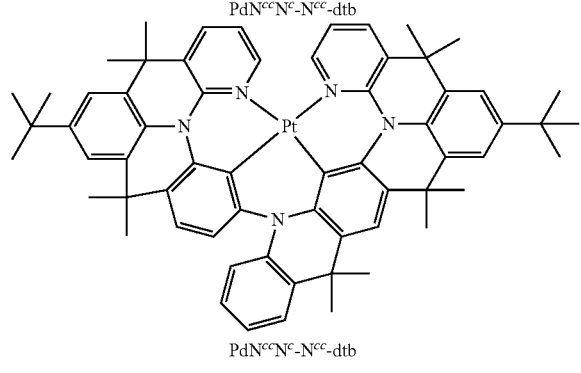

PdN$^{cc}$N$^{c}$-N$^{cc}$-dtb

In the compounds shown in Structure 1-Structure 47, each of R, $R^1$, $R^2$, $R^3$, $R^4$, $R^5$, and $R^6$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In another aspect, each of R, $R^1$, $R^2$, $R^3$, $R^4$, $R^5$, and $R^6$ is independently hydrogen, halogen, hydroxyl, thiol, nitro, cyano; or substituted or unsubstituted: aryl, cycloalkyl, cycloalkenyl, heterocyclyl, heteroaryl, alkyl, alkenyl, alkynyl, or amino. In another aspect, each of R, $R^1$, $R^2$, $R^3$, and $R^4$ is independently hydrogen or substituted or unsubstituted: aryl, cycloalkyl, cycloalkenyl, heterocyclyl, heteroaryl, alkyl, alkenyl, or alkynyl.

Disclosed herein are complexes of Formula BI, Formula BII, Formula BIII, Formula BIV, or Formula BV:

Formula BI

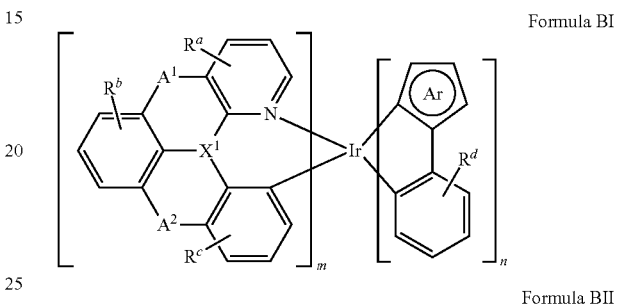

Formula BII

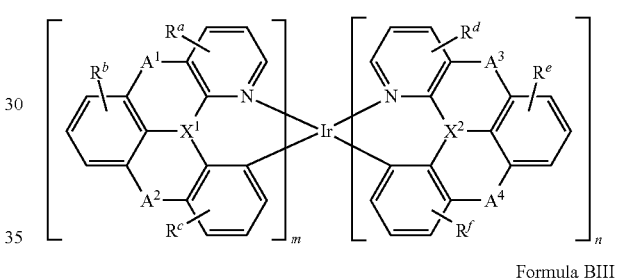

Formula BIII

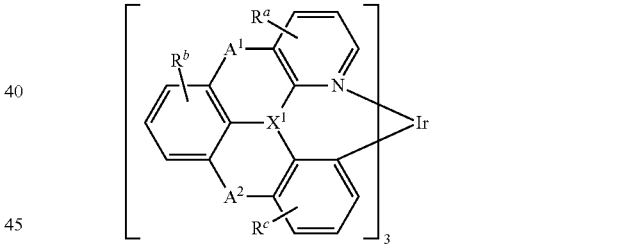

Formula BIV

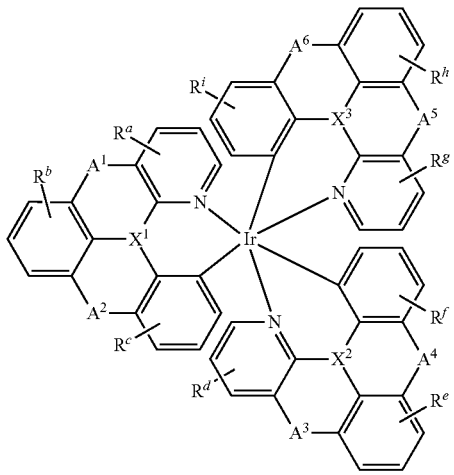

-continued

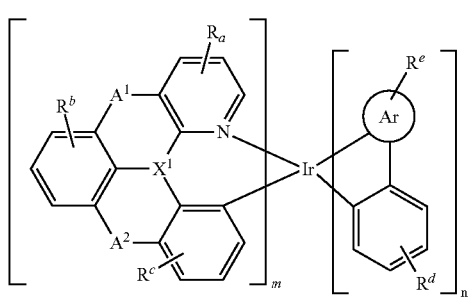

Formula BV wherein:
Ar is substituted or unsubstituted aryl, cycloalkyl, cycloalkenyl, heteroaryl, heterocyclyl, carbene, or N-heterocyclic carbene, each of $A^1$, $A^2$, $A^3$, $A^4$, $A^5$, and $A^6$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$, each of $X^1$, $X^2$, and $X^3$ is independently $CR^1$, $SiR^1$, $GeR^1$, N, P, P=O, As, As=O, B, $R^3Bi$=O or Bi, m=1, n=2 or m=2, n=1, each of $R^a$, $R^b$, $R^c$, $R^d$, $R^e$, $R^f$, $R^g$, $R^h$, and $R^i$ is independently present or absent, and if present each of $R^a$, $R^b$, $R^c$, $R^d$, $R^e$, $R^f$, $R^g$, $R^h$, and $R^i$ is independently a mono-, di-, or tri-substitution, and each of $R^a$, $R^b$, $R^c$, $R^d$, $R^e$, $R^f$, $R^g$, $R^h$, and $R^i$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, metal complexes illustrated in this disclosure can comprise one or more of the following structures. In another aspect, metal complexes illustrated in this disclosure can also comprise other structures or portions thereof not specifically recited herein, and the present disclosure is not intended to be limited to those structures or portions thereof specifically recited.

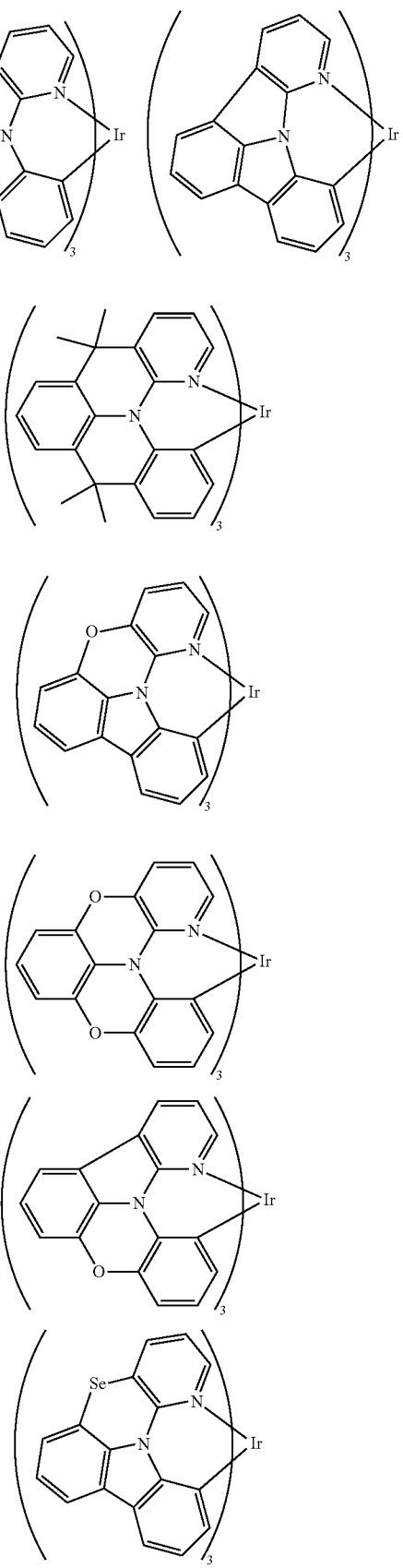

445
-continued
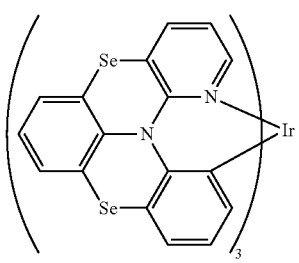
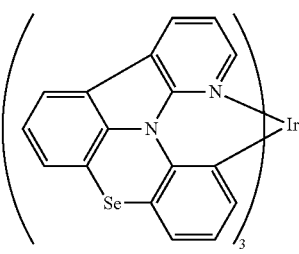
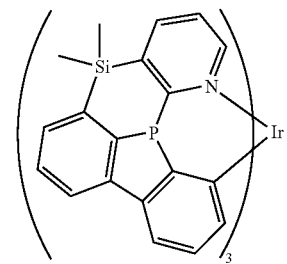
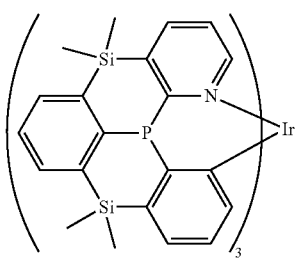
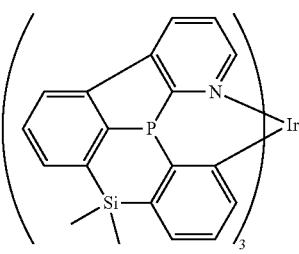
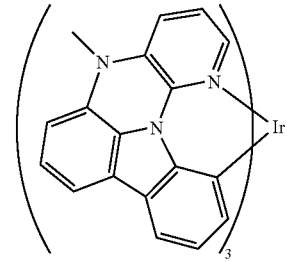
446
-continued
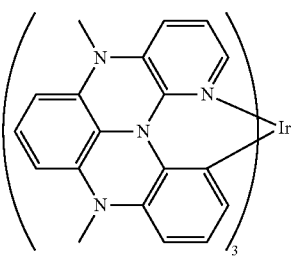
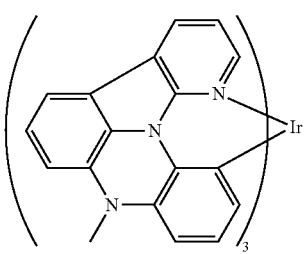
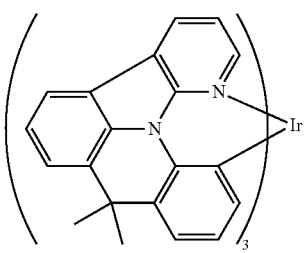
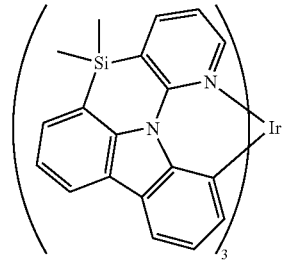
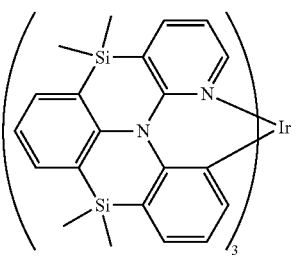
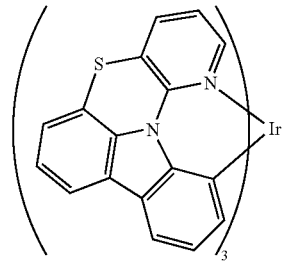

447
-continued
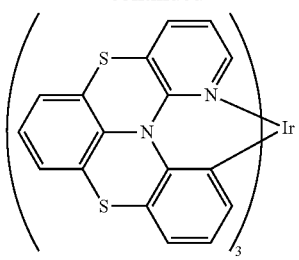
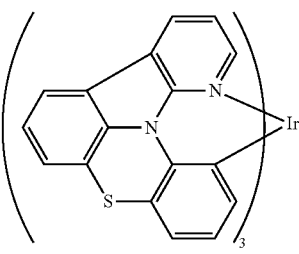
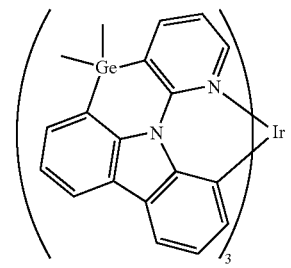
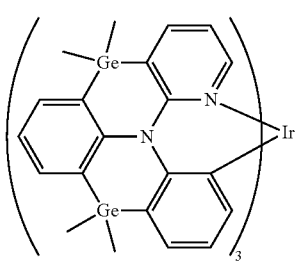
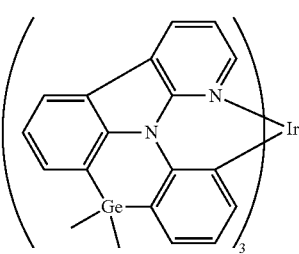
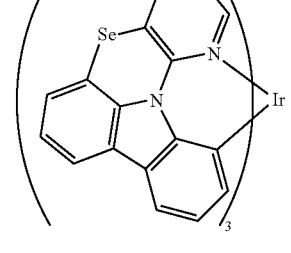
448
-continued
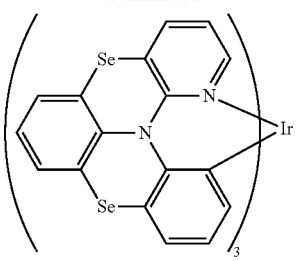
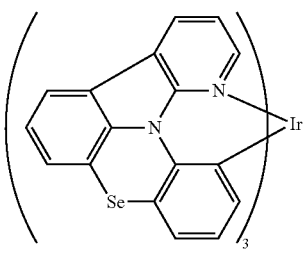
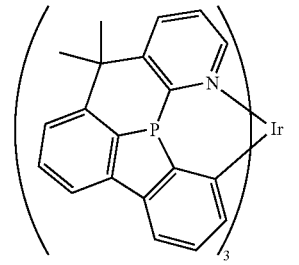
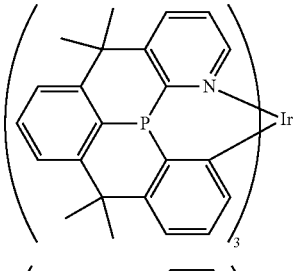
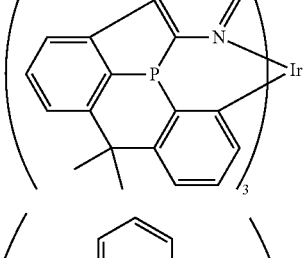
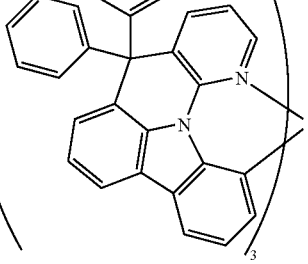

449
-continued
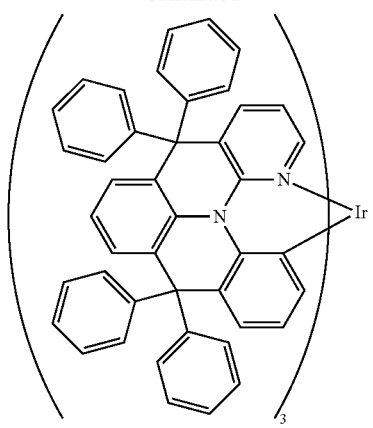
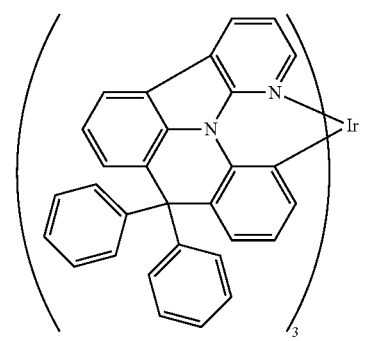
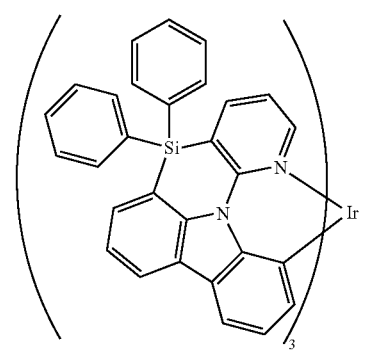
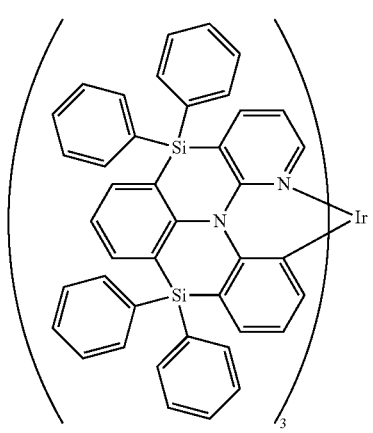
450
-continued
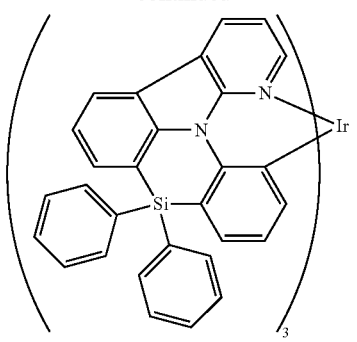
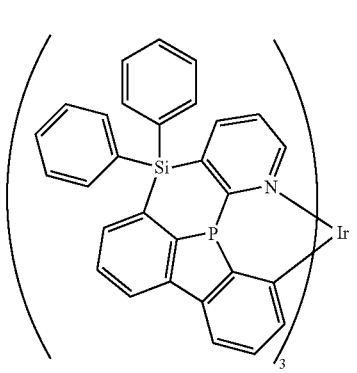
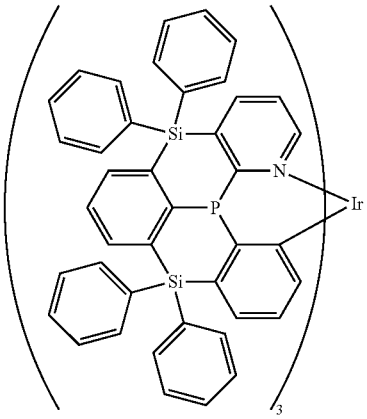
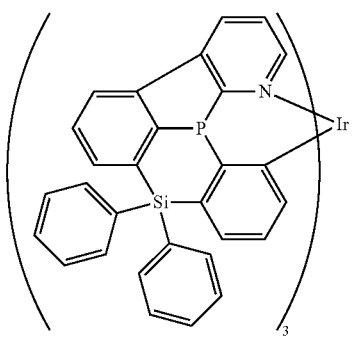

451

-continued

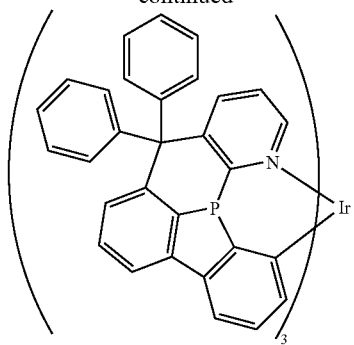

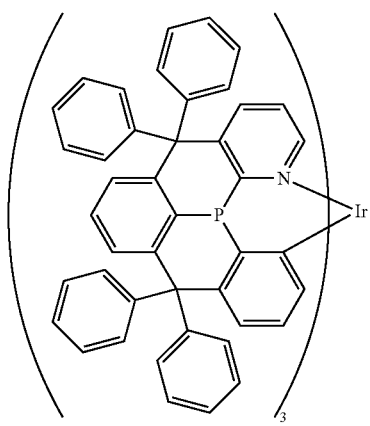

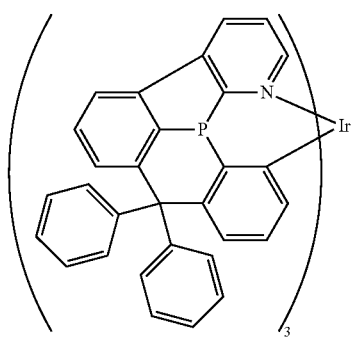

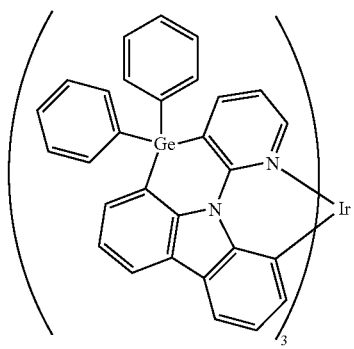

452

-continued

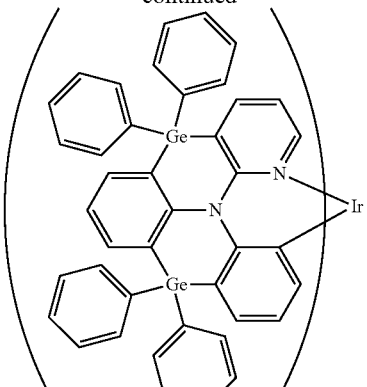

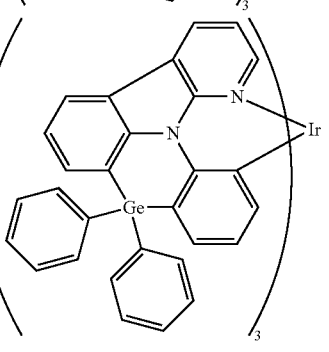

Also disclosed herein are devices including one or more of the complexes disclosed herein.

The complexes disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Complexes described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Complexes described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H NMR spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane (δ=0.00 ppm) as internal reference; $^{13}$C NMR spectra were recorded with CDCl$_3$ (δ=77.00 ppm) as internal reference. If DMSO-d$_6$ was used as solvent, $^1$H NMR spectra were recorded with residual H$_2$O (δ=3.33 ppm) as internal reference; $^{13}$C NMR spectra were recorded with DMSO-d$_6$ (δ=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

General Synthetic Routes

General synthetic routes for L$^3$-L$^4$ (when A$^4$ is a single bond, O or NR) fragments disclosed herein includes:

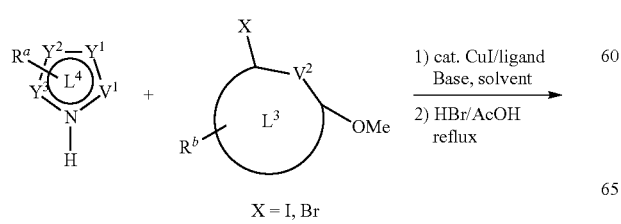

-continued

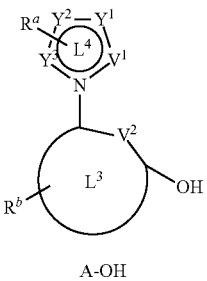

A-OH

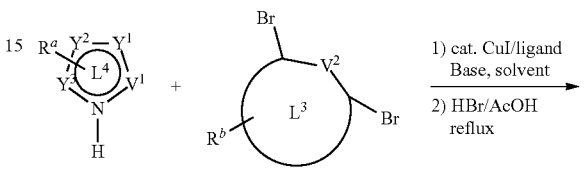

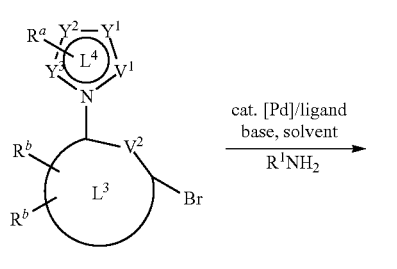

A-Br

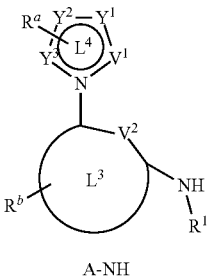

A-NH

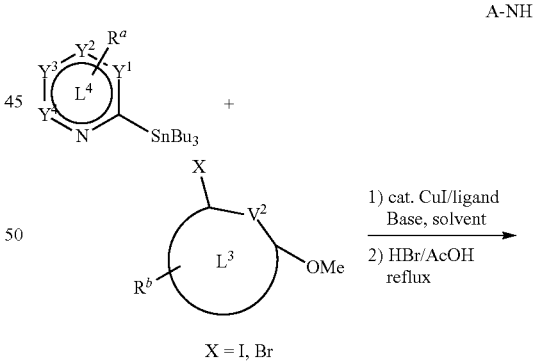

X = I, Br

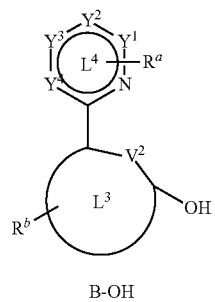

B-OH

-continued
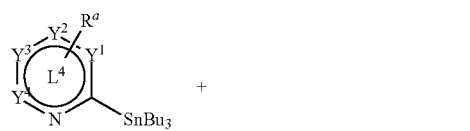
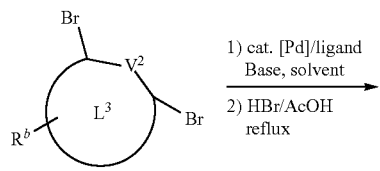
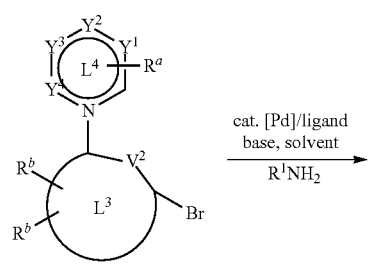
B-Br
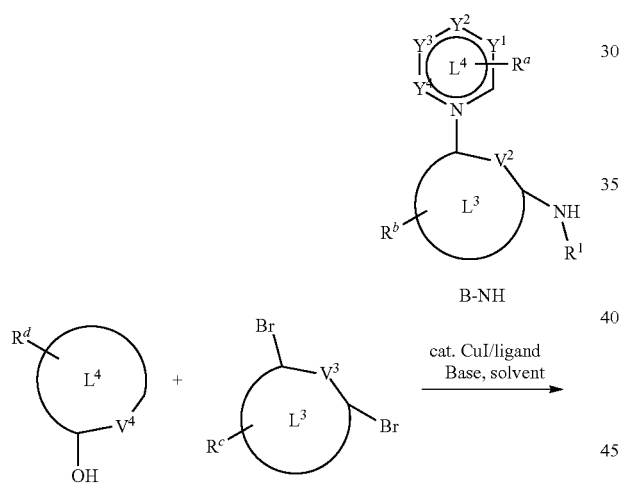
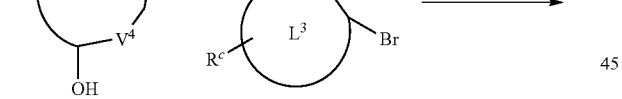
C-Br
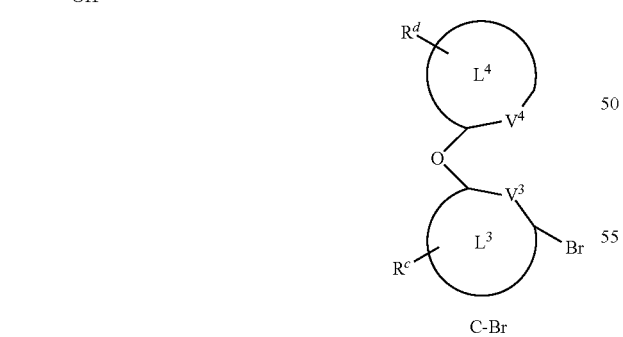
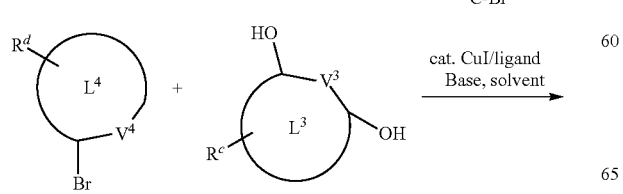
-continued
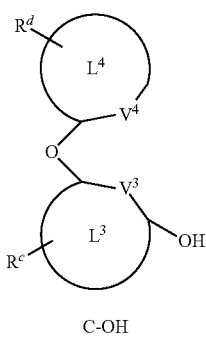
C-OH
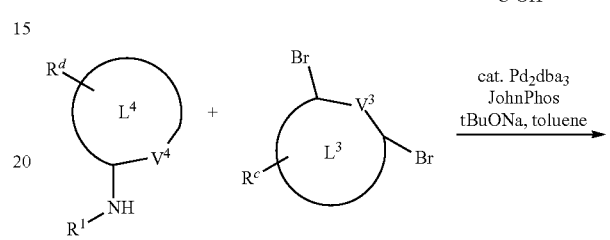
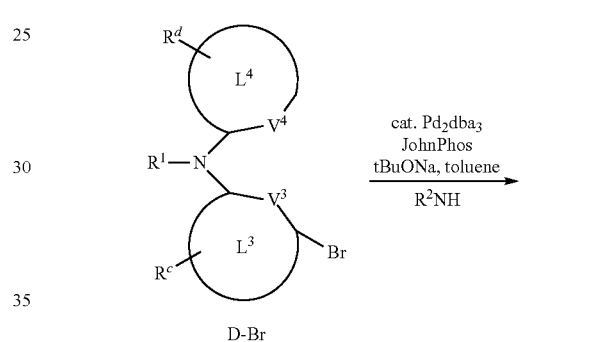
D-Br
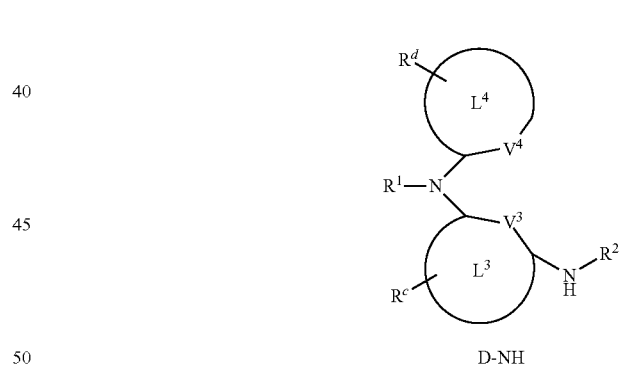
D-NH
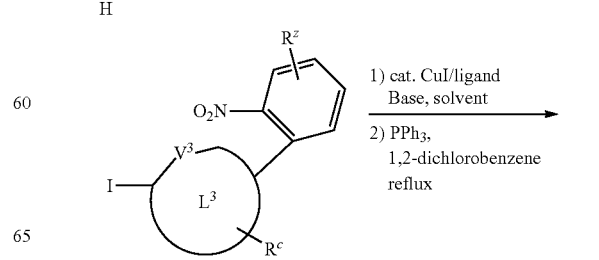

-continued
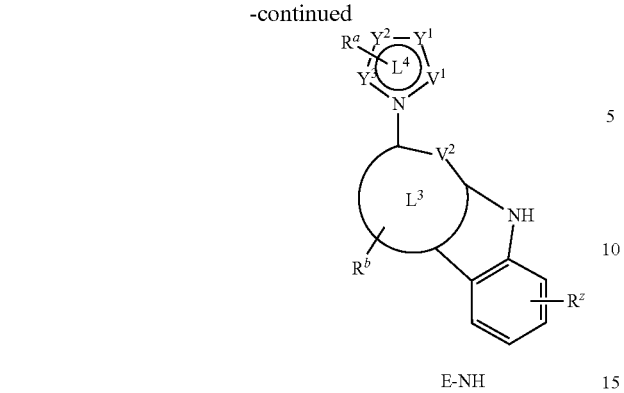
E-NH
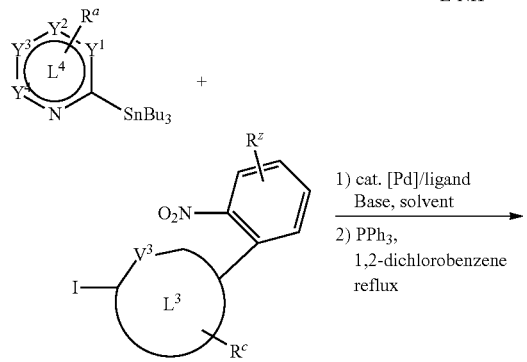
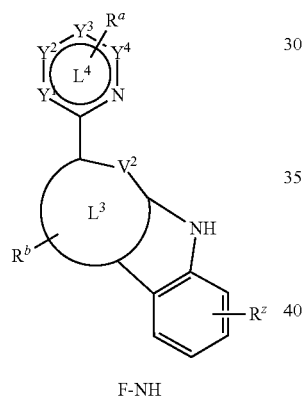
F-NH
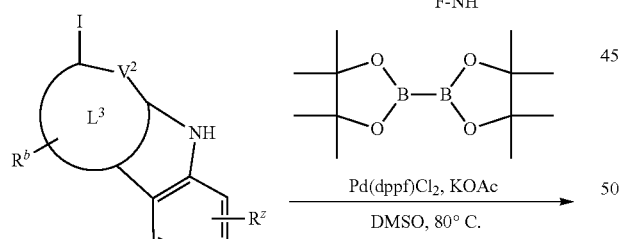
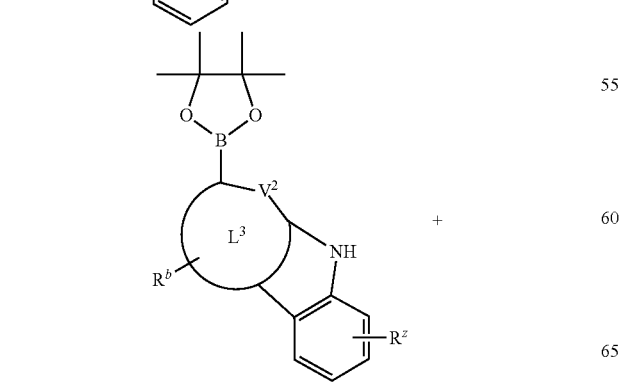
-continued
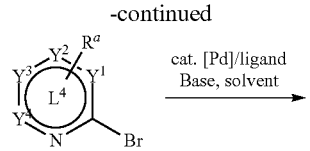
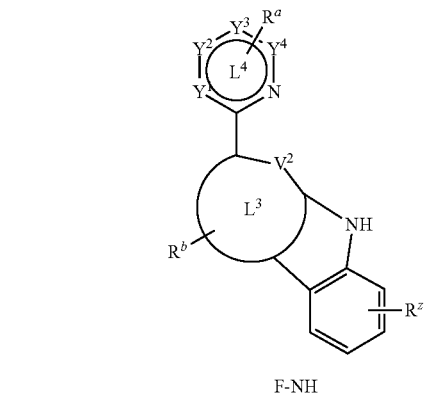
F-NH
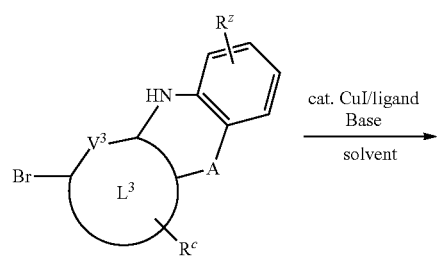
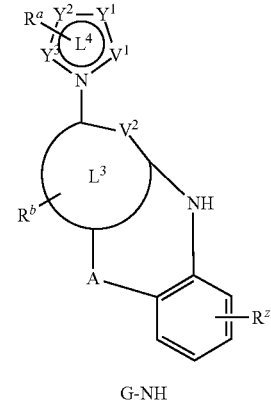
G-NH
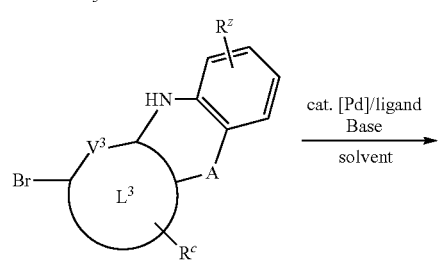

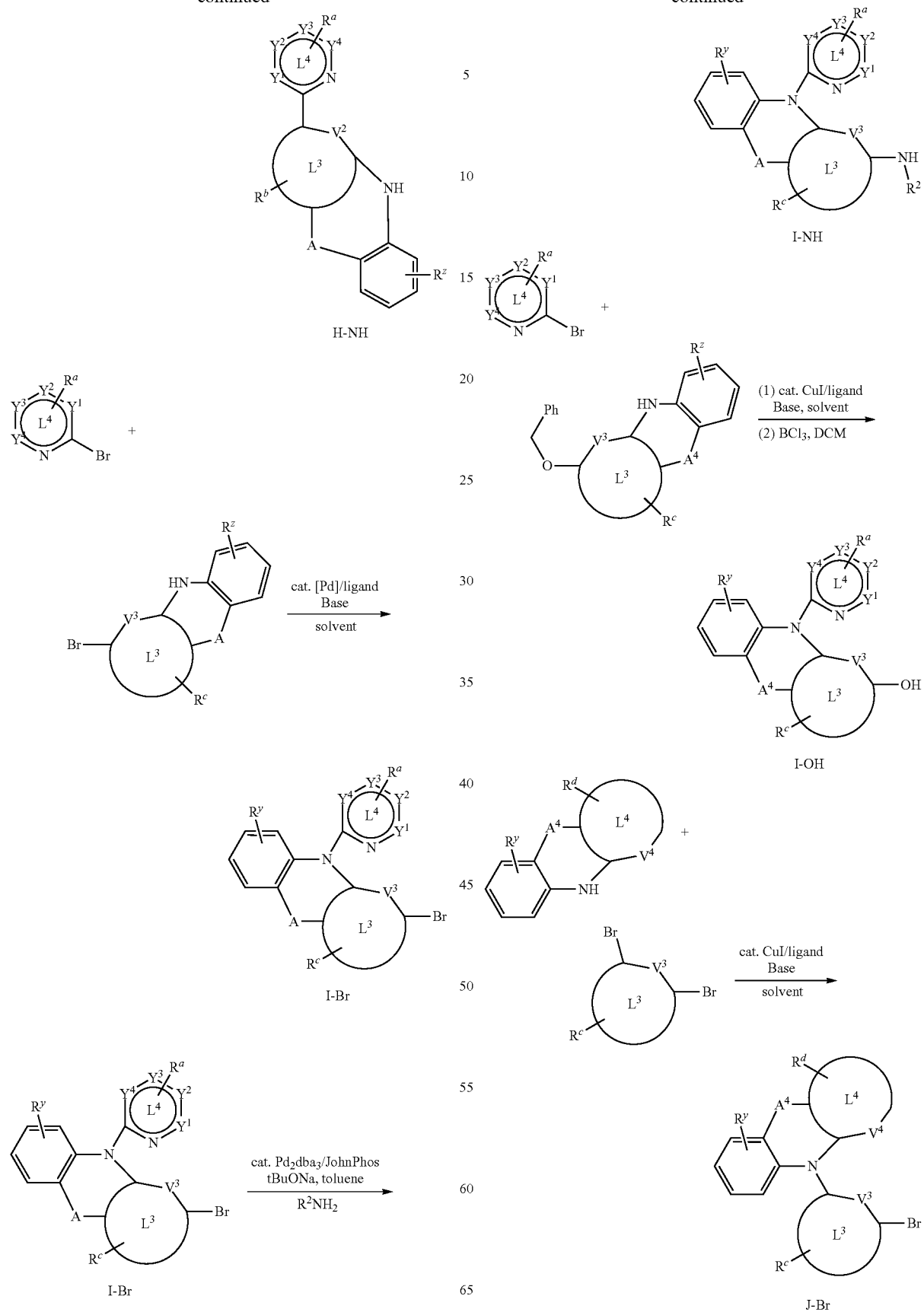

461
-continued
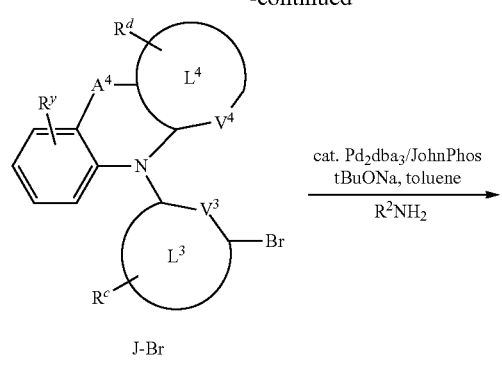
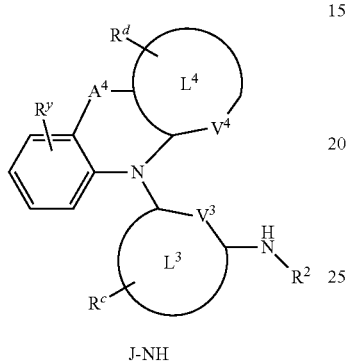
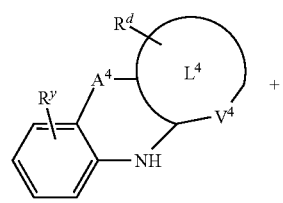
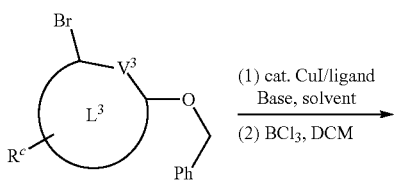
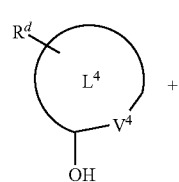
462
-continued
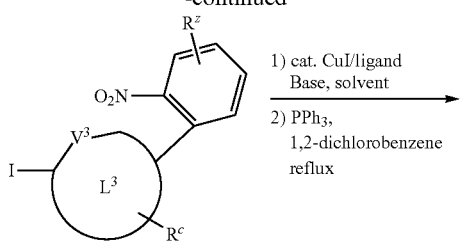
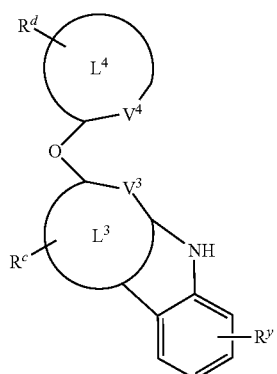
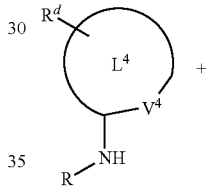
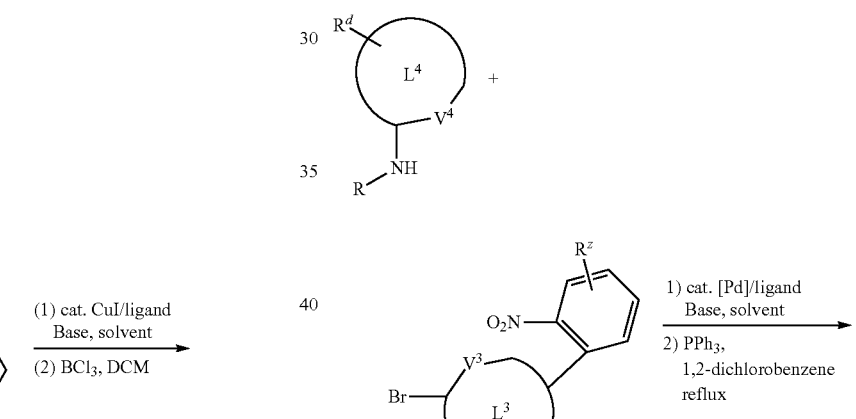
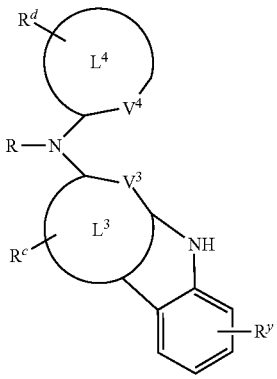
Examples for Synthesis of Some Fragments
The synthetic routes for some fragments are available in the publications and patents listed in the following table.

| Fragments | Publications |
|---|---|
| 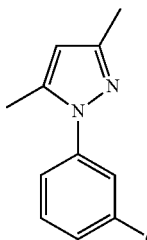<br>A-OH-1DM | *Adv. Mater.* 2014, 26, 7116-7121.<br>US 20140364605 |
| 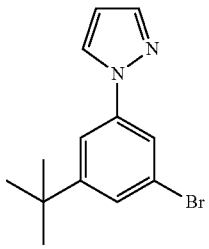 [SMILES: CC(C)(C)c1cc(Br)cc(-n2cccn2)c1]<br>A-Br-7-tBu | *Adv. Mater.* 2014, 26, 7116-7121. |
| 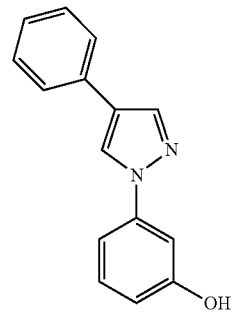 [SMILES: Oc1cccc(-n2cc(-c3ccccc3)cn2)c1]<br>A-OH-6 | *Adv. Mater.* 2014, 26, 7116-7121.<br>US 20140364605 |
| 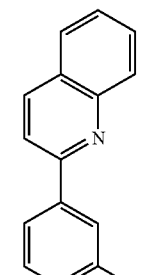<br>B-OH-11 | *Organic Electronics* 2014, 15, 1862-1867. |
| 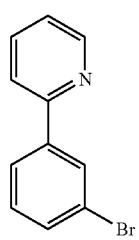 [SMILES: Brc1cccc(-c2ccccn2)c1]<br>B-Br-3 | *Adv. Optical Mater.* 2014, 2015, 3, 390-397. |
-continued
| Fragments | Publications |
|---|---|
| 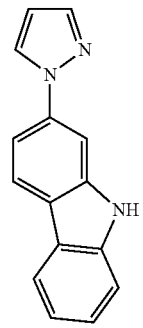 [SMILES: c1ccc2c(c1)[nH]c1cc(-n3cccn3)ccc12]<br>E-NH-1 | *Adv. Optical Mater.* 2014, 2015, 3, 390-397.<br>US 20140364605 |
| 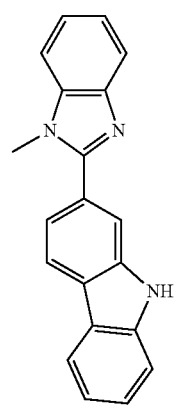 [SMILES: Cn1c(-c2ccc3c(c2)[nH]c2ccccc23)nc2ccccc21]<br>E-NH-8 | *Adv. Optical Mater.* 2014, 2015, 3, 390-397. |
| 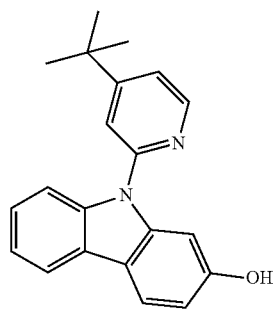 [SMILES: CC(C)(C)c1ccnc(-n2c3ccccc3c3ccc(O)cc32)c1]<br>I-OH-1-tBu | *Adv. Mater.* 2014, 26, 7116-7121.<br>*Adv. Optical Mater.* 2014, 2015, 3, 390-397. |
| 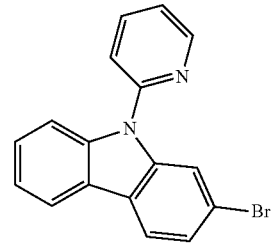 [SMILES: Brc1ccc2c3ccccc3n(-c3ccccn3)c2c1]<br>I-Br-1 | *Adv. Optical Mater.* 2014, 2015, 3, 390-397.<br>US 20140364605 |

Synthesis of 3-(3,5-dimethyl-1H-pyrazol-1-yl)phenol A-OH-1

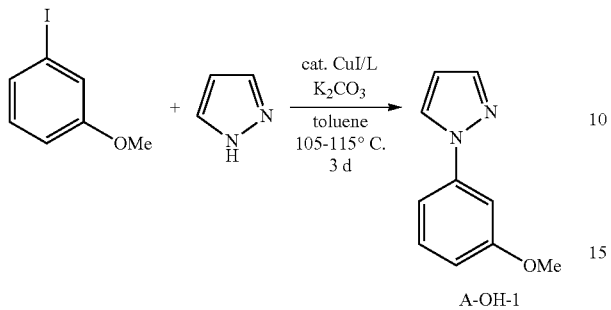

A-OH-1

A mixture of 1-iodo-3-methoxybenzene (8.06 g, 36 mmol, 1.2 eq), 1H-pyrazole (2.04 g, 30 mmol, 1.0 eq), CuI (0.29 g, 1.5 mmol, 0.05 eq), $K_2CO_3$ (13.37 g, 63 mmol, 2.1 eq), and trans-1,2-cyclohexanediamine (0.65 g, 6.0 mmol, 0.2 eq) in toluene (40 mL) was stirred at a temperature of 105-115° C. for 3 days under a nitrogen atmosphere and then cooled to ambient temperature. The solid was filtered and washed with ethyl acetate. The filtrate was concentrated under reduced pressure and the residue was purified through column chromatography on silica gel using hexane and ethyl acetate (10:1) as eluent to obtain a yellow liquid which was used directly in the next step. A solution of the yellow liquid in hydrobromic acid (48%) was refluxed at 110-120° C. for 24 hours under a nitrogen atmosphere. Then the mixture was cooled to ambient temperature and neutralized with a solution of $K_2CO_3$ in water until gas evolution ceased. Then the precipitate was filtered and washed with water several times. The resulting solid was air-dried under reduced pressure to afford the desired product 3-(3,5-dimethyl-1H-pyrazol-1-yl) phenol A-OH-1 as a brown solid 3.32 g in 69% total yield for the two steps. $^1$H NMR (DMSO-$d_6$, 400 MHz): δ 6.49-6.50 (m, 1H), 6.69 (dd, J=6.4, 2.0 Hz, 1H), 7.22-7.27 (m, 3H), 7.70 (d, J=0.8 Hz, 1H), 8.40 (d, J=1.6 Hz, 1H), 9.76 (s, 1H).

Synthesis of 4-(4-(pyridin-3-yl)-1H-pyrazol-1-yl)phenol A-OH-1c

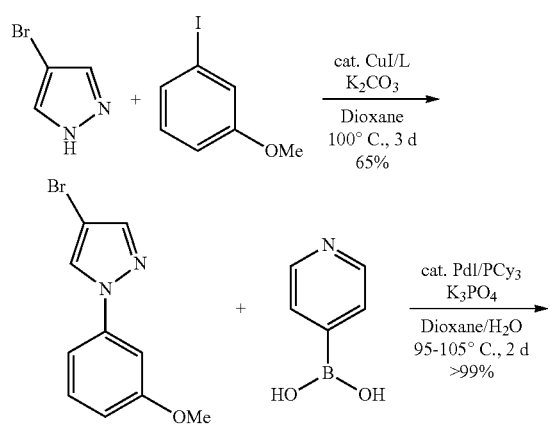

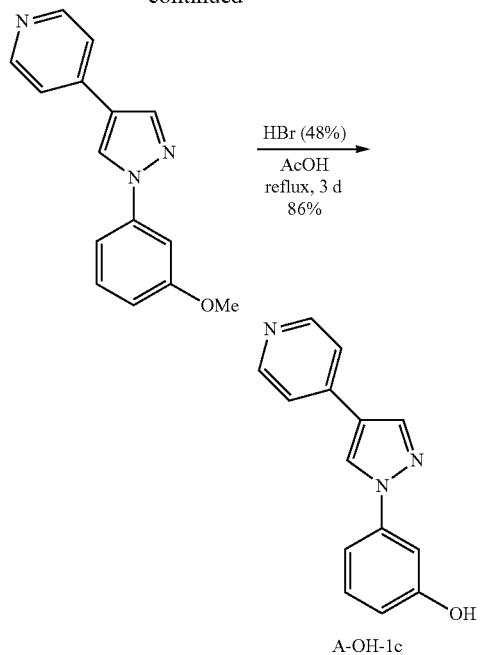

A-OH-1c

Synthesis of 4-bromo-1-(3-methoxyphenyl)-1H-pyrazole: 4-Bromo-1H-pyrazole (3674 mg, 25 mmol, 1.0 eq), CuI (95 mg, 0.5 mmol, 0.02 eq) and $K_2CO_3$ (7256 mg, 52.5 mmol, 2.1 eq) were added to a dry pressure tube equipped with a magnetic stir bar. Then trans-1,2-cyclohexanediamine (570 mg, 5 mmol, 0.2 eq), 1-iodo-3-methoxybenzene (3.57 mL, 30 mmol, 1.2 eq) and dioxane (50 mL) were added in a nitrogen filled glove box. The mixture was sparged with nitrogen for 5 minutes. The tube was sealed before being taken out of the glove box. The mixture was stirred in an oil bath at a temperature of 100° C. for two days. Then the mixture was cooled to ambient temperature, filtered and washed with ethyl acetate. The filtrate was concentrated and the residue was purified through column chromatography on silica gel using hexane and ethyl acetate (20:1-15:1) as eluent to obtain the desired product 4-bromo-1-(3-methoxyphenyl)-1H-pyrazole as a colorless sticky liquid 4.09 g in 65% yield. $^1$H NMR (DMSO-$d_6$, 400 MHz): δ 3.82 (s, 3H), 6.89-6.92 (m, 1H), 7.39-7.41 (m, 3H), 7.86 (s, 1H), 8.81 (s, 1H). $^{13}$C NMR (DMSO-$d_6$, 100 MHz): δ 55.45, 94.92, 104.01, 110.35, 112.54, 128.30, 130.51, 140.26, 141.16, 160.15.

Synthesis of 4-(1-(3-methoxyphenyl)-1H-pyrazol-4-yl) pyridine: To a three-necked flask equipped with a magnetic stir bar and a condenser was added pyridin-4-yl-4-boronic acid (738 mg, 6.0 mmol, 1.2 eq), $Pd_2(dba)_3$ (183 mg, 0.2 mmol, 0.04 eq) and tricyclohexylphosphine (135 mg, 0.48 mmol, 0.096 eq). Then the flask was evacuated and backfilled with nitrogen. The evacuation and backfill procedure was repeated for another two cycles. Then a solution of 4-bromo-1-(3-methoxyphenyl)-1H-pyrazole 3 (1.27 g, 5.0 mmol, 1.0 eq) in dioxane (25 mL) and a solution of $K_3PO_4$ (1804 mg, 8.5 mmol, 1.7 eq) in $H_2O$ (10 mL) were added by syringe independently under nitrogen. The mixture was stirred in an oil bath at a temperature of 95-105° C. for 2 days, cooled to ambient temperature, filtered, and washed with ethyl acetate. The organic layer of the filtrate was separated, dried over sodium sulfate, filtered, and concentrated under reduced pressure. The resulting residue was purified through column chromatography on silica gel using hexane/ethyl acetate (3:1) first, then dichloromethane/methanol (10:1) as eluent to obtain the desired product 4-(1-(3-methoxyphenyl)-1H-pyrazol-4-yl)pyridine as a brown sticky liquid 1.32 g in >99% yield. $^1$H NMR (DMSO-$d_6$, 400 MHz): δ 3.86 (s, 3H), 6.94 (d, J=8.4 Hz, 1H), 7.45-7.48 (m, 3H), 7.72 (dd, J=4.4, 1.6 Hz, 2H), 8.39 (s, 1H), 8.57 (dd, J=4.8, 1.6 Hz, 2H), 9.25 (s, 1H).

Synthesis of 4-(4-(pyridin-3-yl)-1H-pyrazol-1-yl)phenol A-OH-1c: A mixture of 4-(1-(3-methoxyphenyl)-1H-pyrazol-4-yl)pyridine (1.32 g, 4.77 mmol) and hydrobromic acid (10 mL, 48%) in acetic acid (20 mL) was refluxed at 110-120° C. for 2 days under an atmosphere of nitrogen. Then the mixture was cooled to ambient temperature. The organic solvent was removed under reduced pressure and the residue was neutralized with an aqueous solution of $K_2CO_3$ until there was no further gas evolution. Then the precipitate was filtered and washed with water several times. The collected solid was air-dried to afford the product 4-(4-(pyridin-3-yl)-1H-pyrazol-1-yl)phenol A-OH-1c as a brown-grey solid 1.03 g in 86% yield. $^1$H NMR (DMSO-$d_6$, 400 MHz): δ 6.74-6.77 (m, 1H), 7.31-7.32 (m, 3H), 7.72 (dd, J=4.4, 1.6 Hz, 2H), 8.36 (s, 1H), 8.56 (dd, J=4.4, 1.6 Hz, 2H), 9.16 (s, 1H), 9.86 (s, 1H).

Synthesis of 3-(4-(pyridin-3-yl)-1H-pyrazol-1-yl)phenol A-OH-1d

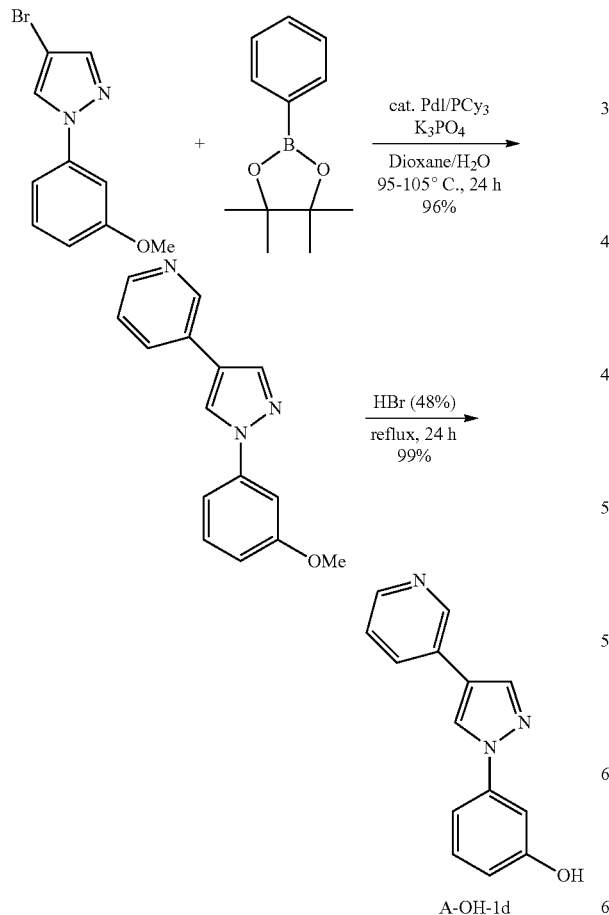

Synthesis of 3-(1-(3-methoxyphenyl)-1H-pyrazol-4-yl)pyridine: To a three-necked flask equipped with a magnetic stir bar and a condenser was added 3-(4,4,5,5-tetramethyl-1,3,2-dioxaborolan-2-yl)pyridine (1.23 g, 6.0 mmol, 1.2 eq), $Pd_2(dba)_3$ (183 mg, 0.2 mmol, 0.04 eq), and tricyclohexylphosphine (135 mg, 0.48 mmol, 0.096 eq). Then the flask was evacuated and backfilled with nitrogen. The evacuation and back fill procedure was repeated for another two cycles. Then a solution of 4-bromo-1-(3-methoxyphenyl)-1H-pyrazole 3 (1266 mg, 5.0 mmol, 1.0 eq) in dioxane (25 mL) and a solution of $K_3PO_4$ (1804 mg, 8.5 mmol, 1.7 eq) in $H_2O$ (10 mL) were added by syringe independently under nitrogen. The mixture was stirred in an oil bath at a temperature of 95-105° C. for 24 hours, cooled to ambient temperature, filtered, and washed with ethyl acetate. The organic layer of the filtrate was separated, dried over sodium sulfate, filtered, and concentrated under reduced pressure. The resulting residue was purified through column chromatography on silica gel using hexane/ethyl acetate (10:1-5:1) first, followed by dichloromethane/methanol (10:1) as consecutive eluents to obtain the desired product 3-(1-(3-methoxyphenyl)-1H-pyrazol-4-yl)pyridine as a brown solid 1.21 g in 96% yield. $^1$H NMR (DMSO-$d_6$, 400 MHz): δ 3.85 (s, 3H), 6.90-6.93 (m, 1H), 7.41-7.48 (m, 4H), 8.10 (dt, J=8.0, 2.0 Hz, 1H), 8.31 (s, 1H), 8.45 (dd, J=4.8, 1.6 Hz, 1H), 8.98 (d, J=1.2 Hz, 1H), 9.13 (s, 1H).

Synthesis of 3-(4-(pyridin-3-yl)-1H-pyrazol-1-yl)phenol A-OH-1d: A solution of 3-(1-(3-methoxyphenyl)-1H-pyrazol-4-yl)pyridine (1.20 g, 4.77 mmol) in hydrobromic acid (15 mL, 48%) was refluxed at 110-120° C. for 24 hours under an atmosphere of nitrogen. Then the mixture was cooled to ambient temperature and neutralized with an aqueous solution of $K_2CO_3$ until there was no further gas evolution. Then the precipitate was filtered and washed with water several times. The collected solid was air-dried to afford the product as a brown solid 1.24 g in 99% yield. $^1$H NMR (DMSO-$d_6$, 400 MHz): δ 6.59 (dt, J=7.2, 2.0 Hz, 1H), 7.11-7.17 (m, 3H), 7.38 (dd, J=7.6, 1.6 Hz, 1H), 8.07 (dt, J=8.0, 2.0 Hz, 1H), 8.15 (s, 1H), 8.33-8.34 (m, 1H), 8.85 (d, J=1.6 Hz, 1H), 8.90 (s, 1H), 9.78 (bs, 1H).

Synthesis of 3-(1-methyl-1H-imidazol-2-yl)phenol A-OH-2

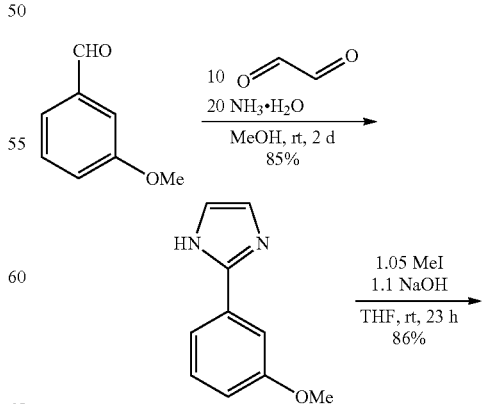

Synthesis of 3-(1H-benzo[d]imidazole-1-yl)phenol A-OH-5

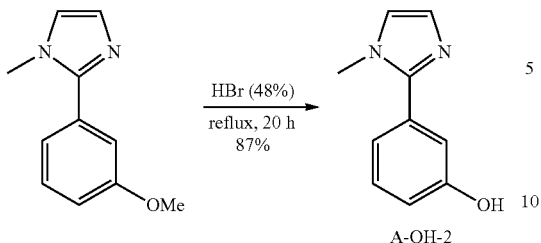

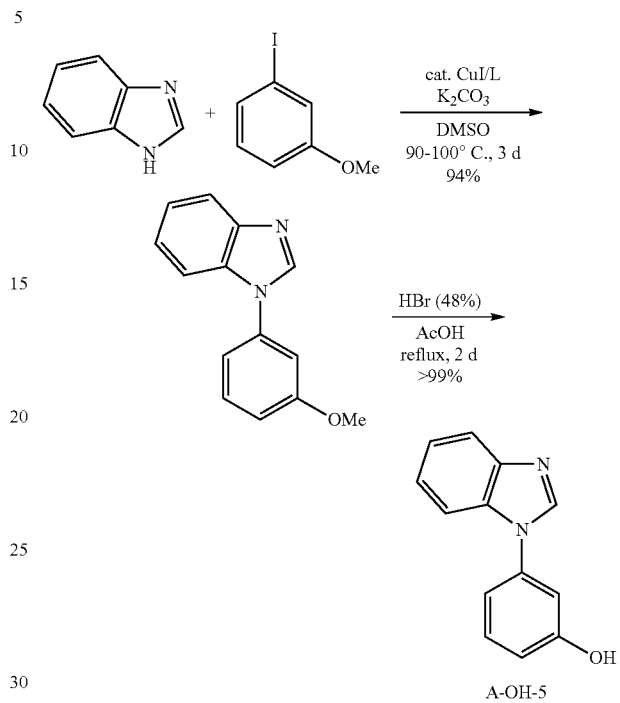

Synthesis of 2-(3-methoxyphenyl)-1H-imidazole: To a three-necked flask equipped with a magnetic stir bar was added oxalaldehyde (114 mL, 1000 mmol, 10 eq, 40% in H$_2$O) to 3-methoxybenzaldehyde (13.62 g, 100 mmol, 1.0 eq) in methanol (375 mL) under nitrogen. Then the mixture was cooled to 0-5° C. in an ice water bath. NH$_3$.H$_2$O (124 mL, 2 mol, 20 eq, 28% in H$_2$O) was added to the mixture slowly. The mixture was stirred at 0° C. for 15 minutes, then warmed to room temperature over two days. The resulting mixture was filtered and concentrated under reduced pressure until about 200 mL solvent was left. The resulting slurry was filtered and washed with water. The collected solid was air-dried to afford the desired product as a brown solid 11.34 g. The filtrate was extracted with dichloromethane three times. The combined organic layers were washed with water and brine, then dried over sodium sulfate, filtered, and concentrated under reduced pressure. The resulting residue was purified through column chromatography on silica gel sequentially using dichloromethane then dichloromethane/methanol (10:1) as eluents to obtain the desired product 3.4 g in 85% total yield. $^1$H NMR (DMSO-d$_6$, 400 MHz): δ 3.79 (s, 3H), 6.87-6.90 (m, 1H), 7.00 (bs, 1H), 7.23 (bs, 1H), 7.31-7.35 (m, 1H), 7.49-7.51 (m, 2H), 12.47 (bs, 1H).

Synthesis of 2-(3-methoxyphenyl)-1-methyl-1H-imidazole: NaOH (1.10 g, 27.4 mmol, 1.1 eq) was added to a solution of 2-(3-methoxyphenyl)-1H-imidazole (4.34 g, 24.9 mmol, 1.0 eq) in THF (90 mL) under nitrogen. Then MeI (1.63 mL, 26.1 mmol, 1.05 eq) was added slowly. The mixture was then stirred at room temperature for 23 hours. The solvent was removed under reduced pressure and the residue was purified through column chromatography on silica gel using dichloromethane/methanol (100:3-100:4) as eluent to obtain the desired product 4.0 g as a brown liquid in 86% yield. $^1$H NMR (DMSO-d$_6$, 400 MHz): δ 3.74 (s, 3H), 3.80 (s, 3H), 6.96 (d, J=0.8 Hz, 1H), 6.97-7.00 (m, 1H), 7.20-7.24 (m, 3H), 7.38 (t, J=8.0 Hz, 1H).

Synthesis of 3-(1-methyl-1H-imidazol-2-yl)phenol A-OH-2: A solution of 2-(3-methoxyphenyl)-1-methyl-1H-imidazole 2 (13.44 g, 71.46 mmol) in hydrobromic acid (75 mL, 48%) was refluxed (110-120° C.) for 20 hours under nitrogen. Then the mixture was cooled down to ambient temperature and neutralized with an aqueous solution of K$_2$CO$_3$ until there was no further gas evolution. Then the precipitate was filtered and washed with water three times. The brown solid was air-dried under reduced pressure and 10.80 g was obtained in 87% yield. $^1$H NMR (DMSO-d$_6$, 400 MHz): δ 3.70 (s, 3H), 6.78-6.81 (m, 1H), 6.93 (d, J=1.2 Hz, 1H), 7.05-7.07 (m, 2H), 7.20 (d, J=0.8 Hz, 1H), 7.24 (t, J=8.0 Hz, 1H), 9.58 (s, H).

Synthesis of 1-(3-methoxyphenyl)-1H-benzo[d]imidazole: To a dry pressure tube equipped with a magnetic stir bar was added 1H-benzo[d]imidazole (3.54 g, 30 mmol, 1.0 eq), 1-iodo-3-methoxybenzene (7.15 mL, 60 mmol, 2.0 eq), CuI (0.57 g, 3.0 mmol, 0.1 eq), K$_2$CO$_3$ (8.29 g, 60 mmol, 2.0 eq) and L-proline (0.69 g, 6 mmol, 0.2 eq). Then the tube was evacuated and backfilled with nitrogen. The evacuation and backfill procedure was repeated for another two cycles. The mixture was stirred in an oil bath at 90-100° C. for 3 days. Then the mixture was cooled to ambient temperature, diluted with ethyl acetate, filtered, and washed with ethyl acetate. The filtrate was concentrated and the residue was purified through column chromatography on silica gel sequentially using hexane and ethyl acetate (10:1), then dichloromethane/methanol (10:1) as eluents to obtain the desired product as a brown sticky liquid 6.34 g in 94% yield. $^1$H NMR (DMSO-d$_6$, 400 MHz): δ 3.85 (s, 3H), 7.06 (dd, J=8.0, 2.4 Hz, 1H), 7.23-7.25 (m, 2H), 7.28-7.35 (m, 2H), 7.53 (t, J =8.4 Hz, 1H), 7.66 (d, J=7.6 Hz, 1H), 7.78 (d, J=6.8 Hz, 1H), 8.60 (s, 1H).

Synthesis of 3-(1H-benzo[d]imidazole-1-yl)phenol A-OH-5: A solution of 1-(3-methoxyphenyl)-H-benzo[d]imidazole (6.30 g, 28.09 mmol) in a mixture of hydrobromicaci (56 mL, 48%) and acetic acid (80 mL) was refluxed at 110-120° C. for 2 days under nitrogen. Then the mixture was cooled to ambient temperature. After removing the organic solvent under reduced pressure, the residue was neutralized with a solution of K$_2$CO$_3$ in water until there was no further gas evolution. Then the precipitate was filtered and washed with water several times. The collected solid was dried in air to afford the product as a brown solid 6.08 g in >99% yield. $^1$H NMR (DMSO-d$_6$, 400 MHz): δ 6.84 (dd, J=8.4, 2.0 Hz, 1H), 6.98 (s, 1H), 7.03 (d, J=8.0 Hz, 1H), 7.28-7.32 (m, 2H), 7.36 (t, J=8.0 Hz, 1H), 7.60 (d, J=4.0 Hz, 1H), 7.75 (bs, 1H), 8.67 (bs, 1H), 9.94 (s, 1H).

Synthesis of 3-(1H-indazol-1-yl)phenol A-OH-12

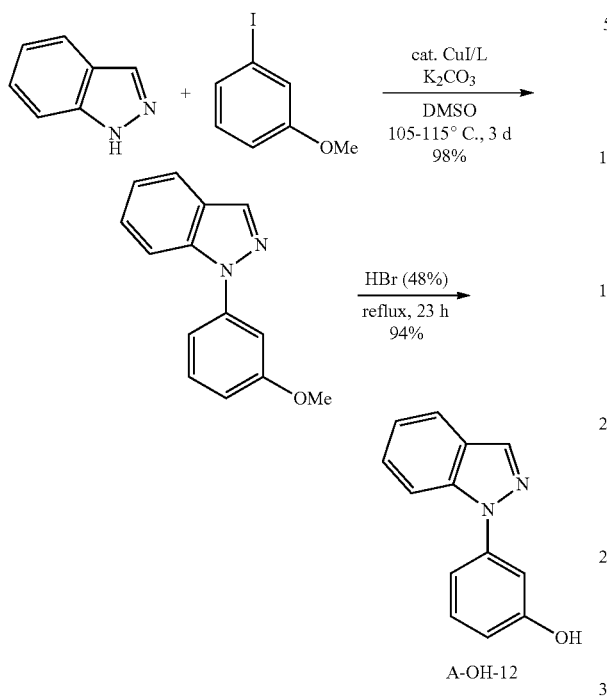

A-OH-12

Synthesis of 1-(3-methoxyphenyl)-1H-indazole: To a dry pressure tube equipped with a magnetic stir bar was added 1H-indazole (3.54 g, 30 mmol, 1.0 eq), 1-iodo-3-methoxybenzene (8.07 g, 36 mmol, 1.2 eq), CuI (0.29 g, 1.5 mmol, 0.05 eq), $K_2CO_3$ (13.37 g, 63 mmol, 2.1 eq) and trans-1,2-cyclohexanediamine (0.65 g, 6 mmol, 0.2 eq). Then the tube was taken into a glove box and solvent toluene (40 mL) was added. The mixture was sparged with nitrogen for 5 minutes and then the tube was sealed. The tube was taken out of the glove box and the mixture was stirred in an oil bath at 105-115° C. for 3 days. Then the mixture was cooled to ambient temperature, diluted with ethyl acetate, filtered, and washed with ethyl acetate. The filtrate was concentrated and the residue was purified through column chromatography on silica gel using hexane and ethyl acetate (20:1-10:1) as eluent to obtain the desired product as a colorless liquid 6.62 g in 98% yield. $^1$H NMR (DMSO-$d_6$, 400 MHz): δ 3.85 (s, 3H), 6.98 (dd, J=8.0, 2.0 Hz, 1H), 7.25-7.30 (m, 2H), 7.35 (dd, J =8.0, 1.6 Hz, 1H), 7.49 (t, J=8.0 Hz, 2H), 7.86 (d, J=8.4 Hz, 1H), 7.89 (d, J=7.6 Hz, 1H), 8.37 (s, 1H). $^{13}$C NMR (DMSO-$d_6$, 100 MHz): δ 55.40, 107.75, 110.59, 112.42, 114.12, 121.49, 121.70, 125.10, 127.55, 130.48, 135.69, 138.13, 140.83, 160.13.

Synthesis of 3-(1H-indazol-1-yl)phenol A-OH-12: A solution of 1-(3-methoxyphenyl)-1H-indazole (6.50 g, 28.98 mmol) in hydrobromic acid (45 mL, 48%) was refluxed 110-120° C. for 23 hours under nitrogen. Then the mixture was cooled to ambient temperature and neutralized with an aqueous solution of $K_2CO_3$ until there was no further gas evolution. Then the precipitate was filtered and washed with water several times. The collected solid was dried in air to afford the product as a brown solid 5.70 g in 94% yield. $^1$H NMR (DMSO-$d_6$, 400 MHz): δ 6.63 (dd, J=8.4, 2.0 Hz, 1H), 7.00-7.03 (m, 2H), 7.08 (t, J=7.6 Hz, 1H), 7.20 (t, J=7.6 Hz, 1H), 7.31 (d, J=7.6 Hz, 1H), 7.65 (d, J=7.2 Hz, 1H), 7.70 (d, J=8.0 Hz, 1H), 8.17 (s, 1H), 9.67 (bs, 1H). $^{13}$C NMR (DMSO-$d_6$, 100 MHz): δ 109.08, 110.54, 112.45, 113.63, 121.48, 121.61, 125.05, 127.42, 130.41, 135.48, 138.02, 140.72, 158.35.

Synthesis of 3-(5-phenyl-1H-indazol-1-yl)phenol A-OH-12Ph

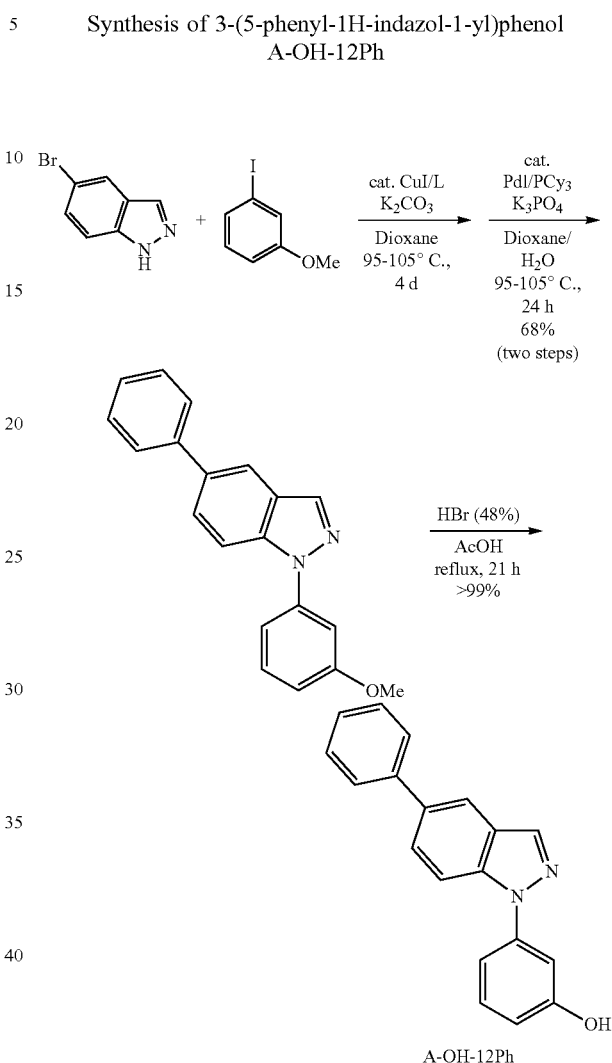

A-OH-12Ph

Synthesis of 1-(3-methoxyphenyl)-5-phenyl-1H-indazole: To a dry pressure tube equipped with a magnetic stir bar was added 5-bromo-1H-indazole (2.50 g, 12.69 mmol, 1.0 eq), CuI (48 mg, 1.5 mmol, 0.25 eq), $K_2CO_3$ (3.68 g, 26.65 mmol, 2.1 eq) and trans-1,2-cyclohexanediamine (140 mg, 1.23 mmol, 0.2 eq). The vessel was evacuated and back filled with nitrogen. This evacuation and backfill procedure was repeated for three cycles. Then 1-iodo-3-methoxybenzene (3.56 g, 15.23 mmol, 1.2 eq) and dioxane (25 mL) were added. The mixture was stirred in an oil bath at 95-105° C. for 3 days. Then the mixture was cooled to ambient temperature, diluted with ethyl acetate, filtered, and washed with ethyl acetate. The filtrate was concentrated and the residue was purified through column chromatography on silica gel using hexane and ethyl acetate (20:1-10:1) as eluent to obtain the desired product as a colorless sticky liquid 2.76 g which was used directly in the next step. The colorless sticky liquid (2.70 g, 8.91 mmol, 1.0 eq), phenylboronic acid (1.41 g, 11.58 mmol, 1.3 eq), $Pd_2(dba)_3$ (0.33 g, 0.36 mmol, 0.04 eq), $PCy_3$ (0.24 g, 0.86 mmol, 0.096 eq) and $K_3PO_4$ (3.21 g, 15.15 mmol, 1.7 eq) were added to a dry three-necked flask equipped with a magnetic stir bar and a condenser. Then the flask was evacuated and backfilled with nitrogen. The evacuation and backfill procedure was repeated for another two cycles. Then dioxane (60 mL) and H$_2$O (27 mL) were added under a nitrogen atmosphere. The flask was then placed into an oil bath and stirred at 95-105° C. for 24 hours. Then the mixture was cooled to ambient temperature, filtered, and washed with ethyl acetate. The organic layer was separated and the aqueous layer was extracted with ethyl acetate. The combined organic layers were washed with water and then dried over sodium sulfate, filtered, and washed with ethyl acetate. The filtrate was concentrated and the residue was purified through column chromatography on silica gel using hexane and ethyl acetate (20:1-10:1)) as eluent to obtain the desired product 1-(3-methoxyphenyl)-5-phenyl-1H-indazole as a brown grey solid 2.56 g in 68% total yield for the two steps. $^1$H NMR (DMSO-d$_6$, 400 MHz): δ 3.87 (s, 3H), 7.00 (dd, J=8.0, 2.0 Hz, 1H), 7.33-7.34 (m, 1H), 7.39 (d, J=8.4 Hz, 2H), 7.46-7.54 (m, 3H), 7.74 (d, J=7.6 Hz, 2H), 7.81-7.83 (m, 1H), 7.96 (d, J=8.4 Hz, 1H), 8.16 (s, 1H), 8.43 (s, 1H).

Synthesis of 3-(5-phenyl-1H-indazol-1-yl)phenol A-OH-12Ph: A mixture of 1-(3-methoxyphenyl)-5-phenyl-1H-indazole (2.53 g, 8.42 mmol) and hydrobromic acid (20 mL, 48%) in acetic acid (30 mL) was refluxed at 110-120° C. for 21 hours under nitrogen. Then the mixture was cooled to ambient temperature and the organic solvent was removed under reduced pressure. The resulting residue was neutralized with an aqueous solution of K$_2$CO$_3$ until there was no further gas evolution. Then the precipitate was filtered and washed with water several times. The brown solid was dried in air under reduced pressure and product 3-(5-phenyl-1H-indazol-1-yl)phenol A-OH-1Ph 2.47 g was obtained in >99% yield. $^1$H NMR (DMSO-d$_6$, 400 MHz): δ 6.74-6.77 (m, 1H), 7.14-7.19 (m, 2H), 7.30-7.35 (m, 2H), 7.44 (t, J=8.0 Hz, 2H), 7.69 (d, J=8.0 Hz, 2H), 7.76 (dd, J=8.8, 1.6 Hz, 1H), 8.85 (d, J=8.8 Hz, 1H), 8.09 (s, 1H), 8.34 (s, 1H), 9.82 (bs, 1H).

Synthesis of 1-(3-bromo-phenyl)-1H-benzo[d]imidazole A-Br-5

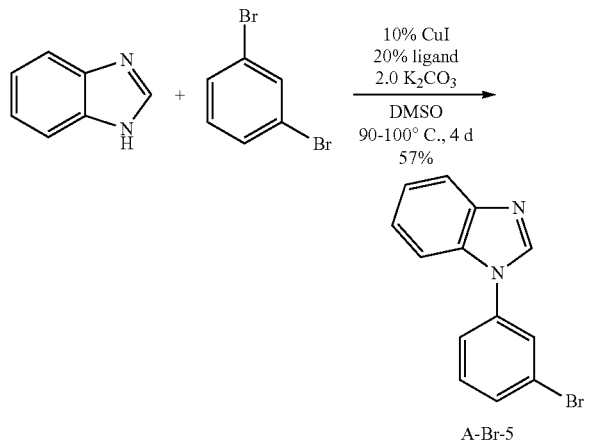

A-Br-5

A mixture of 1,3-dibromobenzene (4.83 mL, 40.0 mmol, 2.0 eq), 1H-benzo[d]imidazole (2.36 g, 20.0 mmol, 1.0 eq), CuI (0.38 g, 2.0 mmol, 0.10 eq), K$_2$CO$_3$ (5.53 g, 40.0 mmol, 2.0 eq) and L-proline (0.46 g, 4.0 mmol, 0.20 eq) in DMSO (20 mL) was stirred at a temperature of 90-100° C. for 4 days under a nitrogen atmosphere. The mixture was then cooled to ambient temperature, diluted with ethyl acetate, filtered, and the resulting solid was washed with ethyl acetate. The filtrate was washed with water three times, dried over sodium sulfate, filtered, and concentrated under reduced pressure. The residue was purified through column chromatography on silica gel using hexane first, then hexane/ethyl acetate (10:1-5:1-3:1) as eluent to obtain the desired product 1-(3-bromophenyl)-1H-benzo[d]imidazole A-Br-5 as a brown solid 3.13 g in 57% yield. $^1$H NMR (DMSO-d$_6$, 400 MHz): δ 7.31-7.38 (m, 2H), 7.60 (t, J=8.4 Hz, 1H), 7.64 (dd, J=6.8, 2.0 Hz, 1H), 7.70-7.80 (m, 3H), 7.96 (t, J=2.0 Hz, 1H), 8.61 (s, 1H).

Synthesis of 1-(3-bromo-5-tert-butylphenyl)-1H-benzo[d]imidazole A-Br-5-tBu

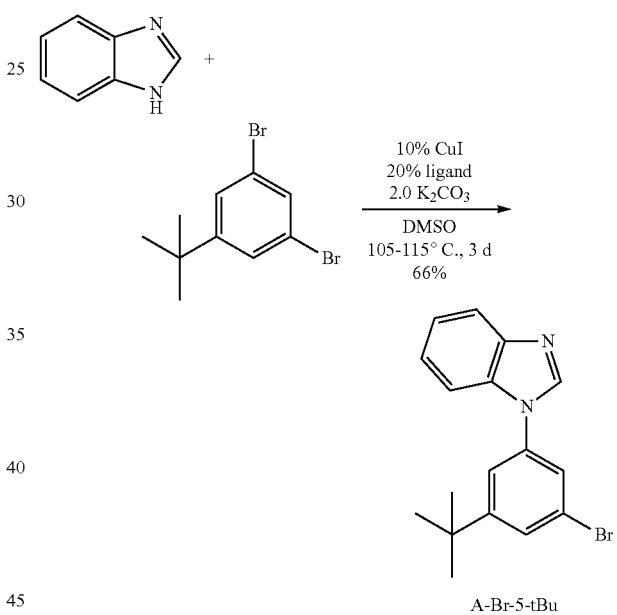

A-Br-5-tBu

A mixture of 1,3-dibromo-5-tert-butylbenzene (8.76 g, 30.0 mmol, 2.0 eq), 1H-benzo[d]imidazole (1.77 g, 15.0 mmol, 1.0 eq), CuI (0.29 g, 1.5 mmol, 0.10 eq), K$_2$CO$_3$ (4.15 g, 30.0 mmol, 2.0 eq) and 2-(dimethylamino)acetic acid (0.31 g, 3.0 mmol, 0.20 eq) in DMSO (30 mL) was stirred at a temperature of 105-115° C. for three days under nitrogen, then cooled to ambient temperature. The mixture was diluted with ethyl acetate, filtered, and the solid was washed with ethyl acetate. The filtrate was washed with water three times, dried over sodium sulfate, filtered, and concentrated under reduced pressure. The residue was purified through column chromatography on silica gel using hexane first, then hexane/ethyl acetate (10:1-3:1) as eluent to obtain the desired product 1-(3-bromo-5-tert-butylphenyl)-1H-benzo[d]imidazole A-Br-5-tBu as a brown sticky liquid 3.26 g in 66% yield. $^1$H NMR (DMSO-d$_6$, 400 MHz): δ 1.35 (s, 9H), 7.32-7.39 (m, 2H), 7.61 (d, J=8.0 Hz, 1H), 7.685-7.689 (m, 2H), 7.77 (t, J=1.6 Hz, 1H), 7.80 (d, J=7.2 Hz, 1H), 8.61 (s, 1H).

Synthesis of 1-(3-bromophenyl)-1H-imidazole A-Br-7

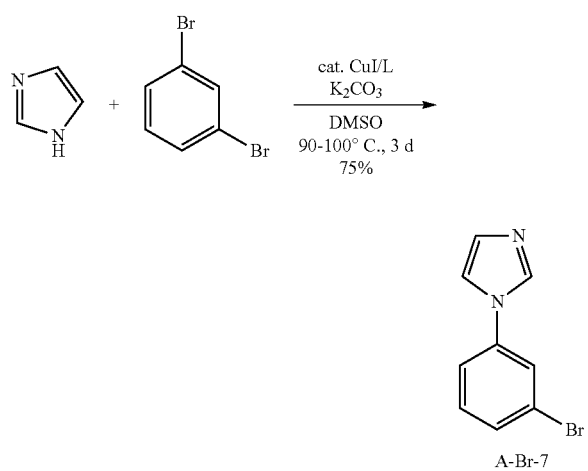

A mixture of 1,3-dibromobenzene (7.25 mL, 60.0 mmol, 2.0 eq), 1H-imidazole (2.04 g, 30.0 mmol, 1.0 eq), CuI (0.57 g, 3.0 mmol, 0.10 eq), K$_2$CO$_3$ (48.29 g, 60.0 mmol, 2.0 eq) and L-proline (0.69 g, 6.0 mmol, 0.20 eq) in DMSO (30 mL) was stirred at a temperature of 90-100° C. for three days under a nitrogen atmosphere, then cooled to ambient temperature. The mixture was diluted with ethyl acetate, filtered, and the solid was washed with ethyl acetate. The filtrate was washed with water three times, dried over sodium sulfate, filtered, and concentrated under reduced pressure. The residue was purified through column chromatography on silica gel using hexane first, then dichloromethane/methanol (20:1-10:1) as eluent to obtain the desired product 1-(3-bromophenyl)-1H-imidazole A-Br-7 as a brown-red liquid 5.00 g in 75% yield. $^1$H NMR (DMSO-d$_6$, 400 MHz): δ 7.15 (bs, 1H), 7.47 (t, J=8.0 Hz, 1H), 7.56 (dd, J=7.2, 0.8 Hz, 1H), 7.71 (dd, J=7.6, 1.2 Hz, 1H), 7.86 (bs, 1H), 7.97 (t, J=2.0 Hz, 1H), 8.37 (bs, 1H).

Synthesis of 1-(3-bromo-5-tert-butylphenyl)-4-phenyl-1H-imidazole A-Br-7-ptb

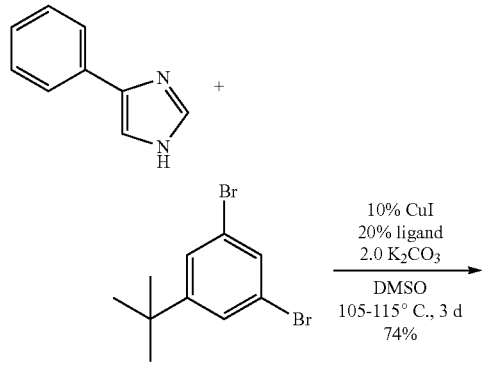

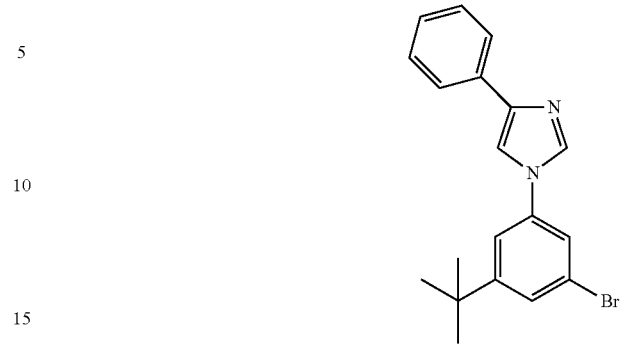

A mixture of 1,3-dibromo-5-tert-butylbenzene (8.76 g, 30.0 mmol, 2.0 eq), 4-phenyl-1H-imidazole (2.16 g, 15.0 mmol, 1.0 eq), CuI (0.29 g, 1.5 mmol, 0.10 eq), K$_2$CO$_3$ (4.15 g, 30.0 mmol, 2.0 eq) and 2-(dimethylamino)acetic acid (0.31 g, 3.0 mmol, 0.20 eq) in DMSO (30 mL) was stirred at a temperature of 105-115° C. for three days under a nitrogen atmosphere, then cooled to ambient temperature. The mixture was diluted with ethyl acetate, filtered, and the solid was washed with ethyl acetate. The filtrate was washed with water three times, dried over sodium sulfate, filtered, and concentrated under reduced pressure. The residue was purified through column chromatography on silica gel using hexane first, then hexane/ethyl acetate (10:1-5:1-3:1) as eluent to obtain the desired product 1-(3-bromo-5-tert-butylphenyl)-4-phenyl-1H-imidazole A-Br-7-ptb as a white solid 3.96 g in 74% yield. $^1$H NMR (DMSO-d$_6$, 400 MHz): δ 1.36 (s, 9H), 7.25-7.28 (m, 1H), 7.40-7.43 (m, 2H), 7.54 (s, 1H), 7.73 (s, 1H), 7.84-7.90 (m, 3H), 8.42 (s, 1H), 8.46 (s, 1H).

Synthesis of 1-(3-bromo-5-tert-butylphenyl)-4-biphenyl-1H-imidazole A-Br-7a-tBu

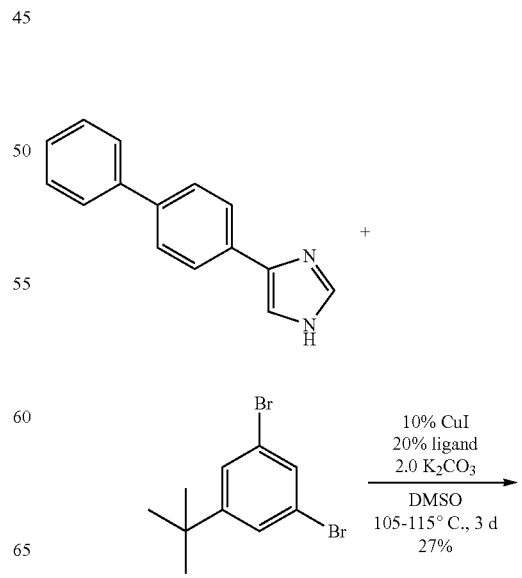

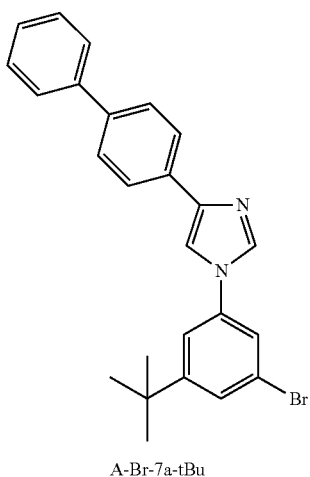

A-Br-7a-tBu

A mixture of 1,3-dibromo-5-tert-butylbenzene (8.00 g, 27.4 mmol, 1.6 eq), 4-biphenyl-1H-imidazole (3.78 g, 17.13 mmol, 1.0 eq), CuI (0.33 g, 1.7 mmol, 0.10 eq), K$_2$CO$_3$ (4.74 g, 34.3 mmol, 2.0 eq) and L-proline (0.39 g, 3.4 mmol, 0.20 eq) in DMSO (35 mL) was stirred at a temperature of 105-115° C. for three days under a nitrogen atmosphere, then cooled to ambient temperature. The mixture was diluted with ethyl acetate, filtered, and the solid was washed with ethyl acetate. The filtrate was washed with water three times, dried over sodium sulfate, filtered, and concentrated under reduced pressure. The residue was purified through column chromatography on silica gel using hexane first, then hexane/ethyl acetate (10:1-5:1-3:1) as eluent to obtain the desired product 1-(3-bromo-5-tert-butylphenyl)-4-biphenyl-1H-imidazole A-Br-7a-tBu as a brown-red solid 2.02 g in 27% yield. $^1$H NMR (DMSO-d$_6$, 400 MHz): δ 1.37 (s, 9H), 7.38 (t, J=7.2 Hz, 1H), 7.49 (t, J=7.6 Hz, 2H), 7.55 (d, J=1.6 Hz, 1H), 7.73-7.76 (m, 5H), 7.89 (d, J=1.2 Hz, 1H), 7.99 (d, J=8.4 Hz, 2H), 8.49 (s, 2H).

Synthesis of 3-(isoquinolin-1-yl)phenol B-OH-10

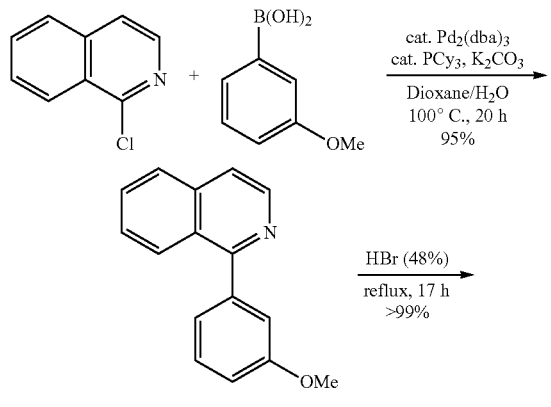

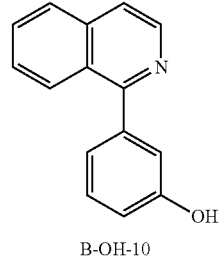

B-OH-10

Synthesis of 1-(3-methoxyphenyl)isoquinoline: 1-Chloroisoquinoline (4.91 g, 30 mmol, 1.0 eq), 3-methoxyphenyl boronic acid (5.47 g, 36 mmol, 1.2 eq), Pd$_2$(dba)$_3$ (0.28 g, 0.3 mmol, 0.01 eq), PCy$_3$ (0.20 g, 0.72 mmol, 0.024 eq) and K$_3$PO$_4$ (10.83 g, 51 mmol, 1.7 eq) were added to a dry 250 mL three-necked flask equipped with a magnetic stir bar and a condenser. Then the flask was evacuated and backfilled with nitrogen. The evacuation and backfill procedure was repeated for another two cycles. Then DME (80 mL) and H$_2$O (40 mL) were added under a nitrogen atmosphere. The flask was then placed into an oil bath and stirred at 100° C. for 20 hours. Then the mixture was cooled to ambient temperature and diluted with ethyl acetate. The organic layer was separated and the aqueous layer was extracted with ethyl acetate. The combined organic layers were washed with water, dried over sodium sulfate, filtered, and washed with ethyl acetate. The filtrate was concentrated and the residue was purified through column chromatography on silica gel using hexane and ethyl acetate (10:1-3:1)) as eluent to obtain the desired product 1-(3-methoxyphenyl) isoquinoline as a brown liquid 6.69 g in 95% yield. $^1$H NMR (DMSO-d$_6$, 400 MHz): δ 3.83 (s, 3H), 7.11 (dd, J=8.0, 2.4 Hz, 1H), 7.19-7.22 (m, 2H), 7.48 (t, J=8.0 Hz, 1H), 7.63-7.67 (m, 1H), 7.78-7.82 (m, 1H), 7.86 (d, J=6.4 Hz, 1H), 8.05 (t, J=7.6 Hz, 2H), 8.58 (d, J=6.0 Hz, 1H).

Synthesis of 3-(isoquinolin-1-yl)phenol B-OH-10: A solution of 1-(3-methoxyphenyl)isoquinoline (6.65 g, 28.26 mmol) in hydrobromic acid (45 mL, 48%) was refluxed at 110-120° C. for 17 hours under nitrogen. Then the mixture was cooled to ambient temperature and neutralized with an aqueous solution of K$_2$CO$_3$ until there was no gas evolution. Then the precipitate was filtered off and washed with water several times. The brown solid was dried in air under reduced pressure and product 3-(isoquinolin-1-yl)phenol B-OH-10 7.68 g was obtained in >99% yield. $^1$H NMR (DMSO-d$_6$, 400 MHz): δ 7.12 (dd, J=8.4, 2.8 Hz, 1H), 7.18-7.21 (m, 2H), 7.50 (t, J=8.0 Hz, 1H), 7.90-7.94 (m, 1H), 8.13 (t, J=7.6 Hz, 1H), 8.19 (d, J=8.8 Hz, 1H), 8.33 (d, J=8.4 Hz, 1H), 8.36 (d, J=6.4 Hz, 1H), 8.64 (d, J=6.4 Hz, 1H), 10.02 (bs, 1H).

Synthesis of N-(3-(3,5-dimethyl-1H-pyrazol-1-yl) phenyl)benzenamine A-NH-1DM

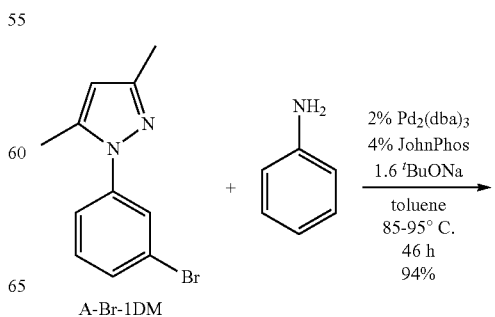

A-Br-1DM

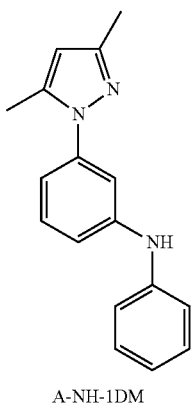

A-NH-1DM

To a Schlenck tube equipped with a magnetic stir bar and a condenser was added 1-(3-bromophenyl)-3,5-dimethyl-1H-pyrazole A-Br-1DM (1507 mg, 6.0 mmol, 1.0 eq), 'BuONa (923 mg, 9.6 mmol, 1.6 eq), Pd$_2$(dba)$_3$ (110 mg, 0.12 mmol, 0.02 eq), JohnPhos (72 mg, 0.24 mmol, 0.04 eq), and toluene (24 mL) under nitrogen. The mixture was stirred in an oil bath at a temperature of 85-95° C. for 46 hours then cooled down to ambient temperature. The solvent was removed and the residue was purified through column chromatography on silica gel using hexane/ethyl acetate (3:1) as eluent to obtain the desired product N-(3-(3,5-dimethyl-1H-pyrazol-1-yl)phenyl)benzenamine A-NH-1DM as a brown liquid 1.48 g in 94% yield. $^1$H NMR (DMSO-d$_6$, 400 MHz): δ 2.16 (s, 3H), 2.30 (s, 3H), 6.04 (s, 1H), 6.87-6.90 (m, 2H), 7.04 (dd, J=7.6, 2.0 Hz, 1H), 7.11-7.13 (m, 3H), 7.25-7.32 (m, 3H), 8.36 (s, 1H).

Synthesis of 3-(pyridin-2-yloxy)phenol C-OH-3

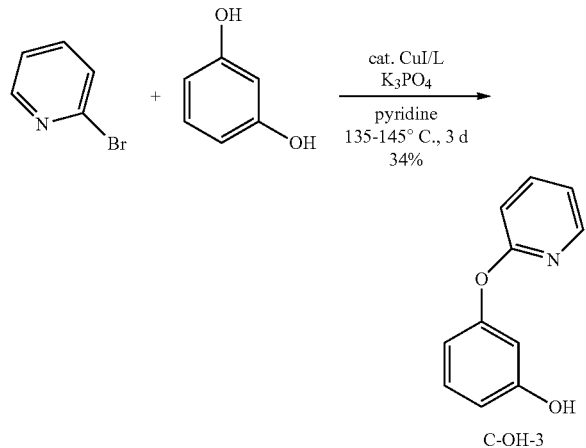

C-OH-3

To a dry pressure tube equipped with a magnetic stir bar was added resorcinol (13.2 g, 120 mmol, 1.2 eq), 2-bromopyridine (9.8 mL, 100 mmol, 1.0 eq), CuI (1.9 g, 10 mmol, 0.1 eq), K$_2$CO$_3$ (27.6 g, 200 mmol, 2.0 eq), pyridine (100 mL), and 1-methyl-1H-imidazole (2.5 mL, 50 mmol, 0.5 eq) under nitrogen. The mixture was sparged with nitrogen for 30 minutes and then the tube was sealed. The mixture was stirred in an oil bath at 135-145° C. for 3 days. Then the mixture was cooled to ambient temperature, filtered, and washed with a mixture of toluene and ethyl acetate (200 mL, 1:1). The filtrate was concentrated under reduced pressure, then diluted with water (150 mL). The organic layer was separated and the aqueous layer was extracted with ethyl acetate three times. The combined organic layers were washed with water three times, dried over sodium sulfate, filtered, and concentrated under reduced pressure. The resulting residue was purified through column chromatography on silica gel using hexane and ethyl acetate (1:1) as eluent to obtain the desired product which was further purified by recrystallization in ethyl acetate to afford the pure product 6.40 g in 34% yield. $^1$H NMR (DMSO-d$_6$, 400 MHz): δ 6.48 (t, J=2.0 Hz, 1H), 6.52 (dd, J=8.0, 2.4 Hz, 1H), 6.61 (dd, J=8.0, 2.4 Hz, 1H), 6.99 (d, J=8.0 Hz, 1H), 7.14 (dd, J=6.8, 4.8 Hz, 1H), 7.19 (t, J=8.0 Hz, 1H), 7.82-7.87 (m, 1H), 8.19 (bs, 1H), 9.60 (s, 1H).

Synthesis of 2-bromo-9-(4-tert-butylpyridin-2-yl)-9H-carbazole I-Br-1-tBu

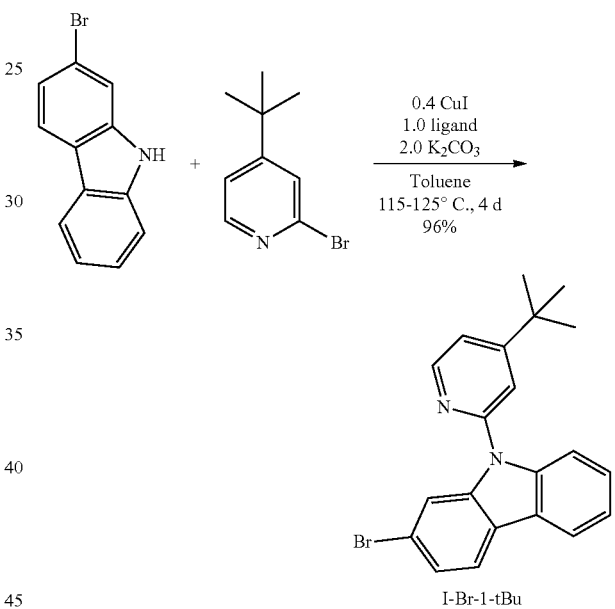

I-Br-1-tBu

To a pressure vessel equipped with a magnetic stir bar was added 2-bromo-9H-carbazole (2461 mg, 10.0 mmol, 1.0 eq), CuI (762 mg, 4.0 mmol, 0.4 eq), and K$_2$CO$_3$ (2764 mg, 20.0 mmol, 2.0 eq). Then the vessel was evacuated and backfilled with nitrogen. The evacuation and back fill procedure was repeated for another two cycles. Then toluene (60 mL), 1-methyl-1H-imidazole (792 uL, 10.0 mmol, 1.0 eq) and 2-bromo-4-tert-butylpyridine (5353 mg, 25.0 mmol, 2.5 eq) were added under nitrogen. The mixture was stirred in an oil bath at a temperature of 115-125° C. for 4 days. Then the mixture was cooled to ambient temperature. The solvent was removed under reduced pressure and the residue was purified through column chromatography on silica gel using dichloromethane as eluent to obtain the desired product 2-bromo-9-(4-tert-butylpyridin-2-yl)-9H-carbazole as a colorless sticky liquid 3635 mg in 96% yield. $^1$H NMR (DMSO-d$_6$, 400 MHz): δ 1.39 (s, 9H), 7.36 (t, J=8.0 Hz, 1H), 7.48-7.55 (m, 3H), 7.71-7.73 (m, 2H), 7.94 (d, J=2.0 Hz, 1H), 8.23 (d, J=8.0 Hz, 1H), 8.28 (d, J=8.0 Hz, 1H), 8.66 (d, J=5.5 Hz, 1H).

Synthesis of 2-(pyridin-2-yl)-9H-carbazole E-NH-3

Synthesis of 2-(4-phenylpyridin-2-yl)-9H-carbazole E-NH-3Ph

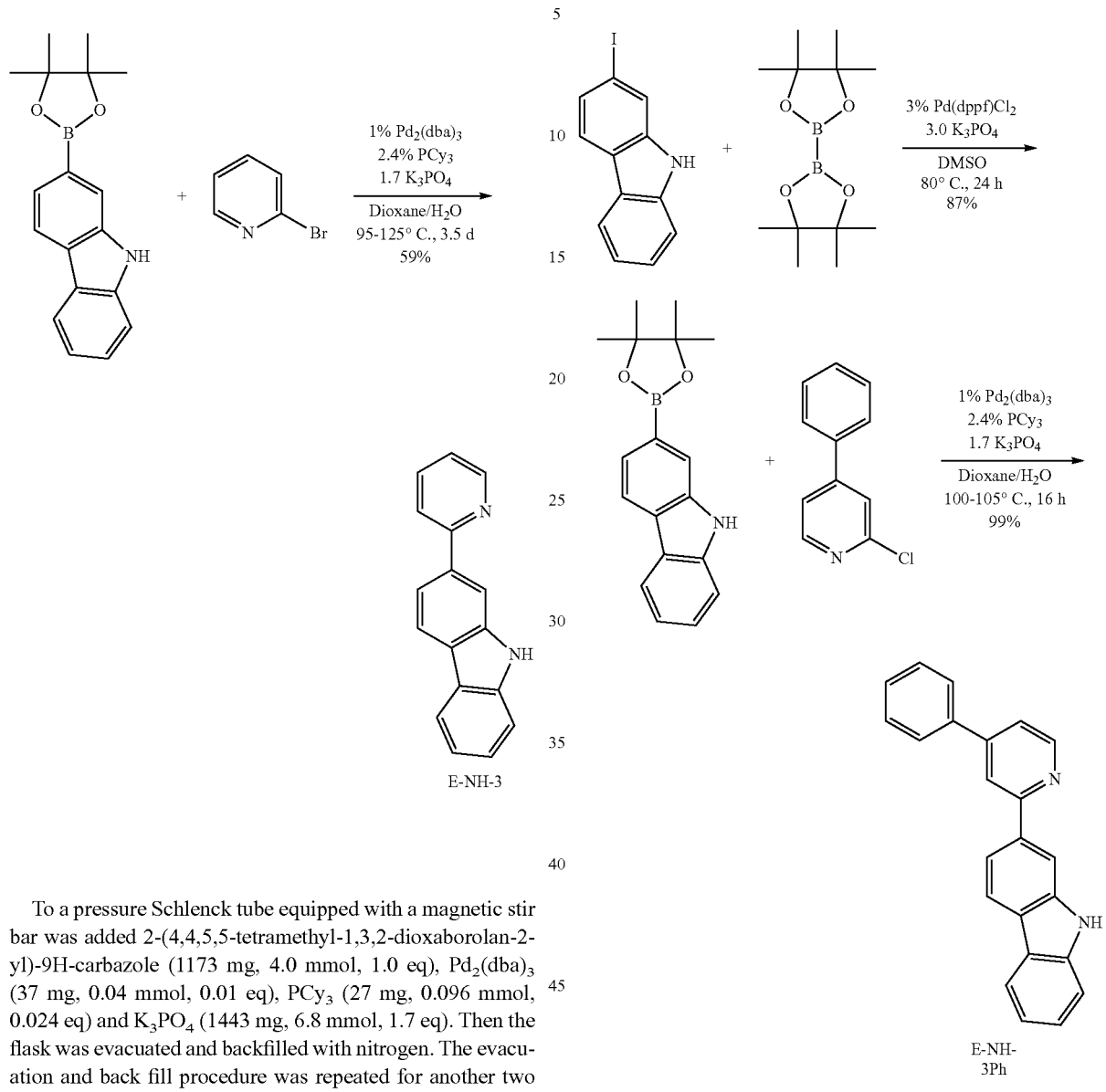

To a pressure Schlenck tube equipped with a magnetic stir bar was added 2-(4,4,5,5-tetramethyl-1,3,2-dioxaborolan-2-yl)-9H-carbazole (1173 mg, 4.0 mmol, 1.0 eq), Pd$_2$(dba)$_3$ (37 mg, 0.04 mmol, 0.01 eq), PCy$_3$ (27 mg, 0.096 mmol, 0.024 eq) and K$_3$PO$_4$ (1443 mg, 6.8 mmol, 1.7 eq). Then the flask was evacuated and backfilled with nitrogen. The evacuation and back fill procedure was repeated for another two cycles. Then dioxane (10.7 mL), water (5.3 mL) and 2-bromopyridine (400 mg, 2.11 mmol, 1.0 eq) were added under nitrogen. The mixture was stirred in an oil bath at a temperature of 95-125° C. for 3.5 days. Then the mixture was cooled to ambient temperature, filtered, and washed with ethyl acetate. The organic layer was separated and dried over sodium sulfate, filtered, and concentrated under reduced pressure. the resulting residue was purified through column chromatography on silica gel using hexane and ethyl acetate (3:1-1:1) as eluent to obtain the desired product 2-(pyridin-2-yl)-9H-carbazole E-NH-3 as a solid 580 mg in 59% yield. $^1$H NMR (DMSO-d$_6$, 400 MHz): δ 7.19 (t, J=7.6 Hz, 1H), 7.36 (dd, J=7.6, 4.8 Hz, 1H), 7.40-7.44 (m, 1H), 7.53 (d, J=8.0 Hz, 1H), 7.89-7.93 (m, 2H), 8.07 (d, J=8.0 Hz, 1H), 8.16 (d, J=8.0 Hz, 1H), 8.21 (d, J=8.4 Hz, 1H), 8.24 (s, 1H), 8.70-8.71 (m, 1H), 11.38 (s, 1H).

Synthesis of 2-(4,4,5,5-tetramethyl-1,3,2-dioxaborolan-2-yl)-9H-carbazole: To a three-necked flask equipped with a magnetic stir bar was added 2-iodo-9H-carbazole (2.93 g, 10.0 mmol, 1.0 eq), 4,4,5,5-tetramethyl-2-(4,4,5,5-tetramethyl-1,3,2-dioxaborolan-2-yl)-1,3,2-dioxaborolane (2.57 g, 11.0 mmol, 1.1 eq), Pd(dppf) Cl$_2$.CH$_2$Cl$_2$ (0.25 g, 0.3 mmol, 0.03 eq) and KOAc (2.94 g, 30.0 mmol, 3.0 eq). Then the flask was evacuated and backfilled with nitrogen. The evacuation and back fill procedure was repeated for three cycles. Then DMSO (40 mL) was added under nitrogen. The mixture was stirred in an oil bath at a temperature of 80° C. for 24 hours. Then the mixture was cooled to ambient temperature and quenched with water, diluted with ethyl acetate, filtered, and washed with ethyl acetate. The organic layer of the filtrate was separated and the aqueous layer was extracted with ethyl acetate three times. The combined organic layers were then washed with water three times, washed with brine three times, dried over sodium sulfate, filtered, and concentrated under reduced pressure. the resulting residue was purified through column chromatography on silica gel using hexane and ethyl acetate (5:1-3:1) as eluent to obtain the desired product 2-(4,4,5,5-tetramethyl-1,3,2-dioxaborolan-2-yl)-9H-carbazole as a white solid 2.54 g in 87% yield. $^1$H NMR (CDCl$_3$, 400 MHz): δ 1.39 (s, 12H), 7.22-7.26 (m, 1H), 7.41-7.47 (m, 2H), 7.69 (d, J=8.0 Hz, 1H), 7.92 (d, J=0.4 Hz, 1H), 8.05 (bs, 1H), 8.08-8.82 (m, 2H).

Synthesis of 2-(4-phenylpyridin-2-yl)-9H-carbazole E-NH-3Ph: To a three-necked flask equipped with a magnetic stir bar was added 2-(4,4,5,5-tetramethyl-1,3,2-dioxaborolan-2-yl)-9H-carbazole (682 mg, 2.32 mmol, 1.1 eq), 2-chloro-4-phenylpyridine (400 mg, 2.11 mmol, 1.0 eq), Pd$_2$(dba)$_3$ (21 mg, 0.023 mmol, 0.01 eq), PCy$_3$ (14 mg, 0.051 mmol, 0.024 eq) and K$_3$PO$_4$ (761 mg, 3.59 mmol, 1.7 eq). Then the flask was evacuated and backfilled with nitrogen. The evacuation and back fill procedure was repeated for another two cycles. Then dioxane (8 mL) and water (3.8 mL) were added under nitrogen. The mixture was stirred in an oil bath at a temperature of 100-105° C. for 16 hours. Then the mixture was cooled to ambient temperature and diluted with ethyl acetate. The organic layer was separated and dried over sodium sulfate, filtered, and concentrated under reduced pressure. The resulting residue was purified through column chromatography on silica gel using hexane and ethyl acetate (5:1-3:1-2:1) as eluent to obtain the desired product 2-(4-phenylpyridin-2-yl)-9H-carbazole as a brown solid 675 mg in 99% yield. $^1$H NMR (DMSO-d$_6$, 400 MHz): δ 7.20 (t, J=7.6 Hz, 1H), 7.41-7.45 (m, 1H), 7.51-7.61 (m, 4H), 7.68 (dd, J=4.8, 1.2 Hz, 1H), 7.96-7.98 (m, 2H), 8.05 (dd, J=7.6, 1.6 Hz, 1H), 8.18 (d, J=7.6 Hz, 1H), 8.24 (d, J=8.0 Hz, 1H), 8.31 (s, 1H), 8.35 (d, J=0.4 Hz, 1H), 8.77 (d, J=5.2 Hz, 1H), 11.37 (s, 1H).

Synthesis of 2-(1H-imidazol-1-yl)-9H-carbazole E-NH-7

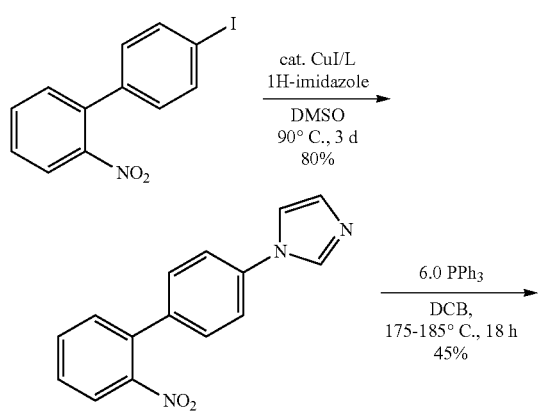

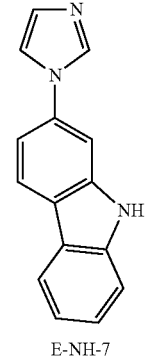

E-NH-7

Synthesis of 1-(2'-nitrobiphenyl-4-yl)-1H-imidazole: To a dry pressure tube equipped with a magnetic stir bar was added 4'-iodo-2-nitrobiphenyl 3 (8.13 g, 25 mmol, 1.0 eq), 1H-imidazole (1.77 g, 26 mmol, 1.05 eq) and K$_2$CO$_3$ (6.91 g, 50 mmol, 2.0 eq). Then the tube was taken into a glove box. CuI (0.48 g, 2.5 mmol, 0.1 eq), L-proline (0.58 g, 5 mmol, 0.2 eq) and solvent DMSO (25 mL) were then added. The mixture was sparged with nitrogen for 5 minutes and then the tube was sealed. The tube was taken out of the glove box and the mixture was stirred in an oil bath at a temperature of 90° C. for three days. Then the mixture was cooled to ambient temperature, diluted with ethyl acetate, filtered, and washed with ethyl acetate. The filtrate was concentrated under reduced pressure and the residue was purified through column chromatography on silica gel using dichloromethane and methanol (20:1) as eluent to obtain the desired product 1-(2'-nitrobiphenyl-4-yl)-1H-imidazole 9 as a off-white solid 5.3 g in 80% yield. $^1$H NMR (DMSO-d$_6$, 400 MHz): δ 7.14 (s, 1H), 7.47-7.50 (m, 2H), 7.60 (dd, J=7.6, 1.6 Hz, 1H), 7.65 (td, J=8.0, 1.6 Hz, 1H), 7.73-7.76 (m, 2H), 7.79 (td, J=7.6, 1.6 Hz, 1H), 7.82 (t, J=1.2 Hz, 1H), 8.01 (dd, J=7.6, 1.2 Hz, 1H), 8.35 (s, 1H).

Synthesis of 2-(1H-imidazol-1-yl)-9H-carbazole E-NH-7: To a three-necked flask equipped with a magnetic stir bar and a condenser was added 1-(2'-nitrobiphenyl-4-yl)-1H-imidazole 9 (5.00 g, 18.85 mmol, 1.0 eq) and PPh$_3$ (29.66 g, 113.09 mmol, 6.0 eq). The flask was evacuated and backfilled with nitrogen. The evacuation and backfill procedure was repeated for another two cycles. Then 1,2-dichlorobenzene (120 mL) was added under nitrogen. The mixture was stirred in an oil bath at a temperature of 175-185° C. for 18 hours then cooled to ambient temperature. The solvent was removed by distillation under high vacuum. The residue was purified through column chromatography on silica gel using dichloromethane and methanol (20:1) as eluent to obtain the desired product 2.00 g in 45% yield. $^1$H NMR (DMSO-d$_6$, 400 MHz): δ 7.08 (s, 1H), 7.12 (t, J=7.6 Hz, 1H), 7.31-7.35 (m, 2H), 7.46 (d, J=8.0 Hz, 1H), 7.61 (d, J=2.4 Hz, 1H), 7.73 (s, 1H), 8.07 (d, J=7.2 Hz, 1H), 8.15 (d, J=8.0 Hz, 1H), 8.24 (s, 1H), 11.42 (s, 1H). $^{13}$C NMR (DMSO-d$_6$, 100 MHz): δ 103.04, 111.15, 111.96, 118.70, 119.05, 120.31, 121.35, 121.37, 121.98, 125.80, 129.75, 134.83, 135.94, 140.11, 140.50.

Synthesis of 2-(quinolin-2-yl)-9H-carbazole E-NH-11

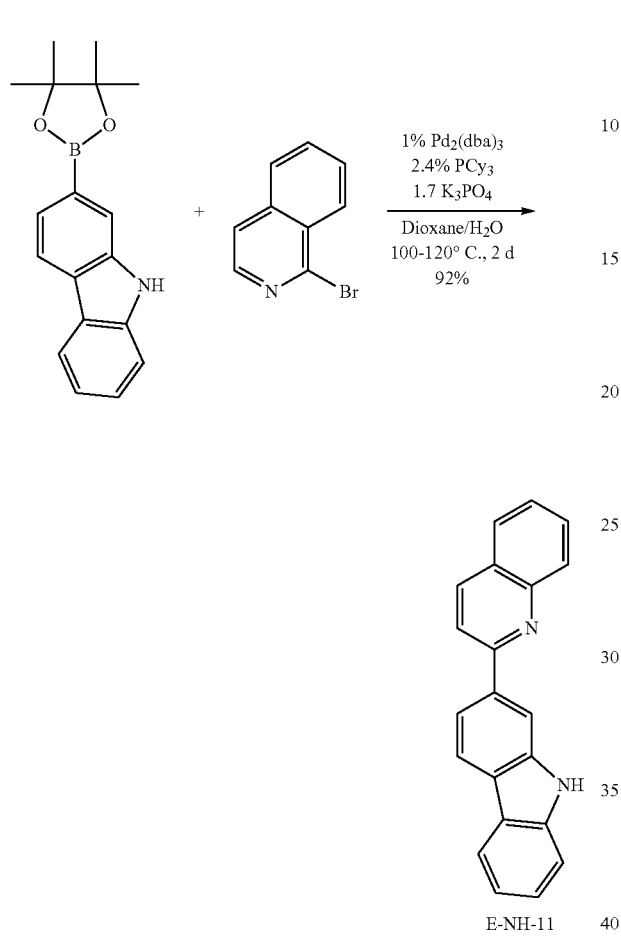

E-NH-11

Synthesis of 2-(1H-indazol-1-yl)-9H-carbazole E-NH-12

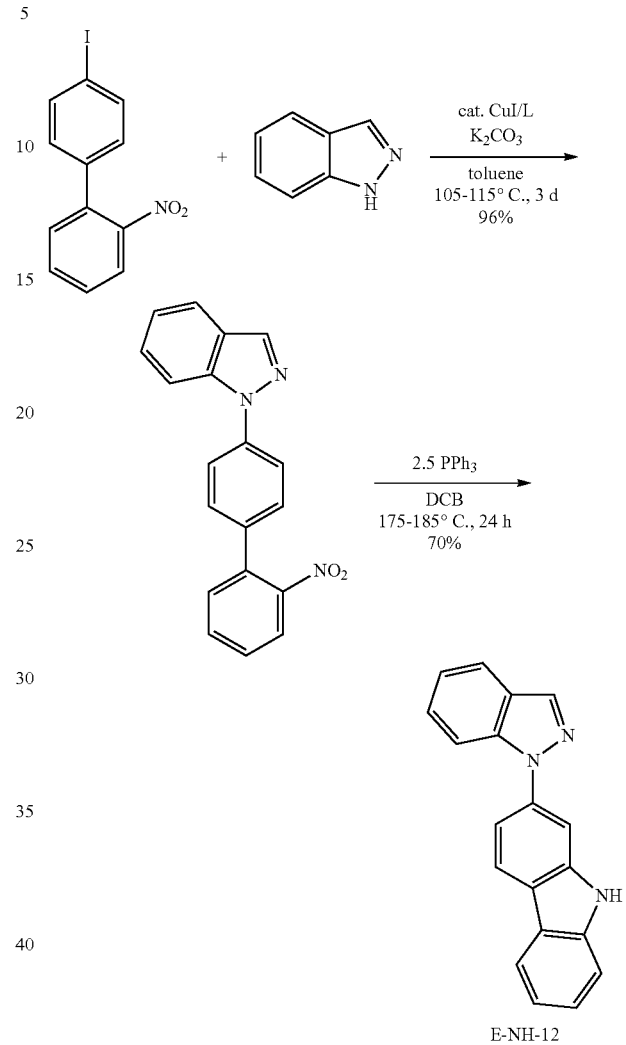

E-NH-12

To a three-necked flask equipped with a magnetic stir bar was added 2-(4,4,5,5-tetramethyl-1,3,2-dioxaborolan-2-yl)-9H-carbazole (147 mg, 0.50 mmol, 1.0 eq), 2-bromoquinoline (114 mg, 0.55 mmol, 1.1 eq), Pd$_2$(dba)$_3$ (4.6 mg, 0.005 mmol, 0.01 eq), PCy$_3$ (3.4 mg, 0.012 mmol, 0.024 eq) and K$_3$PO$_4$ (180 mg, 0.85 mmol, 1.7 eq). Then the flask was evacuated and backfilled with nitrogen. The evacuation and back fill procedure was repeated for another two cycles. Then dioxane (2 mL) and water (0.7 mL) were added under nitrogen. The mixture was stirred in an oil bath at a temperature of 100-120° C. for 2 days. Then the mixture was cooled to ambient temperature. The organic solvent was removed under reduced pressure and the precipitate was filtered off and washed with water. The collected solid was dried in air to obtain the desired product 2-(quinolin-2-yl)-9H-carbazole E-NH-11 as a brown solid 135 mg in 92% yield. $^1$H NMR (DMSO-d$_6$, 400 MHz): δ 7.18 (t, J=8.0 Hz, 1H), 7.40-7.44 (m, 1H), 7.53 (d, J=8.0 Hz, 1H), 7.57-7.60 (m, 1H), 7.78 (td, J=8.4, 1.2 Hz, 1H), 8.00 (d, J=7.6 Hz, 1H), 8.08-8.10 (m, 2H), 8.17 (d, J=7.2 Hz, 1H), 8.24-8.26 (m, 2H), 8.42 (s, 1H), 8.46 (d, J=8.8 Hz, 1H), 11.39 (s, 1H).

Synthesis of 1-(2'-nitrobiphenyl-4-yl)-1H-indazole: 1H-indazole (1.18 g, 10 mmol, 1.0 eq), 4'-iodo-2-nitrobiphenyl (3.90 g, 12 mmol, 1.2 eq), CuI (0.10 g, 0.5 mmol, 0.05 eq) and K$_3$PO$_4$ (4.49 g, 21 mmol, 2.1 eq) were added to a dry pressure tube equipped with a magnetic stir bar. The vessel was then evacuated and back-filled with nitrogen. This evacuation and back-fill procedure was repeated for another two cycles. Then trans-1,2-cyclohexanediamine (0.22 g, 2.0 mmol, 0.2 eq) and toluene (20 mL) were added under nitrogen. The mixture was stirred in an oil bath at a temperature of 105-115° C. for 3 days. Then the mixture was cooled to ambient temperature, filtered, and washed with ethyl acetate. The filtrate was concentrated and the resulting residue was purified through column chromatography on silica gel using hexane and ethyl acetate (10:1-5:1-3:1) as eluent to obtain the desired product 1-(2'-nitrobiphenyl-4-yl)-1H-indazole as a brown solid 3.05 g in 96% yield. $^1$H NMR (DMSO-d$_6$, 400 MHz): δ 7.29 (t, J=7.2 Hz, 1H), 7.50-7.57 (m, 3H), 7.64-7.68 (m, 2H), 7.80 (td, J=8.0, 1.2 Hz, 1H), 7.88-7.93 (m, 4H), 8.03 (d, J=8.0 Hz, 1H), 8.43 (s, 1H). $^{13}$C NMR (DMSO-d$_6$, 100 MHz): δ 110.58, 121.61, 121.89, 122.00, 124.25, 125.26, 127.71, 129.06, 129.17, 131.90, 133.08, 134.30, 134.84, 136.21, 138.02, 139.62, 148.83.

Synthesis of 2-(1H-indazol-1-yl)-9H-carbazole E-NH-12: To a three-necked flask equipped with a magnetic stir bar and a condenser was added 1-(2'-nitrobiphenyl-4-yl)-1H-indazole (2.90 g, 9.20 mmol, 1.0 eq) and PPh$_3$ (6.03 g, 23.00 mmol, 2.5 eq). The flask was evacuated and backfilled with nitrogen. The evacuation and backfill procedure was repeated for another two cycles. Then 1,2-dichlorobenzene (40 mL) was added under nitrogen. The mixture was stirred in an oil bath at a temperature of 175-185° C. for 24 hours, then cooled to ambient temperature. The solvent was removed by distillation under high vacuum. The residue was purified through column chromatography on silica gel using hexane/ethyl acetate (10:1-5:1-3:1) as eluent to obtain the desired product as a white solid 1.83 g in 70% yield. $^1$H NMR (DMSO-d$_6$, 400 MHz): δ 7.19 (t, J=7.2 Hz, 1H), 7.26 (t, J=7.6 Hz, 1H), 7.40 (t, J=7.6 Hz, 1H), 7.49 (t, J=8.0 Hz, 1H), 7.52-7.56 (m, 2H), 7.81 (d, J=1.6 Hz, 1H), 7.89 (d, J=8.8 Hz, 2H), 8.17 (d, J=8.0 Hz, 1H), 8.27 (d, J=8.4 Hz, 1H), 8.39 (s, 1H), 11.42 (s, 1H). $^{13}$C NMR (DMSO-d$_6$, 100 MHz): δ 104.92, 110.49, 111.10, 113.53, 119.00, 120.29, 121.03, 121.06, 121.46, 121.56, 122.08, 125.01, 125.74, 127.36, 135.36, 137.40, 138.36, 140.08, 140.44.

Synthesis of 2-(9H-carbazol-2-yl)benzo[d]oxazole E-NH-13

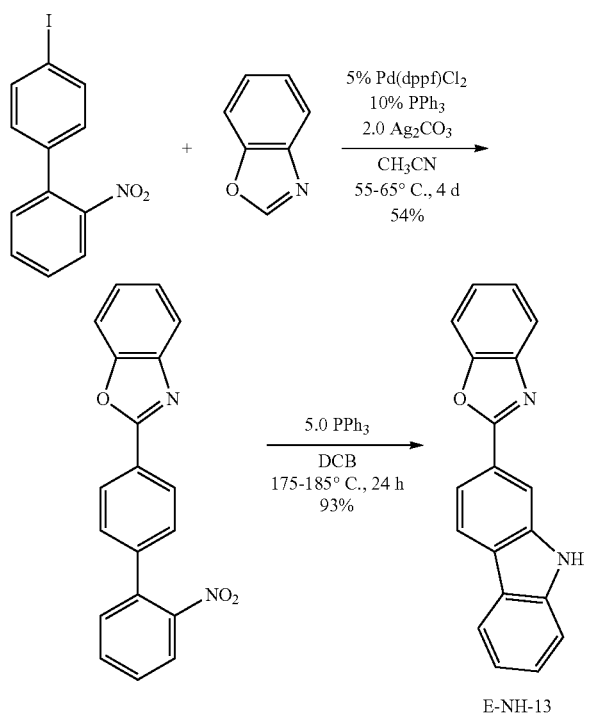

Synthesis of 2-(2'-nitrobiphenyl-4-yl)benzo[d]oxazole: To a three-necked flask equipped with a magnetic stir was added 4'-iodo-2-nitrobiphenyl (1.63 g, 5.0 mmol, 1.0 equiv), benzo[d]oxazole (0.72 g, 6.0 mmol, 1.2 equiv), Ag$_2$CO$_3$ (2.76 g, 10.0 mmol, 2.0 eq), Pd(dppf)Cl$_2$·CH$_2$Cl$_2$ (0.20 g, 0.25 mmol, 0.05 eq), and PPh$_3$ (0.13 g, 0.5 mmol, 0.1 eq). The tube was evacuated and back-filled with nitrogen. This evacuation and back-fill procedure was repeated for another two cycles. Then CH$_3$CN (25 mL) was added under nitrogen. The mixture was stirred in an oil bath at a temperature of 55-65° C. for 4 days and then cooled to ambient temperature. The solid was filtered through a pad of celite, washed with ethyl acetate, and concentrated under reduced pressure. the resulting residue was purified through column chromatography on silica gel using hexane and ethyl acetate (10:1-5:1) as eluent to afford the desired product 2-(2'-nitrobiphenyl-4-yl)benzo[d]oxazole 0.85 g in 54% yield. $^1$H NMR (DMSO-d$_6$, 400 MHz): δ 7.43-7.49 (m, 2H), 7.61-7.63 (m, 2H), 7.66 (d, J=7.6 Hz, 1H), 7.69-7.73 (m, 1H), 7.83-7.87 (m, 3H), 8.08 (d, J=8.8 Hz, 1H), 8.30 (dd, J=8.0, 1.2 Hz, 2H).

Synthesis of 2-(9H-carbazol-2-yl)benzo[d]oxazole E-NH-13: To a three-necked flask equipped with a magnetic stir bar and a condenser was added 2-(2'-nitrobiphenyl-4-yl)benzo[d]oxazole (1.08 g, 3.41 mmol, 1.0 eq) and PPh$_3$ (4.48 g, 17.07 mmol, 5.0 eq). The flask was evacuated and backfilled with nitrogen. The evacuation and backfill procedure was repeated for another two cycles. Then 1,2-dichlorobenzene (20 mL) was added under nitrogen. The mixture was stirred in an oil bath at a temperature of 175-185° C. for 24 hours, cooled, and the solvent was removed by distillation under high vacuum. Some ethyl acetate and dichloromethane was added to the residue and stirred at room temperature overnight, filtered, and washed with dichloromethane. The collected solid was dried in air to yield the desired product as an off-white solid 809 mg. The filtrate was concentrated and the residue was purified through column chromatography on silica gel using hexane and ethyl acetate (10:1-5:1-3:1) as eluent to obtain the desired product 117 mg, in 96% total yield. $^1$H NMR (DMSO-d$_6$, 400 MHz): δ 7.25 (t, J=7.6 Hz, 1H), 7.41-7.52 (m, 3H), 7.60 (d, J=8.4 Hz, 1H), 7.82-7.86 (m, 2H), 8.05 (dd, J=8.4, 1.2 Hz, 1H), 8.24 (d, J=7.2 Hz, 1H), 8.34-8.37 (m, 2H), 11.63 (s, 1H).

Synthesis of 2-(9H-carbazol-2-yl)benzo[d]thiazole E-NH-14

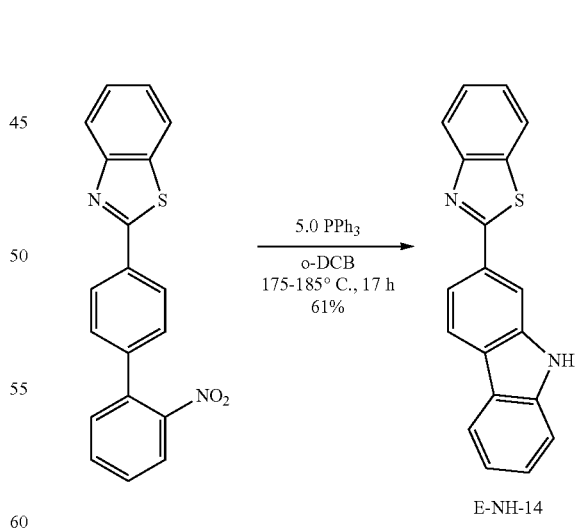

Synthesis of E-NH-14: To a three-necked flask equipped with a magnetic stir bar and a condenser was added 2-(2'-nitrobiphenyl-4-yl)benzo[d]thiazole (230 mg, 0.69 mmol, 1.0 eq) and PPh$_3$ (904 mg, 3.45 mmol, 5.0 eq). The flask was evacuated and backfilled with nitrogen. The evacuation and backfill procedure was repeated for another two cycles. Then 1,2-dichlorobenzene (20 mL) was added under nitrogen. The mixture was stirred in an oil bath at a temperature of 175-185° C. for 17 hours, then cooled. The solvent was removed by distillation under high vacuum. The residue was diluted with some ethyl acetate, filtered, and washed ethyl acetate. The filtrate was concentrated under reduced pressure and the resulting residue was purified through column chromatography on silica gel sequentially using hexane and ethyl acetate (10:1), then hexane/dichloromethane (1:1) as eluents to obtain the desired product as a brown solid 125 mg in 61% yield. $^1$H NMR (DMSO-d$_6$, 400 MHz): δ 7.24 (t, J=7.2 Hz, 1H), 7.46-7.50 (m, 2H), 7.56-7.59 (m, 2H), 7.92 (dd, J=8.4, 1.2 Hz, 1H), 8.10 (d, J=7.6 Hz, 1H), 8.18 (dd, J=7.6, 0.8 Hz, 1H), 8.22 (d, J=8.0 Hz, 1H), 8.24-8.25 (m, 1H), 8.31 (d, J=8.0 Hz, 1H), 11.54 (s, 1H).

Synthesis of 9,9-dimethyl-3-(1H-pyrazol-1-yl)-9,10-dihydroacridine G-NH-1

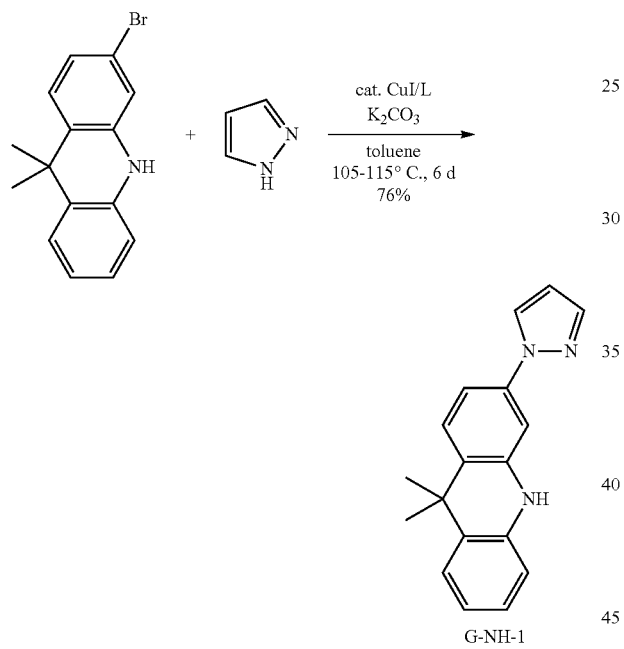

G-NH-1

Pyrazole (242 mg, 3.56 mmol, 1.2 eq), 3-bromo-9,9-dimethyl-9,10-dihydroacridine (948 mg, 2.96 mmol, 1.0 eq), CuI (29 mg, 0.15 mmol, 0.05 eq), K$_2$CO$_3$ (858 mg, 6.22 mmol, 2.1 eq) and trans-1,2-cyclohexanediamine (84 mg, 0.59 mmol, 0.2 eq) were added to a dry pressure tube equipped with a magnetic stir bar. Then the tube was taken into a glove box and toluene (4 mL) was added. The mixture was sparged with nitrogen for 2 minutes and the tube was sealed. The tube was taken out of the glove box and the mixture was stirred in an oil bath at 105-115° C. for 6 days. Then the mixture was cooled to ambient temperature. The mixture was concentrated under reduced pressure and the residue was purified through column chromatography on silica gel using hexane and ethyl acetate (10:1-5:1) as eluent to obtain the pure desired product as a yellow solid 664 mg in 73% yield. $^1$H NMR (DMSO-d$_6$, 400 MHz): δ 1.51 (s, 6H), 6.51 (t, J=2.0 Hz, 1H), 6.78 (d, J=8.0 Hz, 1H), 6.82 (td, J=8.0, 1.6 Hz, 1H), 7.07 (dd, J=7.6, 1.6 Hz, 1H), 7.19 (dd, J=8.0, 2.0 Hz, 1H), 7.26 (d, J=2.8 Hz, 1H), 7.36 (d, J=7.6 Hz, 1H), 7.43 (d, J=8.4 Hz, 1H), 7.71 (d, J=1.6 Hz, 1H), 8.35 (d, J=2.4 Hz, 1H), 9.06 (s, 1H).

Synthesis of 9-(pyridin-2-yl)-9H-carbazol-2-ol I-OH-1

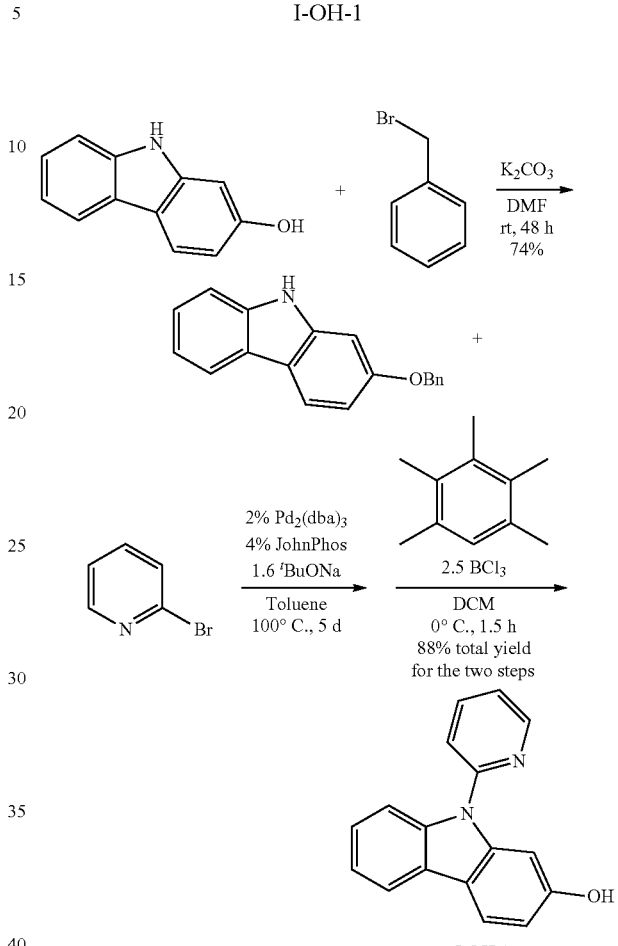

I-OH-1

Synthesis of 2-(benzyloxy)-9H-carbazole: A mixture of 9H-carbazol-2-ol (5.00 g, 27.30 mmol, 1.0 eq), BnBr (3.25 mL, 27.30 mmol, 1.0 eq), K$_2$CO$_3$ (3.77 g, 27.30 mmol, 1.0 eq) in DMF (40 mL) was stirred at room temperature for 2 days. The mixture was then diluted with water (150 mL), then stirred at room temperature for 10 minutes. The precipitate was filtered off and washed with water three times, then washed with ethyl acetate. The collected solid was dried in air to afford the desired product as a white solid 5.47 g in 74% yield. $^1$H NMR (DMSO-d$_6$, 500 MHz): δ 5.19 (s, 2H), 6.85 (dd, J=8.0, 2.0 Hz, 1H), 7.04 (d, J=1.5 Hz, 1H), 7.10 (t, J=7.0 Hz, 1H), 7.28 (t, J=8.5 Hz, 1H), 7.33 (t, J=7.5 Hz, 1H), 7.39-7.42 (m, 3H), 7.50 (d, J=7.5 Hz, 2H), 7.97 (t, J=8.5 Hz, 2H), 11.10 (s, 1H).

Synthesis of I-OH-1: To a three-necked flask equipped with a magnetic stir bar and a condenser was added 2-(benzyloxy)-9H-carbazole (3.69 g, 13.50 mmol, 1.0 eq), Pd$_2$(dba)$_3$ (0.25 g, 0.27 mmol, 0.02 eq), and JohnPhos (0.16 g, 0.54 mmol, 0.04 eq), $^t$BuONa (2.08 g, 21.60 mmol, 1.6 eq). The flask was evacuated and backfilled with nitrogen. This evacuation and backfill procedure was repeated for three cycles. Then toluene (40 mL) and 2-bromopyridine (1.54 mL, 16.20 mmol, 1.2 eq) were added. The mixture was stirred at 95-105° C. in an oil bath for 5 days. Then the mixture was cooled down to ambient temperature and diluted with ethyl acetate. The mixture was concentrated and the residue was purified through column chromatography on silica gel using hexane and ethyl acetate (10:1-5:1-3:1) as eluent to obtain the desired product as a sticky liquid which was used directly for the next step. A solution of BCl$_3$ (33.75 mL, 33.75 mmol, 2.5 eq) was slowly added to a solution of the sticky liquid (~13.5 mmol) and 1,2,3,4,5-pentamethylbenzene (6.00 g, 40.5 mmol, 3.0 eq) in dichloromethane (100 mL) at 0° C. The mixture was then stirred at 0° C. for 1.5 hours, quenched with water, and diluted with dichloromethane. The resulting mixture was washed with aqueous NaHCO$_3$, dried over sodium sulfate, filtered, and concentrated under reduced pressure. The resulting residue was purified through column chromatography on silica gel sequentially using hexane/ethyl acetate (10:1-3:1), then dichloromethane/methanol (10:1) as eluents to obtain the desired product as a grey solid 3.19 g in 88% total yield for the two steps. $^1$H NMR (DMSO-d$_6$, 400 MHz): δ 6.69 (dd, J=8.0, 2.0 Hz, 1H), 7.07 (d, J=2.0 Hz, 1H), 7.12-7.16 (m, 1H), 7.22 (td, J=8.4, 1.2 Hz, 1H), 7.35-7.38 (m, 1H), 7.59 (d, J=8.4 Hz, 1H), 7.64 (d, J=8.4 Hz, 1H), 7.88 (d, J=8.0 Hz, 1H), 7.95 (d, J=7.2 Hz, 1H), 8.01 (td, J=8.0, 2.0 Hz, 1H), 8.62 (dd, J=4.8, 1.2 Hz, 1H), 9.56 (bs, 1H).

Synthetic routes for the critical fragments LI-Br, LI-NH, LI-OH, II-Br, LII-NH, LII-OH, LIII-NH and LIV-NH disclosed herein includes:

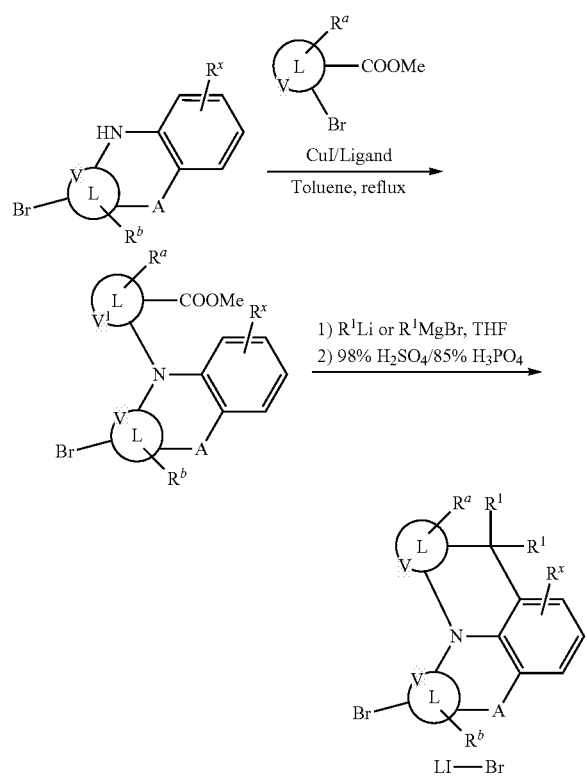

For example, LI-Br-1 can be synthesized as follows:

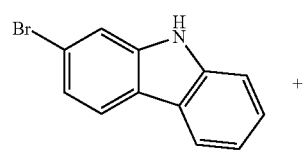

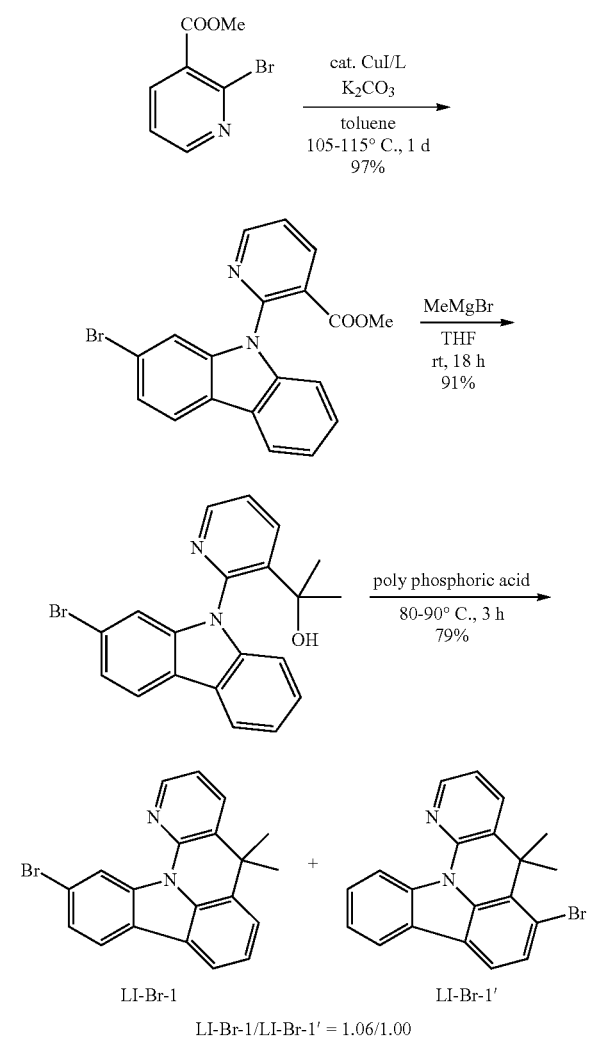

Synthesis of methyl 2-(2-bromo-9H-carbazol-9-yl)pyridine-3-carboxylate: A mixture of 2-bromo-9H-carbazole (1.23 g, 10 mmol, 1.0 eq), methyl 2-bromopyridine-3-carboxylate (1.51 g, 7 mmol, 1.4 eq), CuI (0.19 g, 1.0 mmol, 0.2 eq), K$_2$CO$_3$ (1.38 g, 10 mmol, 2.0 eq), and L-proline (0.12 g, 1.0 mmol, 0.2 eq) in toluene (15 mL) was stirred at 105-115° C. for 1 day under nitrogen then cooled to ambient temperature. The solvent was removed under reduced pressure and the residue was purified through column chromatography on silica gel using dichloromethane as eluent to obtain a sticky liquid 1.85 g in 97% yield. $^1$H NMR (DMSO-d$_6$, 400 MHz): δ 3.32 (s, 3H), 7.22 (d, J=8.0 Hz, 1H), 7.31 (t, J=7.2 Hz, 1H), 7.41 (d, J=8.0 Hz, 1H), 7.45 (dd, J=8.4, 16 Hz, 1H), 7.48 (d, J=1.6 Hz, 1H), 7.74 (dd, J=8.0, 4.8 Hz, 1H), 8.19 (d, J=8.0 Hz, 1H), 8.24 (d, J=8.0 Hz, 1H), 8.49 (d, J=8.0, 2.0 Hz, 1H), 8.93 (d, J=8.4, 2.0 Hz, 1H).

Synthesis of 2-(2-(2-bromo-9H-carbazol-9-yl)pyridin-3-yl)propan-2-ol: MeMgBr (40.0 mL, 40.0 mmol, 4.0 eq, 1.0 M in THF) was added to 2-(2-bromo-9H-carbazol-9-yl)pyridine-3-carboxylate (10.0 mmol, 1.0 eq) at room temperature under nitrogen. Then the mixture was stirred at room temperature for 20 hours and monitored by TLC until the reaction was complete. The mixture was quenched with a saturated aqueous solution of NH$_4$Cl, extracted with ethyl acetate, dried over sodium sulfate, filtered, and washed with ethyl acetate. The filtrate was concentrated and the residue was purified through column chromatography on silica gel sequentially using hexane and ethyl acetate (5:1-3:1), then dichloromethane/methanol (10:1) as eluent to obtain the desired product as a white solid 3.48 g in 91%. $^1$H NMR (DMSO-d$_6$, 400 MHz): δ 1.13 (s, 3H), 1.19 (s, 3H), 6.85 (d, J=8.0 Hz, 1H), 6.98 (s, 1H), 7.27 (d, J=8.0 Hz, 1H), 7.37-7.40 (m, 2H), 7.67-7.70 (m, 1H), 8.17 (d, J=8.4 Hz, 1H), 8.22 (d, J=7.6 Hz, 1H), 8.49 (dd, J=8.0, 2.0 Hz, 1H), 8.52-8.83 (m, 1H).

Synthesis of LI-Br-1 and LI-Br-1': A mixture of 2-(2-(2-bromo-9H-carbazol-9-yl)pyridin-3-yl)propan-2-ol (1.76 g, 4.62 mmol) and polyphosphoric acid (about 30 g) was stirred at 80-90° C. for 3 hours under nitrogen, then cooled and quenched with water. The mixture was then extracted with ethyl acetate three times. The combined organic layers were dried over sodium sulfate, filtered, and concentrated under reduced pressure. The resulting residue was purified through column chromatography on silica gel using hexane/ethyl acetate (50:1-30:1) as eluent to obtain a brown solid 1.33 g in 79% for the LI-Br-1 and LI-Br-1' as a mixture with a ratio of 1.06:1.00 from $^1$H NMR. $^1$H NMR (DMSO-d$_6$, 500 MHz): δ 1.72 (s, 3H), 2.00 (s, 3H), 7.26-7.29 (m, 2H), 7.38-7.43 (m, 2H), 7.54 (dd, J=7.5, 2.0 Hz, 1H), 7.58-7.61 (m, 2H), 7.63 (d, J=7.5 Hz, 1H), 8.00 (d, J=8.0 Hz, 1H), 8.05 (d, J=6.0 Hz, 1H), 8.16-8.20 (m, 3H), 8.23 (d, J=8.0 Hz, 1H), 8.42 (dd, J=4.5, 2.0 Hz, 1H), 8.45 (dd, J=4.5, 2.0 Hz, 1H), 9.06 (d, J=8.5 Hz, 1H), 9.19 (d, J=2.0 Hz, 1H).

For another example, LI-OH-2-tBu can be synthesized as follows:

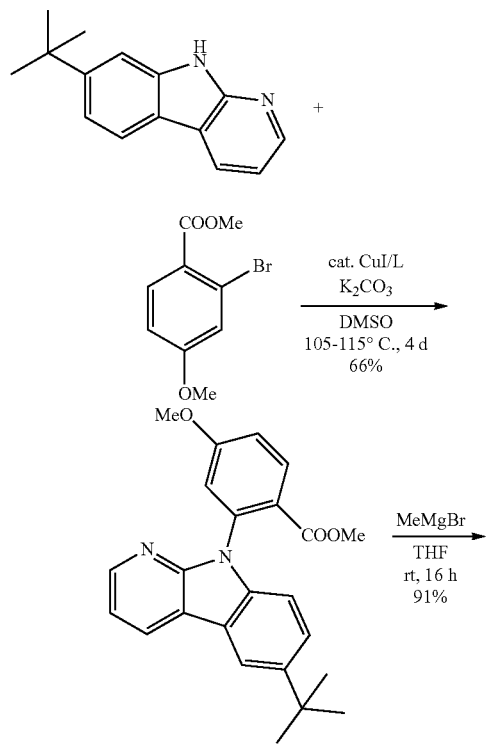

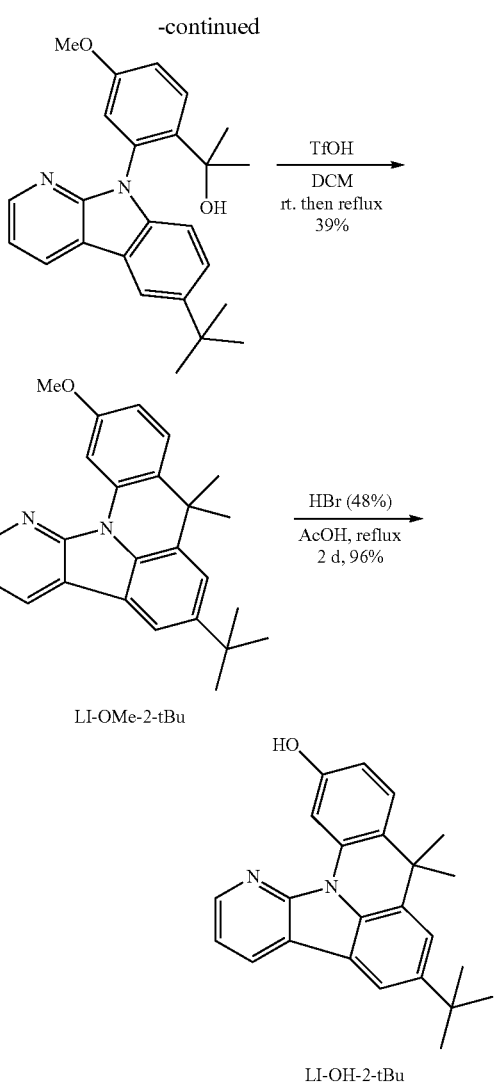

Synthesis of methyl 2-(6-tert-butyl-9H-pyrido[2,3-b]indol-9-yl)-4-methoxybenzoate: A mixture of 7-tert-butyl-9H-pyrido[2,3-b]indole (3.07 g, 13.68 mmol, 1.0 eq), methyl 2-methyl 2-bromo-4-methoxybenzoate (5.03 g, 20.52 mmol, 1.5 eq), CuI (0.13 g, 0.68 mmol, 0.05 eq), K$_2$CO$_3$ (3.97 g, 28.73 mmol, 2.1 eq), trans-N$^1$,N$^2$-dimethylcyclohexane-1,2-diamine (0.39 g, 2.74 mmol, 0.2 eq) in DMSO (35 mL) was stirred at a temperature of 105-115° C. for 4 days under a nitrogen atmosphere and then cooled to ambient temperature. The mixture was diluted with ethyl acetate and filtered. The filtrate was washed with water three times, dried over sodium sulfate, filtered, and concentrated under reduced pressure. The resulting residue was purified through column chromatography on silica gel using hexane/ethyl acetate (10:1-5:1-3:1) as eluent to obtain the desired product as a yellow solid 3.52 g in 66% yield. $^1$H NMR (DMSO-d$_6$, 400 MHz): δ 1.44 (s, 9H), 3.21 (s, 3H), 3.91 (s, 3H), 7.23-7.29 (m, 4H), 7.57 (dd, J=8.8, 2.0 Hz, 1H), 8.06 (d, J=9.2 Hz, 1H), 8.31-8.32 (m, 2H), 8.65 (d, J=8.0, 1.6 Hz, 1H).

Synthesis of 2-(2-(6-tert-butyl-9H-pyrido[2,3-b]indol-9-yl)-4-methoxyphenyl)propan-2-ol: MeMgBr (30.0 mL, 30.0 mmol, 1.0 M in THF) was added to methyl 2-(6-tert-butyl-9H-pyrido[2,3-b]indol-9-yl)-4-methoxybenzoate (2.44 g, 6.28 mmol) at room temperature under an atmosphere of nitrogen. Then the mixture was stirred at room temperature for 16 hours and monitored by TLC until the reaction was complete. The mixture was quenched with a saturated aqueous solution of $NH_4Cl$, extracted with ethyl acetate, dried over sodium sulfate, filtered, and washed with ethyl acetate. The filtrate was concentrated and the residue was purified through column chromatography on silica gel using hexane and ethyl acetate (3:1-2:1), then dichloromethane/methanol (10:1) as eluent to obtain the desired product as a brown solid 2.21 g in 91%. $^1$H NMR (DMSO-$d_6$, 500 MHz): δ 0.98 (s, 3H), 1.07 (s, 3H), 1.41 (s, 9H), 3.70 (s, 3H), 4.96 (s, 1H), 6.54 (d, J=3.0 Hz, 1H), 6.92 (d, J=8.5 Hz, 1H), 7.16 (dd, J=8.5, 2.5 Hz, 1H), 7.26 (dd, J=7.5, 4.0 Hz, 1H), 7.54 (dd, J=8.5, 2.5 Hz, 1H), 7.96 (d, J=9.5 Hz, 1H), 8.28 (d, J=1.0 Hz, 1H), 8.34 (dd, J=5.0, 2.0 Hz, 1H), 8.63 (dd, J=8.0, 2.0 Hz, 1H).

Synthesis of LI-OMe-2-tBu: A mixture of 2-(2-(6-tert-butyl-9H-pyrido[2,3-b]indol-9-yl)-4-methoxyphenyl)propan-2-ol (2.10 g, 5.405 mmol) and TfOH (3.5 mL) was stirred at room temperature for 2 hours, then refluxed about 2-3 hours under nitrogen until the starting material was consumed completely, then cooled down and quenched with $Et_3N$. The solvent was evaporated under reduced pressure and the residue was purified through column chromatography on silica gel using hexane/ethyl acetate (3:1) as eluent to obtain the desired product as a colorless solid 0.77 g in 39% yield. $^1$H NMR (DMSO-$d_6$, 500 MHz): δ 1.44 (s, 9H), 1.71 (s, 6H), 3.87 (s, 3H), 6.82 (dd, J=7.5, 2.0 Hz, 1H), 7.38 (dd, J=8.0, 5.0 Hz, 1H), 7.64 (d, J=9.0 Hz, 1H), 7.70 (d, J=2.0 Hz, 1H), 8.08 (d, J=2.0 Hz, 1H), 8.59 (dd, J=5.5, 2.0 Hz, 1H), 8.66 (dd, J=8.0, 1.5 Hz, 1H), 9.12 (d, J=3.0 Hz, 1H).

Synthesis of LI-OH-2-tBu: A mixture of LI-OMe-2-tBu (0.77 g, 2.078 mmol) and hydrobromic acid (5 mL, 48%) in acetic acid (10 mL) was refluxed for 2 days, then cooled to ambient temperature. The solvent was removed under reduced pressure and the residue was neutralized with an aqueous solution of $K_2CO_3$ until there was no further gas evolution. The precipitate was filtered and washed with water three times. The collected solid was dried in air to give the desired product as a brown solid 0.71 g in 96% yield. $^1$H NMR (DMSO-$d_6$, 500 MHz): δ 1.35 (s, 9H), 1.60 (s, 6H), 6.55 (dd, J=8.0, 2.5 Hz, 1H), 7.28 (dd, J=8.0, 4.5 Hz, 1H), 7.41 (d, J=9.0 Hz, 1H), 7.60 (s, 1H), 7.99 (s, 1H), 8.49 (dd, J=4.5, 1.5 Hz, 1H), 8.57 (dd, J=8.0, 1.5 Hz, 1H), 8.87 (d, J=2.5 Hz, 1H), 9.49 (bs, 1H).

In yet another example, LI-OH-3 can be synthesized as follows:

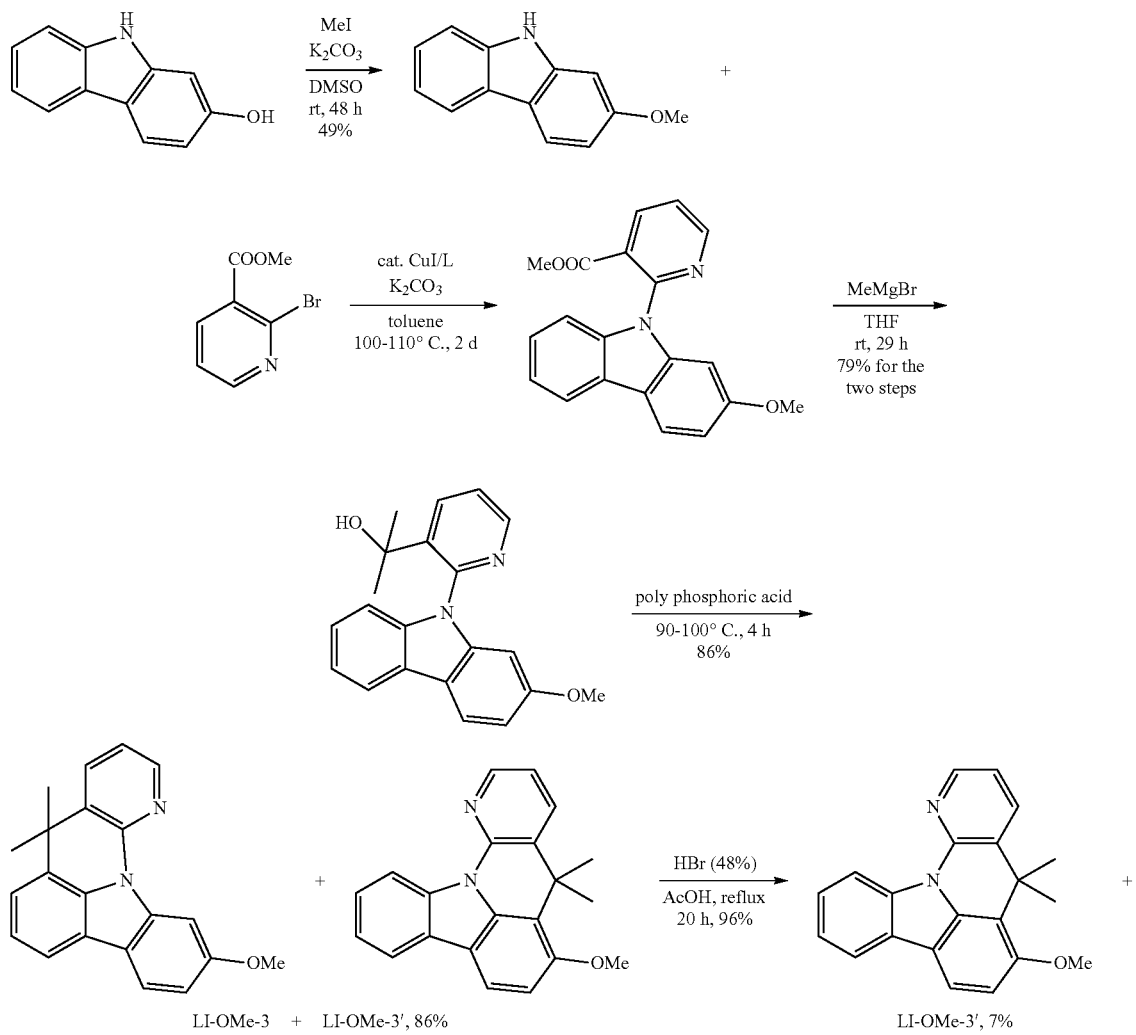

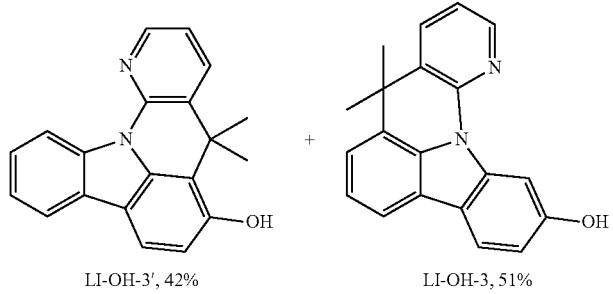

LI-OH-3', 42%    LI-OH-3, 51%

Synthesis of 2-methoxy-9H-carbazole: MeI (1.25 mL, 20 mmol, 1.0 eq) was added to a mixture of 9H-carbazol-2-ol (3.66 g, 20 mmol, 1.0 eq) and $K_2CO_3$ (2.76 g, 20 mmol, 1.0 eq) in DMF (40 mL). The mixture was stirred at room temperature for 23 hours, then quenched by water. The precipitate was filtered off and washed with ethyl acetate, and the collected solid was dried in air to afford the desired product as a white solid 1.94 g in 49% yield. $^1$H NMR (CDCl$_3$, 500 MHz): δ 3.91 (s, 3H), 6.86 (dd, J=8.0, 2.5 Hz, 1H), 6.92 (d, J=2.0 Hz, 1H), 7.21 (t, J=8.0 Hz, 1H), 7.34 (t, J=8.0 Hz, 1H), 7.35 (d, J=7.5 Hz, 1H), 7.93-7.98 (m, 3H).

Synthesis of methyl 2-(2-methoxy-9H-carbazol-9-yl)pyridine-3-carboxylate: A mixture of 2-methoxy-9H-carbazole (1.94 g, 9.8 mmol, 1.0 eq), methyl 2-bromopyridine-3-carboxylate (3.24 g, 15.0 mmol, 1.5 eq), CuI (0.38 g, 2.0 mmol, 0.2 eq), $K_2CO_3$ (2.76 g, 20.0 mmol, 2.0 eq) and L-proline (0.23 g, 2.0 mmol, 0.2 eq) in toluene (30 mL) was stirred at a temperature of 100-110° C. for 2 days under a nitrogen atmosphere and then cooled down to ambient temperature. The solvent was removed under reduced pressure and the residue was purified through column chromatography on silica gel using hexane/ethyl acetate (10:1-5:1) as eluent to obtain the desired product as a colorless liquid. $^1$H NMR (CDCl$_3$, 500 MHz): δ 3.25 (s, 3H), 3.83 (s, 3H), 6.90-6.92 (m, 2H), 7.24-7.27 (m, 1H), 7.29-7.34 (m, 2H), 7.48-7.50 (m, 1H), 7.96 (d, J=9.5 Hz, 1H), 8.00 (d, J=7.0 Hz, 1H), 8.40 (dd, J=8.0, 2.5 Hz, 1H), 8.86 (dd, J=5.0, 2.0 Hz, 1H).

Synthesis of 2-(2-(2-methoxy-9H-carbazol-9-yl)pyridin-3-yl)propan-2-ol: MeMgBr (40.0 mL, 40.0 mmol, 1.0 M in THF) was added to methyl 2-(2-methoxy-9H-carbazol-9-yl)pyridine-3-carboxylate (obtained in last step) at room temperature under an atmosphere of nitrogen. Then the mixture was stirred at room temperature for 29 hours and monitored by TLC until the reaction was complete. The mixture was quenched with water and then extracted with ethyl acetate, dried over sodium sulfate, filtered, and washed with ethyl acetate. The filtrate was concentrated and the residue was purified through column chromatography on silica gel using hexane and ethyl acetate (5:1-2:1), then dichloromethane/methanol (10:1) as eluent to obtain the desired product as a slight yellow solid 2.56 g in a total yield of 79% for the two steps. $^1$H NMR (CDCl$_3$, 500 MHz): δ 1.45 (s, 3H), 1.46 (s, 3H), 2.08 (s, 1H), 3.78 (s, 3H), 6.37 (d, J=2.5 Hz, 1H), 6.86 (d, J=7.0 Hz, 1H), 6.88 (dd, J=8.5, 2.0 Hz, 1H), 7.22-7.29 (m, 2H), 7.51 (dd, J=8.0, 5.0 Hz, 1H), 7.98 (d, J=9.0 Hz, 1H), 8.01 (d, J=8.0 Hz, 1H), 8.39 (d, J=8.0, 2.5 Hz, 1H), 8.59 (dd, J=5.0, 2.0 Hz, 1H).

Synthesis of LI-OMe-3: A mixture of 2-(2-(2-methoxy-9H-carbazol-9-yl)pyridin-3-yl)-propan-2-ol (2.50 g, 7.52 mmol) and poly phosphoric acid (about 25 g) was stirred at 90-100° C. for 4 hours, then cooled down and quenched by water. The mixture was extracted with ethyl acetate three times. The combined organic layer was washed with NaHCO$_3$ solution twice, then dried over sodium sulfate, filtered and washed with ethyl acetate. The filtrate was evaporated under reduced pressure and the residue was purified through column chromatography on silica gel using hexane/ethyl acetate (10:1) as eluent to obtain a mixture of LI-OMe-3 and LI-OMe-3' as a white solid 2.04 g in 86% yield. $^1$H NMR (DMSO-d$_6$, 500 MHz, mixture): δ 1.71 (s, 6H), 1.84 (s, 6H), 3.92 (s, 3H), 3.97 (s, 3H), 6.99-7.01 (m, 1H), 7.11 (d, J=7.5 Hz, 1H), 7.19-7.25 (m, 2H), 7.30-7.36 (m, 2H), 7.44-7.50 (m, 2H), 7.90 (d, J=7.5 Hz, 1H), 7.99 (d, J=8.5 Hz, 1H), 8.08-8.14 (m, 2H), 8.37 (d, J=4.5 Hz, 1H), 8.41 (d, J=4.5 Hz, 1H), 8.59 (d, J=2.0 Hz, 1H), 8.96 (d, J=8.0, Hz, 1H).

Synthesis of LI-OH-3: A mixture of LI-OMe-3 and LI-OMe-3' (2.00 g, 6.36 mmol) in HBr (25 mL, 48%) and acetic acid (50 mL) refluxed for 20 hours, then cooled down. The solvent was removed under reduced pressure and the residue was diluted with water, then neutralized by a solution of NaHCO$_3$ in water until there was no gas to generate. The mixture was then extracted with ethyl acetate, dried over sodium sulfate, filtered and washed with ethyl acetate. The filtrate was evaporated under reduced pressure and the residue was purified through column chromatography on silica gel using hexane/ethyl acetate (10:1) as eluent to obtain LI-OMe-3' as a brown solid 104 mg in 7% yield; LI-OH-3' as a grey solid 811 mg in 42% yield; LI-OH-3 as a brown solid 1040 mg in 51% yield. $^1$H NMR (DMSO-d$_6$, 500 MHz) for LI-OMe-3': 1.84 (s, 6H), 3.97 (s, 3H), 7.12 (d, J=8.0 Hz, 1H), 7.21 (dd, J=7.5, 4.5 Hz, 1H), 7.30-7.33 (m, 1H), 7.44-7.48 (m, 1H), 7.99 (d, J=9.0 Hz, 1H), 8.09-8.11 (m, 2H), 8.37 (dd, J=5.0, 1.5 Hz, 1H), 8.96 (d, J=8.0, Hz, 1H). $^1$H NMR (DMSO-d$_6$, 500 MHz) for LI-OH-3': 1.86 (s, 6H), 6.88 (d, J=8.5 Hz, 1H), 7.19 (dd, J=7.5, 4.5 Hz, 1H), 7.27 (t, J=7.5 Hz, 1H), 7.40 (t, J=7.5 Hz, 1H), 7.79 (d, J=8.5 Hz, 1H), 8.00 (d, J=7.0, Hz, 1H), 8.07 (dd, J=7.5, 1.0 Hz, 1H), 8.36 (dd, J=4.5, 1.5 Hz, 1H), 8.93 (d, J=8.0 Hz, 1H), 9.87 (s, 1H). $^1$H NMR (DMSO-d$_6$, 500 MHz) for LI-OH-3: 1.70 (s, 6H), 6.82 (dd, J=8.5, 2.0 Hz, 1H), 7.22 (dd, J=7.5, 5.0 Hz, 1H), 7.31 (t, J=8.0 Hz, 1H), 7.44 (d, J=7.0 Hz, 1H), 7.83 (d, J=7.0 Hz, 1H), 7.96 (d, J=8.5, Hz, 1H), 8.12 (dd, J=7.5, 1.5 Hz, 1H), 8.38 (dd, J=4.5, 2.0 Hz, 1H), 8.44 (d, J=2.0 Hz, 1H), 9.71 (s, 1H).

General Synthetic Routes, Examples, and Designed Synthetic Routes for the Platinum and Palladium Complexes A general synthesis route for the disclosed Pt and Pd compounds of Formula AI herein includes:

```
A-OH  +  LI-Br
A-OH  +  LII-Br
A-Br  +  LI-OH
A-Br  +  LII-OH
B-OH  +  LI-Br
B-OH  +  LII-Br
B-Br  +  LI-OH
B-Br  +  LII-OH
C-OH  +  LI-Br
C-OH  +  LII-Br
C-Br  +  LI-OH
C-Br  +  LII-OH
D-Br  +  LI-OH
D-Br  +  LII-OH
```

10% CuI
20% picolinic acid
2.0 K$_3$PO$_4$
DMSO
95-105° C.
3 days

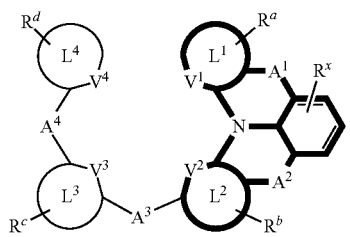

$A^3$ = O or NR
$A^4$ = O or NR

K$_2$PtCl$_4$
cat. $^n$Bn$_4$NBr
AcOH, reflux
$A^3$ = O or NR
$A^4$ = O or NR

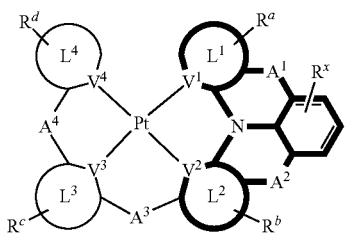

Pt-I

```
A-NH  +  LI-Br
A-NH  +  LII-Br
B-NH  +  LI-Br
B-NH  +  LII-Br
D-NH  +  LI-Br
D-NH  +  LII-Br
```

2% Pd$_2$dba$_3$
4% John Phos
1.7 $^t$BuONa
dioxane/toluene
105-115° C.
1-3 days Pd(OAc)$_2$
cat. $^n$Bn$_4$NBr
AcOH, reflux
$A^3$ = O or NR
$A^4$ = O or NR

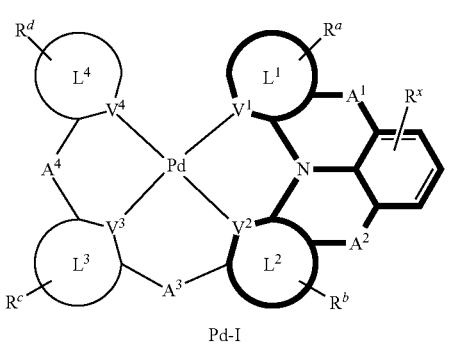

Pd-I

For example, in one aspect PtON$^C$1 can be synthesized as follows:

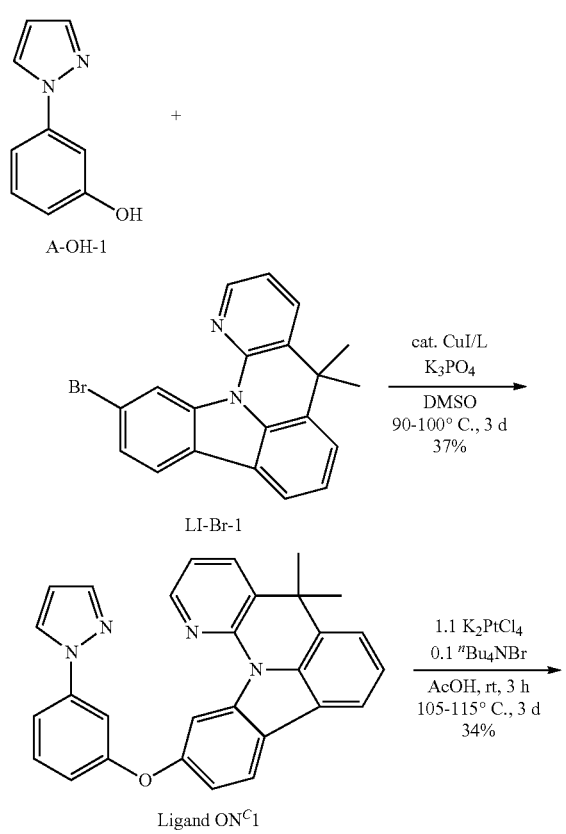

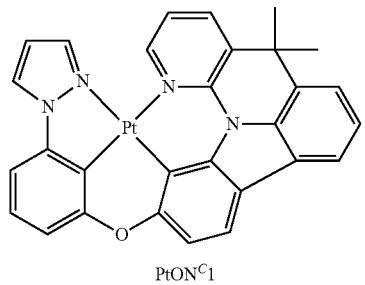

PtON$^C$1

Synthesis of Ligand ON$^C$1: To a dry Schlenck tube equipped with a magnetic stir bar was added 3-(1H-pyrazol-1-yl)phenol A-OH-1 (60 mg, 0.37 mmol, 1.0 eq), LI-Br-1 and LI-Br-1' (135 mg, 0.37 mmol, 1.0 eq), CuI (7 mg, 0.037 mmol, 0.1 eq), picolinic acid (9 mg, 0.074 mmol, 0.2 eq) and K$_3$PO$_4$ (157 mg, 0.74 mmol, 2.0 eq). The tube was evacuated and backfilled with nitrogen. The evacuation and backfill procedure was repeated for three cycles. Then DMSO (3 mL) was added under nitrogen. The mixture was stirred in an oil bath at a temperature of 90-100° C. for 3 days and then cooled to ambient temperature. Water was added to dissolve the resulting solid. The mixture was extracted with ethyl acetate three times. The combined organic layers were washed with water three times, dried over sodium sulfate, filtered, and concentrated under reduced pressure. The resulting residue was purified through column chromatography on silica gel using hexane/ethyl acetate (10:1-5:1-3:1)

as eluent to obtain the desired product Ligand ON$^C$1 as a brown solid 60 mg in 37% yield which was used directly for the next step.

Figure 2:
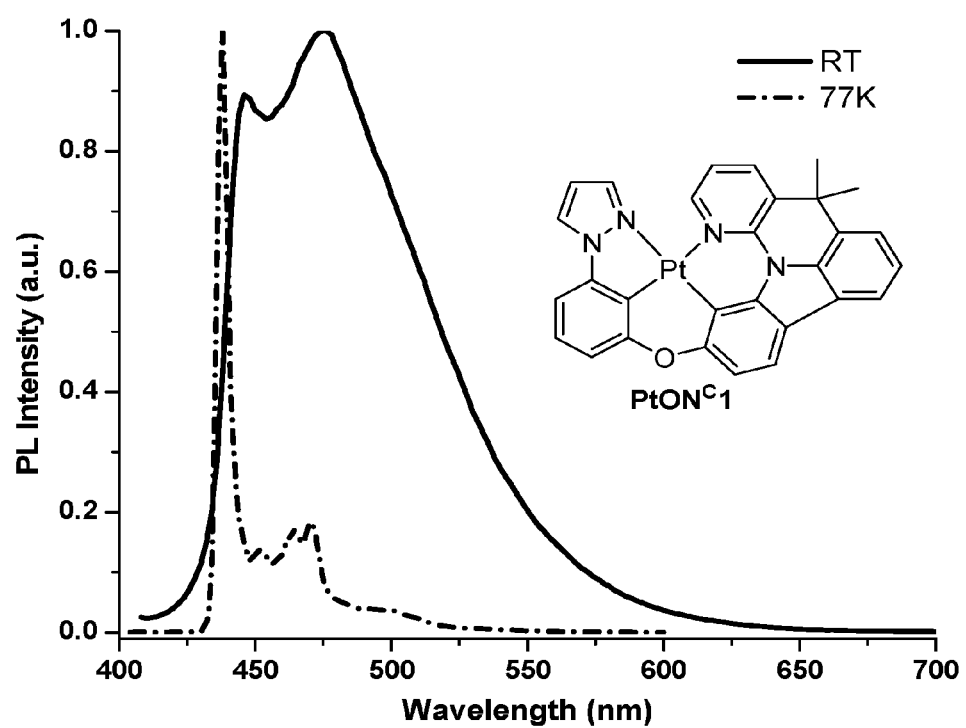
FIG. 2 shows emission spectra of $PtON^C1$ in $CH_2Cl_2$ at room temperature and in 2-methyltetrahydrofuran at 77K.

Synthesis of PtON$^C$1: To a three necked flask equipped with a magnetic stir bar and a condenser was added Ligand ON$^C$1 (6 mg, 0.136 mmol, 1.0 eq), K$_2$PtCl$_4$ (62 mg, 0.149 mmol, 1.1 eq), and $^n$Bu$_4$NBr (5 mg, 0.014 mmol, 0.1 eq). The flask was evacuated and backfilled with nitrogen. The evacuation and backfill procedure was repeated for three cycles. Then acetic acid (10 mL) was added under nitrogen. The mixture was stirred at room temperature for 3 hours and then in an oil bath at a temperature of 105-115° C. for another 3 days. The resulting mixture was cooled to ambient temperature. The solvent was removed under reduced pressure and the residue was purified through flash column chromatography on silica gel using dichloromethane/hexane (2:1) as eluent to obtain the desired product PtON$^C$1 as a yellow solid 30 mg in 34% yield. $^1$H NMR (DMSO-d$_6$, 400 MHz): δ 1.79 (s, 6H), 6.90 (t, J=2.4 Hz, 1H), 6.99 (d, J=7.6 Hz, 1H), 7.23-7.27 (m, 2H), 7.39-7.45 (m, 2H), 7.55 (d, J=7.6 Hz, 2H), 7.91 (d, J=8.4 Hz, 1H), 7.95 (d, J=7.2 Hz, 1H), 8.09 (d, J=2.0 Hz, 1H), 8.50 (d, J=8.4 Hz, 1H), 8.93 (d, J=2.4 Hz, 1H), 9.08 (d, J=6.4 Hz, 1H). Emission spectra of PtON$^C$1 at room temperature in CH$_2$Cl$_2$ and at 77K in 2-methyltetrahydrofuran are shown in FIG. 2.

In another aspect, PdON$^C$1 can be synthesized as follows:

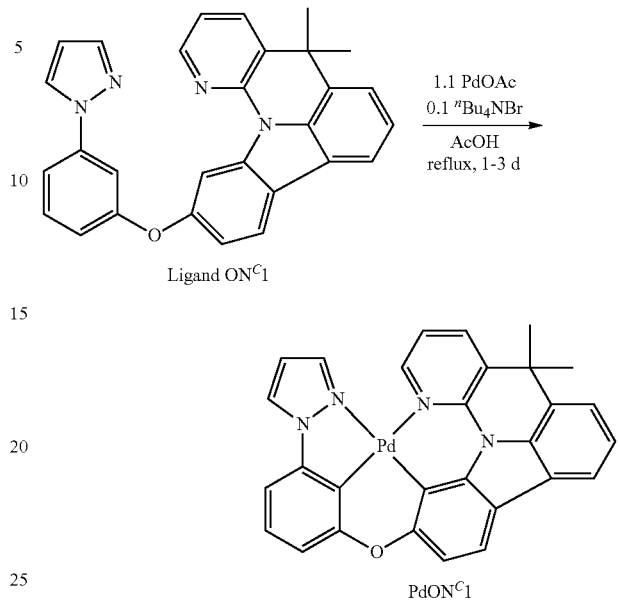

In another aspect, PtON$^C$1-DM and PdON$^C$1-DM can be synthesized as follows:

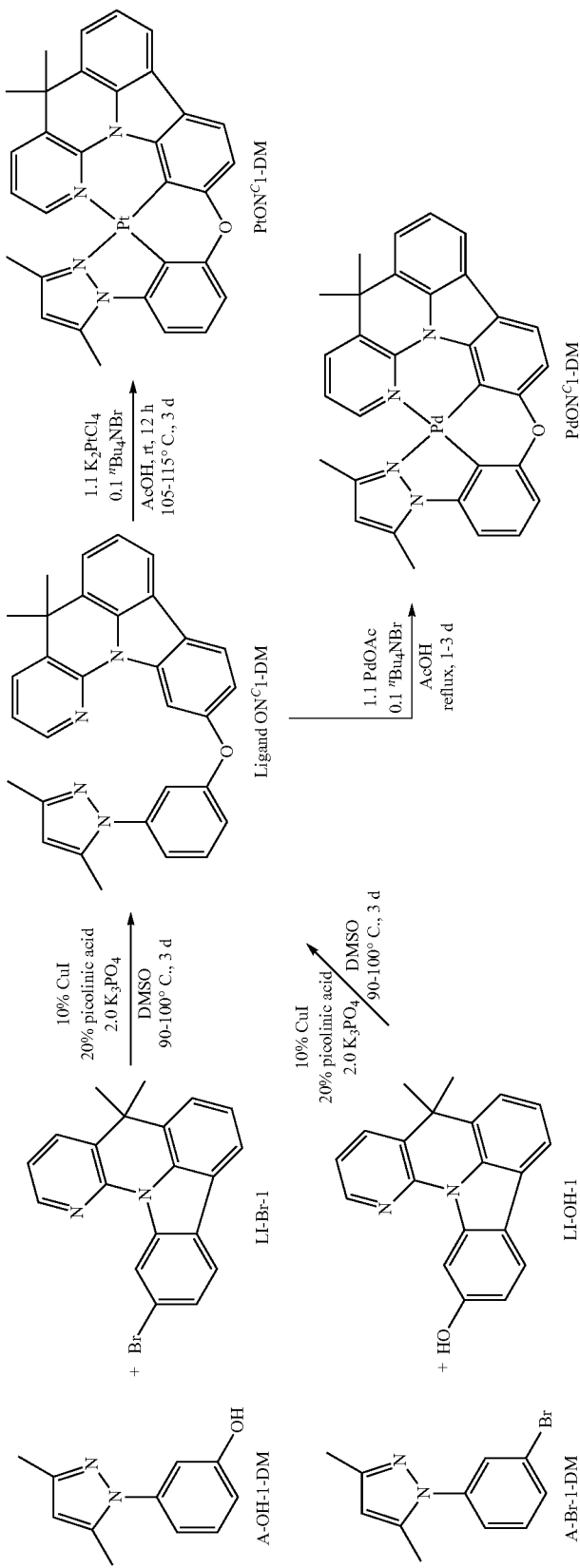

In another aspect, $PtON^C2$ and $PdON^C2$ can be synthesized as follows:

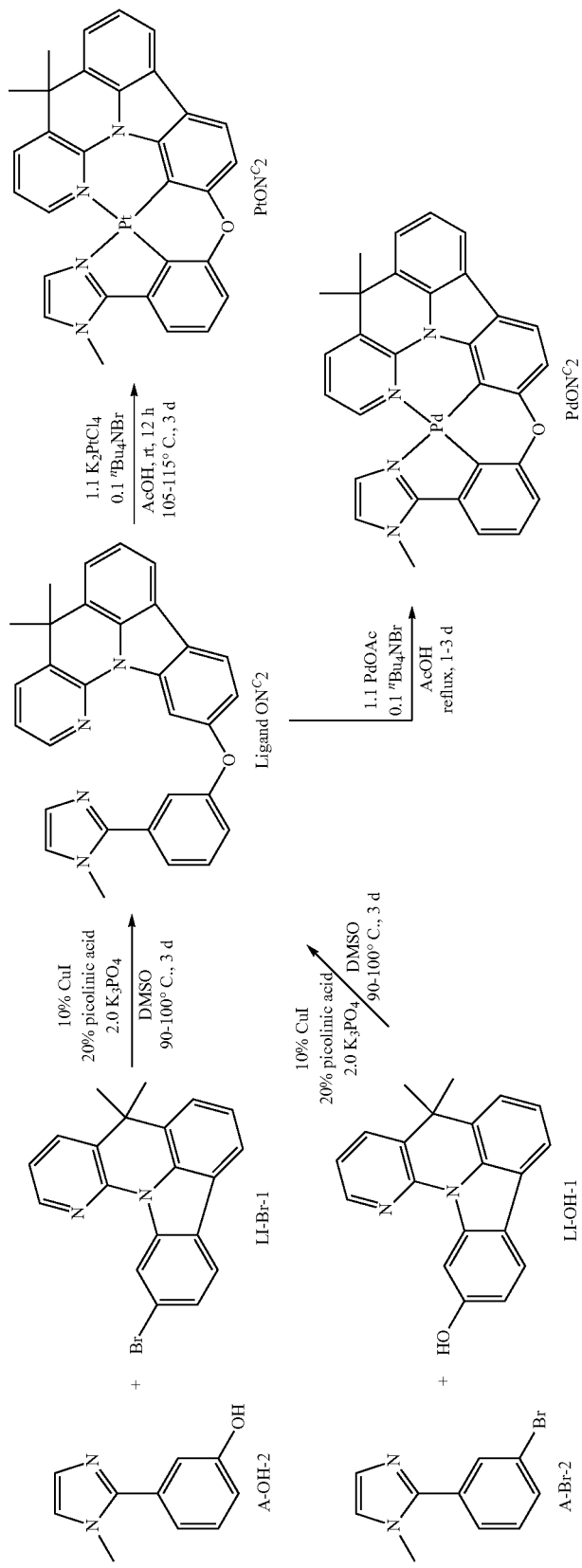

In another aspect, PtON$^C$3 and PdON$^C$3 can be synthesized as follows:

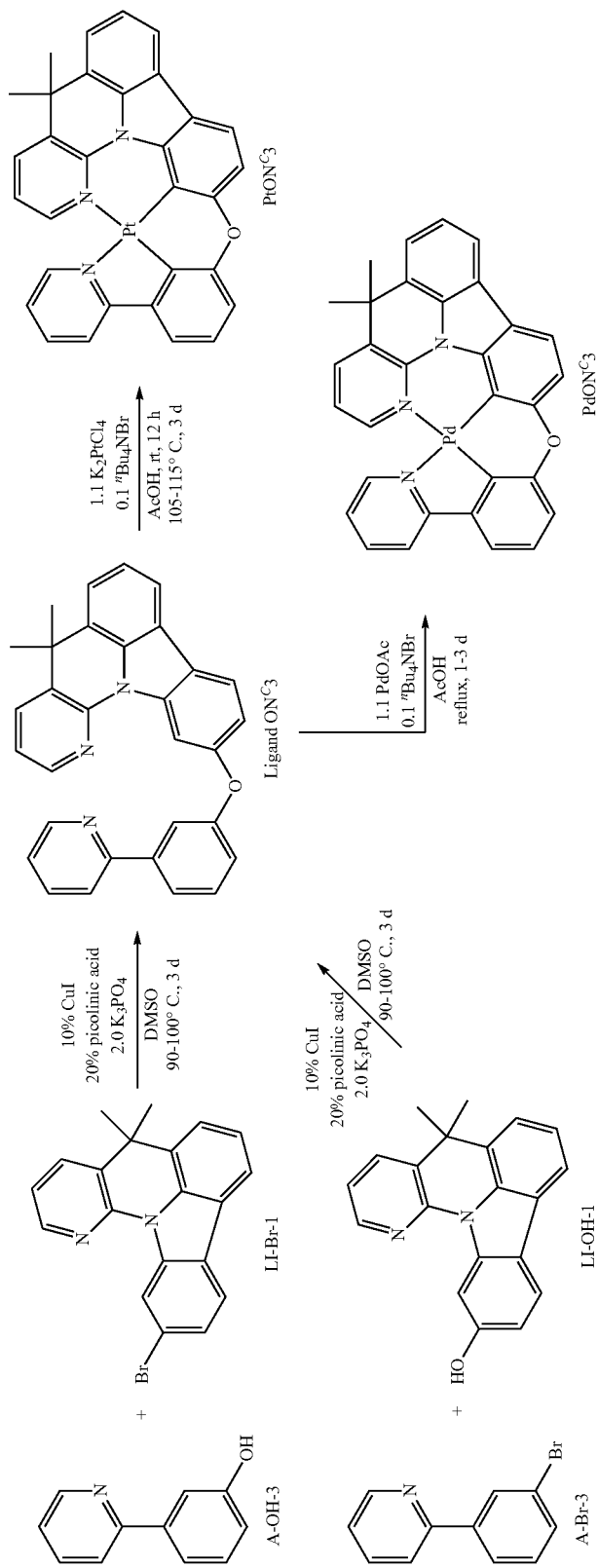

In yet another aspect, PtON$^C$5-tBu can be synthesized as follows:

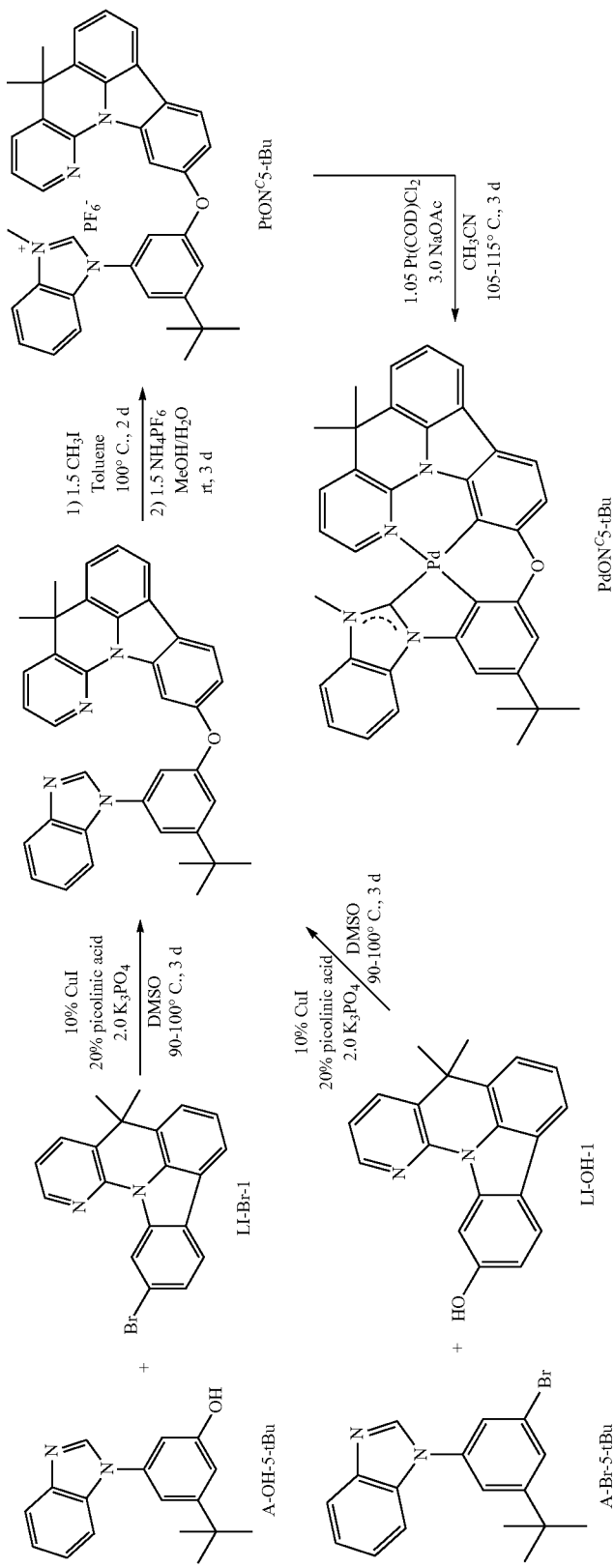

In another aspect, PtON$^C$6 and PdON$^C$6 can be synthesized as follows:
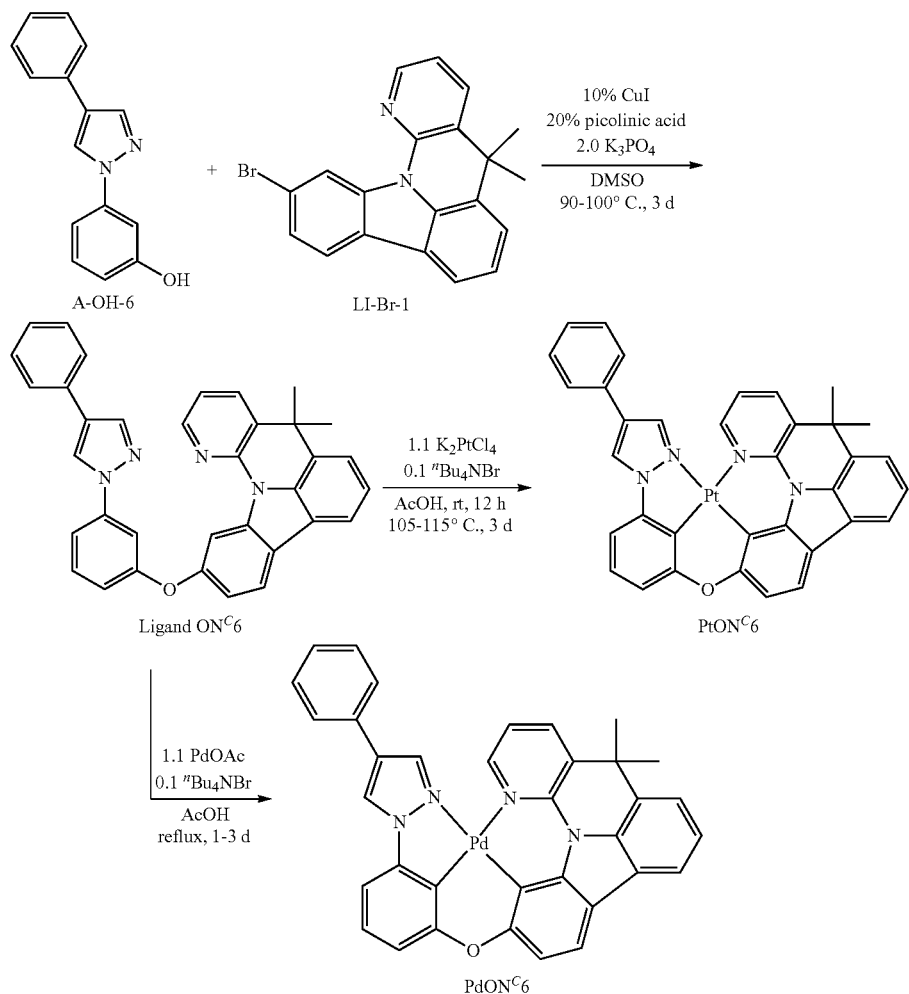
In another aspect, PtON$^C$7-tBu can be synthesized as follows:

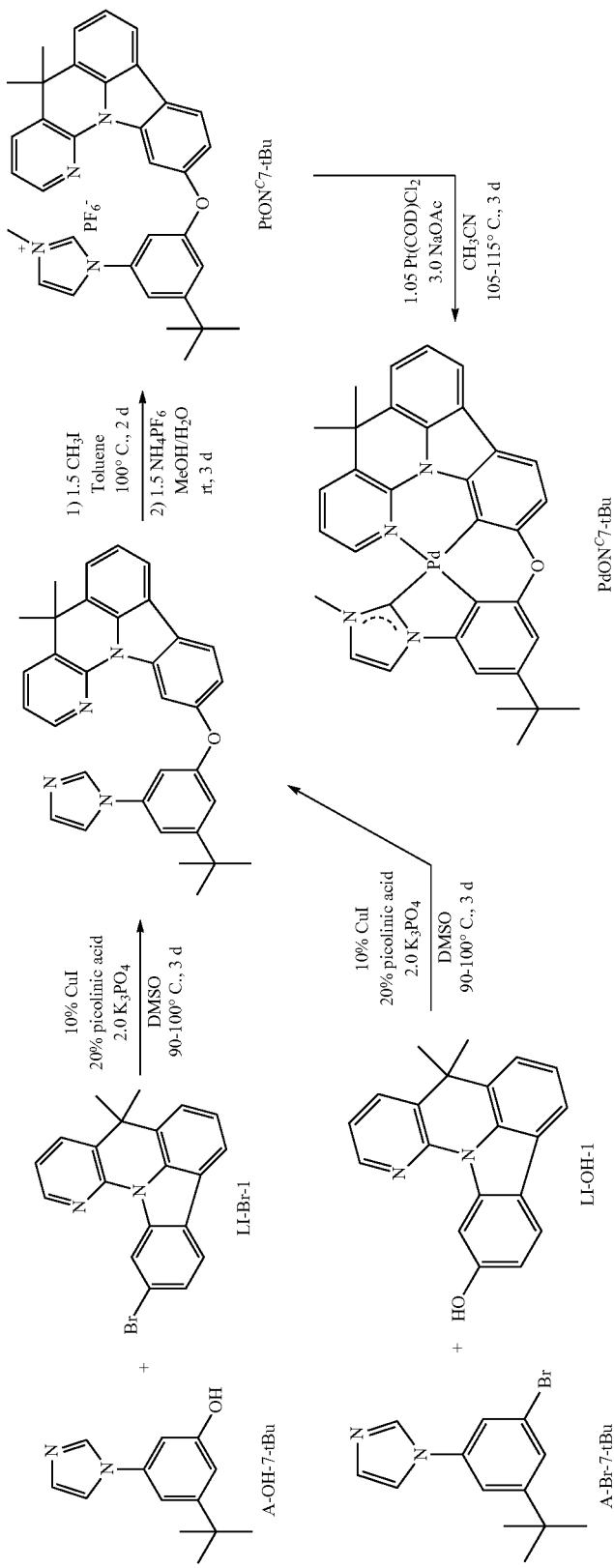

In yet another aspect, PtON$^C$8 and PdON$^C$8 can be synthesized as follows:
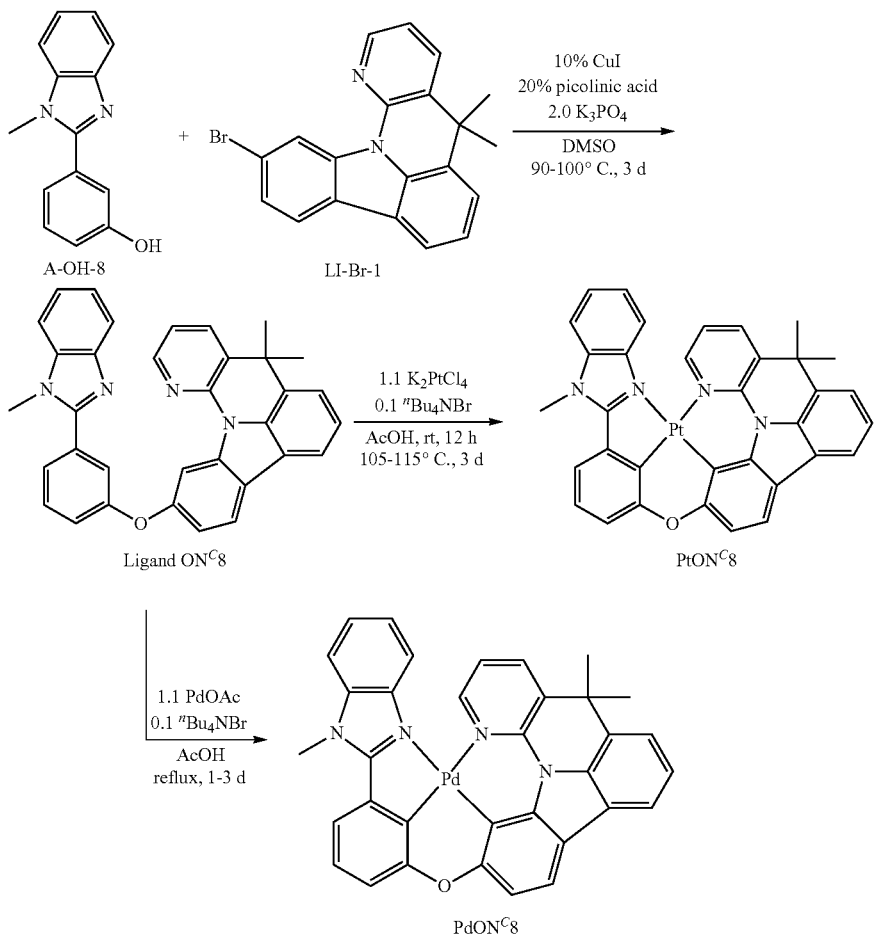
In yet another aspect, PtON$^C$10 and PdON$^C$10 can be synthesized as follows:
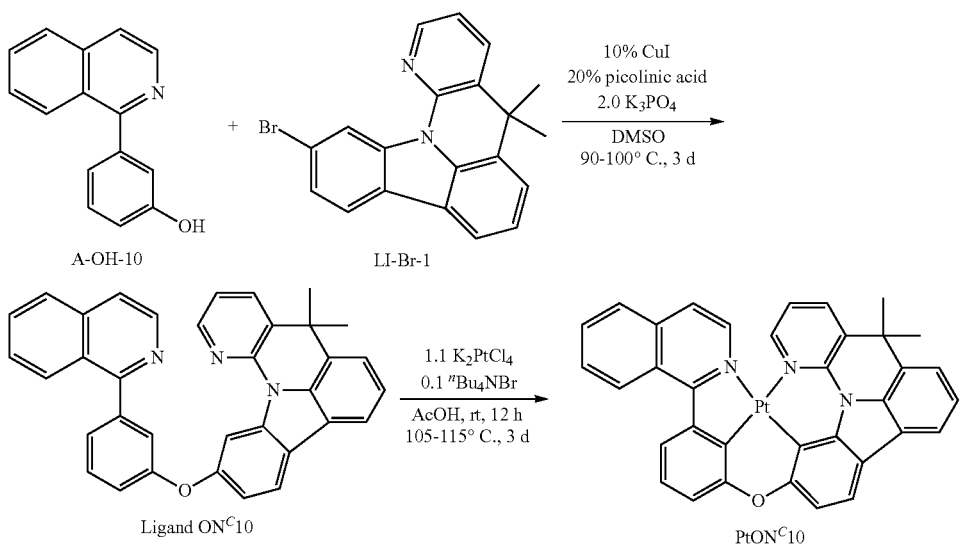

-continued
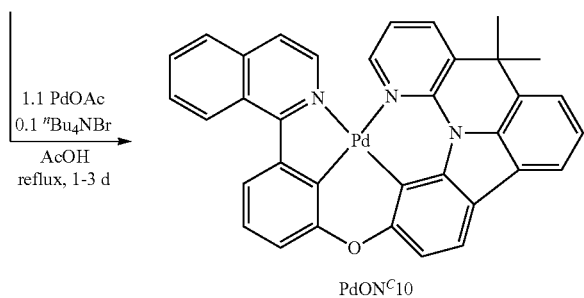
In yet another aspect, PtON$^C$11 and PdON$^C$11 can be synthesized as follows:
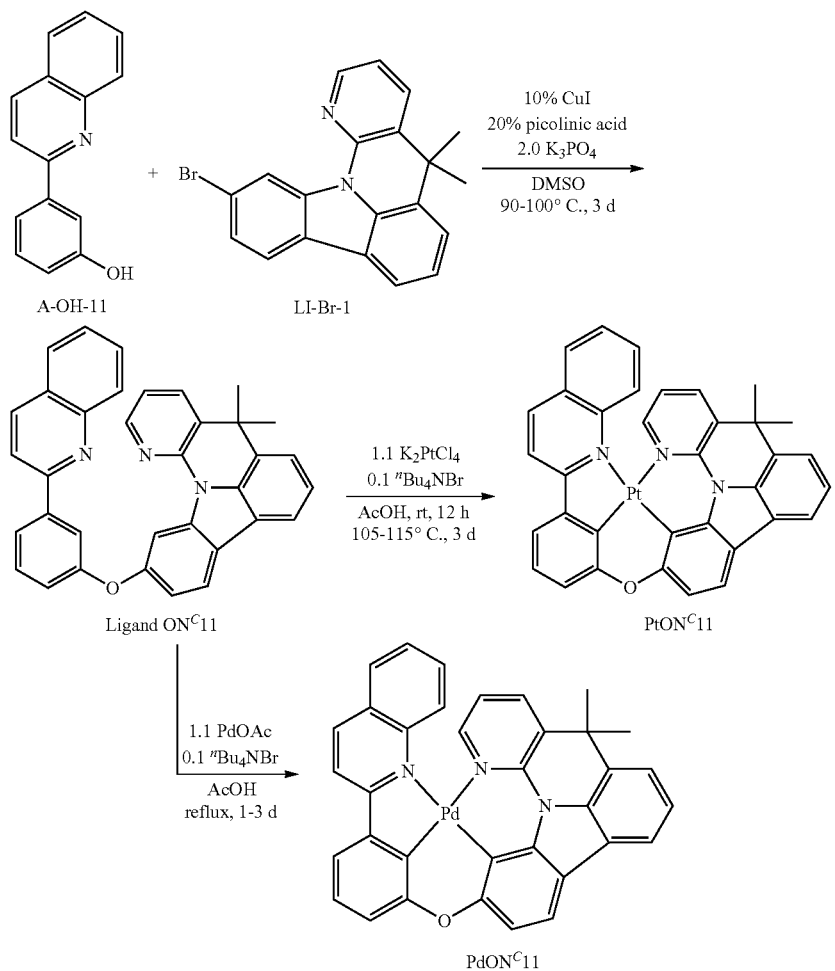
In yet another aspect, PtON$^C$12 and PdON$^C$12 can be synthesized as follows:

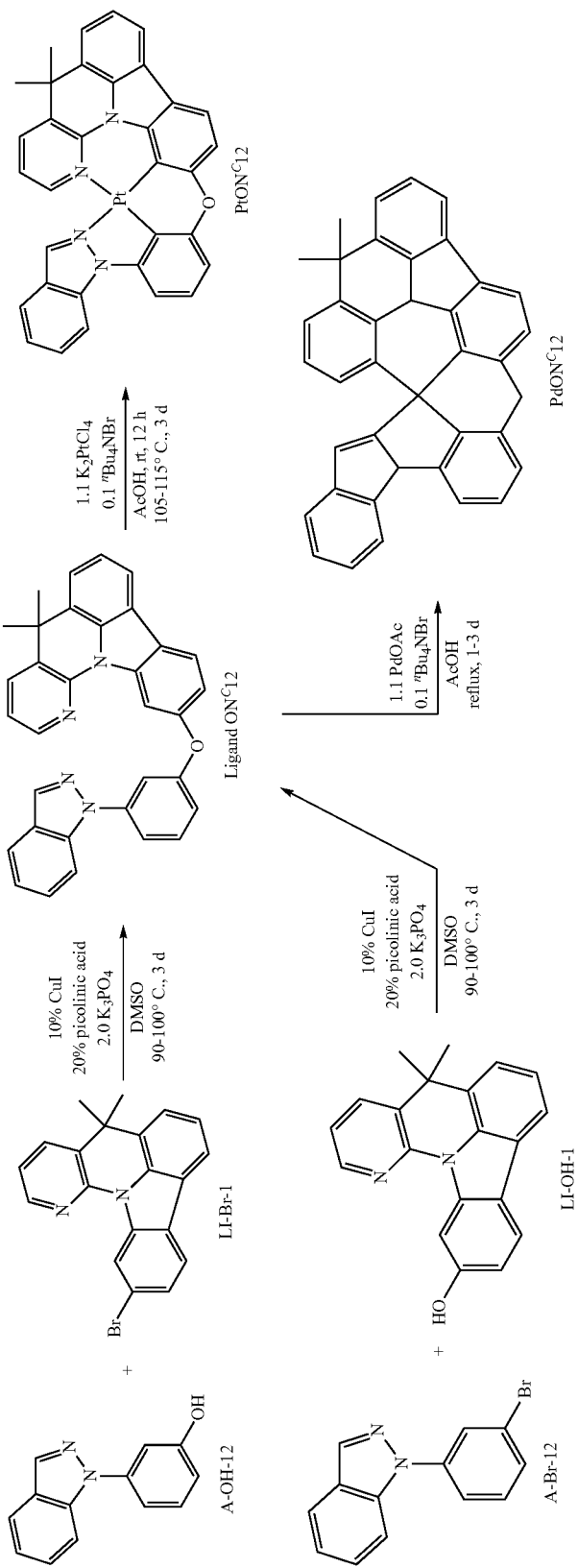

In yet another aspect, PtON^C12Ph and PdON^C12Ph can be synthesized as follows:
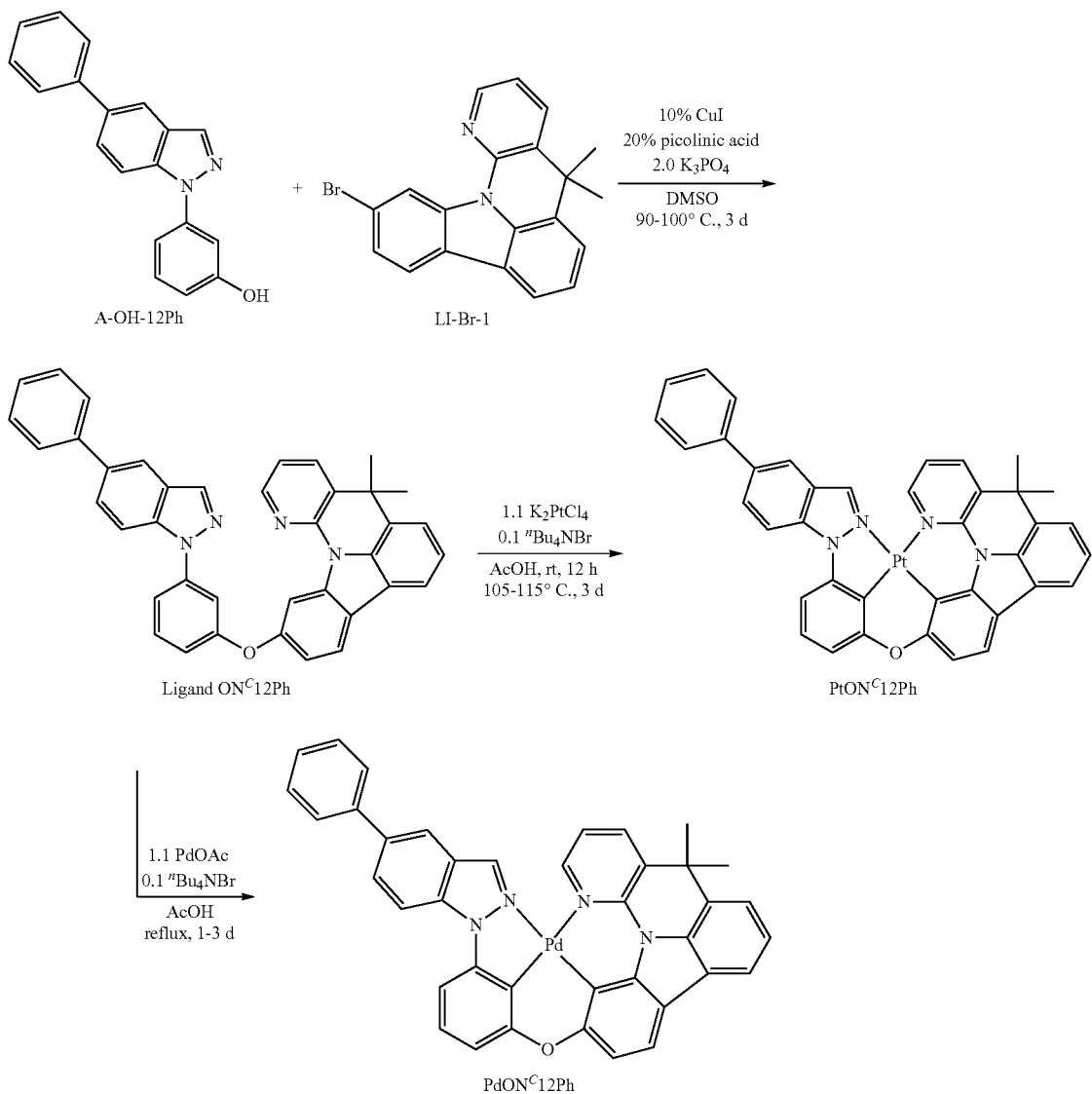
In yet another aspect, PtON^C1c and PdON^C1c can be synthesized as follows:
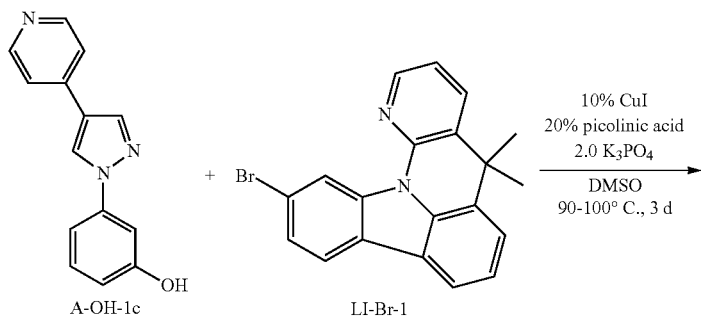

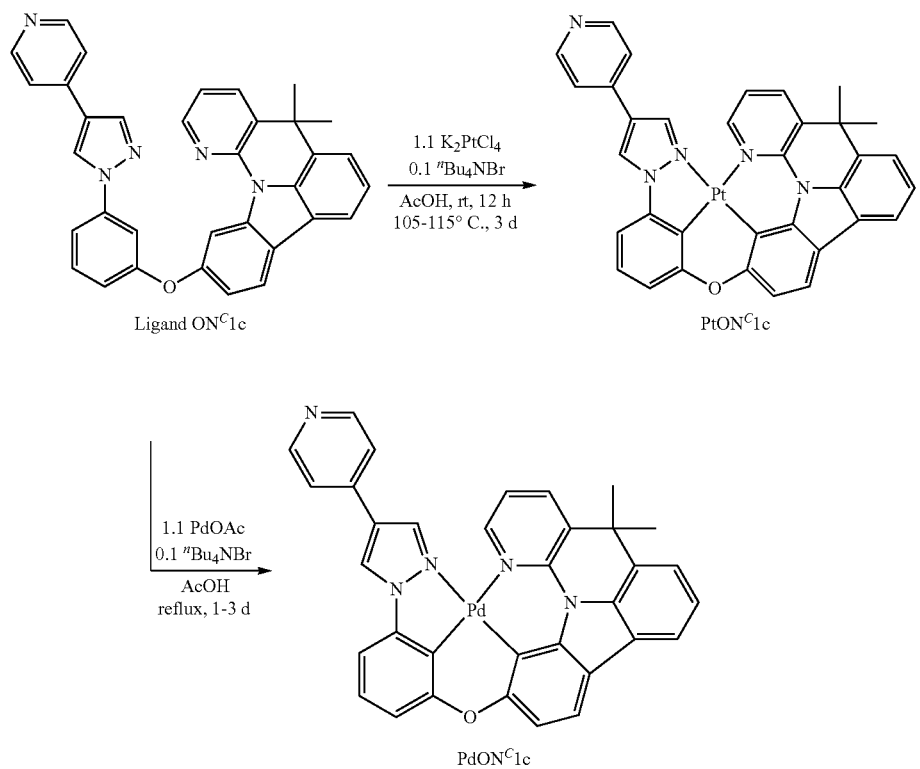
In yet another aspect, PtON$^C$1d and PdON$^C$1d can be synthesized as follows:
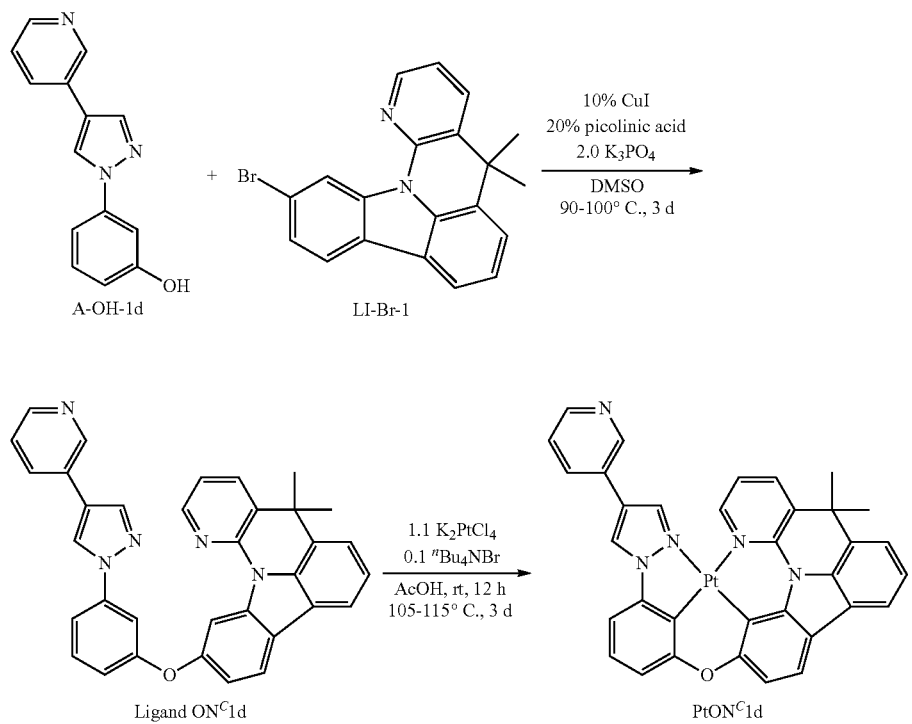

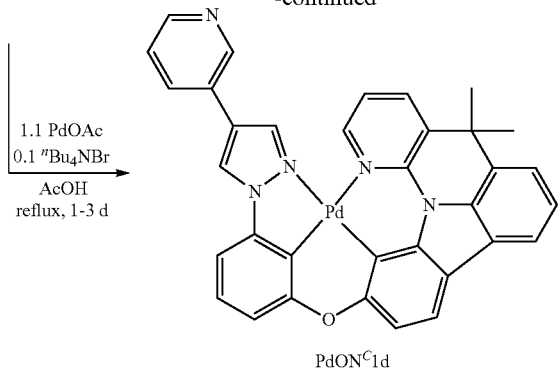
In yet another aspect, PtOON$^C$3 and PdOON$^C$3 can be synthesized as follows:

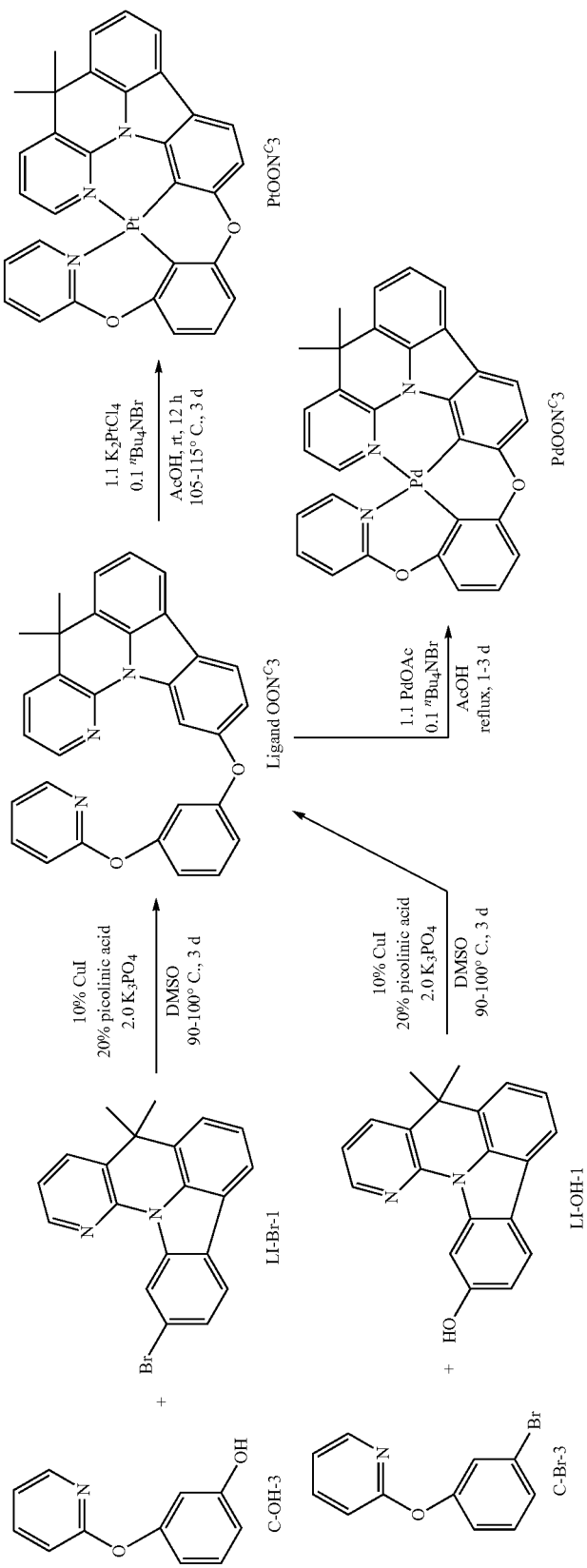

In yet another aspect, PtON$^{C'}$1-DM and PdON$^{C'}$1-DM can be synthesized as follows:

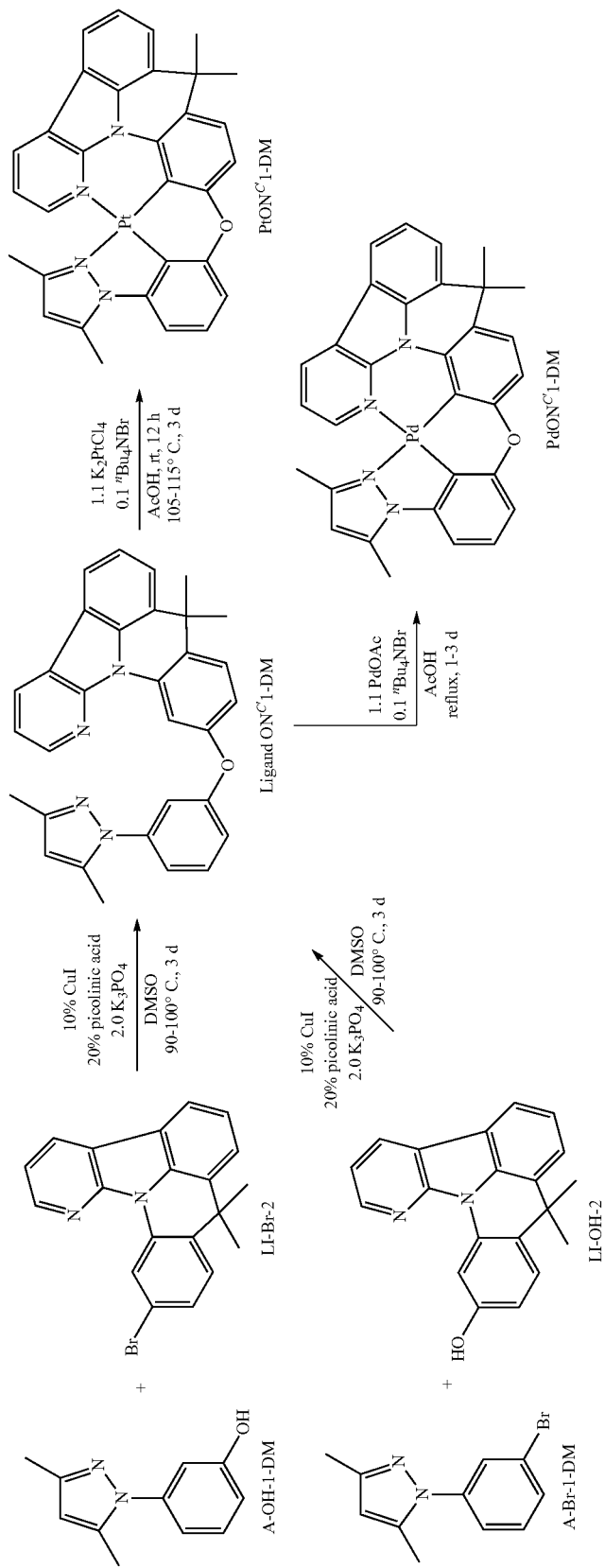

In yet another aspect, PtON$^{CC}$1-DM and PdON$^{CC}$1-DM can be synthesized as follows:
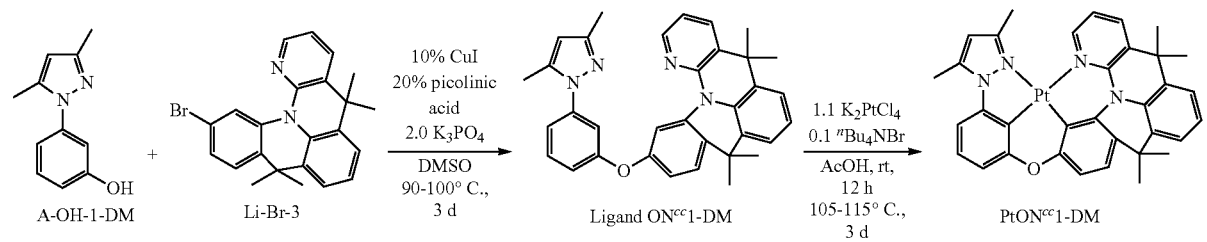
In yet another aspect, PtN$^C$N-DM and PdN$^C$N-DM can be synthesized as follows:
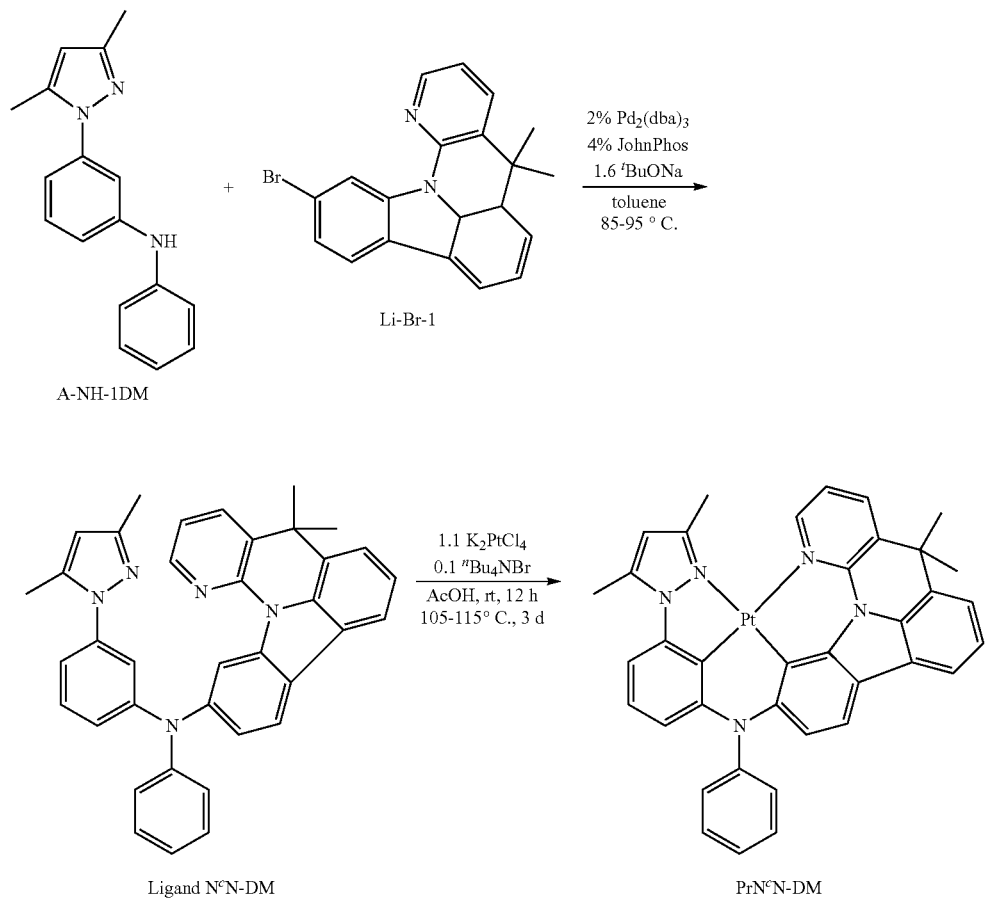

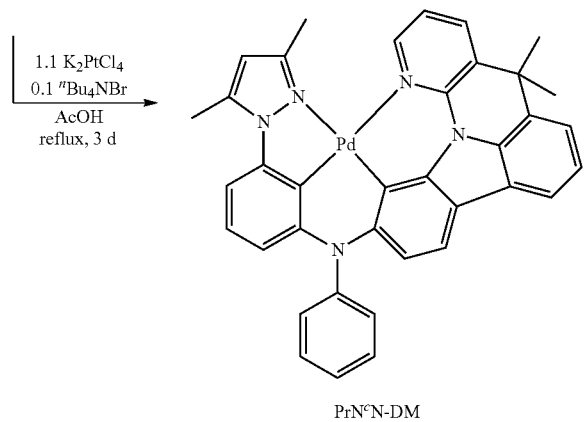
PrN<sup>c</sup>N-DM
A general synthetic route for the disclosed Pt and Pd complexes of Formula AII herein includes:
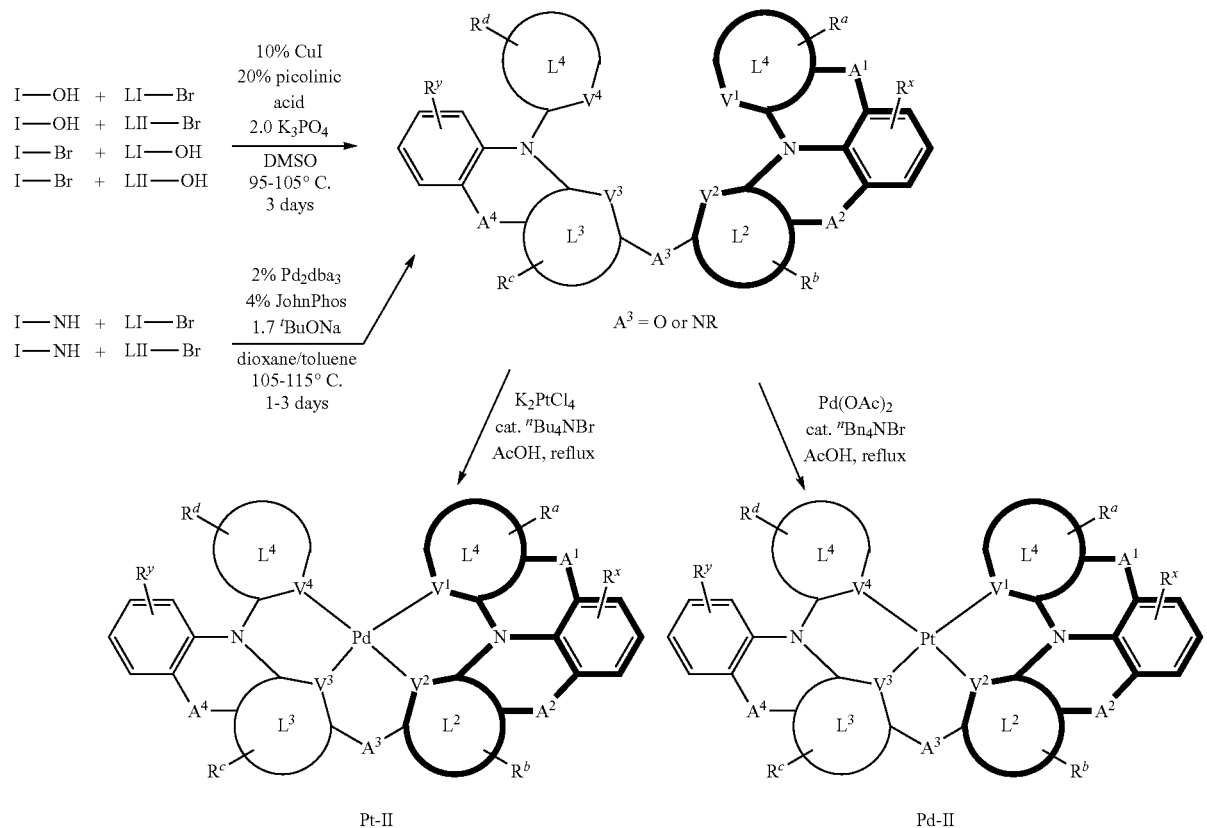
For example, in one aspect, PtNON<sup>C</sup> and PdNON<sup>C</sup> can be synthesized as follows:

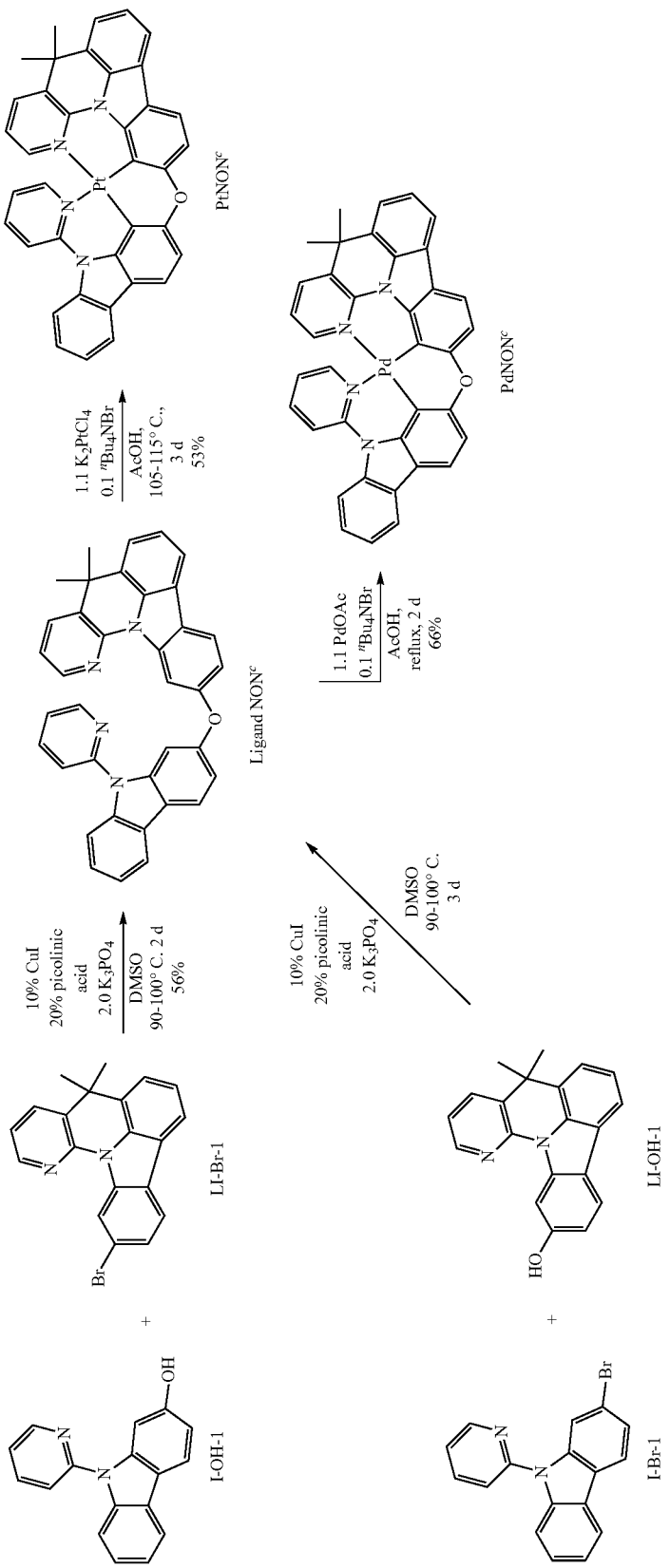

Synthesis of Ligand NON$^C$: 9-(Pyridin-2-yl)-9H-carbazol-2-ol I-OH-1 (326 mg, 1.25 mmol, 1.0 eq), LI-Br-1 and LI-Br-1' (500 mg, 1.38 mmol, 1.1 eq, LI-Br-1 and LI-Br-1' as a mixture with a ratio of 1.06:1.00 from $^1$H NMR), CuI (33 mg, 0.125 mmol, 0.1 eq), picolinic acid (31 mg, 0.250 mmol, 0.2 eq) and K$_3$PO$_4$ (531 mg, 2.50 mmol, 2.0 eq) were added to a dry Schlenck tube equipped with a magnetic stir bar. The tube was evacuated and backfilled with nitrogen. The evacuation and backfill procedure was repeated for three cycles. Then DMSO (6 mL) was added under nitrogen. The mixture was stirred in an oil bath at a temperature of 90-100° C. for 2 days and then cooled to ambient temperature. Water was added to dissolve the resulting solid. The mixture was extracted with ethyl acetate three times. The combined organic layers were washed with water three times, dried over sodium sulfate, filtered, and concentrated under reduced pressure. The resulting residue was purified through column chromatography on silica gel using hexane/ethyl acetate (10:1-5:1) as eluent to obtain the desired product Ligand NON$^C$ as a colorless solid 210 mg in 56% yield based on the one isomer of LI-Br-1. 260 mg of LI-Br-1 and LI-Br-1' was recycled with a ratio of about 2:1 from $^1$H NMR. $^1$H NMR for the Ligand NON$^C$ (DMSO-d$_6$, 500 MHz): δ 1.72 (s, 6H), 7.09-7.12 (m, 2H), 7.19 (dd, J=8.0, 5.0 Hz, 1H), 7.34-7.47 (m, 4H), 7.55-7.57 (m, 2H), 7.79 (t, J=8.0 Hz, 2H), 7.98 (d, J=8.0 Hz, 1H), 8.03-8.06 (m, 1H), 8.13 (dd, J=7.5, 2.0 Hz, 1H), 8.20-8.24 (m, 2H), 8.27-8.29 (m, 2H), 8.66 (dd, J=5.0, 1.0 Hz, 1H), 8.74 (d, J=2.0 Hz, 1H).

Figure 3:
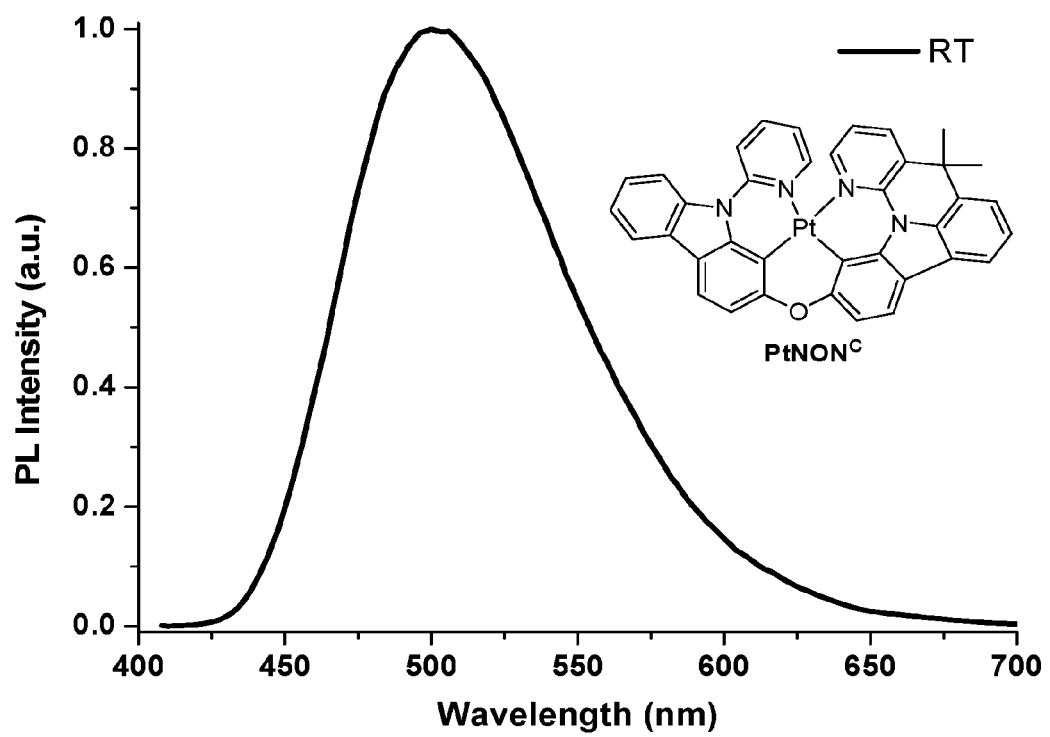
FIG. 3 shows emission spectrum of $PtNON^C$ in $CH_2Cl_2$ at room temperature.

Synthesis of PtNON$^C$: Ligand NON$^C$ (140 mg, 0.258 mmol, 1.0 eq), K$_2$PtCl$_4$ (119 mg, 0.284 mmol, 1.1 eq), and $^n$Bu$_4$NBr (8 mg, 0.0258 mmol, 0.1 eq) were added to a three necked flask equipped with a magnetic stir bar and a condenser. The flask was evacuated and backfilled with nitrogen. The evacuation and backfill procedure was repeated for three cycles. Then acetic acid (16 mL) was added under nitrogen. The mixture was stirred at 105-115° C. for another 3 days, cooled to ambient temperature, and the solvent was removed under reduced pressure. The resulting residue was purified through flash column chromatography on silica gel using dichloromethane/hexane (1:1-2:1) as eluent to obtain the desired product PtNON$^C$ as a yellow solid 100 mg in 53% yield. $^1$H NMR (DMSO-d$_6$, 500 MHz): δ 1.82 (s, 6H), 7.15-7.18 (m, 2H), 7.21 (d, J=7.5 Hz, 1H), 7.27 (td, J=4.0, 1.5 Hz, 1H), 7.40-7.44 (m, 2H), 7.49-7.54 (m, 2H), 7.90 (d, J=8.0 Hz, 1H), 7.93 (t, J=8.0 Hz, 2H), 8.08-8.15 (m, 3H), 8.18 (d, J=8.0 Hz, 1H), 8.41 (dd, J=2.5, 1.0 Hz, 1H), 8.64 (t, J=4.5 Hz, 2H). Emission spectra of PtNON$^C$ at room temperature in CH$_2$Cl$_2$ is shown in FIG. 3. Synthesis of PdNON$^C$:

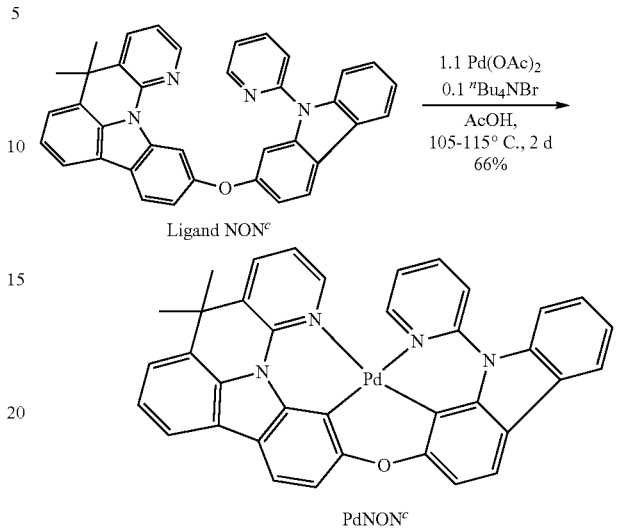

Figure 4:
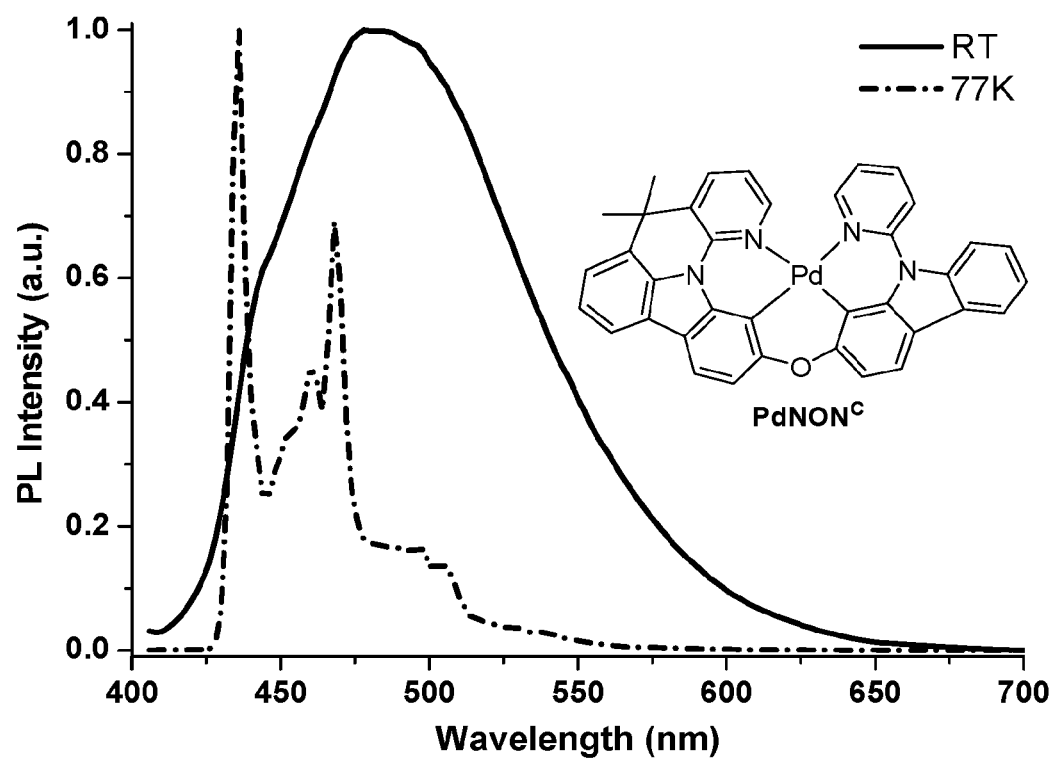
FIG. 4 shows emission spectra of $PdNON^C$ in $CH_2Cl_2$ at room temperature and in 2-methyltetrahydrofuran at 77K.

Synthesis of PdNON$^C$: Ligand NON$^C$ (70 mg, 0.129 mmol, 1.0 eq), Pd(OAc)$_2$ (32 mg, 0.142 mmol, 1.1 eq), and $^n$Bu$_4$NBr (4 mg, 0.0129 mmol, 0.1 eq) were added to a three necked flask equipped with a magnetic stir bar and a condenser. The flask was evacuated and backfilled with nitrogen. The evacuation and backfill procedure was repeated for three cycles. Then acetic acid (8 mL) was added under nitrogen. The mixture was stirred at 105-115° C. for 2 days, then cooled to ambient temperature. The solvent was removed under reduced pressure and the residue was purified through flash column chromatography on silica gel using dichloromethane/hexane (1:1-2:1) as eluent to obtain the desired product PdNON$^C$ as a white solid 55 mg in 66% yield. $^1$H NMR (DMSO-d$_6$, 500 MHz): δ 1.81 (s, 6H), 7.20-7.24 (m, 3H), 7.29-7.32 (m, 1H), 7.39-7.43 (m, 2H), 7.49-7.53 (m, 2H), 7.93 (d, J=3.5 Hz, 1H), 7.97 (t, J=8.0 Hz, 2H), 8.07-8.09 (m, 3H), 8.19 (d, J=7.0 Hz, 1H), 8.34 (dd, J=7.5, 1.5 Hz, 1H), 8.47 (dd, J=6.5, 1.5 Hz, 1H), 8.50 (d, J=6.0 Hz, 1H). Emission spectra of PdNON$^C$ at room temperature in CH$_2$Cl$_2$ and at 77K in 2-methyltetrahydrofuran are shown in FIG. 4.

In another aspect, PtNON$^{C'}$-tBu and PdNON$^{C'}$-tBu can be synthesized as follows:

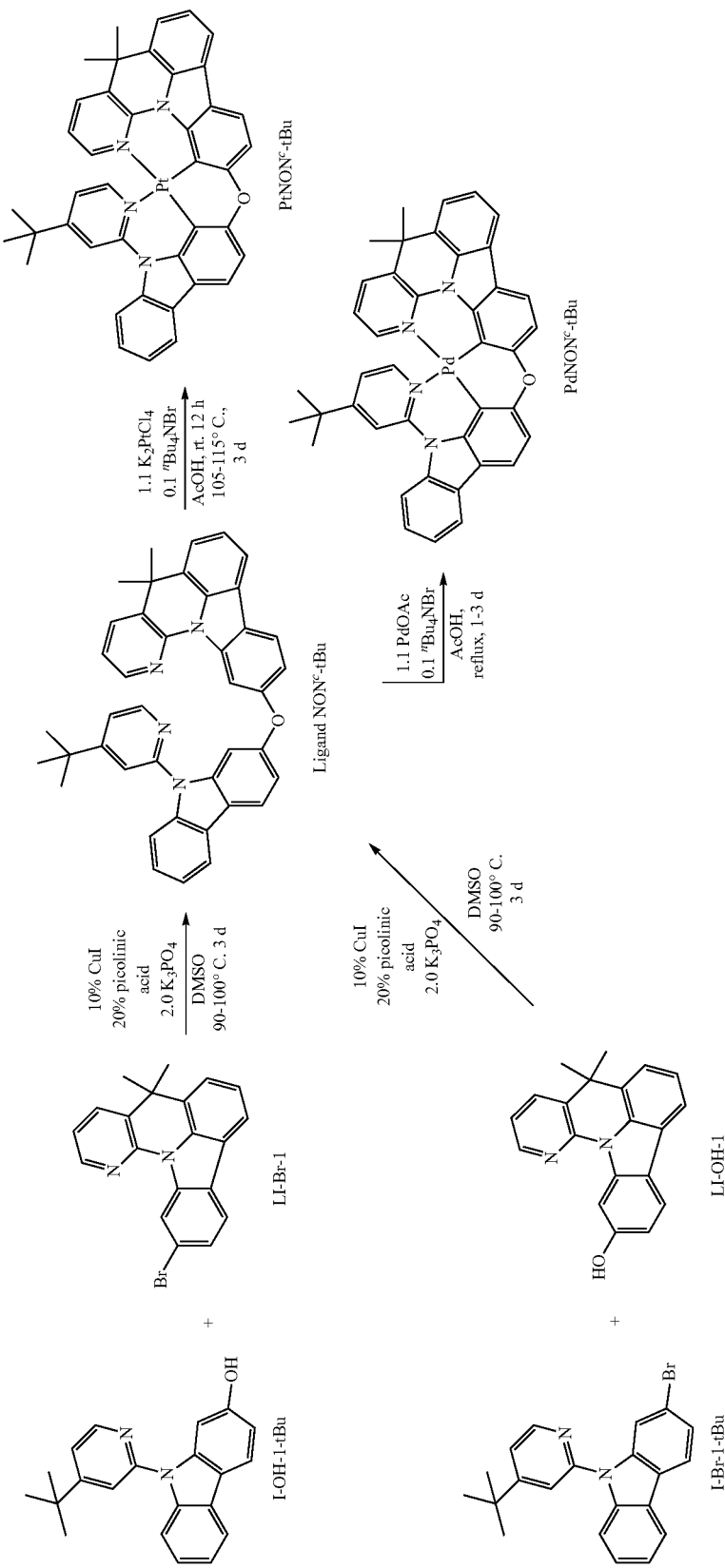

In another aspect, PtNON$^{C'}$ and PdNON$^{C'}$ can be synthesized as follows:

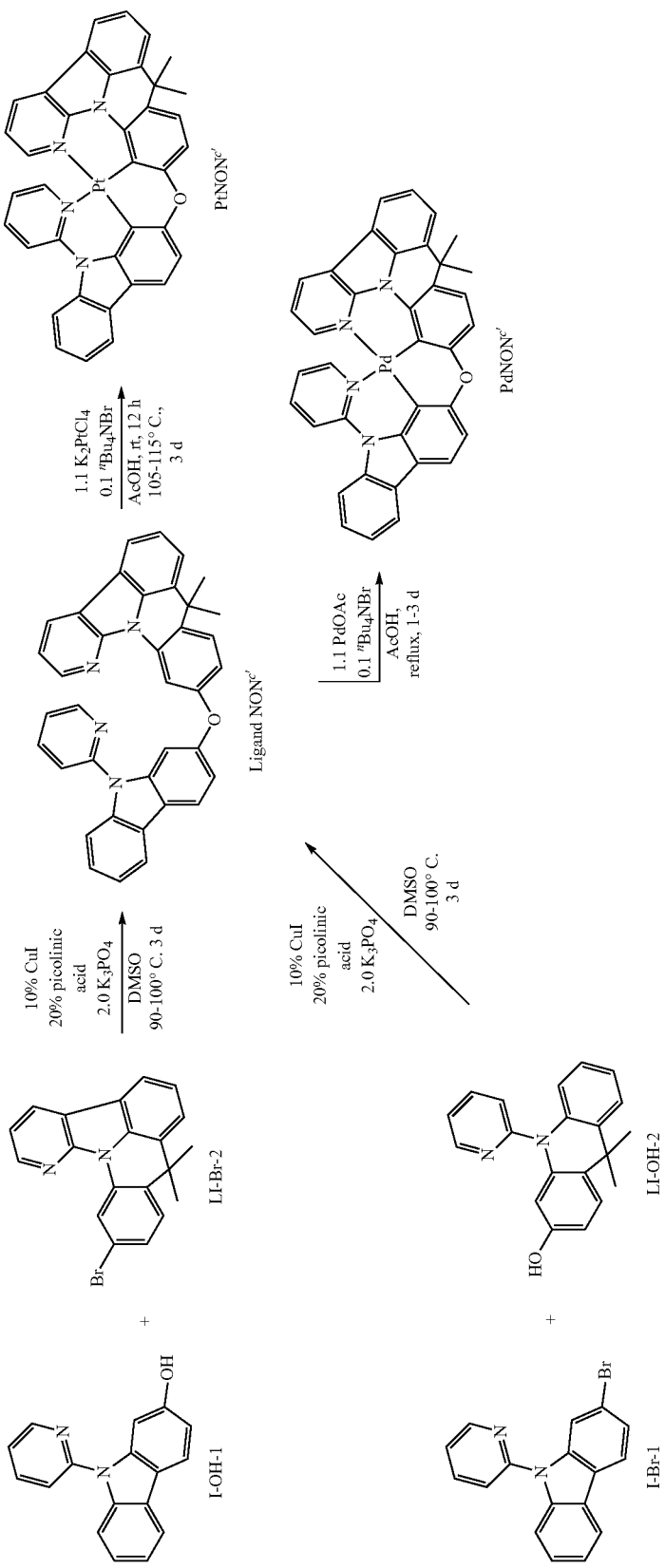

In another aspect, PtNON$^{C'}$-tBu can be synthesized as follows:

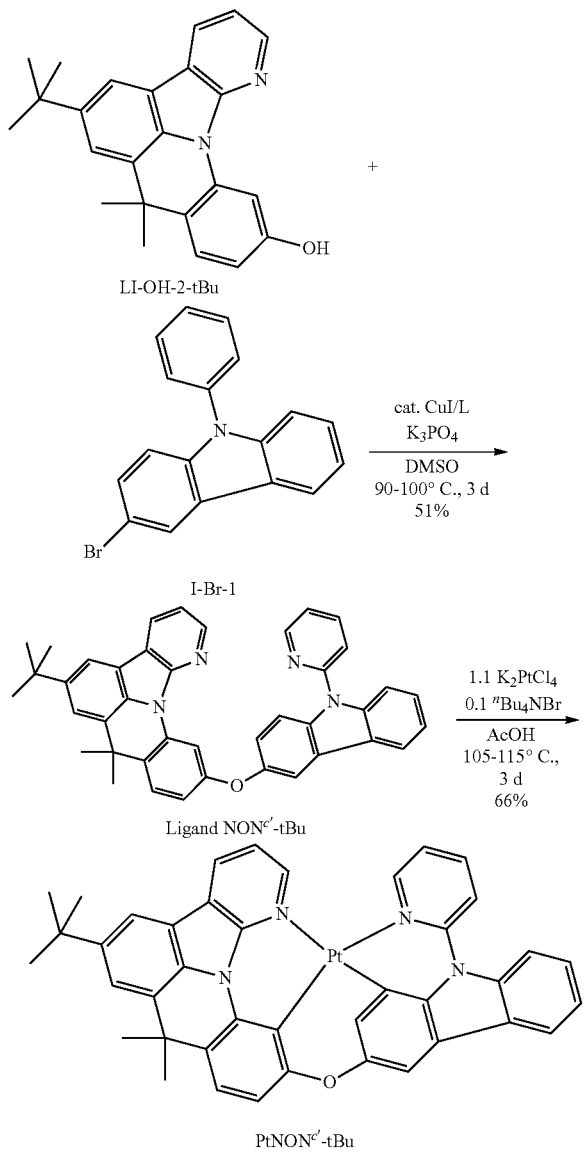

Synthesis of Ligand NON$^{C'}$-tBu: 2-Bromo-9-(pyridin-2-yl)-9H-carbazole I-Br-1 (163 mg, 0.51 mmol, 1.2 eq), LI-OH-2-tBu (150 mg, 0.42 mmol, 1.0 eq), CuI (8 mg, 0.042 mmol, 0.1 eq), picolinic acid (10 mg, 0.084 mmol, 0.2 eq) and K$_3$PO$_4$ (178 mg, 0.84 mmol, 2.0 eq) were added to a dry Schlenck tube equipped with a magnetic stir bar. The tube was evacuated and backfilled with nitrogen. The evacuation and backfill procedure was repeated for three cycles. Then DMSO (4 mL) was added under nitrogen. The mixture was stirred in an oil bath at a temperature of 95-105° C. for 3 days and then cooled to ambient temperature. Water was added to dissolve solid. The mixture was extracted with ethyl acetate three times. The combined organic layers were washed with water three times, dried over sodium sulfate, filtered, and concentrated under reduced pressure. The resulting residue was purified through column chromatography on silica gel using hexane/ethyl acetate (10:1-5:1) as eluent to obtain the desired product Ligand NON$^{C'}$-tBu as a brown solid 128 mg in 51% yield. $^1$H NMR (DMSO-d$_6$, 500 MHz): δ 1.45 (s, 9H), 1.74 (s, 6H), 6.83 (dd, J=8.5, 3.0 Hz, 1H), 7.13 (dd, J=8.5, 2.5 Hz, 1H), 7.32-7.37 (m, 2H), 7.42-7.48 (m, 2H), 7.59 (d, J=2.5 Hz, 1H), 7.72 (dd, J=5.0, 3.5 Hz, 2H), 7.80-7.82 (m, 2H), 8.03 (td, J=8.0, 2.0 Hz, 1H), 8.09 (d, J=1.5 Hz, 1H), 8.24 (d, J=7.0 Hz, 1H), 8.29 (d, J=8.5 Hz, 1H), 8.44 (dd, J=5.0, 2.0 Hz, 1H), 8.64-8.67 (m, 2H), 9.30 (d, J=2.5 Hz, 1H).

Figure 5:
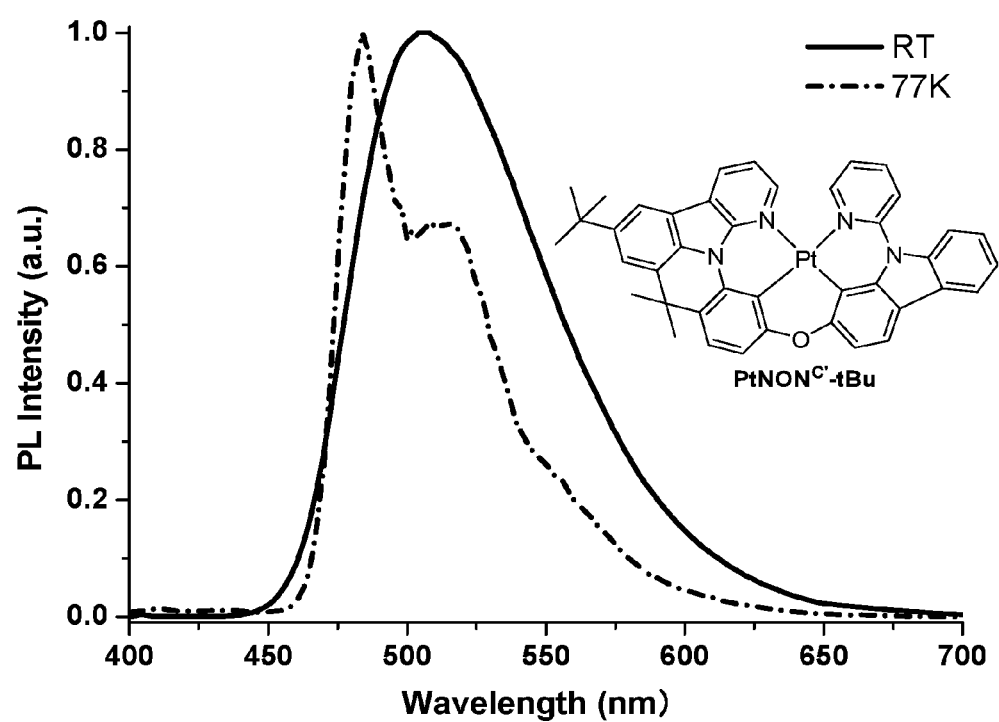
FIG. 5 shows emission spectra of $PtNON^{C'}$-tBu in $CH_2Cl_2$ at room temperature and in 2-methyltetrahydrofuran at 77K.

Synthesis of PtNON$^{C'}$-tBu: Ligand NON$^{C'}$-tBu (60 mg, 0.10 mmol, 1.0 eq), K$_2$PtCl$_4$ (46 mg, 0.11 mmol, 1.1 eq), and $^n$Bu$_4$NBr (3 mg, 0.01 mmol, 0.1 eq) were added to a three necked flask equipped with a magnetic stir bar and a condenser. The flask was evacuated and backfilled with nitrogen. The evacuation and backfill procedure was repeated for three cycles. Then acetic acid (10 mL) was added under nitrogen. The mixture was stirred at 105-115° C. for 3 days, cooled to ambient temperature, and concentrated under reduced pressure. The resulting residue was purified through flash column chromatography on silica gel using dichloromethane/hexane (2:1) as eluent to obtain the desired product PtNON$^{C'}$-tBu as a yellow solid 52.5 mg in 66% yield. $^1$H NMR (DMSO-d$_6$, 500 MHz): δ 1.48 (s, 9H), 1.79 (s, 6H), 7.07 (t, J=8.5 Hz, 2H), 7.25-7.27 (m, 1H), 7.39-7.43 (m, 2H), 7.49-7.52 (m, 1H), 7.55 (d, J=9.5 Hz, 1H), 7.81 (s, 1H), 7.82 (d, J=9.5 Hz, 1H), 8.09 (d, J=7.5 Hz, 1H), 8.14-8.15 (m, 3H), 8.22 (d, J=1.5 Hz, 1H), 8.53-8.54 (m, 1H), 8.75 (d, J=6.0 Hz, 1H), 8.96 (dd, J=7.5, 1.5 Hz, 1H). Emission spectra of PtNON$^{C'}$-tBu at room temperature in CH$_2$Cl$_2$ and at 77K in 2-methyltetrahydrofuran are shown in FIG. 5.

In another aspect, PdNON$^{C'}$-tBu can be synthesized as follows:

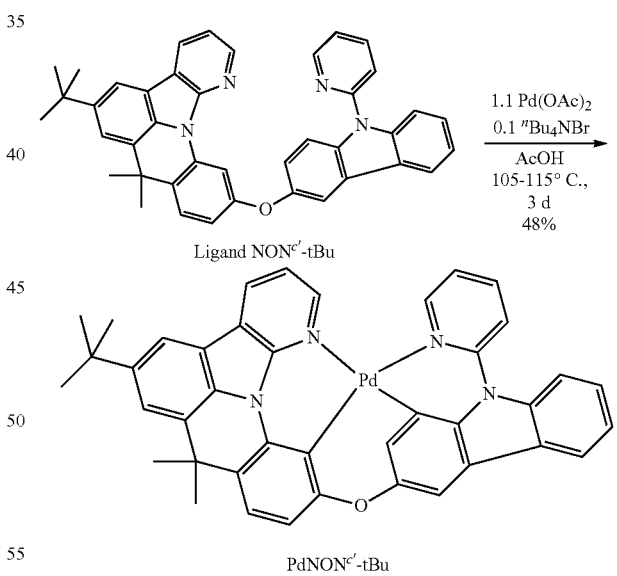

Figure 6:
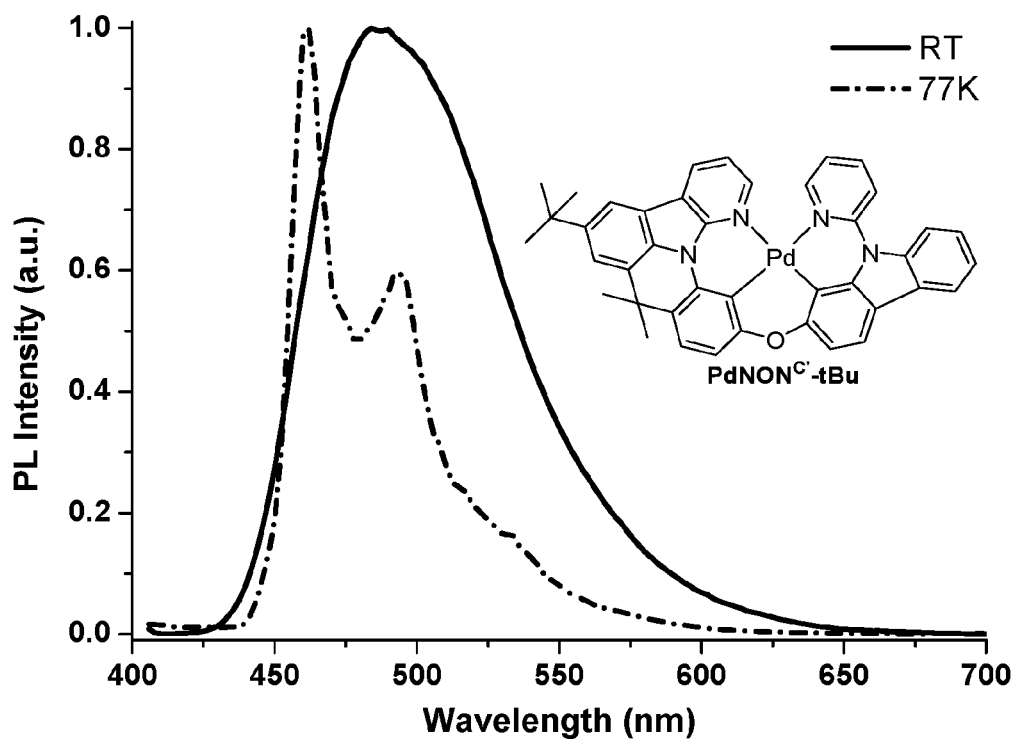
FIG. 6 shows emission spectra of $PdNON^{C'}$-tBu in $CH_2Cl_2$ at room temperature and in 2-methyltetrahydrofuran at 77K, in accordance with various aspects of the present disclosure.

Synthesis of PdNON$^{C'}$-tBu: Ligand NON$^{C'}$-tBu (60 mg, 0.10 mmol, 1.0 eq), Pd(OAc)$_2$ (25 mg, 0.11 mmol, 1.1 eq), and $^n$Bu$_4$NBr (3 mg, 0.0129 mmol, 0.1 eq) were added to a three necked flask equipped with a magnetic stir bar and a condenser. The flask was evacuated and backfilled with nitrogen. The evacuation and backfill procedure was repeated for three cycles. Then acetic acid (10 mL) was added under nitrogen. The mixture was stirred at 105-115° C. for 3 days, cooled to ambient temperature, and concentrated under reduced pressure. The resulting residue was purified through flash column chromatography on silica gel using dichloromethane/hexane (1:1) as eluent to obtain the desired product PdNON$^{C'}$-tBu as a slight yellow solid 33.5 mg in 48% yield. $^1$H NMR (DMSO-d$_6$, 500 MHz): δ 1.48 (s, 9H), 1.79 (s, 6H), 7.08 (d, J=6.0 Hz, 1H), 7.10 (d, J=6.5 Hz, 1H), 7.25-7.31 (m, 1H), 7.39-7.45 (m, 2H), 7.49-7.52 (m, 1H), 7.59 (d, J=9.0 Hz, 1H), 7.80 (d, J=1.0, Hz, 1H), 7.90 (d, J=7.5 Hz, 1H), 8.09 (d, J=8.0 Hz, 1H), 8.116 (s, 1H), 8.12 (d, J=0.5 Hz, 1H), 8.16 (d, J=8.0 Hz, 1H), 8.21 (d, J=2.0 Hz, 1H) 8.37 (dd, J=5.5, 1.0 Hz, 1H), 8.64 (d, J=6.0 Hz, 1H), 8.89 (dd, J=7.5, 1.5 Hz, 1H). Emission spectra of PdNON$^{C'}$-tBu at room temperature in CH$_2$Cl$_2$ and at 77K in 2-methyltetrahydrofuran are shown in FIG. 6

In yet another aspect, PtNON$^{CC}$ and PdNON$^{CC}$ can be synthesized as follows:

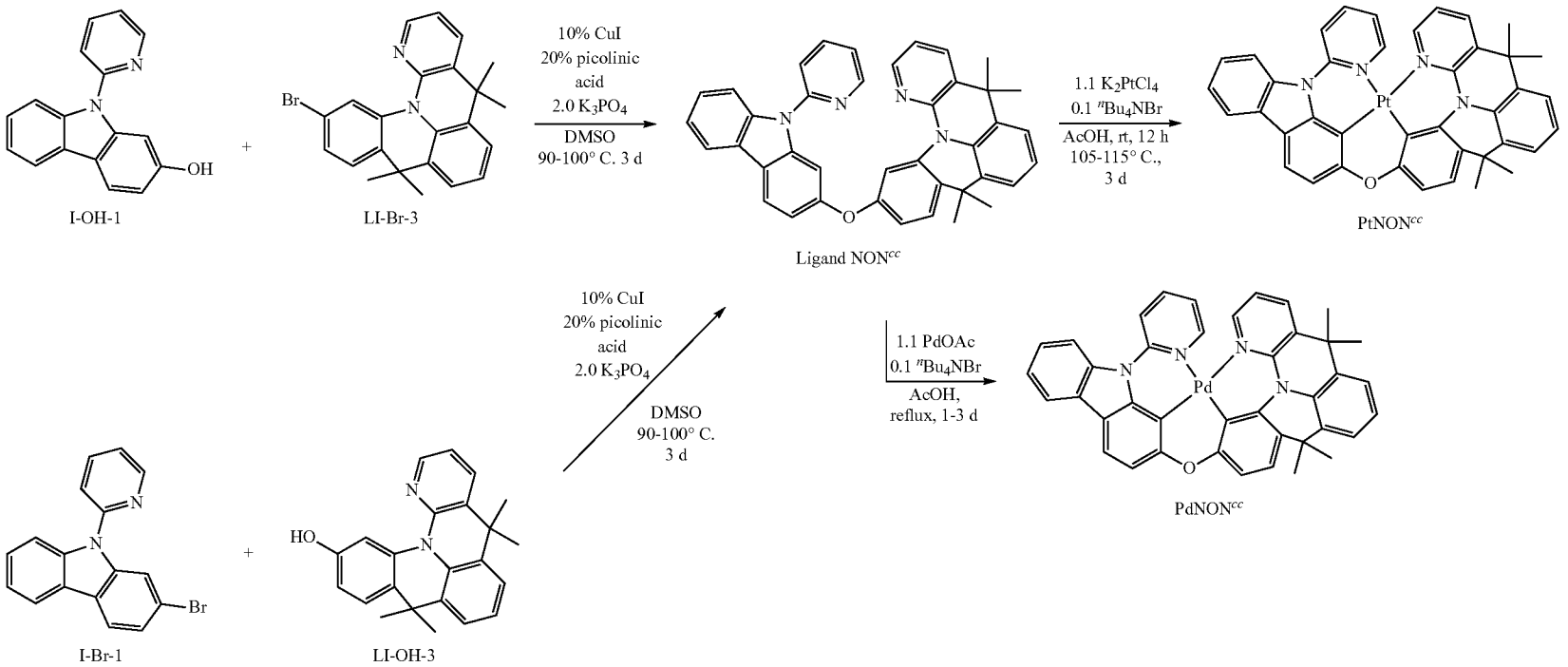

In yet another aspect, PtNON$^{C'}$ and PdNON$^{C'}$ can be synthesized as follows:

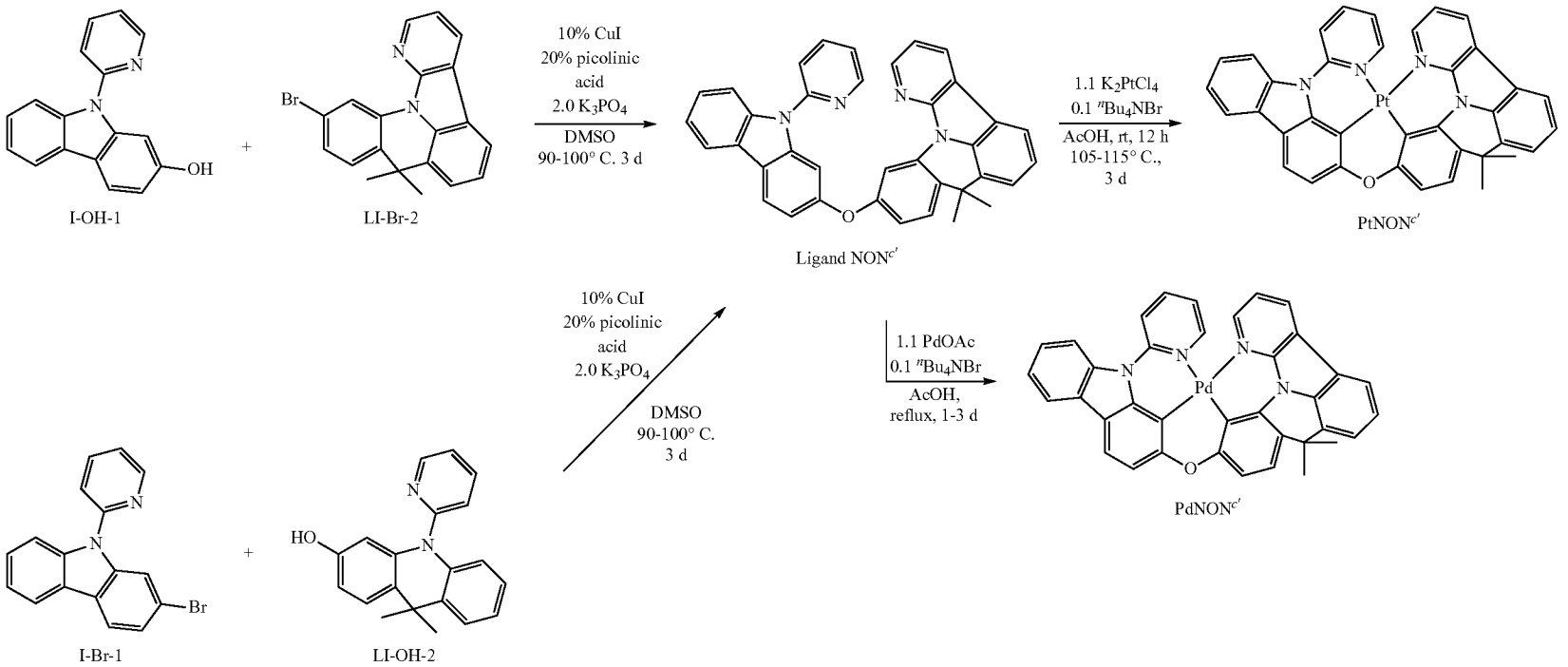

In yet another aspect, PtN$^{C'}$ON$^C$ and PdN$^{C'}$ON$^C$ can be synthesized as follows:

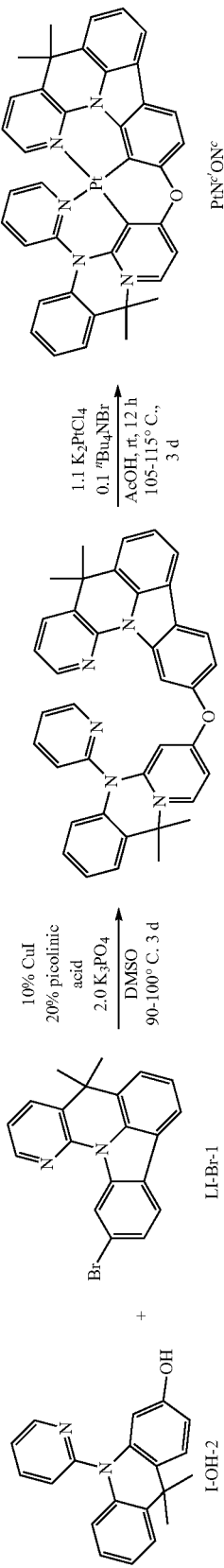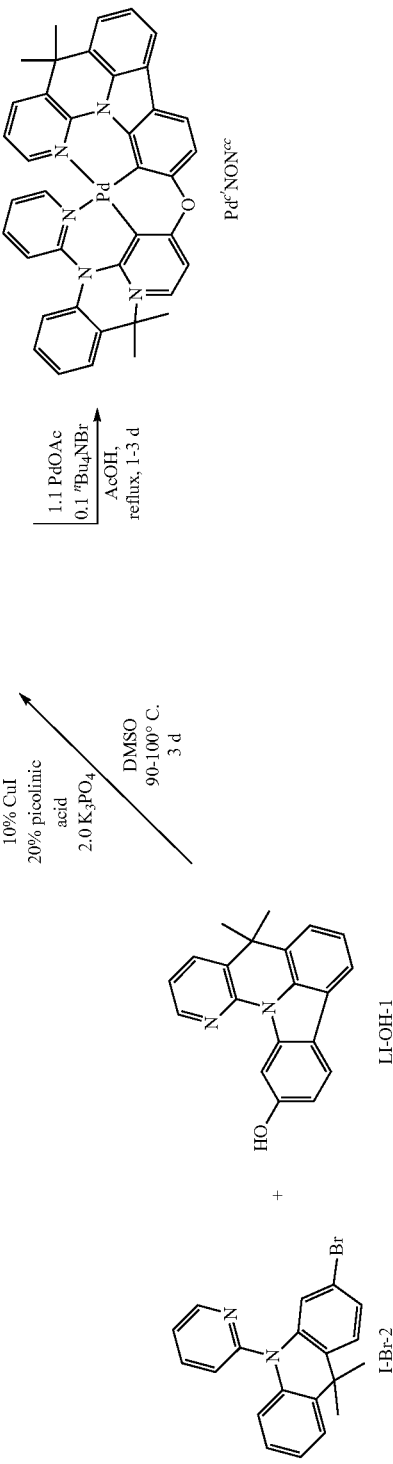

A general synthesis route for the disclosed Pt and Pd complexes of Formula AIII herein includes:
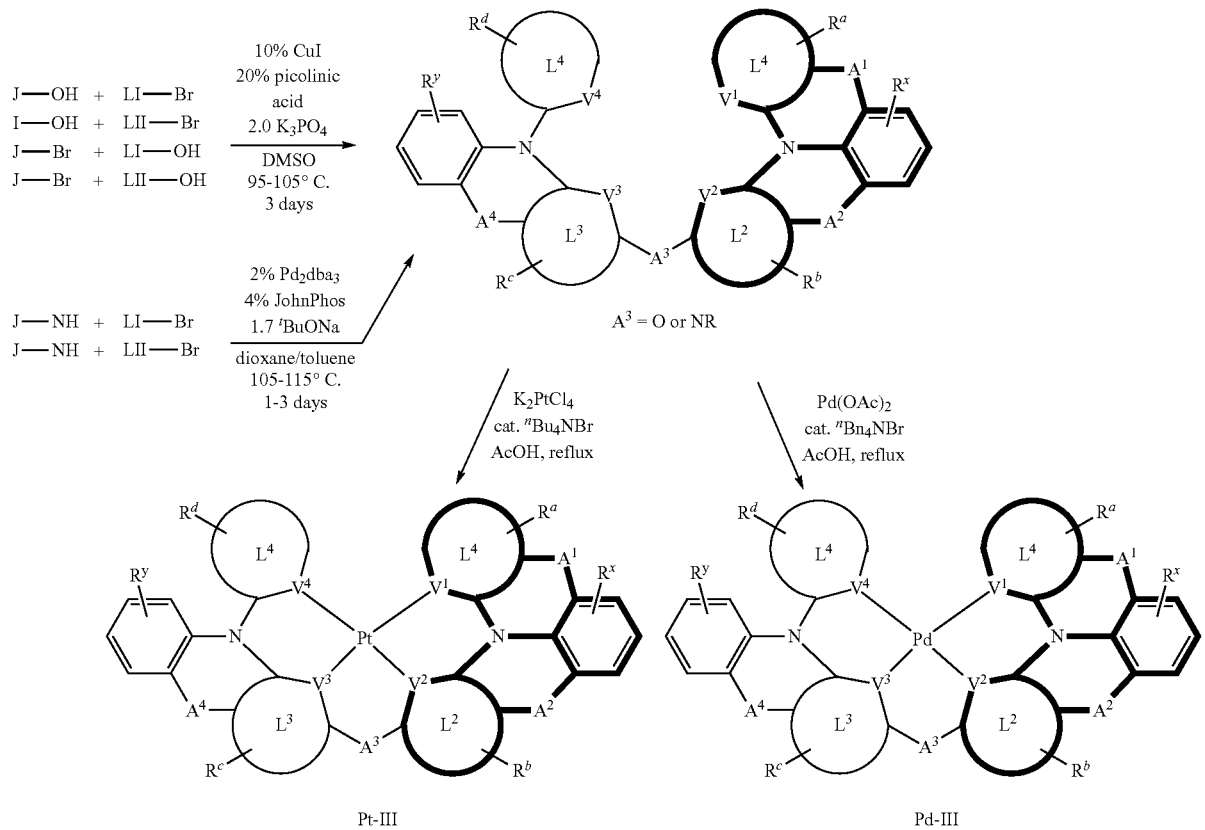
For example, in one aspect, PtN$^C$ON' and PdN$^C$ON' can be synthesized as follows:

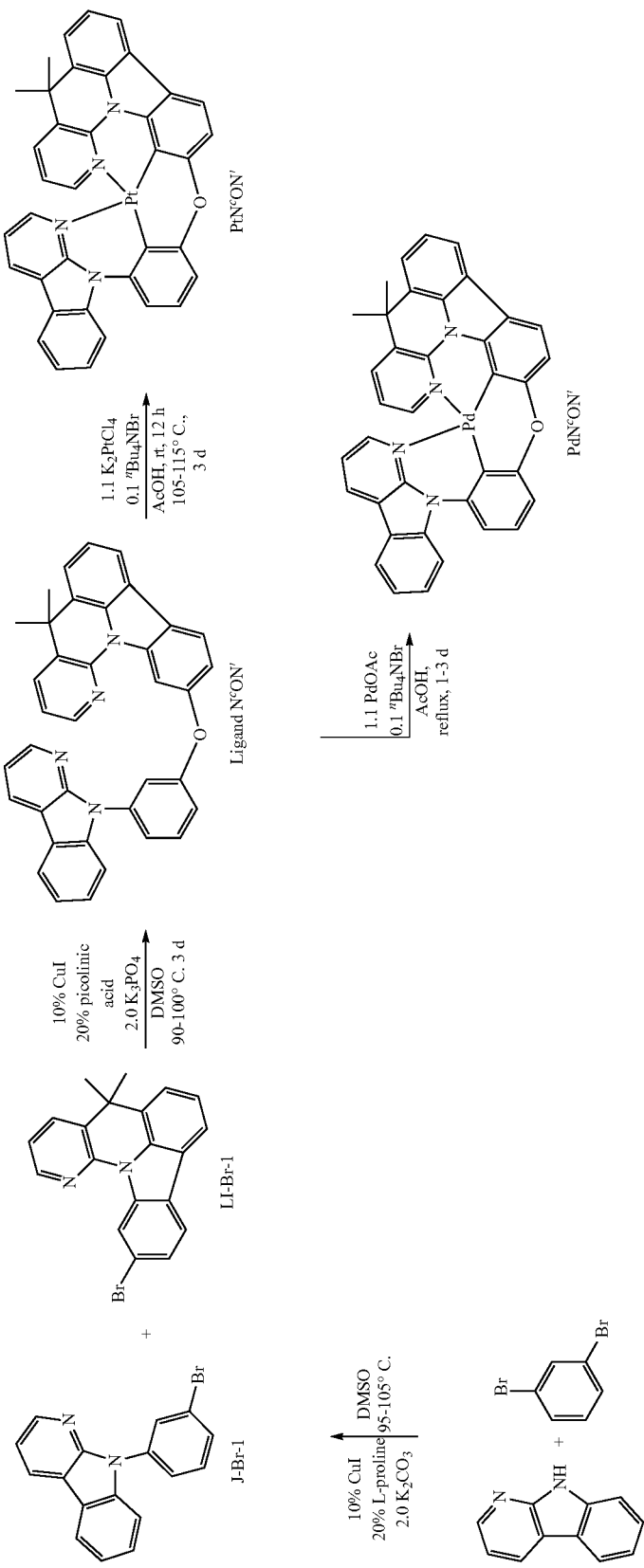

In another aspect, PtN$^C$ON'-tBu and PdN$^C$ON'-tBu can be synthesized as follows:

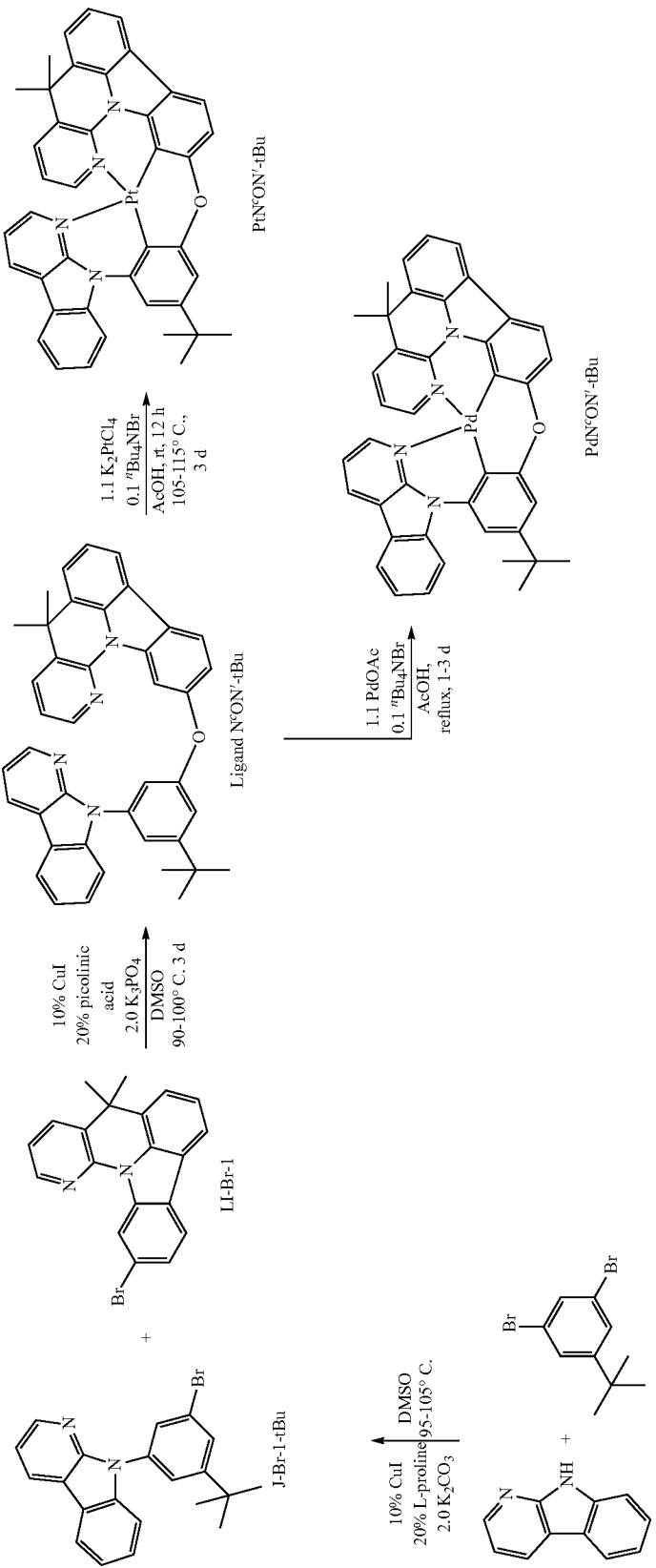

In yet another aspect, PtN'ON$^{C'}$ and PdN'ON$^{C'}$ can be synthesized as follows:

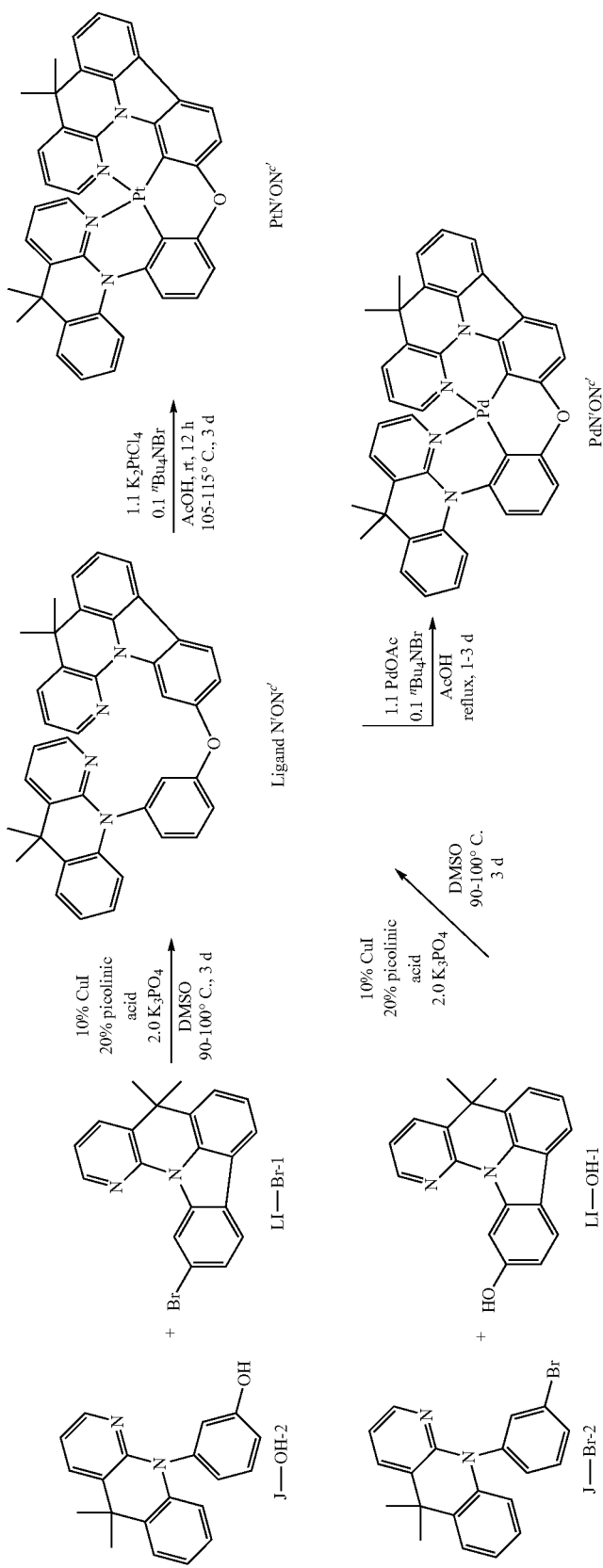

A general synthesis route for the disclosed Pt and Pd complexes of Formula AIV herein includes:
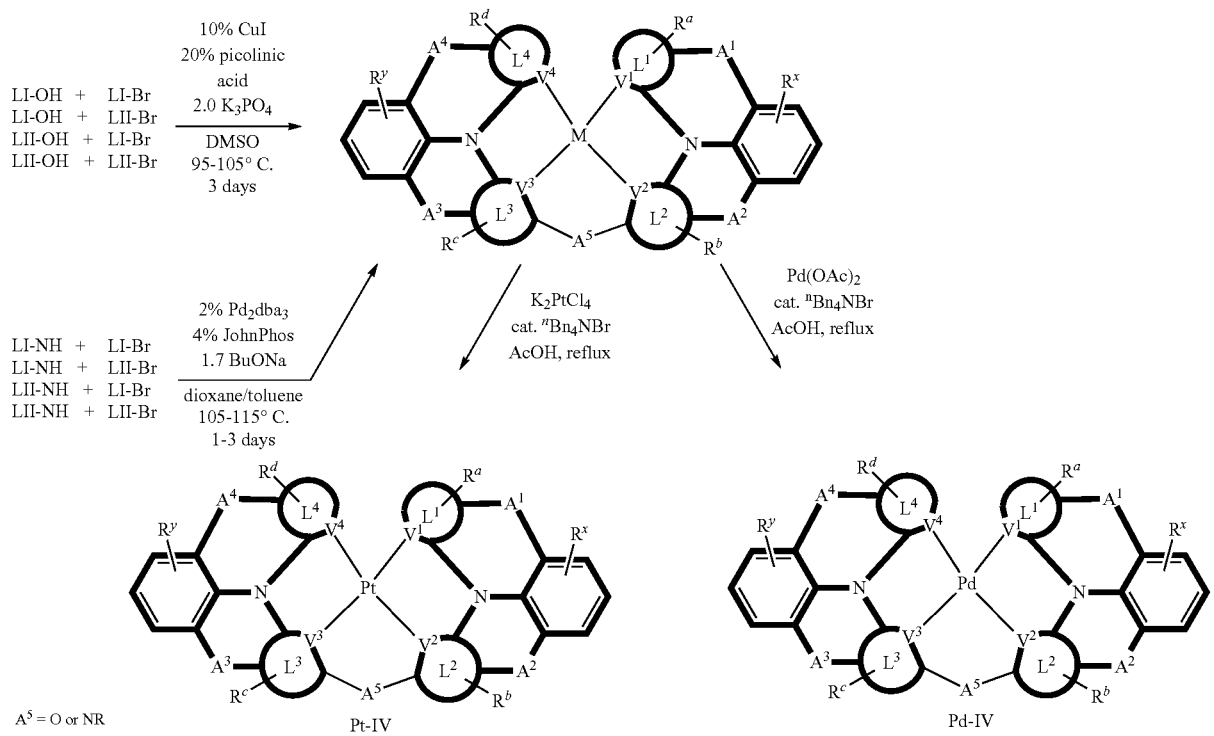
For example, in other aspects, PtN$^C$ON$^C$ and PdN$^C$ON$^C$ can be synthesized as follows:
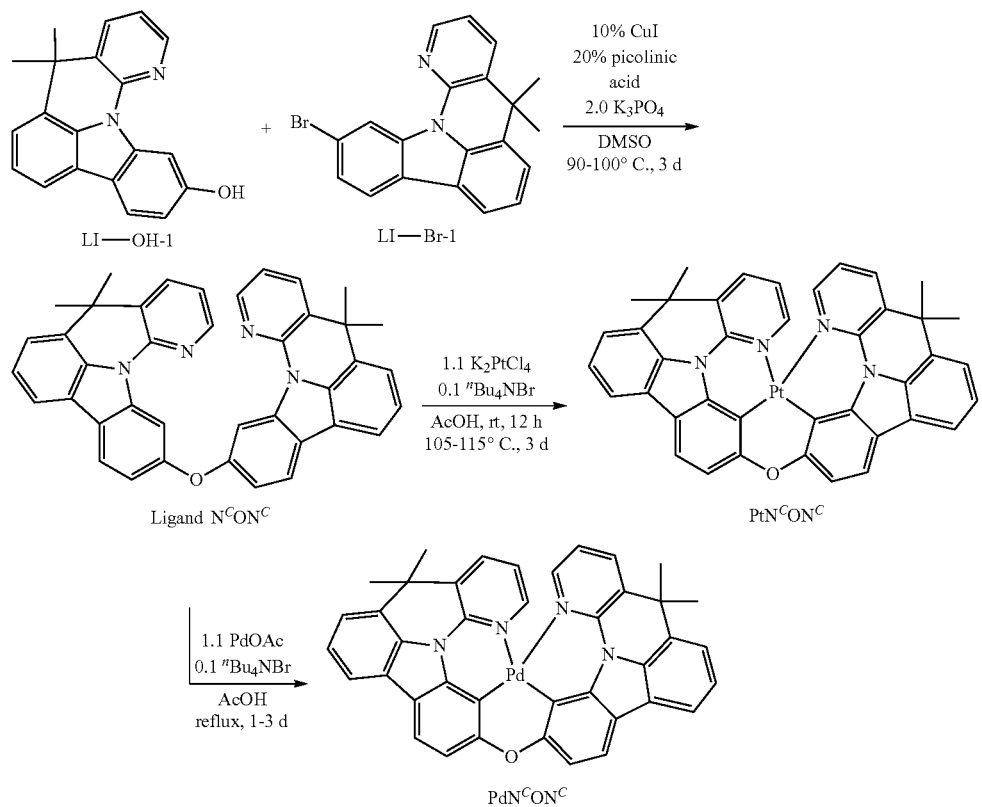

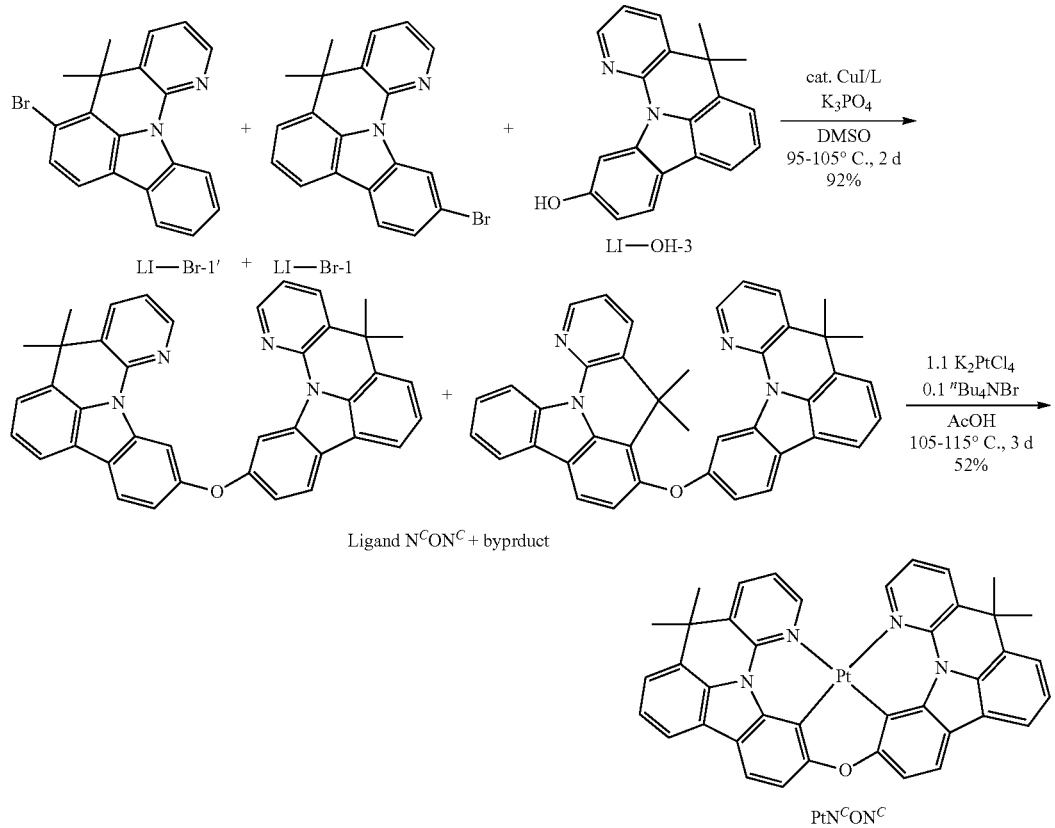

Synthesis of Ligand N$^C$ON$^C$: LI-OH-3 (413 mg, 1.38 mmol, 1.0 eq), LI-Br-1 and LI-Br-1' (1000 mg, 2.75 mmol, 2.0 eq, LI-Br-1 and LI-Br-1' as a mixture with a ratio of 1.06:1.00 from $^1$H NMR), CuI (53 mg, 0.28 mmol, 0.2 eq), picolinic acid (69 mg, 0.56 mmol, 0.4 eq) and K$_3$PO$_4$ (583 mg, 2.75 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (6 mL) was added under the protection of nitrogen. The mixture was stirred in an oil bath at a temperature of 95-105° C. for 2 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (10:1) as and eluent to obtain a mixture of the desired product Ligand N$^C$ON$^C$+by-product as a brown solid 0.74 g in 92% yield. $^1$H NMR (DMSO-d$_6$, 500 MHz) for the Ligand N$^C$ON$^C$: δ 1.73 (s, 12H), 7.14 (dd, J=10.0, 2.5 Hz, 2H), 7.19 (dd, J=9.5, 6.0 Hz, 2H), 7.40 (t, J=10.0 Hz, 2H), 7.57 (d, J=9.0 Hz, 2H), 8.00 (d, J=9.0 Hz, 2H), 8.13 (dd, J=10.0, 2.0 Hz, 2H), 8.24 (d, J=10.0 Hz, 2H), 8.27 (dd, J=6.0, 2.0 Hz, 2H), 8.76 (d, J=2.0 Hz, 2H).

Figure 7:
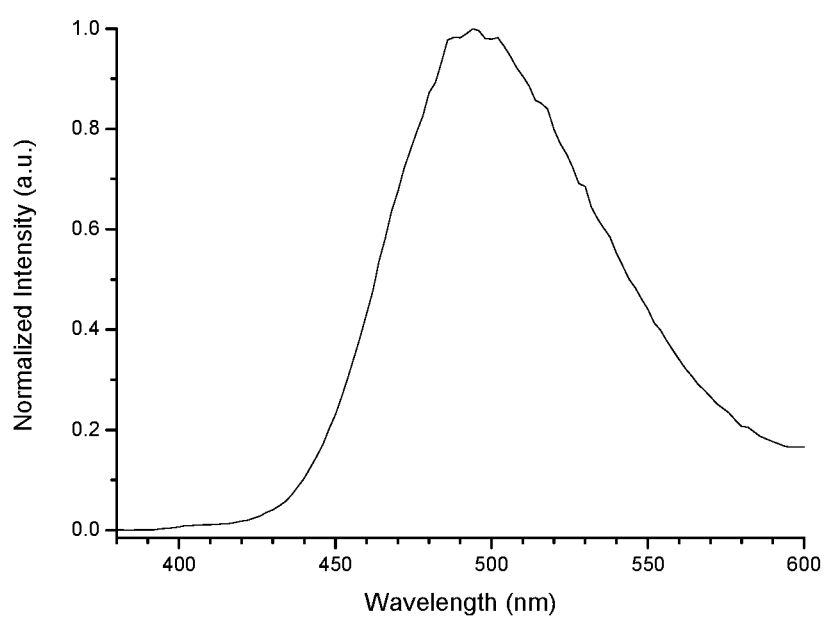
FIG. 7 shows an emission spectrum of $PtN^cON^c$ at room temperature in dichloromethane.

Synthesis of PtN$^C$ON$^C$: Ligand N$^C$ON$^C$+by-product (720 mg, 1.23 mmol, 1.0 eq), K$_2$PtCl$_4$ (570 mg, 1.36 mmol, 1.1 eq), $^n$Bu$_4$NBr (39 mg, 0.12 mmol, 0.1 eq) were added to a three necked flask equipped with a magnetic stir bar and a condenser. The flask was evacuated and backfilled with nitrogen. The evacuation and backfill procedure was repeated for a total of three times. Then solvent acetic acid (74 mL) was added under the protection of nitrogen. The mixture was stirred at 105-115° C. for another 3 days, cooled down to ambient temperature. The solvent was removed under reduced pressure and the residue was purified through flash column chromatography on silica gel using dichloromethane/hexane (1:1-2:1) as eluent to obtain the desired product PtN$^C$ON$^C$ as a solid 500 mg in 52% yield. $^1$H NMR (DMSO-d$_6$, 500 MHz): δ 1.82 (s, 12H), 7.11 (t, J=6.0 Hz, 2H), 7.20 (d, J=8.5 Hz, 2H), 7.43 (t, J=7.5 Hz, 2H), 7.54 (d, J=7.0 Hz, 2H), 7.92 (d, J=8.5 Hz, 2H), 7.94 (d, J=8.0 Hz, 2H), 8.14 (d, J=6.0 Hz, 2H), 8.34 (d, J=7.5 Hz, 2H). FIG. 7 shows an emission spectrum of PtN$^C$ON$^C$ at room temperature in dichloromethane.

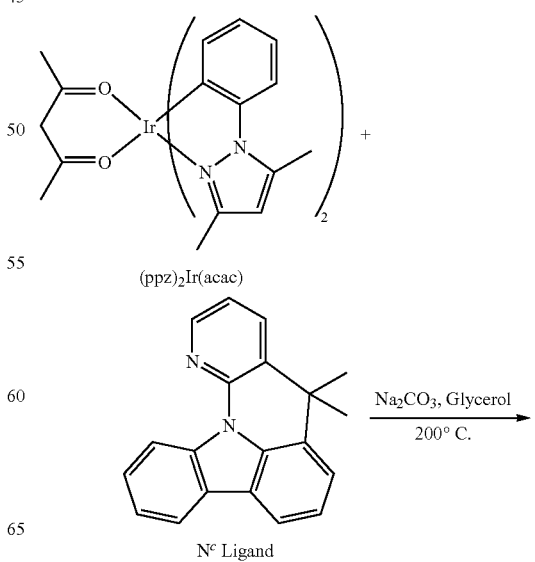

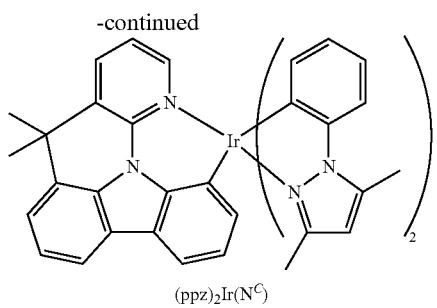

(ppz)$_2$Ir(N$^C$)

To a 100 ml three-neck round bottom flask were added (ppz)$_2$Ir(acac) (150 mg, 0.24 mmol), 5,5-dimethyl-5H-[1,8] naphthyridino[3,2,1-jk]carbazole (N$^c$ ligand, 79 mg, 0.26 mmol), Na$_2$CO$_3$ (36 mg, 0.6 mmol). The flask was evacuated and backfilled with nitrogen three times. Glycerol (20 ml) was added under the protection of nitrogen, and the reaction mixture was stirred at 200° C. under nitrogen atmosphere for 24 hours. After cooling to room temperature, water (30 ml) was added and the mixture was extracted three times with 30 ml of DCM. The combined organic layer was dried with anhydrous Na$_2$SO$_4$, filtered, concentrated under reduced pressure, and purified by column chromatography with DCM as eluent to afford the desired product (ppz)$_2$Ir(N$^c$) as a light yellow solid. MS (LC-MS) for C$_{42}$H$_{37}$IrN$_6$ [M]$^+$: calcd 818.27, found 819.2.

In another aspect, PtN$^{C'}$ON$^{C'}$ and PdN$^{C'}$ON$^{C'}$ can be synthesized as follows:

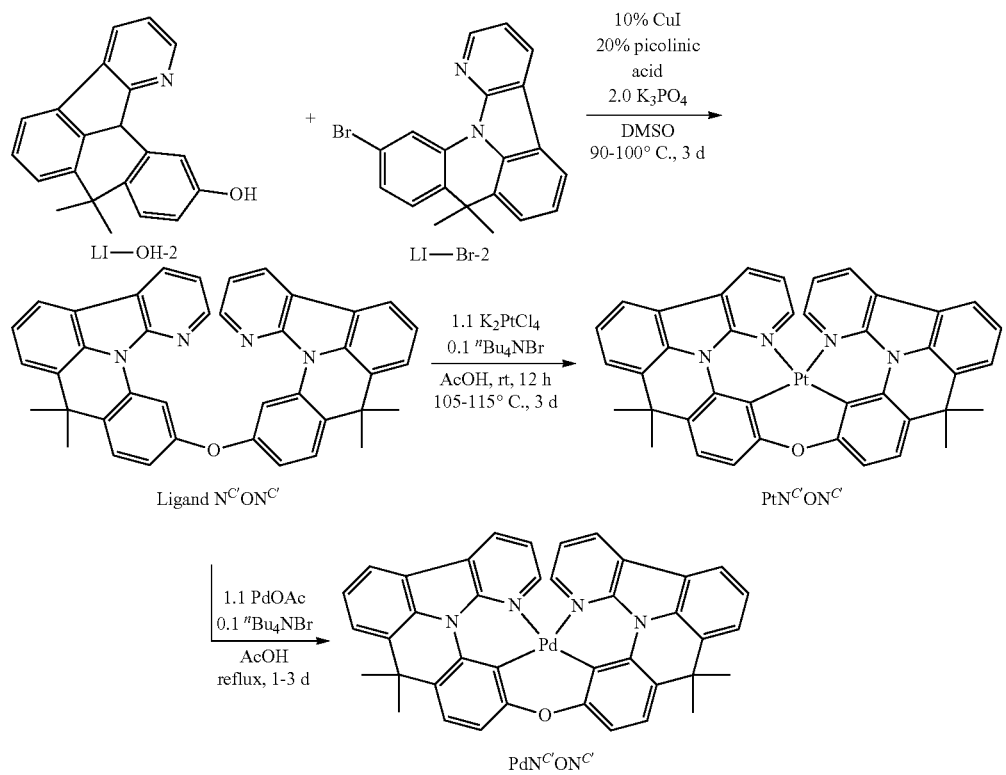

In yet another aspect, PtN$^{CC}$ON$^{CC}$ and PdN$^{CC}$ON$^{CC}$ can be synthesized as follows:

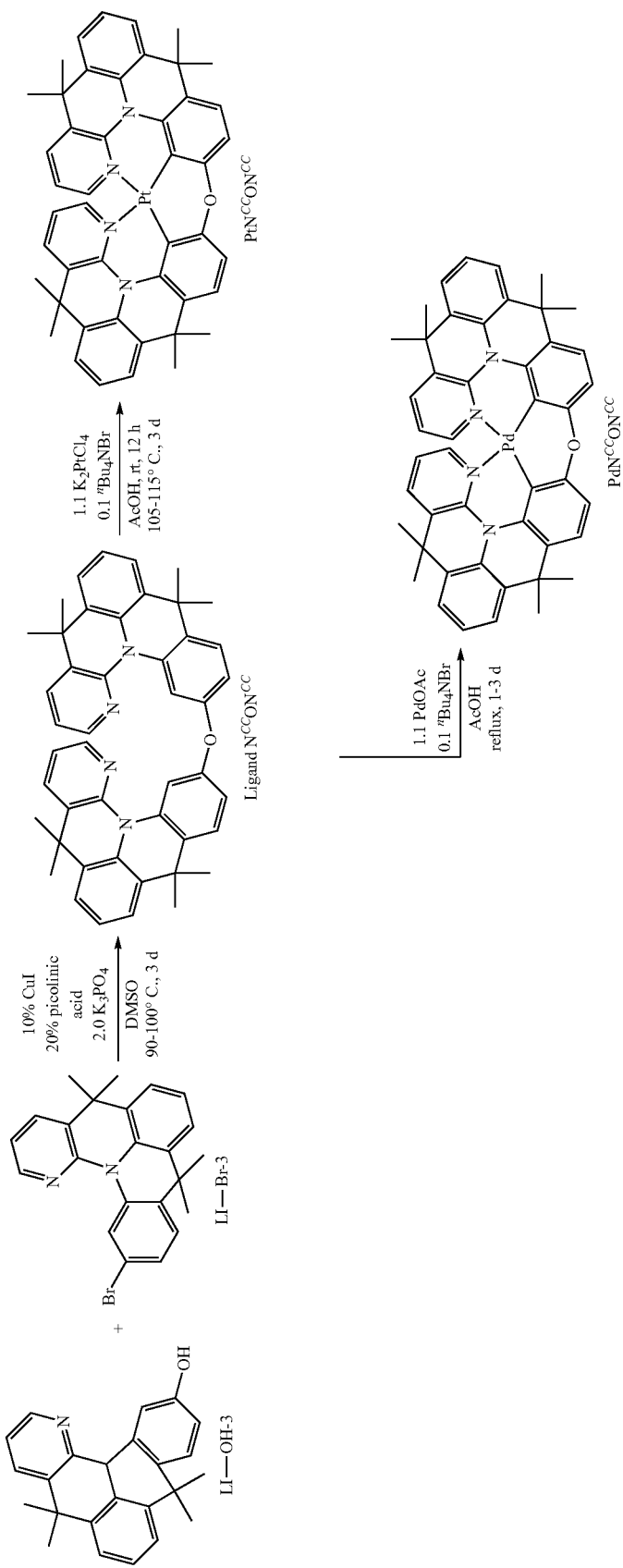

In yet another aspect, $PtN^CON^{C'}$ and $PdN^CON^{C'}$ can be synthesized as follows:

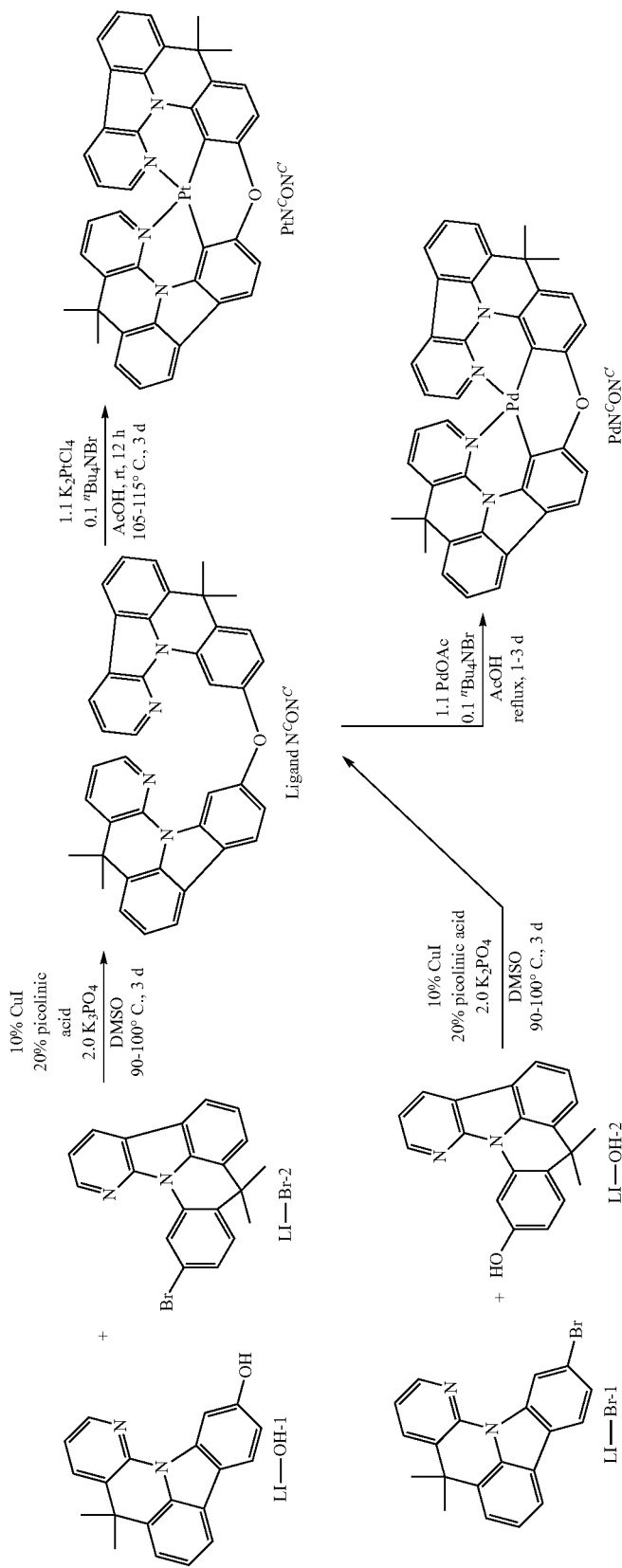

In yet another aspect, PtN$^C$ON$^{CC}$ and PdN$^C$ON$^{CC}$ can be synthesized as follows:

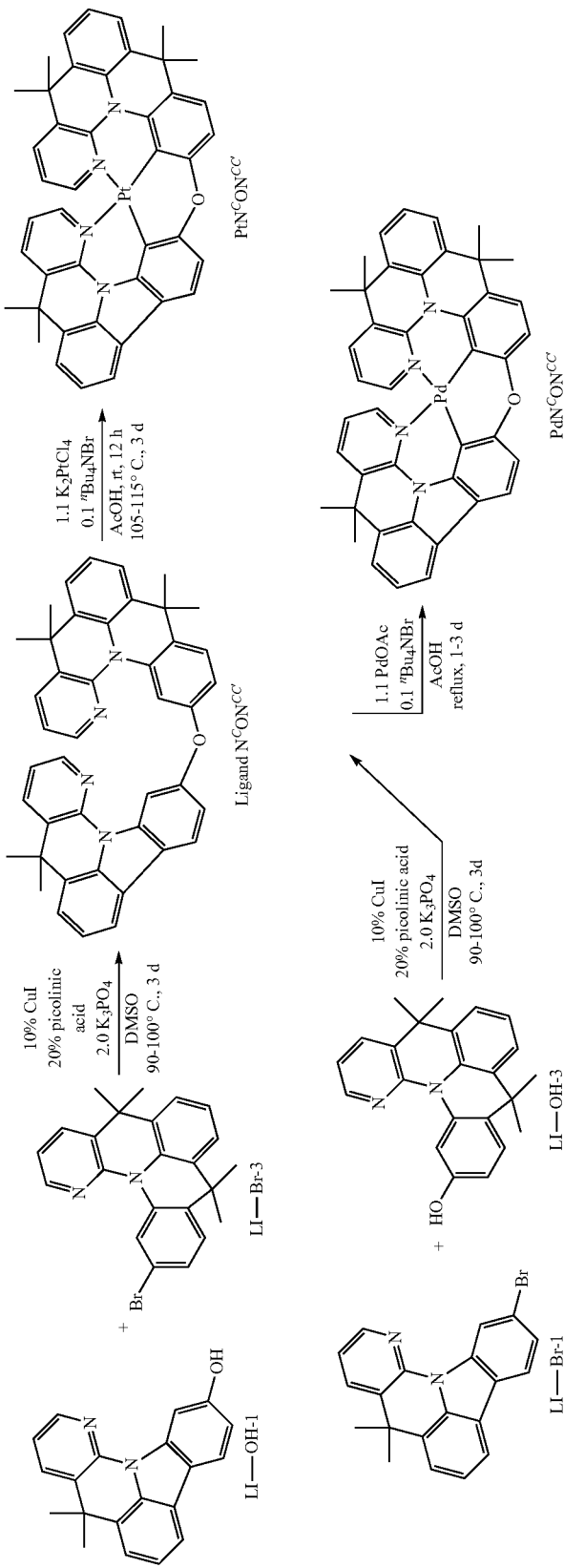

In yet another aspect, $PtN^{C'}ON^{CC}$ and $PdN^{C'}ON^{CC}$ can be synthesized as follows:

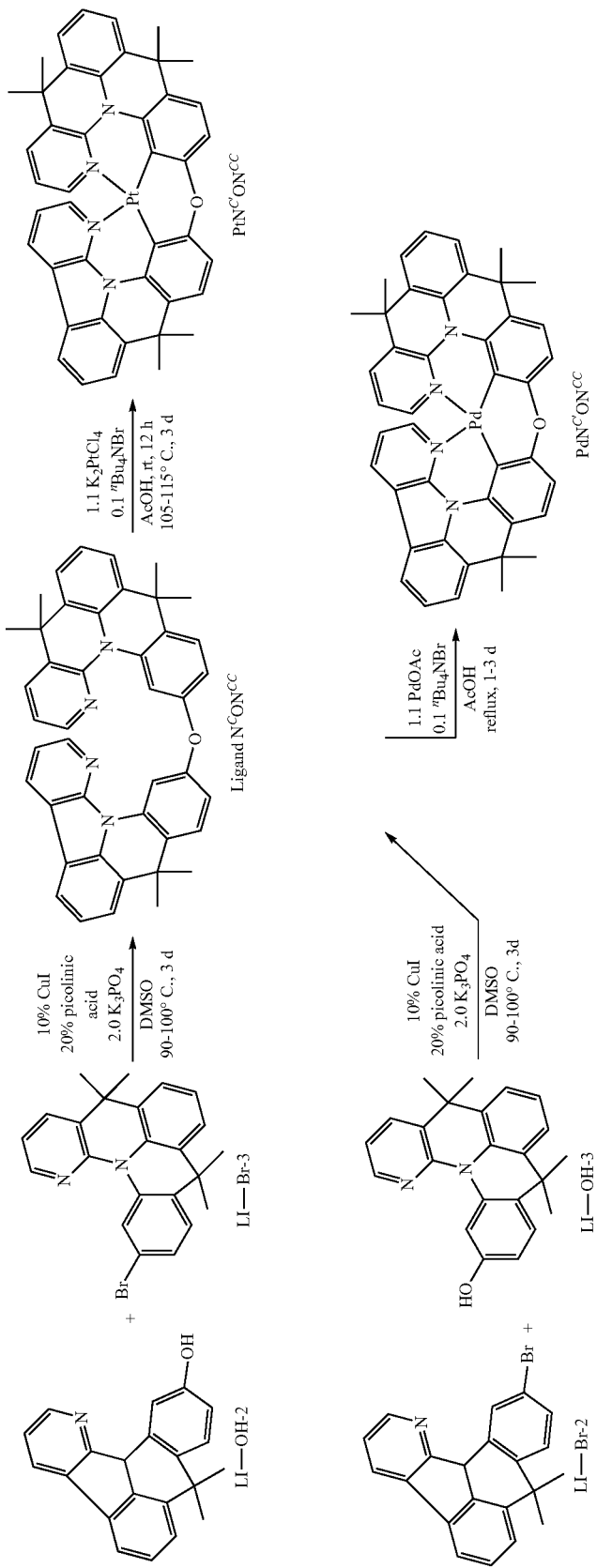

In yet another aspect, PtN$^C$NN$^C$ and PdN$^C$NN$^C$ can be synthesized as follows:

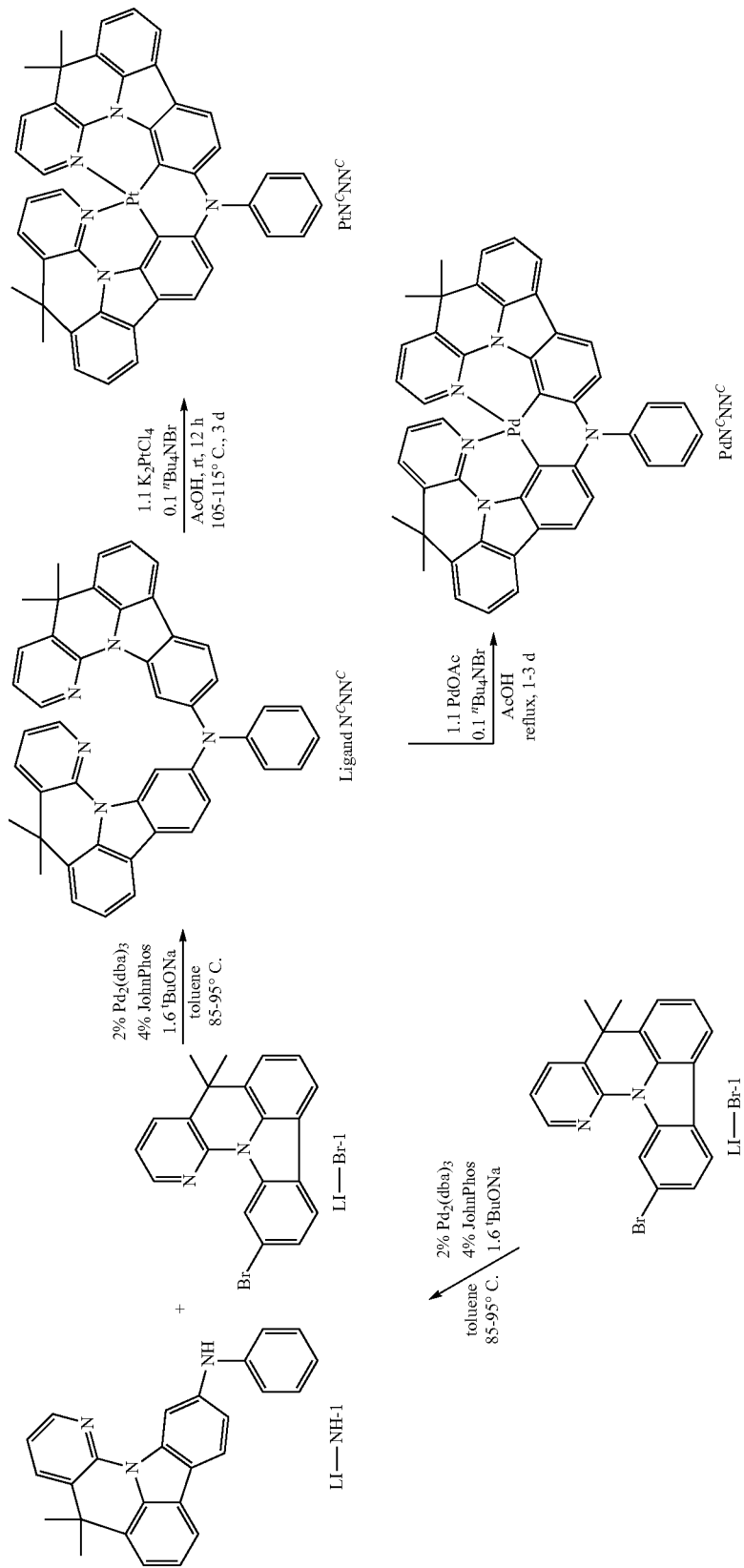

A general synthesis route for the disclosed Pt and Pd complexes of Formula AV herein includes:
E-NH + LI-Br
F-NH + LI-Br
G-NH + LI-Br
H-NH + LI-Br
K-NH + LI-Br
L-NH + LI-Br
E-NH + LII-Br
F-NH + LII-Br
G-NH + LII-Br
H-NH + LII-Br
K-NH + LII-Br
L-NH + LII-Br
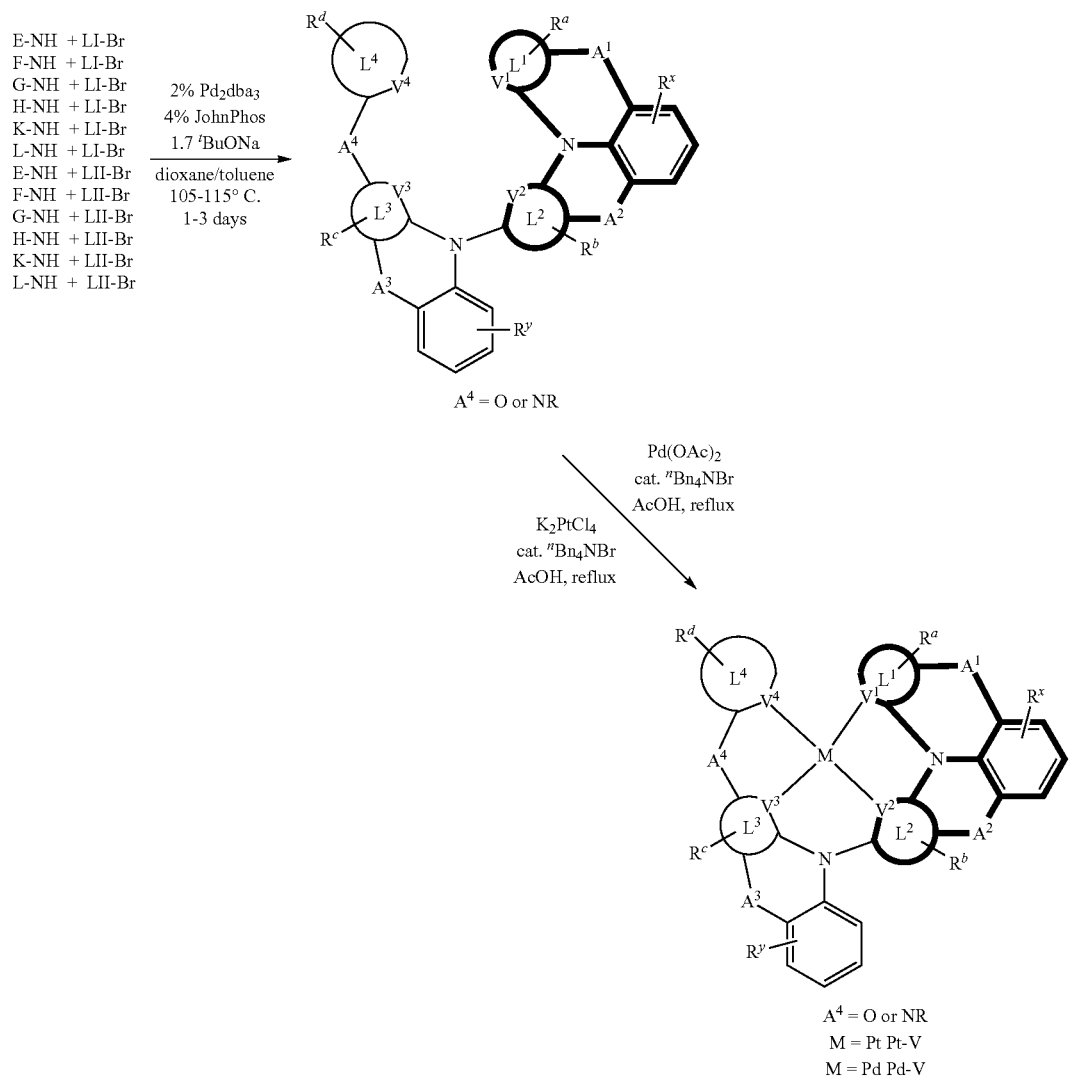
For example, in one aspect, PtN$^C$1N-DM and PdN$^C$1N-DM can be synthesized as follows:
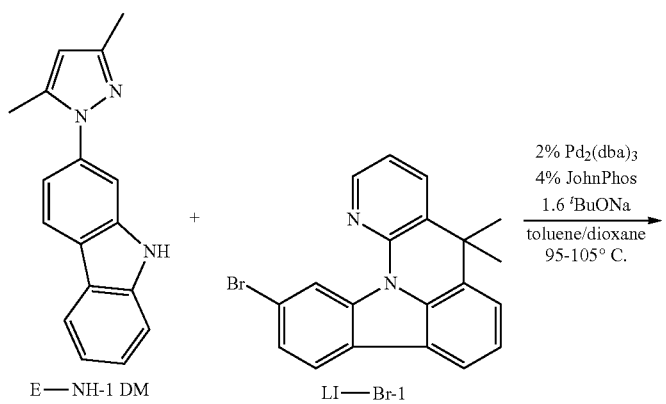

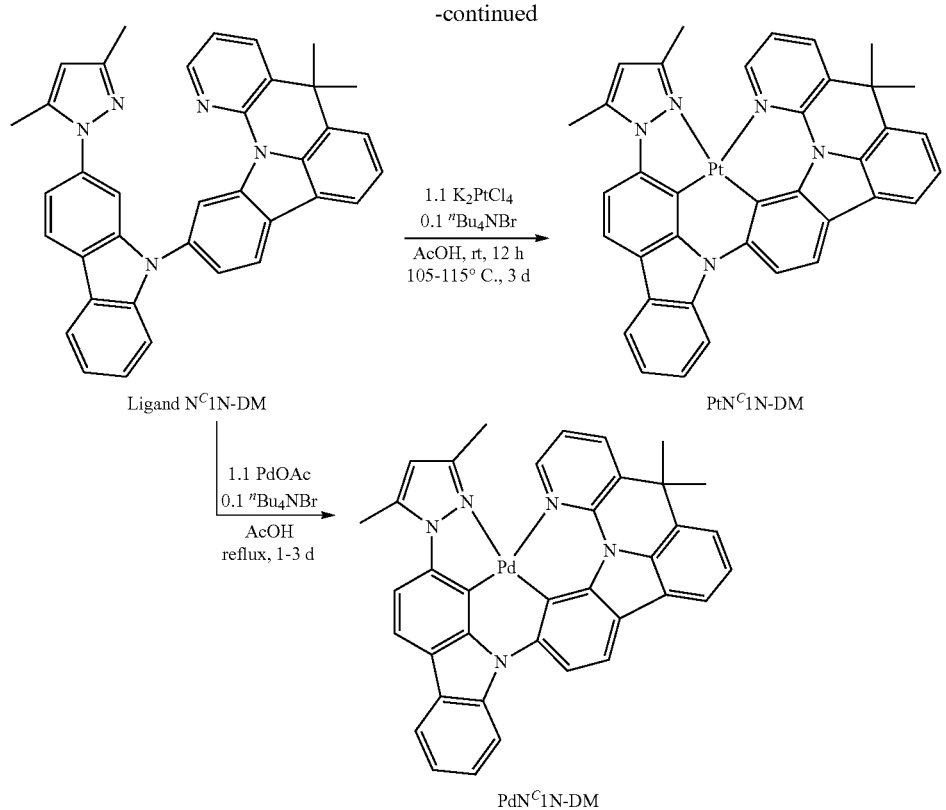
In another aspect, PtN$^C$1N and PdN$^C$1N can be synthesized as follows:
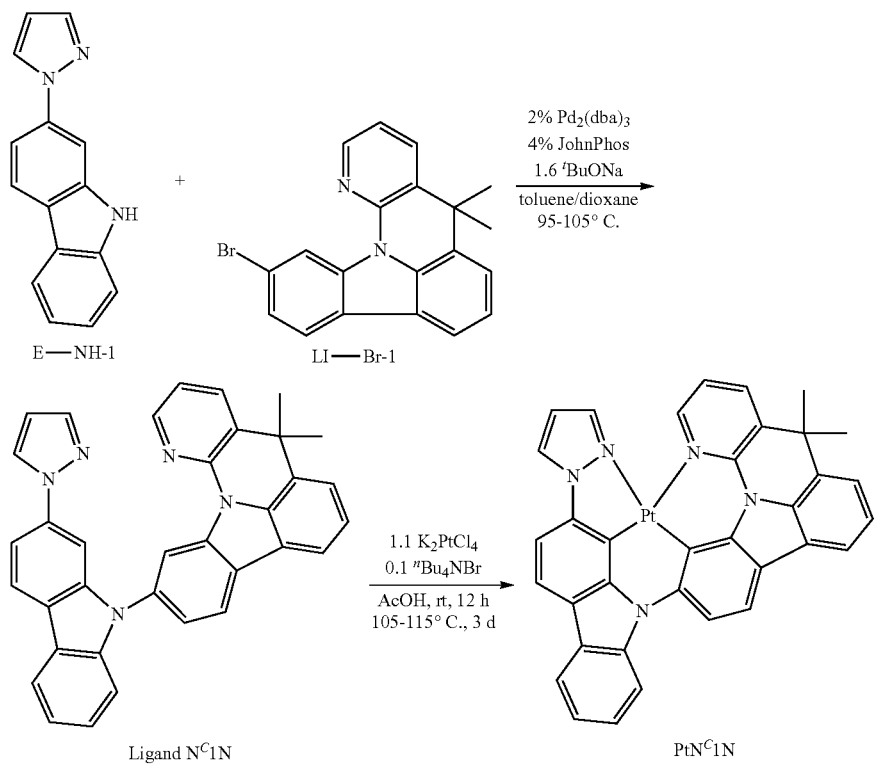

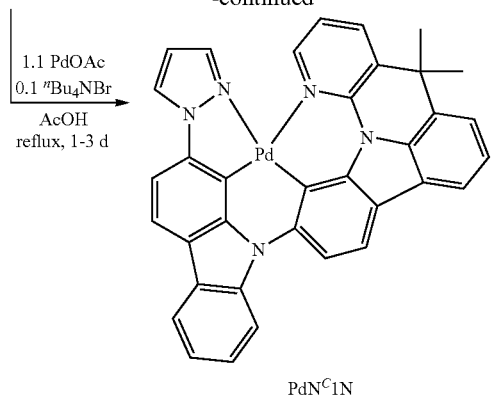
In yet another aspect, PtN$^C$3N and PdN$^C$3N can be synthesized as follows:
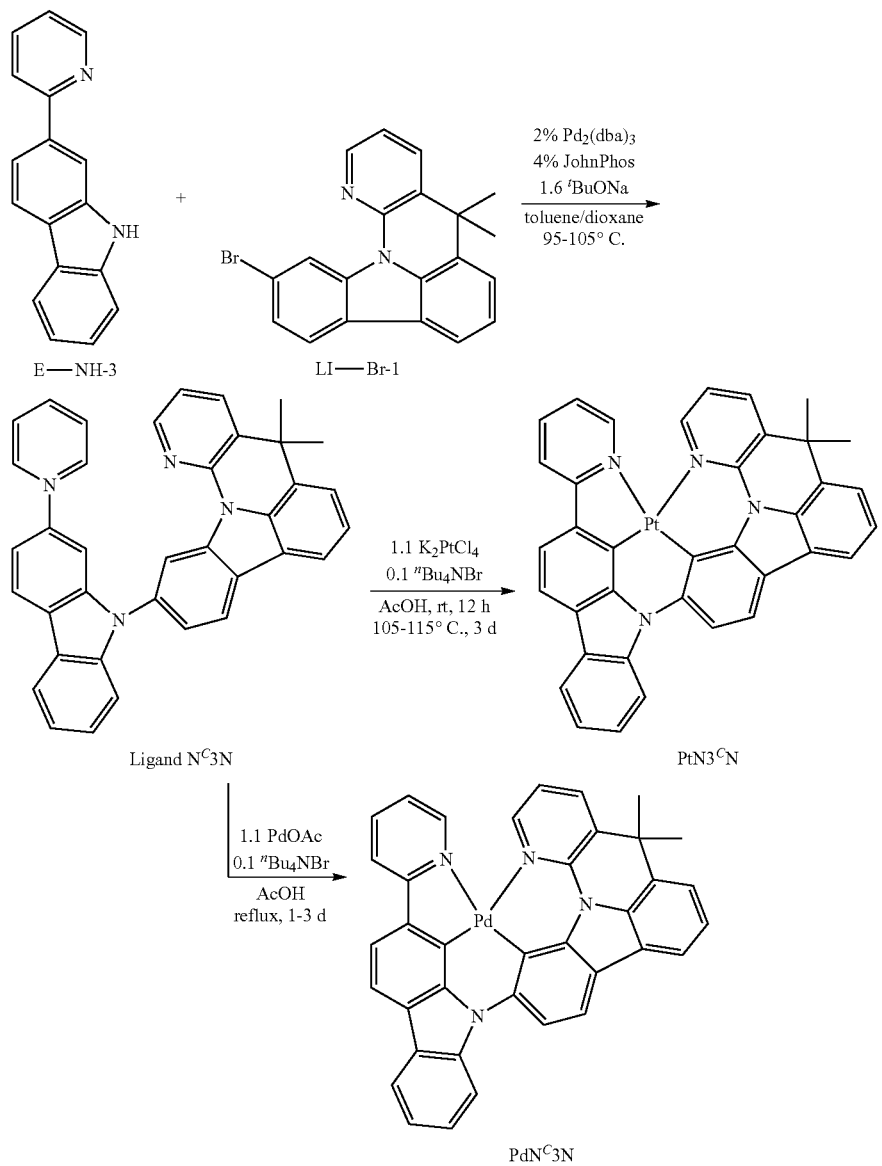

In yet another aspect, PtN$^C$3N-Ph and PdN$^C$3N-Ph can be synthesized as follows:
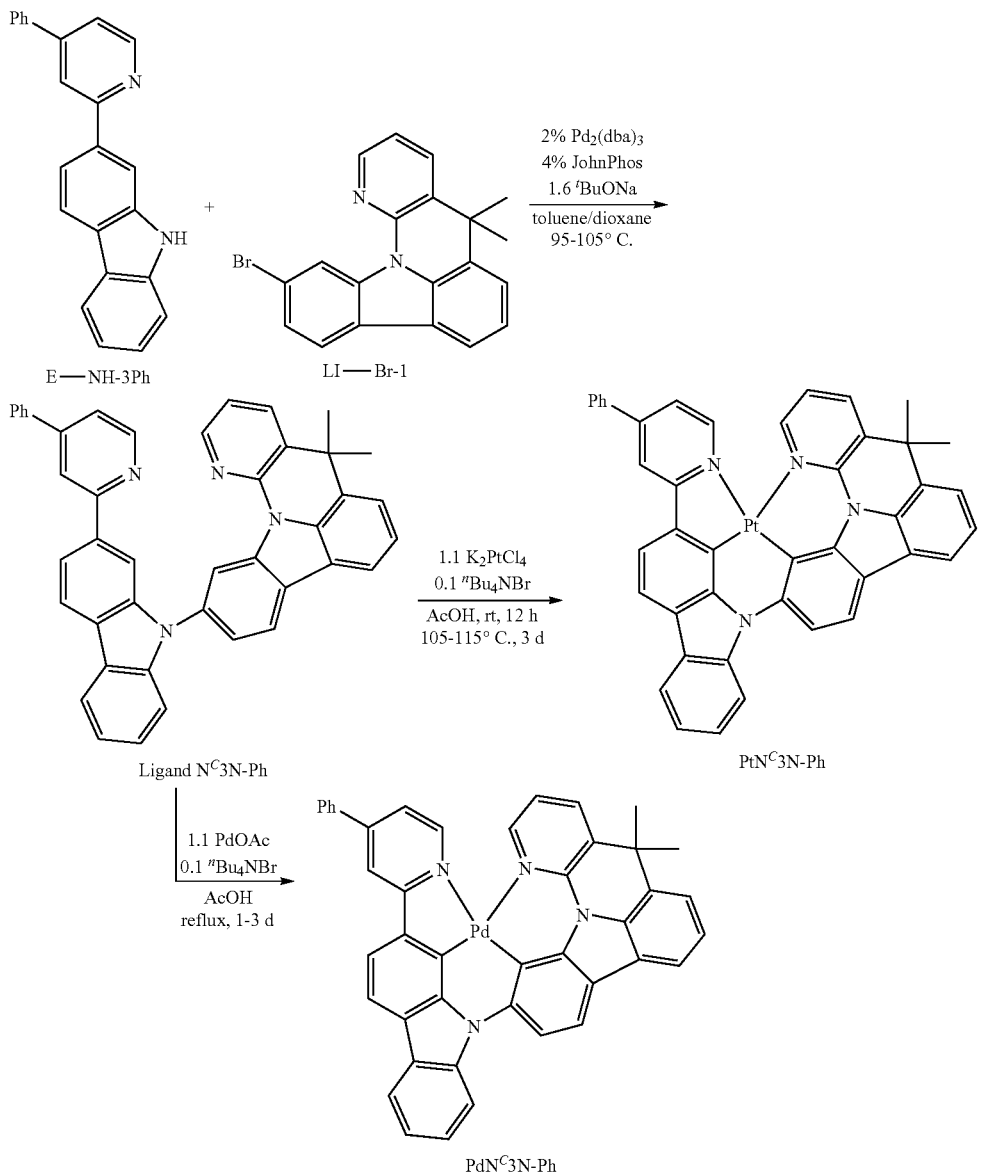
In yet another aspect, PtN$^C$7N can be synthesized as follows:
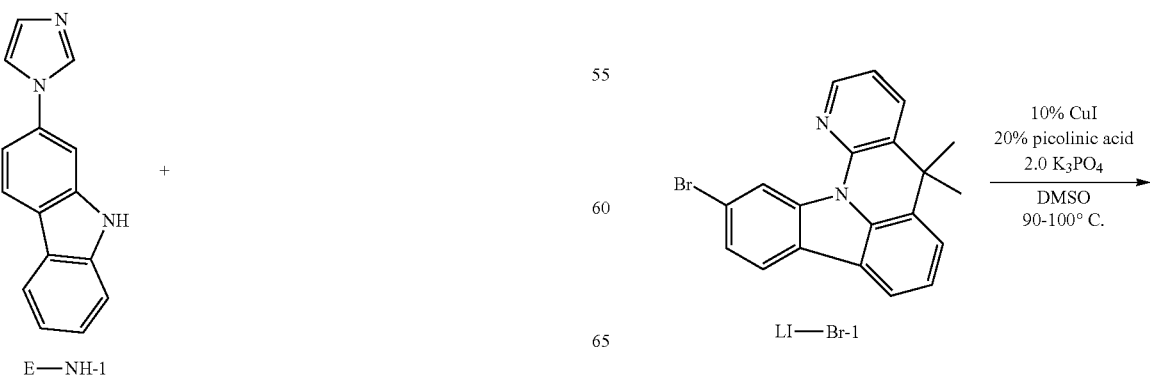

611
-continued
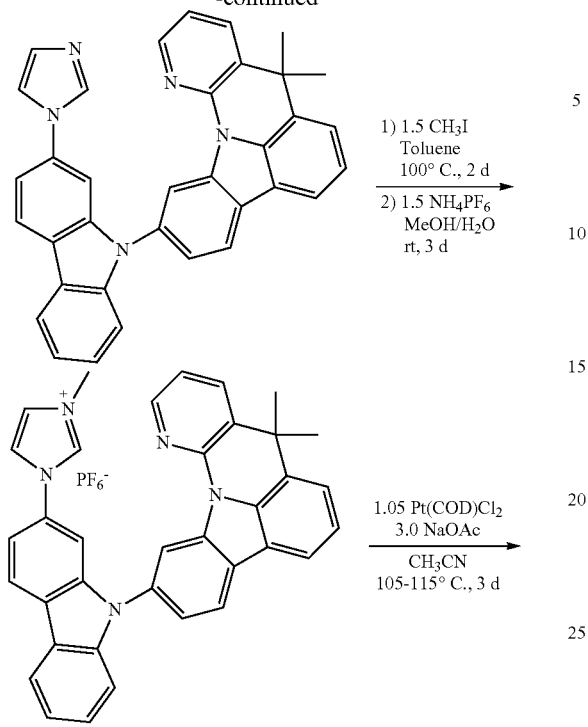
612
-continued
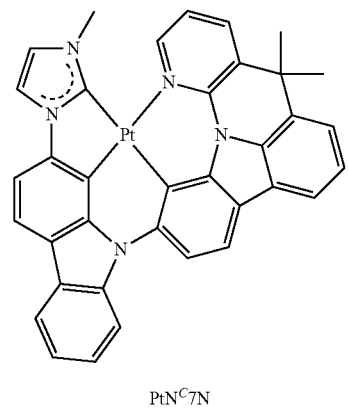
In yet another aspect, PtN$^C$12N and PdN$^C$12N can be synthesized as follows:
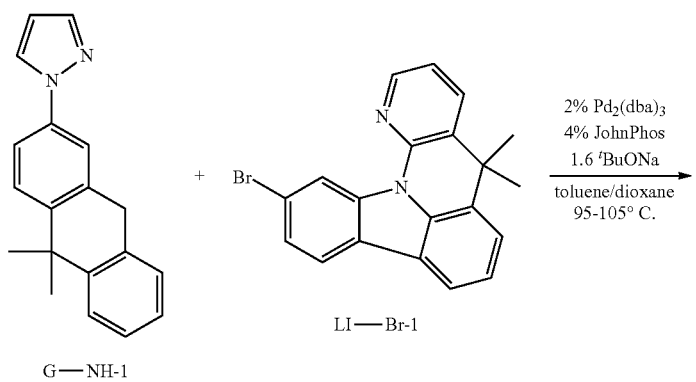
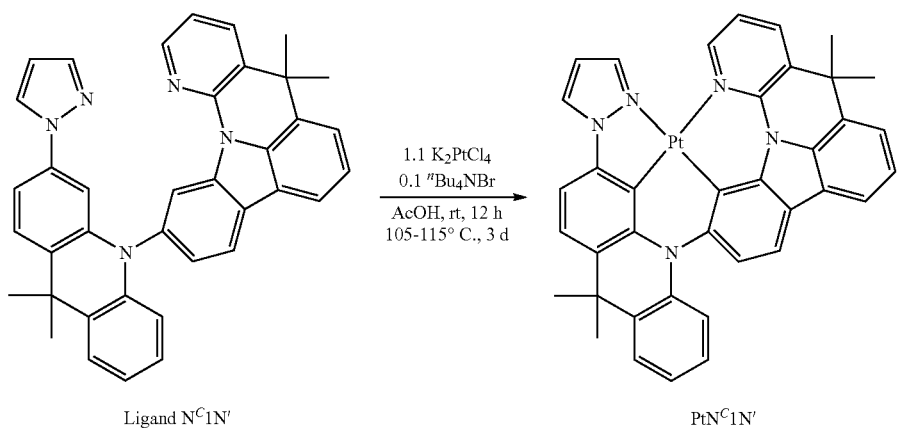

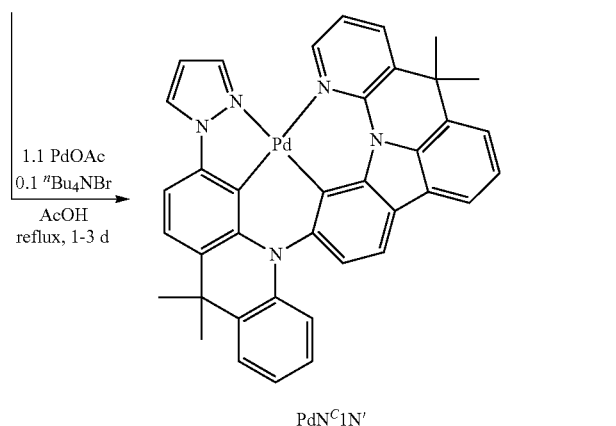
PdN<sup>C</sup>1N'
In one aspect, PtN<sup>C</sup>1N' and PdN<sup>C</sup>1N' can be synthesized as follows:
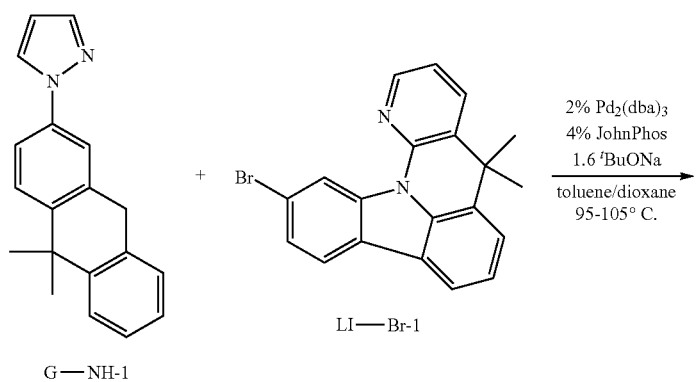
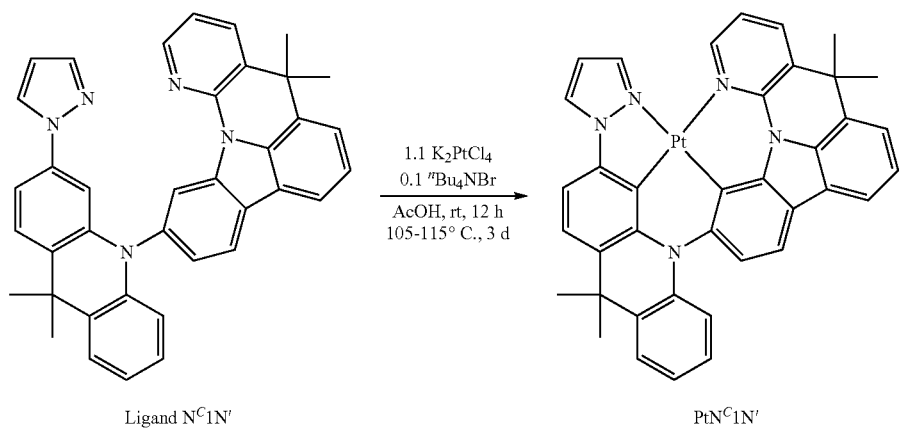

-continued
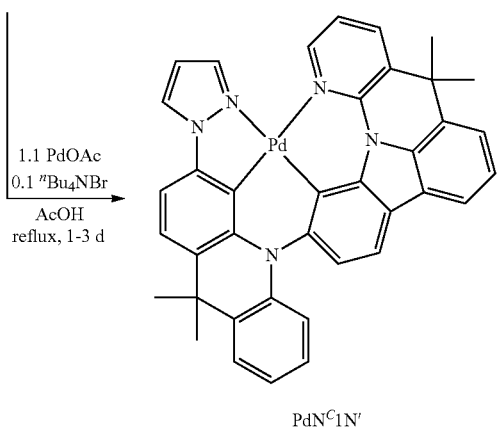
PdN^C1N'
In another aspect, PtN^C3N' and PdN^C3N' can be synthesized as follows:
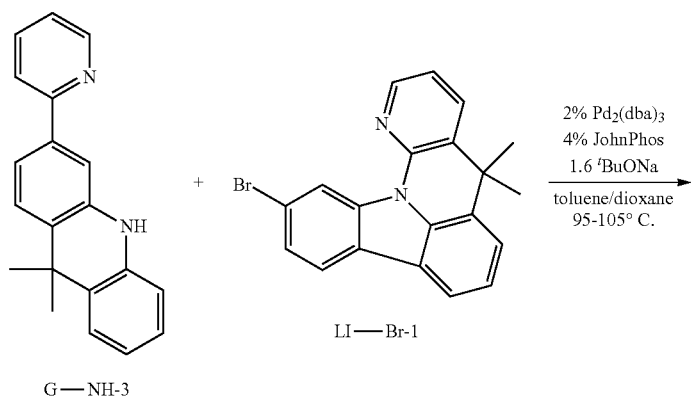
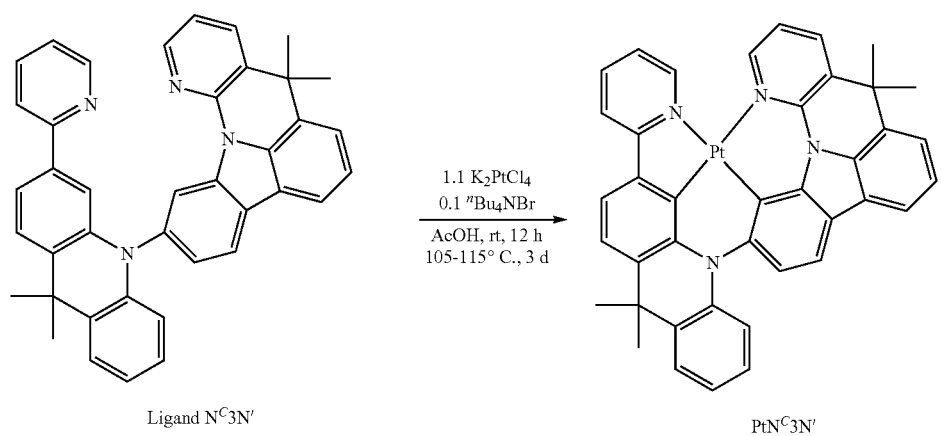

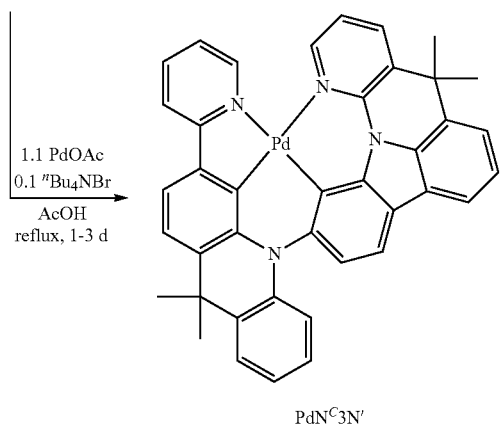
PdN^C3N'
In yet another aspect, PtN^{CC}1N and PdN^{CC}1N can be synthesized as follows:
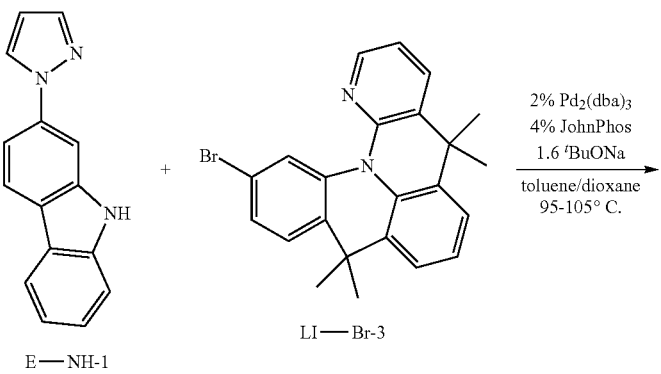
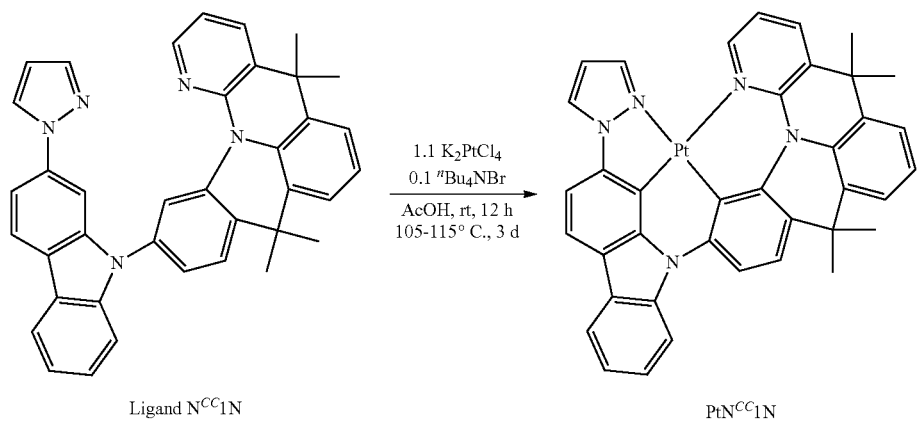

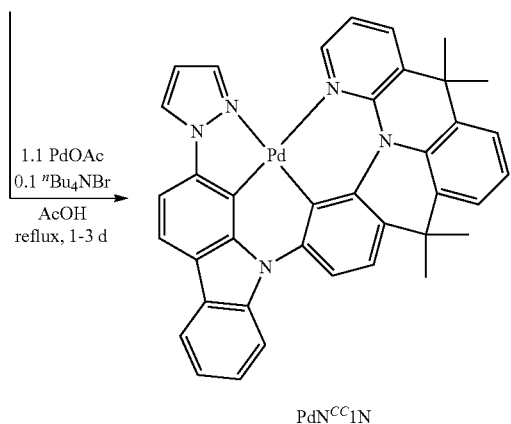
PdN$^{CC}$1N
In yet another aspect, PtN$^{CC}$3N' and PdN$^{CC}$3N' can be synthesized as follows:
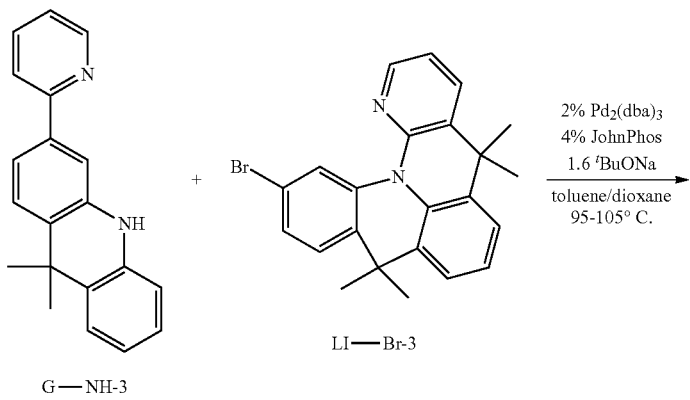
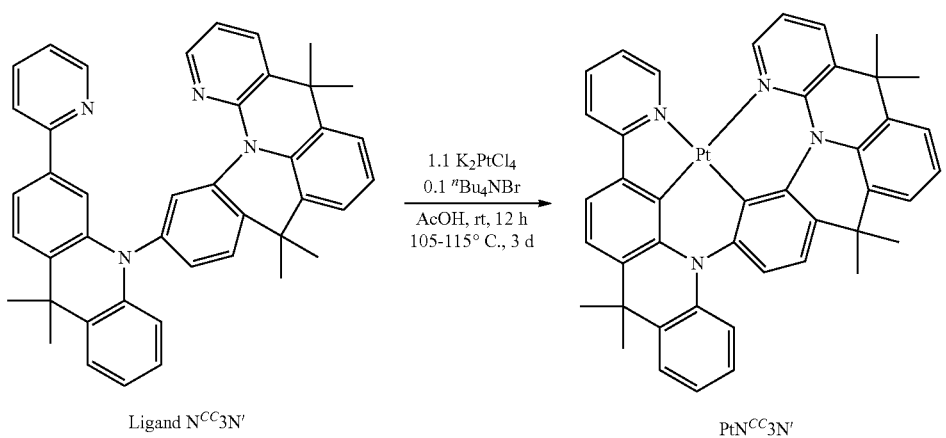

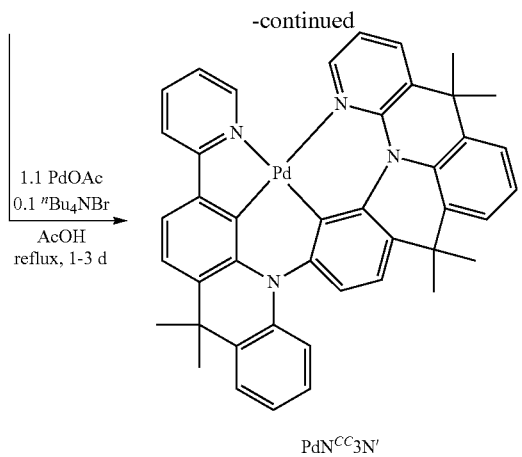
PdN$^{CC}$3N′
A general synthesis route for the disclosed Pt and Pd complexes of Formula AVI herein includes:
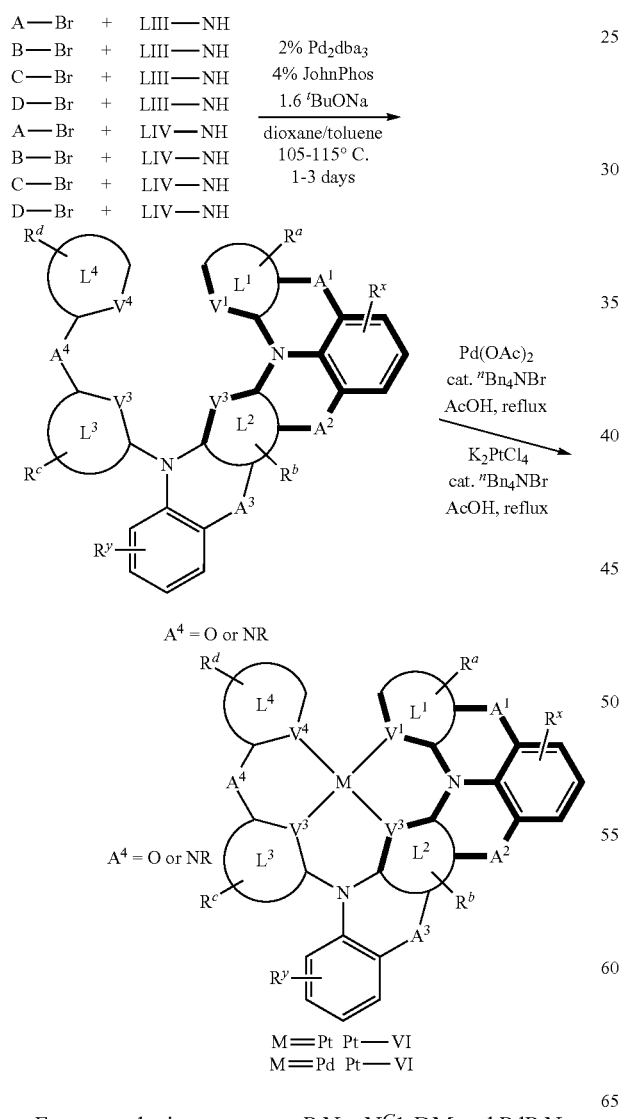
$A^4$ = O or NR
$A^4$ = O or NR
M=Pt  Pt—VI
M=Pd  Pt—VI
For example, in one aspect, PtN—N$^C$1-DM and PdPtN—N$^C$1-DM can be synthesized as follows:
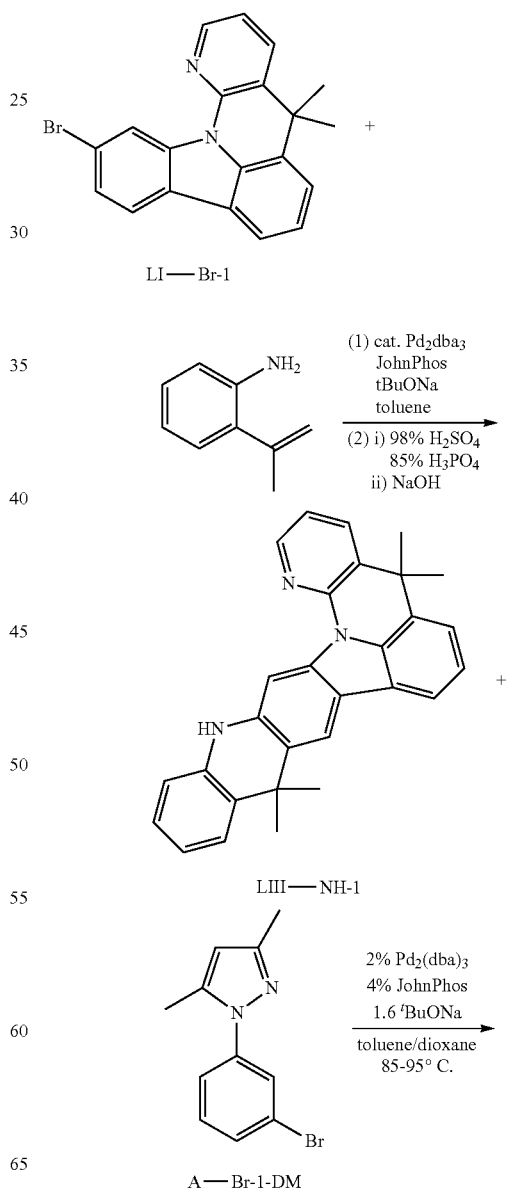
LI—Br-1
LIII—NH-1
A—Br-1-DM 623
-continued
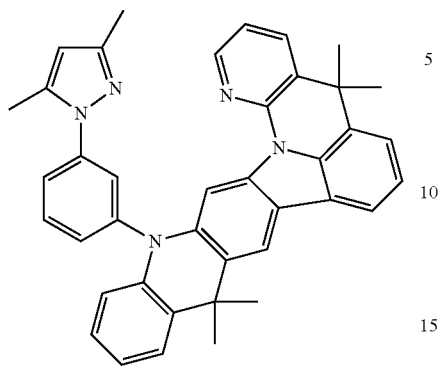
Ligand N—N^C1-DM
1.1 K₂PtCl₄ | AcOH, rt, 12 h
0.1 ⁿBu₄NBr | 105-115° C., 3 d
↓
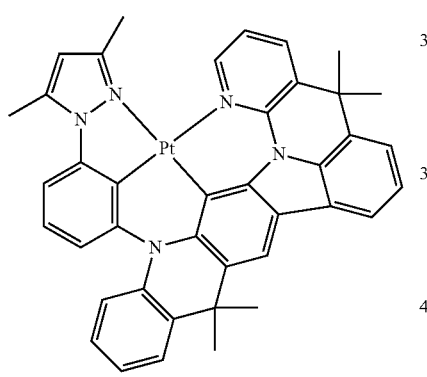
PtN—N^C1-DM
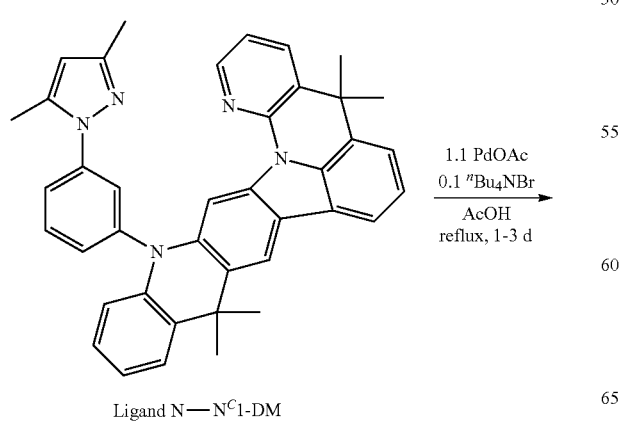
Ligand N—N^C1-DM
1.1 PdOAc
0.1 ⁿBu₄NBr
―――――
AcOH
reflux, 1-3 d
624
-continued
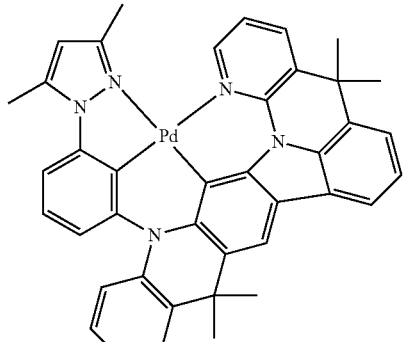
PdN—N^C1-DM
In yet another aspect, PtN—N^{C'}1-DM and PdPtN—N^{C'}1-DM can be synthesized as follows:
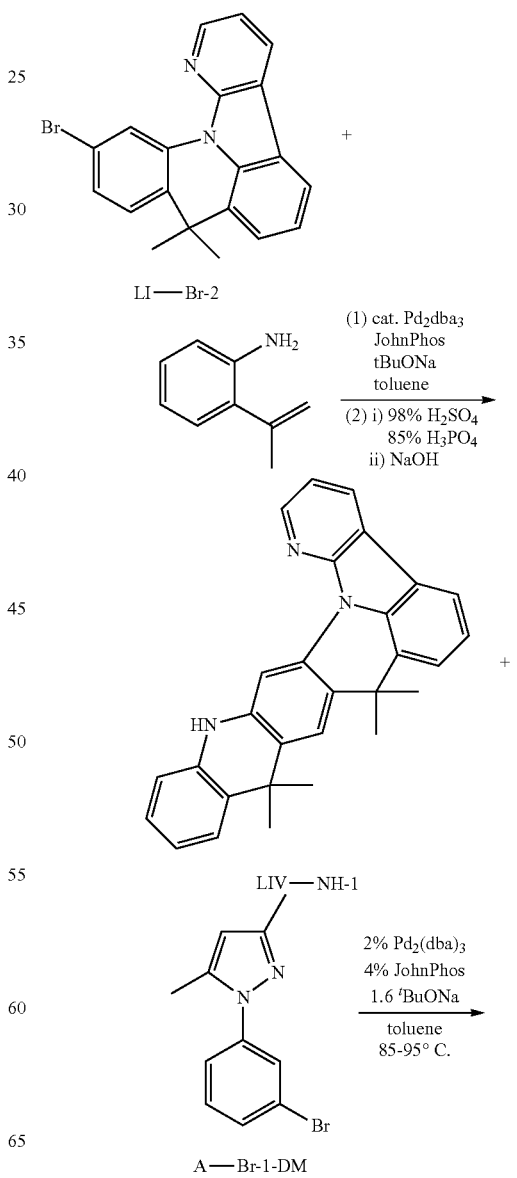

625
-continued

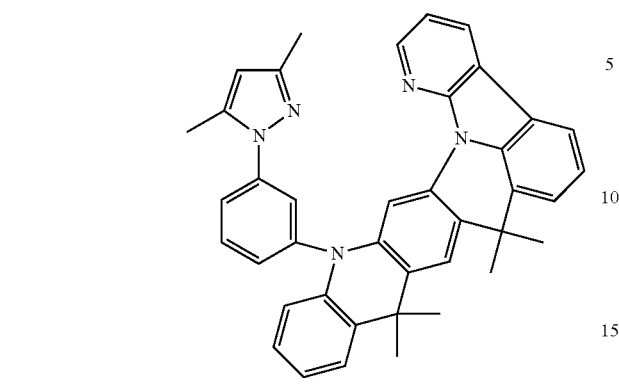

Ligand N—N$^C$1-DM $\Big\downarrow$ 1.1 K$_2$PtCl$_4$  AcOH, rt, 12 h
0.1 $^n$Bu$_4$NBr  105-115° C., 3 d

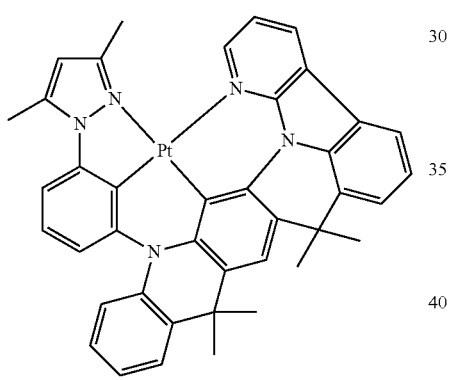

PtN—N$^C$1-DM

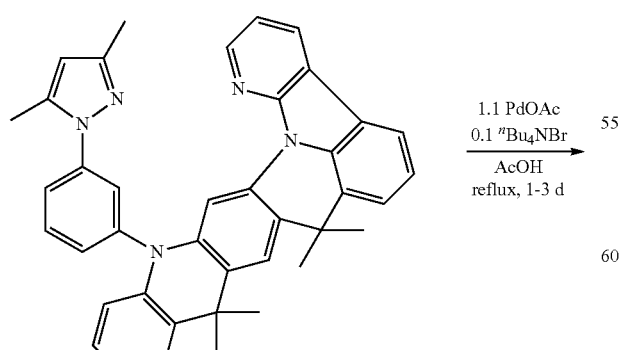

Ligand N—N$^C$1-DM $\xrightarrow[\text{reflux, 1-3 d}]{\substack{1.1\ \text{PdOAc} \\ 0.1\ ^n\text{Bu}_4\text{NBr} \\ \text{AcOH}}}$ 626
-continued

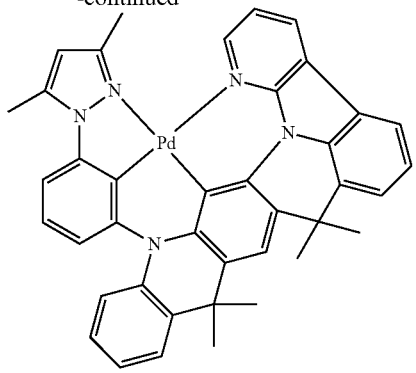

PdN—N$^C$1-DM

In yet another aspect, PtN—N$^{CC}$1-DM and PdPtN—N$^{CC}$1-DM can be synthesized as follows:

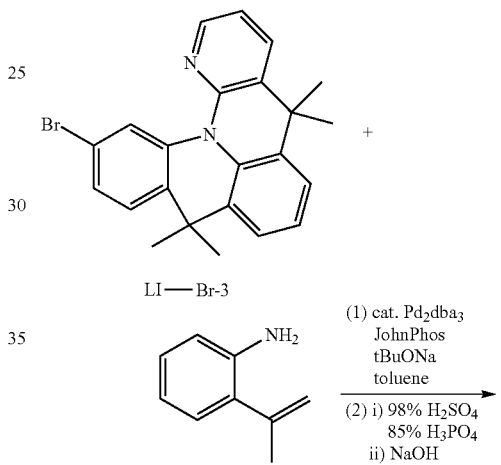

LI—Br-3

$\xrightarrow[\substack{\text{(2) i) 98\% H}_2\text{SO}_4 \\ \text{85\% H}_3\text{PO}_4 \\ \text{ii) NaOH}}]{\substack{\text{(1) cat. Pd}_2\text{dba}_3 \\ \text{JohnPhos} \\ \text{tBuONa} \\ \text{toluene}}}$

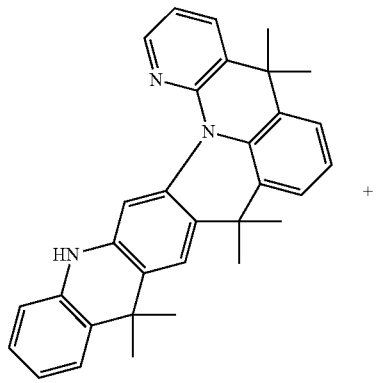

LV—NH-1

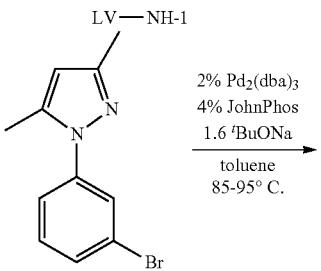

A—Br-1-DM $\xrightarrow[\substack{\text{toluene} \\ 85\text{-}95°\ \text{C.}}]{\substack{2\%\ \text{Pd}_2(\text{dba})_3 \\ 4\%\ \text{JohnPhos} \\ 1.6\ ^t\text{BuONa}}}$

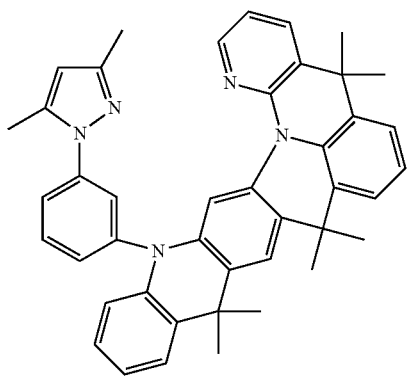
Ligand N—N^{CC}1-DM
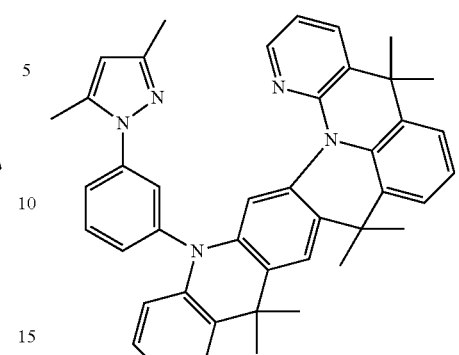
Ligand N—N^{CC}1-DM
1.1 K$_2$PtCl$_4$ | AcOH, rt, 12 h
0.1 $^n$Bu$_4$NBr | 105–115° C., 3 d
1.1 PdOAc
0.1 $^n$Bu$_4$NBr
AcOH
reflux, 1–3 d
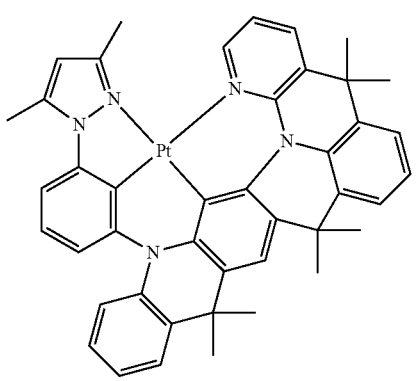
PtN—N^{CC}1-DM
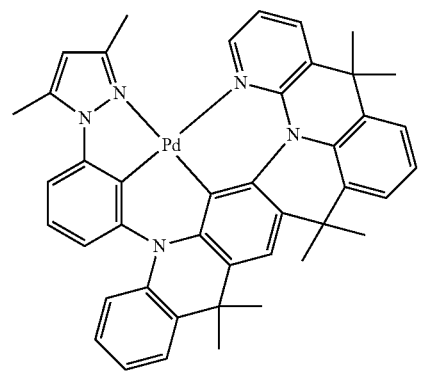
PdN—N^{CC}1-DM
A general synthesis route for the disclosed Pt and Pd complexes of Formula AVII herein includes:
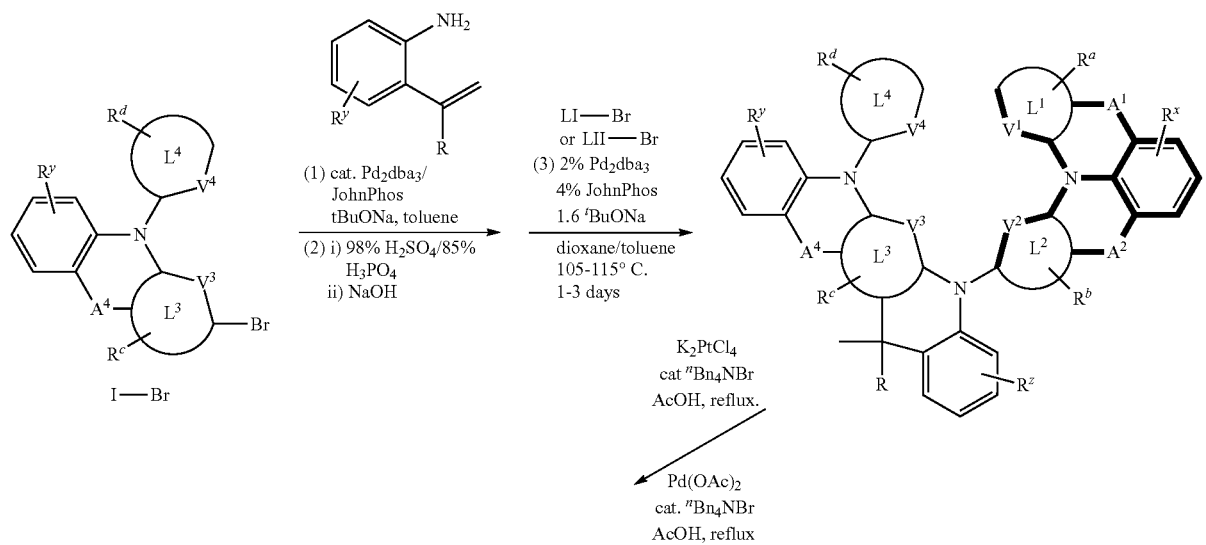

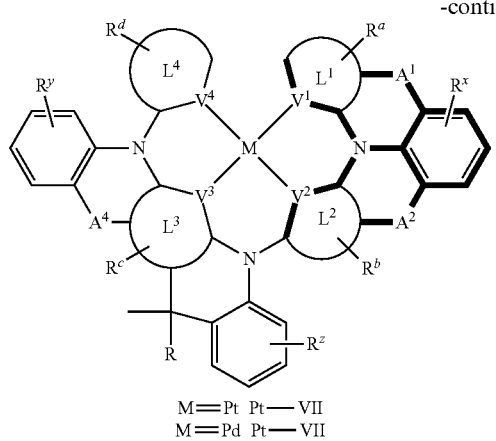
M=Pt Pt—VII
M=Pd Pt—VII
For example, in one aspect, PtN—N$^C$N$^C$ and PdPtN—N$^C$N$^C$ can be synthesized as follows:
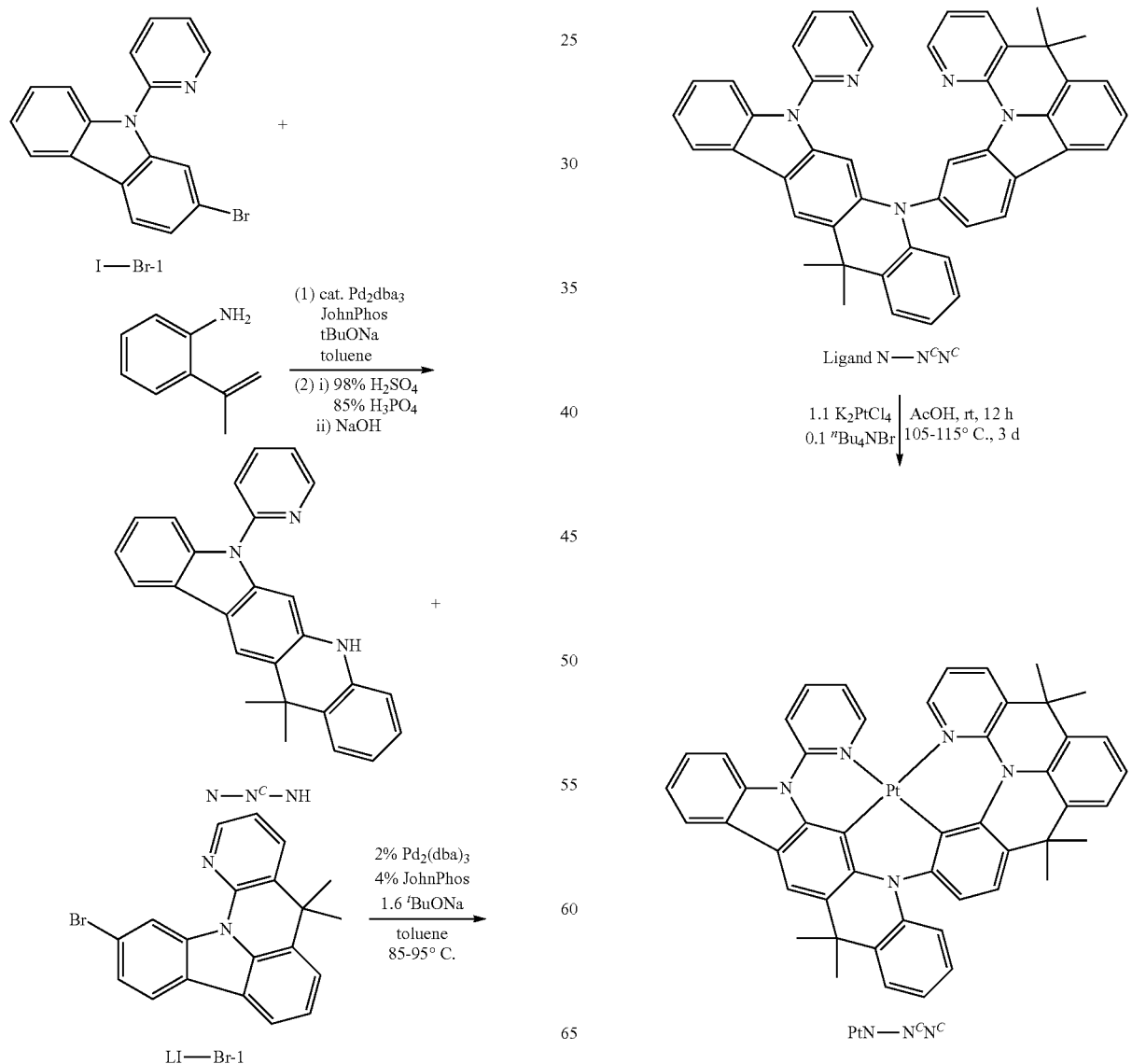

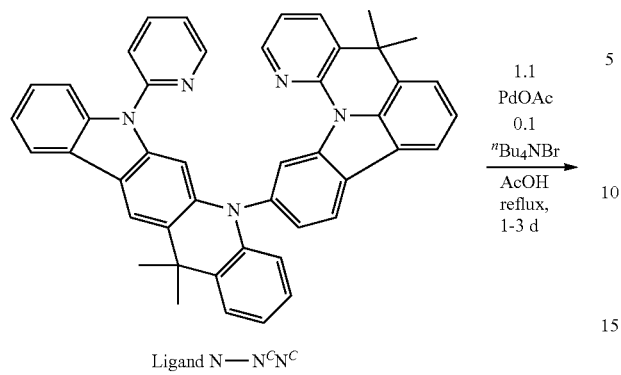
Ligand N—N^C N^C
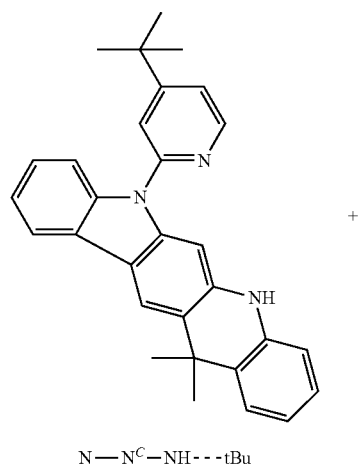
N—N^C—NH---tBu
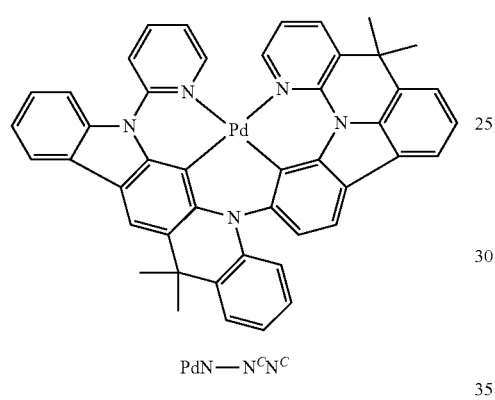
PdN—N^C N^C
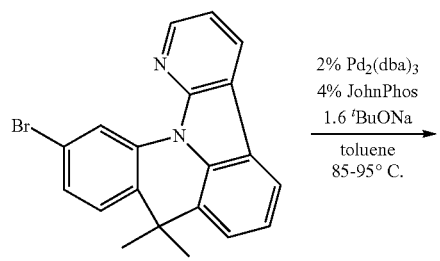
LI—Br-2
In another aspect, PtN—N^C N^{C'}-tBu and PdPtN—N^C N^{C'}-tBu can be synthesized as follows:
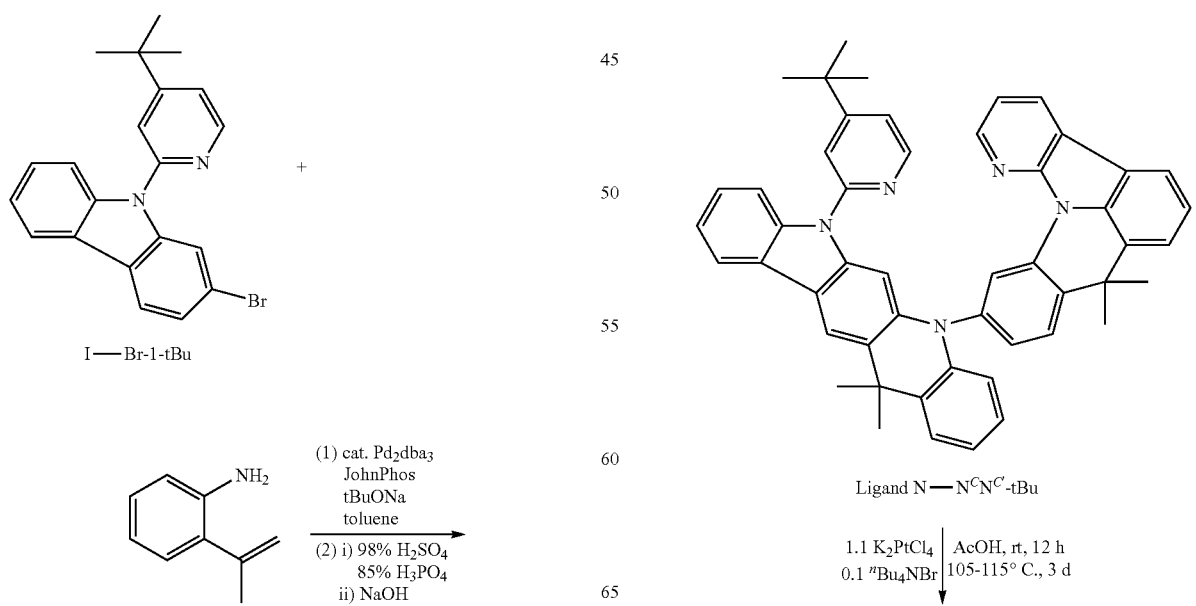
Ligand N—N^C N^{C'}-tBu
1.1 K$_2$PtCl$_4$ | AcOH, rt, 12 h
0.1 $^n$Bu$_4$NBr | 105-115° C., 3 d

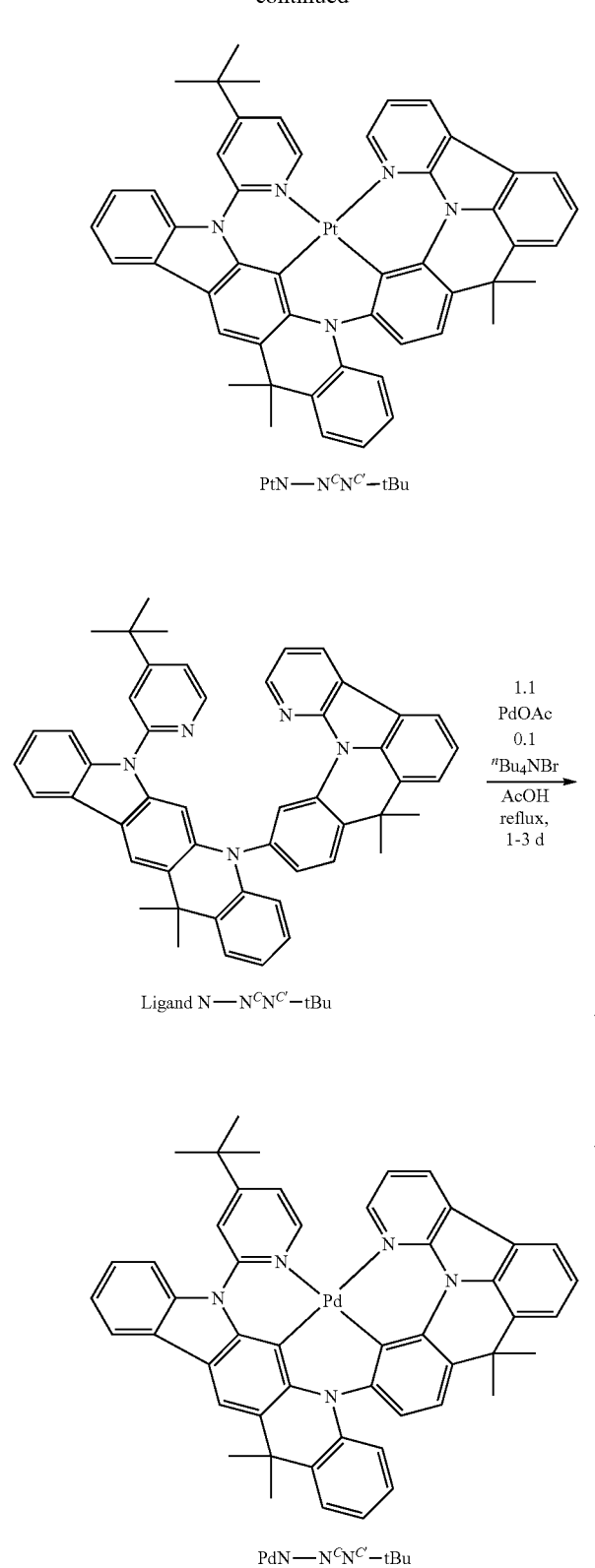
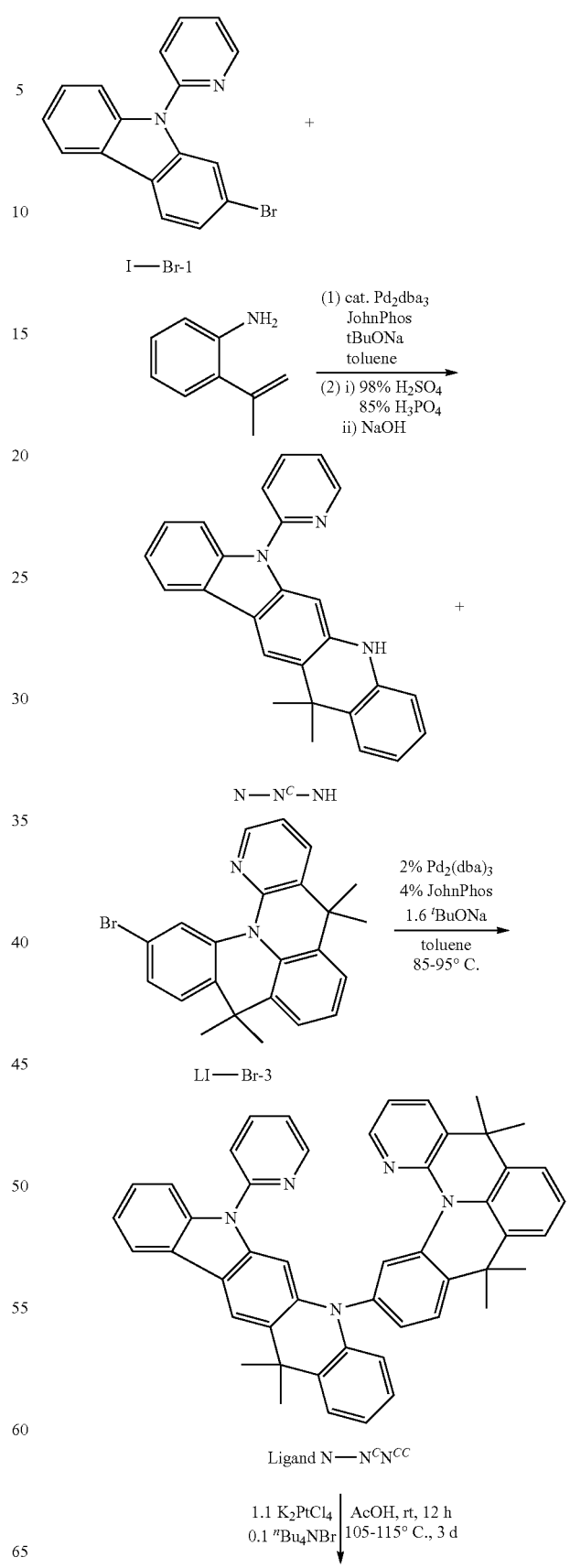
In yet another aspect, PtN—N$^C$N$^{CC}$ and PdPtN—N$^C$N$^{CC}$ can be synthesized as follows:

635
-continued
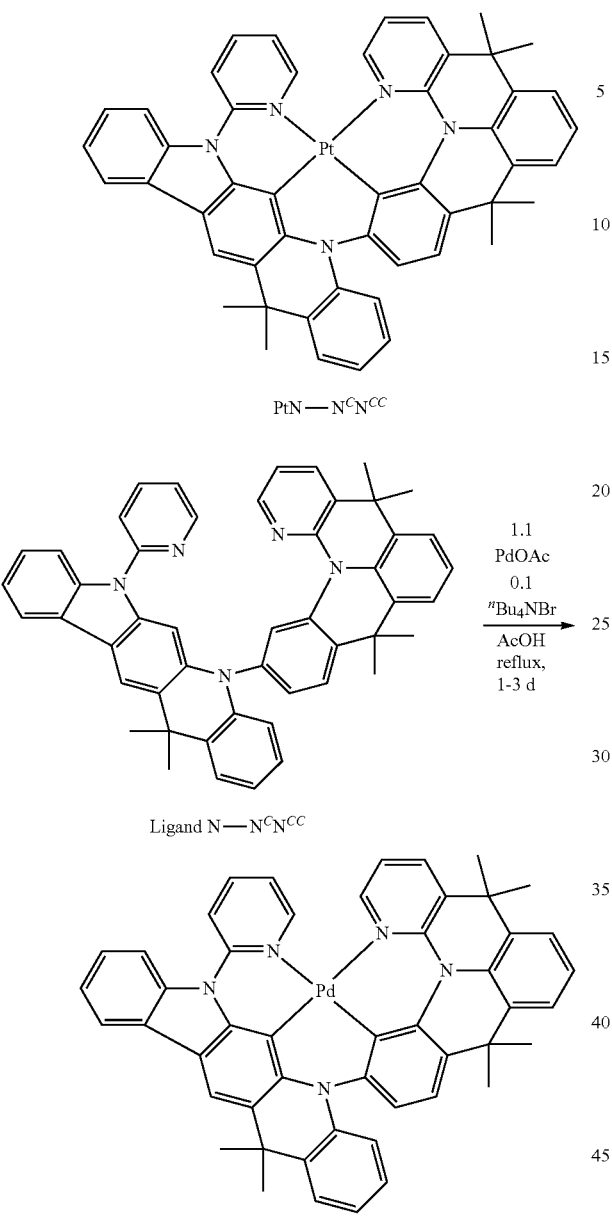
PtN—N$^C$N$^{CC}$
Ligand N—N$^C$N$^{CC}$
PdN—N$^C$N$^{CC}$
In yet another aspect, PtN$^C$—N$^C$N$^{CC}$ and PdPtN$^C$—N$^C$-N$^{CC}$ can be synthesized as follows:
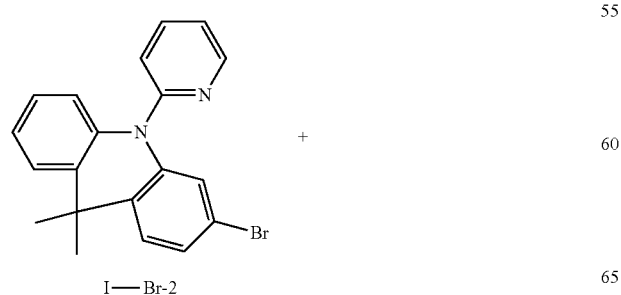
I—Br-2
636
-continued
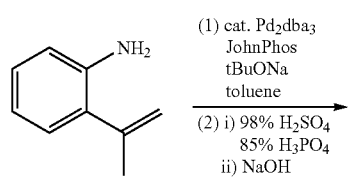
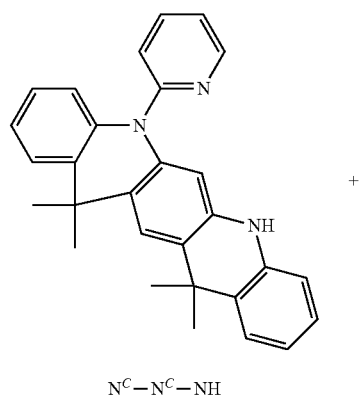
N$^C$—N$^C$—NH
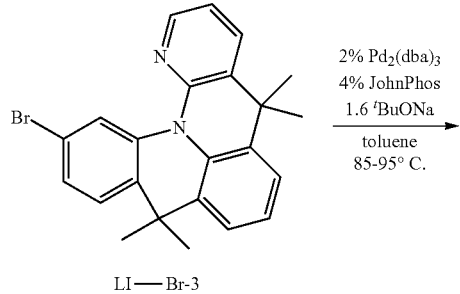
LI—Br-3
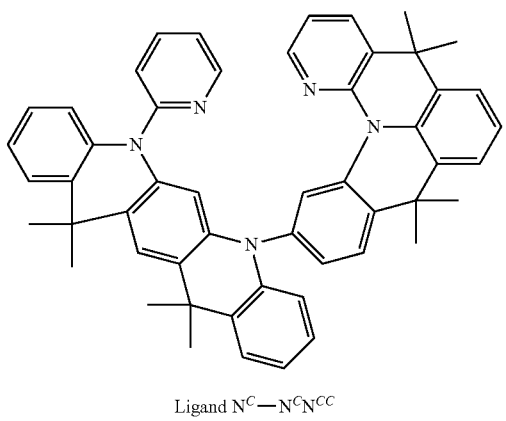
Ligand N$^C$—N$^C$N$^{CC}$
1.1 K$_2$PtCl$_4$ | AcOH, rt, 12 h
0.1 $^n$Bu$_4$NBr | 105-115° C., 3 d 637
-continued
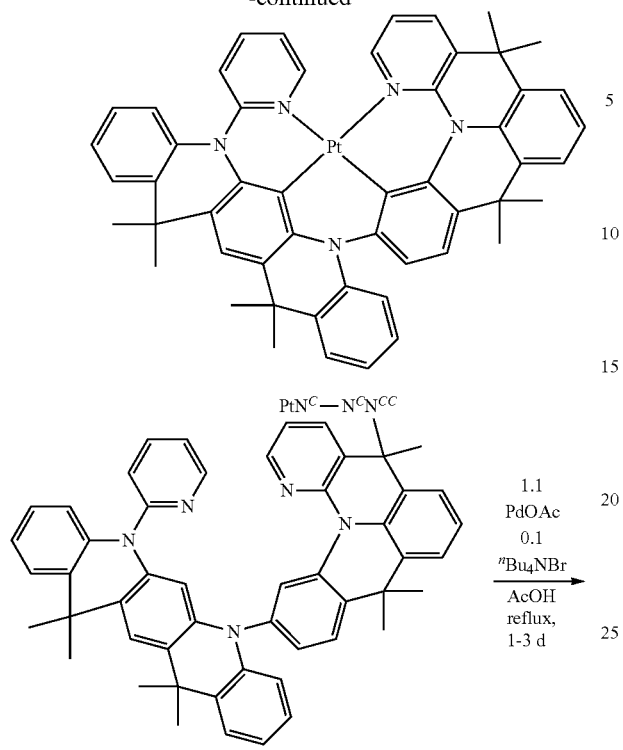
638
-continued
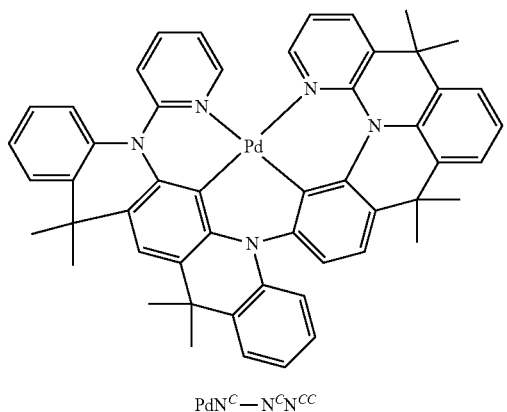
A general synthesis route for the disclosed Pt and Pd complexes of Formula AVIII herein includes:
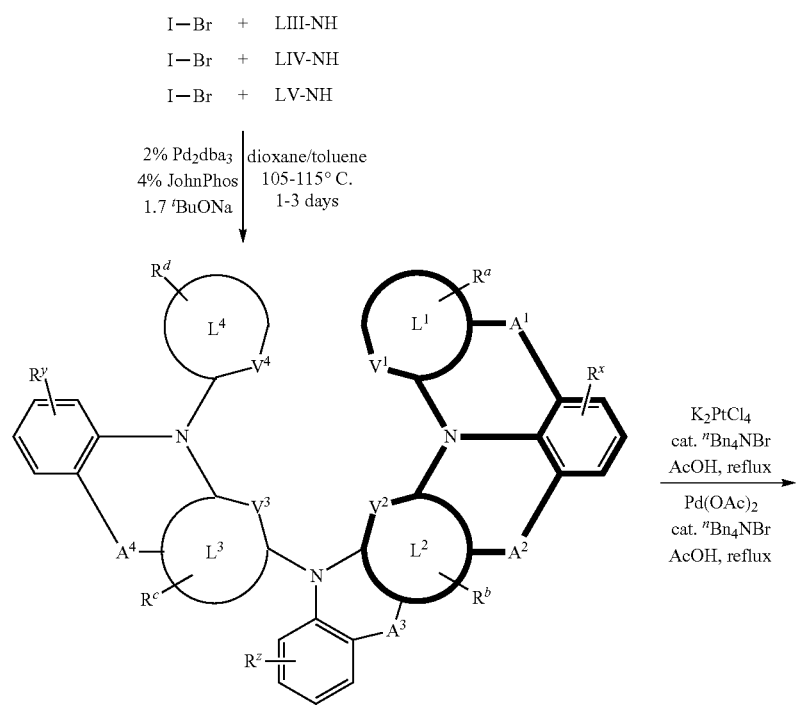

-continued
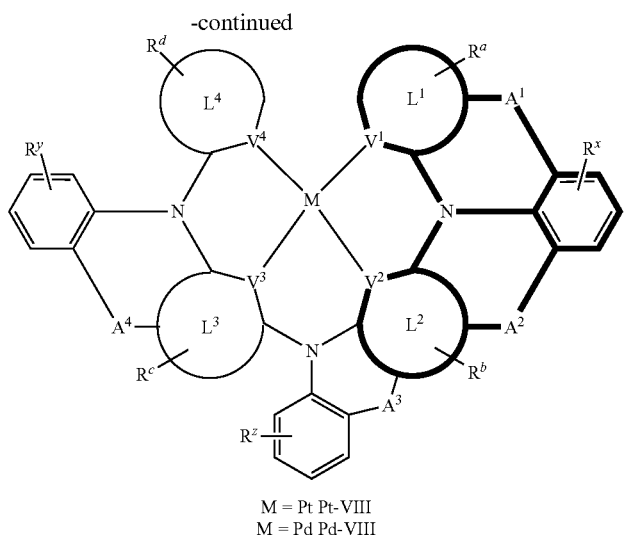
M = Pt Pt-VIII
M = Pd Pd-VIII
For example, in one aspect, PtNN$^C$—N$^C$ and PdPtNN$^C$—N$^C$ can be synthesized as follows:

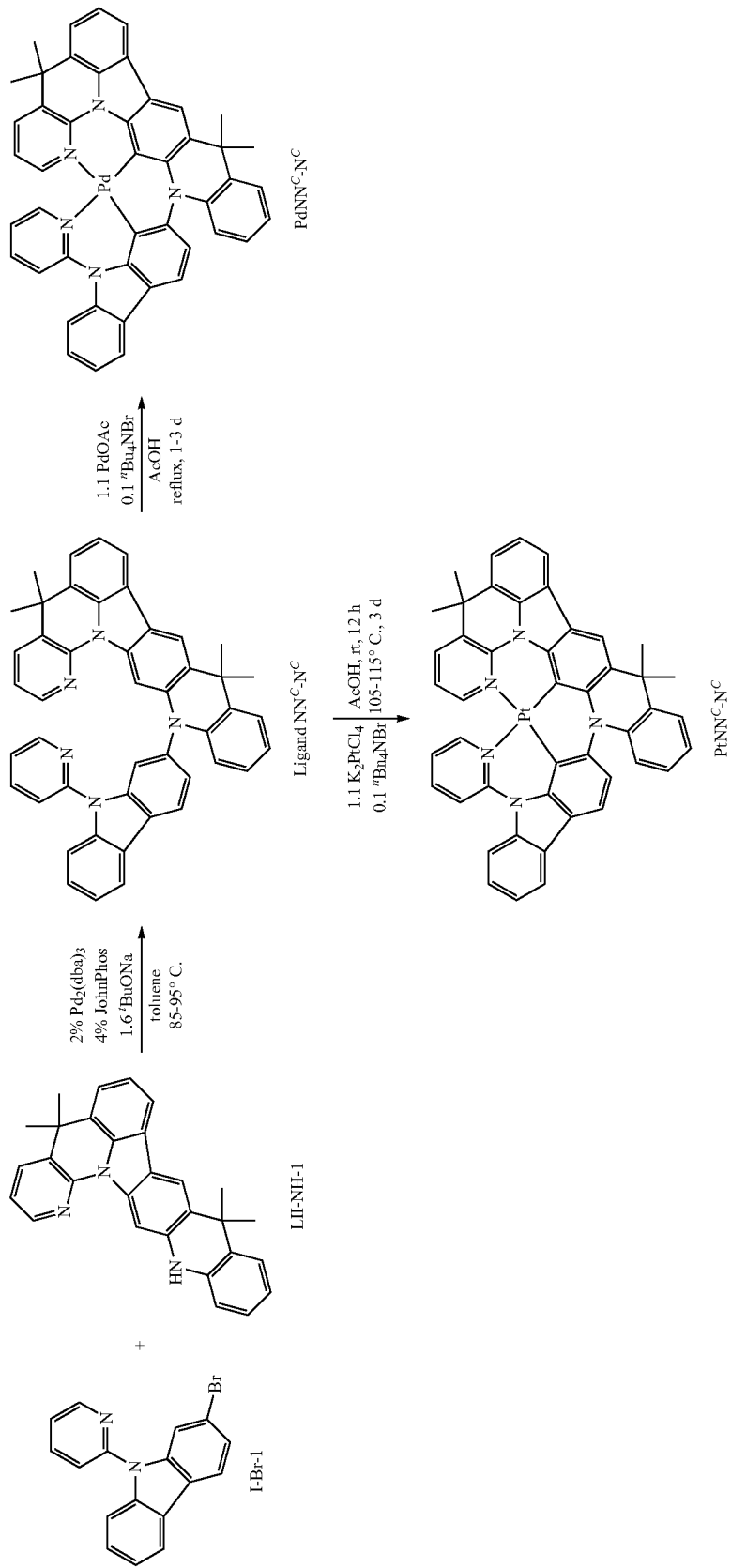

In yet another aspect, PtNN$^C$—N$^{C'}$ and PdPtNN$^C$—N$^{C'}$ can be synthesized as follows:

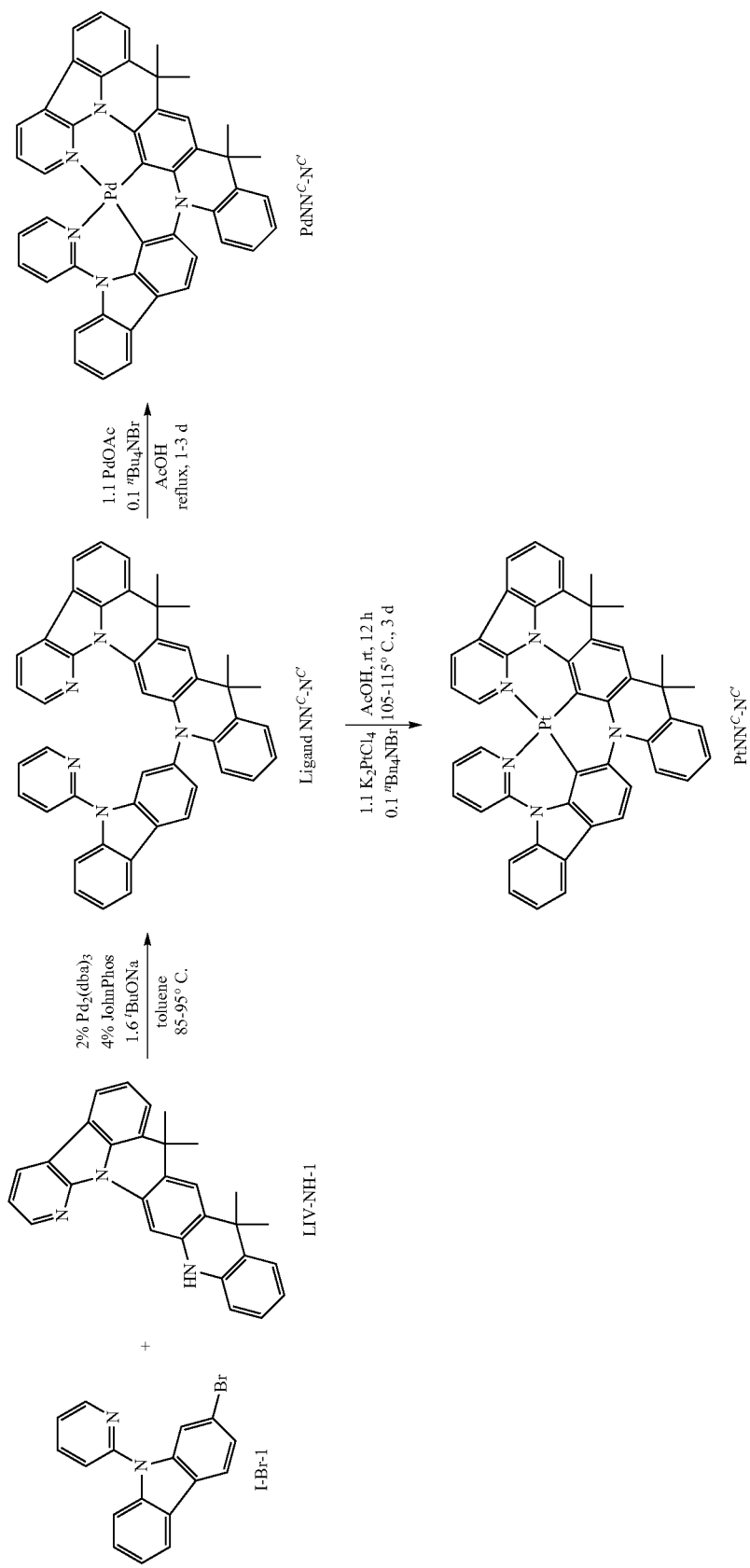

In yet another aspect, PtNN$^C$—N$^{CC}$ and PdPtNN$^C$—N$^{CC}$ can be synthesized as follows:

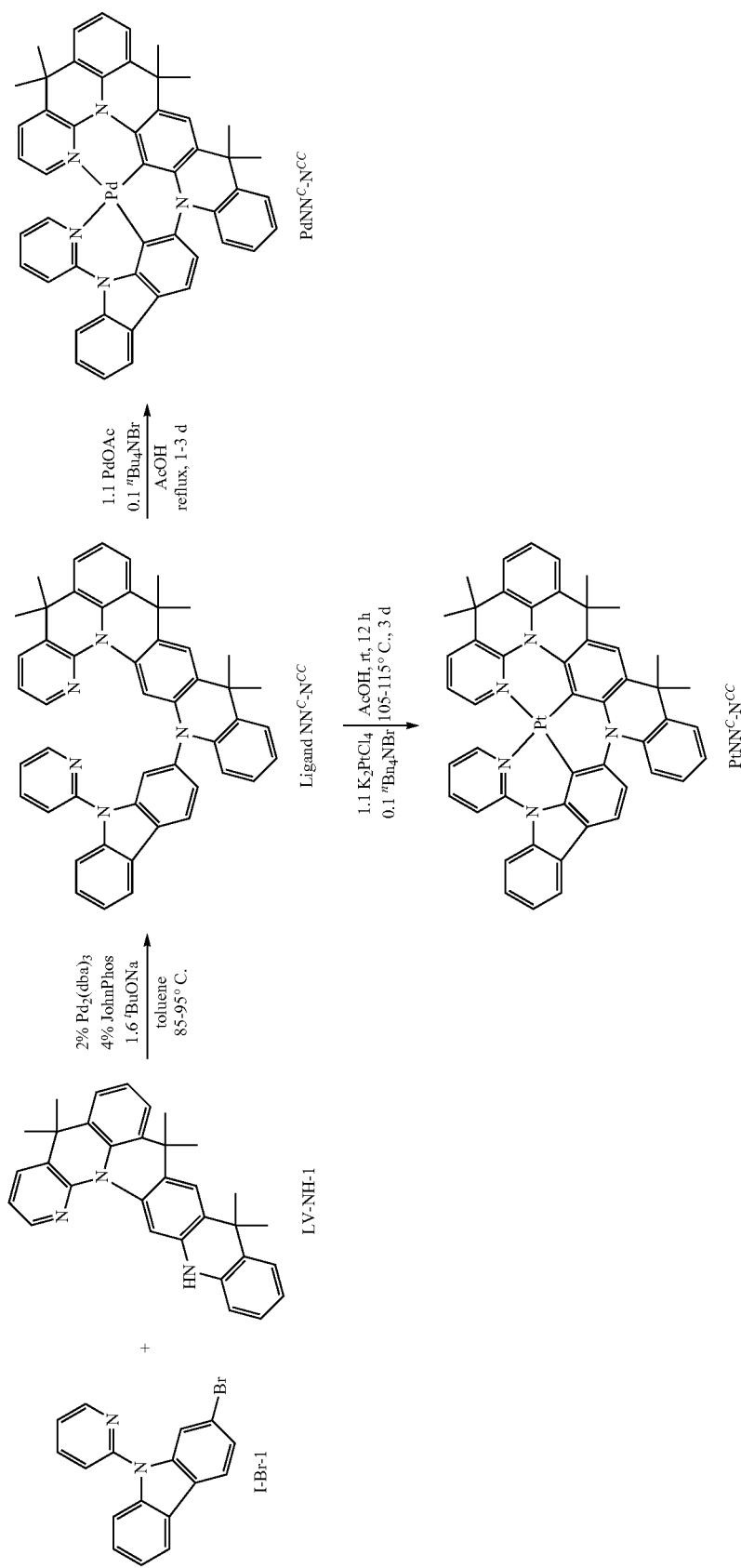

In yet another aspect, $PtN^CN^C\text{—}N^{CC}$ and $PdPtN^CN^C\text{—}N^{CC}$ can be synthesized as follows:

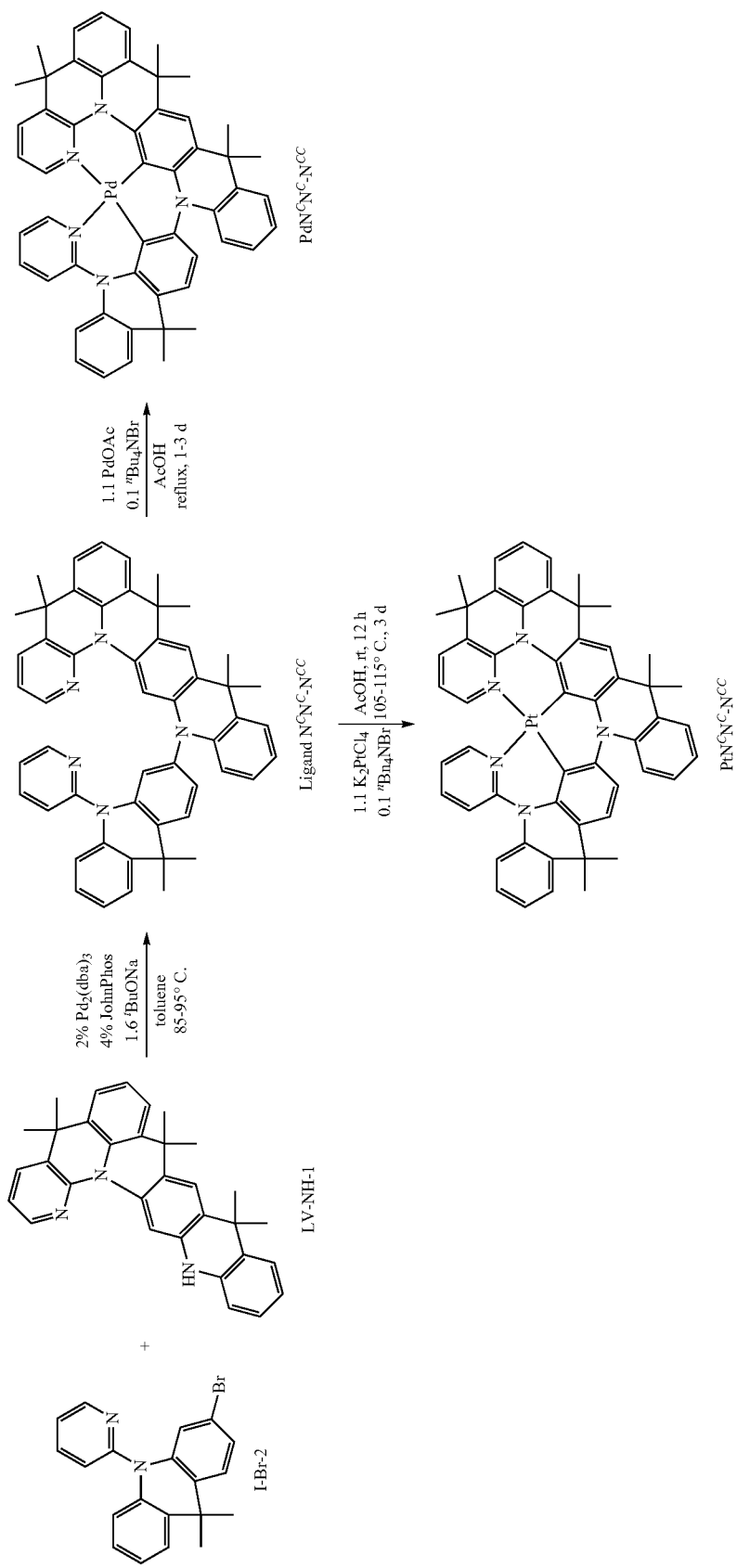

A general synthesis route for the disclosed Pt and Pd complexes of Formula AIX herein includes:
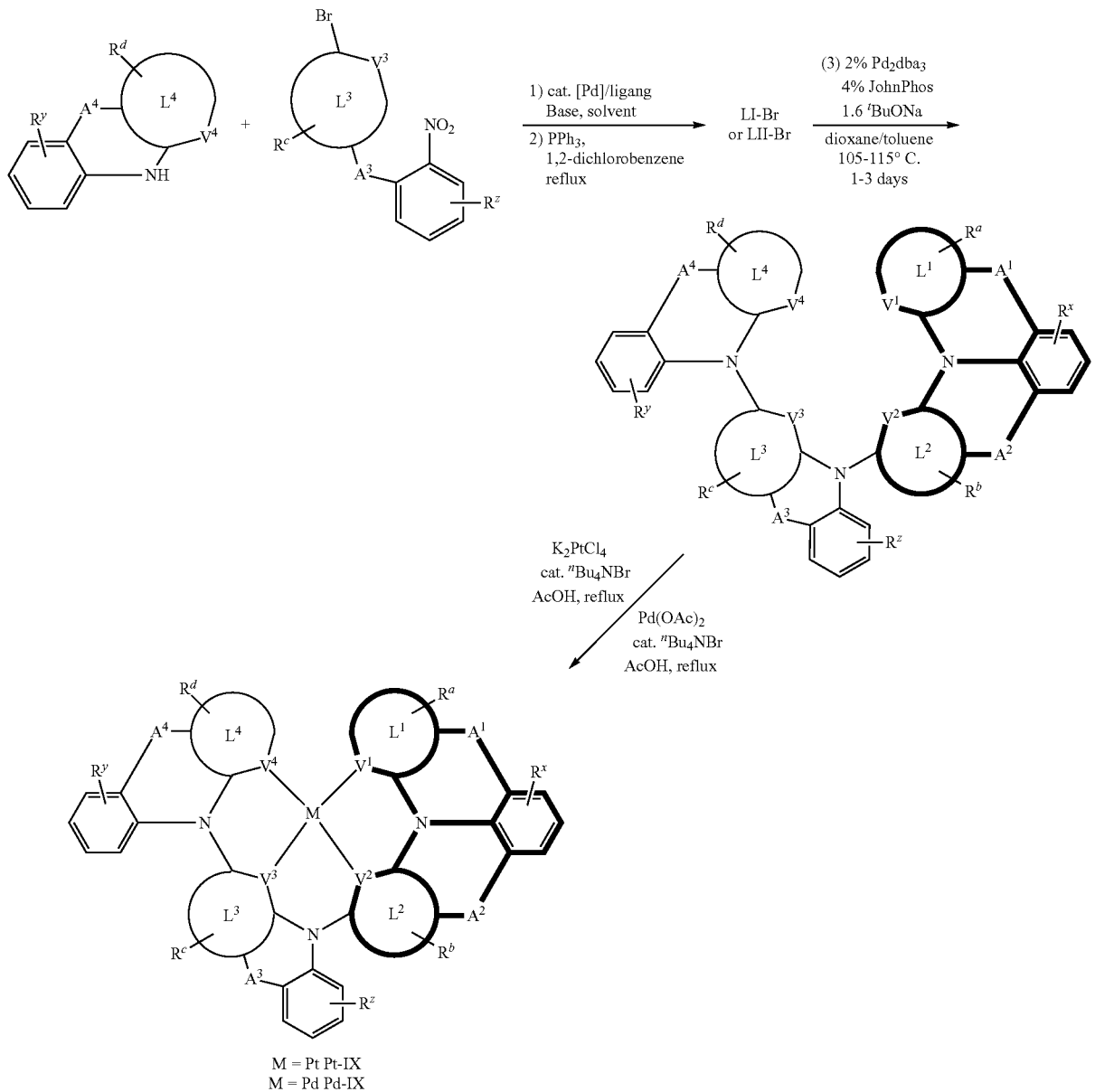
M = Pt Pt-IX
M = Pd Pd-IX
For example, in one aspect, PtN'NN$^C$ and PdPtN'NN$^C$ can be synthesized as follows:
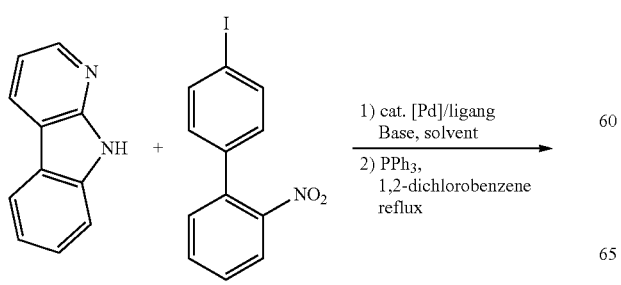
-continued
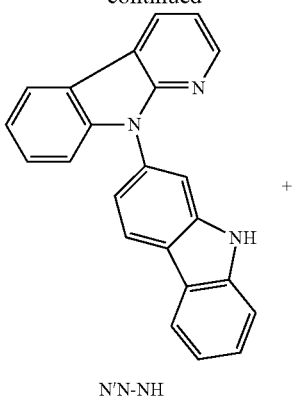
N'N-NH 657
-continued
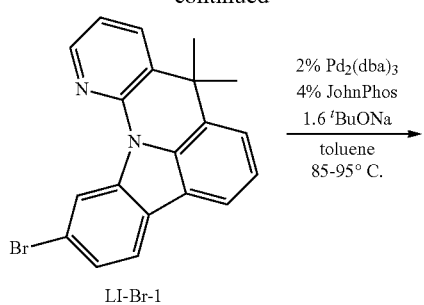
LI-Br-1
2% Pd₂(dba)₃
4% JohnPhos
1.6 ᵗBuONa
toluene
85-95° C.
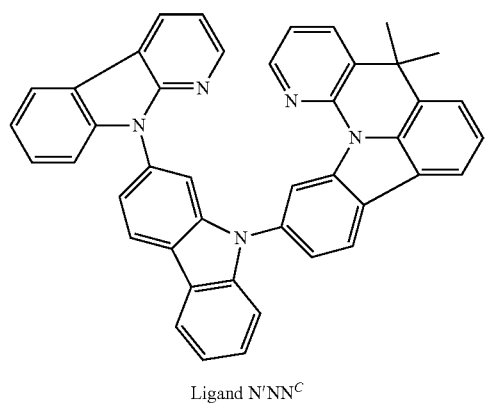
Ligand N'NN^C
1.1 K₂PtCl₄  AcOH, rt, 12 h
0.1 ⁿBn₄NBr  105-115° C., 3 d
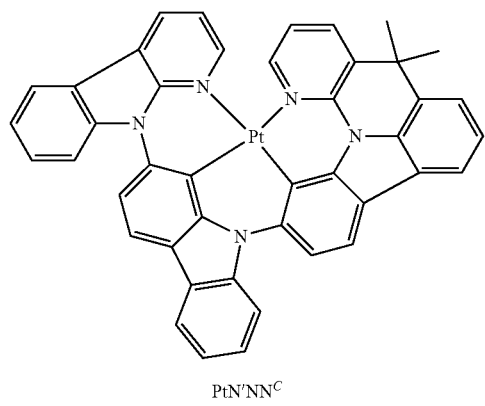
PtN'NN^C
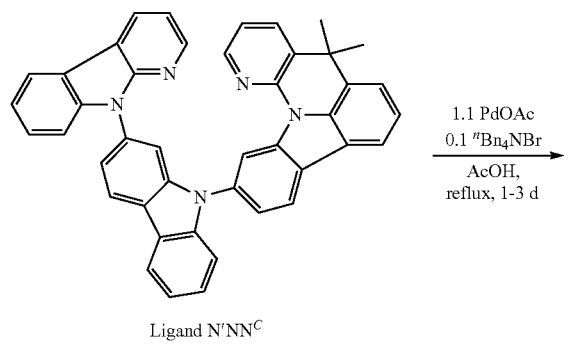
Ligand N'NN^C
1.1 PdOAc
0.1 ⁿBn₄NBr
AcOH,
reflux, 1-3 d
658
-continued
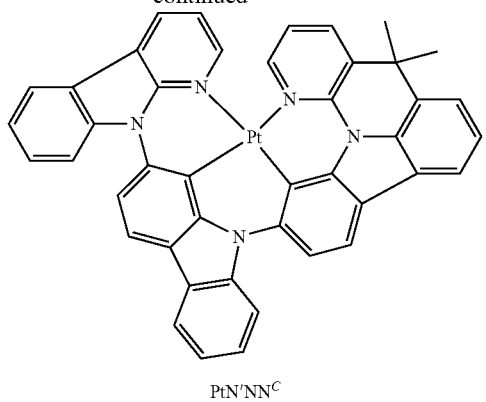
PtN'NN^C
In yet another aspect, PtN'NN^{C'} and PdPtN'NN^{C'} can be synthesized as follows:
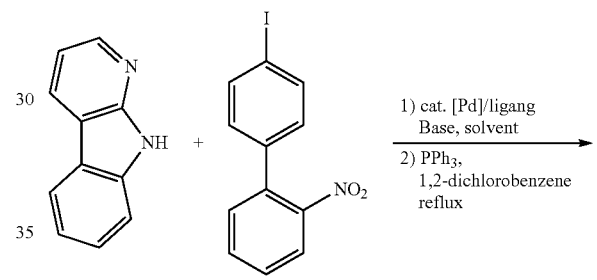
1) cat. [Pd]/ligang
   Base, solvent
2) PPh₃,
   1,2-dichlorobenzene
   reflux
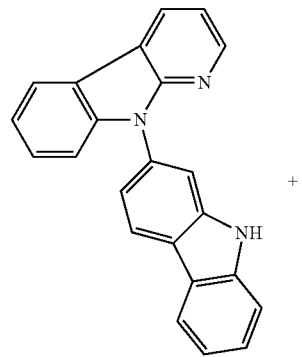
N'N-NH
+
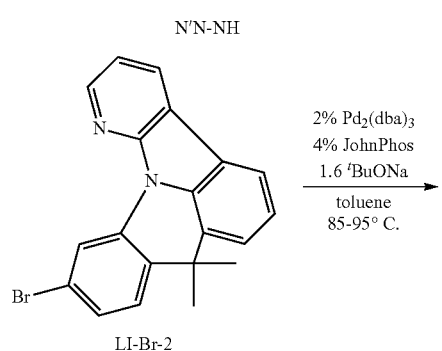
LI-Br-2
2% Pd₂(dba)₃
4% JohnPhos
1.6 ᵗBuONa
toluene
85-95° C.

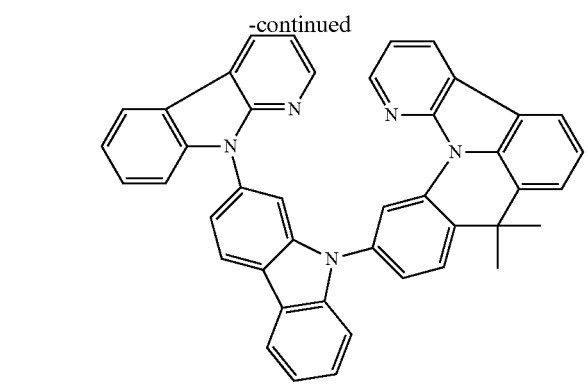

Ligand N'NN$^{C'}$

↓ 1.1 K$_2$PtCl$_4$  AcOH, rt, 12 h
   0.1 $^n$Bn$_4$NBr  105-115° C., 3 d

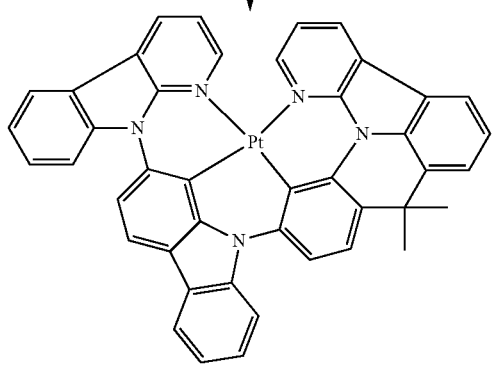

PtN'NN$^{C'}$

↓ 1.1 PdOAc
   0.1 $^n$Bn$_4$NBr
   AcOH,
   reflux, 1-3 d

Ligand N'NN$^{C'}$

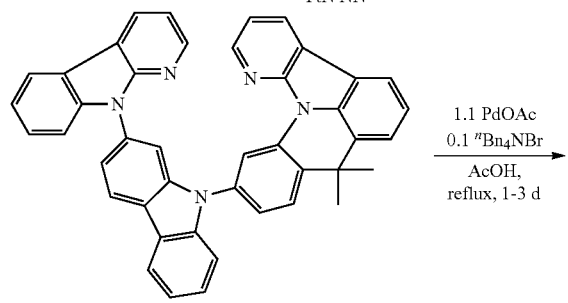

PtN'NN$^{C'}$

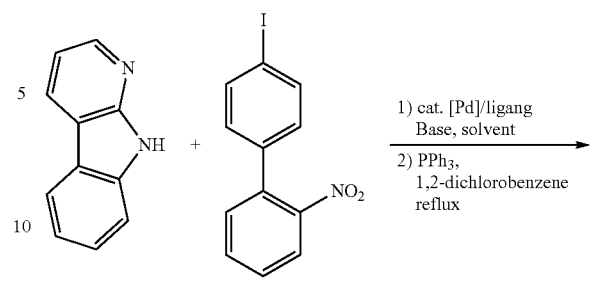

1) cat. [Pd]/ligang Base, solvent
2) PPh$_3$, 1,2-dichlorobenzene reflux
→

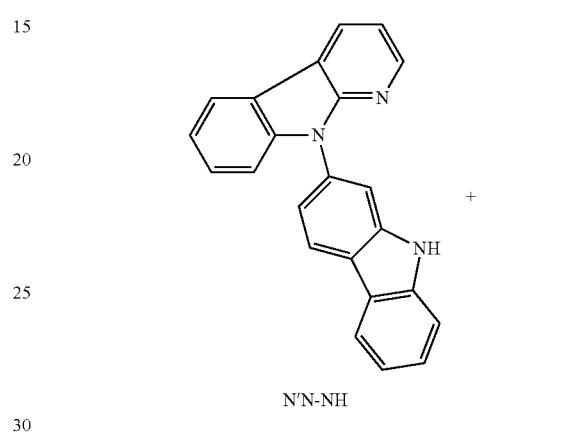

N'N-NH

2% Pd$_2$(dba)$_3$
4% JohnPhos
1.6 $^t$BuONa
toluene
85-95° C.

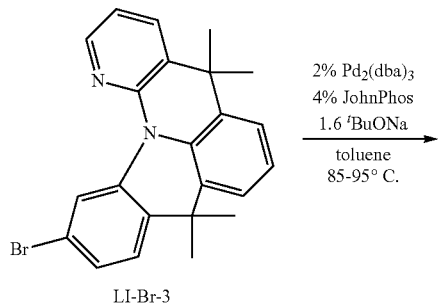

LI-Br-3

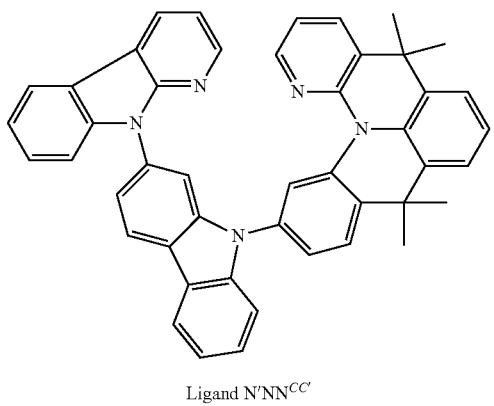

Ligand N'NN$^{CC'}$

↓ 1.1 K$_2$PtCl$_4$  AcOH, rt, 12 h
   0.1 $^n$Bn$_4$NBr  105-115° C., 3 d

In yet another aspect, PtN'NN$^{CC'}$ and PdPtN'NN$^{CC'}$ can be synthesized as follows:

661
-continued
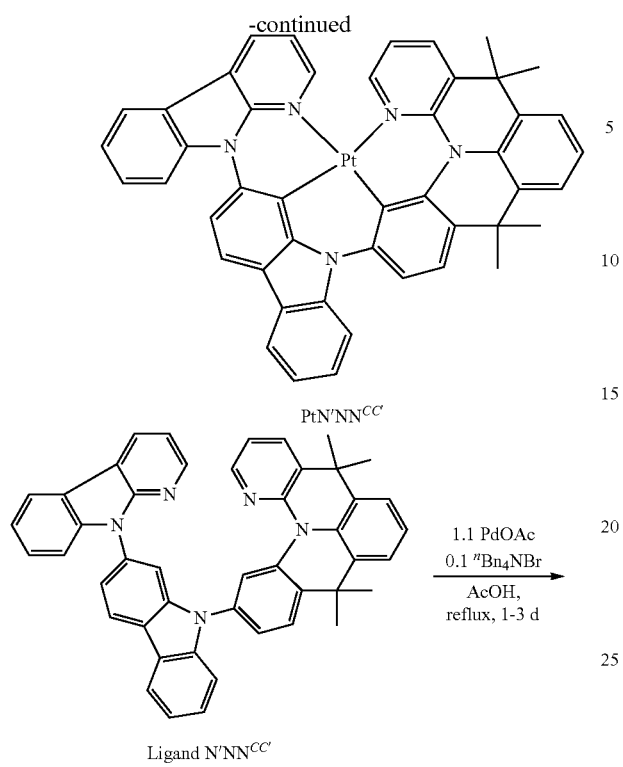
662
-continued
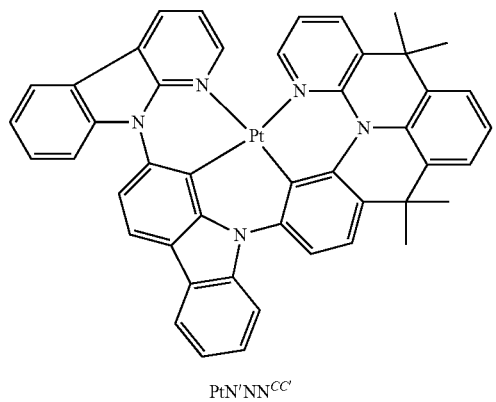
A general synthesis route for the disclosed Pt and Pd complexes of Formula AX herein includes:
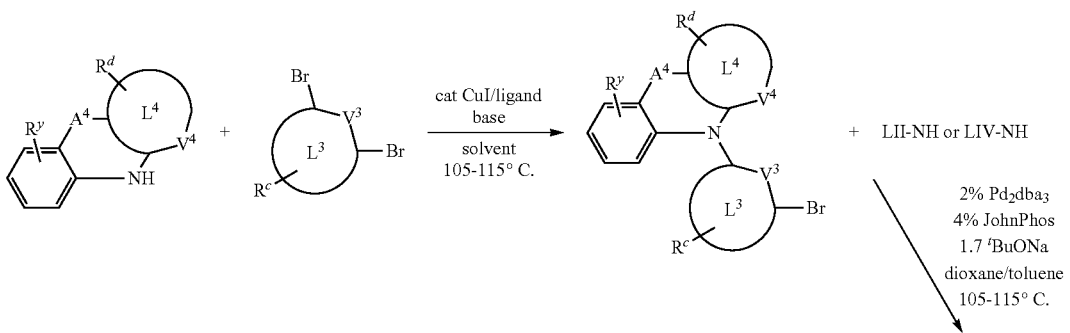
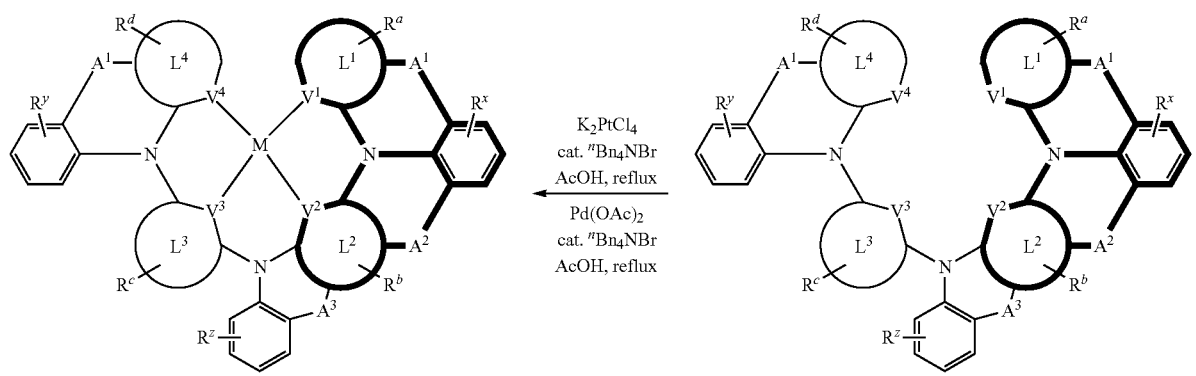

For example, in one aspect, PtN'N—N$^C$ and PdPtN'N—N$^C$ can be synthesized as follows:
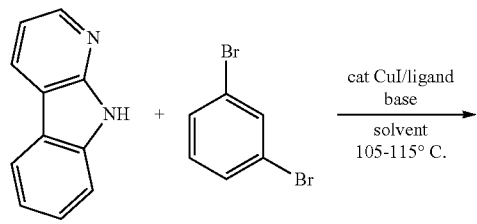
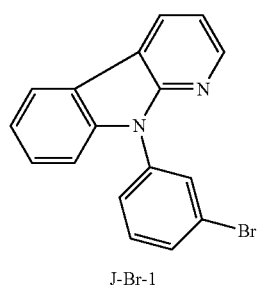
J-Br-1
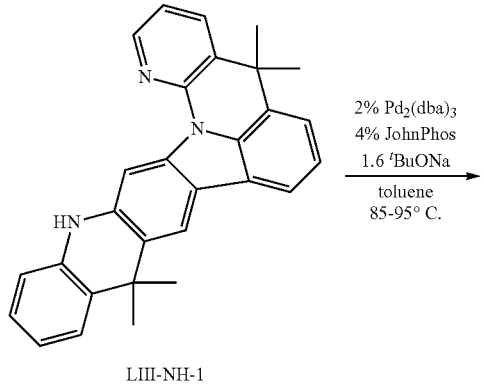
LIII-NH-1
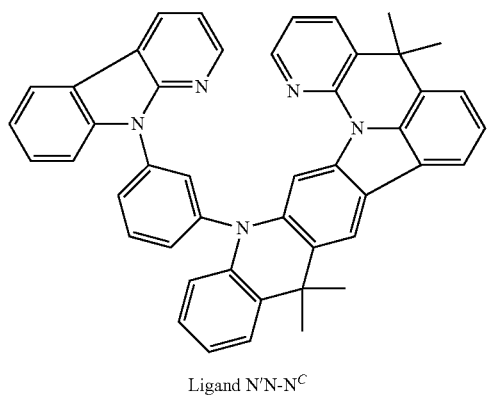
Ligand N'N-N$^C$
1.1 K$_2$PtCl$_4$ | AcOH, rt, 12 h
0.1 $^n$Bu$_4$NBr | 105-115° C., 3 d
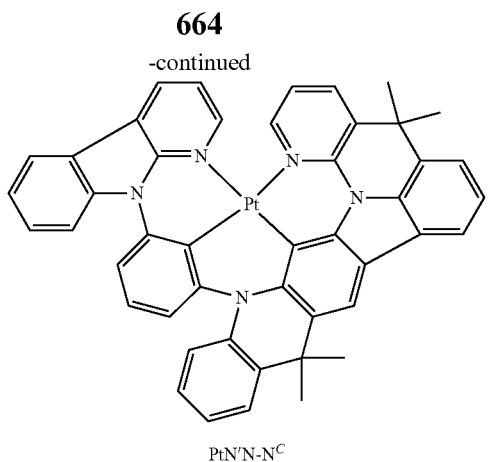
PtN'N-N$^C$
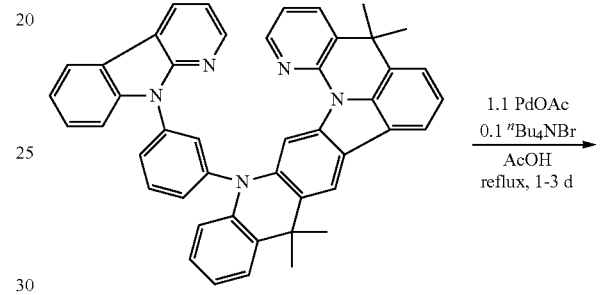
Ligand N'N-N$^C$
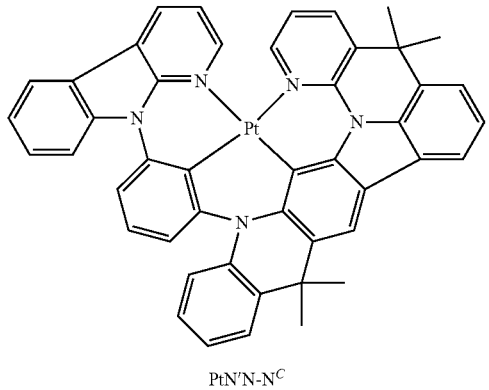
PtN'N-N$^C$
In another aspect, PtN'N—N$^{C'}$ and PdPtN'N—N$^{C'}$ can be synthesized as follows:
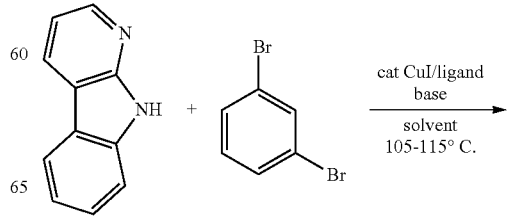

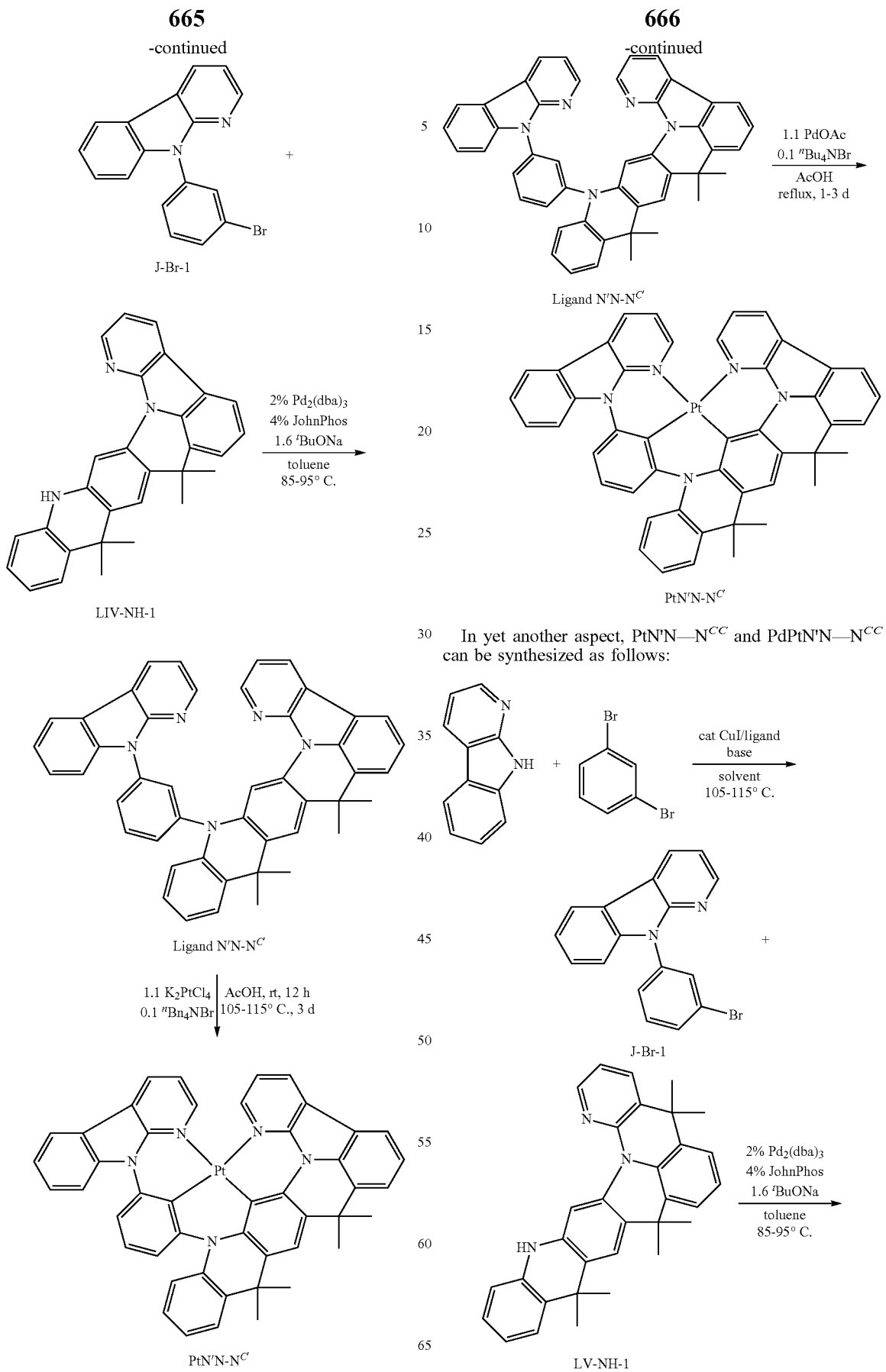
In yet another aspect, PtN'N—$N^{CC}$ and PdPtN'N—$N^{CC}$ can be synthesized as follows:

667
-continued
668
-continued
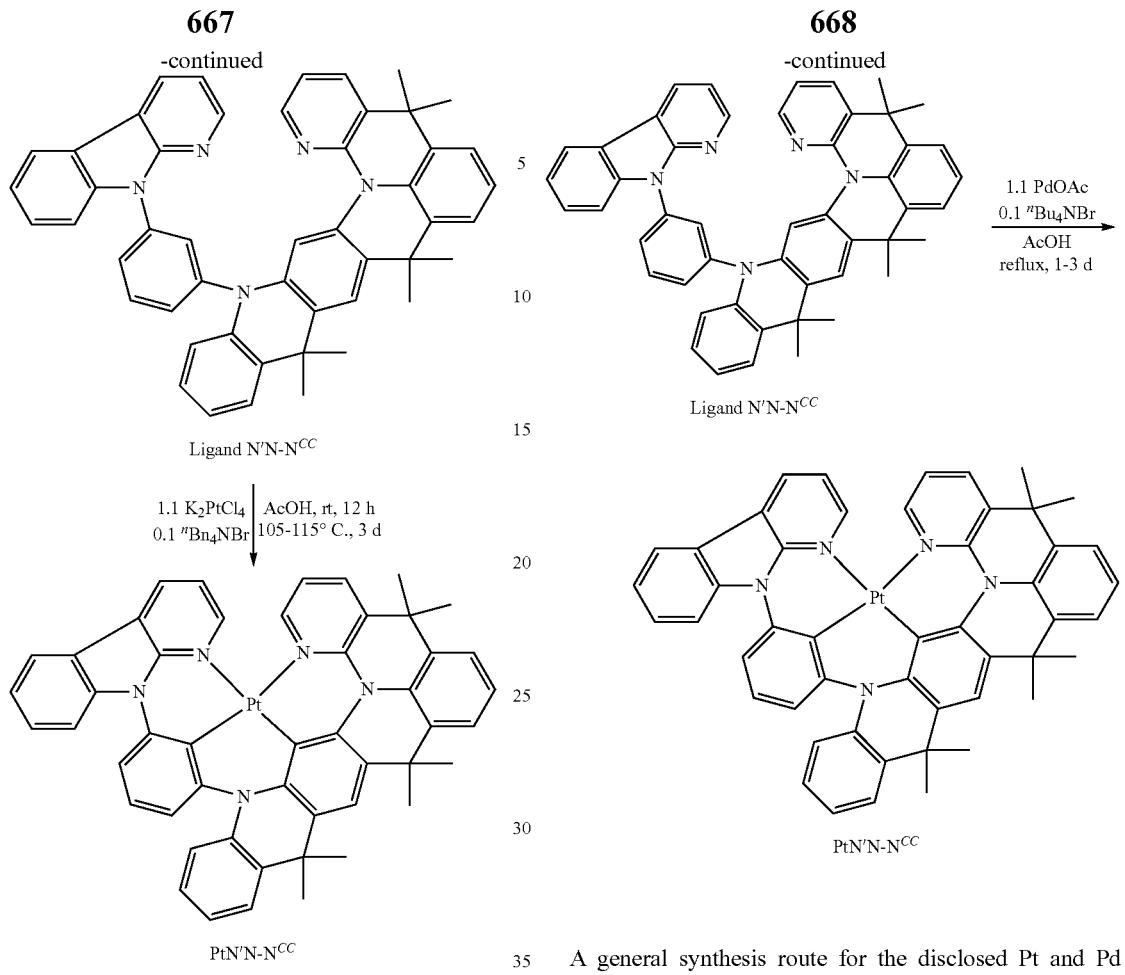
A general synthesis route for the disclosed Pt and Pd complexes of Formula AXI herein includes:
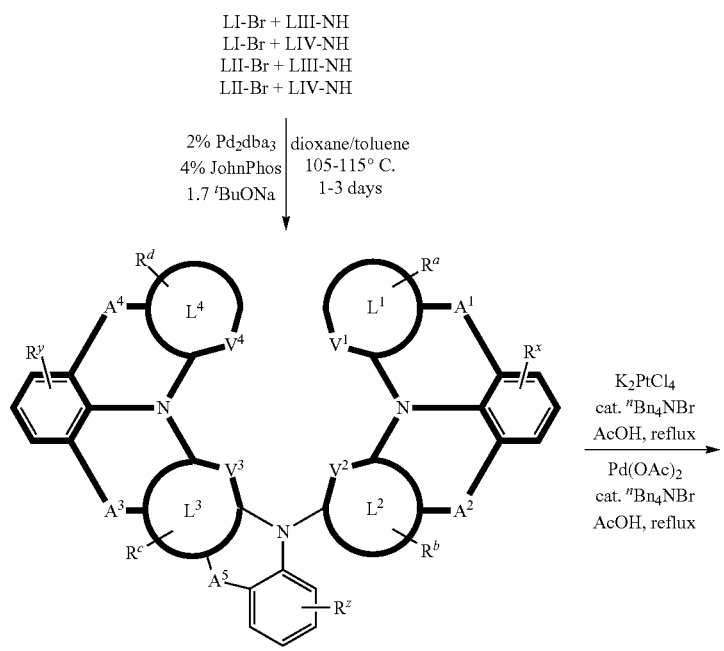

-continued
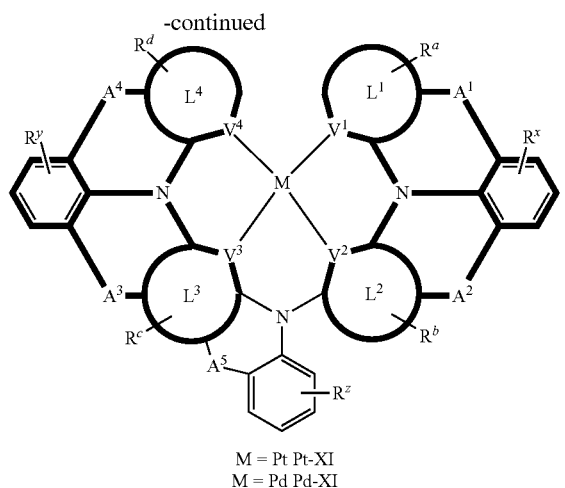
M = Pt Pt-XI
M = Pd Pd-XI
For example, in one aspect, $PtN^C$—$NN^{CC}$ and $PdPtN^C$—$NN^{CC}$ can be synthesized as follows:

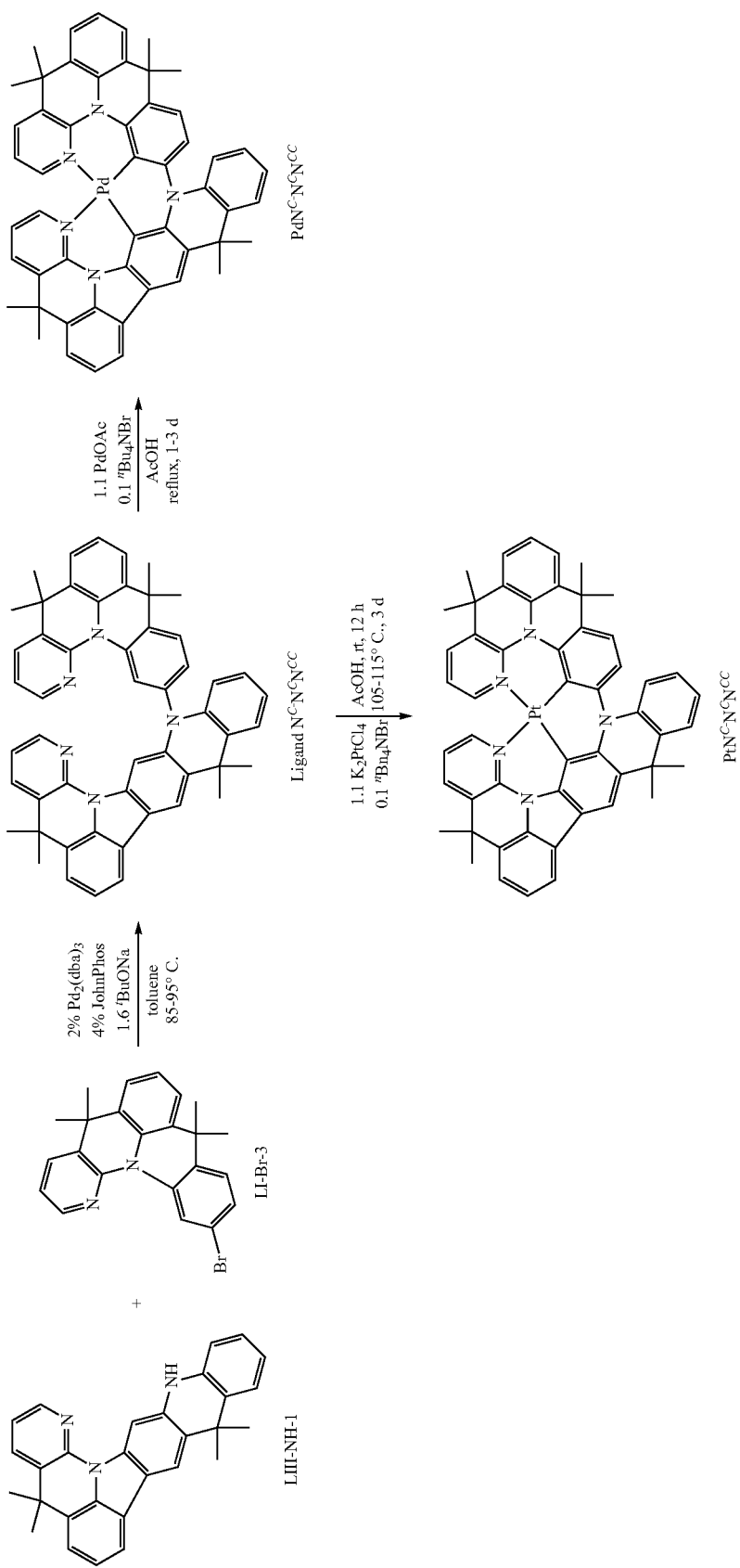

In another aspect, PtN$^{C'}$—NN$^{CC}$ and PdPtN$^{C'}$—NN$^{CC}$ can be synthesized as follows:
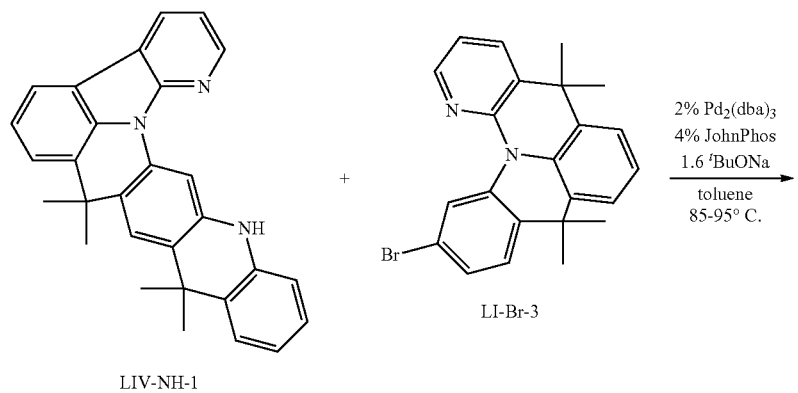
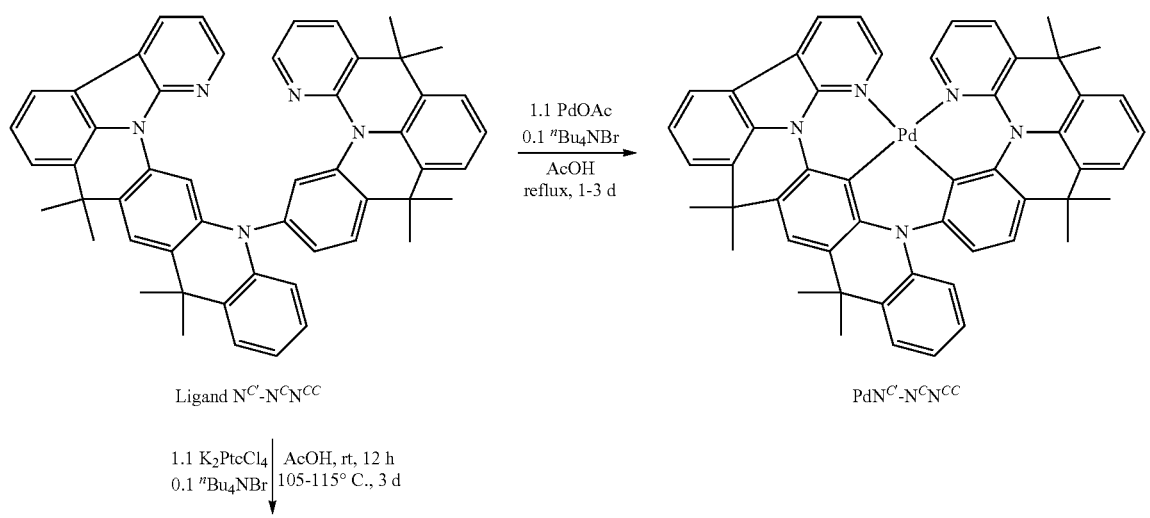
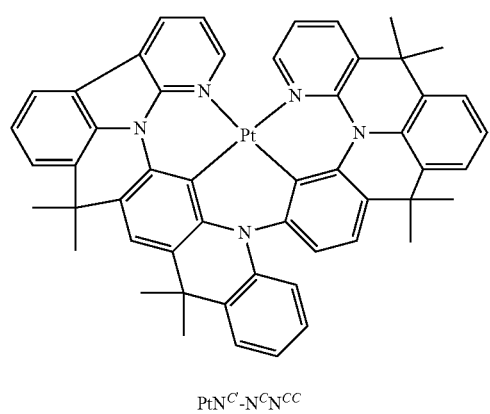
A general synthesis route for the disclosed Pt and Pd complexes of Formula AXII herein includes:

LI-Br + LIII-NH
LI-Br + LIV-NH
LII-Br + LIII-NH
LII-Br + LIV-NH
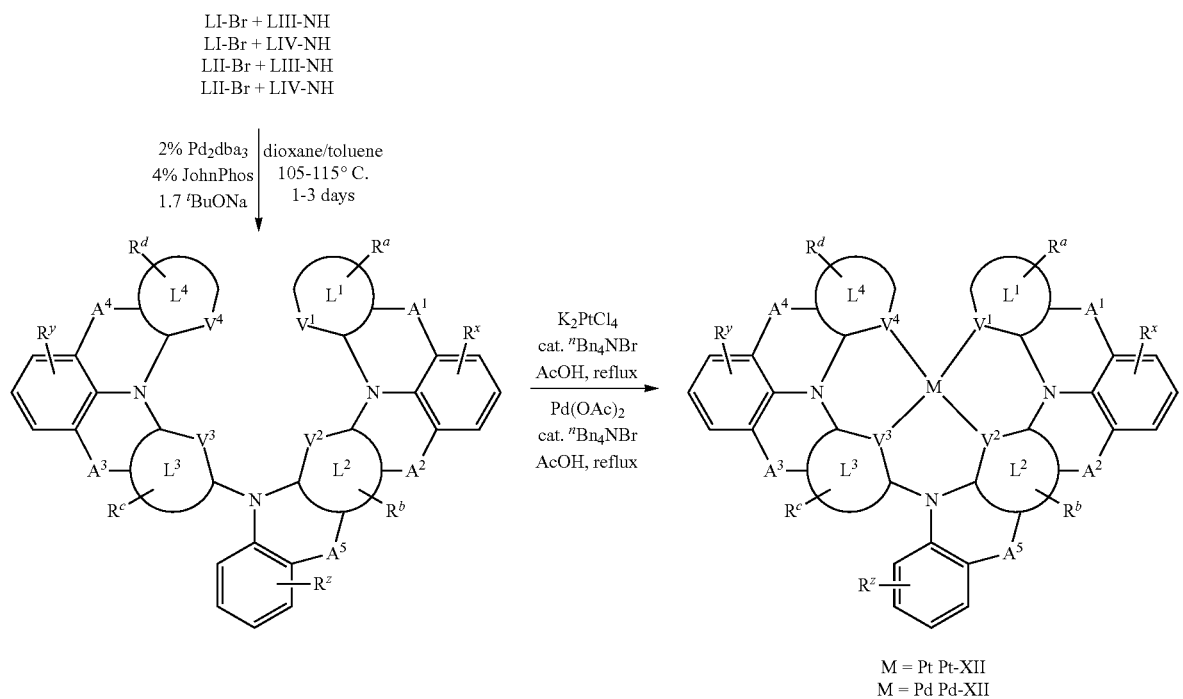
For example, in one aspect, $PtN^CN^C\text{—}N^{CC}$ and $PdPtN^CN^C\text{—}N^{CC}$ can be synthesized as follows:
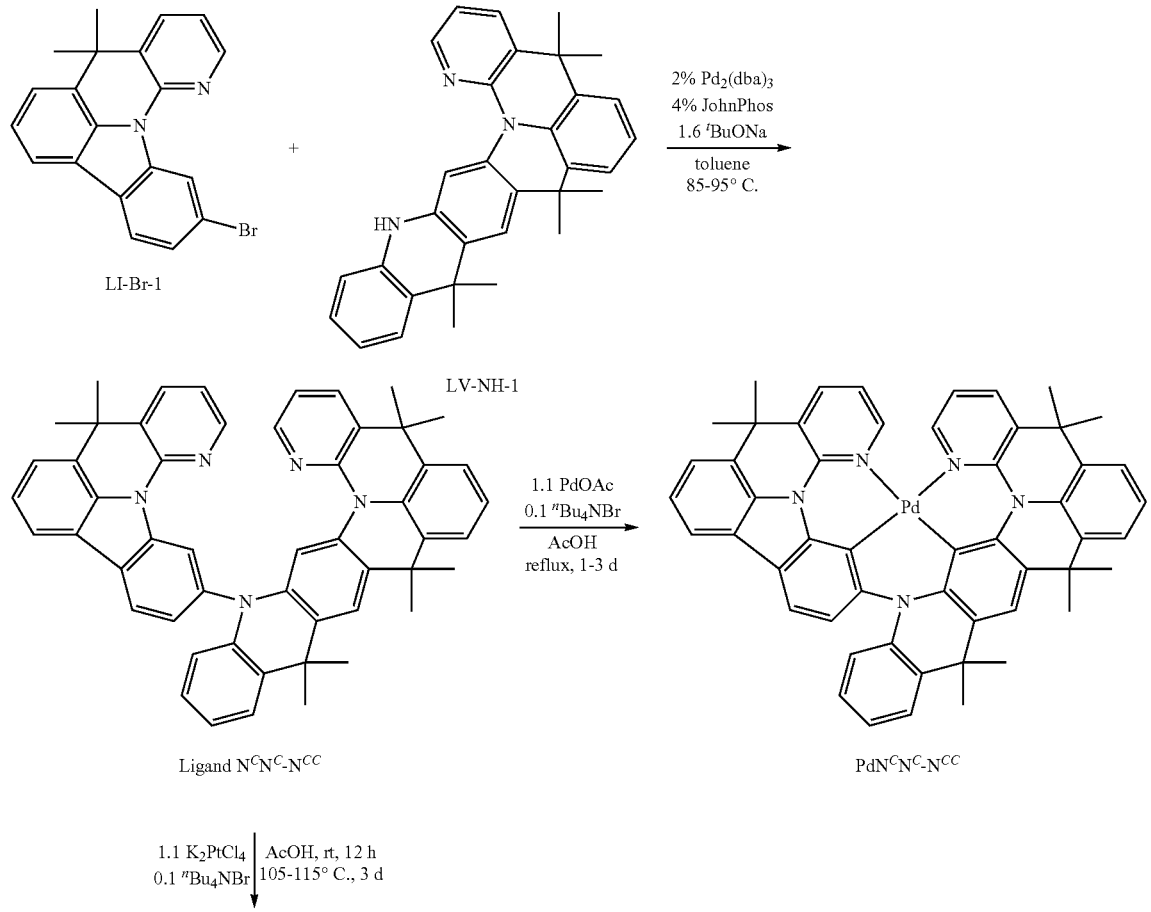

-continued
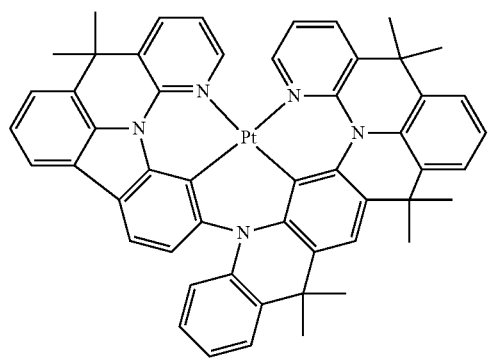
PtN$^{C'}$N$^C$-N$^{CC}$
In another aspect, PtN$^{C'}$N$^C$—N$^{CC}$ and PdPtN$^{C'}$N$^C$—N$^{CC}$ can be synthesized as follows:
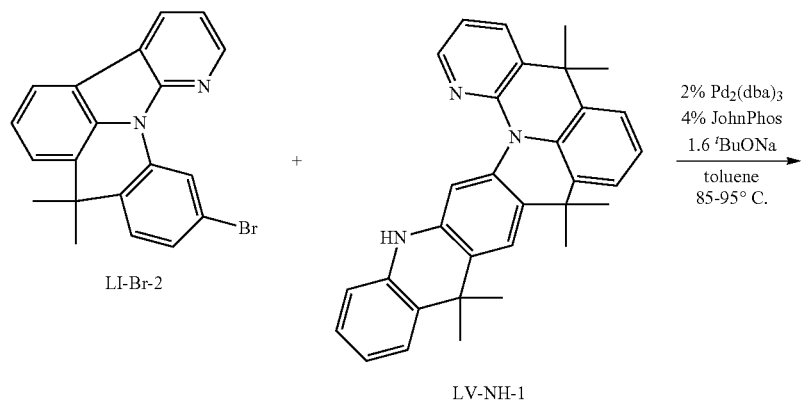
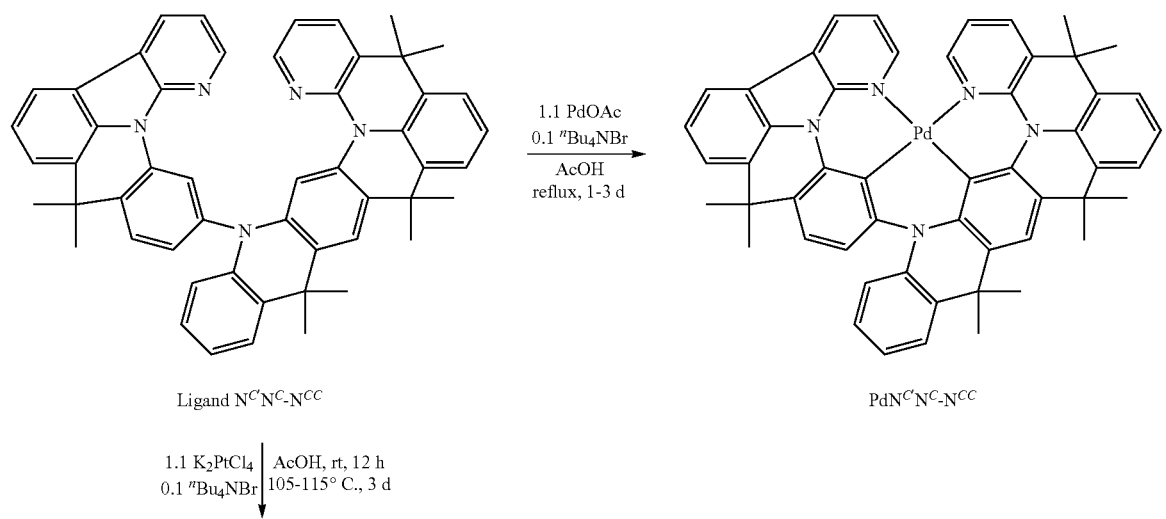

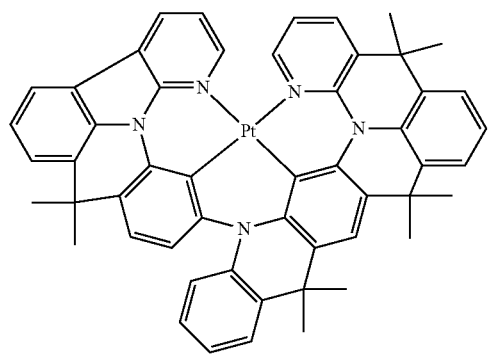
PtN^C'N^C-N^CC
In yet another aspect, PtN^CC N^C—N^CC and PdPtN^CC N^C—N^CC can be synthesized as follows:
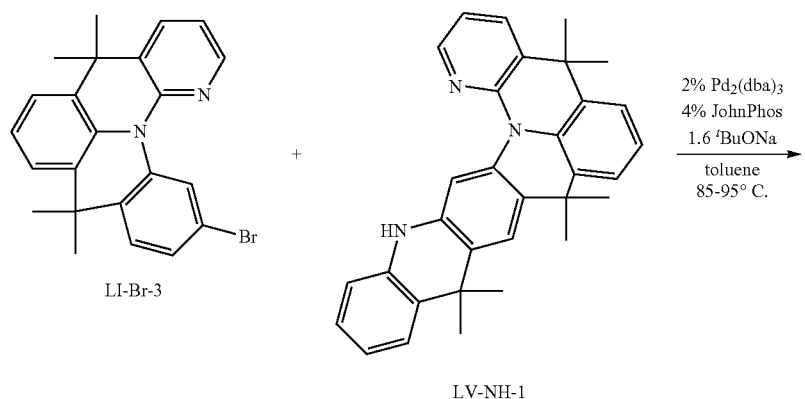
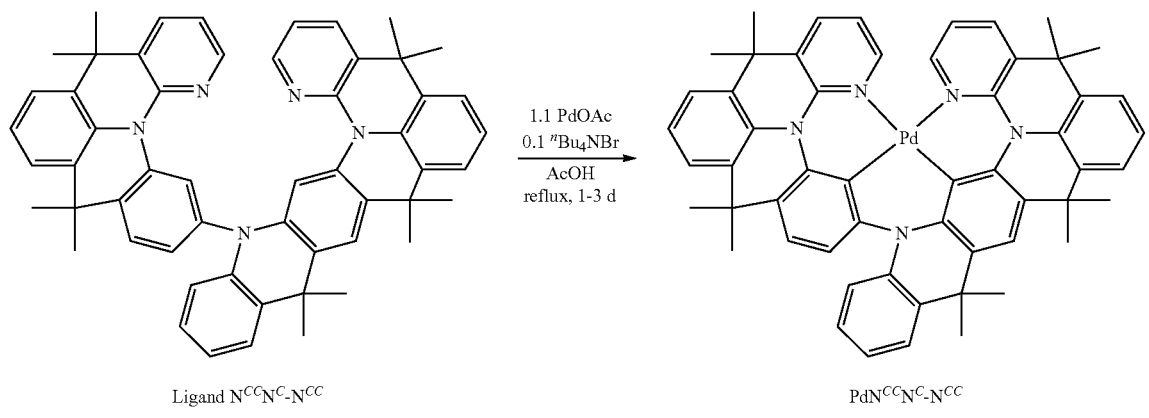

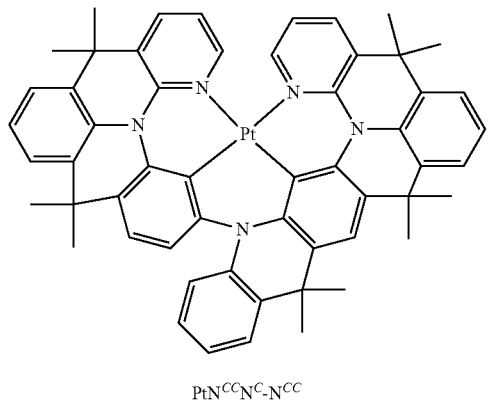

PtN^{CC}N^{C}-N^{CC} wherein each of $Y^1$, $Y^2$, $Y^3$, and $Y^4$ is independently C, N, O, or S.

wherein each of R, $R^1$, and $R^2$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Figure 8:
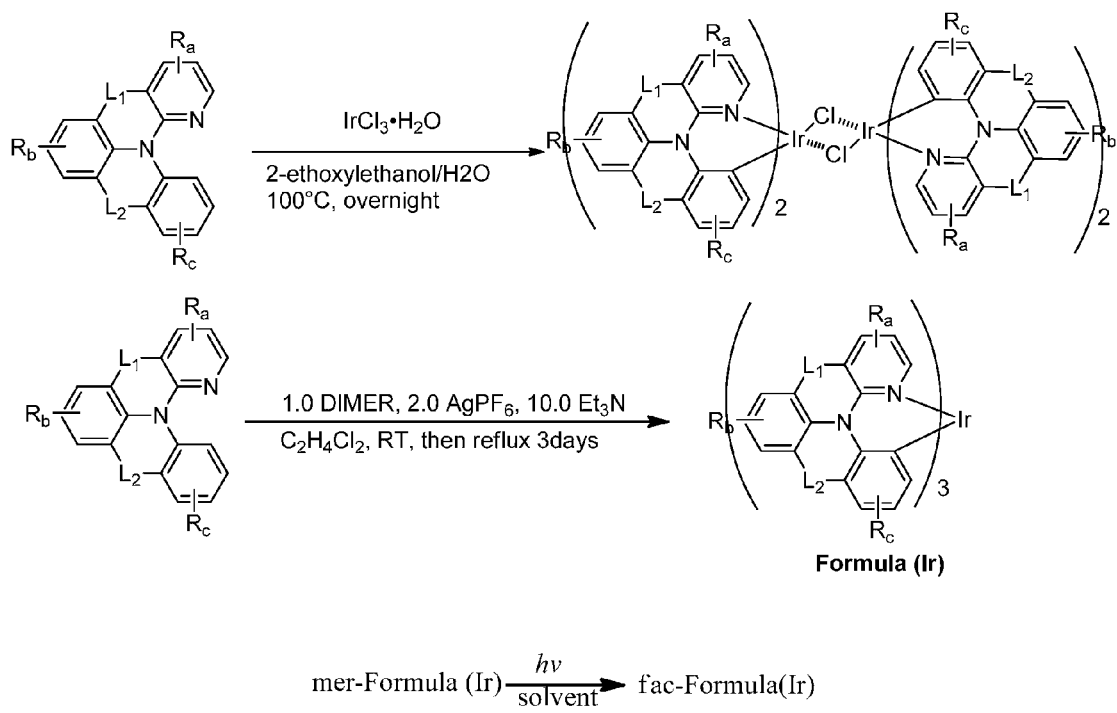
FIG. 8 depicts a synthetic scheme for the synthesis of Ir and Rh complexes.

A synthetic scheme for the synthesis of Ir and Rh complexes is depicted in FIG. 8.

Figure 9:
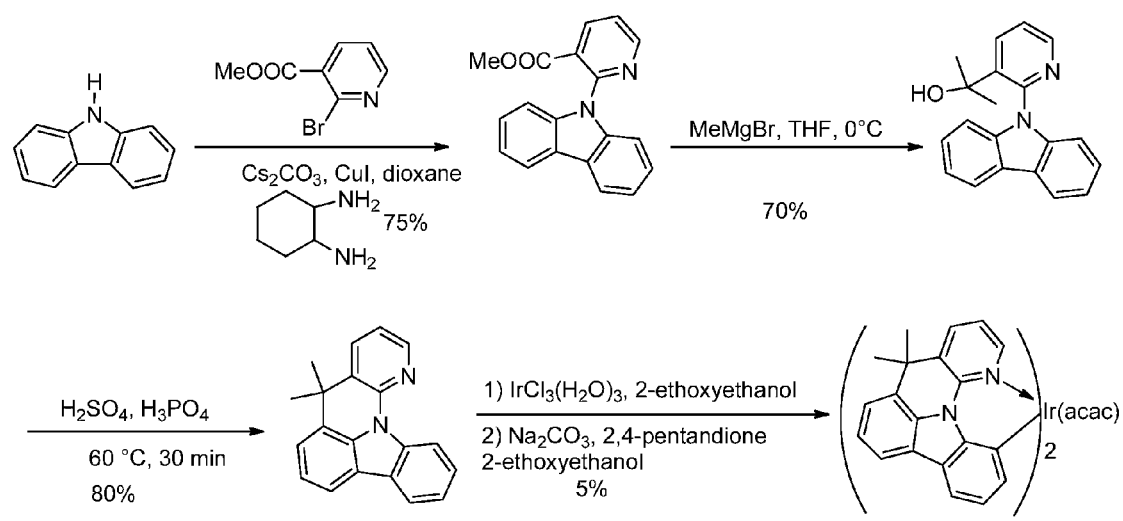
FIG. 9 depicts a synthetic scheme for the synthesis of $Ir(N^c)_2(acac)$.

A synthetic scheme for the synthesis of Ir($N^c$)$_2$(acac) is depicted in FIG. 9.

Synthesis of Ir($N^c$)$_2$(acac)

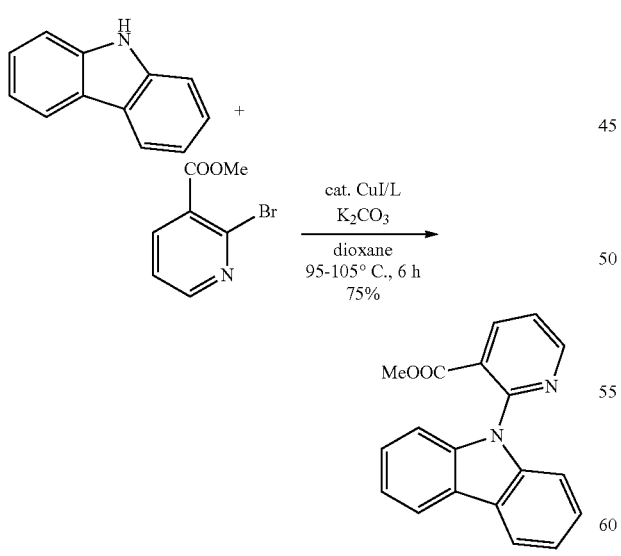

Methyl 2-(9H-carbazol-9-yl)pyridine-3-carboxylate

Methyl 2-bromo pyridine-3-carboxylate (1.70 g, 7.8 mmol, 1.00 eq), carbazole (1.3 g, 7.8 mmol, 1.00 eq), CuI (0.15 g, 0.78 mmol, 0.10 eq), and (±)-cyclohexane-1, 2-diamine (0.09 g, 0.78 mmol, 0.10 eq) were added to a dry pressure tube equipped with a magnetic stir bar. The tube was then taken into a glove box. $K_2CO_3$ (2.38 g, 17.2 mmol. 2.21 eq) and dry dioxane (10 mL) were added. The mixture was sparged with nitrogen for 10 minutes and then the tube was sealed. The tube was taken out of the glove box and heated to 95° C.-105° C. in an oil bath. The reaction was monitored by TLC and about 6 hours later the starting was consumed completely. Then the mixture was cooled to ambient temperature, diluted with ethyl acetate and washed with water. The organic phase was dried over sodium sulfate, filtered, and concentrated under reduced pressure. The residue was purified by silica gel column chromatography, using a mixture of hexanes and dichloromethane as eluent, in a ratio of 1:4 in volume, giving a white solid 1.8 g in yield of 75%. $^1$H NMR (400 MHz, $d_6$-DMSO): δ 9.05-9.03 (m, 1H), 8.45-8.40 (m, 1H), 8.35-8.30 (m, 1H), 7.55-7.50 (m, 2H), 7.45-7.38 (m, 2H), 7.00-7.10 (m, 4H), 3.43 (s, 3H).

2-(2-(9H-carbazol-9-yl)pyridin-3-yl)propan-2-ol (3)

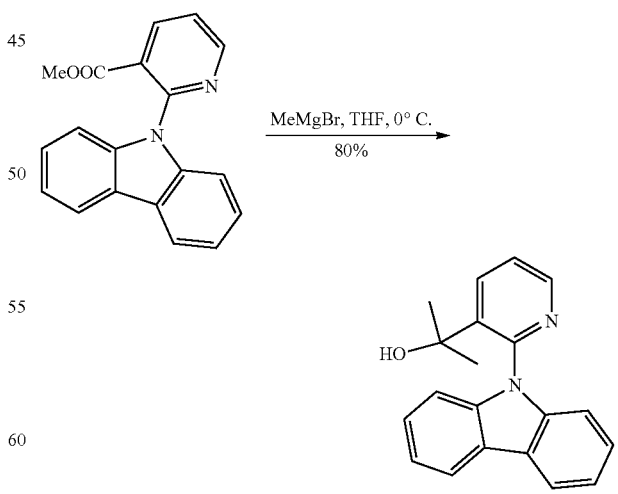

A solution of methyl 2-(9H-carbazol-9-yl)pyridine-3-carboxylate (4.2 g, 14 mmol) was added to a solution of methylmagnesium bromide in tetrahydrofuran (1 mol/L, 56 mL) at 0° C., then stirred to room temperature overnight.

The reaction was quenched with saturated aqueous ammonium chloride solution, extracted with dichloromethane, dried over sodium sulfate, filtered, and concentrated under vacuum. The residue was purified by silica gel column chromatography, using a mixture of hexanes and dichloromethane as eluent, in a ratio of 1:4 in volume, giving a white solid 3.5 g in yield of 80%.

5,5-Dimethyl-5H-[1,8]naphthyridino[3,2,1-jk]carbazole

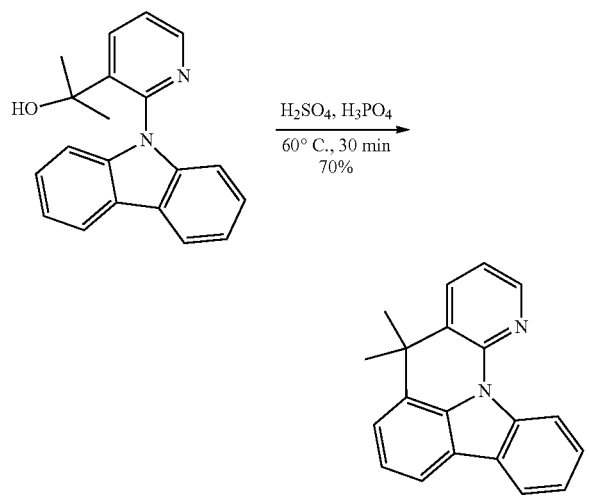

2-(2-(9H-carbazol-9-yl)pyridin-3-yl)propan-2-ol (1.00 g, 2.80 mmol) was added to a mixture of 98% concentrated sulfuric acid (5 mL) and phosphoric acid (5 mL) at 60° C. The resulting dark solution was stirred for 15 min, then cooled to room temperature and quenched with water. A white precipitate formed, and the slurry extracted with ethyl acetate. Then the organic phase was separated and dried over sodium sulfate, filtered, and concentrated under vacuum. The residue was purified by silica gel column chromatography using a mixture of ethyl acetate and hexane as eluent in a ratio of 1:4 in volume, giving a white solid 0.75 g in a yield of 70%. $^1$H NMR (400 MHz, d$_6$-DMSO): δ, 8.98 (d, 1H, J=9.0 Hz), 8.40 (d, 1H, J=1.5 Hz), 8.39 (d, 1H J=2.0 Hz), 8.21 (d, 1H, J=9.0 Hz), 8.13-8.11 (m, 2H), 8.01-8.00 (d, 1H, J=9.0 Hz), 7.58-7.53 (m, 2H), 7.39-7.35 (m, 2H), 7.24-7.21 (m, 1H), 1.70 (m, 6H).

Ir(N$^c$)$_2$(acac)

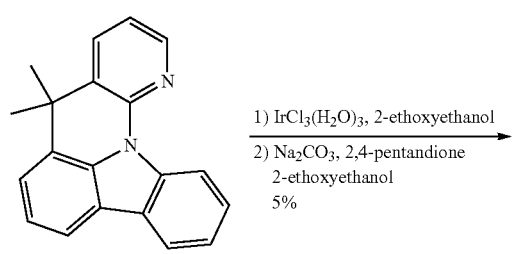

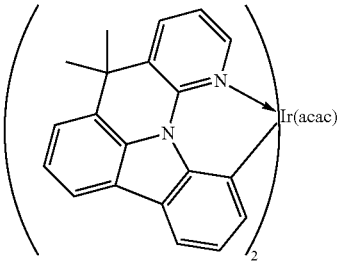

A mixture of organic ligand 5, 5-Dimethyl-5H-[1,8]naphthyridino[3,2,1-jk]carbazole (1.12 g, 3 mmol) and IrCl$_3$•3H$_2$O (0.2 g 0.67 mmol) in 2-ethoxyethanol (12 ml) and water (4 ml) was stirred at 120° C. for 48 h under nitrogen and cooled to room temperature. The precipitate was collected by filtration and washed with water, ethanol, and hexanes successively, then dried under vacuum to give a cyclometallated Ir(III) 1-chloro-bridged dimer.

The Ir(III) 1-chloro-bridged dimer (0.2 g, 0.19 mmol), pentane-2,4-dione (1 mL, 0.58 mmol), and Na$_2$CO$_3$ (0.20 g, 1.9 mmol) were dissolved in 2-ethoxyethanol (10 ml) and the mixture was then stirred under argon at 100° C. for 16 h. After cooling to room temperature, the precipitate was filtered and successively washed with water, ethanol, and hexane. The crude product was flash chromatographed on silica gel using CH$_2$Cl$_2$ as eluent to afford the desired Ir(III) complex 19 mg as yellow solid in a yield of 5%. $^1$H NMR (400 MHz, d$_6$-DMSO): δ 9.07 (2H, m), 8.06 (2H, m), 7.25 (2H, s), 6.95 (2H, t) 6.76 (2H, m), 6.64 (2H, m) 6.40 (2H, m), 6.30 (2H, m), 5.79 (2H, m), 5.25 (s, 1H), 1.9 (6H, s), 1.6 (12H, m).

Synthesis of complex 5 and complex 6

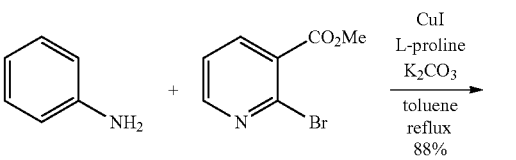

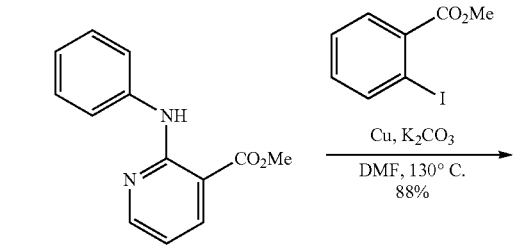

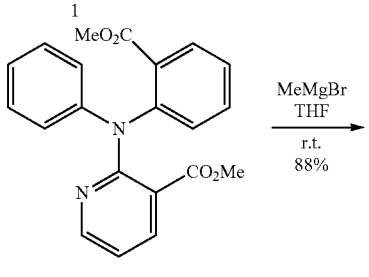

-continued

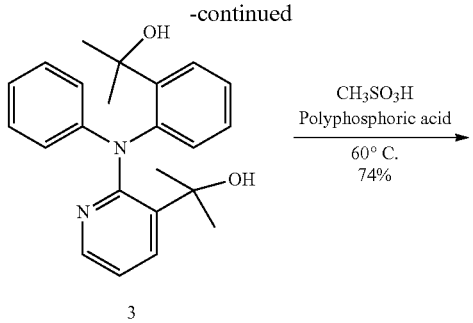

3

4

Methyl 2-(phenylamino)nicotinate

Aniline (93 mg, 1 mmol, 1.0 eq), methyl 2-bromonicotinate (216 mg, 68 mmol, 2.0 eq), L-proline (35 mg, 0.3 mmol, 0.3 eq) and $K_2CO_3$ (276 mg, 2 mmol, 2 eq) were added to a dry pressure tube equipped with a magnetic stir bar. Then the tube was taken into a glove box. CuI (57 mg, 0.3 mmol, 0.3 eq) and solvent toluene (10 mL) were added. The mixture was bubbled with nitrogen for 10 minutes. The tube was sealed before being taken out of the glove box and the mixture was stirred in an oil bath at a temperature of 120° C. for 1 day, cooled down to ambient temperature and quenched with water (50 mL). Then the mixture was extracted with ethyl acetate three times and the combined organic layer was washed with water three times, dried over magnesium sulphate, then filtered and washed with ethyl acetate. The filtrate was concentrated and the residue was purified through column chromatography on silica gel using hexane and ethyl acetate (20:1-10:1) as eluent to obtain the desired product methyl 2-(phenylamino)nicotinate 1 as yellow oil 200 mg in 88% yield. $^1$H NMR (500 MHz, $d_6$-DMSO) δ 10.10 (s, 1H), 8.42 (dd, J=4.7, 2.0 Hz, 1H), 8.26 (dd, J=7.8, 2.0 Hz, 1H), 7.71 (dd, J=8.6, 1.0 Hz, 2H), 7.34 (t, J=8.6 Hz, 2H), 7.03 (tt, J=7.6, 1.0 Hz, 1H), 6.90 (dd, J=7.8, 4.7 Hz, 1H), 3.91 (s, 3H).

Methyl 2-((2-(methoxycarbonyl)phenyl)(phenyl)amino)nicotinate 1 (2.1 g, 9.2 mmol, 1.0 eq), methyl 2-iodobenzoate (2.89 g, 11 mmol, 1.2 eq) and $K_2CO_3$ (3.23 g, 23 mmol, 2.5 eq) were added to a dry pressure tube equipped with a magnetic stir bar. Then the tube was taken into a glove box. Cu (585 mg, 9.2 mmol, 1 eq) and solvent DMF (100 mL) were added. The mixture was bubbled with nitrogen for 10 minutes. The tube was sealed before being taken out of the glove box and the mixture was stirred in an oil bath at a temperature of 130° C. for 2 days, cooled down to ambient temperature and quenched with water (200 mL). Then the mixture was extracted with ethyl acetate three times and the combined organic layer was washed with water three times, dried over magnesium sulphate, then filtered and washed with ethyl acetate. The filtrate was concentrated and the residue was purified through column chromatography on silica gel using hexane and ethyl acetate (5:1) as eluent to obtain the desired product methyl 2-((2-(methoxycarbonyl)phenyl)(phenyl)amino)nicotinate 2 as white solid 2.9 g in 88% yield. $^1$H NMR (500 MHz, $d_6$-DMSO) δ 8.27 (dd, J=4.7, 1.8 Hz, 1H), 7.86 (dd, J=7.6, 1.8 Hz, 1H), 7.66 (dd, J=7.7, 1.3 Hz, 1H), 7.52 (t, J=7.7 Hz, 1H), 7.31-7.21 (m, 3H), 7.08-7.00 (m, 3H), 6.86 (d, J=7.7 Hz, 2H), 3.33 (s, 3H), 3.20 (s, 3H).

2-(2-((2-(2-Hydroxypropan-2-yl)phenyl)(phenyl)amino)pyridin-3-yl)propan-2-ol 2 (1.82 g, 5 mmol, 1.0 eq) was dissolved in solvent THF (30 ml) and MeMgBr (30 ml, 1 mol/l, 6.0 eq) was added dropwise at room temperature. The mixture was stirred for 1 day and quenched with saturated $NH_4Cl$ aqueous (50 mL). Then the mixture was extracted with ethyl acetate three times and the combined organic layer was washed with water three times, dried over magnesium sulphate, then filtered and washed with ethyl acetate. The filtrate was concentrated and the residue was purified through column chromatography on silica gel using hexane and ethyl acetate (1:1) as eluent to obtain the desired product methyl 2-(2-((2-(2-hydroxypropan-2-yl)phenyl)(phenyl)amino)pyridin-3-yl)propan-2-ol 3 as white solid 1.6 g in 88% yield.

5,5,9,9-Tetramethyl-5,9-dihydro-[1,8]naphthyridino[3,2,1-de]acridine 3 (1.50 g, 4 mmol) was added to a mixture of $CH_3SO_3H$ (10 mL) and polyphosphoric acid (20 mL) at 60° C. The resulting solution was stirred for 2 hours, then cooled to room temperature and neutralized with a solution of $K_2CO_3$. Then the mixture was extracted with ethyl acetate three times and the combined organic layer was washed with water three times, dried over magnesium sulphate, then filtered and washed with ethyl acetate. The filtrate was concentrated and the residue was purified through column chromatography on silica gel using hexane and ethyl acetate (2:1) as eluent to obtain the desired product 5,5,9,9-tetramethyl-5,9-dihydro-[1,8]naphthyridino[3,2,1-de]acridine 4 as white solid 1.0 g in 74% yield. $^1$H NMR (500 MHz, $d_6$-DMSO) δ 12.93 (dd, J=4.5, 1.2 Hz, 1H), 12.67 (d, J=7.5 Hz, 1H), 12.27 (d, J=7.9 Hz, 1H), 12.21 (d, J=8.0 Hz, 1H), 12.14 (t, J=7.7 Hz, 2H), 12.02-11.85 (m, 4H), 6.60 (s, 6H), 5.91 (s, 6H).

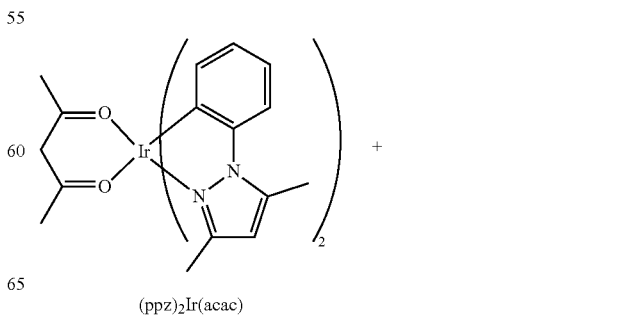

(ppz)$_2$Ir(acac)

-continued

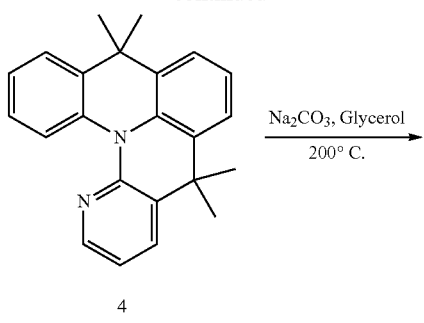

4

Na₂CO₃, Glycerol
⎯⎯⎯⎯⎯⎯⎯⎯→
200° C.

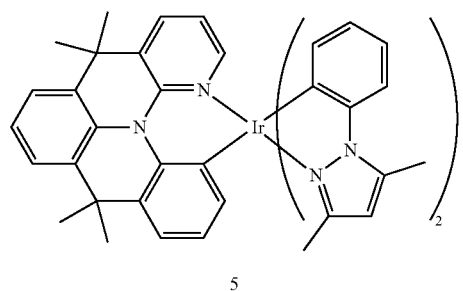

5

Complex 5:

To a 100 ml three-neck round bottom flask were added (ppz)₂Ir(acac) (150 mg, 0.24 mmol), 4 (85 mg, 0.26 mmol), Na₂CO₃ (36 mg, 0.6 mmol). The flask was evacuated and backfilled with nitrogen three times. Glycerol (20 ml) was added under the protection of nitrogen, and the reaction mixture was stirred at 200° C. under nitrogen atmosphere for 24 hours. After cooling to room temperature, water (30 ml) was added and the mixture was extracted three times with 30 ml of DCM. The combined organic layer was dried with anhydrous Na₂SO₄, filtered, concentrated under reduced pressure, and purified by column chromatography with DCM as eluent to afford the desired product.

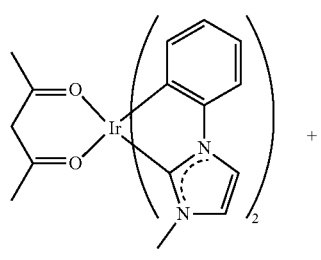

A

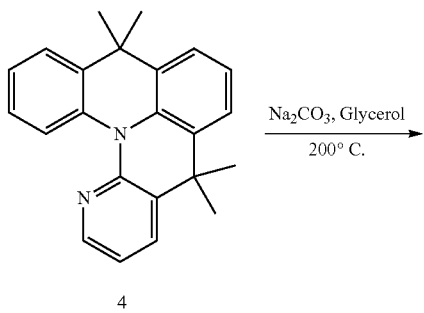

4

Na₂CO₃, Glycerol
⎯⎯⎯⎯⎯⎯⎯⎯→
200° C.

-continued

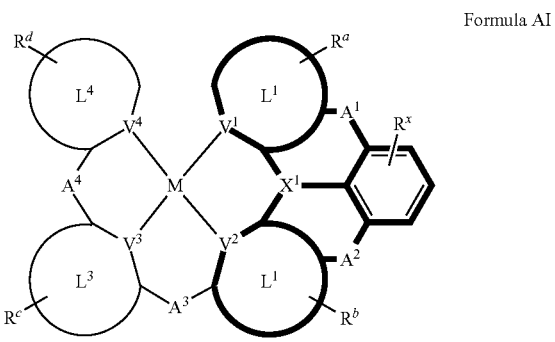

6

Complex 6:

To a 100 ml three-neck round bottom flask were added A (108 mg, 0.24 mmol), 4 (85 mg, 0.26 mmol), Na₂CO₃ (36 mg, 0.6 mmol). The flask was evacuated and backfilled with nitrogen three times. Glycerol (20 ml) was added under the protection of nitrogen, and the reaction mixture was stirred at 200° C. under nitrogen atmosphere for 24 hours. After cooling to room temperature, water (30 ml) was added and the mixture was extracted three times with 30 ml of DCM. The combined organic layer was dried with anhydrous Na₂SO₄, filtered, concentrated under reduced pressure, and purified by column chromatography with DCM as eluent to afford the desired product.

A number of embodiments have been described. Nevertheless, it will be understood that various modifications may be made without departing from the spirit and scope of the disclosure. Accordingly, other embodiments are within the scope of the following claims.

What is claimed is:

1. A complex of Formula AIV:

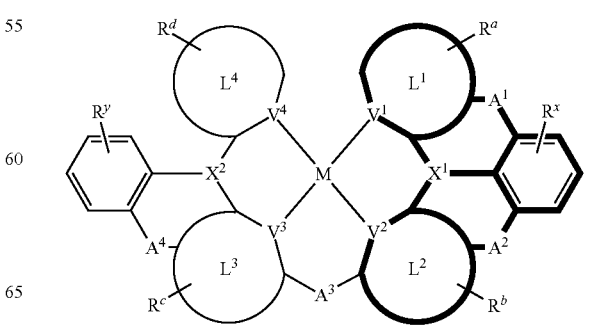

Formula AI

Formula AII

-continued

Formula AIII

Formula AIV wherein:
M is Pt or Pd,
$V^1$ and $V^4$ are N,
$V^2$ and $V^3$ are C,
$L^1$ and $L^4$ are pyridyl;
$L^2$ and $L^3$ are phenyl;
each of $A^1$, $A^2$, $A^3$, and $A^4$ is independently a single bond, $CR^1R^2$, C=O, $SiR^1R^2$, $GeR^1R^2$, $NR^3$, $PR^3$, $R^3P$=O, $AsR^3$, $R^3As$=O, O, S, S=O, $SO_2$, Se, Se=O, $SeO_2$, $BR^3$, $R^3Bi$=O, or $BiR^3$,
$A^5$ is O, $NR^3$, $CR^1R^2$, or C=O,
$X^1$ and $X^2$ are N,
each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof,
each of $R^x$ and $R^y$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination, and each of $R^1$, $R^2$ and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; wherein le and le are optionally linked together.

2. The complex of claim 1, wherein the complex has a neutral charge.

3. A complex represented by one of the chemical structures:

691
-continued
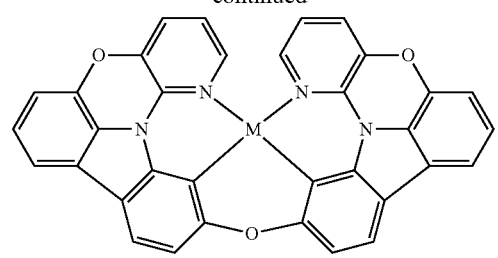
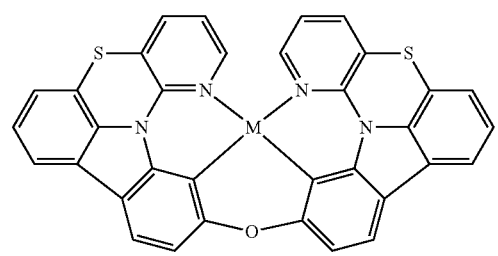
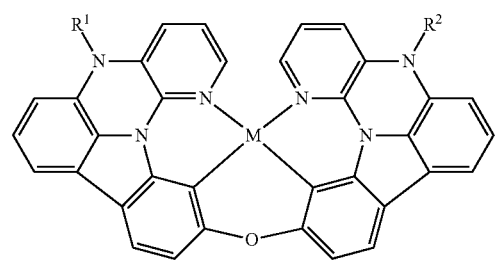
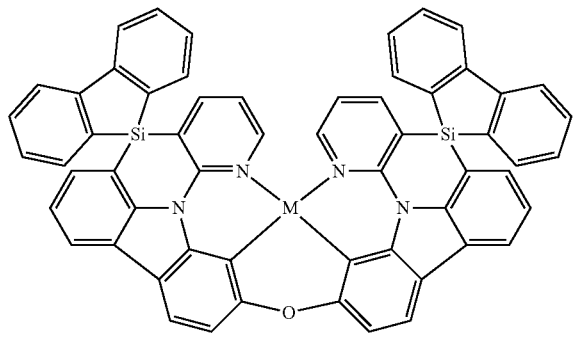
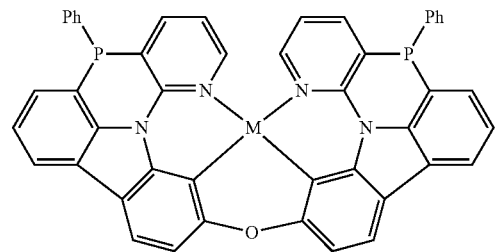
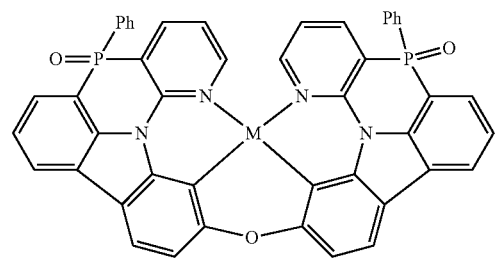
692
-continued
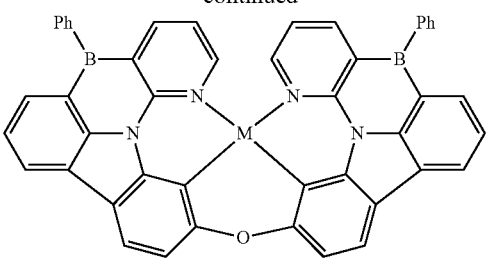
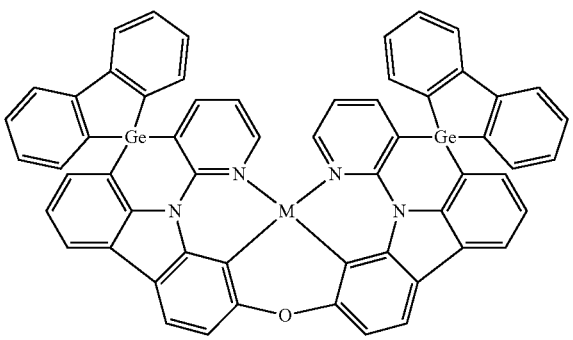
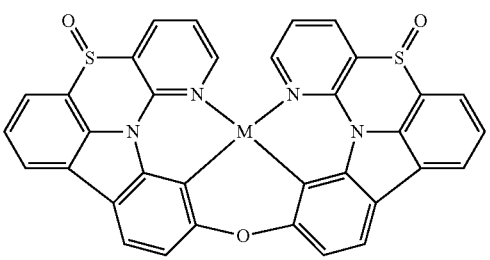
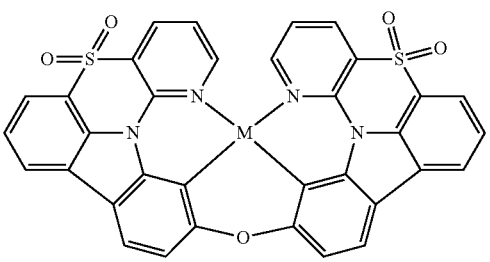
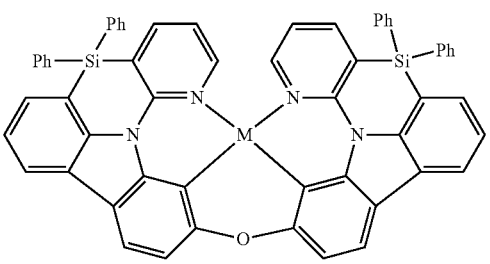
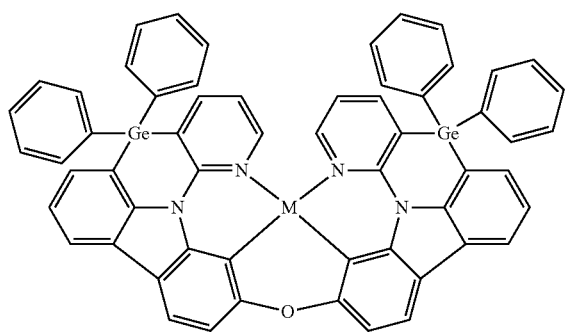

693
-continued
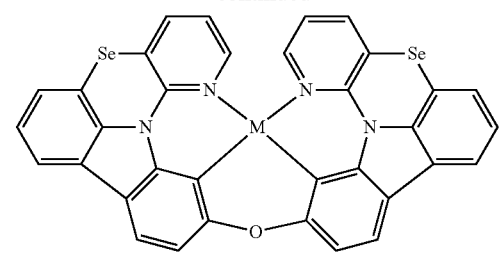
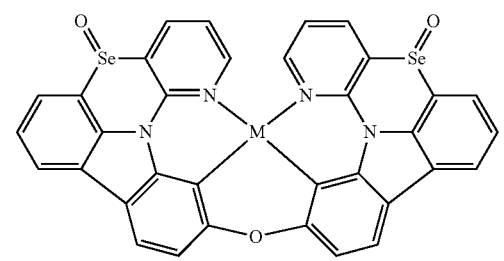
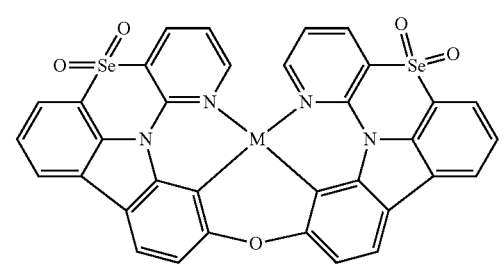
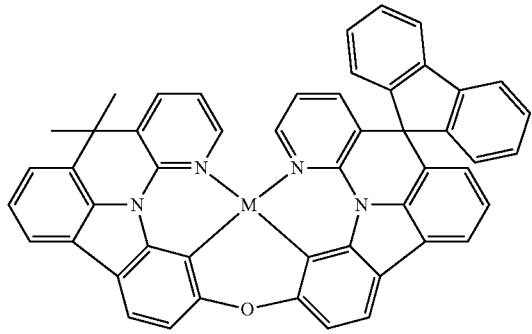
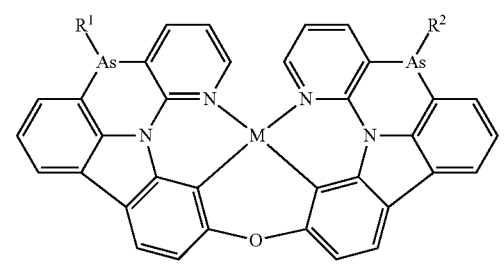
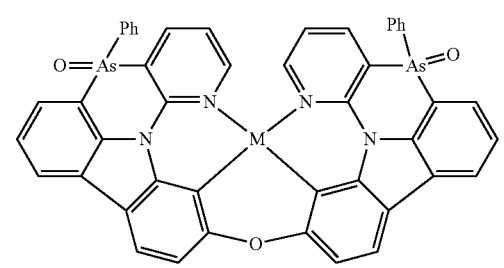
694
-continued
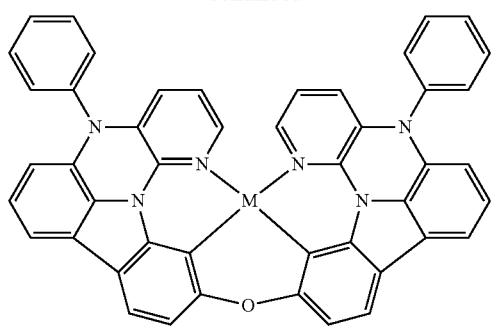
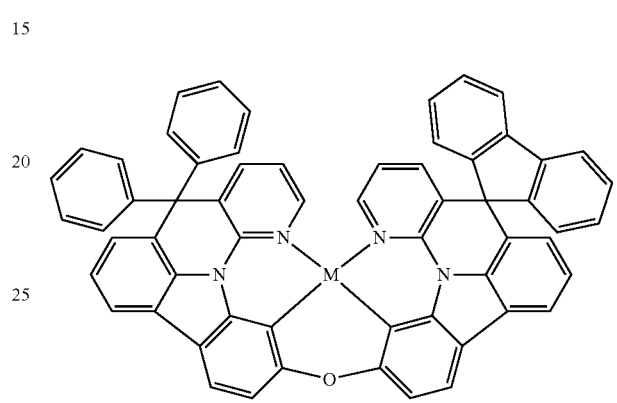
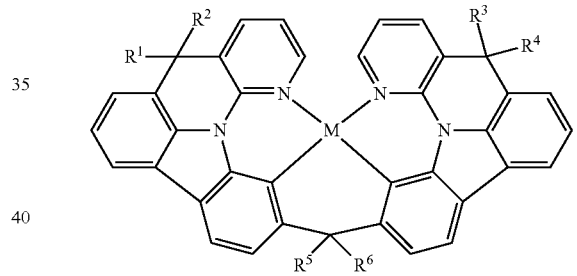
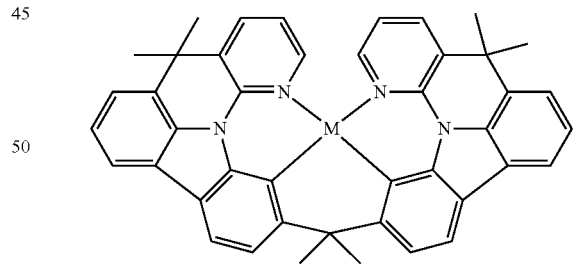
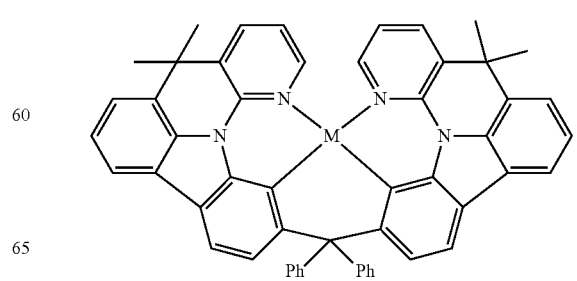

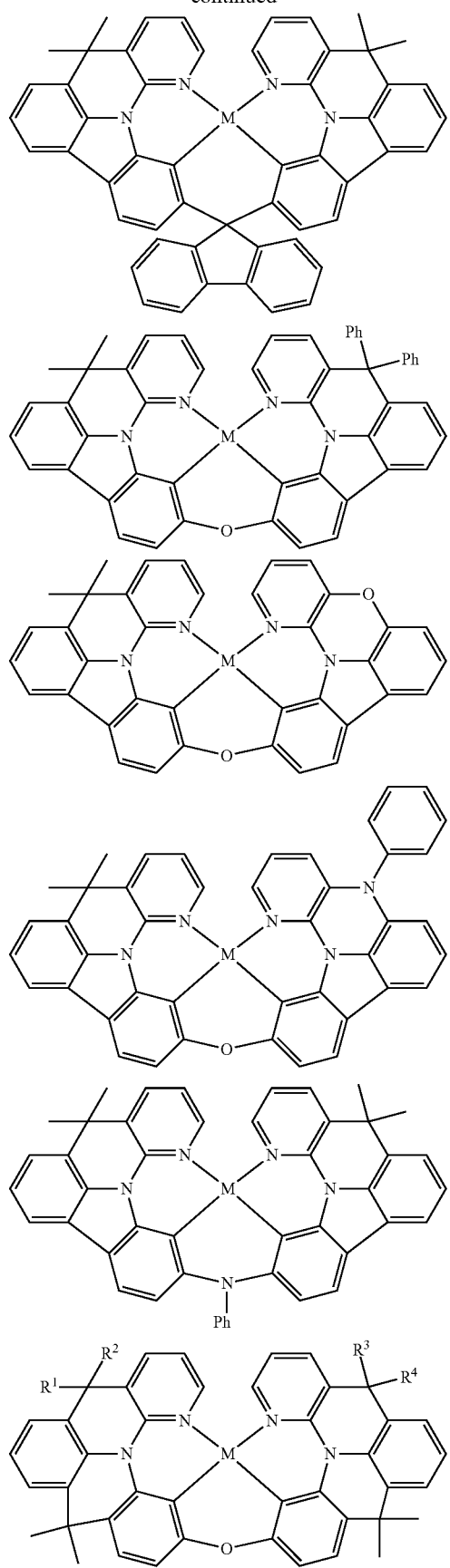
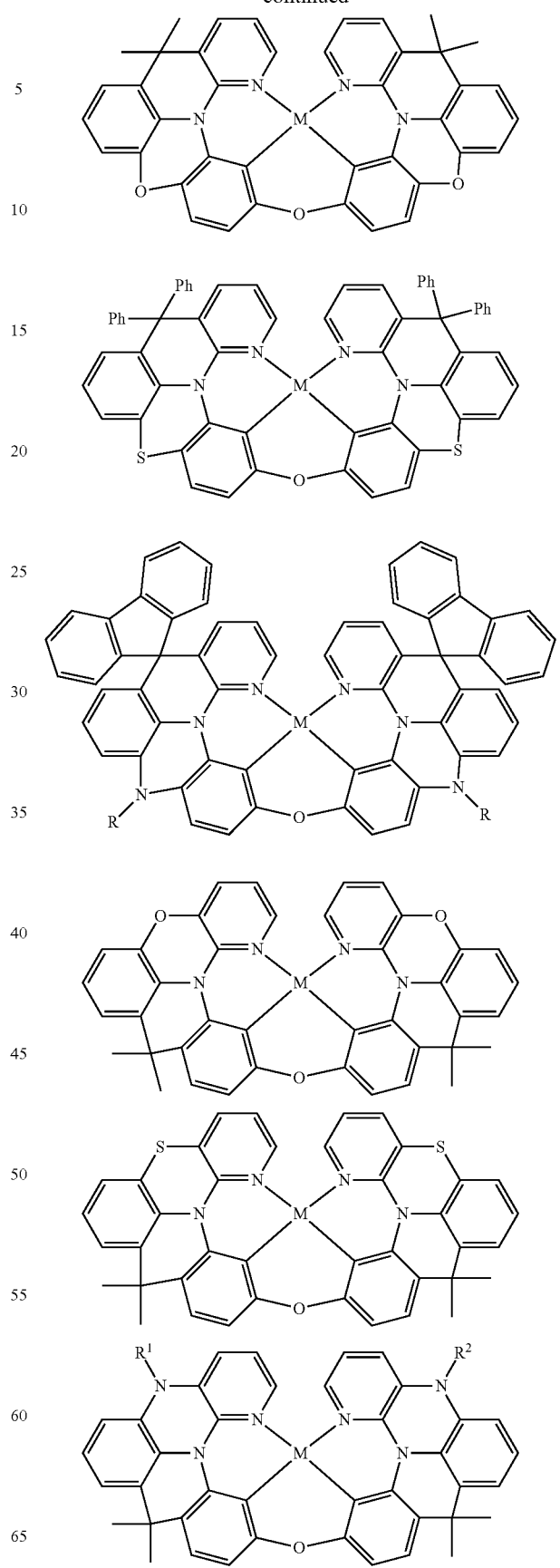

697
-continued
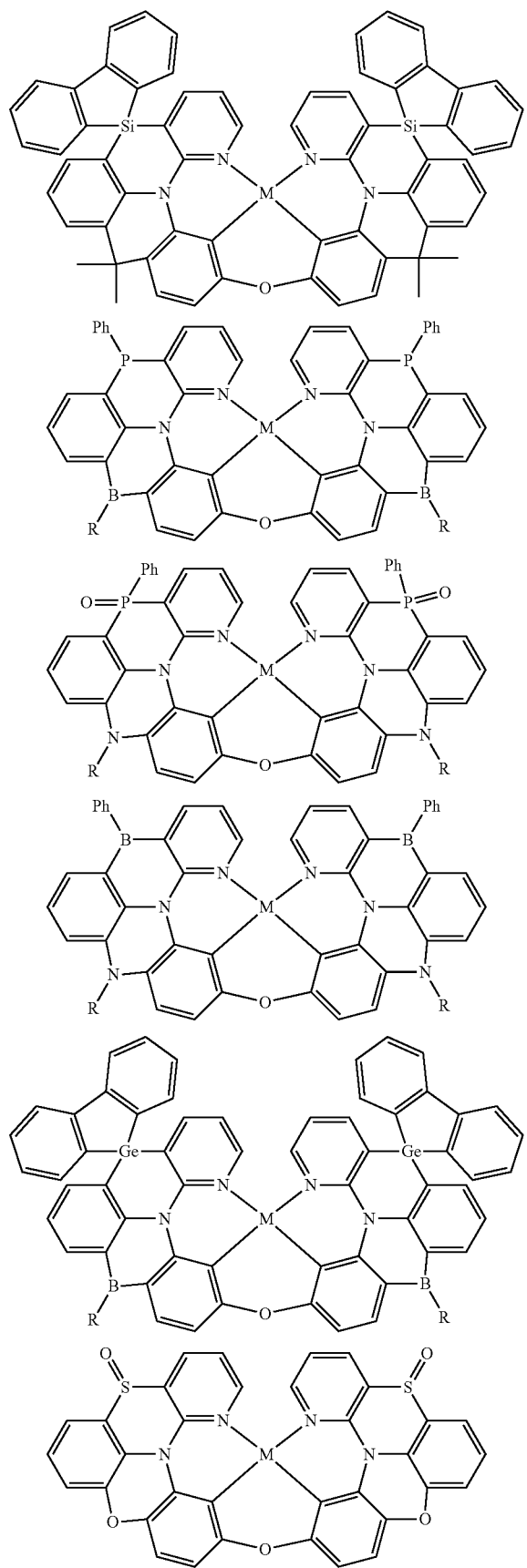
698
-continued
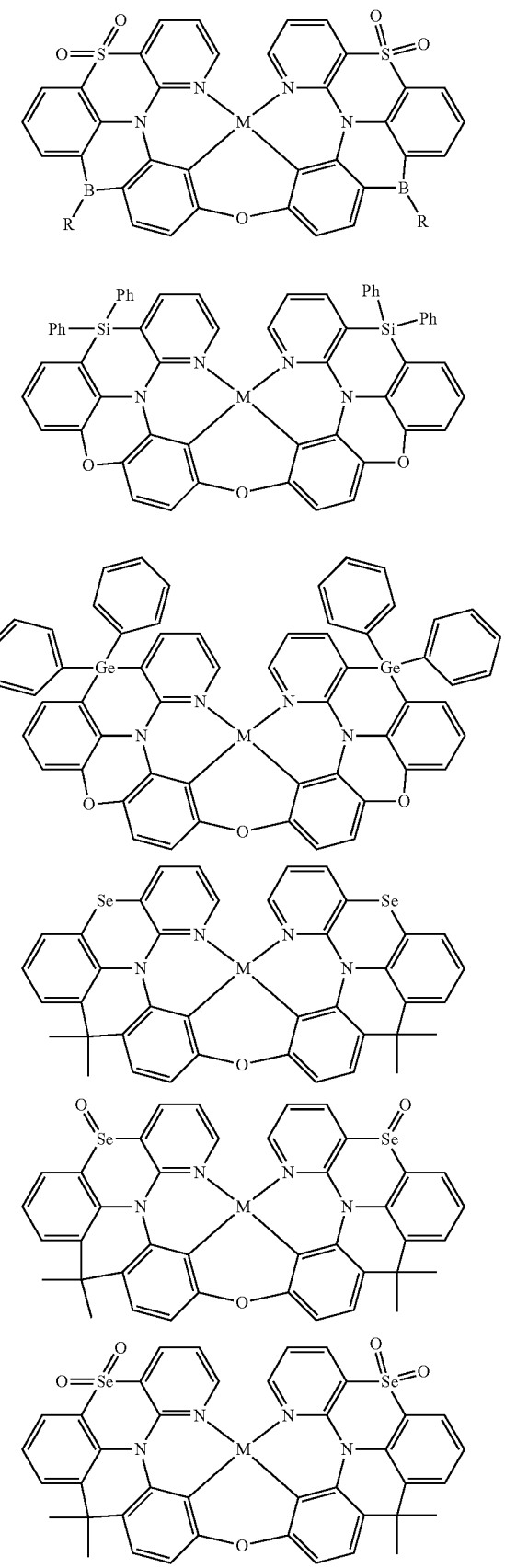

699
-continued
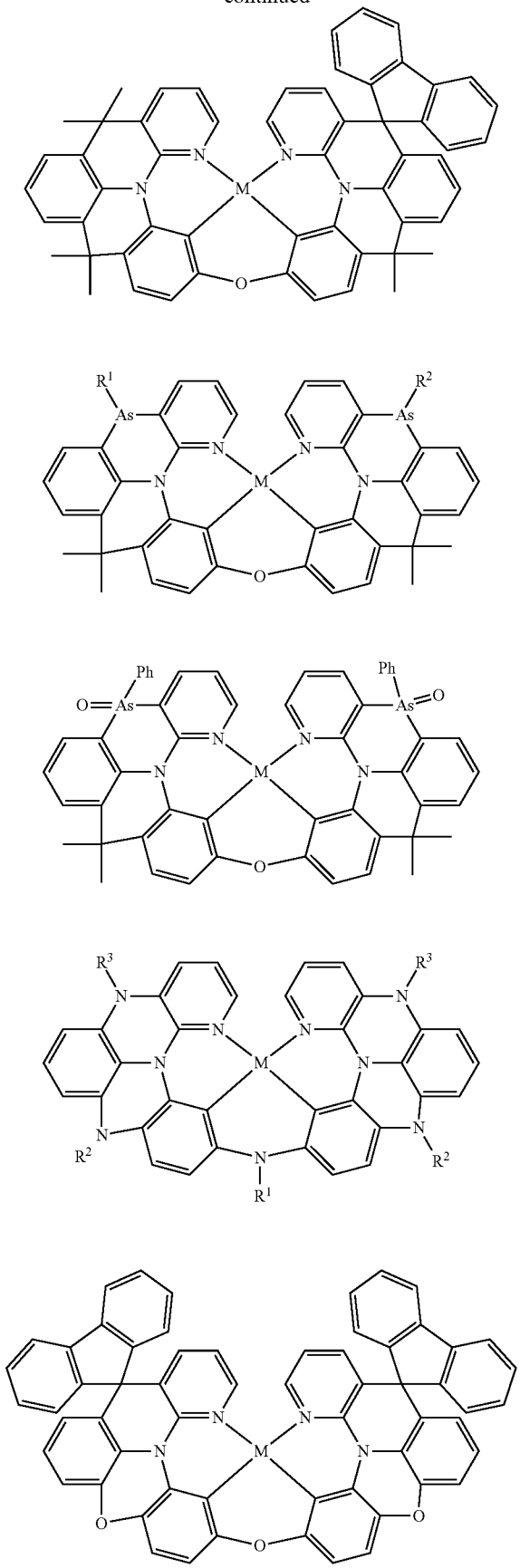
700
-continued
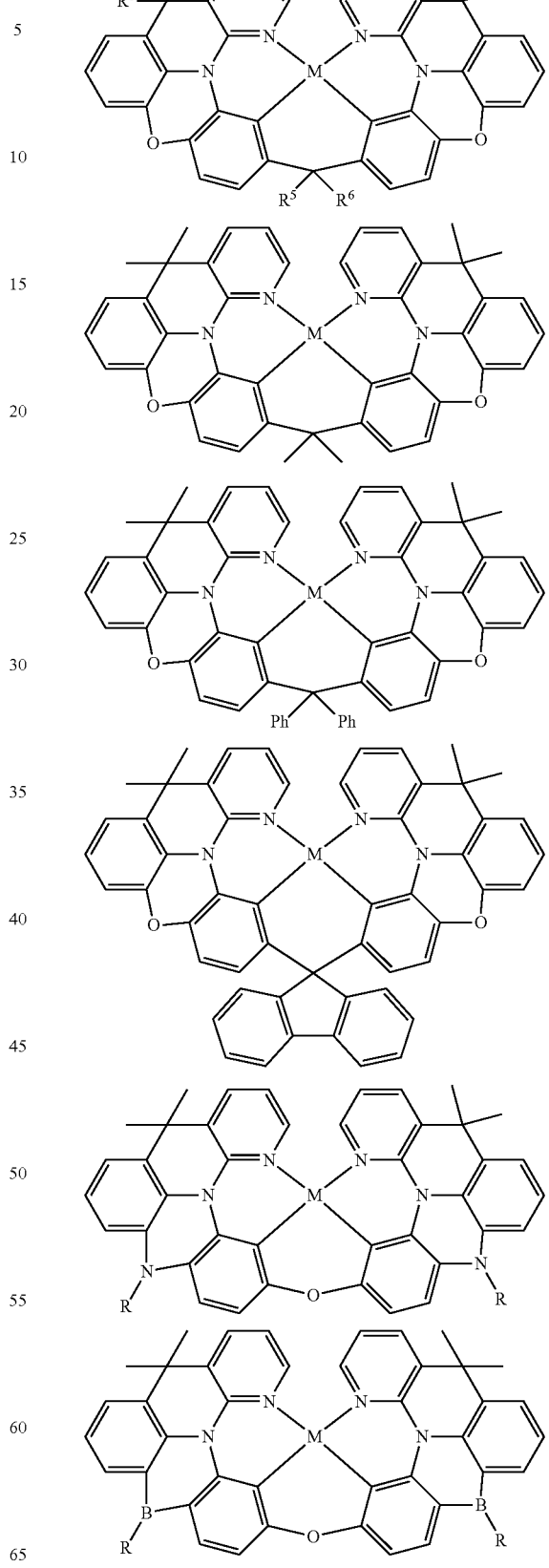

701
-continued
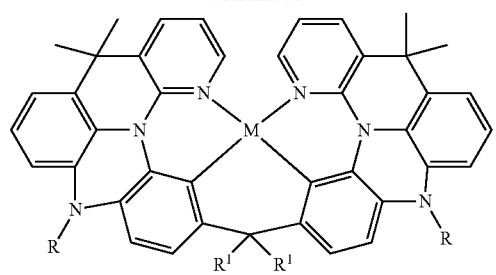
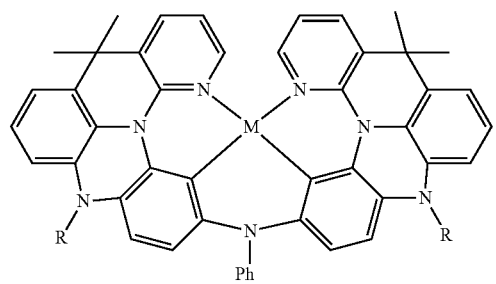
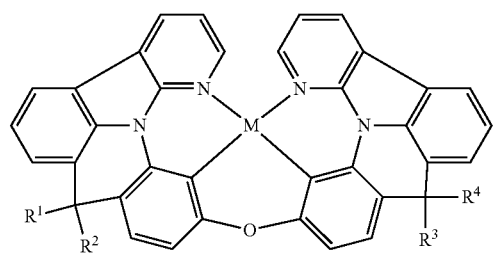
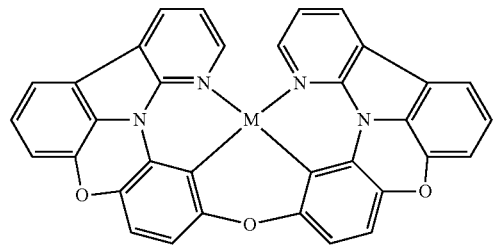
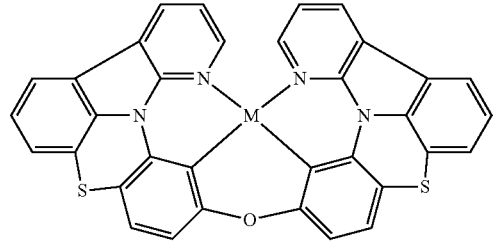
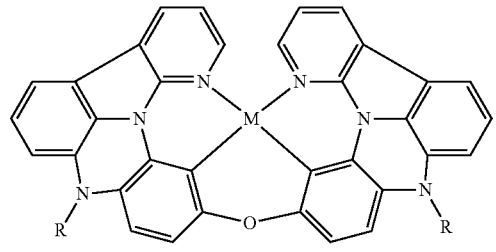
702
-continued
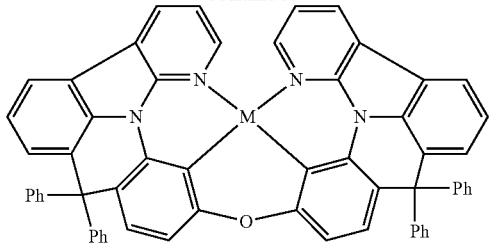
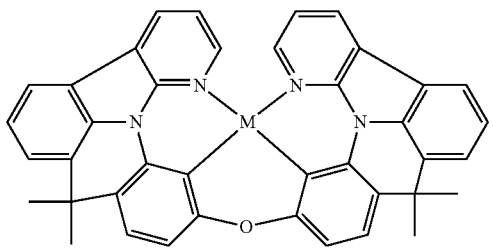
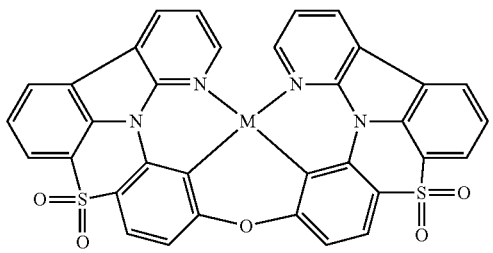
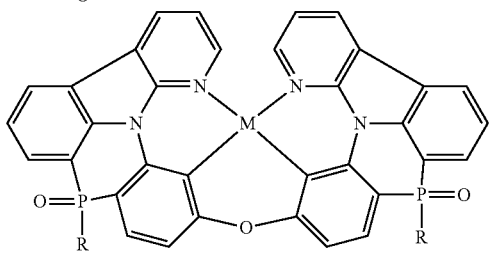
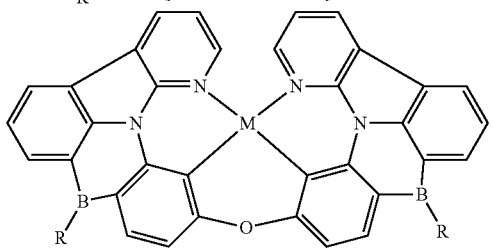
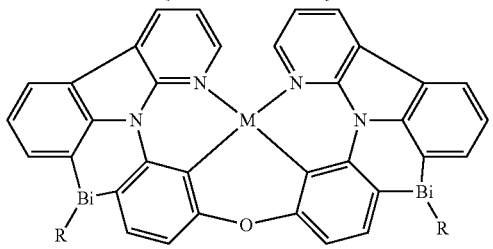
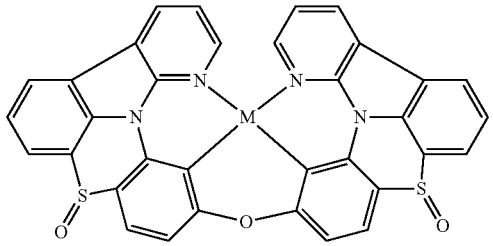

703
-continued
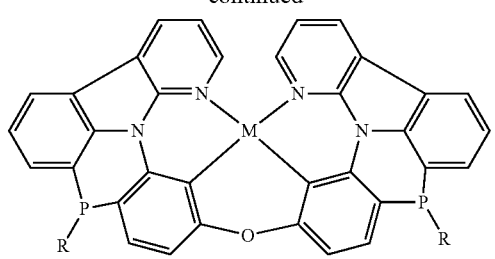
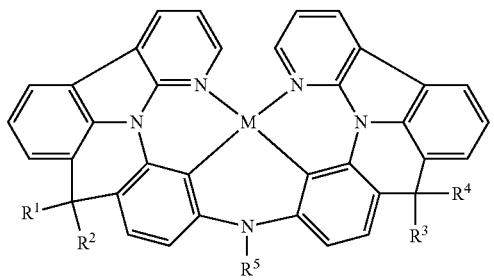
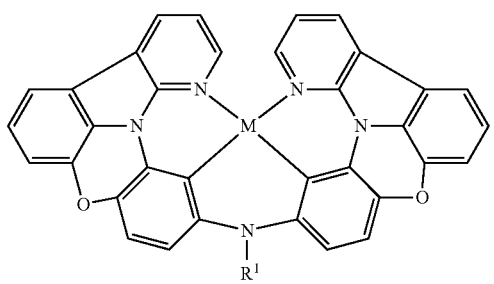
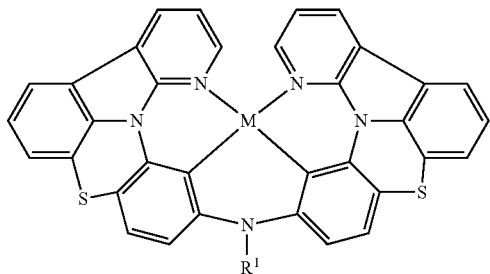
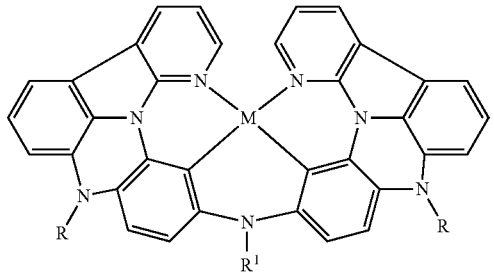
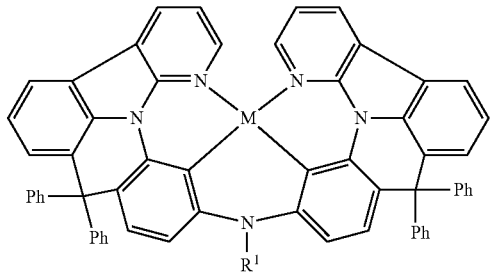
704
-continued
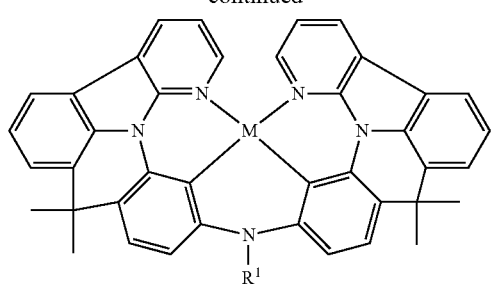
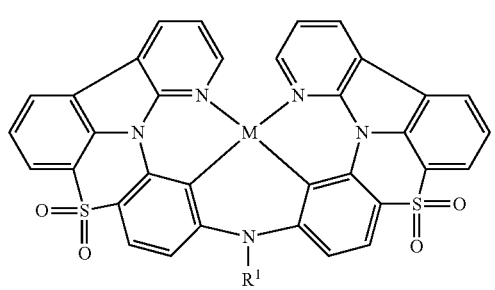
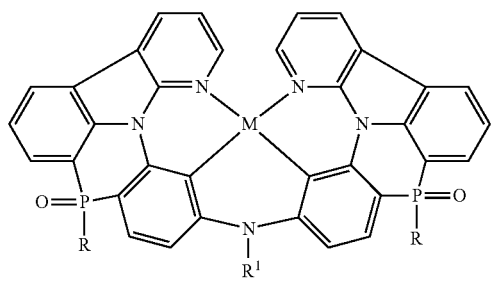
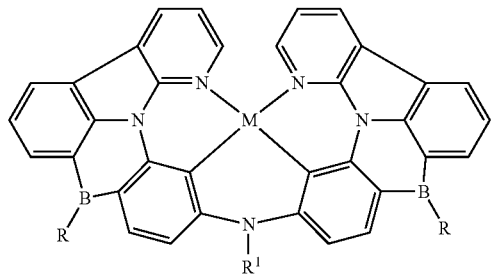
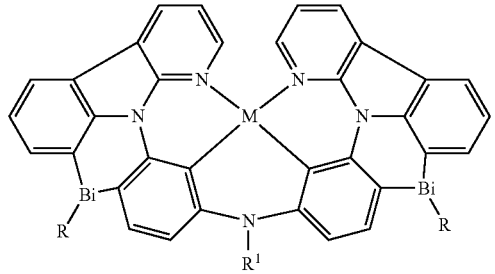
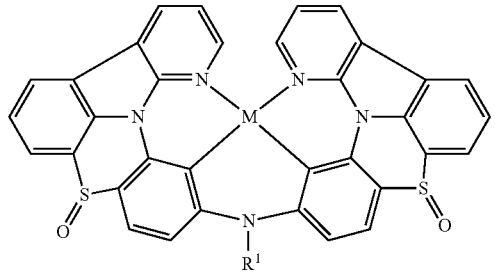

705
-continued
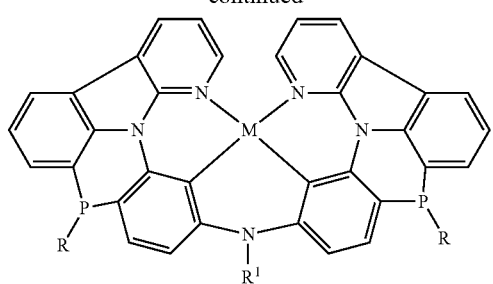
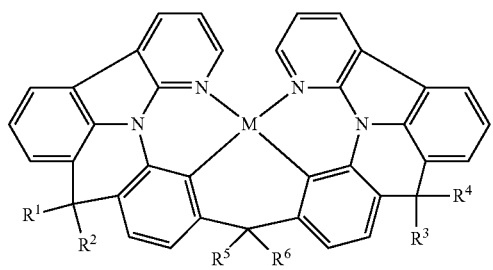
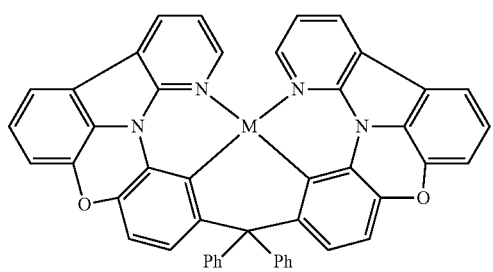
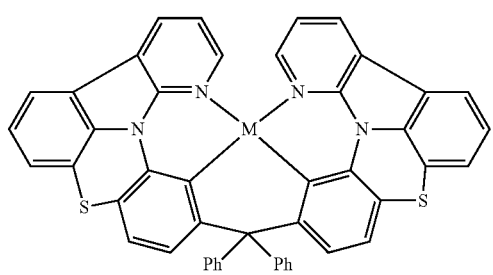
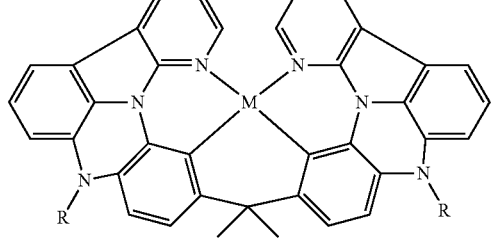
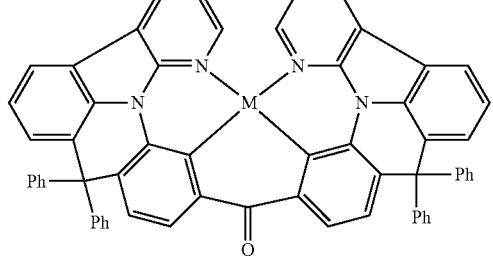
706
-continued
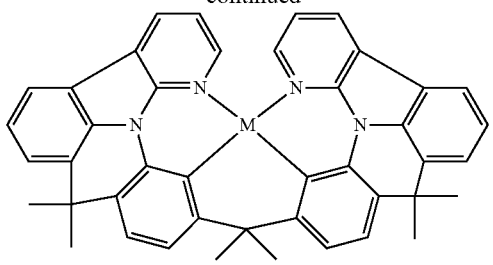
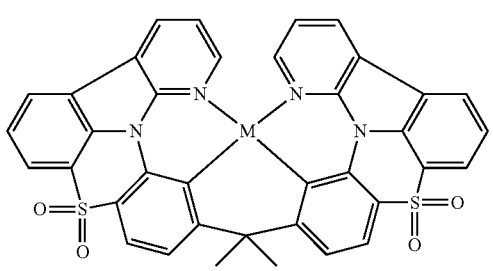
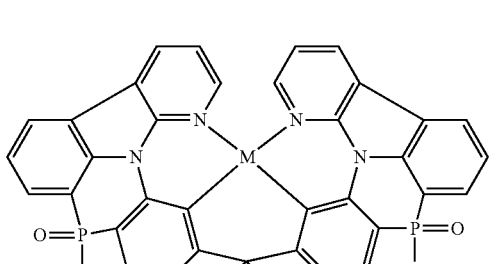
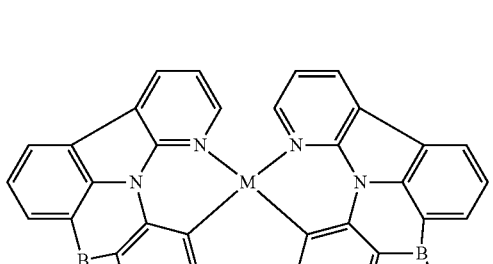
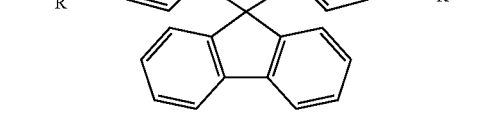
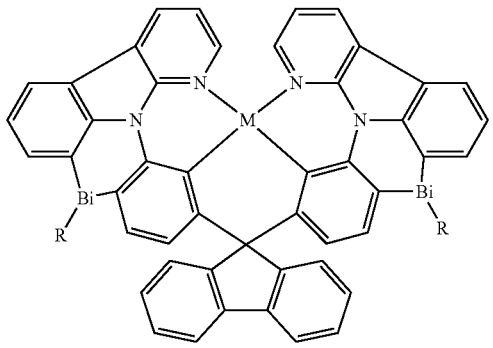

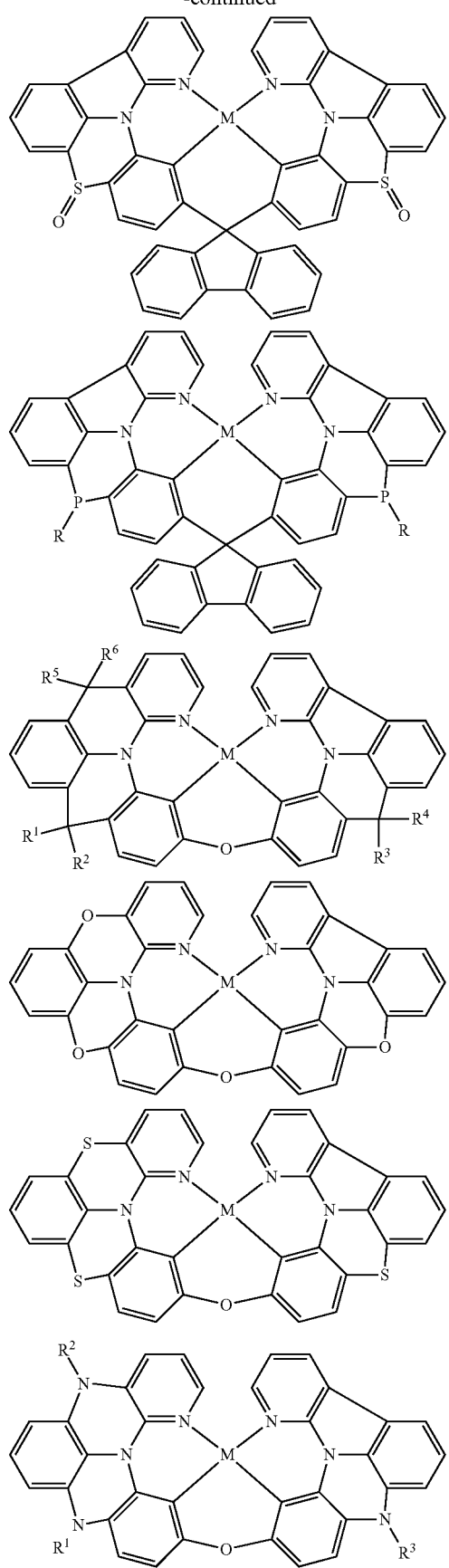
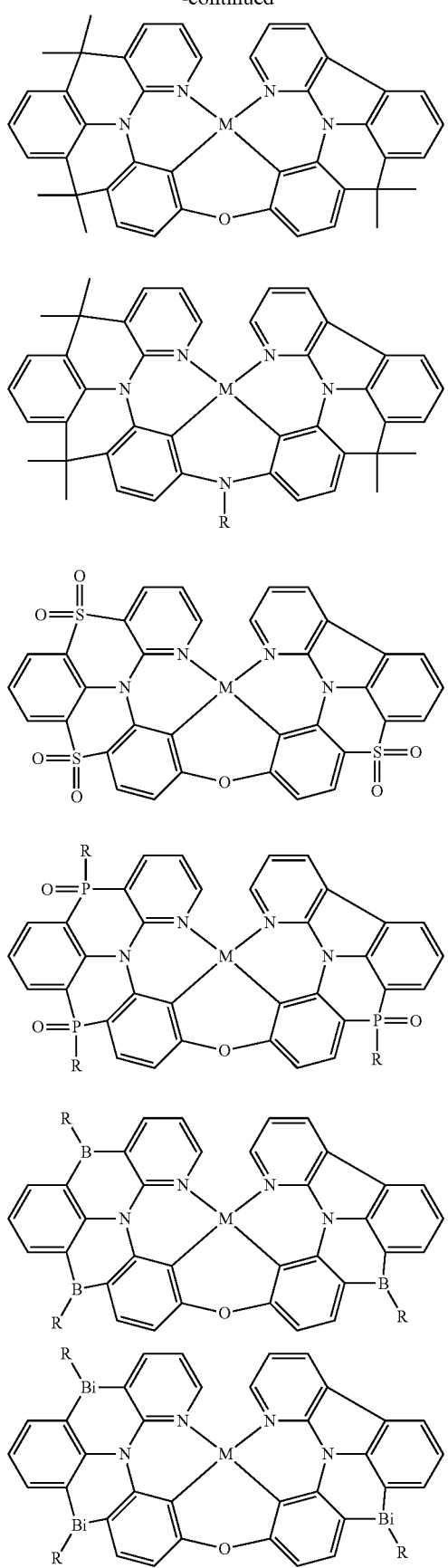

709
-continued
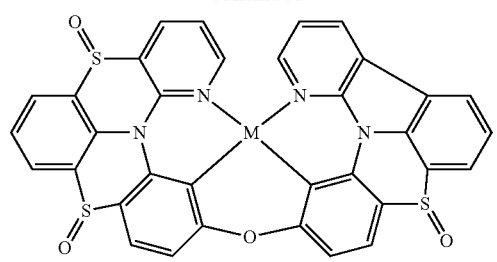
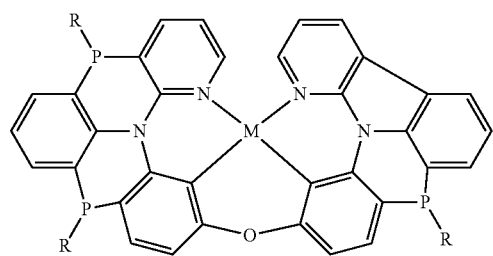
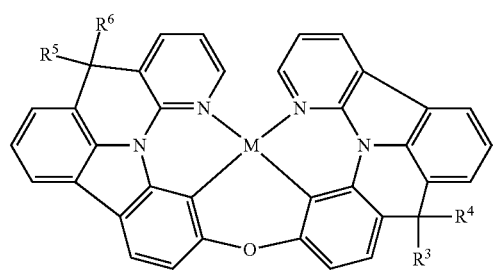
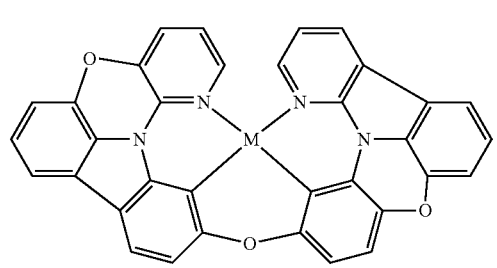
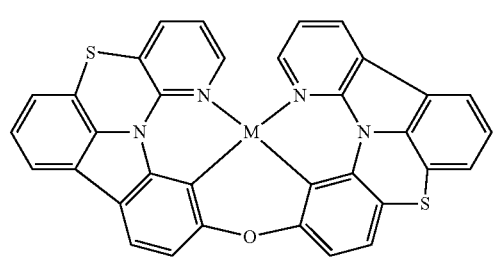
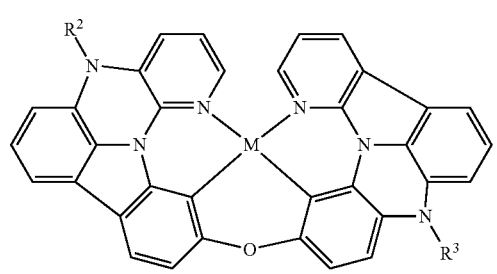
710
-continued
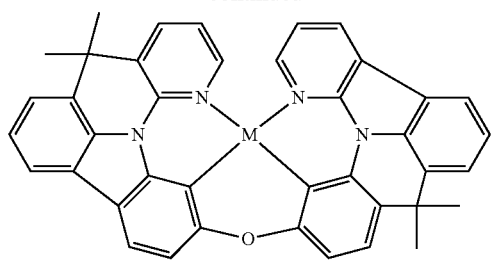
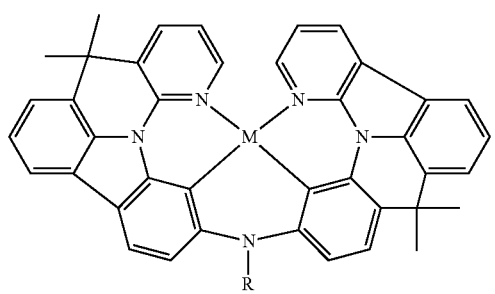
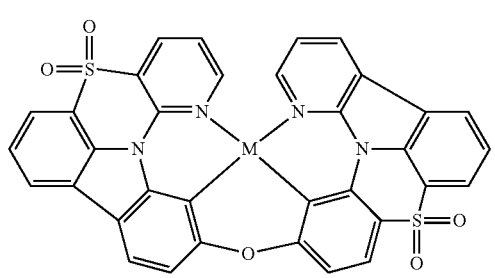
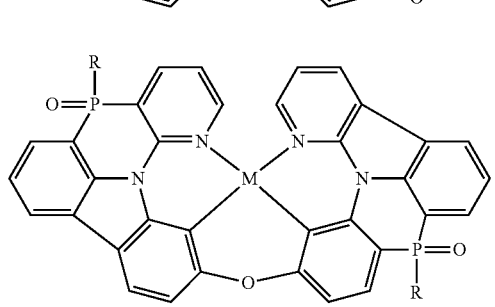
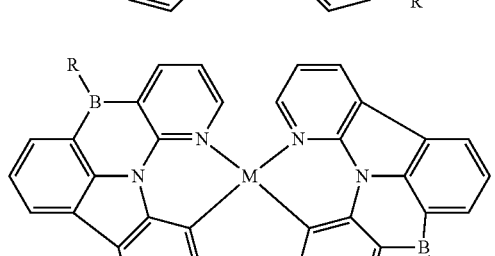
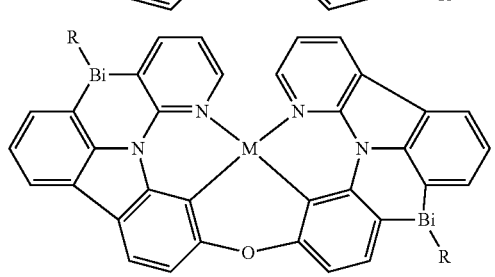

711
-continued
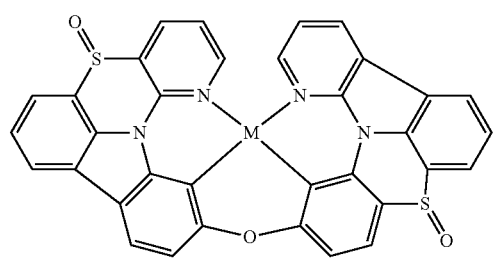
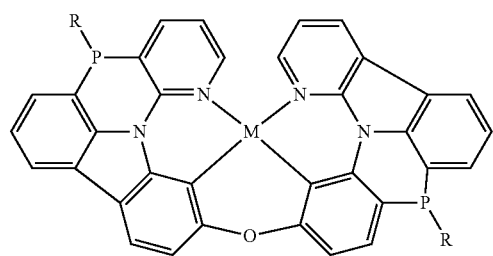
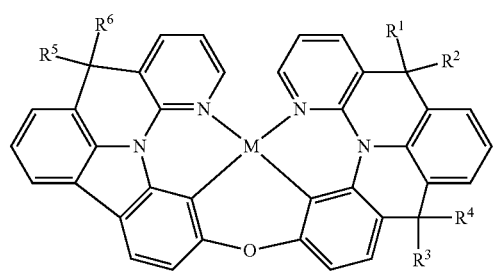
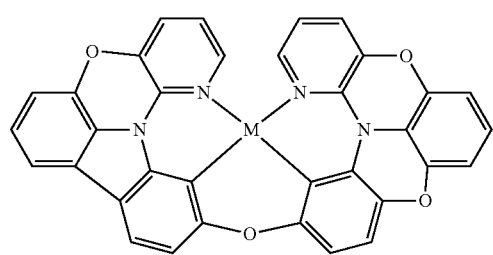
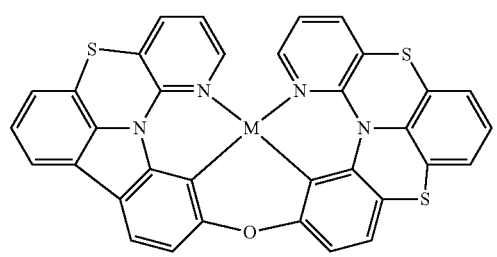
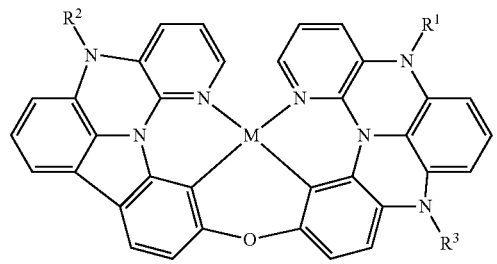
712
-continued
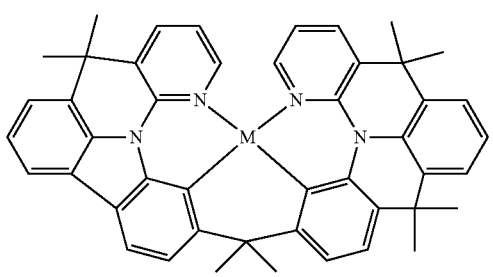
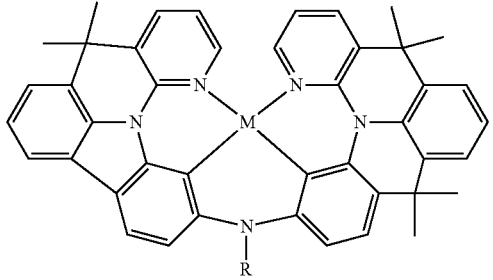
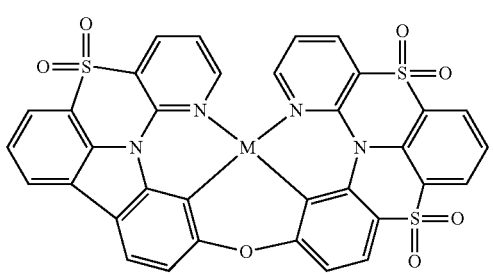
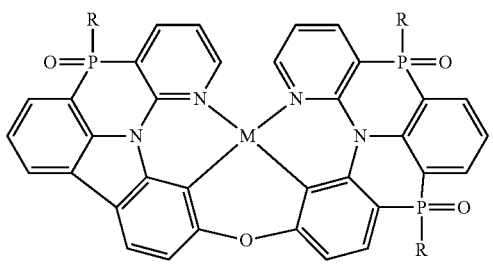
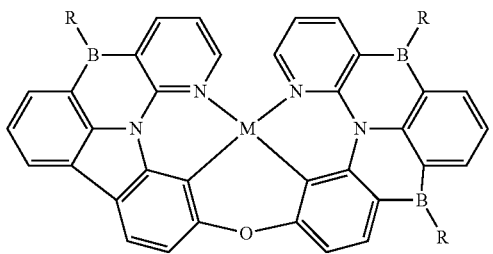
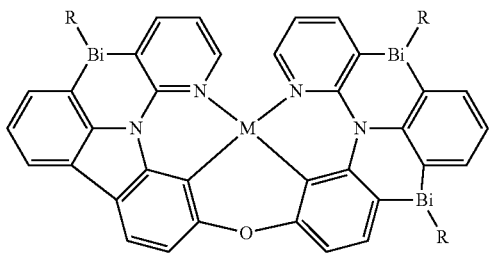

713
-continued
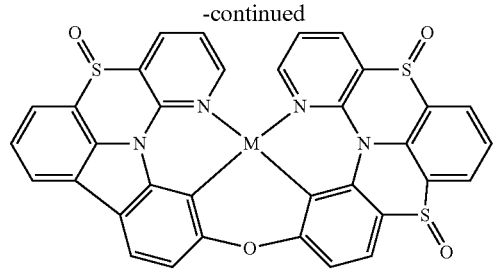
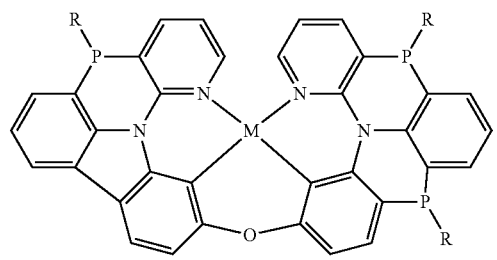
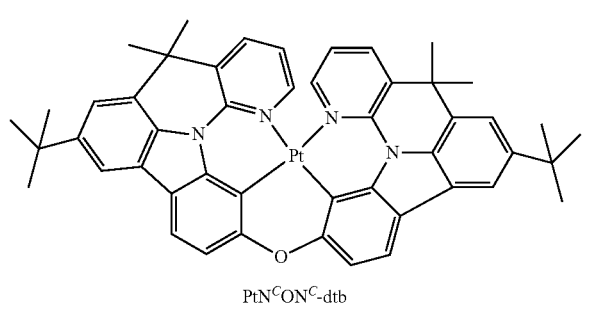
PtN^C ON^C -dtb
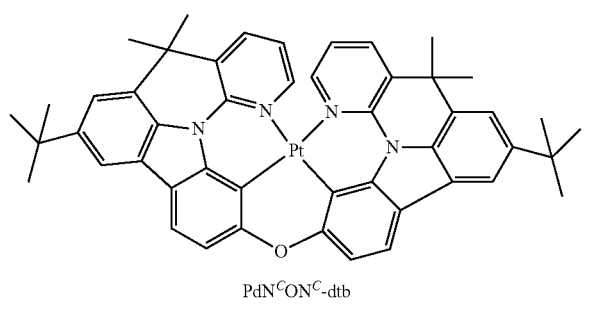
PdN^C ON^C -dtb
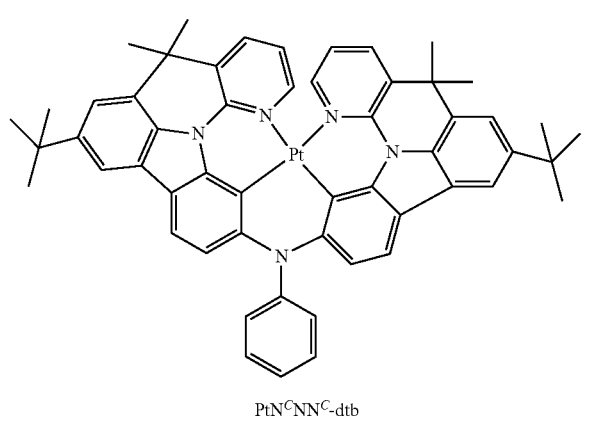
PtN^C NN^C -dtb
714
-continued
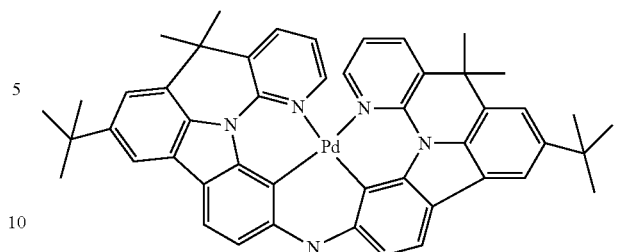
PdN^C NN^C -dtb
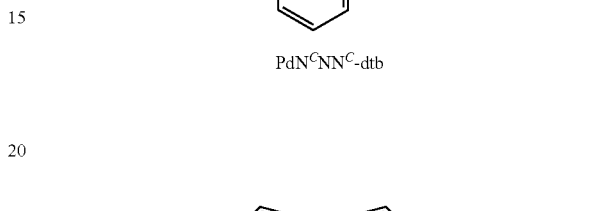
PtN^C ON^{C'} -dtb
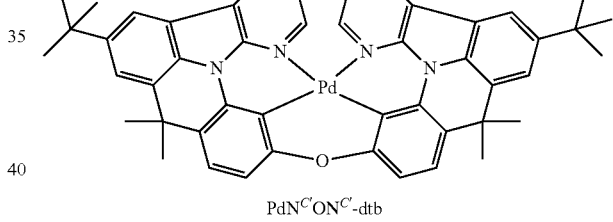
PdN^C ON^{C'} -dtb
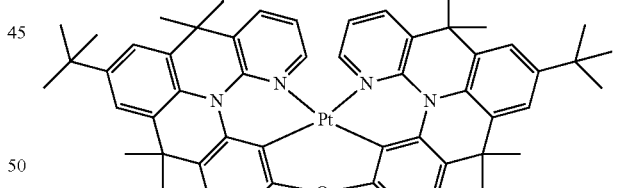
PtN^{CC} ON^{CC} -dtb
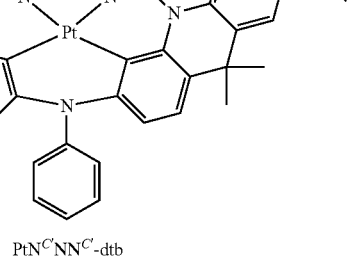
PtN^C NN^{C'} -dtb

715
-continued
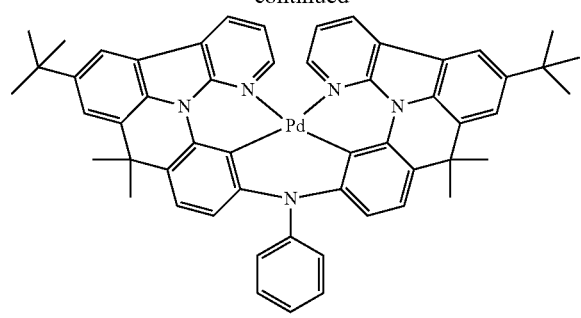
PdN^C'NN^C'-dtb
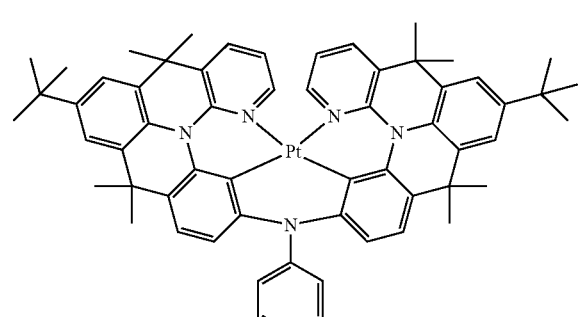
PtN^CC NN^CC -dtb
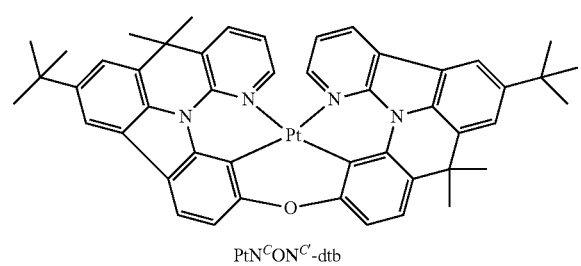
PtN^C ON^C' -dtb
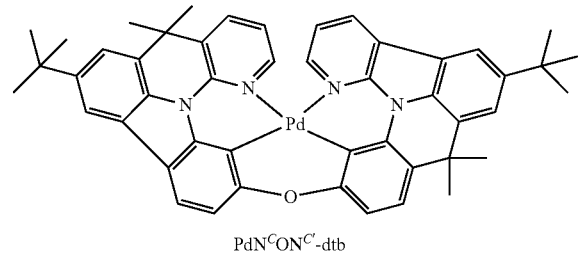
PdN^C ON^C' -dtb
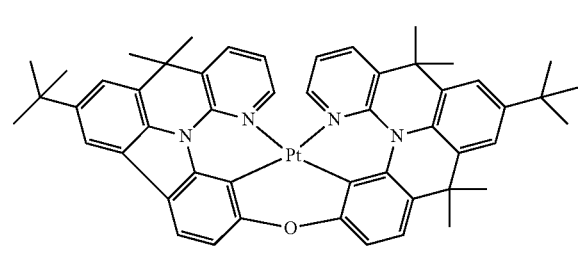
PtN^C ON^CC -dtb
716
-continued
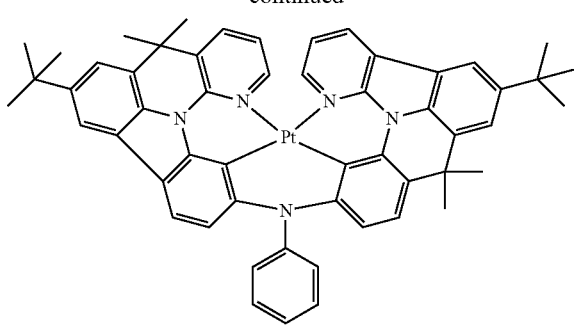
PtN^C NN^C' -dtb
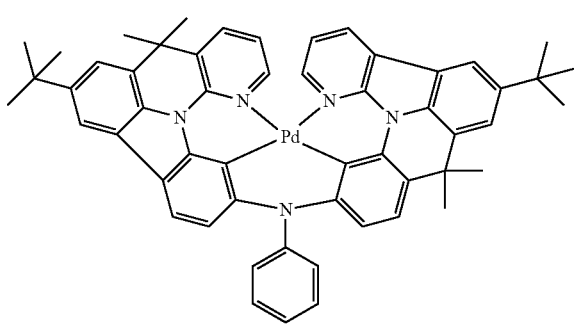
PdN^C NN^C' -dtb
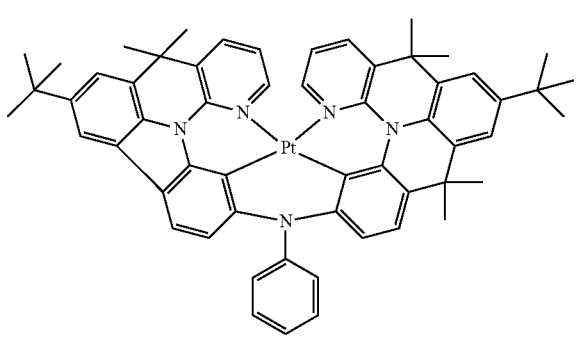
PtN^C' NN^CC -dtb
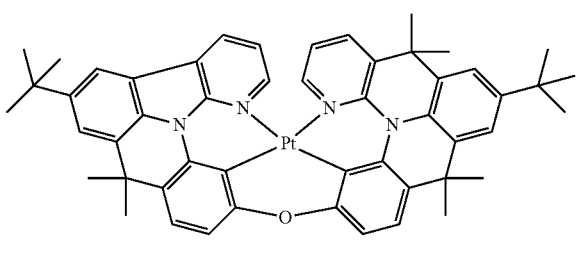
PtN^C' ON^CC -dtb
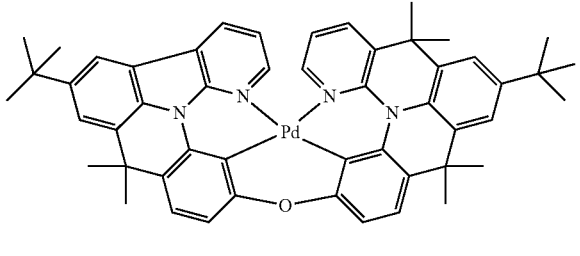
PdN^C ON^CC -dtb 717
-continued

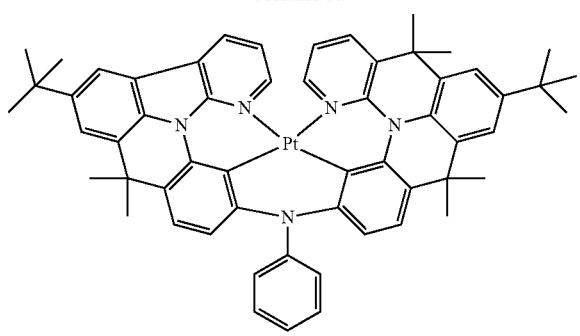

PtN^C NN^{CC}-dtb

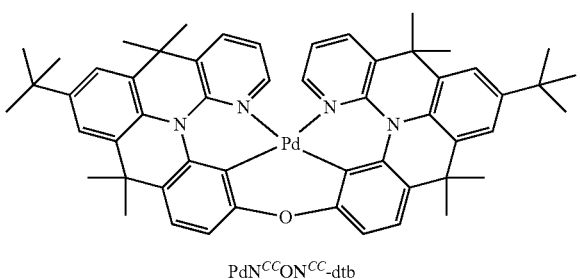

PdN^{CC}ON^{CC}-dtb

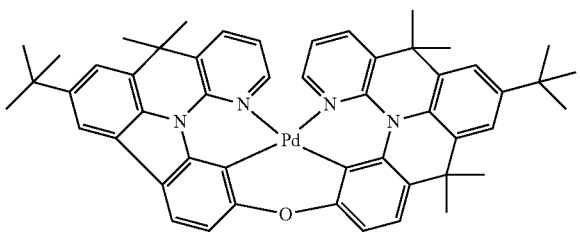

PdN^C ON^{CC}-dtb

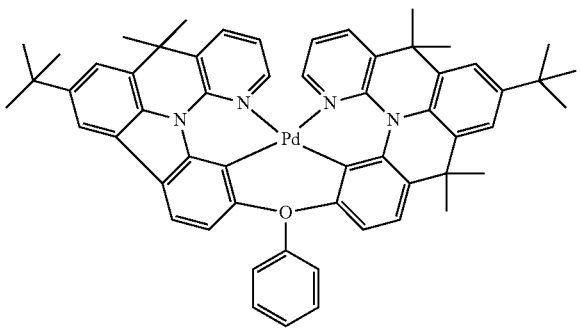

PdN^C NN^{CC}-dtb

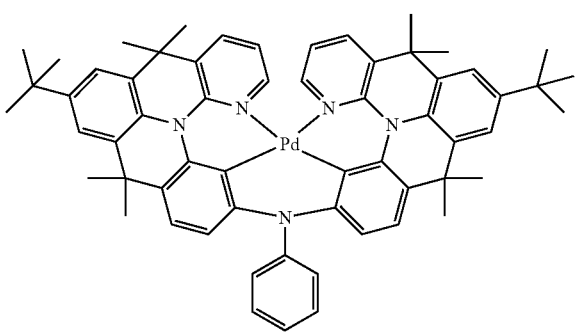

PdN^{CC}NN^{CC}-dtb

718
-continued

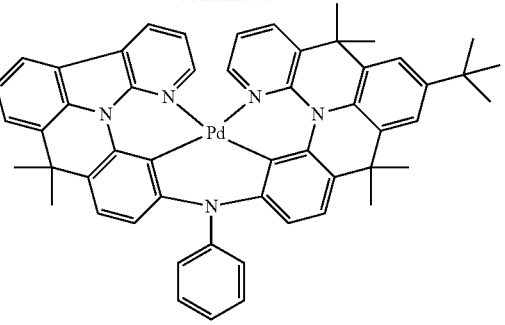

PdN^C NN^{CC}-dtb wherein M is Pt or Pd, and
each of R, $R^1$, $R^2$, $R^3$, $R^4$, $R^5$ and $R^6$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

4. The complex of claim 1, wherein each of

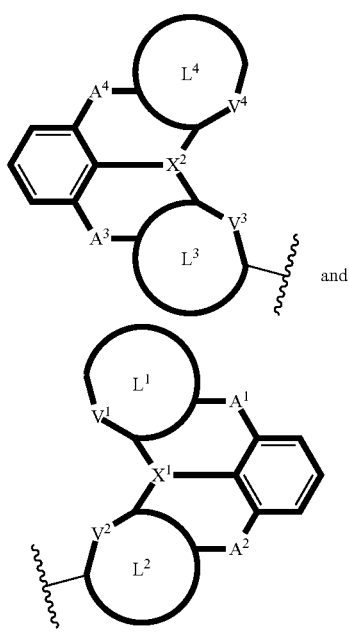

is independently one of the following structures:

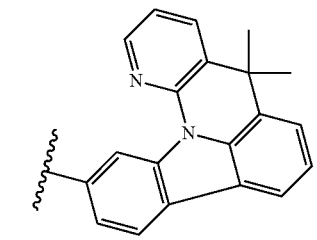

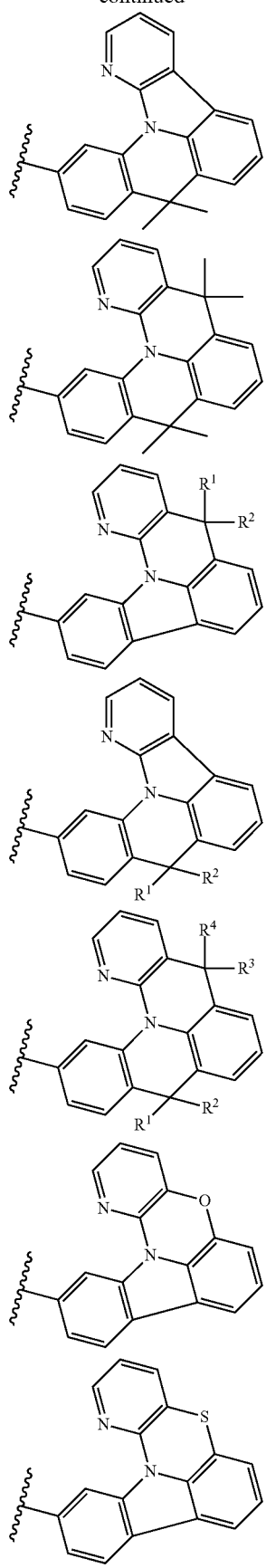
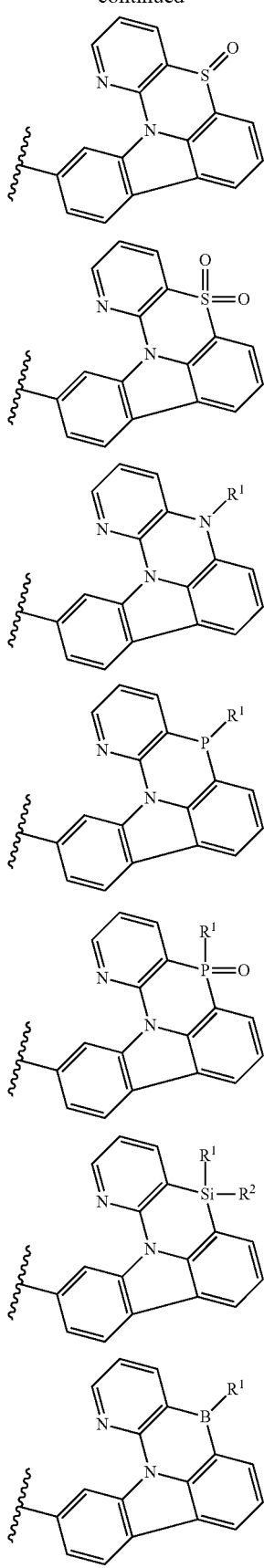

721
-continued
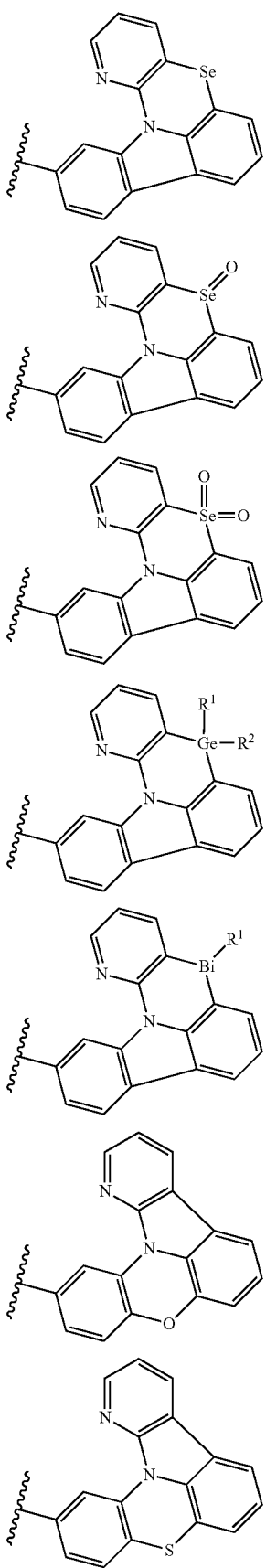
722
-continued
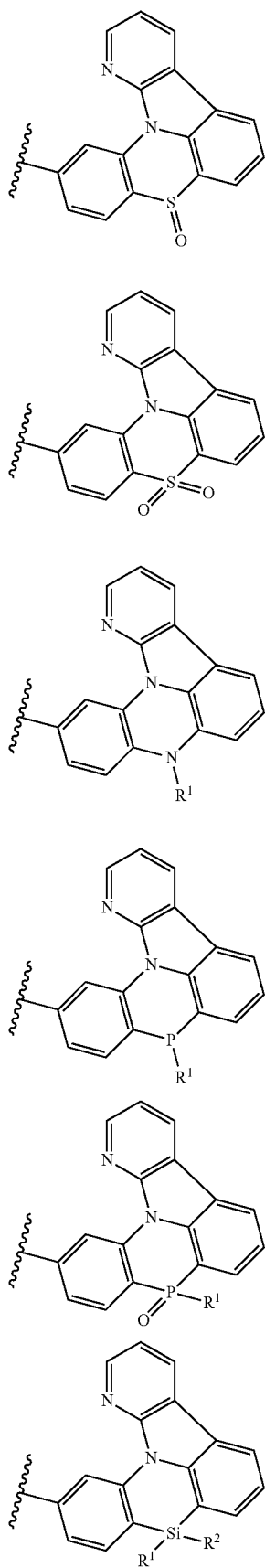

723
-continued
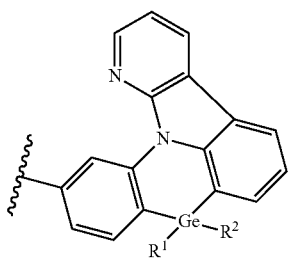
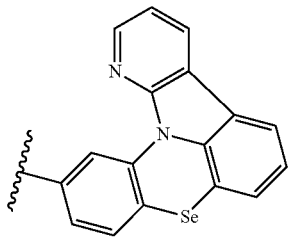
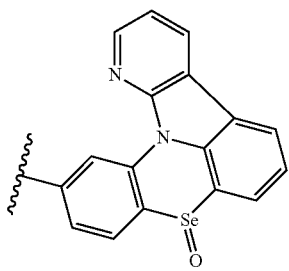
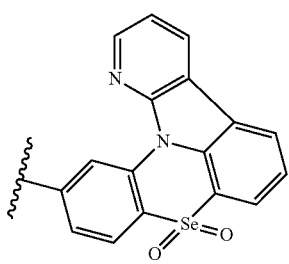
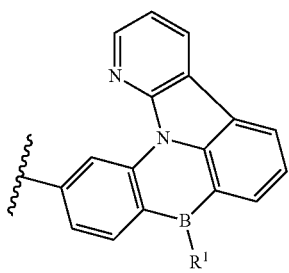
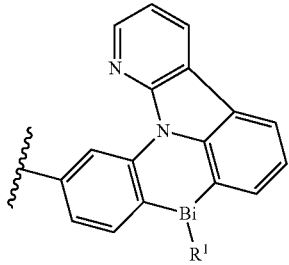
724
-continued
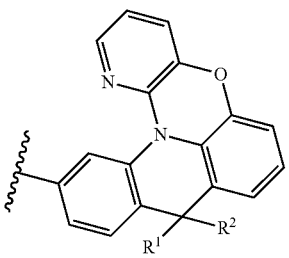
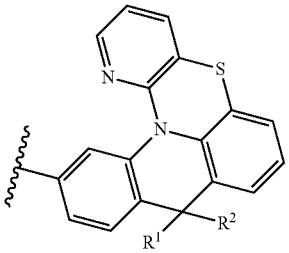
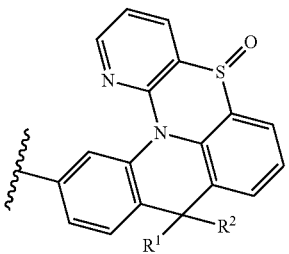
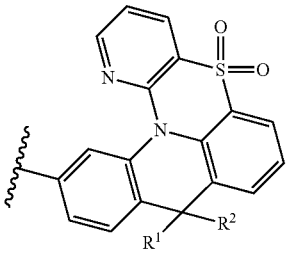
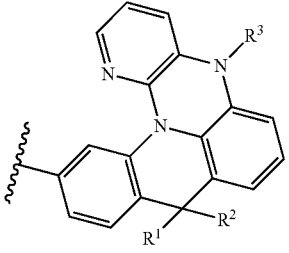
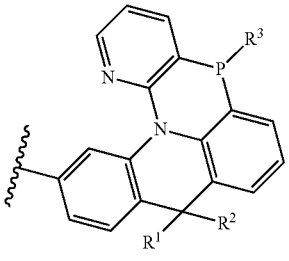

725
-continued
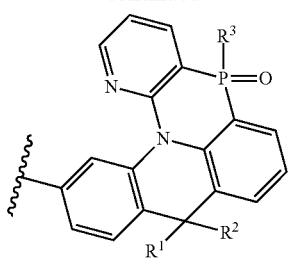
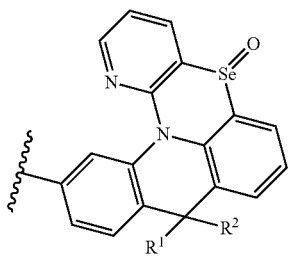
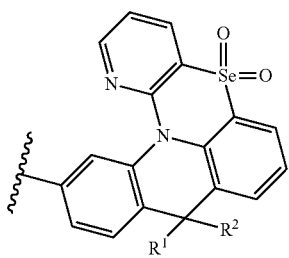
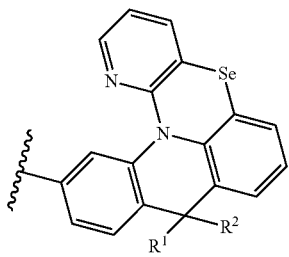
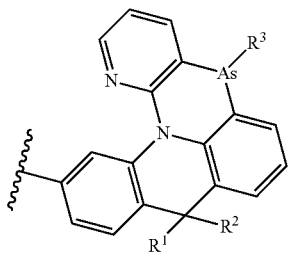
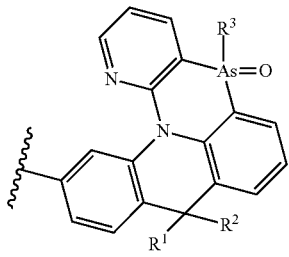
726
-continued
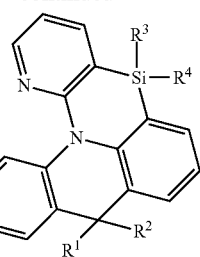
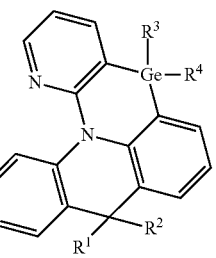
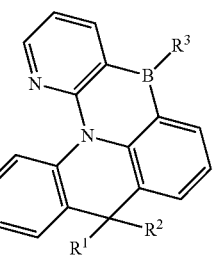
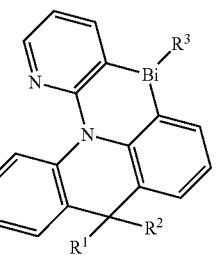
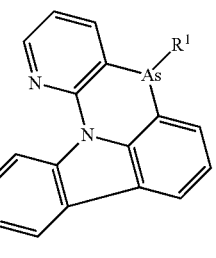
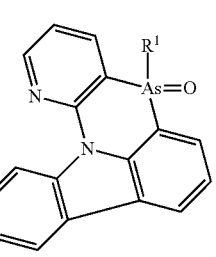

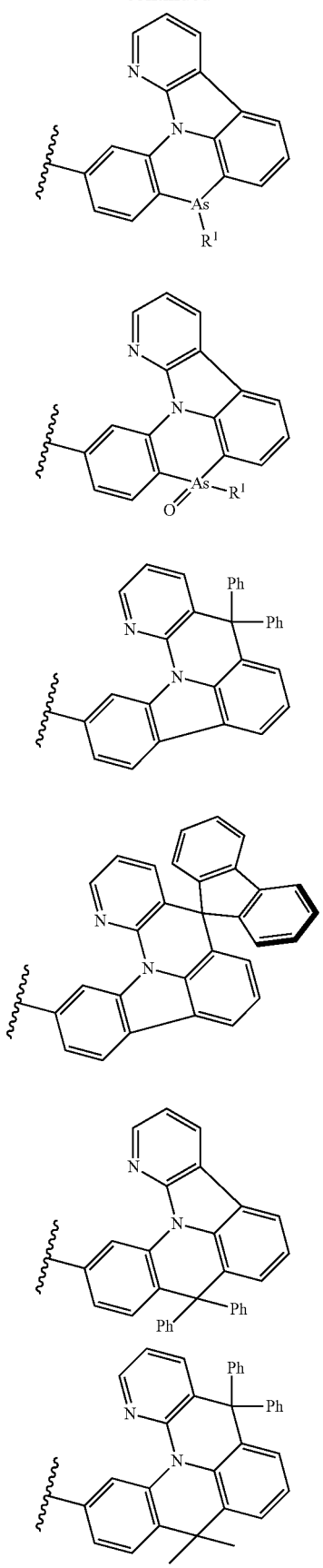
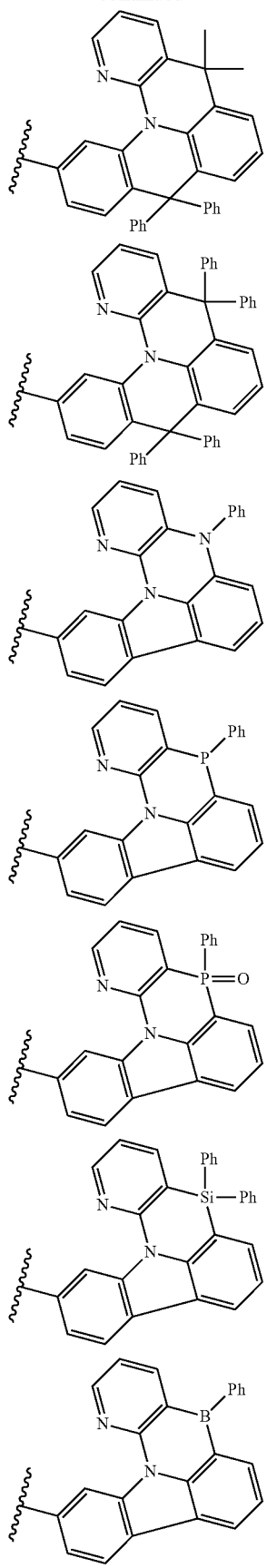

729
-continued
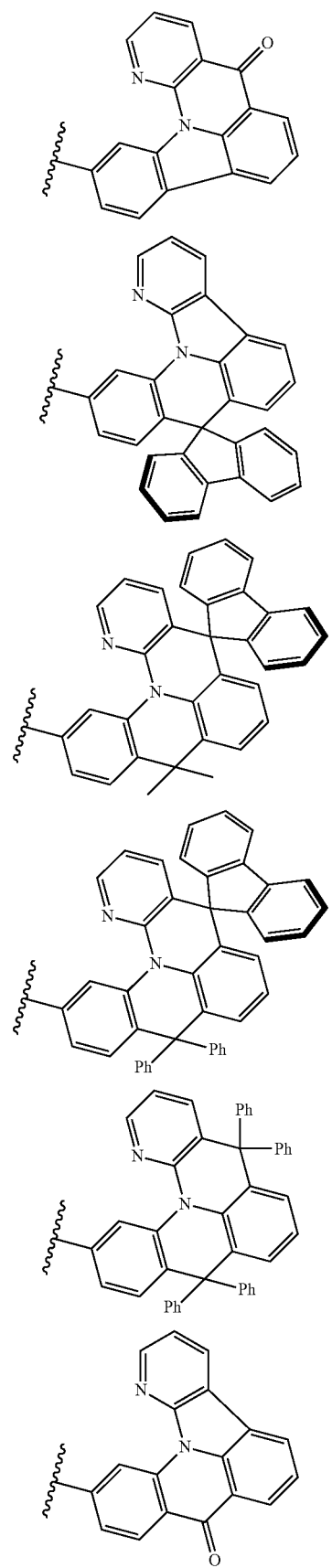
730
-continued
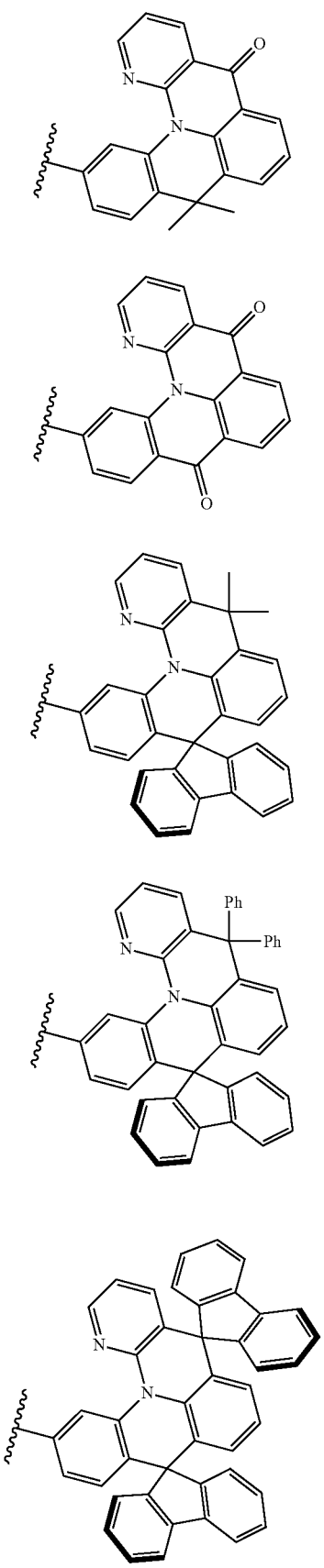

731
-continued
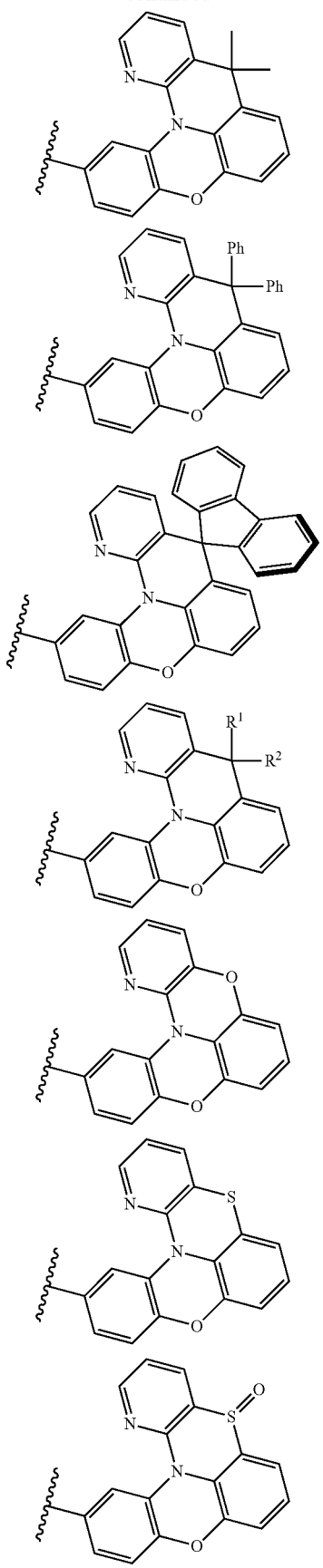
732
-continued
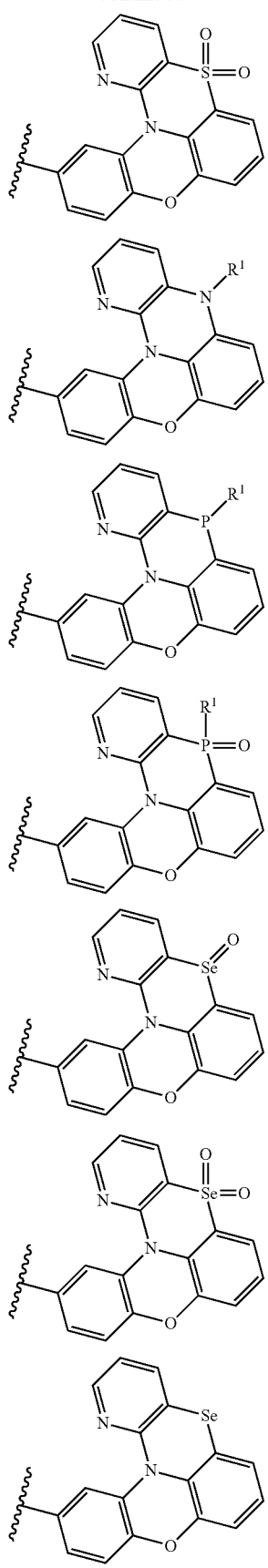

733
-continued
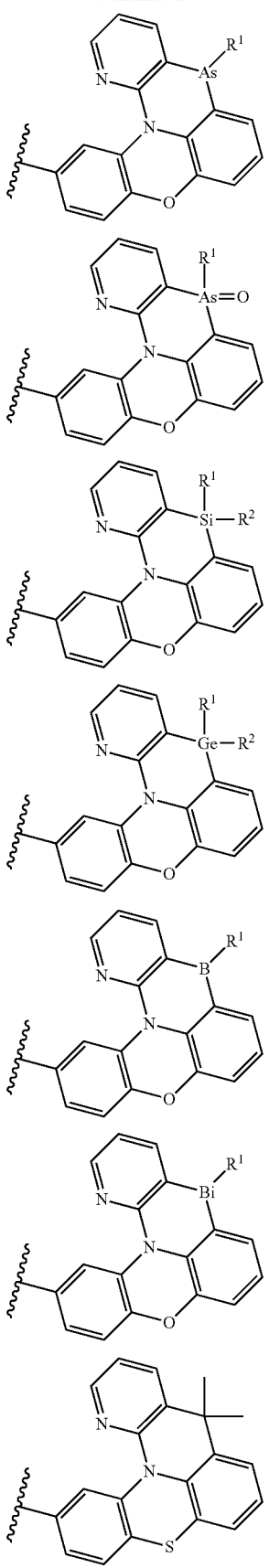
734
-continued
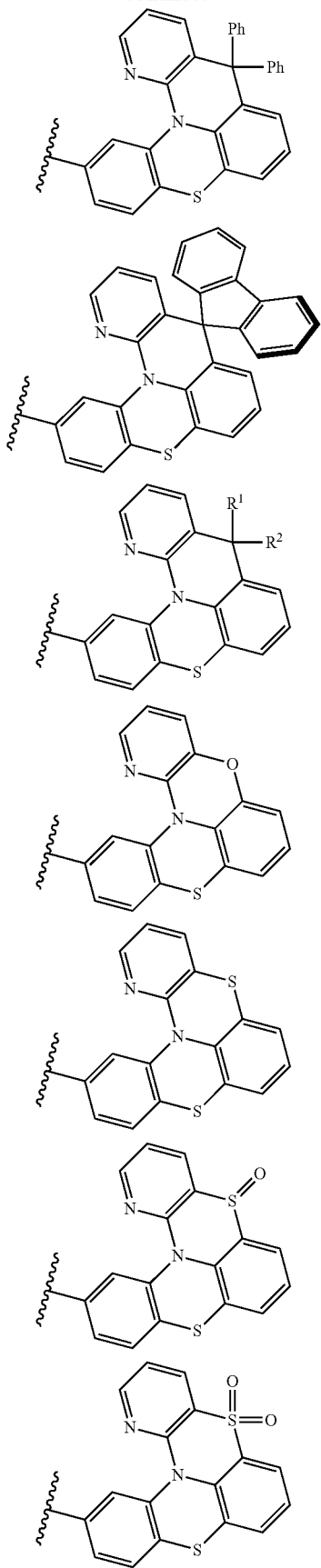

735
-continued
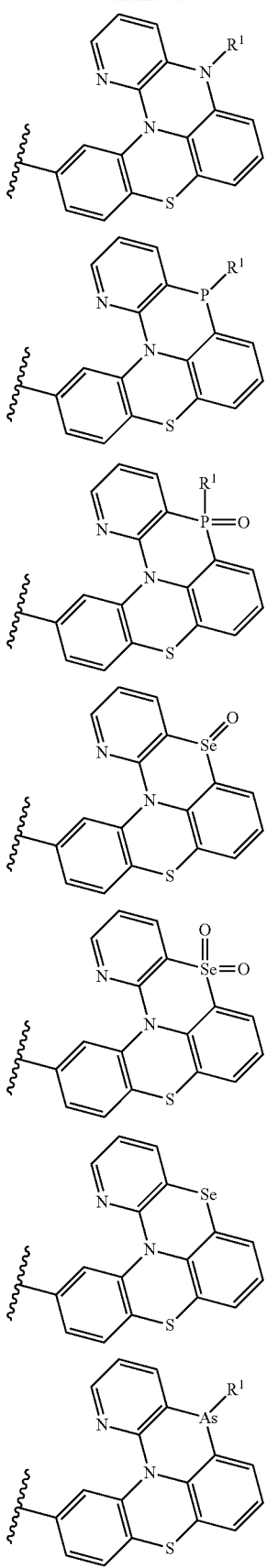
736
-continued
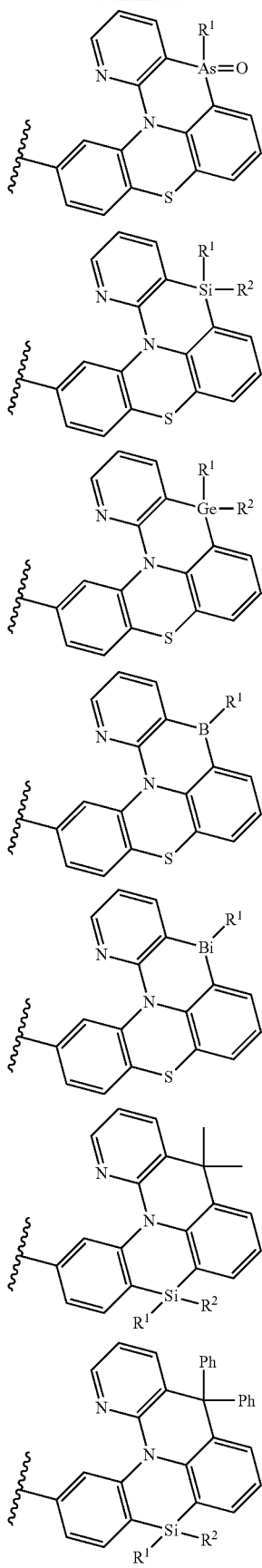

737
-continued
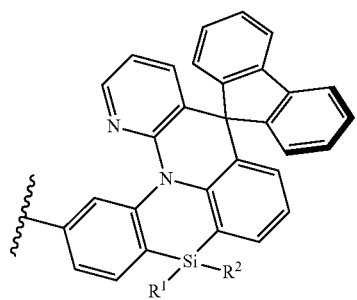
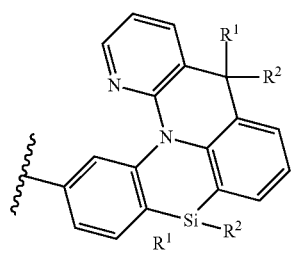
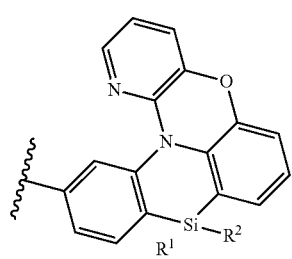
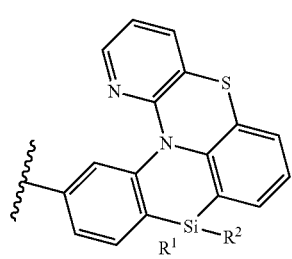
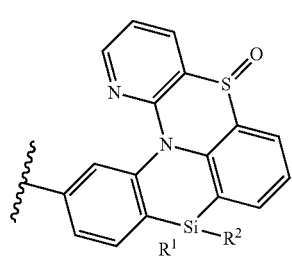
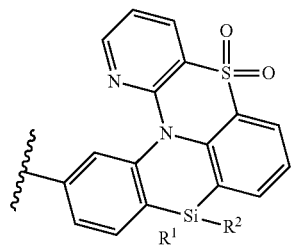
738
-continued
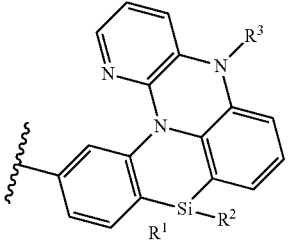
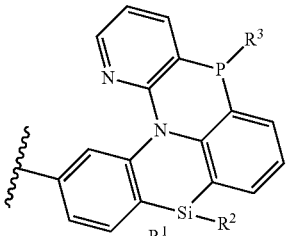
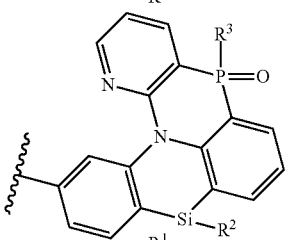
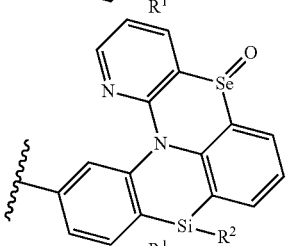
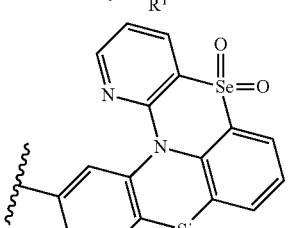
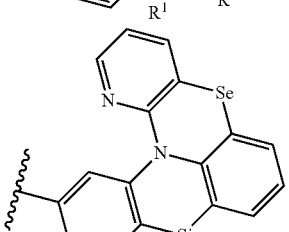
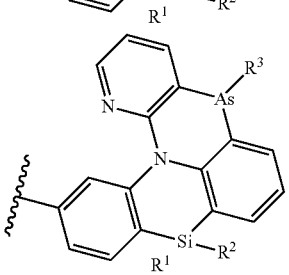

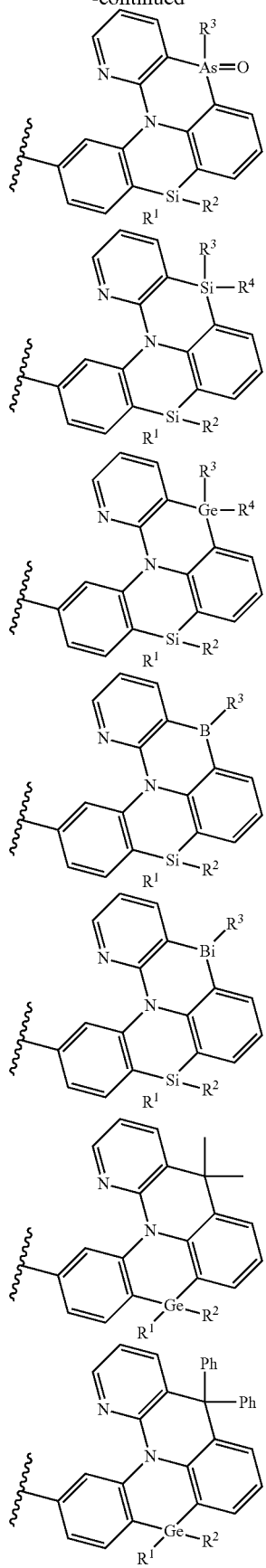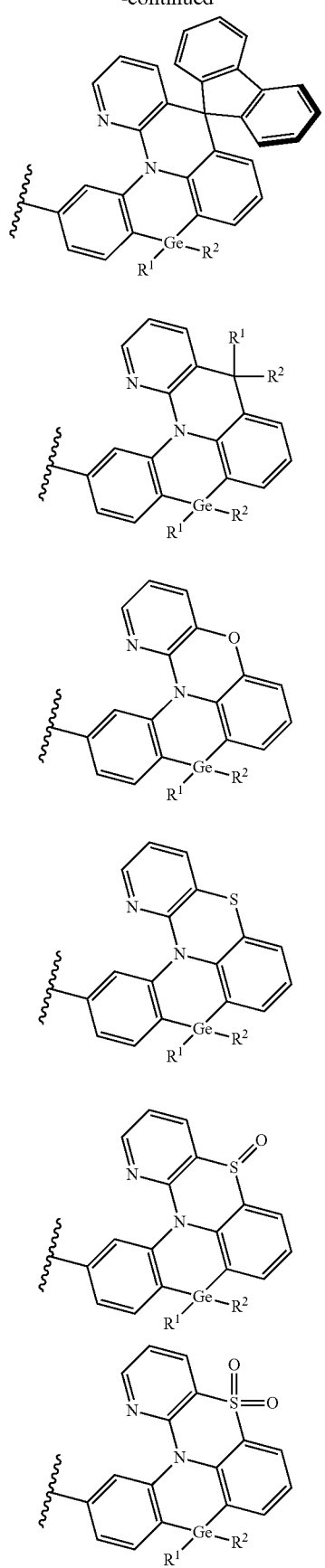

741
-continued
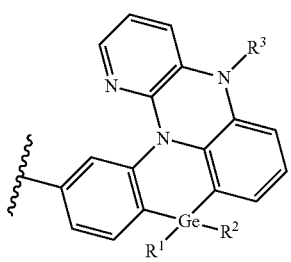
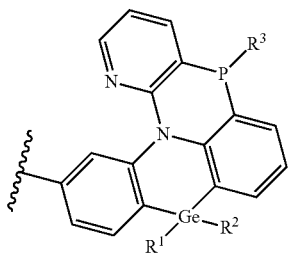
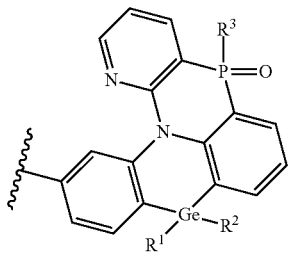
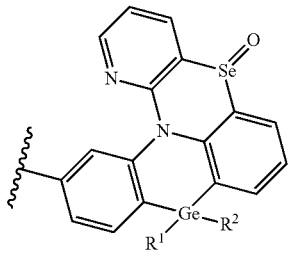
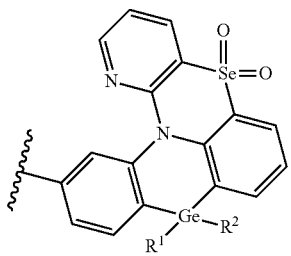
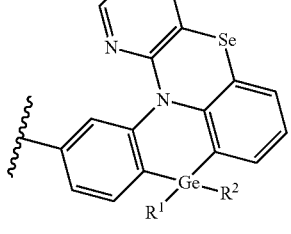
742
-continued
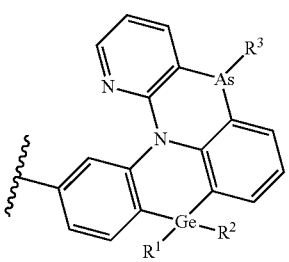
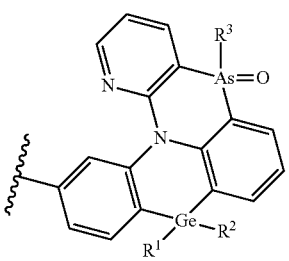
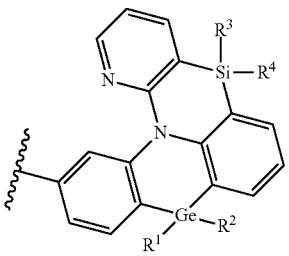
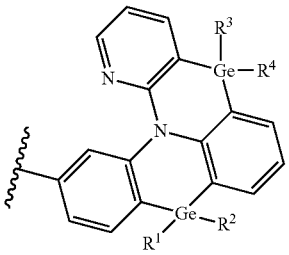
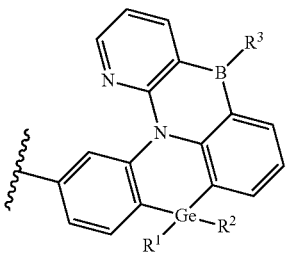
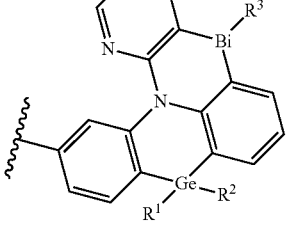

743
-continued
744
-continued
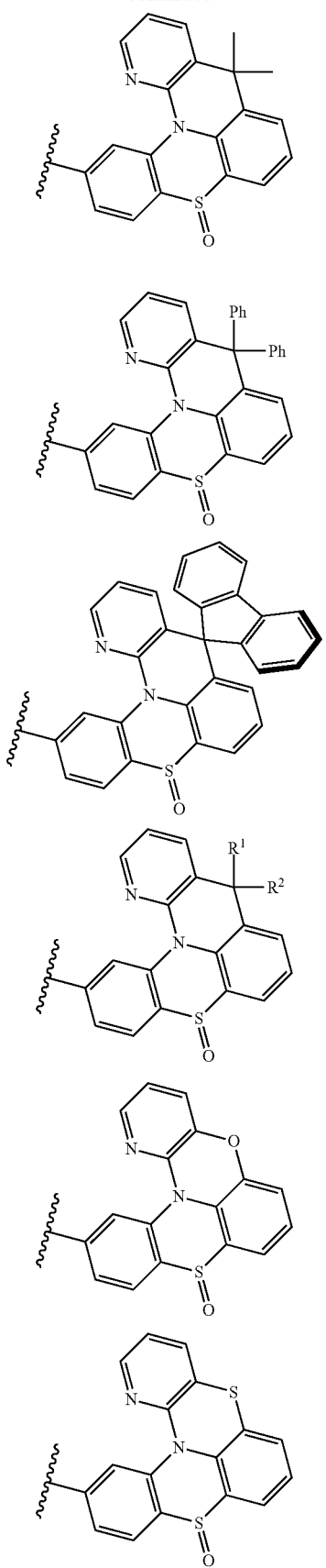
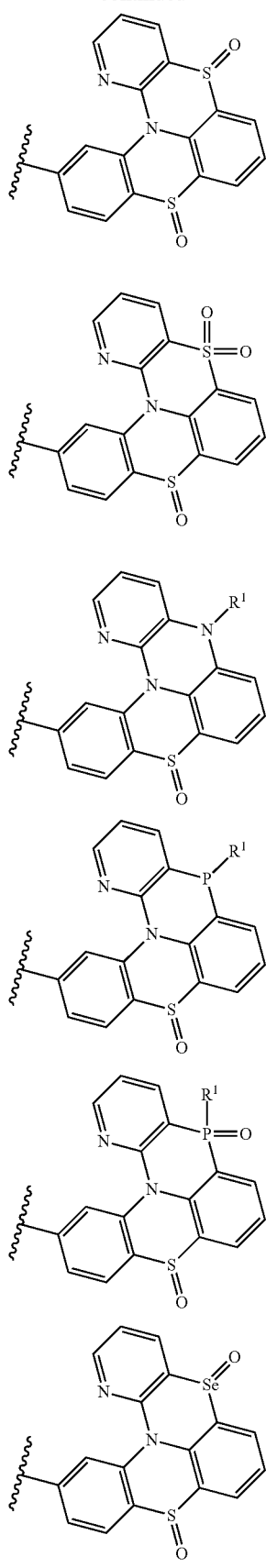

745
-continued
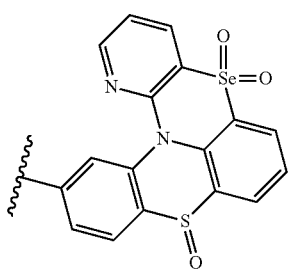
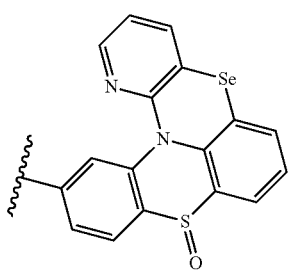
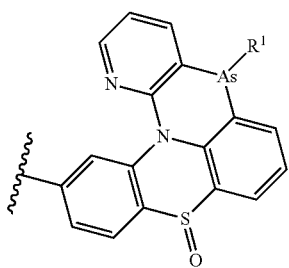
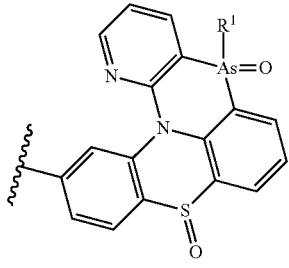
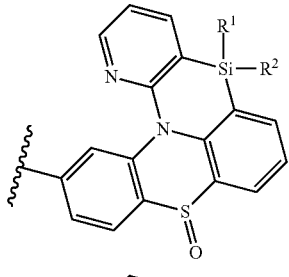
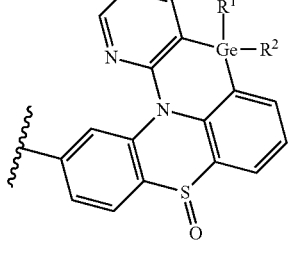
746
-continued
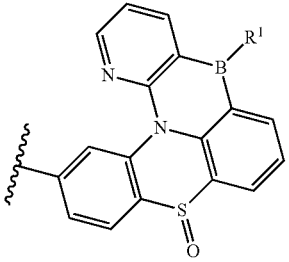
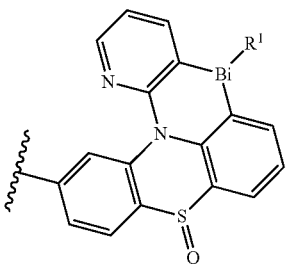
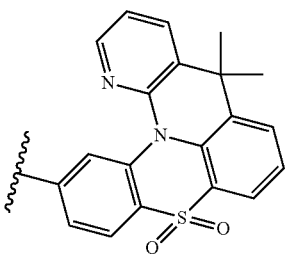
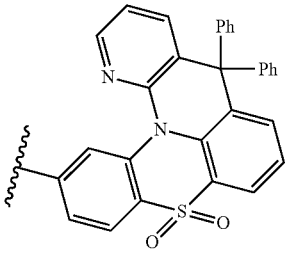
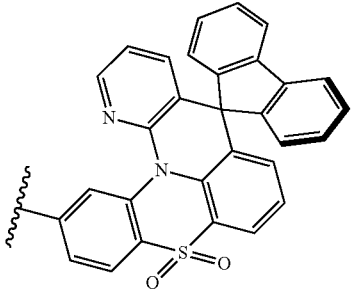
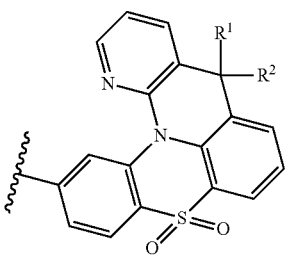

747
-continued
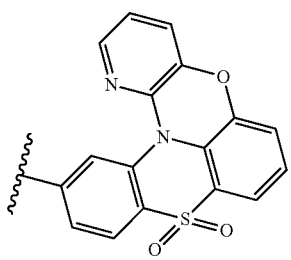
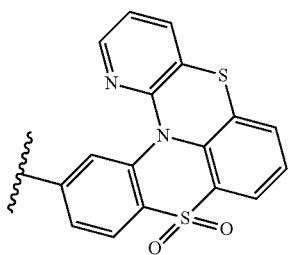
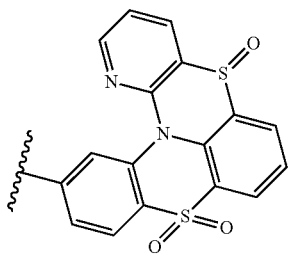
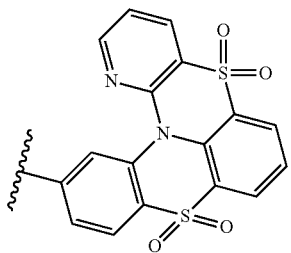
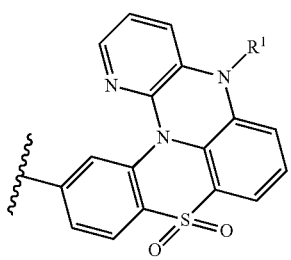
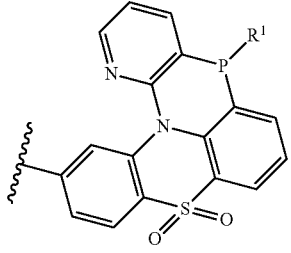
748
-continued
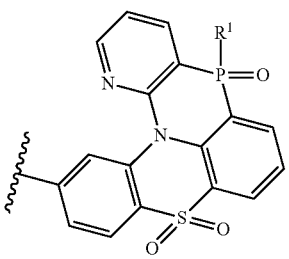
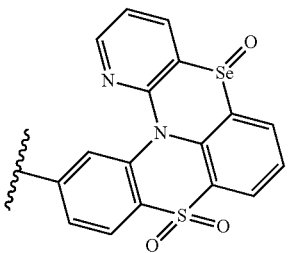
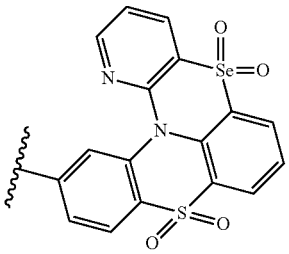
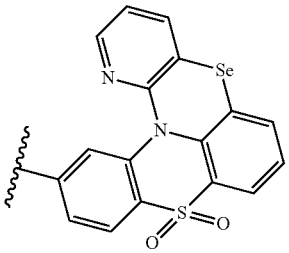
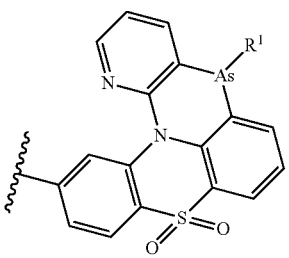
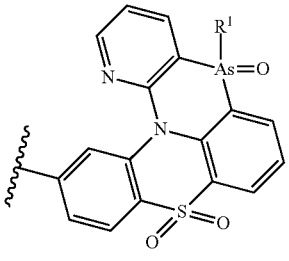

749
-continued
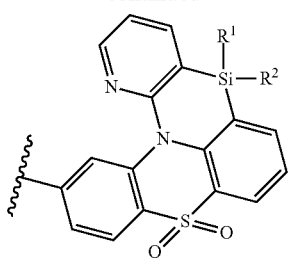
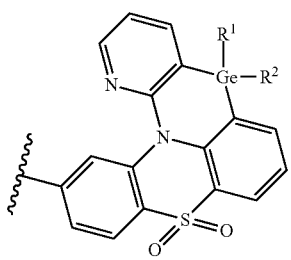
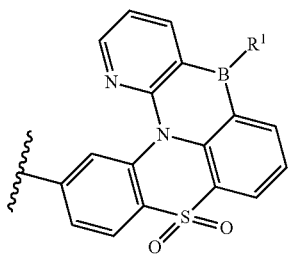
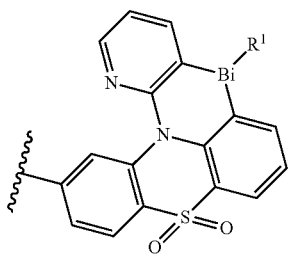
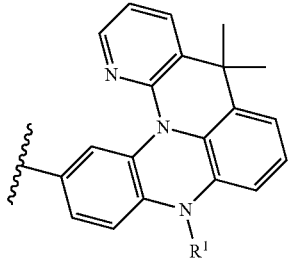
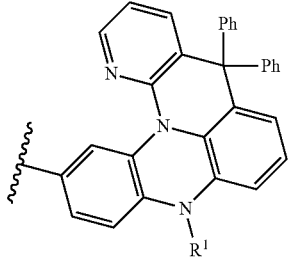
750
-continued
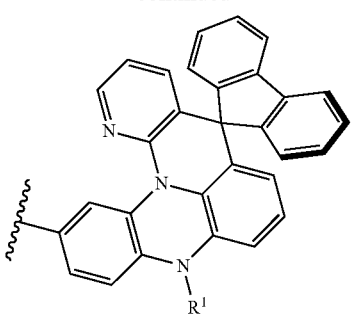
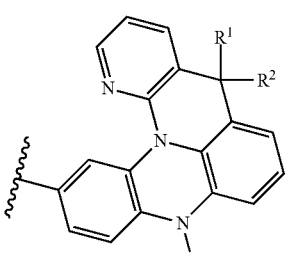
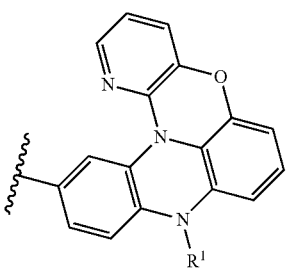
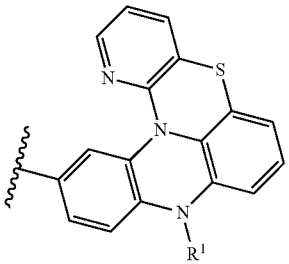
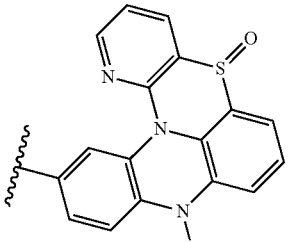
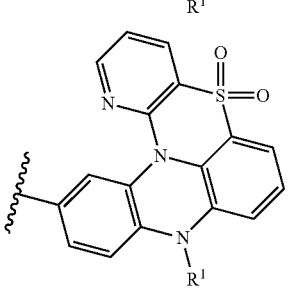

751
-continued
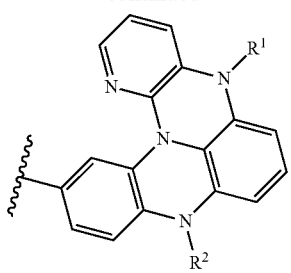
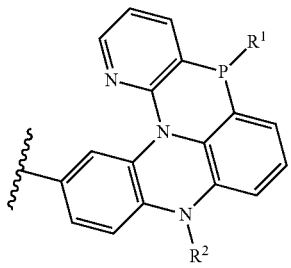
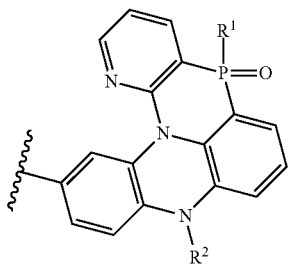
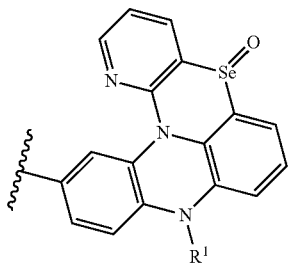
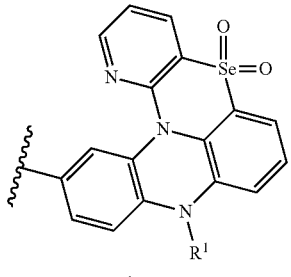
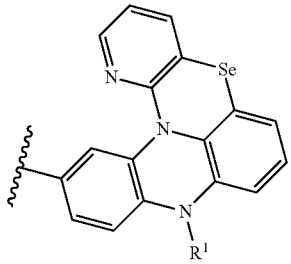
752
-continued
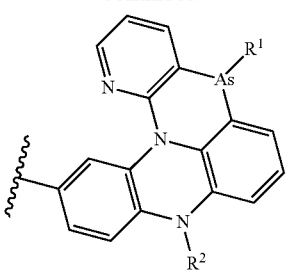
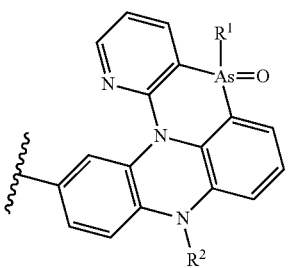
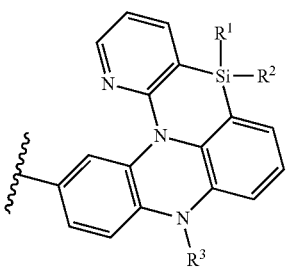
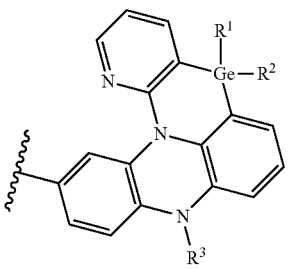
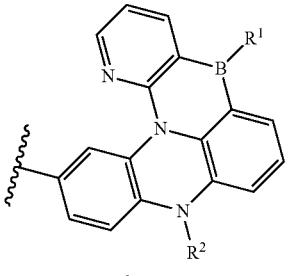
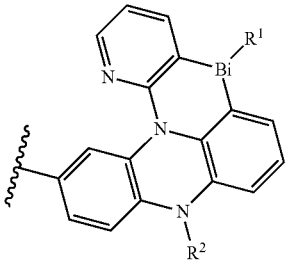

753
-continued
754
-continued
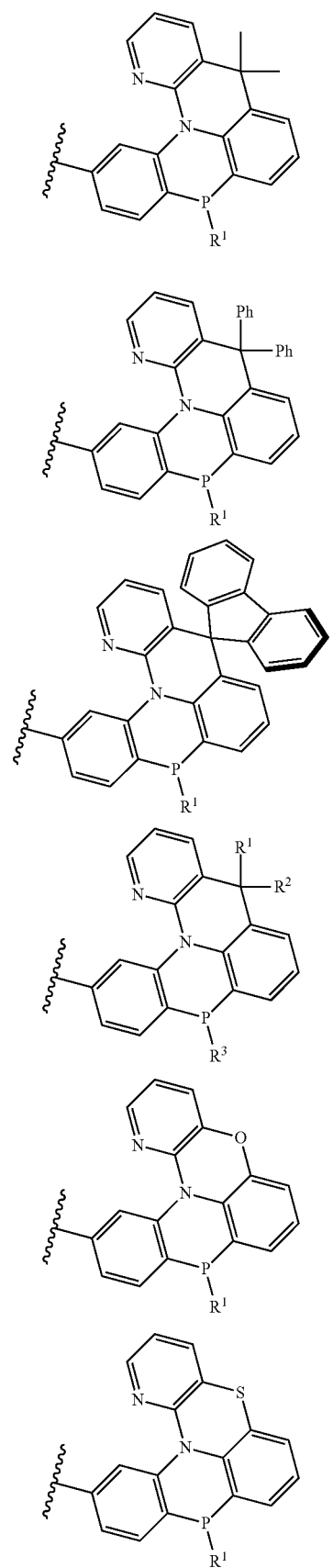
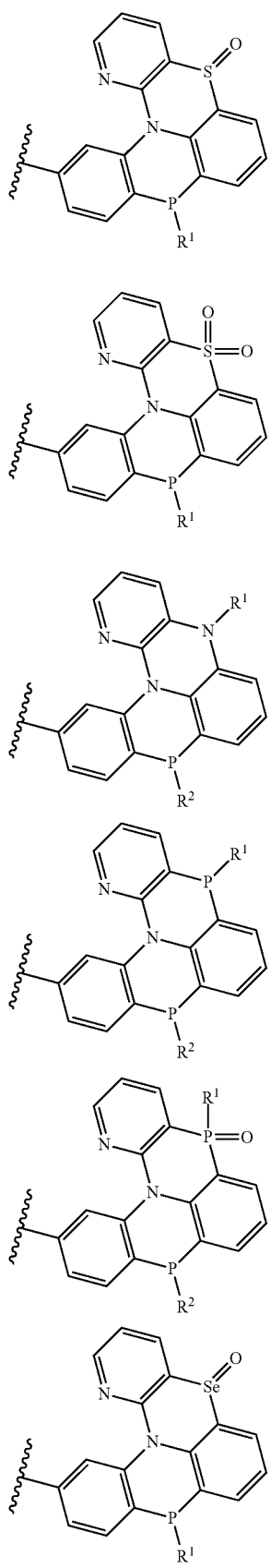

755
-continued
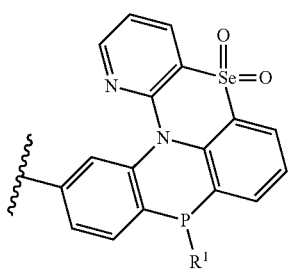
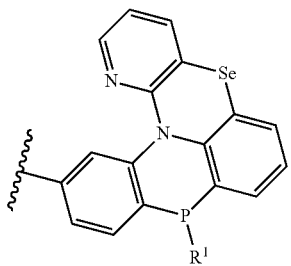
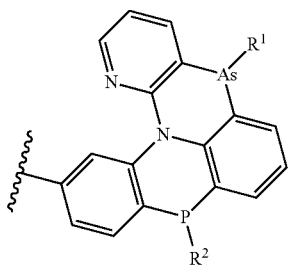
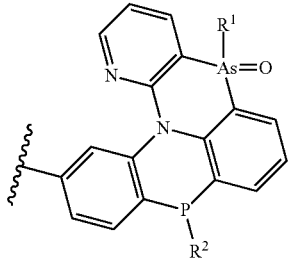
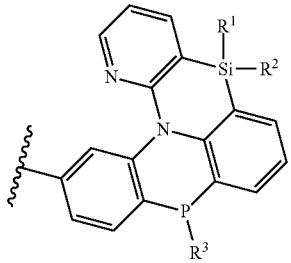
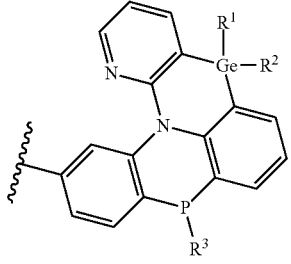
756
-continued
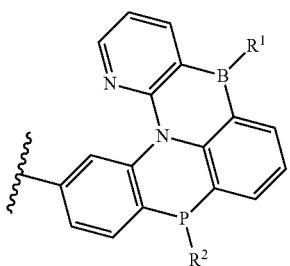
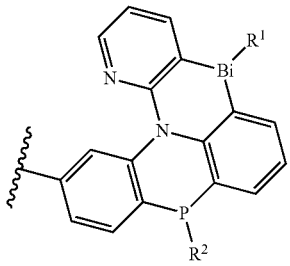
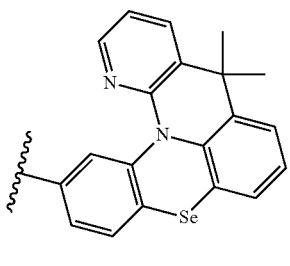
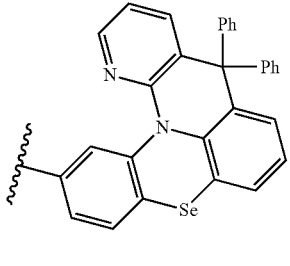
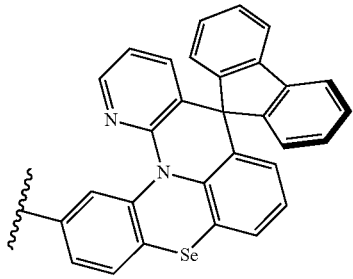
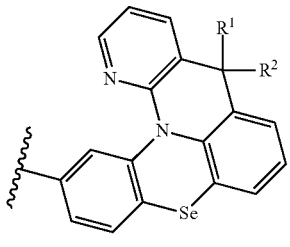

757
-continued
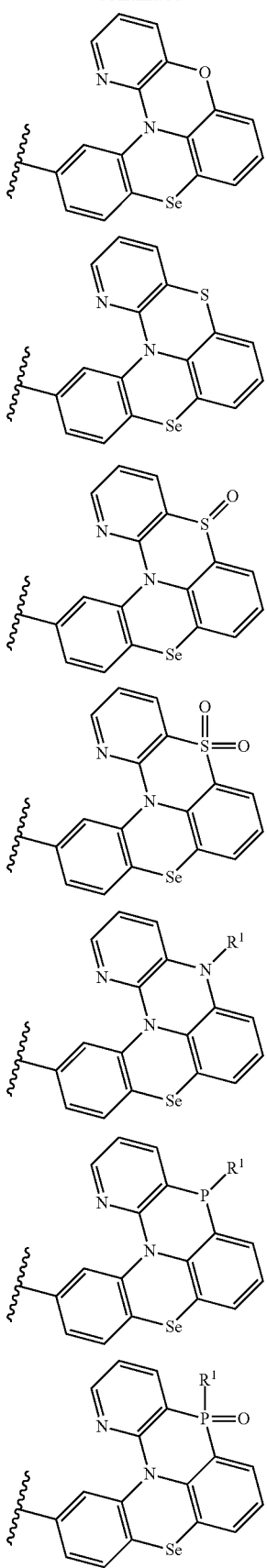
758
-continued
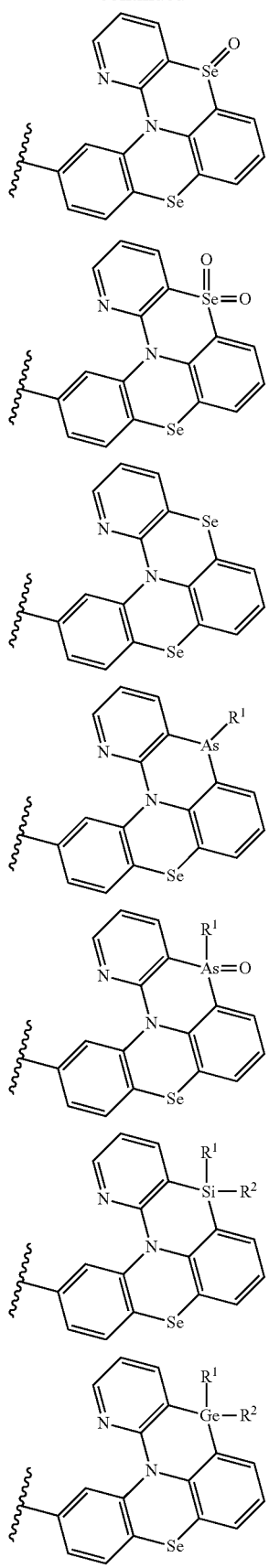

759
-continued
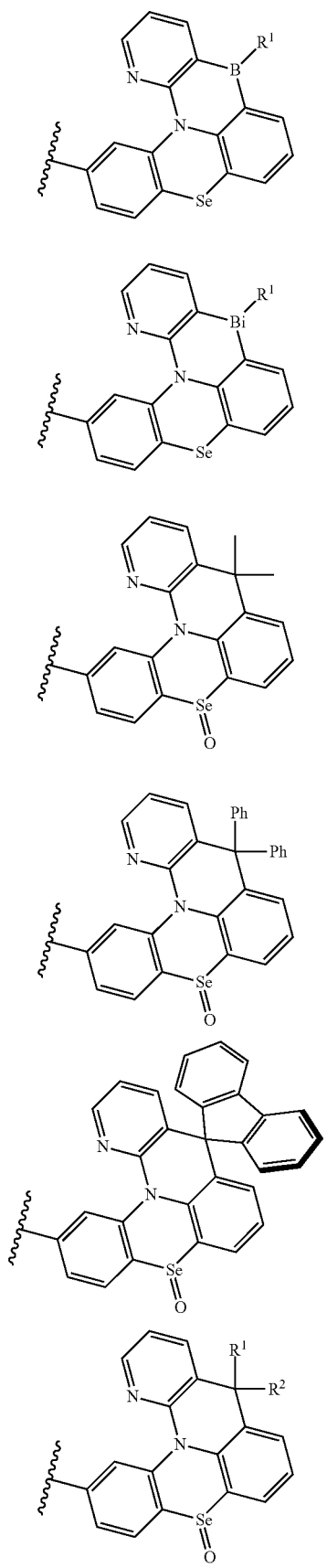
760
-continued
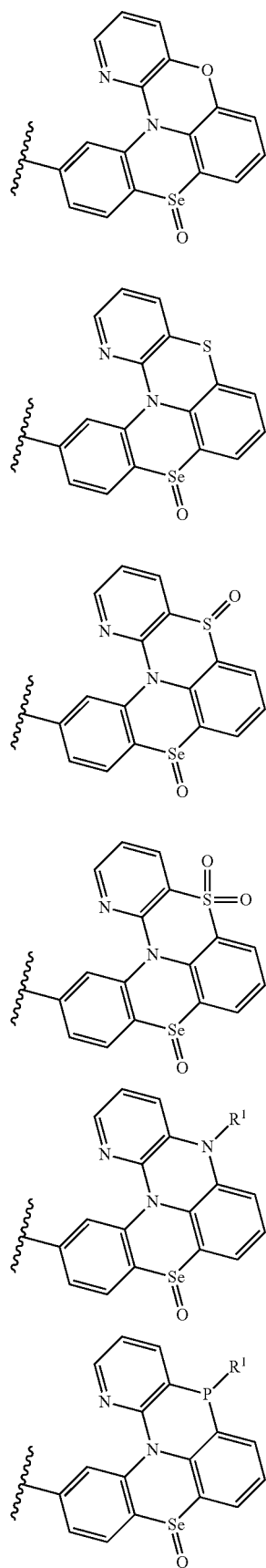

761
-continued
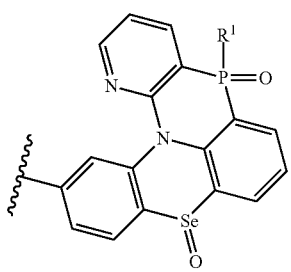
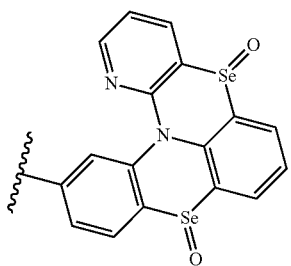
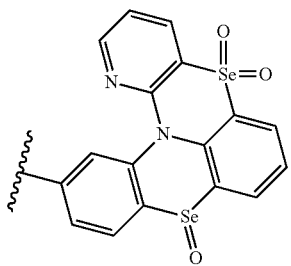
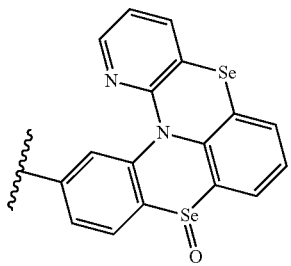
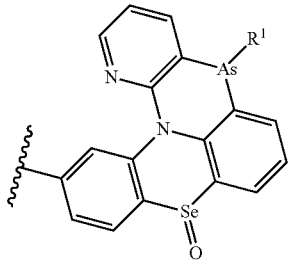
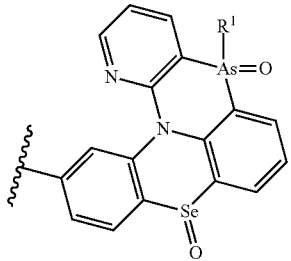
762
-continued
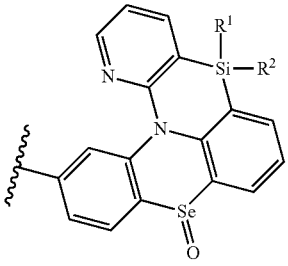
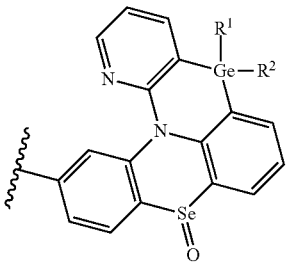
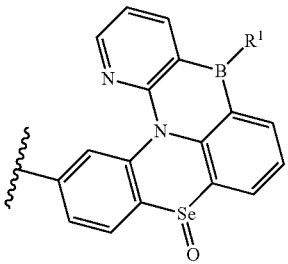
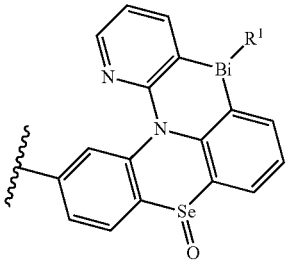
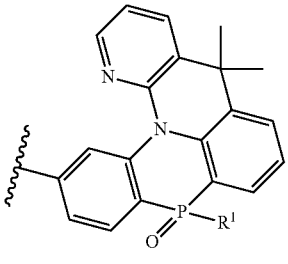
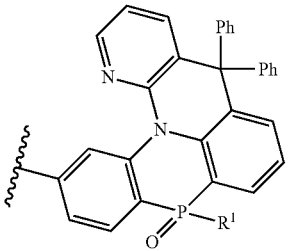

763
-continued
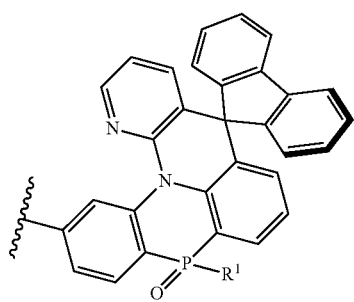
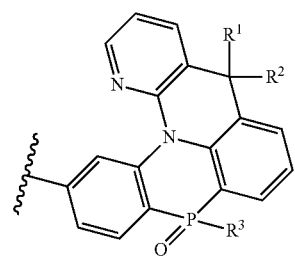
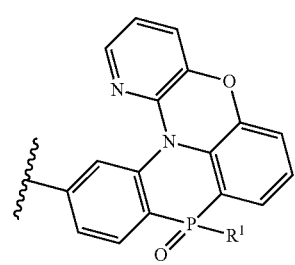
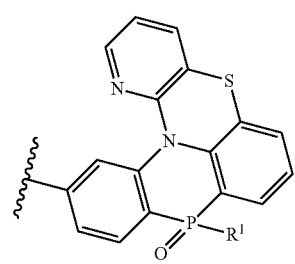
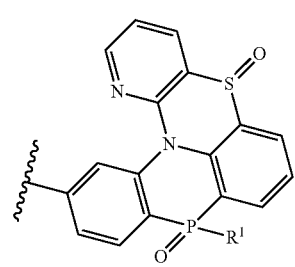
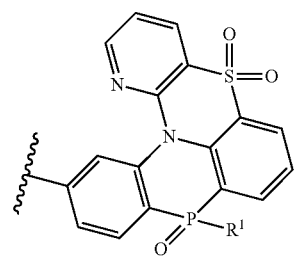
764
-continued
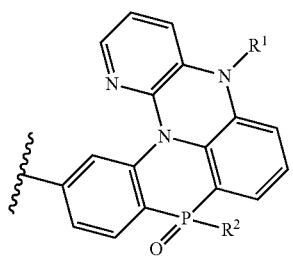
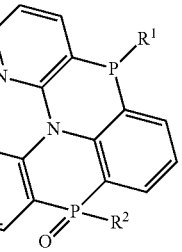
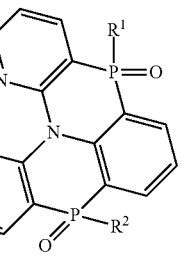
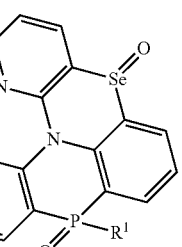
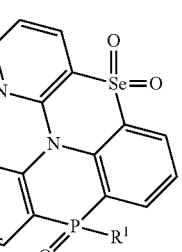
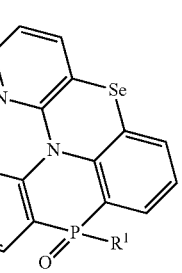

-continued
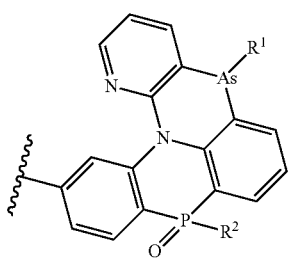
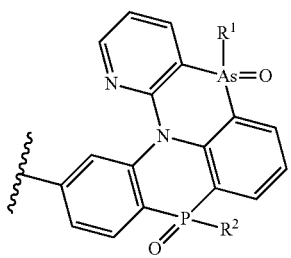
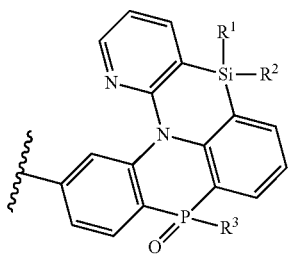
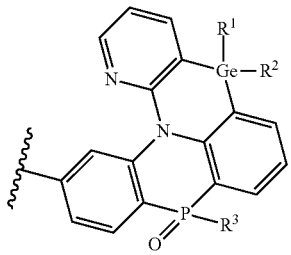
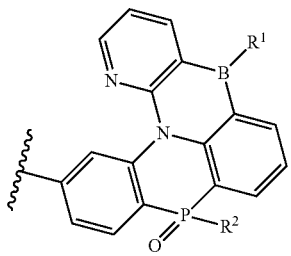
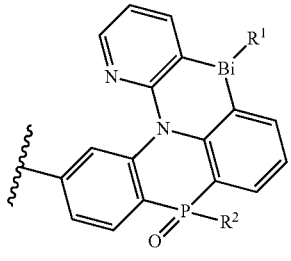
-continued
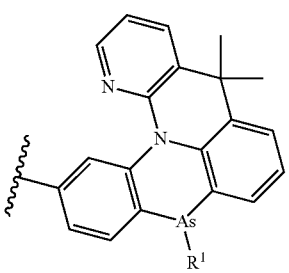
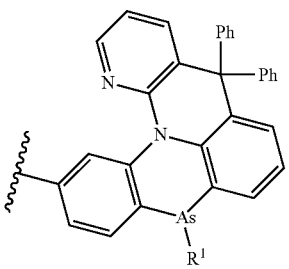
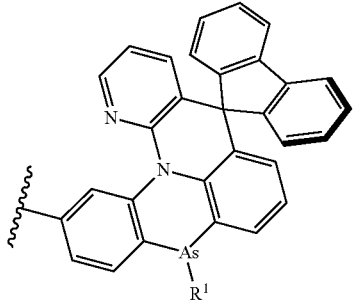
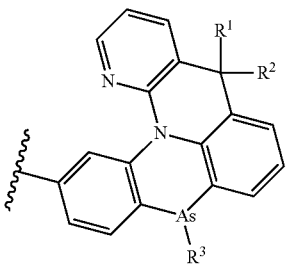
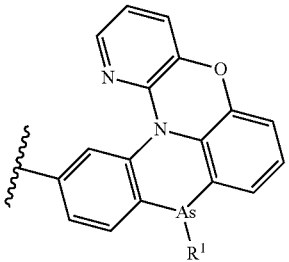
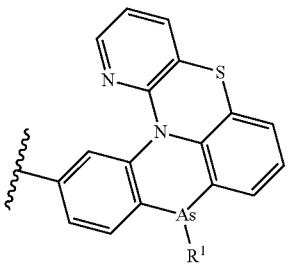

767
-continued
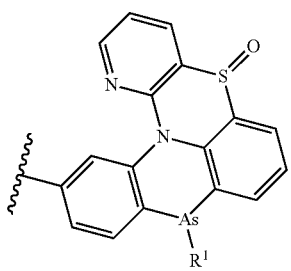
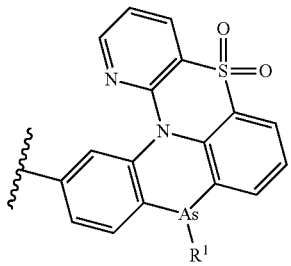
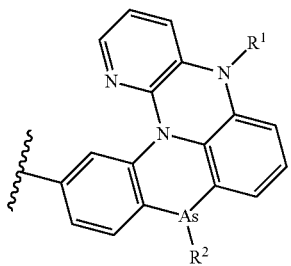
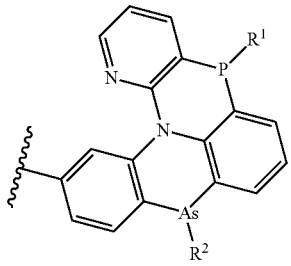
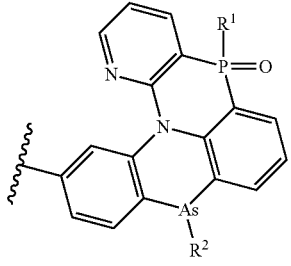
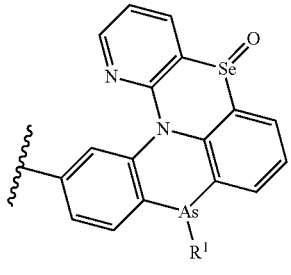
768
-continued
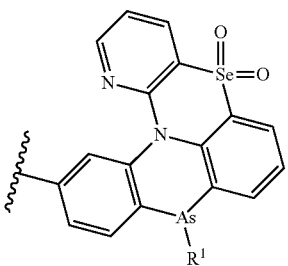
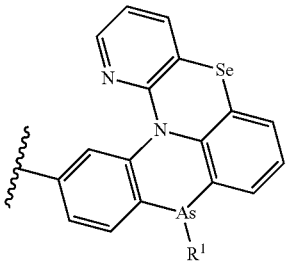
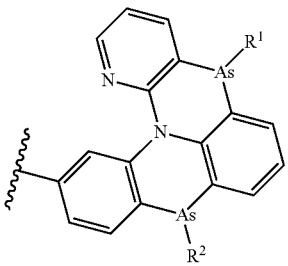
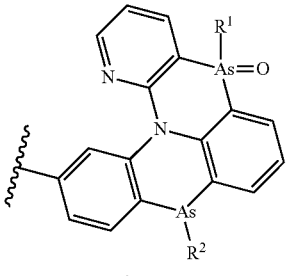
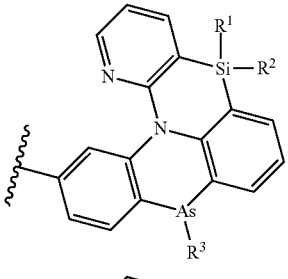
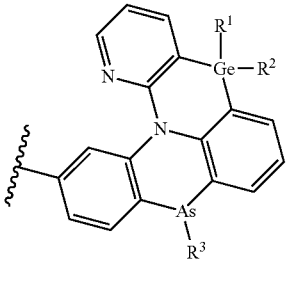

-continued
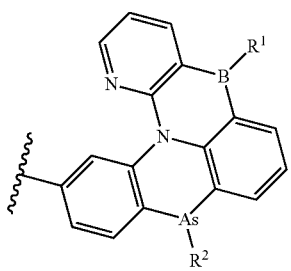
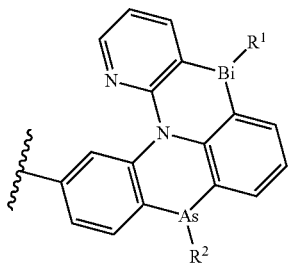
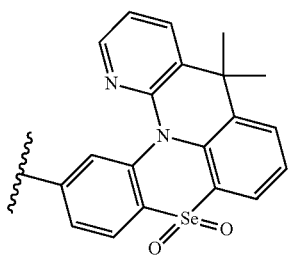
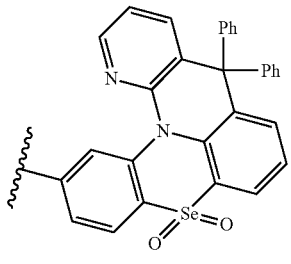
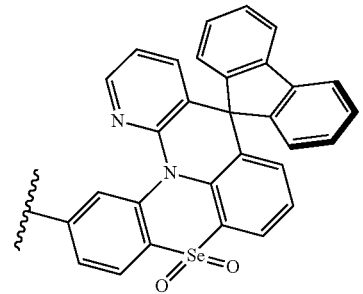
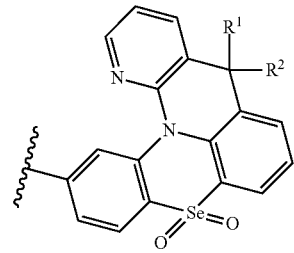
-continued
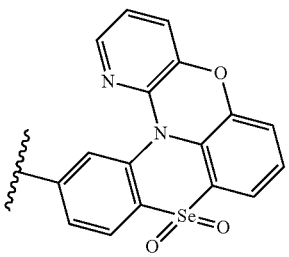
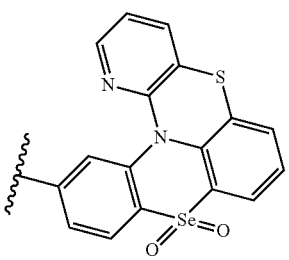
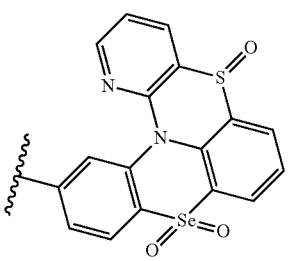
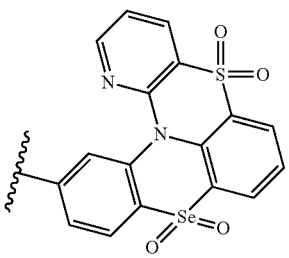
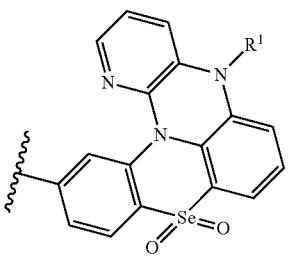
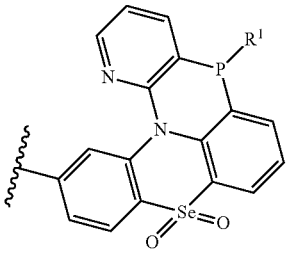

771
-continued
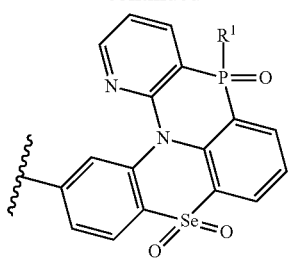
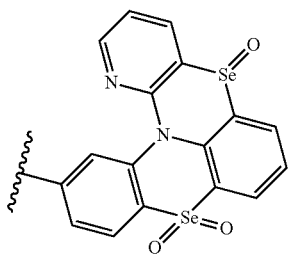
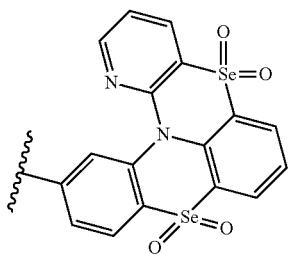
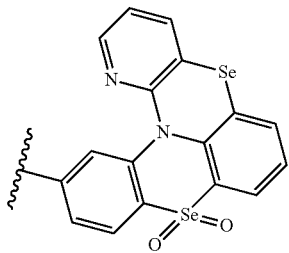
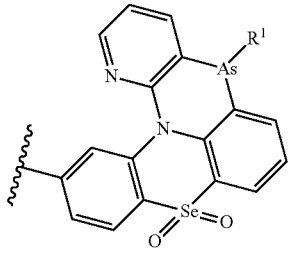
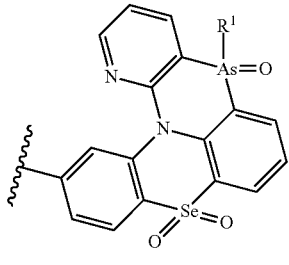
772
-continued
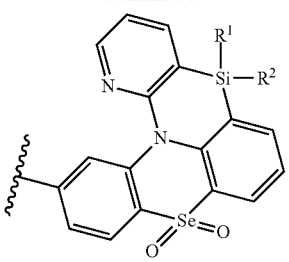
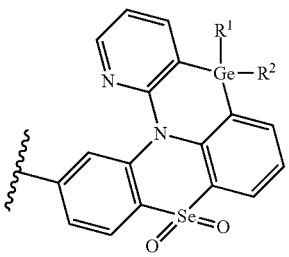
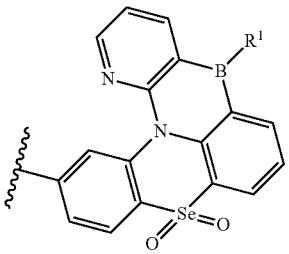
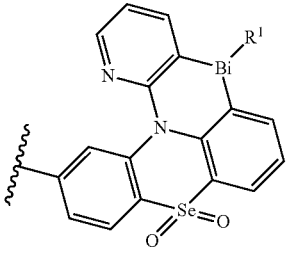
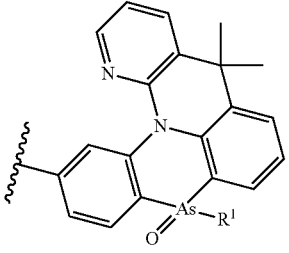
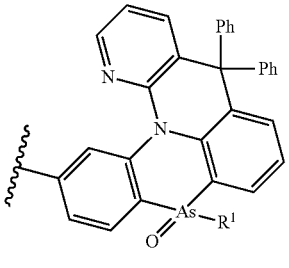

-continued
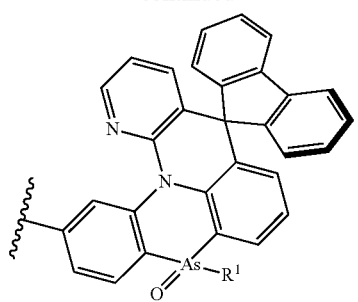
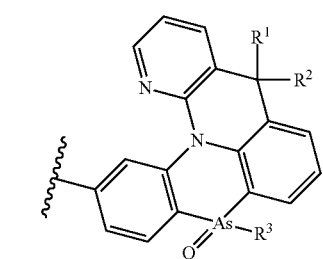
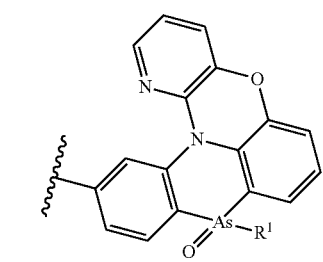
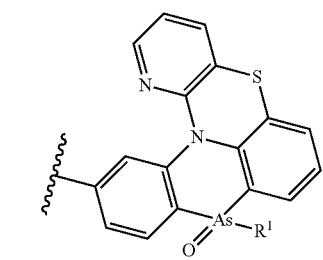
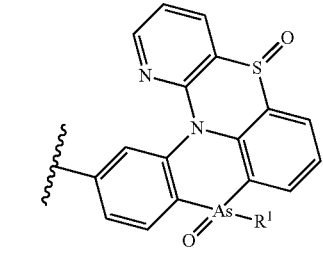
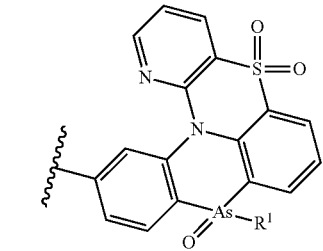
-continued
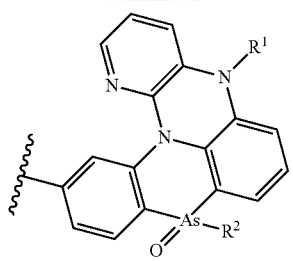
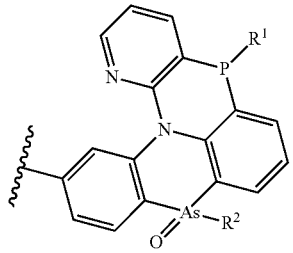
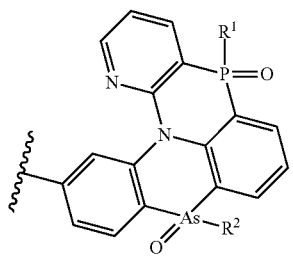
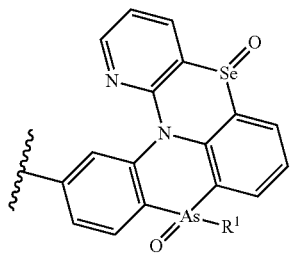
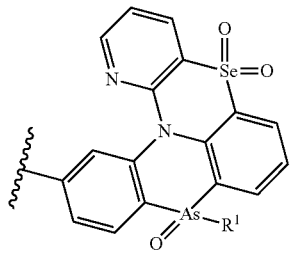
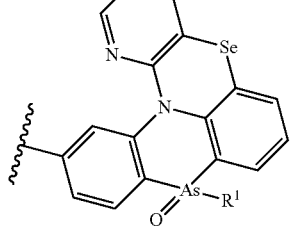

775
-continued
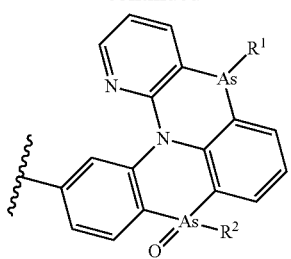
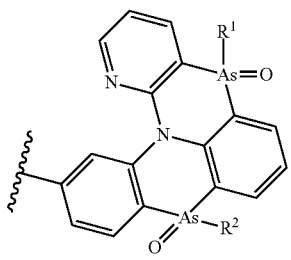
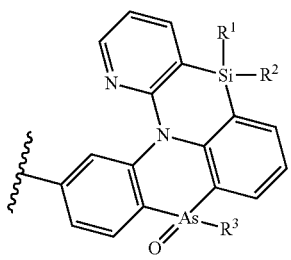
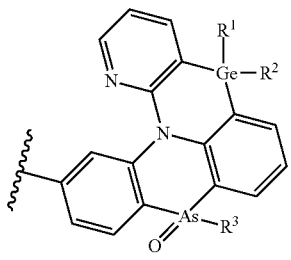
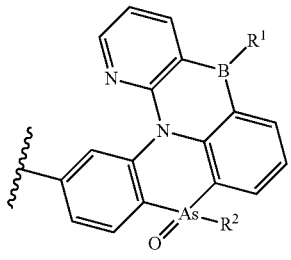
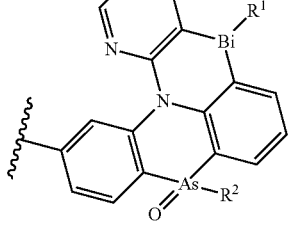
776
-continued
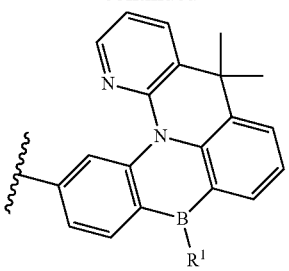
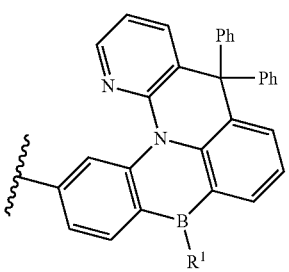
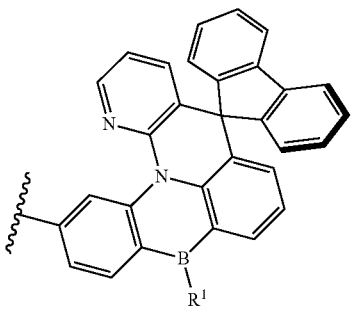
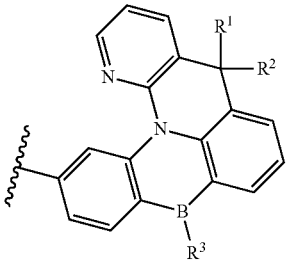
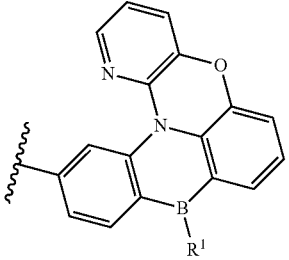
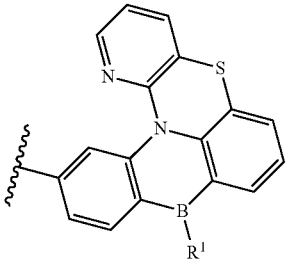

777
-continued
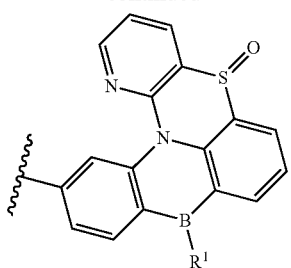
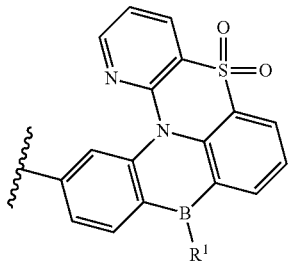
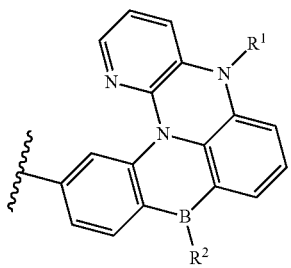
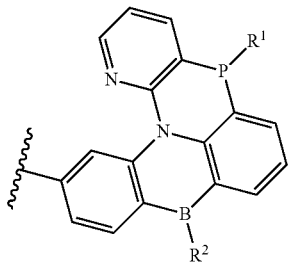
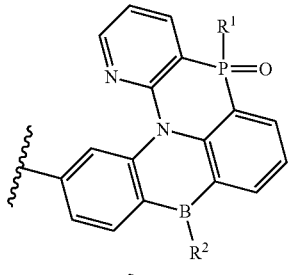
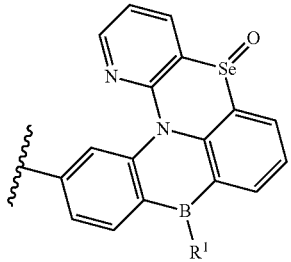
778
-continued
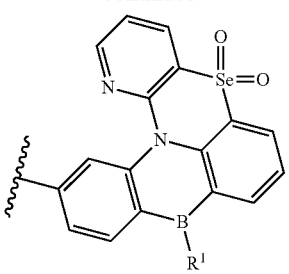
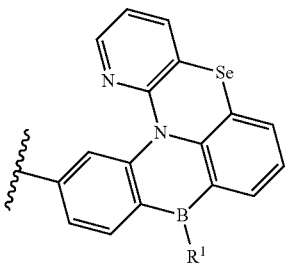
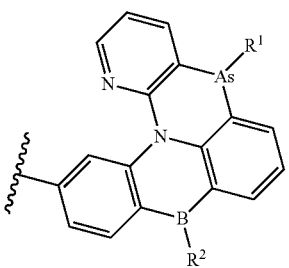
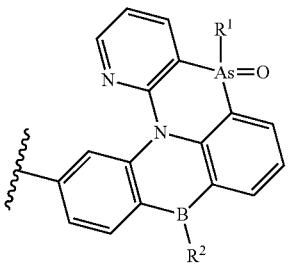
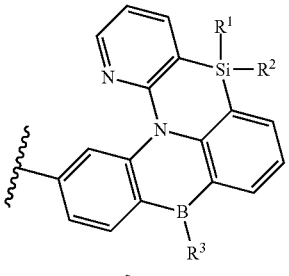
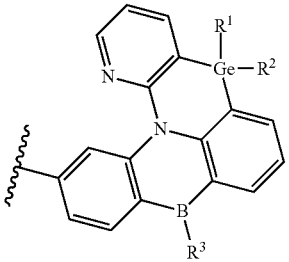

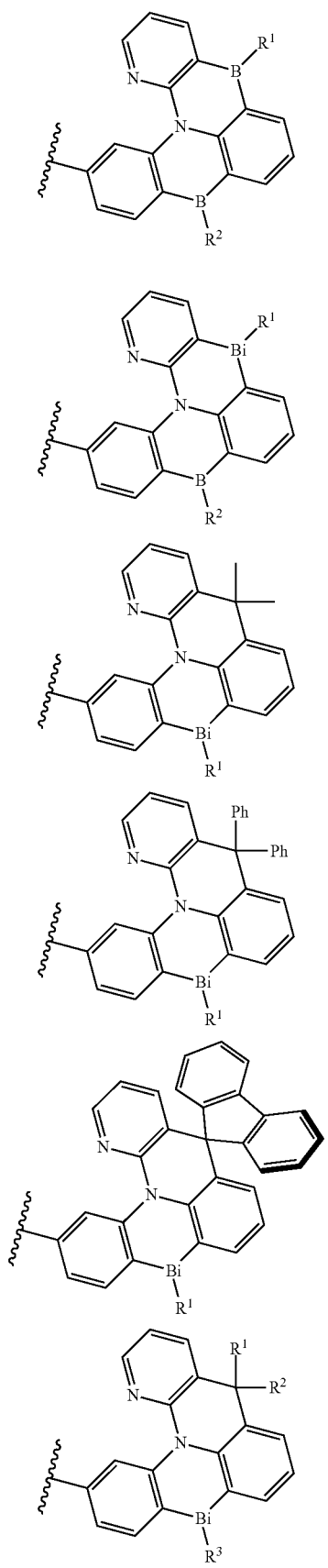
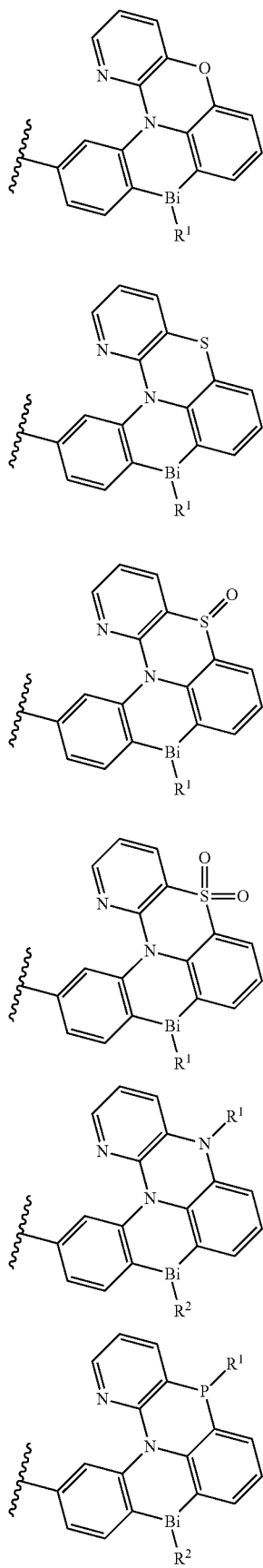

781
-continued
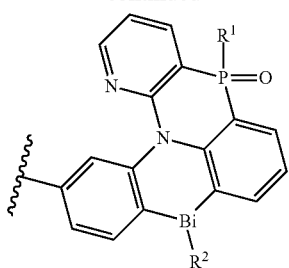
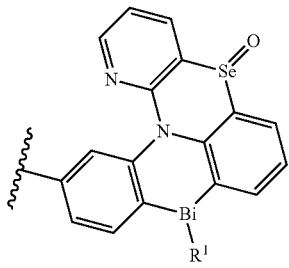
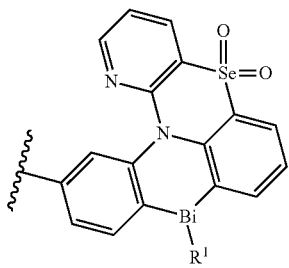
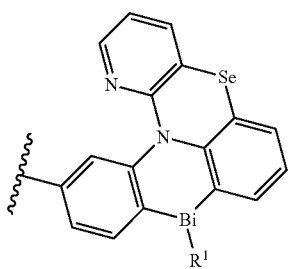
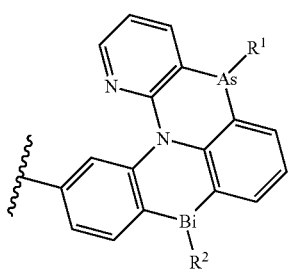
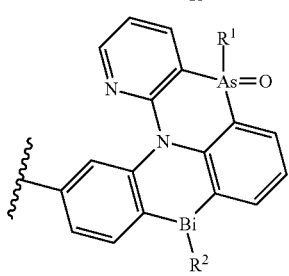
782
-continued
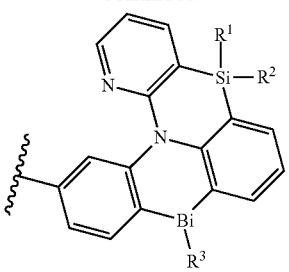
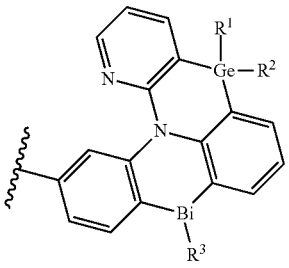
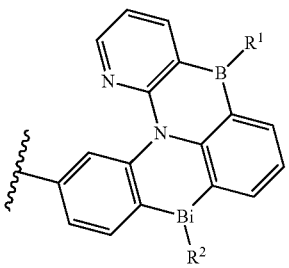
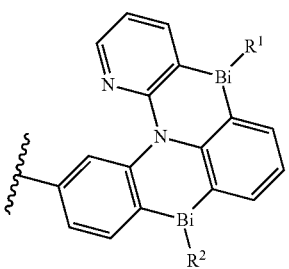
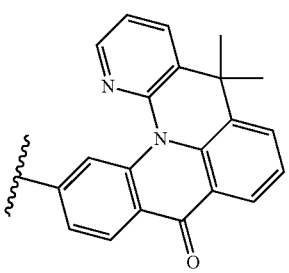
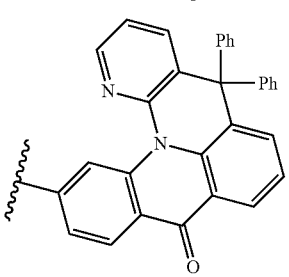

783
-continued
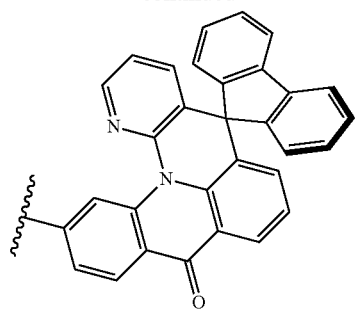
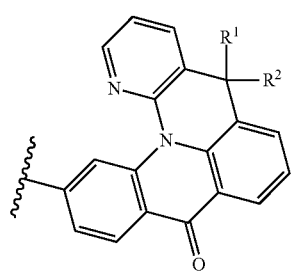
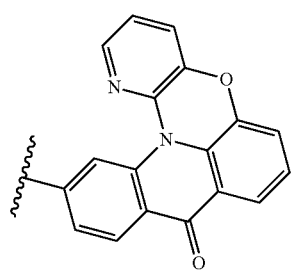
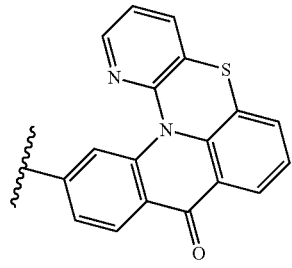
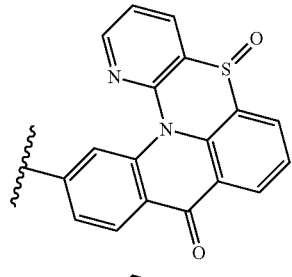
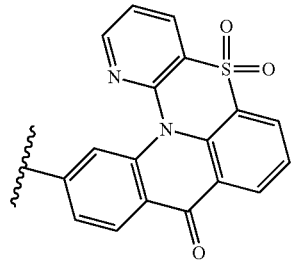
784
-continued
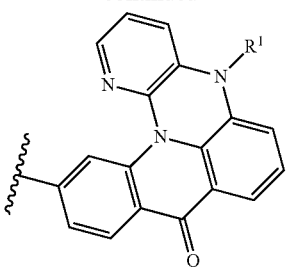
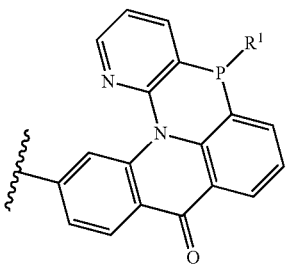
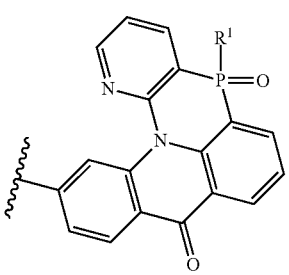
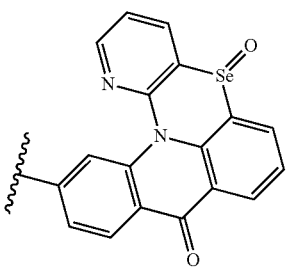
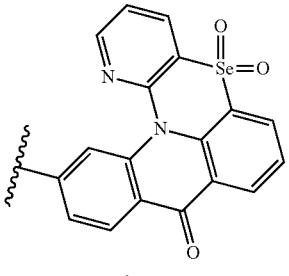
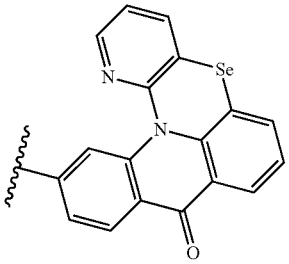

785
-continued
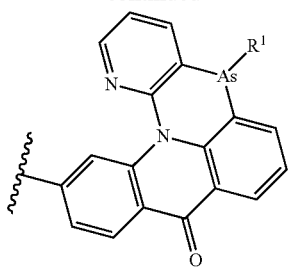
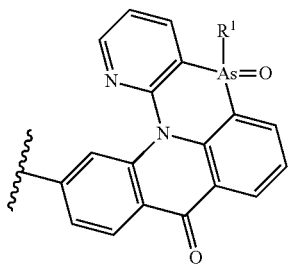
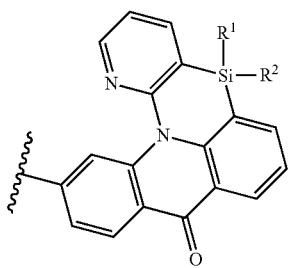
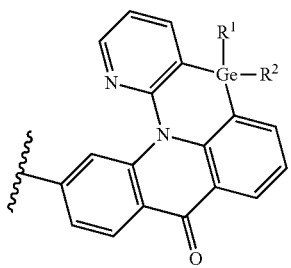
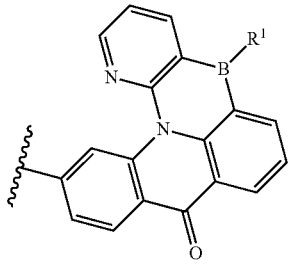
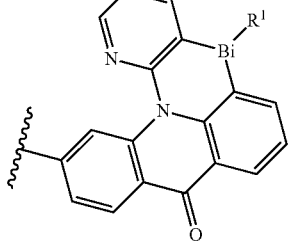
786
-continued
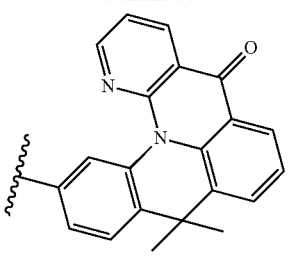
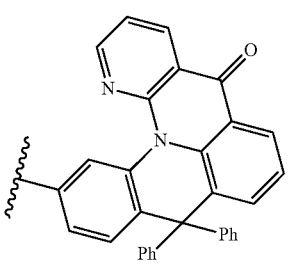
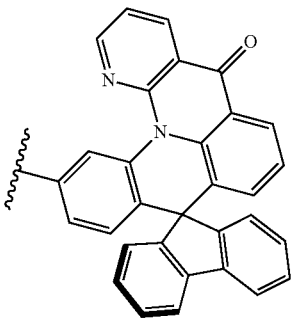
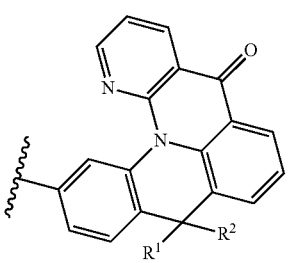
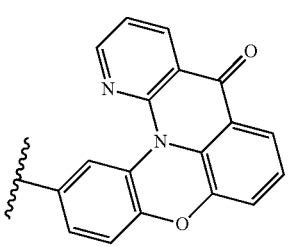
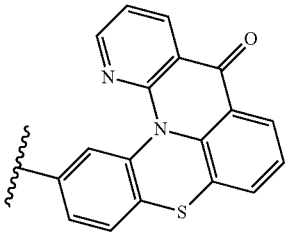

787
-continued
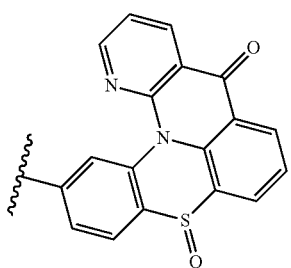
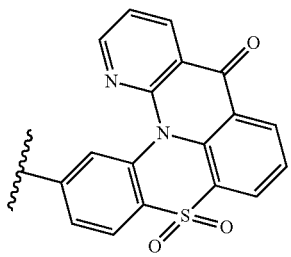
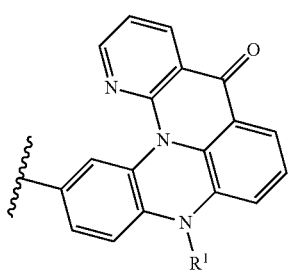
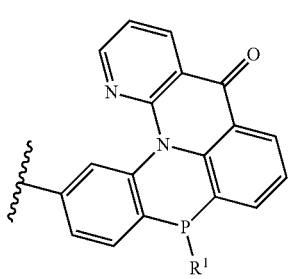
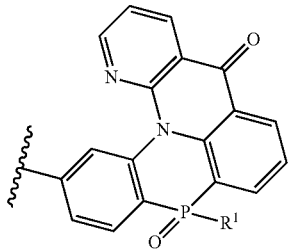
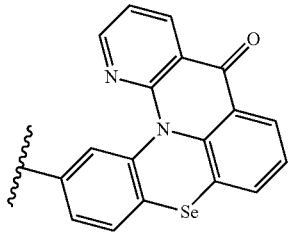
788
-continued
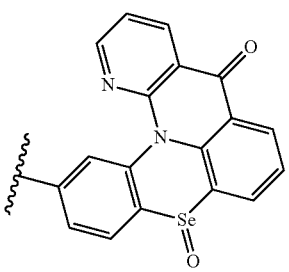
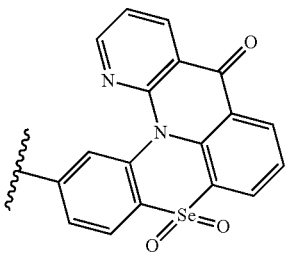
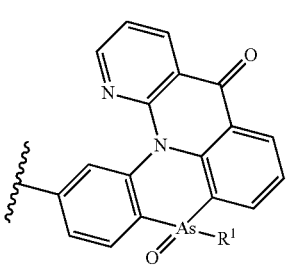
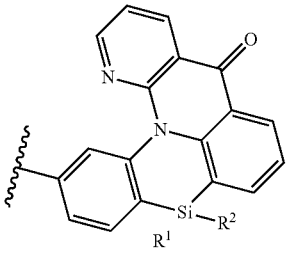
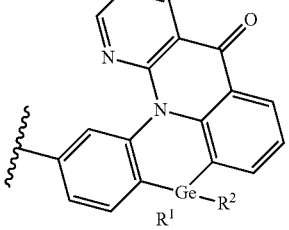

-continued

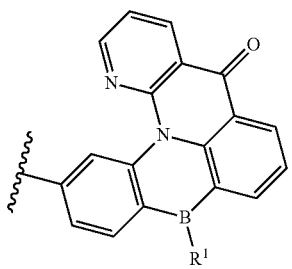

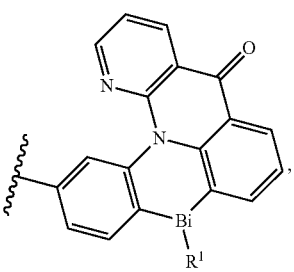

wherein each of $R^1$, $R^2$, $R^3$ and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

5. An emitter comprising the complex of claim 3.

6. An emitter comprising the complex of claim 1, wherein the emitter is a delayed fluorescent and phosphorescent emitter.

7. An emitter comprising the complex of claim 1, wherein the emitter is a phosphorescent emitter.

8. An emitter comprising the complex of claim 1, wherein the emitter is a delayed fluorescent emitter.

9. The complex of claim 1, wherein polymeric comprises polyalkylene, polyester, or polyether.

10. The complex of claim 9, wherein polymeric comprises —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COOCH$_2$CH$_3$)]$_n$—CH$_3$, or —[CH$_2$CH(COO$^t$Bu)]$_n$—CH$_3$, where n is an integer.

11. A device comprising a complex of claim 1.

12. The complex of claim 1, wherein each of $A^1$, $A^2$, $A^3$, and $A^4$ is independently a single bond, $CR^1R^2$, C=O, $SiR^1R^2$, $NR^3$, O, S, S=O, or SO$_2$.

13. The complex of claim 1, wherein each of $A^1$, $A^2$, $A^3$, and $A^4$ is independently a single bond, $CR^1R^2$, $NR^3$, or O.

14. The complex of claim 1, wherein each of $A^1$, $A^2$, $A^3$, and $A^4$ is independently a single bond or $CR^1R^2$.

15. The complex of claim 1, wherein $A^5$ is O, $NR^3$, or $CR^1R^2$.

16. The complex of claim 1, wherein $A^5$ is O.

17. The complex of claim 1, wherein each $R^1$, $R^2$ and $R^3$ is independently hydrogen, deuterium, halogen, hydroxyl; substituted or unsubstituted: aryl, cycloalkyl, cycloalkenyl, heterocyclyl, heteroaryl, alkyl, alkenyl, alkynyl, alkoxy, aryloxy, or haloalkyl.

18. The complex of claim 1, wherein each $R^1$, $R^2$ and $R^3$ is independently hydrogen; substituted or unsubstituted: aryl, alkyl, alkenyl, or alkynyl.

19. The complex of claim 1, wherein each of $R^a$, $R^b$, $R^c$, and $R^d$ is independently present or absent, and if present each of $R^a$, $R^b$, $R^c$, and $R^d$ is independently a mono-, di-, or tri-substitution as valency permits, and each of $R^a$, $R^b$, $R^c$, and $R^d$ is independently hydrogen, halogen, hydroxyl; substituted or unsubstituted: aryl, heteroaryl, alkyl, alkenyl, or alkynyl, and each of $R^x$ and $R^y$ is independently hydrogen, halogen, hydroxyl; substituted or unsubstituted: aryl, heteroaryl, alkyl, alkenyl, or alkynyl.

20. The complex of claim 1, wherein the complex is

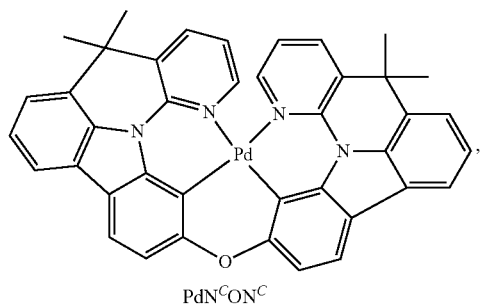

PdN$^C$ON$^C$

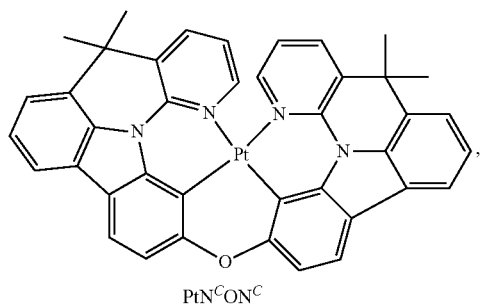

PtN$^C$ON$^C$

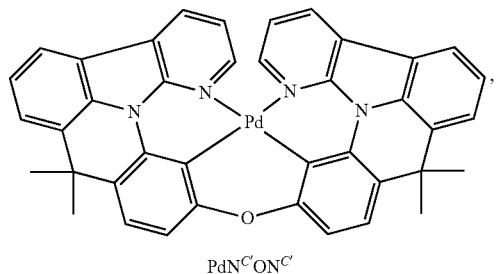

PdN$^C$ON$^C$

-continued
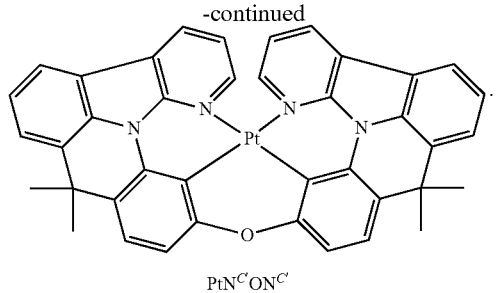
PtN^C ON^C'
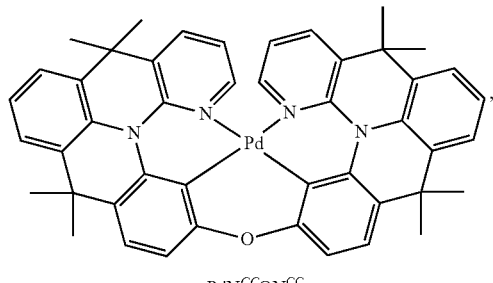
PdN^{CC}ON^{CC}
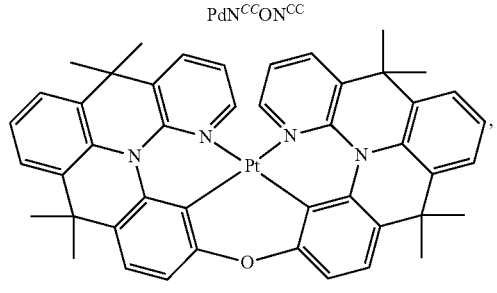
PtN^{CC}ON^{CC}
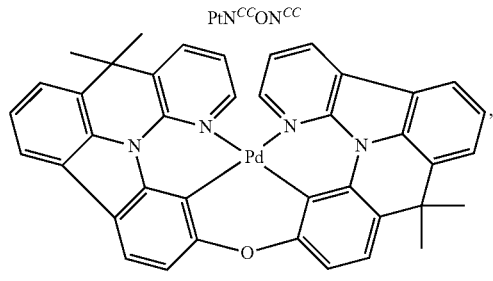
PdN^C ON^C'
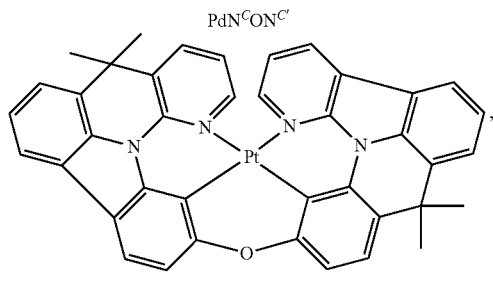
PtN^C ON^C'
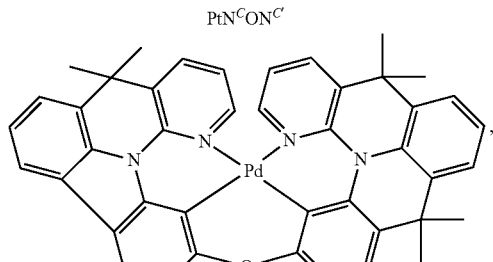
PdN^C ON^{CC}
-continued
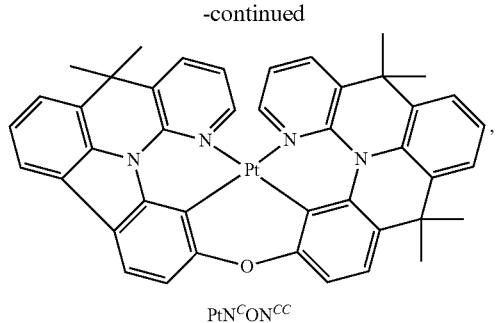
PtN^C ON^{CC}
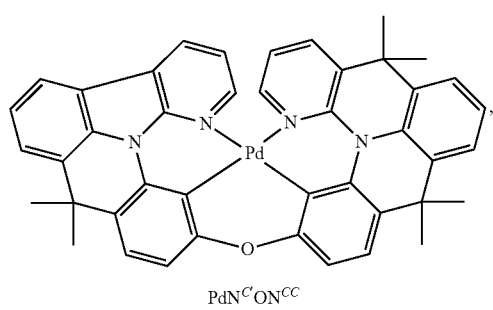
PdN^C' ON^{CC}
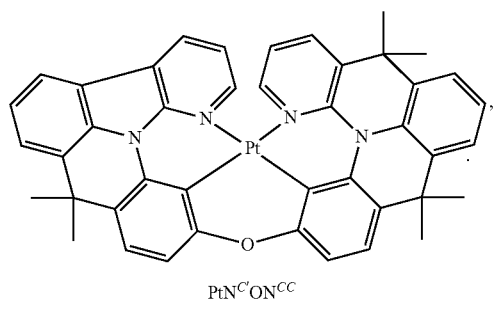
PtN^C' ON^{CC}
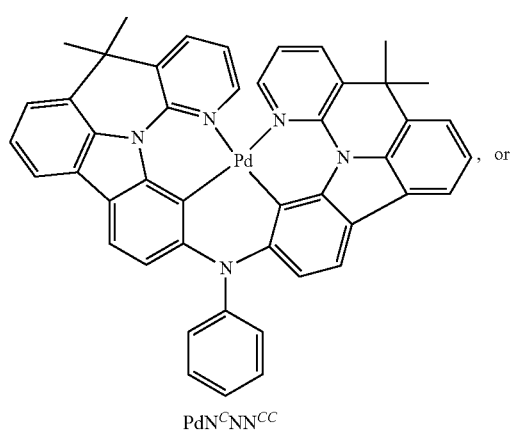
PdN^C NN^{CC}
, or -continued
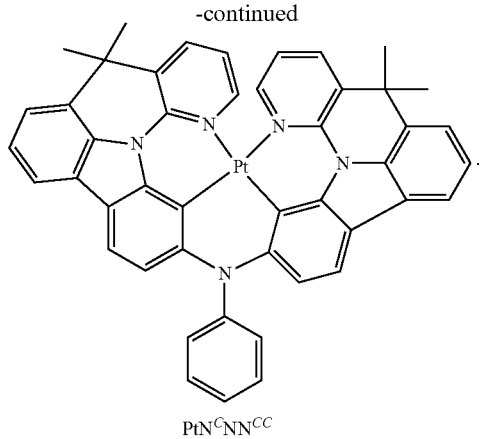
PtN<sup>C</sup>NN<sup>CC</sup>
* * * * *

UNITED STATES PATENT AND TRADEMARK OFFICE
CERTIFICATE OF CORRECTION

PATENT NO. : 9,879,039 B2  
APPLICATION NO. : 15/168942  
DATED : January 30, 2018  
INVENTOR(S) : Jian Li and Guijie Li Page 1 of 2

It is certified that error appears in the above-identified patent and that said Letters Patent is hereby corrected as shown below:

In the Claims

In Claim 1, Column 688-689, Line 40-66 (Column 688) 2-14 (Approx.) (Column 689) below "Formula AIV:" delete

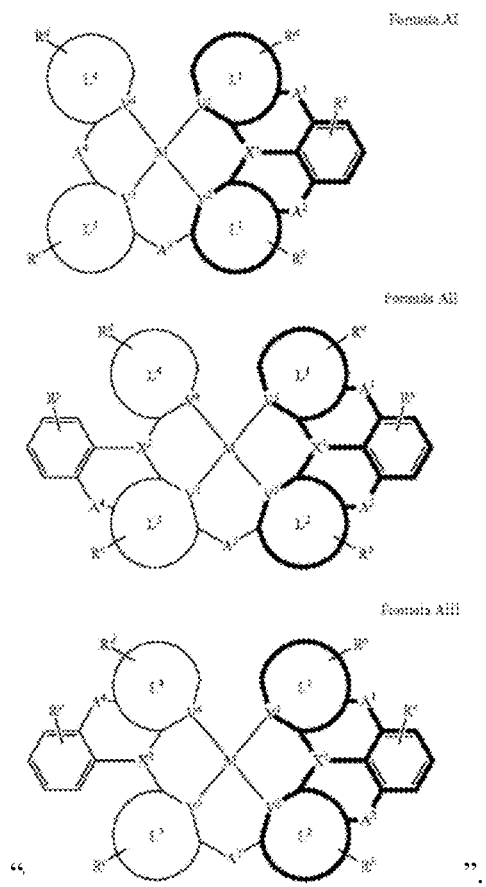

".

Signed and Sealed this  
Eighth Day of May, 2018

Andrei Iancu  
*Director of the United States Patent and Trademark Office*

CERTIFICATE OF CORRECTION (continued)
U.S. Pat. No. 9,879,039 B2

In Claim 1, Column 690, Line 16 delete "le and le" and insert -- $R^1$ and $R^2$ --, therefor.

In Claim 3, Column 716, Line 42 (Approx.) delete "PtN$^{C'}$NN$^{CC}$-dtb" and insert -- PtN$^C$NN$^{CC}$-dtb --, therefor.